US009957271B2

(12) United States Patent
Casaubon et al.

(10) Patent No.: US 9,957,271 B2
(45) Date of Patent: May 1, 2018

(54) SUBSTITUTED BICYCLIC AZA-HETEROCYCLES AND ANALOGUES AS SIRTUIN MODULATORS

(71) Applicant: GlaxoSmithKline, LLC, Wilmington, DE (US)

(72) Inventors: Rebecca L. Casaubon, Cambridge, MA (US); Radha Narayan, Belmont, MA (US); Christopher Oalmann, Watertown, MA (US); Chi B. Vu, Arlington, MA (US)

(73) Assignee: GLAXOSMITHKLINE LLC, Wilmington, DE (US)

(*) Notice: Subject to any disclaimer, the term of this patent is extended or adjusted under 35 U.S.C. 154(b) by 0 days. days.

(21) Appl. No.: 14/353,096

(22) PCT Filed: Oct. 19, 2012

(86) PCT No.: PCT/US2012/061015
§ 371 (c)(1),
(2) Date: Apr. 21, 2014

(87) PCT Pub. No.: WO2013/059587
PCT Pub. Date: Apr. 25, 2013

(65) Prior Publication Data
US 2014/0349993 A1 Nov. 27, 2014

(51) Int. Cl.
C07D 487/04 (2006.01)
A61K 45/06 (2006.01)
A61K 31/5025 (2006.01)
A61K 31/506 (2006.01)
A61K 31/519 (2006.01)
A61K 31/5377 (2006.01)
C07D 491/107 (2006.01)
C07D 495/10 (2006.01)
C07D 519/00 (2006.01)

(52) U.S. Cl.
CPC .......... C07D 487/04 (2013.01); A61K 31/506 (2013.01); A61K 31/5025 (2013.01); A61K 31/519 (2013.01); A61K 31/5377 (2013.01); A61K 45/06 (2013.01); C07D 491/107 (2013.01); C07D 495/10 (2013.01); C07D 519/00 (2013.01)

(58) Field of Classification Search
CPC .................................................. C07D 487/04
See application file for complete search history.

(56) References Cited

U.S. PATENT DOCUMENTS 5,707,997 A   1/1998  Shoji et al.
7,662,826 B2  2/2010  Seno et al.
7,750,000 B2  7/2010  Prien et al.
2004/0043998 A1  3/2004  Kato et al.
2006/0089362 A1  4/2006  Seno et al.
2007/0037809 A1  2/2007  Nunes et al.
2007/0037865 A1  2/2007  Nunes et al.
2007/0093490 A1  4/2007  Prien et al.
2008/0039455 A1  2/2008  Ince et al.
2008/0153813 A1  6/2008  Chen et al.
2009/0163545 A1  6/2009  Goldfarb
2010/0029657 A1  2/2010  Levin et al.
2010/0056529 A1  3/2010  Harbeson
2010/0130488 A1  5/2010  Rice et al.
2010/0216798 A1  8/2010  Nakai et al.
2011/0046127 A1  2/2011  Pevarello et al.
2011/0077248 A1  3/2011  Vu et al.
2011/0237564 A1  9/2011  Sanchez et al.
2011/0237580 A1  9/2011  Gijsen et al.
2014/0249147 A1  9/2014  Blum et al.
2014/0288052 A1  9/2014  Blum et al.

FOREIGN PATENT DOCUMENTS

EP  1 334 973 A1  8/2003
EP  1 505 068 A1  2/2005
EP  1 900 739 A1  3/2008
EP  2 014 281 A1  1/2009
WO  WO 2006/068954 A2  6/2006
WO  WO 2006/084634 A1  8/2006
WO  WO 2006/094235 A1  9/2006

(Continued)

OTHER PUBLICATIONS

Chi B. Vu "Discovery of Imidazo[1,2-b]thiazole Derivatives as Novel SIRT1 Activators" Journal of Medicinal Chemistry, 2009, vol. 52, No. 5. 1275-1283.*
George A. Patani "Bioisosterism: A Rational Approach in Drug Design" Chemical Reviews 1996, 96, 3147-3176.*
Wermuth, Camille G. "Molecular Variation Based on Isosteric Replacements" in Chapter 13, The Practice of Medicinal Chemistry, Academic: 1996.*
Nakamura, Toshio "Imidazole derivatives as new potent and selective 20-HETE synthase inhibitors." Bioorganic & Medicinal Chemistry Letters 2004, 14, 333-336.*
Li, Bing et. al. "N-(Arylacetyl)-biphenylalanines as Potent VLA-4 Antagonists" Bioorganic & Medicinal Chemistry Letters 2002, 12, 2141-2144.*

(Continued)

Primary Examiner — David K O'Dell
(74) Attorney, Agent, or Firm — Nicole Ho; Andrea Lockenour

(57) ABSTRACT

Provided herein are novel substituted bicyclic aza-heterocycle sirtuin-modulating compounds and methods of use thereof. The sirtuin-modulating compounds may be used for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity. Also provided are compositions comprising a sirtuin-modulating compound in combination with another therapeutic agent.

4 Claims, No Drawings

(56) References Cited

FOREIGN PATENT DOCUMENTS

| WO | WO 2009060197 A1 * | 5/2009 | ............ C07D 487/04 |
|---|---|---|---|
| WO | WO 2009/146358 A1 | 12/2009 | |
| WO | WO 2010/070008 A1 | 6/2010 | |
| WO | WO 2010/086040 A1 | 8/2010 | |
| WO | WO 2010/089292 A1 | 8/2010 | |
| WO | WO 2010/101949 A1 | 9/2010 | |
| WO | WO 2010/139483 A1 | 12/2010 | |
| WO | WO 2012/078855 A1 | 6/2012 | |
| WO | WO 2013/059589 A1 | 4/2013 | |
| WO | WO 2013/059594 | 4/2013 | |

OTHER PUBLICATIONS

Kim, et al. "Structure based design and syntheses of amino-1H-pyrazole amide derivates as selective Raf kinase inhibitors in melanoma cells" Bioorganic & Medicinal Chemistry, vol. 19, Issue 6, Mar. 2011, pp. 1915-1923.

Database CAPLUS [online] Chemical Abstracts Service, Goldfarb, David Scott, "Method using lifespan-altering compounds for altering the lifespan of eukaryotic organisms, and screening for such compounds" XP002736489, retrieved form STN Database accession No. 2009:846108.

Dalinger, et al., "Liquid-phase synthesis of combinatorial libraries based on 7-trifluoromethyl-substituted pyrazolo[1,5-a] Pyrimidine scaffold", Journal of Combinatorial Chemistry, 7(2):236-245 (2005).

EP 12842012 Search Report dated Mar. 5, 2015.
EP 12840924.0 Search Report dated Jun. 6, 2015.
EP 12840924.0 Search Report dated Feb. 2, 2016.
EP 12842273.0 Search Report dated Aug. 5, 2015.

* cited by examiner

SUBSTITUTED BICYCLIC AZA-HETEROCYCLES AND ANALOGUES AS SIRTUIN MODULATORS

This application is a 371 of International Application No. PCT/US2012/061015, filed Oct. 19, 2012, which claims the benefit of 61/549,370 filed Oct. 20, 2011.

BACKGROUND

The Silent Information Regulator (SIR) family of genes represents a highly conserved group of genes present in the genomes of organisms ranging from archaebacteria to eukaryotes. The encoded SIR proteins are involved in diverse processes from regulation of gene silencing to DNA repair. A well-characterized gene in this family is *S. cerevisiae* SIR2, which is involved in silencing HM loci that contain information specifying yeast mating type, telomere position effects and cell aging. The yeast Sir2 protein belongs to a family of histone deacetylases. The proteins encoded by members of the SIR gene family show high sequence conservation in a 250 amino acid core domain. The Sir2 homolog, CobB, in *Salmonella typhimurium*, functions as an NAD (nicotinamide adenine dinucleotide)-dependent ADP-ribosyl transferase.

The Sir2 protein is a class III deacetylase which uses NAD as a cosubstrate. Unlike other deacetylases, many of which are involved in gene silencing, Sir2 is insensitive to class I and II histone deacetylase inhibitors like trichostatin A (TSA).

Deacetylation of acetyl-lysine by Sir2 is tightly coupled to NAD hydrolysis, producing nicotinamide and a novel acetyl-ADP ribose compound. The NAD-dependent deacetylase activity of Sir2 is essential for its functions, which can connect its biological role with cellular metabolism in yeast. Mammalian Sir2 homologs have NAD-dependent histone deacetylase activity.

Biochemical studies have shown that Sir2 can readily deacetylate the amino-terminal tails of histones $H_3$ and H4, resulting in the formation of 2'/3'-O-acetyl-ADP-ribose (OAADPR) and nicotinamide. Strains with additional copies of SIR2 display increased rDNA silencing and a 30% longer life span. It has also been shown that additional copies of the *C. elegans* SIR2 homolog, sir-2.1, and the *D. melanogaster* dSir2 gene extend life span in those organisms. This implies that the SIR2-dependent regulatory pathway for aging arose early in evolution and has been well conserved. Today, Sir2 genes are believed to have evolved to enhance an organism's health and stress resistance to increase its chance of surviving adversity.

In humans, there are seven Sir2-like genes (SIRT1-SIRT7) that share the conserved catalytic domain of Sir2. SIRT1 is a nuclear protein with the highest degree of sequence similarity to Sir2. SIRT1 regulates multiple cellular targets by deacetylation including the tumor suppressor p53, the cellular signaling factor NF-κB, and the FOXO transcription factor.

SIRT3 is a homolog of SIRT1 that is conserved in prokaryotes and eukaryotes. The SIRT3 protein is targeted to the mitochondrial cristae by a unique domain located at the N-terminus. SIRT3 has $NAD^+$-dependent protein deacetylase activity and is ubiquitously expressed, particularly in metabolically active tissues. Upon transfer to the mitochondria, SIRT3 is believed to be cleaved into a smaller, active form by a mitochondrial matrix processing peptidase (MPP).

Caloric restriction has been known for over 70 years to improve the health and extend the lifespan of mammals. Yeast life span, like that of metazoans, is also extended by interventions that resemble caloric restriction, such as low glucose. The discovery that both yeast and flies lacking the SIR2 gene do not live longer when calorically restricted provides evidence that SIR2 genes mediate the beneficial health effects of a restricted calorie diet. Moreover, mutations that reduce the activity of the yeast glucose-responsive cAMP (adenosine 3',5'-monophosphate)-dependent (PKA) pathway extend life span in wild type cells but not in mutant sir2 strains, demonstrating that SIR2 is likely to be a key downstream component of the caloric restriction pathway.

SUMMARY

Provided herein are novel sirtuin-modulating compounds and methods of use thereof.

In one aspect, the invention provides sirtuin-modulating compounds of Structural Formulas (I) and (II) as are described in detail below.

In another aspect, the invention provides methods for using sirtuin-modulating compounds, or compositions comprising sirtuin-modulating compounds. In certain embodiments, sirtuin-modulating compounds that increase the level and/or activity of a sirtuin protein may be used for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, chemotherapeutic-induced neuropathy, neuropathy associated with an ischemic event, ocular diseases and/or disorders, cardiovascular disease, blood clotting disorders, inflammation, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating compounds that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As described further below, the methods comprise administering to a subject in need thereof a pharmaceutically effective amount of a sirtuin-modulating compound.

In certain aspects, the sirtuin-modulating compounds may be administered alone or in combination with other compounds, including other sirtuin-modulating compounds, or other therapeutic agents.

DETAILED DESCRIPTION

1. Definitions

As used herein, the following terms and phrases shall have the meanings set forth below. Unless defined otherwise, all technical and scientific terms used herein have the same meaning as commonly understood to one of ordinary skill in the art.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues.

The term "bioavailable", when referring to a compound, is art-recognized and refers to a form of a compound that allows for all or a portion of the amount of compound administered to be absorbed by, incorporated into, or otherwise physiologically available to a subject or patient to whom it is administered.

"Biologically active portion of a sirtuin" refers to a portion of a sirtuin protein having a biological activity, such as the ability to deacetylate ("catalytically active"). Catalytically active portions of a sirtuin may comprise the core domain of sirtuins. Catalytically active portions of SIRT1 having GenBank Accession No. NP_036370 that encompass the NAD$^+$ binding domain and the substrate binding domain, for example, may include without limitation, amino acids 240-664 or 240-505 of GenBank Accession No. NP_036370, which are encoded by the polynucleotide of GenBank Accession No. NM_012238. Therefore, this region is sometimes referred to as the core domain. Other catalytically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238. Another "biologically active" portion of SIRT1 is amino acids 62-293 or 183-225 of GenBank Accession No. NP_036370, which comprise a domain N-terminal to the core domain that is important to the compound binding site.

The term "companion animals" refers to cats and dogs. As used herein, the term "dog(s)" denotes any member of the species *Canis familiaris*, of which there are a large number of different breeds. The term "cat(s)" refers to a feline animal including domestic cats and other members of the family Felidae, genus *Felis*.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "$ED_{50}$" refers to the art-recognized measure of effective dose. In certain embodiments, $ED_{50}$ means the dose of a drug which produces 50% of its maximum response or effect, or alternatively, the dose which produces a predetermined response in 50% of test subjects or preparations, such as isolated tissue or cells. The term "$LD_{50}$" refers to the art-recognized measure of lethal dose. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol-related disorders, such as gallstones, cholecystitis and cholelithiasis, gout, obstructive sleep apnea and respiratory problems, osteoarthritis, and bone loss, e.g., osteoporosis in particular.

The term "livestock animals" refers to domesticated quadrupeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*.

The term "mammal" is known in the art, and exemplary mammals include humans, primates, livestock animals (including bovines, porcines, etc.), companion animals (e.g., canines, felines, etc.) and rodents (e.g., mice and rats).

"Obese" individuals or individuals suffering from obesity are generally individuals having a body mass index (BMI) of at least 25 or greater. Obesity may or may not be associated with insulin resistance.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

A "patient", "subject", "individual" or "host" refers to either a human or a non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress (for example, heatshock, osmotic stress, high energy radiation, chemically-induced stress, DNA damage, inadequate salt level, inadequate nitrogen level, or inadequate nutrient level). Lifespan can be increased by at least about 10%, 20%, 30%, 40%, 50%, 60% or between 20% and 70%, 30% and 60%, 40% and 60% or more using methods described herein.

"Sirtuin-modulating compound" refers to a compound that increases the level of a sirtuin protein and/or increases at least one activity of a sirtuin protein. In an exemplary embodiment, a sirtuin-modulating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

"Sirtuin protein" refers to a member of the sirtuin deacetylase protein family, or preferably to the sir2 family, which include yeast Sir2 (GenBank Accession No. P53685), *C. elegans* Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

"SIRT1 protein" refers to a member of the sir2 family of sirtuin deacetylases. In certain embodiments, a SIRT1 protein includes yeast Sir2 (GenBank Accession No. P53685), *C. elegans* Sir-2.1 (GenBank Accession No. NP_501912), human SIRT1 (GenBank Accession No. NM_012238 or NP_036370 (or AF083106)), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In certain embodiments, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In certain embodiments, a SIRT3 protein includes a fragment of SIRT3 protein that is produced by cleavage with a mitochondrial matrix processing peptidase (MPP) and/or a mitochondrial intermediate peptidase (MIP).

The term "steroisomer" as used herein is art-recognized and refers to any of two or more isomers that have the same molecular constitution and differ only in the three-dimensional arrangement of their atomic groupings in space. When used herein to describe a compounds or genus of compounds, stereoisomer includes any portion of the compound or the compound in its entirety. For example, diastereomers and enantiomers are stereoisomers.

The terms "systemic administration" and "administered systemically," are art-recognized and refer to the administration of a subject composition, therapeutic or other material enterally or parenterally.

The term "tautomer" as used herein is art-recognized and refers to any one of the possible alternative structures that may exist as a result of tautomerism, which refers to a form of constitutional isomerism in which a structure may exist in two or more constitutional arrangements, particularly with respect to the position of hydrogens bonded to oxygen. When used herein to describe a compound or genus of compounds, it is further understood that a "tautomer" is readily interconvertible and exists in equilibrium. For example, keto and enol tautomers exist in proportions determined by the equilibrium position for any given condition, or set of conditions:

The term "therapeutic agent" is art-recognized and refers to any biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a beneficial local or systemic effect in animals, particularly mammals, and more particularly humans, caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of skill in the art. For example, certain compositions described herein may be administered in a sufficient amount to produce a desired effect at a reasonable benefit/risk ratio applicable to such treatment.

"Treating" a condition or disease refers to curing as well as ameliorating at least one symptom of the condition or disease.

The term "vision impairment" refers to diminished vision, which is often only partially reversible or irreversible upon treatment (e.g., surgery). Particularly severe vision impairment is termed "blindness" or "vision loss", which refers to a complete loss of vision, vision worse than 20/200 that cannot be improved with corrective lenses, or a visual field of less than 20 degrees diameter (10 degrees radius).

2. Compounds

In one aspect, the invention provides novel compounds for treating and/or preventing a wide variety of diseases and disorders including, for example, diseases or disorders related to aging or stress, diabetes, obesity, neurodegenerative diseases, ocular diseases and disorders, cardiovascular disease, blood clotting disorders, inflammation, cancer, and/or flushing, etc. Subject compounds, such as sirtuin-modulating compounds that increase the level and/or activity of a sirtuin protein, may also be used for treating a disease or disorder in a subject that would benefit from increased mitochondrial activity, for enhancing muscle performance, for increasing muscle ATP levels, or for treating or preventing muscle tissue damage associated with hypoxia or ischemia. Compounds disclosed herein may be suitable for use in pharmaceutical compositions and/or one or more methods disclosed herein.

In certain embodiments, compounds of the invention are represented by Structural Formula (I):

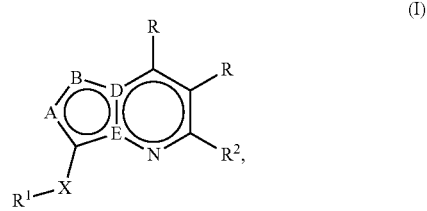

wherein one of D and E is N and the other is C; and
when D is N, one of A and B is N and the other is CR; and
when E is N, B is N and A is N or CR;
or a salt thereof, wherein:

each R is independently selected from hydrogen, halo, OH, C≡N, $C_1$-$C_4$ alkyl, halo-substituted $C_2$-$C_4$ alkyl, $C_1$-$C_4$ alkoxy-substituted $C_1$-$C_4$ alkyl, hydroxy-substituted $C_1$-$C_8$ alkyl, $OR^3$, O—($C_1$-$C_4$ alkyl)-$OR^3$, S—($C_1$-$C_2$ alkyl), S-(halo-substituted $C_1$-$C_4$ alkyl), N(hydroxy-substituted $C_1$-$C_4$ alkyl)$_2$, N(methoxy-substituted $C_1$-$C_4$ alkyl)$_2$, N($C_1$-$C_4$ alkyl)(hydroxy-substituted $C_1$-$C_4$ alkyl), N($C_1$-$C_4$ alkyl)(methoxy-substituted $C_1$-$C_4$ alkyl), N(hydroxy-substituted $C_1$-$C_4$ alkyl)(methoxy-substituted $C_1$-$C_4$ alkyl), $C_5$-$C_7$ cycloalkyl, and 4- to 8-membered non-aromatic heterocycle, and when one or both of E and A is N, then R can additionally be selected from halo-substituted methyl and $C_3$-$C_4$ cycloalkyl;

$R^1$ is an aromatic heterocycle or a fused carbocycle, wherein $R^1$ is optionally substituted with one or more substituents independently selected from halo, C≡N, $C_1$-$C_4$ alkyl, halo-substituted $C_1$-$C_4$ alkyl, $C_1$-$C_4$ alkoxy-substituted $C_1$-$C_4$ alkyl, hydroxy-substituted $C_1$-$C_8$ alkyl, O—$R^3$, O—($C_1$-$C_4$ alkyl)-$OR^3$, =O, $C_3$-$C_7$ cycloalkyl, $SO_2R^3$, S—$R^3$, ($C_1$-$C_4$ alkyl)-N($R^3$)($R^3$), N($R^3$)($R^3$), O—($C_1$-$C_4$ alkyl)-N($R^3$)($R^3$), O—($C_0$-$C_4$ alkyl)-$CR^3R^3$—($C_0$-$C_4$ alkyl), ($C_1$-$C_4$ alkyl)-O—($C_1$-$C_4$ alkyl)-N($R^3$)($R^3$), C(O)—N($R^3$)($R^3$), ($C_1$-$C_4$ alkyl)-C(=O)—N($R^3$)($R^3$), O—($C_0$-$C_4$ alkyl)-$CR^xR^x$—($C_0$-$C_4$ alkyl), $CR^xR^x$, phenyl, O-phenyl, second heterocycle, O-(second heterocycle), 3,4-methylenedioxy, halo-substituted 3,4-methylenedioxy, 3,4-ethylenedioxy, and halo-substituted 3,4-ethylenedioxy, wherein any phenyl, saturated heterocycle, or second heterocycle substituent of $R^1$ is optionally substituted with one or more substituents independently selected from halo, C≡N, $C_1$-$C_4$ alkyl, halo-substituted $C_1$-$C_4$ alkyl, O-(halo-substituted $C_1$-$C_4$ alkyl), O—($C_1$-$C_4$ alkyl), S—($C_1$-$C_4$ alkyl), and S-(halo-substituted $C_1$-$C_4$ alkyl);

$R^2$ is a carbocycle or a heterocycle, wherein $R^2$ is optionally substituted with one or more substituents independently selected from halo, C≡N, $C_1$-$C_4$ alkyl, halo-substituted $C_1$-$C_4$ alkyl, $C_1$-$C_4$ alkoxy-substituted $C_1$-$C_4$ alkyl, hydroxy-substituted $C_1$-$C_8$ alkyl, O—$R^3$, O—($C_1$-$C_4$ alkyl)-$OR^3$, =O, $C_3$-$C_7$ cycloalkyl, $SO_2R^3$, S—$R^3$, ($C_1$-$C_4$ alkyl)-N($R^3$)($R^3$), N($R^3$)($R^3$), O—($C_1$-$C_4$ alkyl)-N($R^3$)($R^3$), O—($C_0$-$C_4$ alkyl)-$CR^3R^3$—($C_0$-$C_4$ alkyl), ($C_1$-$C_4$ alkyl)-O—($C_1$-$C_4$ alkyl)-N($R^3$)($R^3$), C(O)—N($R^3$)($R^3$), ($C_1$-$C_4$ alkyl)-C(O)—N($R^3$)($R^3$), O-phenyl, O-(second heterocycle), 3,4-methylenedioxy, halo-substituted 3,4-methylenedioxy, 3,4-ethylenedioxy, and halo-substituted 3,4-ethylenedioxy, and when E is N, substituents on $R^2$ can be additionally selected from a second heterocycle, and when both D and A are N, substituents on $R^2$ can additionally be selected from phenyl and a second heterocycle, wherein any phenyl, saturated heterocycle or second heterocycle substituent of $R^2$ is optionally substituted with one or more substituents independently selected from halo, C≡N, $C_1$-$C_4$ alkyl, halo-substituted $C_1$-$C_4$ alkyl, O-(halo-substituted $C_1$-$C_4$ alkyl), O—($C_1$-$C_4$ alkyl), S—($C_1$-$C_4$ alkyl), and S-(halo-substituted $C_1$-$C_4$ alkyl);

each $R^3$ is independently selected from hydrogen and $C_1$-$C_4$ alkyl optionally substituted with one or more of OH, —O—($C_1$-$C_4$ alkyl), halo, $NH_2$, NH($C_1$-$C_4$ alkyl), N($C_1$-$C_4$ alkyl)$_2$, NH(methoxy-substituted $C_1$-$C_4$ alkyl), NH(hydroxy-substituted $C_1$-$C_4$ alkyl), N(methoxy-substituted $C_1$-$C_4$ alkyl)(hydroxy-substituted $C_1$-$C_4$ alkyl), N(hydroxy-substituted $C_1$-$C_4$ alkyl)$_2$ and N(methoxy-substituted $C_1$-$C_4$ alkyl)$_2$; or two $R^3$ are taken together with the nitrogen or carbon atom to which they are bound to form a 4- to 8-membered saturated heterocycle optionally comprising one additional heteroatom selected independently from N, S, S(=O), S(=O)$_2$, and O, wherein the heterocycle formed by two $R^3$ is optionally substituted at any carbon atom with one or more of OH, halo, $C_1$-$C_4$ alkyl, halo-substituted $C_1$-$C_4$ alkyl, $NH_2$, NH($C_1$-$C_4$ alkyl), N($C_1$-$C_4$ alkyl)$_2$, O($C_1$-$C_4$ alkyl), NH(hydroxy-substituted $C_1$-$C_4$ alkyl), N(hydroxy-substituted $C_1$-$C_4$ alkyl)$_2$, N(methoxy-substituted $C_1$-$C_4$ alkyl)(hydroxy-substituted $C_1$-$C_4$ alkyl), NH(methoxy-substituted $C_1$-$C_4$ alkyl), or N(methoxy-substituted $C_1$-$C_4$ alkyl)$_2$, and optionally substituted at any substitutable nitrogen atom with $C_1$-$C_4$ alkyl or halo-substituted $C_1$-$C_4$ alkyl;

two $R^x$ taken together with the carbon atom to which they are bound form a 4- to 8-membered carbocycle or heterocycle optionally comprising one or two heteroatoms independently selected from N, S, S(=O), S(=O)$_2$, and O, wherein the carbocycle or heterocycle is optionally substituted at any carbon atom with one or more of OH, halo, $C_1$-$C_4$ alkyl, halo-substituted $C_1$-$C_4$ alkyl, $NH_2$, and N($R^3$)($R^3$) and optionally substituted at any substitutable nitrogen atom with $C_1$-$C_4$ alkyl or halo-substituted $C_1$-$C_4$ alkyl; and when D is N, A is CR, and B is N, then X is selected from C(=O)—NH-†, NH—C(=O)-†, S(=O)—NH-†, S(=O)$_2$—NH-†, and NH—C(=O)—O—$CR^4R^5$-†; and when E is N, B is N, and A is N or CR, then X is selected from C(=O)—NH-†, NH—C(=O)-†, S(=O)—NH-†, S(=O)$_2$—NH-†, NH—C(=S)-†, C(=S)—NH-†, NH—S(=O)-†, NH—S(=O)$_2$-†, NH—S(=O)$_2$—$NR^4$-†, $NR^4$—S(=O)$_2$—NH-†, NH—C(=O)—O-†, O—C(=O)—NH-†, NH—C(=O)—NH-†, NH—C(=O)—$NR^4$-†, $NR^4$—C(=O)—NH-†, $CH_2$—NH—C(=O)-†, NH—C(=S)—$CR^4R^5$-†, $CR^4R^5$—C(=S)—NH-†, NH—S(=O)—$CR^4R^5$-†, $CR^4R^5$—S(=O)—NH-†, NH—S(=O)$_2$—$CR^4R^5$-†, $CR^4R^5$—S(=O)$_2$—NH-†, $CR^4R^5$—O—C(=O)—NH-†, NH—C(=O)—$CR^4R^5$-†, NH—C(O)—$CR^4R^5$—NH-†, $CR^4R^5$—NH—C(O)—O-† and NH—C(O)—O—$CR^4R^5$—; and when D is N, A is N, and B is CR, then X is selected from C(=O)—NH-†, NH—C(=O)-†, NH—$CR^4R^5$-†, C(=O)—NH—$CR^4R^5$-†, S(=O)—NH-†, S(=O)$_2$—NH-†, $CR^4R^5$—NH-†, NH—C(=O)—O—$CR^4R^5$-†, NH-†, NH—C(=S)-†, C(=S)—NH-†, NH—S(=O)-†, NH—S(=O)$_2$-†, NH—S(=O)$_2$—$NR^4$-†, $NR^4$—S(O)$_2$—NH-†, NH—C(=O)—O-†, O—C(=O)—NH-†, NH—C(=O)—NH-†, NH—C(=O)—$NR^4$-†, $NR^4$—C(=O)—NH-†, $CR^4R^5$—NH—C(O)-†, NH—C(=S)—$CR^4R^5$-†, $CR^4R^5$—C(=S)—NH-†, NH—S(=O)—$CR^4R^5$-†, $CR^4R^5$—S(=O)—NH-†, NH—S(=O)$_2$—$CR^4R^5$-†, $CR^4R^5$—S(=O)$_2$—NH-†, $CR^4R^5$—O—C(=O)—NH-†, NH—C(=O)—$CR^4R^5$-†, NH—C(O)—$CR^4R^5$—NH† and $CR^4R^5$—NH—C(O)—O-†;

wherein:

† represents where X is bound to $R^1$; and each $R^4$ and $R^5$ is independently selected from hydrogen, $C_1$-$C_4$ alkyl, $CF_3$ and ($C_1$-$C_3$ alkyl)-$CF_3$.

In certain embodiments both E and B are N. In particular embodiments, E, B and A are N. In such embodiments, the compound of Structural Formula (I) is represented by Structural Formula (Ia):

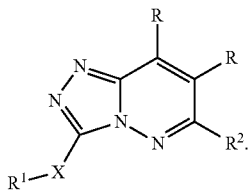
(Ia)

In other embodiments, E and B are N and A is CR. In such embodiments, the compound of Structural Formula (I) is represented by Structural Formula (Ib):

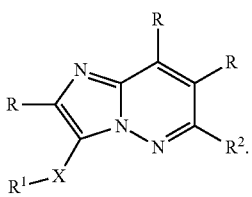
(Ib)

In certain embodiments both D and B are N and A is CR. In such embodiments, the compound of Structural Formula (I) is represented by Structural Formula (Ic):

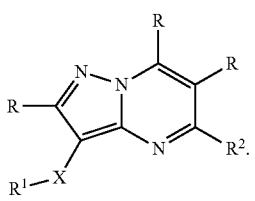
(Ic)

In certain embodiments both D and A are N and B is CR. In such embodiments, the compound of Structural Formula (I) is represented by Structural Formula (Id):

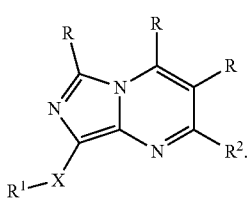
(Id)

For any of Structural Formulas (I), (Ia), (Ib), (Ic), or (Id), R at each occurrence may be selected from hydrogen, halo, $C_1$-$C_4$ alkyl, O—$R^3$ and 4- to 8-membered non-aromatic heterocycle, such as selected from hydrogen, $C_1$-$C_4$ alkyl, and 4- to 8-membered non-aromatic heterocycle. For any of Structural Formulas (I), (Ia), (Ib), (Ic), or (Id), $R^1$ may be selected from optionally substituted aromatic heterocycle, such as pyridinyl, thiazolyl, oxazolyl, pyrimidinyl, pyrazole, triazole, imidazole, pyrazine and pyridazine. For any of Structural Formulas (I), (Ia), (Ib), (Ic), or (Id), $R^1$ may be selected from optionally substituted

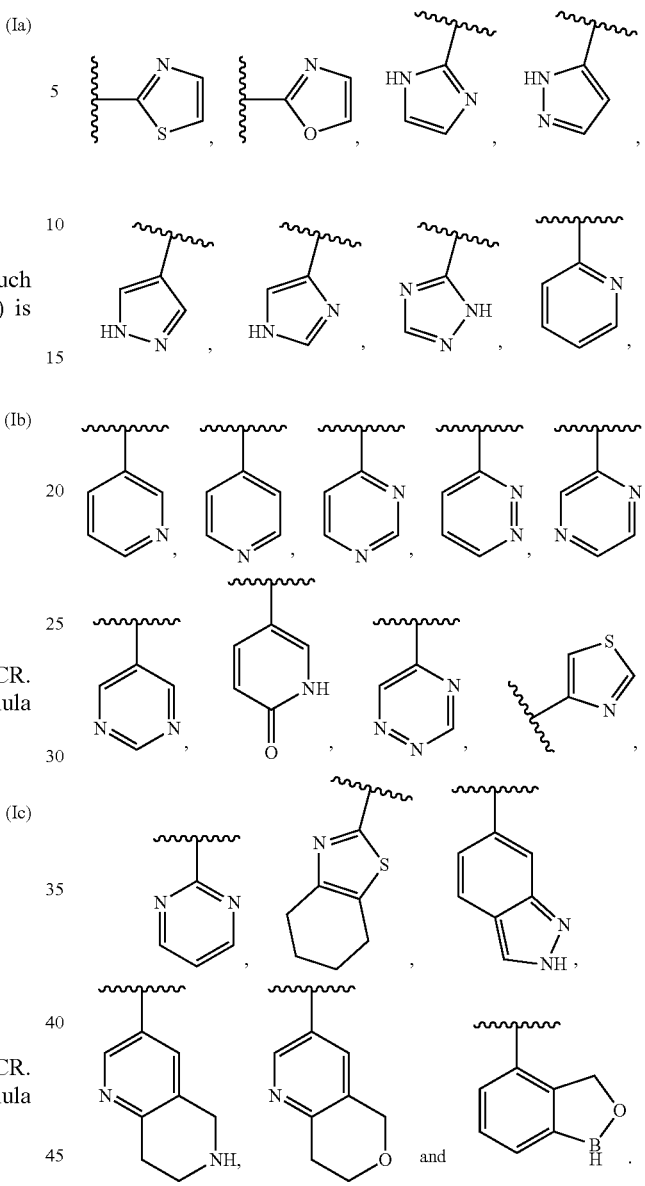

For any of Structural Formulas (I), (Ia), (Ib), (Ic), or (Id), $R^1$ may be selected from

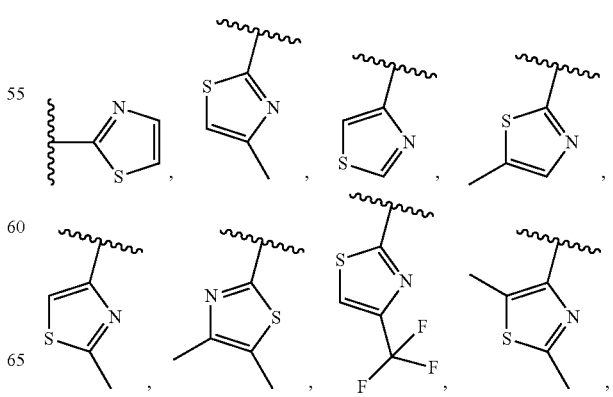

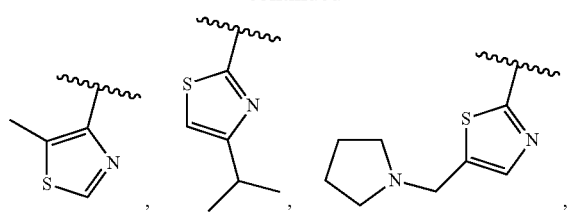
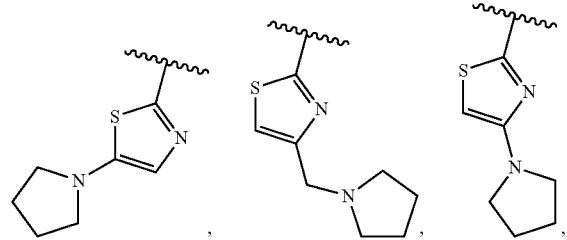
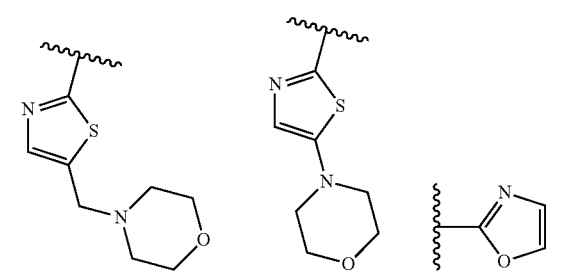
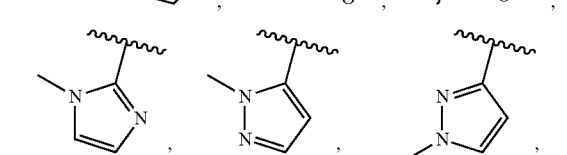
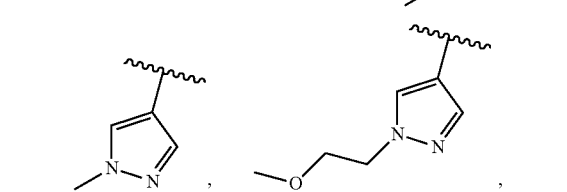
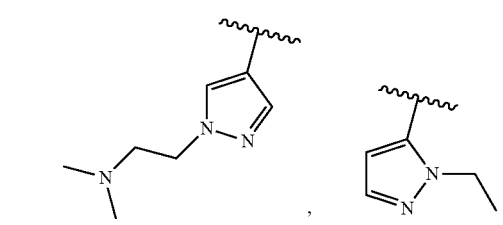
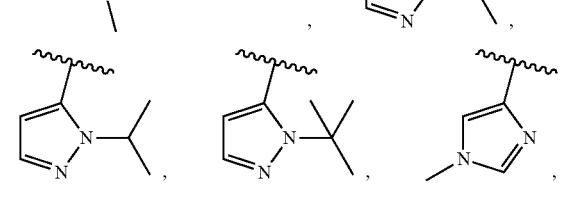
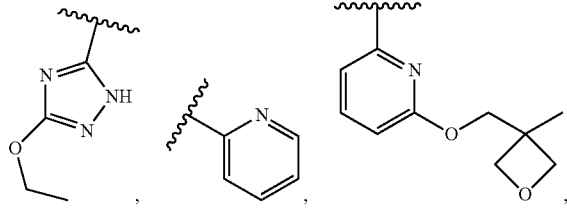
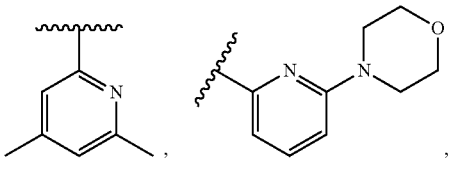
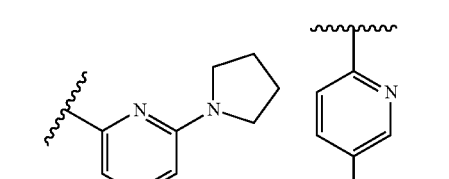
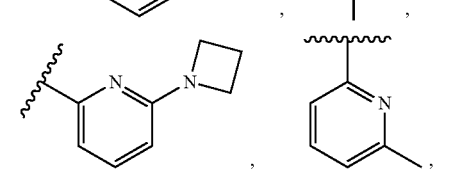
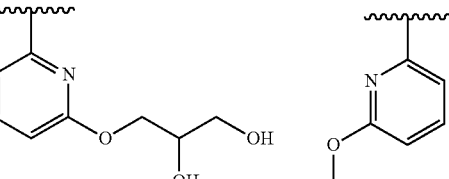
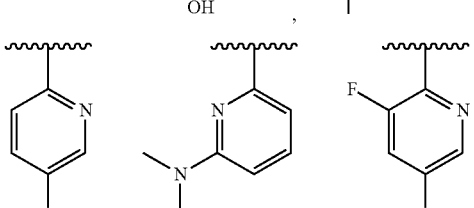
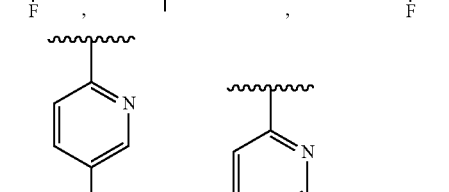
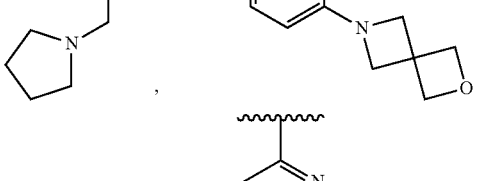
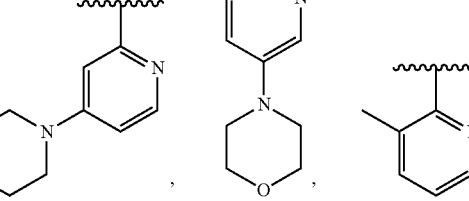
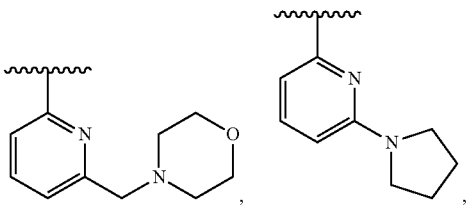

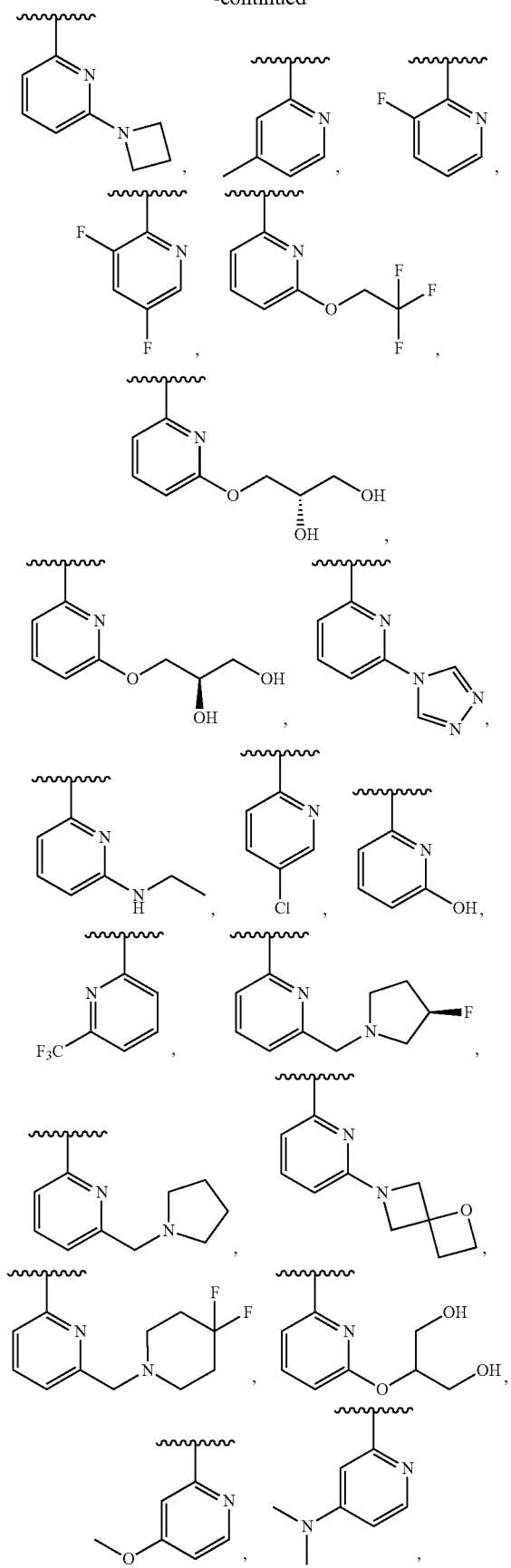
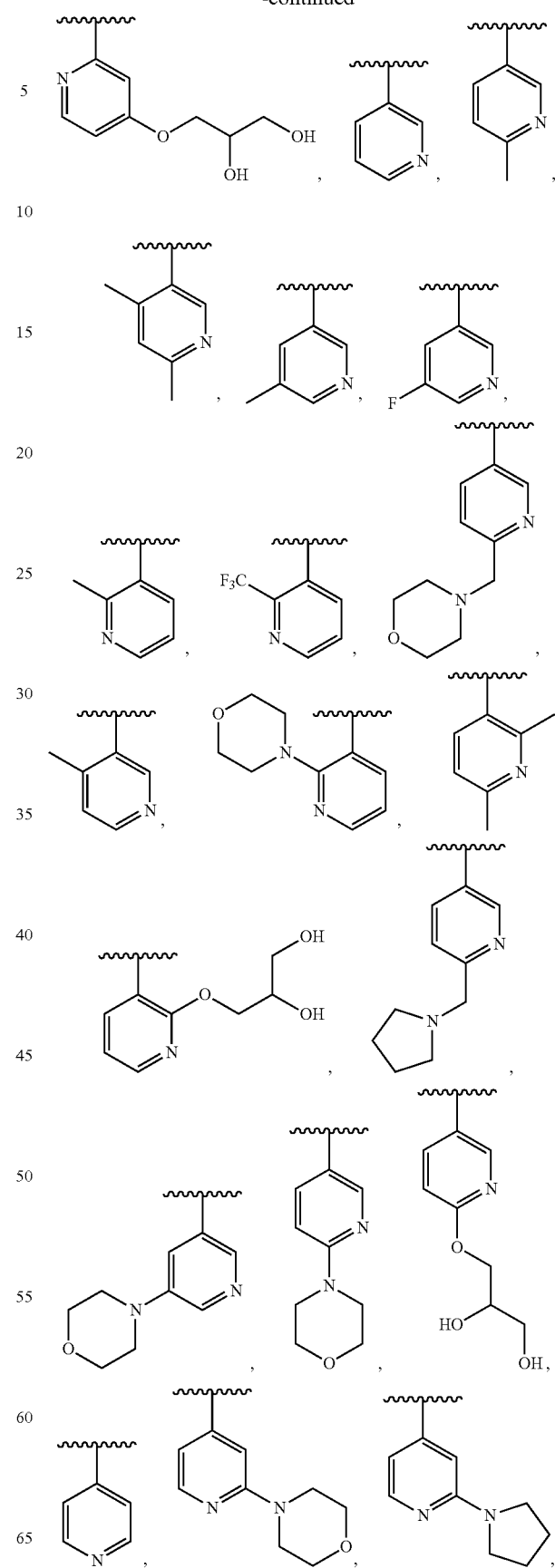

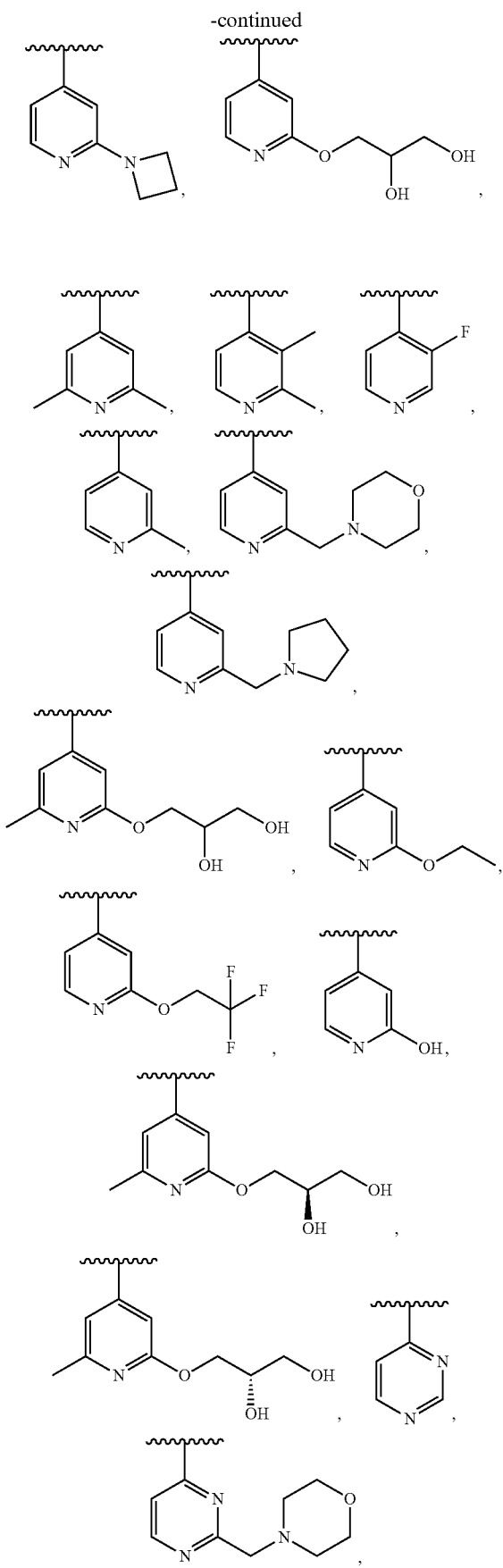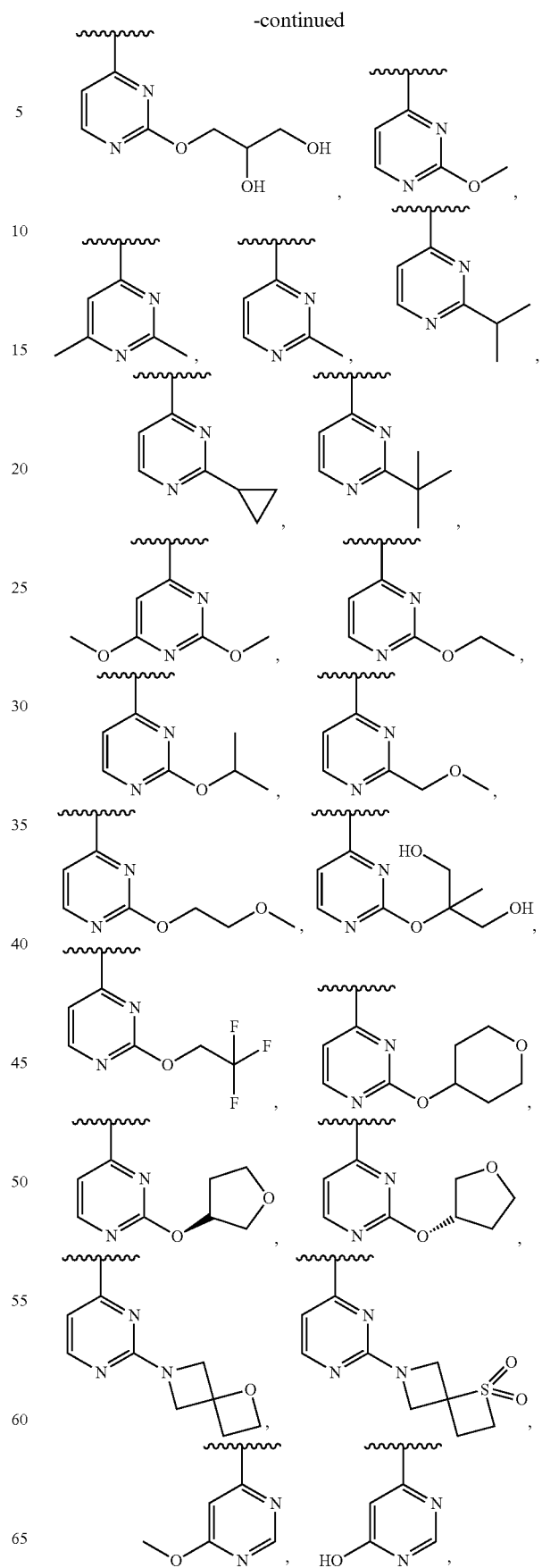

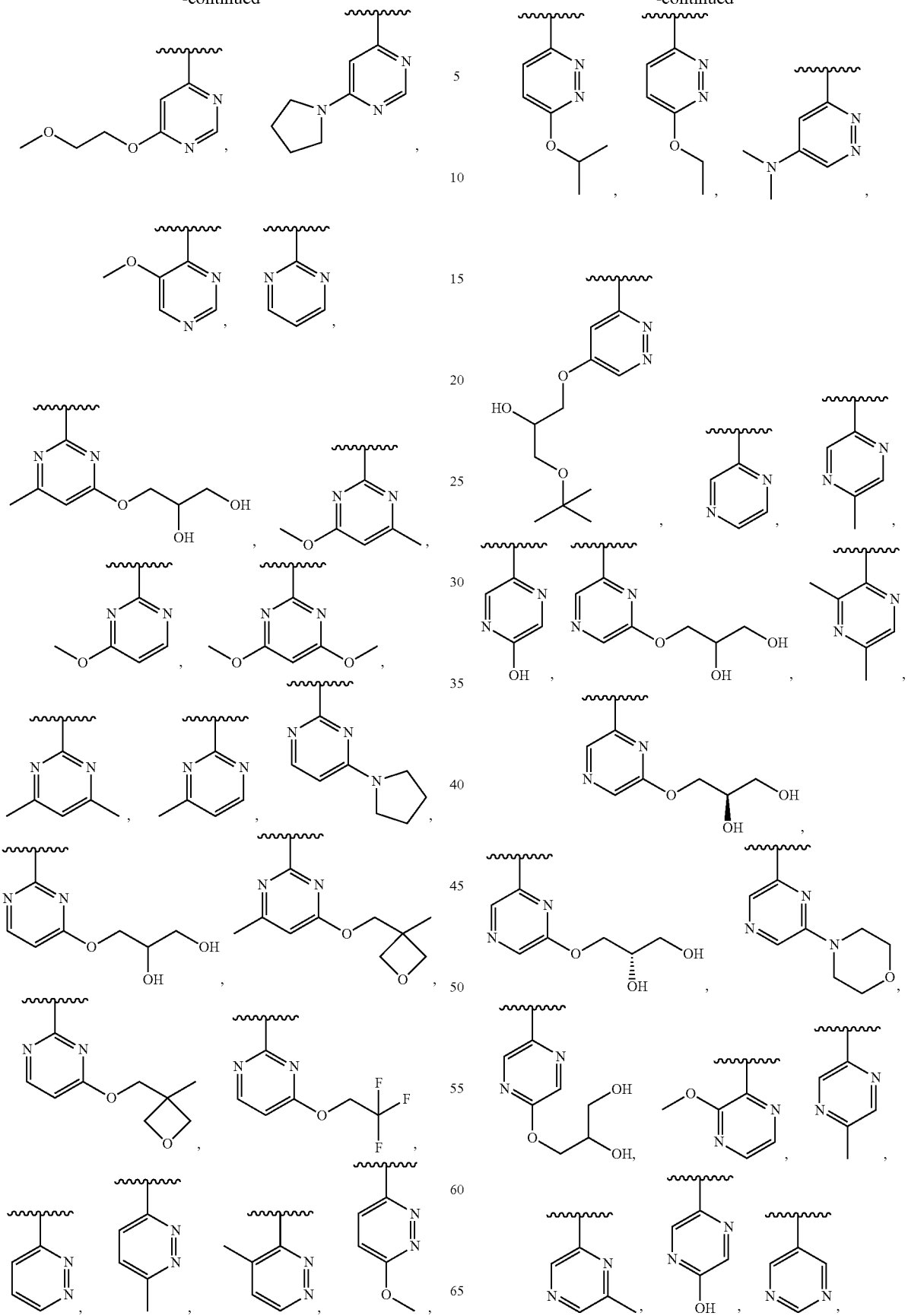

21
-continued
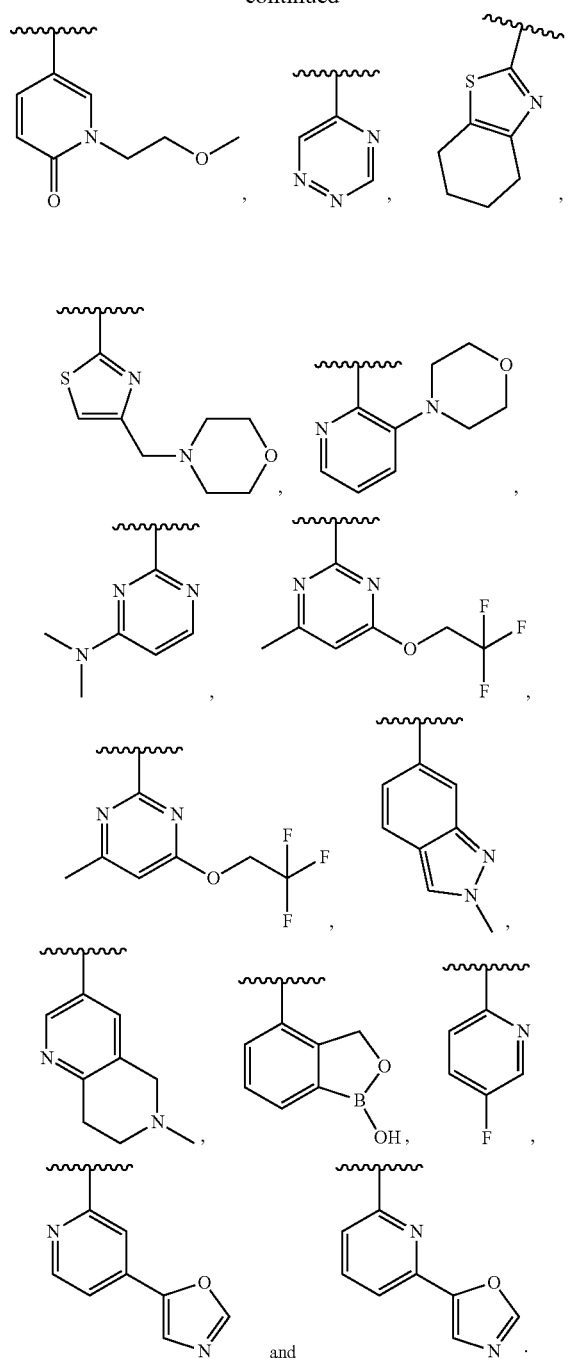
In more particular embodiments, R[1] is selected from:
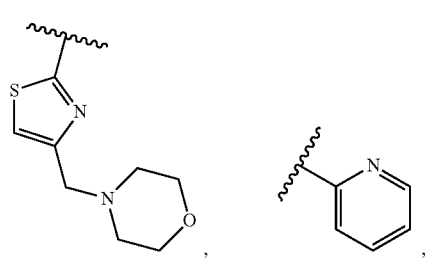
22
-continued
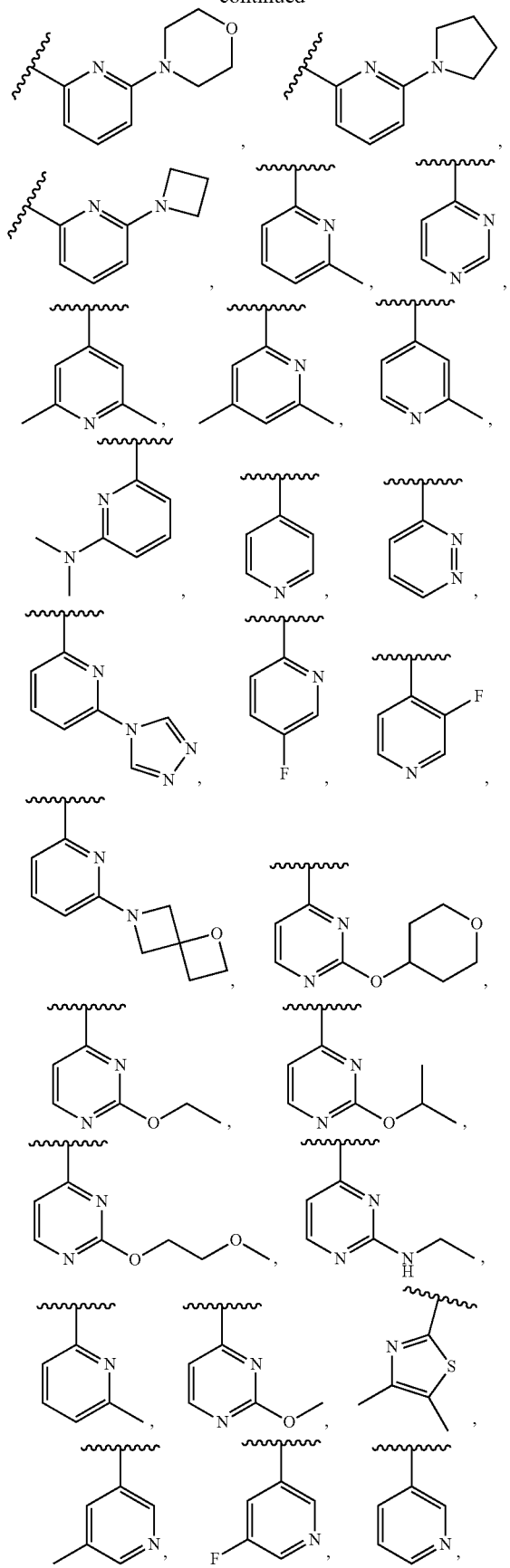

-continued

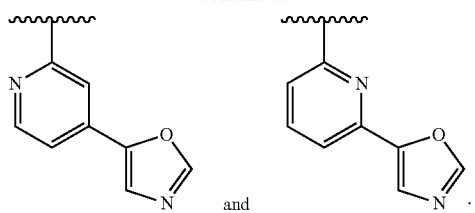
and

For any of Structural Formulas (I), (Ia), (Ib), (Ic), or (Id), $R^2$ may be selected from optionally substituted carbocycle and optionally substituted non-aromatic heterocycle. In particular, $R^2$ may be selected from optionally substituted aromatic carbocycle and optionally substituted non-aromatic heterocycle. For any of Structural Formulas (I), (Ia), (Ib), (Ic), or (Id), $R^2$ may be selected from optionally substituted non-aromatic carbocycle and optionally substituted non-aromatic heterocycle. For example, $R^2$ may be selected from an optionally substituted non-aromatic heterocycle and $R^2$ may be attached to the remainder of the compound by a nitrogen atom of $R^2$.

For any of Structural Formulas (I), (Ia), (Ib), (Ic), or (Id), $R^2$ may be selected from optionally substituted aromatic carbocycle, such as phenyl. For any of Structural Formulas (I), (Ia), (Ib), (Ic), or (Id), $R^2$ may be selected from optionally substituted non-aromatic heterocycle, e.g., nitrogen-containing heterocycles, such as pyrrolidine, piperidine and azetidine.

For any of Structural Formulas (I), (Ia), (Ib), (Ic), or (Id), $R^2$ may be selected from optionally substituted

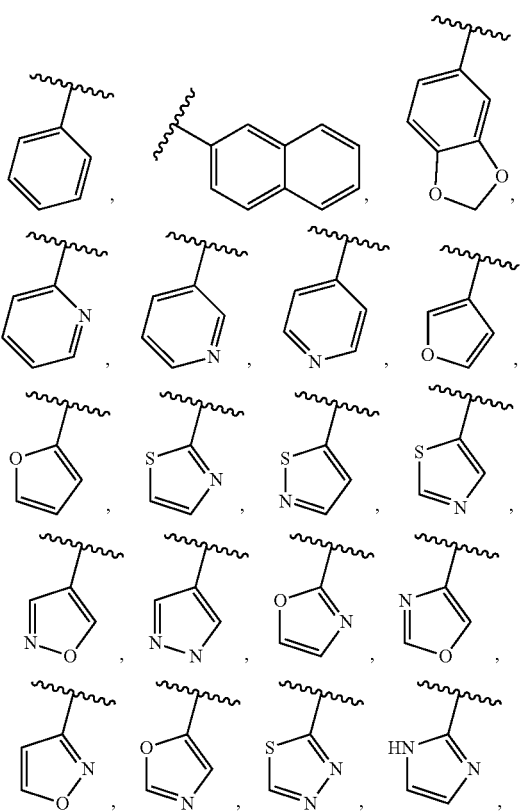

-continued

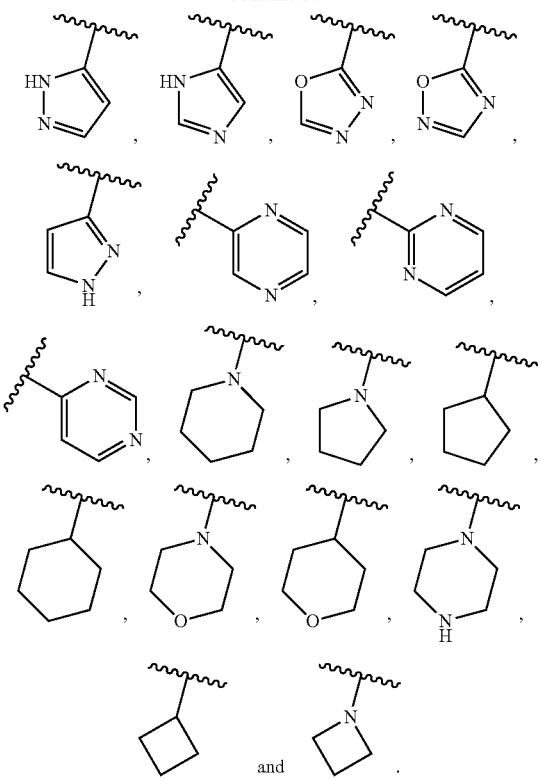
and

In particular, $R^2$ may be selected from:

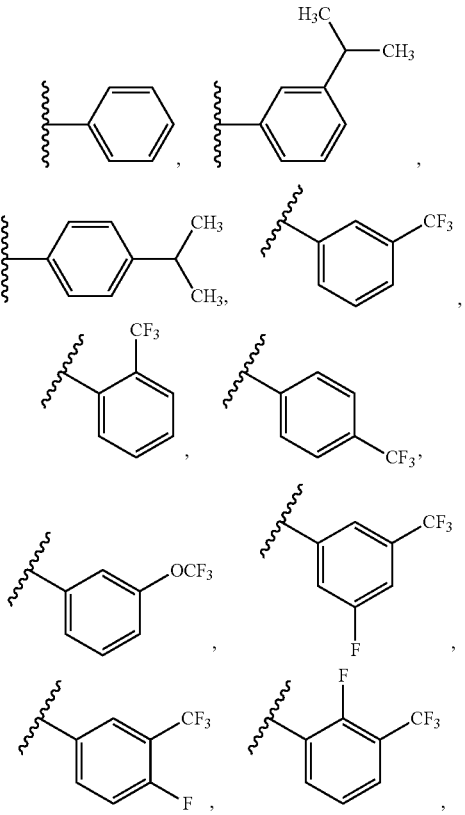

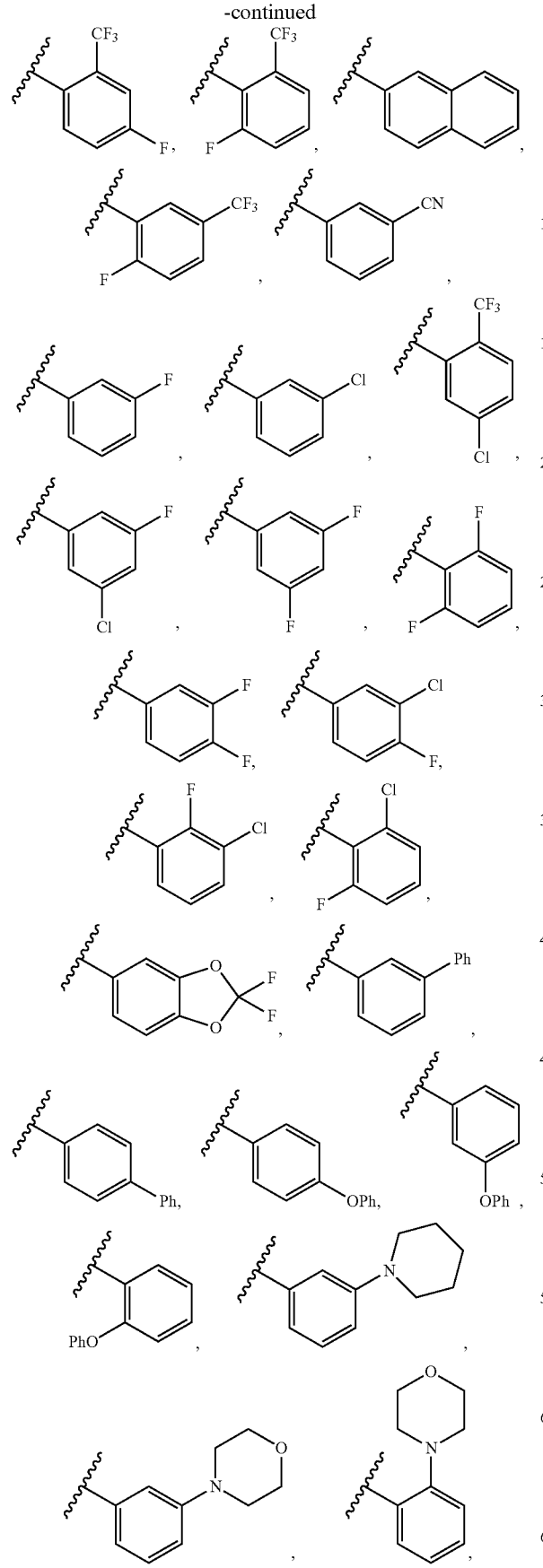
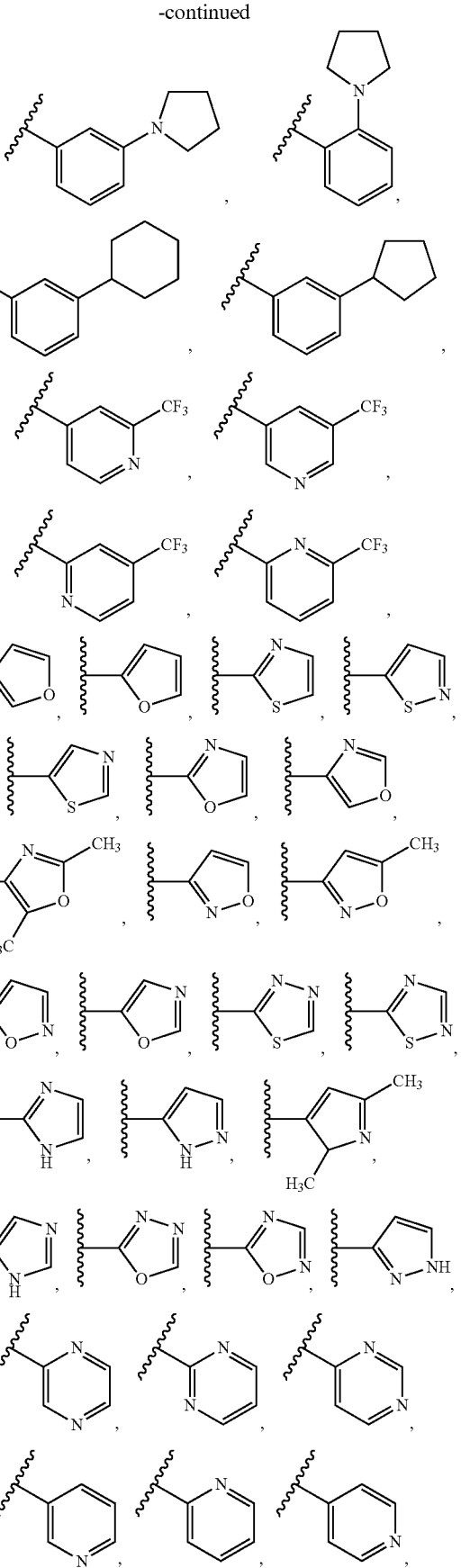

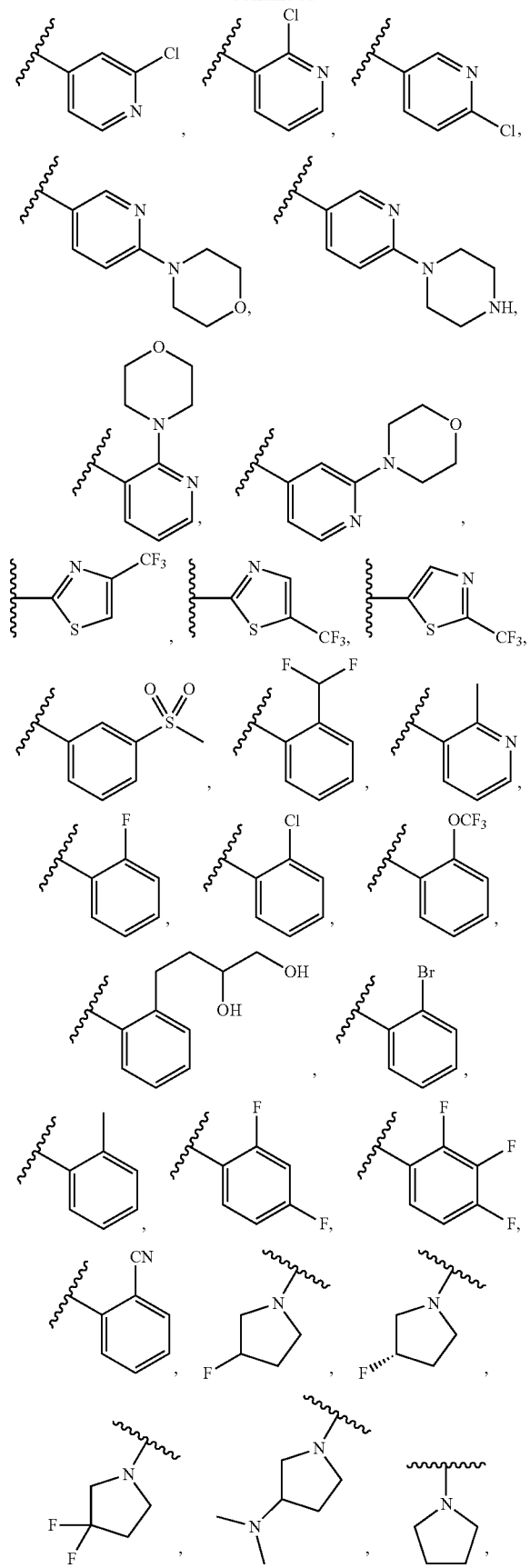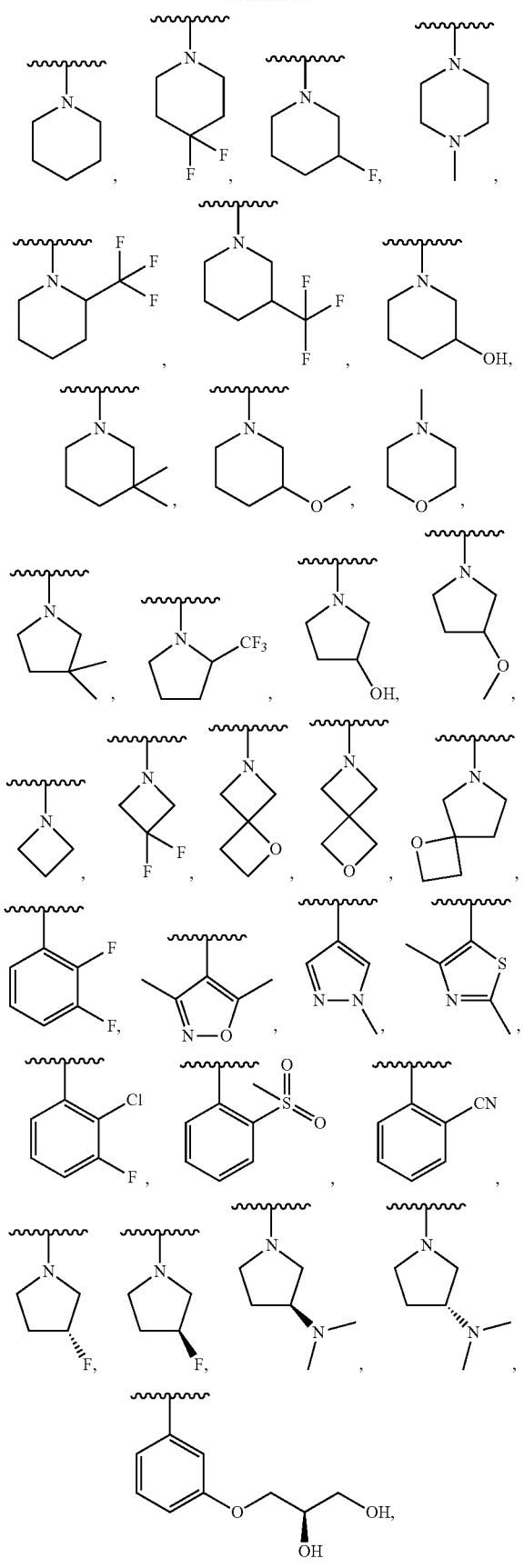

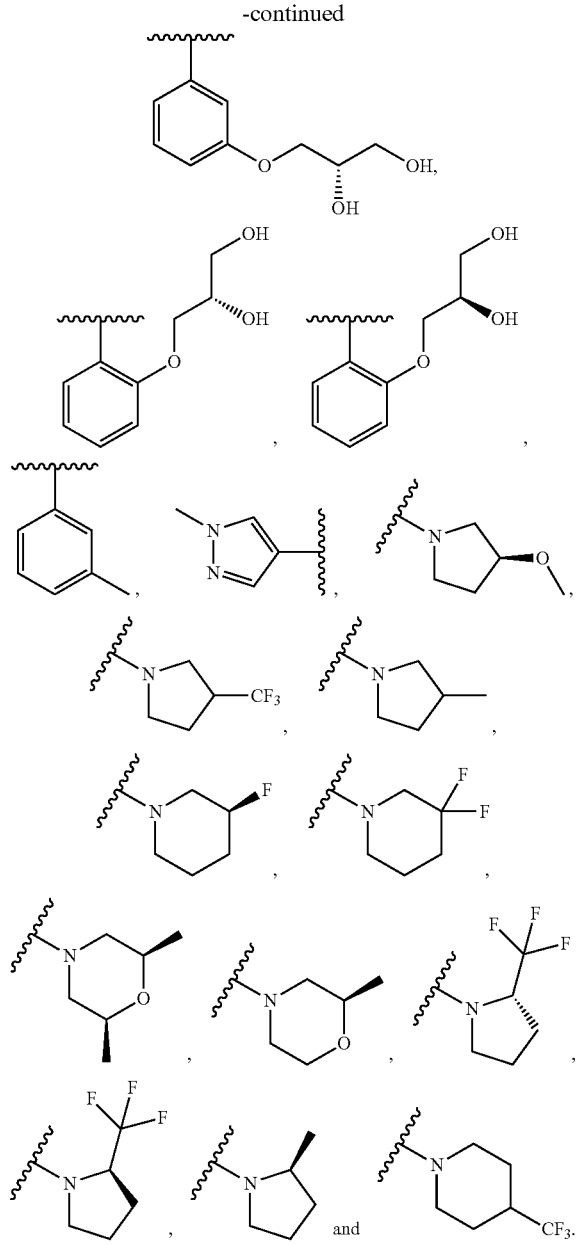
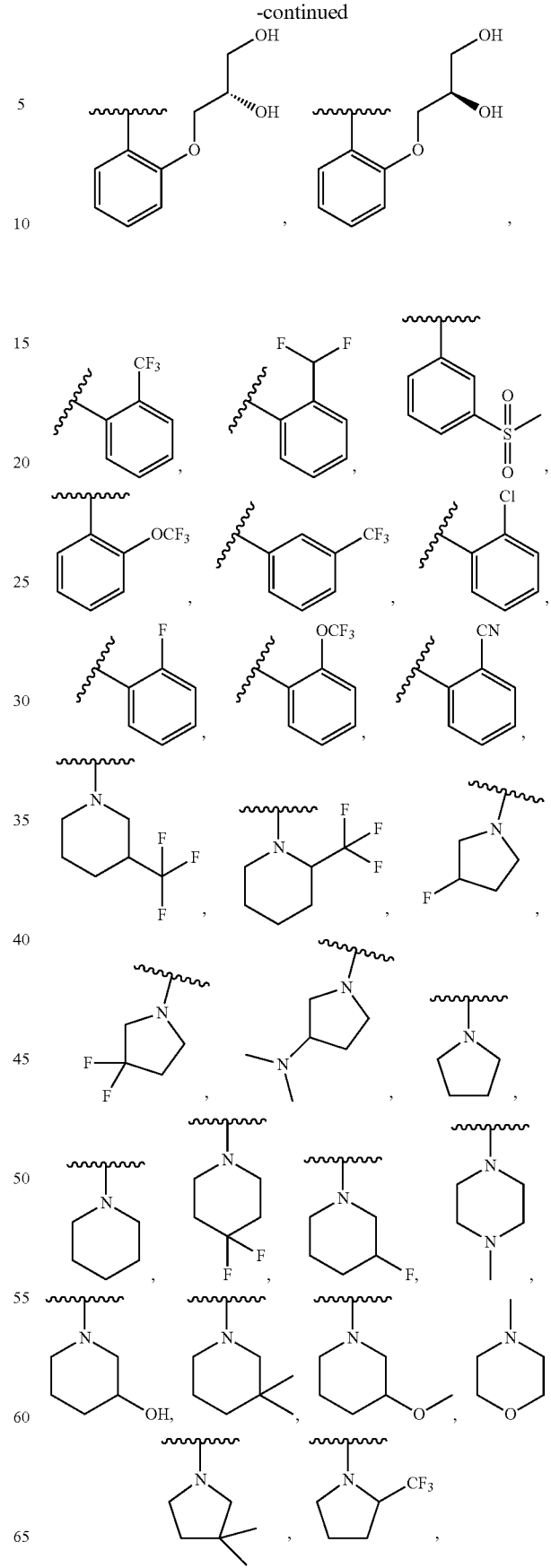
In more particular embodiments, R² is selected from

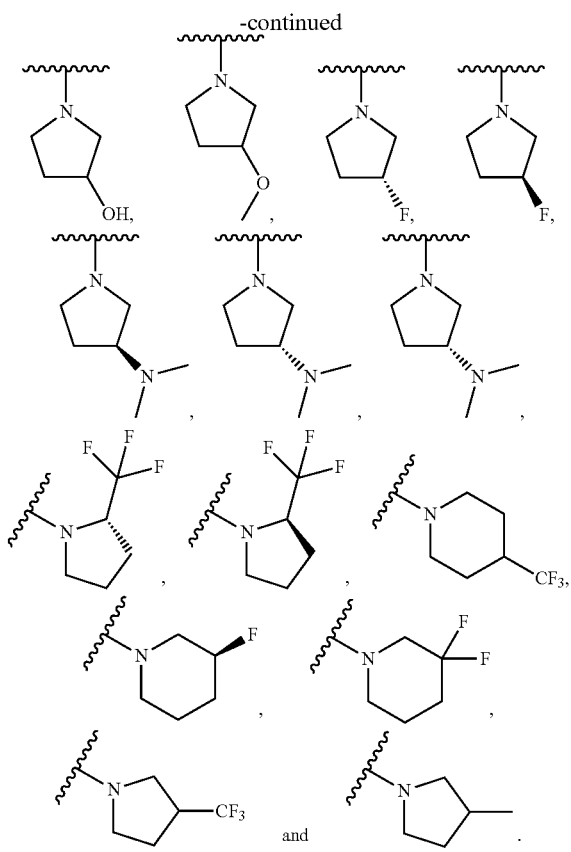

and

For any of Structural Formulas (I), (Ia), (Ib), (Ic), or (Id), X may be selected from amide such as C(=O)—NH-† or NH—C(=O)†. In particular embodiments, X is C(=O)—NH-†. In particular embodiments, X is —NH—C(=O)-†.

In any of the preceding embodiments, R at each occurrence may be selected from hydrogen, halo, OH, C≡N, $C_1$-$C_4$ alkyl, halo-substituted $C_2$-$C_4$ alkyl, $C_1$-$C_4$ alkoxy-substituted $C_1$-$C_4$ alkyl, hydroxy-substituted $C_1$-$C_8$ alkyl, $OR^3$, O—($C_1$-$C_4$ alkyl)-$OR^3$, S—($C_1$-$C_2$ alkyl), S-(halo-substituted $C_1$-$C_4$ alkyl), N(hydroxy-substituted $C_1$-$C_4$ alkyl)$_2$, N(methoxy-substituted $C_1$-$C_4$ alkyl)$_2$, N($C_1$-$C_4$ alkyl)(hydroxy-substituted $C_1$-$C_4$ alkyl), $C_5$-$C_7$ cycloalkyl, and 4- to 8-membered non-aromatic heterocycle, and when one or both of E and A is N, then R can additionally be selected from halo-substituted methyl and $C_3$-$C_4$ cycloalkyl.

In certain embodiments, the compound is any one of Compound Numbers 14, 94, 97, 98, 99, 100, 105, 119, 143, 159, 164, 165, 224, 225, 226, 230, 233, 301, 308, 318, 342, 344, 355, 370, 379, 424, 474, 479, 537, 577, 581, 586, 601, 638, 661, 665, 668, 684, 703, 761, 801, 806, 811, 812, 870, 880, 890, 918, 924, 925 928, 945, 953, 957, 958, 959, 966, 968, 969, 970, 974, 978, 979, 986, 990, 994, 998, 999, 1000, 1001, 1005, 1007, 1009, 1010, 1011, 1012, 1013, 1014, 1015, 1016, 1017, 1018, 1020, 1024, 1025, 1026, 1027, 1028, 1029, 1030, 1031, 1032, 1033, 1034, 1035, 1036, 1046, 1047, 1048, 1049, 1050, 1060, 1062, 1063, 1064, 1066, 1069, 1071, 1072, 1073, 1074, 1077, 1080, 1081, 1082, 1083, 1085, 1086, 1087, 1092, 1096 and 1098 in Table 1.

The invention includes pharmaceutical compositions of any of the compounds of Structural Formulas (I), (Ia), (Ib), (Ic), or (Id), or as otherwise set forth above. The pharmaceutical composition of the compound of Structural Formulas (I), (Ia), (Ib), (Ic), or (Id), may comprise one or more pharmaceutically acceptable carriers or diluents.

In certain embodiments, compounds of the invention are represented by Structural Formula (II):

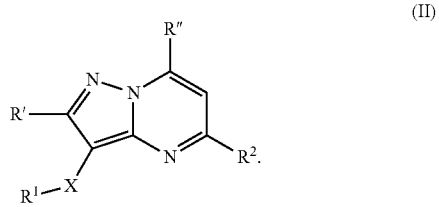

(II)

or a salt thereof, wherein:

each R' is independently selected from hydrogen, halo, C≡N, $C_1$-$C_4$ alkyl, halo-substituted $C_1$-$C_4$ alkyl, O—$R^3$, O—($C_1$-$C_4$ alkyl)-$OR^3$, S—($C_1$-$C_4$ alkyl), S-(halo-substituted $C_1$-$C_4$ alkyl), $C_1$-$C_4$ alkoxy-substituted $C_1$-$C_4$ alkyl, hydroxy-substituted $C_1$-$C_8$ alkyl, N(hydroxy-substituted $C_1$-$C_4$ alkyl)$_2$, N(methoxy-substituted $C_1$-$C_4$ alkyl)$_2$, N($C_1$-$C_4$ alkyl)(hydroxy-substituted $C_1$-$C_4$ alkyl), N($C_1$-$C_4$ alkyl)(methoxy-substituted $C_1$-$C_4$ alkyl), N(hydroxy-substituted $C_1$-$C_4$ alkyl)(methoxy-substituted $C_1$-$C_4$ alkyl), $C_3$-$C_7$ cycloalkyl and 4- to 8-membered non-aromatic heterocycle;

each R" is independently selected from hydrogen, halo, C≡N, chloro- or bromo-substituted $C_1$-$C_4$ alkyl, O-(halo-substituted $C_1$-$C_4$ alkyl), O—($C_1$-$C_4$ alkyl)-$OR^3$, $C_1$-$C_4$ alkoxy-substituted $C_1$-$C_4$ alkyl, hydroxy-substituted $C_1$-$C_8$ alkyl, S—($C_1$-$C_4$ alkyl), S-(halo-substituted $C_1$-$C_4$ alkyl), N(hydroxy-substituted $C_1$-$C_4$ alkyl)$_2$, N(methoxy-substituted $C_1$-$C_4$ alkyl)$_2$, N($C_1$-$C_4$ alkyl)(hydroxy-substituted $C_1$-$C_4$ alkyl), N($C_1$-$C_4$ alkyl)(methoxy-substituted $C_1$-$C_4$ alkyl), N(hydroxy-substituted $C_1$-$C_4$ alkyl)(methoxy-substituted $C_1$-$C_4$ alkyl), $C_3$-$C_7$ cycloalkyl and 4- to 8-membered non-aromatic heterocycle;

$R^1$ is an aromatic heterocycle, wherein $R^1$ is optionally substituted with one or more substituents independently selected from halo, C≡N, $C_1$-$C_4$ alkyl, halo-substituted $C_1$-$C_4$ alkyl, $C_1$-$C_4$ alkoxy-substituted $C_1$-$C_4$ alkyl, hydroxy-substituted $C_1$-$C_8$ alkyl, O—$R^3$, —O—($C_1$-$C_4$ alkyl)-$OR^3$, =O, $C_3$-$C_7$ cycloalkyl, $SO_2R^3$, S—$R^3$, ($C_1$-$C_4$ alkyl)-N($R^3$)($R^3$), N($R^3$)($R^3$), O—($C_1$-$C_4$ alkyl)-N($R^3$)($R^3$), O—($C_0$-$C_4$ alkyl)-$CR^3R^3$($C_0$-$C_4$ alkyl), ($C_1$-$C_4$ alkyl)-O—($C_1$-$C_4$ alkyl)-N($R^3$)($R^3$), C(O)—N($R^3$)($R^3$), ($C_1$-$C_4$ alkyl)-C(O)—N($R^3$)($R^3$), O($C_0$-$C_4$ alkyl)-$CR^xR^x$—($C_0$-$C_4$ alkyl), $CR^xR^x$, phenyl, O-phenyl, second heterocycle, O-(second heterocycle), 3,4-methylenedioxy, halo-substituted 3,4-methylenedioxy, 3,4-ethylenedioxy, and halo-substituted 3,4-ethylenedioxy, wherein any phenyl, saturated heterocycle, or second heterocycle substituent of $R^1$ is optionally substituted with halo, C≡N, $C_1$-$C_4$ alkyl, halo-substituted $C_1$-$C_2$ alkyl, O-(halo-substituted $C_1$-$C_4$ alkyl), O—($C_1$-$C_4$ alkyl), S—($C_1$-$C_4$ alkyl), S-(halo-substituted $C_1$-$C_4$ alkyl), and N($R^3$)($R^3$);

$R^2$ is a carbocycle or a heterocycle, wherein $R^2$ is optionally substituted with one or more substituents independently selected from halo, C≡N, $C_1$-$C_4$ alkyl, halo-substituted $C_1$-$C_4$ alkyl, $C_1$-$C_4$ alkoxy-substituted $C_1$-$C_4$ alkyl, hydroxy-substituted $C_1$-$C_8$, O—$R^3$, O—($C_1$-$C_4$ alkyl)-$OR^3$, =O, $C_3$-$C_7$ cycloalkyl, $SO_2R^3$, S—$R^3$, ($C_1$-$C_4$ alkyl)-N($R^3$)($R^3$), N($R^3$)($R^3$), O—($C_1$-$C_4$ alkyl)-N($R^3$)($R^3$), O—($C_0$-$C_4$ alkyl)-$CR^3R^3$—($C_0$-$C_4$ alkyl), ($C_1$-$C_4$ alkyl)-O—($C_1$-$C_4$ alkyl)-N($R^3$)($R^3$), C(O)—N($R^3$)($R^3$), ($C_1$-$C_4$ alkyl)-C(O)—N($R^3$)($R^3$), O-phenyl, O-(second heterocycle), 3,4- methylenedioxy, halo-substituted 3,4-methylenedioxy, 3,4-ethylenedioxy, and halo-substituted 3,4-ethylenedioxy, wherein any phenyl, saturated heterocycle or second heterocycle substituent of $R^2$ is optionally substituted with one or more substituents independently selected from halo, C≡N, $C_1$-$C_4$ alkyl, halo-substituted $C_1$-$C_4$ alkyl, O-(halo-substituted $C_1$-$C_4$ alkyl), O—($C_1$-$C_4$ alkyl), S—($C_1$-$C_4$ alkyl), S-(halo-substituted $C_1$-$C_4$ alkyl), and $N(R^3)(R^3)$;

each $R^3$ is independently selected from hydrogen and $C_1$-$C_4$ alkyl optionally substituted with one or more of OH, O—($C_1$-$C_4$ alkyl), halo, $NH_2$, $NH(C_1$-$C_4$ alkyl), $N(C_1$-$C_4$ alkyl)$_2$, NH(methoxy-substituted $C_1$-$C_4$ alkyl), NH(hydroxy-substituted $C_1$-$C_4$ alkyl), N(methoxy-substituted $C_1$-$C_4$ alkyl)(hydroxy-substituted $C_1$-$C_4$ alkyl), N(hydroxy-substituted $C_1$-$C_4$ alkyl)$_2$ and N(methoxy-substituted $C_1$-$C_4$ alkyl)$_2$; or two $R^3$ are taken together with the nitrogen or carbon atom to which they are bound to form a 4- to 8-membered saturated heterocycle optionally comprising one additional heteroatom independently selected from N, S, S(=O), S(=O)$_2$, and O, wherein the heterocycle formed by two $R^3$ is optionally substituted at any carbon atom with one or more of OH, halo, $C_1$-$C_4$ alkyl, halo-substituted $C_1$-$C_4$ alkyl, $NH_2$, $NH(C_1$-$C_4$ alkyl), $N(C_1$-$C_4$ alkyl)$_2$, NH(methoxy-substituted $C_1$-$C_4$ alkyl), NH(hydroxy-substituted $C_1$-$C_4$ alkyl), N(methoxy-substituted $C_1$-$C_4$ alkyl)(hydroxy-substituted $C_1$-$C_4$ alkyl), N(hydroxy-substituted $C_1$-$C_4$ alkyl)$_2$ and N(methoxy-substituted $C_1$-$C_4$ alkyl)$_2$, and optionally substituted at any substitutable nitrogen atom with $C_1$-$C_4$ alkyl or halo-substituted $C_1$-$C_4$ alkyl;

two $R^x$ taken together with the carbon atom to which they are bound form a 4- to 8-membered carbocycle or heterocycle optionally comprising one or two heteroatoms independently selected from N, S, S(=O), S(=O)$_2$, and O, wherein the carbocycle or heterocycle is optionally substituted at any carbon atom with one or more of OH, halo, $C_1$-$C_4$ alkyl, halo-substituted $C_1$-$C_4$ alkyl, $N(R^3)(R^3)$, and optionally substituted at any substitutable nitrogen atom with $C_1$-$C_4$ alkyl or halo-substituted $C_1$-$C_4$ alkyl; and X is selected from NH—C(=S)-†, NH—S(=O)-†, NH—S(=O)$_2$-†, NH—S(=O)$_2$—$NR^4$-†, $NR^4$—S(=O)$_2$—NH-†, NH—C(=O)O-†, O—C(=O)—NH-†, NH—C(=O)NH-†, NH—C(=O)$NR^4$-†, $NR^4$—C(=O)NH-†, $CR^4R^5$—NH—C(=O)-†, NH—C(=S)—$CR^4R^5$-†, $CR^4R^5$—C(=S)—NH-†, NH—S(=O)—$CR^4R^5$-†, $CR^4R^5$—S(=O)—NH-†, NH—S(=O)$_2$—$CR^4R^5$-†, $CR^4R^5$—S(=O)$_2$—NH-†, $CR^4R^5$—O—C(=O)—NH-†, NH—C(=O)—$CR^4R^5$-†, NH—C(=O)—$CR^4R^5$—NH† and $CR^4R^5$—NH—C(=O)—O-†, wherein:

† represents where X is bound to $R^1$; and each $R^4$ and $R^5$ is independently hydrogen, $C_1$-$C_4$ alkyl, $CF_3$ or ($C_1$-$C_3$ alkyl)-$CF_3$.

In any of the preceding embodiments, a $C_1$-$C_4$ alkoxy-substituted group may include one or more alkoxy substituents such as one, two or three methoxy groups or a methoxy group and an ethoxy group, for example. Exemplary $C_1$-$C_4$ alkoxy substituents include methoxy, ethoxy, isopropoxy, and tert-butoxy.

In any of the preceding embodiments, a hydroxy-substituted group may include one or more hydroxy substituents, such as two or three hydroxy groups.

In any of the preceding embodiments, a "halo-substituted" group includes from one halo substituent up to perhalo substitution. Exemplary halo-substituted $C_1$-$C_4$ alkyl includes $CFH_2$, $CClH_2$, $CBrH_2$, $CF_2H$, $CCl_2H$, $CBr_2H$, $CF_3$, $CCl_3$, $CBr_3$, $CH_2CH_2F$, $CH_2CH_2Cl$, $CH_2CH_2Br$, $CH_2CHF_2$, $CHFCH_3$, $CHClCH_3$, $CHBrCH_3$, $CF_2CHF_2$, $CF_2CHCl_2$, $CF_2CHBr_2$, $CH(CF_3)_2$, and $C(CF_3)_3$. Perhalo-substituted $C_1$-$C_4$ alkyl, for example, includes $CF_3$, $CCl_3$, $CBr_3$, $CF_2CF_3$, $CCl_2CF_3$ and $CBr_2CF_3$.

In any of the preceding embodiments, a "carbocycle" group may refer to a monocyclic carbocycle embodiment and/or a polycyclic carbocycle embodiment, such as a fused, bridged or bicyclic carbocycle embodiment. "Carbocycle" groups of the invention may further refer to an aromatic carbocycle embodiment and/or a non-aromatic carbocycle embodiment, or, in the case of polycyclic embodiments, a carbocycle having both one or more aromatic rings and/or one or more non-aromatic rings. Polycyclic carbocycle embodiments may be a bicyclic ring, a fused ring or a bridged bicycle. Non-limiting exemplary carbocycles include phenyl, cyclohexane, cyclopentane, or cyclohexene, amantadine, cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene, adamantane, decalin, naphthalene, 1,2,3,4-tetrahydronaphthalene, norbornane, decalin, spiropentane, memantine, biperiden, rimantadine, camphor, cholesterol, 4-phenylcyclohexanol, bicyclo[4.2.0]octane, memantine and 4,5,6,7-tetrahydro-1H-indene and bicyclo[4.1.0]hept-3-ene.

In any of the preceding embodiments, a "heterocycle" group may refer to a monocyclic heterocycle embodiment and/or a polycyclic heterocyclic embodiment, such as a fused, bridged or bicyclic heterocycle embodiment. "Heterocycle" groups of the invention may further refer to an aromatic heterocycle embodiment and/or a non-aromatic heterocycle embodiment, or, in the case of polycyclic embodiments, a heterocycle having both one or more aromatic rings and/or one or more non-aromatic rings. Polycyclic heterocycle embodiments may be a bicyclic ring, a fused ring or a bridged bicycle. Non-limiting exemplary heterocycles include pyridyl, pyrrolidine, piperidine, piperazine, pyrrolidine, morpholine, pyrimidine, benzofuran, indole, quinoline, lactones, lactams, benzodiazepine, indole, quinoline, purine, adenine, guanine, 4,5,6,7-tetrahydrobenzo[d]thiazole, hexamine and methenamine.

Certain compounds of the present invention may exist in particular geometric or stereoisomeric forms. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Compounds of the invention, including novel compounds of the invention, can also be used in the methods described herein.

The compounds and salts thereof described herein can also be present as the corresponding hydrates (e.g., hemihydrate, monohydrate, dihydrate, trihydrate, tetrahydrate) or solvates. Suitable solvents for preparation of solvates and hydrates can generally be selected by a skilled artisan.

The compounds and salts thereof can be present in amorphous or crystalline (including co-crystalline and polymorph) forms.

Sirtuin-modulating compounds of the invention advantageously modulate the level and/or activity of a sirtuin protein, particularly the deacetylase activity of the sirtuin protein.

Separately or in addition to the above properties, certain sirtuin-modulating compounds of the invention do not substantially have one or more of the following activities:

inhibition of PI3-kinase, inhibition of aldoreductase, inhibition of tyrosine kinase, transactivation of EGFR tyrosine kinase, coronary dilation, or spasmolytic activity, at concentrations of the compound that are effective for modulating the deacetylation activity of a sirtuin protein (e.g., such as a SIRT1 and/or a SIRT3 protein).

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_4$ straight chained or branched alkyl group is also referred to as a "lower alkyl" group.

The terms "alkenyl" ("alkene") and "alkynyl" ("alkyne") refer to unsaturated aliphatic groups analogous in length and possible substitution to the alkyl groups described above, but that contain at least one double or triple bond respectively.

The term "aromatic carbocycle" refers to an aromatic hydrocarbon ring system containing at least one aromatic ring. The ring may be fused or otherwise attached to other aromatic carbocyclic rings or non-aromatic carbocyclic rings. Examples of aromatic carbocycle groups include carbocyclic aromatic groups such as phenyl, naphthyl, and anthracyl.

"Azabicyclo" refers to a bicyclic molecule that contains a nitrogen atom in the ring skeleton. The two rings of the bicycle may be fused at two mutually bonded atoms, e.g., indole, across a sequence of atoms, e.g., azabicyclo[2.2.1]heptane, or joined at a single atom, e.g., spirocycle.

"Bicycle" or "bicyclic" refers to a two-ring system in which one, two or three or more atoms are shared between the two rings. Bicycle includes fused bicycles in which two adjacent atoms are shared by each of the two rings, e.g., decalin, indole. Bicycle also includes spiro bicycles in which two rings share a single atom, e.g., spiro[2.2]pentane, 1-oxa-6-azaspiro[3.4]octane. Bicycle further includes bridged bicycles in which at least three atoms are shared between two rings, e.g., norbornane.

"Bridged bicycle" compounds are bicyclic ring systems in which at least three atoms are shared by both rings of the system, i.e., they include at least one bridge of one or more atoms connecting two bridgehead atoms. Bridged azabicyclo refers to a bridged bicyclic molecule that contains a nitrogen atom in at least one of the rings.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from non-aromatic and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from non-aromatic aromatic rings. In an exemplary embodiment, an aromatic ring, e.g., phenyl, may be fused to a non-aromatic or aromatic ring, e.g., cyclohexane, cyclopentane, or cyclohexene. Any combination of non-aromatic and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantine. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated (non-aromatic). Typically, a cycloalkyl group has from 3 to about 10 carbon atoms, more typically 3 to 8 carbon atoms unless otherwise defined. A "cycloalkenyl" group is a cyclic hydrocarbon containing one or more double bonds.

A "halogen" designates F, Cl, Br or I.

A "halogen-substitution" or "halo" substitution designates replacement of one or more hydrogens with F, Cl, Br or I.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocyclyl. Heteroaryl groups include, for example, pyrrole, furan, thiophene, imidazole, oxazole, thiazole, pyrazole, pyridine, pyrazine, pyridazine, and pyrimidine.

The terms "heterocycle", and "heterocyclic", as used herein, refers to a non-aromatic or aromatic ring comprising one or more heteroatoms selected from, for example, N, O, B and S atoms, preferably N, O, or S. The term "heterocycle" includes both "aromatic heterocycles" and "non-aromatic heterocycles." Heterocycles include 4-7 membered monocyclic and 8-12 membered bicyclic rings. Heterocycle includes bicyclic molecules in which one, two or three or more atoms are shared between the two rings. Each ring of a bicyclic heterocycle may be selected from non-aromatic and aromatic rings. The term "fused heterocycle" refers to a bicyclic heterocycle in which each of the rings shares two adjacent atoms with the other ring. Each ring of a fused heterocycle may be selected from non-aromatic and aromatic rings. In an exemplary embodiment, an aromatic ring, e.g., pyridyl, may be fused to a non-aromatic or aromatic ring, e.g., cyclohexane, cyclopentane, pyrrolidine, 2,3-dihydrofuran or cyclohexene. "Heterocycle" groups include, for example, piperidine, piperazine, pyrrolidine, morpholine, pyrimidine, benzofuran, indole, quinoline, lactones, and lactams. Exemplary "fused heterocycles" include benzodiazepine, indole, quinoline, purine, and 4,5,6,7-tetrahydrobenzo[d]thiazole. "Heterocycles" may be substituted at any one or more positions capable of bearing a hydrogen atom.

"Monocyclic rings" include 5-7 membered aromatic carbocycle or heteroaryl, 3-7 membered cycloalkyl or cycloalkenyl, and 5-7 membered non-aromatic heterocyclyl. Exemplary monocyclic groups include substituted or unsubstituted heterocycles or carbocycles such as thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, cyclohexyl, cyclopentyl, cyclopropyl, cyclobutyl, cycloheptanyl, azetidinyl, oxetanyl, thiiranyl, oxiranyl, aziridinyl, and thiomorpholinyl.

As used herein, "substituted" means substituting a hydrogen atom in a structure with an atom or molecule other than hydrogen. A substitutable atom such as a "substitutable nitrogen" is an atom that bears a hydrogen atom in at least one resonance form. The hydrogen atom may be substituted for another atom or group such as a $CH_3$ or an OH group. For example, the nitrogen in a piperidine molecule is substitutable if the nitrogen is bound to a hydrogen atom. If, for example, the nitrogen of a piperidine is bound to an atom other than hydrogen, the nitrogen is not substitutable. An atom that is not capable of bearing a hydrogen atom in any resonance form is not substitutable.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

The compounds disclosed herein also include partially and fully deuterated variants. In certain embodiments, deuterated variants may be used for kinetic studies. One of skill in the art can select the sites at which such deuterium atoms are present.

Also included in the present invention are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

According to another embodiment, the present invention provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

In an exemplary embodiment, a therapeutic compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to INF-induced apoptosis.

In certain embodiments, a sirtuin-modulating compound does not have any substantial ability to inhibit a histone deacetylase (HDAC) class I, and/or an HDAC class II at concentrations (e.g., in vivo) effective for modulating the deacetylase activity of the sirtuin. For instance, in preferred embodiments, the sirtuin-modulating compound is a sirtuin-modulating compound and is chosen to have an $EC_{50}$ for activating sirtuin deacetylase activity that is at least 5 fold less than the $EC_{50}$ for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, a sirtuin-modulating compound does not have any substantial ability to modulate sirtuin homologs. In certain embodiments, an activator of a human sirtuin protein may not have any substantial ability to activate a sirtuin protein from lower eukaryotes, particularly yeast or human pathogens, at concentrations (e.g., in vivo) effective for activating the deacetylase activity of human sirtuin. For example, a sirtuin-modulating compound may be chosen to have an $EC_{50}$ for activating a human sirtuin, such as SIRT1 and/or SIRT3, deacetylase activity that is at least 5 fold less than the $EC_{50}$ for activating a yeast sirtuin, such as Sir2 (such as *Candida*, *S. cerevisiae*, etc.), and even more preferably at least 10 fold, 100 fold or even 1000 fold less. In another embodiment, an inhibitor of a sirtuin protein from lower eukaryotes, particularly yeast or human pathogens, does not have any substantial ability to inhibit a sirtuin protein from humans at concentrations (e.g., in vivo) effective for inhibiting the deacetylase activity of a sirtuin protein from a lower eukaryote. For example, a sirtuin-inhibiting compound may be chosen to have an $IC_{50}$ for inhibiting a human sirtuin, such as SIRT1 and/or SIRT3, deacetylase activity that is at least 5 fold less than the $IC_{50}$ for inhibiting a yeast sirtuin, such as Sir2 (such as *Candida, S. cerevisiae*, etc.), and even more preferably at least 10 fold, 100 fold or even 1000 fold less.

In certain embodiments, a sirtuin-modulating compound may have the ability to modulate one or more sirtuin protein homologs, such as, for example, one or more of human SIRT1, SIRT2, SIRT3, SIRT4, SIRT5, SIRT6, or SIRT7. In some embodiments, a sirtuin-modulating compound has the ability to modulate both a SIRT1 and a SIRT3 protein.

In other embodiments, a SIRT1 modulator does not have any substantial ability to modulate other sirtuin protein homologs, such as, for example, one or more of human SIRT2, SIRT3, SIRT4, SIRT5, SIRT6, or SIRT7, at concentrations (e.g., in vivo) effective for modulating the deacetylase activity of human SIRT1. For example, a sirtuin-modulating compound may be chosen to have an $ED_{50}$ for modulating human SIRT1 deacetylase activity that is at least 5 fold less than the $ED_{50}$ for modulating one or more of human SIRT2, SIRT3, SIRT4, SIRT5, SIRT6, or SIRT7, and even more preferably at least 10 fold, 100 fold or even 1000 fold less. In some embodiments, a SIRT1 modulator does not have any substantial ability to modulate a SIRT3 protein.

In other embodiments, a SIRT3 modulator does not have any substantial ability to modulate other sirtuin protein homologs, such as, for example, one or more of human SIRT1, SIRT2, SIRT4, SIRT5, SIRT6, or SIRT7, at concentrations (e.g., in vivo) effective for modulating the deacetylase activity of human SIRT3. For example, a sirtuin-modulating compound may be chosen to have an $ED_{50}$ for modulating human SIRT3 deacetylase activity that is at least 5 fold less than the $ED_{50}$ for modulating one or more of human SIRT1, SIRT2, SIRT4, SIRT5, SIRT6, or SIRT7, and even more preferably at least 10 fold, 100 fold or even 1000 fold less. In some embodiments, a SIRT3 modulator does not have any substantial ability to modulate a SIRT1 protein.

In certain embodiments, a sirtuin-modulating compound may have a binding affinity for a sirtuin protein of about $10^{-9}$M, $10^{-10}$M, $10^{-11}$M, $10^{-12}$M or less. A sirtuin-modulating compound may reduce (activator) or increase (inhibitor) the apparent Km of a sirtuin protein for its substrate or $NAD^+$ (or other cofactor) by a factor of at least about 2, 3, 4, 5, 10, 20, 30, 50 or 100. In certain embodiments, Km values are determined using the mass spectrometry assay described herein. Preferred activating compounds reduce the Km of a sirtuin for its substrate or cofactor to a greater extent than caused by resveratrol at a similar concentration or reduce the Km of a sirtuin for its substrate or cofactor similar to that caused by resveratrol at a lower concentration. A sirtuin-modulating compound may increase the Vmax of a sirtuin protein by a factor of at least about 2, 3, 4, 5, 10, 20, 30, 50 or 100. A sirtuin-modulating compound may have an $ED_{50}$ for modulating the deacetylase activity of a SIRT1 and/or SIRT3 protein of less than about 1 nM, less than about 10 nM, less than about 100 nM, less than about 1 μM, less than about 10 μM, less than about 100 μM, or from about 1-10 nM, from about 10-100 nM, from about 0.1-1 μM, from about 1-10 μM or from about 10-100 μM. A sirtuin-modulating compound may modulate the deacetylase activity of a SIRT1 and/or SIRT3 protein by a factor of at least about 5, 10, 20, 30, 50, or 100, as measured in a cellular assay or in a cell based assay. A sirtuin-modulating compound may cause at least about 10%, 30%, 50%, 80%, 2 fold, 5 fold, 10 fold, 50 fold or 100 fold greater induction of the deacetylase activity of a sirtuin protein relative to the same concentration of resveratrol. A sirtuin-modulating compound may have an $ED_{50}$ for modulating SIRT5 that is at least about 10 fold, 20 fold, 30 fold, 50 fold greater than that for modulating SIRT1 and/or SIRT3.

3. Exemplary Uses

In certain aspects, the invention provides methods for modulating the level and/or activity of a sirtuin protein and methods of use thereof.

In certain embodiments, the invention provides methods for using sirtuin-modulating compounds wherein the sirtuin-modulating compounds activate a sirtuin protein, e.g., increase the level and/or activity of a sirtuin protein. Sirtuin-modulating compounds that increase the level and/or activity of a sirtuin protein may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a sirtuin-modulating compound, e.g., a sirtuin-modulating compound.

Without wishing to be bound by theory, it is believed that activators of the instant invention may interact with a sirtuin at the same location within the sirtuin protein (e.g., active site or site affecting the Km or Vmax of the active site). It is believed that this is the reason why certain classes of sirtuin activators and inhibitors can have substantial structural similarity.

In certain embodiments, the sirtuin-modulating compounds described herein may be taken alone or in combination with other compounds. In certain embodiments, a mixture of two or more sirtuin-modulating compounds may be administered to a subject in need thereof. In another embodiment, a sirtuin-modulating compound that increases the level and/or activity of a sirtuin protein may be administered with one or more of the following compounds: resveratrol, butein, fisetin, piceatannol, or quercetin. In an exemplary embodiment, a sirtuin-modulating compound that increases the level and/or activity of a sirtuin protein may be administered in combination with nicotinic acid or nicotinamide riboside. In another embodiment, a sirtuin-modulating compound that decreases the level and/or activity of a sirtuin protein may be administered with one or more of the following compounds: nicotinamide (NAM), suramin; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8,3',4'-hexahydroxyflavone), sirtinol; and splitomicin. In yet another embodiment, one or more sirtuin-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, aging, stress, etc. In various embodiments, combination therapies comprising a sirtuin-modulating compound may refer to (1) pharmaceutical compositions that comprise one or more sirtuin-modulating compounds in combination with one or more therapeutic agents (e.g., one or more therapeutic agents described herein); and (2) co-administration of one or more sirtuin-modulating compounds with one or more therapeutic agents wherein the sirtuin-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the compound(s) and other therapeutic agent(s) are in separate vessels). When using separate formulations, the sirtuin-modulating compound may be administered simultaneous with, intermittent with, staggered with, prior to, subsequent to, or combinations thereof, the administration of another therapeutic agent.

In certain embodiments, methods for reducing, preventing or treating diseases or disorders using a compound described herein may also comprise increasing the protein level of a sirtuin, such as human SIRT1, SIRT2 and/or SIRT3, or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370 and/or increasing the level of SIRT3 by introducing a nucleic acid encoding the amino acid sequence set forth in GenBank Accession No. AAH01042.

A nucleic acid that is introduced into a cell to increase the protein level of a sirtuin may encode a protein that is at least about 80%, 85%, 90%, 95%, 98%, or 99% identical to the sequence of a sirtuin, e.g., SIRT1 and/or SIRT3 protein. For example, the nucleic acid encoding the protein may be at least about 80%, 85%, 90%, 95%, 98%, or 99% identical to a nucleic acid encoding a SIRT1 (e.g. GenBank Accession No. NM_012238) and/or SIRT3 (e.g., GenBank Accession No. BC001042) protein. The nucleic acid may also be a nucleic acid that hybridizes, preferably under stringent hybridization conditions, to a nucleic acid encoding a wild-type sirtuin, e.g., SIRT1 and/or SIRT3 protein. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM_012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using a sirtuin-modulating compound may also comprise decreasing the protein level of a sirtuin, such as human SIRT1, SIRT2 and/or SIRT3, or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one aspect, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a sirtuin-modulating compound of the invention that increases the level and/or activity of a sirtuin protein. In an exemplary embodiment, the methods comprise contacting the cell with a sirtuin-modulating compound.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one aspect, cells that are intended to be preserved for long periods of time may be treated with a sirtuin-modulating compound that increases the level and/or activity of a sirtuin protein. The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using a sirtuin-modulating compound that increases the level and/or activity of a sirtuin protein. Other cells that may be treated to extend their lifespan or protect against apoptosis include cells for consumption, e.g., cells from non-human mammals (such as meat) or plant cells (such as vegetables).

Sirtuin-modulating compounds that increase the level and/or activity of a sirtuin protein may also be applied during developmental and growth phases in mammals, plants, insects or microorganisms, in order to, e.g., alter, retard or accelerate the developmental and/or growth process.

In another aspect, sirtuin-modulating compounds that increase the level and/or activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the sirtuin-modulating compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a sirtuin-modulating compound or may have a subset of cells/tissue treated locally with a sirtuin-modulating compound that increases the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a sirtuin-modulating compound that increases the level and/or activity of a sirtuin protein in vivo, e.g., to increase their lifespan or prevent apoptosis. For example, skin can be protected from aging (e.g., developing wrinkles, loss of elasticity, etc.) by treating skin or epithelial cells with a sirtuin-modulating compound that increases the level and/or activity of a sirtuin protein. In an exemplary embodiment, skin is contacted with a pharmaceutical or cosmetic composition comprising a sirtuin-modulating compound that increases the level and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, sirtuin-modulating compounds that increase the level and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

Sirtuin-modulating compounds may be delivered locally or systemically to a subject. In certain embodiments, a sirtuin-modulating compound is delivered locally to a tissue or organ of a subject by injection, topical formulation, etc.

In another embodiment, a sirtuin-modulating compound that increases the level and/or activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin-modulating compound that increases the level and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

Sirtuin-modulating compounds that increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. Sirtuin-modulating compounds that increase the level and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

Sirtuin-modulating compounds that increase the level and/or activity of a sirtuin protein can also be administered to a subject suffering from an acute disease, e.g., damage to an organ or tissue, e.g., a subject suffering from stroke or myocardial infarction or a subject suffering from a spinal cord injury. Sirtuin-modulating compounds that increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof a sirtuin-modulating compound that increases the level and/or activity of a sirtuin protein.

Cardiovascular diseases that can be treated or prevented using the sirtuin-modulating compounds that increase the level and/or activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The sirtuin-modulating compounds that increase the level and/or activity of a sirtuin protein may also be used for increasing HDL levels in plasma of an individual.

Yet other disorders that may be treated with sirtuin-modulating compounds that increase the level and/or activity of a sirtuin protein include restenosis, e.g., following coronary intervention, and disorders relating to an abnormal level of high density and low density cholesterol.

In certain embodiments, a sirtuin-modulating compound that increases the level and/or activity of a sirtuin protein may be administered as part of a combination therapy with another cardiovascular agent. In certain embodiments, a sirtuin-modulating compound that increases the level and/or activity of a sirtuin protein may be administered as part of a combination therapy with an anti-arrhythmia agent. In another embodiment, a sirtuin-modulating compound that increases the level and/or activity of a sirtuin protein may be administered as part of a combination therapy with another cardiovascular agent.

Cell Death/Cancer

Sirtuin-modulating compounds that increase the level and/or activity of a sirtuin protein may be administered to subjects who have recently received or are likely to receive a dose of radiation or toxin. In certain embodiments, the dose of radiation or toxin is received as part of a work-related or medical procedure, e.g., administered as a prophylactic measure. In another embodiment, the radiation or toxin exposure is received unintentionally. In such a case, the compound is preferably administered as soon as possible after the exposure to inhibit apoptosis and the subsequent development of acute radiation syndrome.

Sirtuin-modulating compounds may also be used for treating and/or preventing cancer. In certain embodiments, sirtuin-modulating compounds that increase the level and/or activity of a sirtuin protein may be used for treating and/or preventing cancer. Calorie restriction has been linked to a reduction in the incidence of age-related disorders including cancer. Accordingly, an increase in the level and/or activity of a sirtuin protein may be useful for treating and/or preventing the incidence of age-related disorders, such as, for example, cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Chemotherapeutic agents may be co-administered with modulating compounds described herein as having anti-cancer activity, e.g., compounds that induce apoptosis, compounds that reduce lifespan or compounds that render cells sensitive to stress. Chemotherapeutic agents may be used by themselves with a sirtuin-modulating compound described herein as inducing cell death or reducing lifespan or increasing sensitivity to stress and/or in combination with other chemotherapeutics agents. In addition to conventional chemotherapeutics, the sirtuin-modulating compounds described herein may also be used with antisense RNA, RNAi or other polynucleotides to inhibit the expression of the cellular components that contribute to unwanted cellular proliferation.

Combination therapies comprising sirtuin-modulating compounds and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with a sirtuin-modulating compound is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a sirtuin-modulating compound described herein can be at least 2 fold greater than the TI for conventional chemotherapeutic regimen alone, and even more preferably at 5 fold, 10 fold or even 25 fold greater.

Neuronal Diseases/Disorders

In certain aspects, sirtuin-modulating compounds that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Sirtuin-modulating compounds that increase the level and/or activity of a sirtuin protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. PD is a CNS disorder that results in uncontrolled body movements, rigidity, tremor, and dyskinesia, and is associated with the death of brain cells in an area of the brain that produces dopamine. ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipids substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with sirtuin-modulating compounds of the invention.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a sirtuin-modulating compound that increases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, a sirtuin-modulating compound that increases the level and/or activity of a sirtuin protein may be used to treat or prevent multiple sclerosis (MS), including relapsing MS and monosymptomatic MS, and other demyelinating conditions, such as, for example, chronic inflammatory demyelinating polyneuropathy (CIDP), or symptoms associated therewith.

In yet another embodiment, a sirtuin-modulating compound that increases the level and/or activity of a sirtuin protein may be used to treat trauma to the nerves, including, trauma due to disease, injury (including surgical intervention), or environmental trauma (e.g., neurotoxins, alcoholism, etc.).

Sirtuin-modulating compounds that increase the level and/or activity of a sirtuin protein may also be useful to prevent, treat, and alleviate symptoms of various PNS disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with sirtuin-modulating compounds that increase the level and/or activity of a sirtuin protein include: diabetes, leprosy, Charcot-Marie-Tooth disease, Guillain-Barré syndrome and Brachial Plexus Neuropathies (diseases of the cervical and first thoracic roots, nerve trunks, cords, and peripheral nerve components of the brachial plexus.

In another embodiment, a sirtuin-modulating compound may be used to treat or prevent a polyglutamine disease. Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In certain embodiments, apoptotic or necrotic cell death may be prevented. In still a further embodiment, ischemic-mediated damage, such as cytotoxic edema or central nervous system tissue anoxemia, may be prevented. In each embodiment, the central nervous system cell may be a spinal cell or a brain cell.

Another aspect encompasses administrating a sirtuin-modulating compound to a subject to treat a central nervous system ischemic condition. A number of central nervous system ischemic conditions may be treated by the sirtuin-modulating compounds described herein. In certain embodiments, the ischemic condition is a stroke that results in any type of ischemic central nervous system damage, such as apoptotic or necrotic cell death, cytotoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, a sirtuin-modulating compound may be administered to reduce infarct size of the ischemic core following a central nervous system ischemic condition. Moreover, a sirtuin-modulating compound may also be beneficially administered to reduce the size of the ischemic penumbra or transitional zone following a central nervous system ischemic condition.

In certain embodiments, a combination drug regimen may include drugs or compounds for the treatment or prevention of neurodegenerative disorders or secondary conditions associated with these conditions. Thus, a combination drug regimen may include one or more sirtuin activators and one or more anti-neurodegeneration agents.

Blood Coagulation Disorders

In other aspects, sirtuin-modulating compounds that increase the level and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a sirtuin-modulating compound that increases the level and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, a combination drug regimen may include drugs or compounds for the treatment or prevention of blood coagulation disorders or secondary conditions associated with these conditions. Thus, a combination drug regimen may include one or more sirtuin-modulating compounds that increase the level and/or activity of a sirtuin protein and one or more anti-coagulation or anti-thrombosis agents.

Weight Control

In another aspect, sirtuin-modulating compounds that increase the level and/or activity of a sirtuin protein may be used for treating or preventing weight gain or obesity in a subject. For example, sirtuin-modulating compounds that increase the level and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, sirtuin-modulating compounds that increase the level and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self-esteem). Finally, patients with AIDS can develop lipodystrophy or insulin resistance in response to combination therapies for AIDS.

In another embodiment, sirtuin-modulating compounds that increase the level and/or activity of a sirtuin protein may be used for inhibiting adipogenesis or fat cell differentiation, whether in vitro or in vivo. Such methods may be used for treating or preventing obesity.

In other embodiments, sirtuin-modulating compounds that increase the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In an exemplary embodiment, sirtuin-modulating compounds that increase the level and/or activity of a sirtuin protein may be administered as a combination therapy for treating or preventing weight gain or obesity. For example, one or more sirtuin-modulating compounds that increase the level and/or activity of a sirtuin protein may be administered in combination with one or more anti-obesity agents.

In another embodiment, sirtuin-modulating compounds that increase the level and/or activity of a sirtuin protein may be administered to reduce drug-induced weight gain. For example, a sirtuin-modulating compound that increases the level and/or activity of a sirtuin protein may be administered as a combination therapy with medications that may stimulate appetite or cause weight gain, in particular, weight gain due to factors other than water retention.

Metabolic Disorders/Diabetes

In another aspect, sirtuin-modulating compounds that increase the level and/or activity of a sirtuin protein may be used for treating or preventing a metabolic disorder, such as insulin-resistance, a pre-diabetic state, type II diabetes, and/or complications thereof. Administration of a sirtuin-modulating compound that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, sirtuin-modulating compounds that increase the level and/or activity of a sirtuin protein may be administered as a combination therapy for treating or preventing a metabolic disorder. For example, one or more sirtuin-modulating compounds that increase the level and/or activity of a sirtuin protein may be administered in combination with one or more anti-diabetic agents.

Inflammatory Diseases

In other aspects, sirtuin-modulating compounds that increase the level and/or activity of a sirtuin protein can be used to treat or prevent a disease or disorder associated with inflammation. Sirtuin-modulating compounds that increase the level and/or activity of a sirtuin protein may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

In another embodiment, sirtuin-modulating compounds that increase the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, sirtuin-modulating compounds that increase the level and/or activity of a sirtuin protein may be used to treat autoimmune diseases, and/or inflammation associated with autoimmune diseases, such as arthritis, including rheumatoid arthritis, psoriatic arthritis, and ankylosing spondylitis, as well as organ-tissue autoimmune diseases (e.g., Raynaud's syndrome), ulcerative colitis, Crohn's disease, oral mucositis, scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, one or more sirtuin-modulating compounds that increase the level and/or activity of a sirtuin protein may be taken alone or in combination with other compounds useful for treating or preventing inflammation.

Flushing

In another aspect, sirtuin-modulating compounds that increase the level and/or activity of a sirtuin protein may be used for reducing the incidence or severity of flushing and/or hot flashes which are symptoms of a disorder. For instance, the subject method includes the use of sirtuin-modulating compounds that increase the level and/or activity of a sirtuin protein, alone or in combination with other agents, for reducing incidence or severity of flushing and/or hot flashes in cancer patients. In other embodiments, the method provides for the use of sirtuin-modulating compounds that increase the level and/or activity of a sirtuin protein to reduce the incidence or severity of flushing and/or hot flashes in menopausal and post-menopausal woman.

In another aspect, sirtuin-modulating compounds that increase the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one sirtuin-modulating compound that increases the level and/or activity of a sirtuin protein. In other embodiments, a method for treating drug induced flushing comprises separately administering one or more compounds that induce flushing and one or more sirtuin-modulating compounds, e.g., wherein the sirtuin-modulating compound and flushing inducing agent have not been formulated in the same compositions. When using separate formulations, the sirtuin-modulating compound may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, raloxifene, antidepressants, anti-psychotics, chemotherapeutics, calcium channel blockers, and antibiotics.

In certain embodiments, sirtuin-modulating compounds that increase the level and/or activity of a sirtuin protein may be used to reduce flushing side effects of a vasodilator or an antilipemic agent (including anticholesteremic agents and lipotropic agents). In an exemplary embodiment, a sirtuin-modulating compound that increases the level and/or activity of a sirtuin protein may be used to reduce flushing associated with the administration of niacin.

In another embodiment, the invention provides a method for treating and/or preventing hyperlipidemia with reduced flushing side effects. In another representative embodiment, the method involves the use of sirtuin-modulating compounds that increase the level and/or activity of a sirtuin protein to reduce flushing side effects of raloxifene. In another representative embodiment, the method involves the use of sirtuin-modulating compounds that increase the level and/or activity of a sirtuin protein to reduce flushing side effects of antidepressants or anti-psychotic agent. For instance, sirtuin-modulating compounds that increase the level and/or activity of a sirtuin protein can be used in conjunction (administered separately or together) with a serotonin reuptake inhibitor, or a 5HT2 receptor antagonist.

In certain embodiments, sirtuin-modulating compounds that increase the level and/or activity of a sirtuin protein may be used as part of a treatment with a serotonin reuptake inhibitor (SRI) to reduce flushing. In still another representative embodiment, sirtuin-modulating compounds that increase the level and/or activity of a sirtuin protein may be used to reduce flushing side effects of chemotherapeutic agents, such as cyclophosphamide and tamoxifen.

In another embodiment, sirtuin-modulating compounds that increase the level and/or activity of a sirtuin protein may be used to reduce flushing side effects of calcium channel blockers, such as amlodipine.

In another embodiment, sirtuin-modulating compounds that increase the level and/or activity of a sirtuin protein may be used to reduce flushing side effects of antibiotics. For example, sirtuin-modulating compounds that increase the level and/or activity of a sirtuin protein can be used in combination with levofloxacin.

Ocular Disorders

One aspect of the present invention is a method for inhibiting, reducing or otherwise treating vision impairment by administering to a patient a therapeutic dosage of sirtuin modulator selected from a compound disclosed herein, or a pharmaceutically acceptable salt, prodrug or a metabolic derivative thereof.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g., Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g., *Candida* choroiditis, histoplasmosis), protozoal infections (e.g., toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, or a drug that raises intraocular pressure, such as a steroid), by administering to the subject in need of such treatment a therapeutic dosage of a sirtuin modulator disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of a sirtuin modulator disclosed herein. Ocular surgeries include cataract, iridotomy and lens replacements.

Another aspect of the invention is the treatment, including inhibition and prophylactic treatment, of age related ocular diseases include cataracts, dry eye, age-related macular degeneration (AMD), retinal damage and the like, by administering to the subject in need of such treatment a therapeutic dosage of a sirtuin modulator disclosed herein.

Another aspect of the invention is the prevention or treatment of damage to the eye caused by stress, chemical insult or radiation, by administering to the subject in need of such treatment a therapeutic dosage of a sirtuin modulator disclosed herein. Radiation or electromagnetic damage to the eye can include that caused by CRT's or exposure to sunlight or UV.

In certain embodiments, a combination drug regimen may include drugs or compounds for the treatment or prevention of ocular disorders or secondary conditions associated with these conditions. Thus, a combination drug regimen may include one or more sirtuin activators and one or more therapeutic agents for the treatment of an ocular disorder.

In certain embodiments, a sirtuin modulator can be administered in conjunction with a therapy for reducing intraocular pressure. In another embodiment, a sirtuin modulator can be administered in conjunction with a therapy for treating and/or preventing glaucoma. In yet another embodiment, a sirtuin modulator can be administered in conjunction with a therapy for treating and/or preventing optic neuritis. In certain embodiments, a sirtuin modulator can be administered in conjunction with a therapy for treating and/or preventing CMV Retinopathy. In another embodiment, a sirtuin modulator can be administered in conjunction with a therapy for treating and/or preventing multiple sclerosis.

Mitochondrial-Associated Diseases and Disorders

In certain embodiments, the invention provides methods for treating diseases or disorders that would benefit from increased mitochondrial activity. The methods involve administering to a subject in need thereof a therapeutically effective amount of a sirtuin-modulating compound. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods for treating diseases or disorders that would benefit from increased mitochondrial activity may comprise identifying a subject suffering from a mitochondrial dysfunction. Methods for diagnosing a mitochondrial dysfunction may involve molecular genetics, pathologic and/or biochemical analyses. Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods for treating a disease or disorder that would benefit from increased mitochondrial activity that involves administering to a subject in need thereof one or more sirtuin-modulating compounds in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods for treating diseases or disorders that would benefit from increased mitochondrial activity by administering to a subject a therapeutically effective amount of a sirtuin-modulating compound. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

Muscular dystrophy refers to a family of diseases involving deterioration of neuromuscular structure and function, often resulting in atrophy of skeletal muscle and myocardial dysfunction, such as Duchenne muscular dystrophy. In certain embodiments, sirtuin-modulating compounds may be used for reducing the rate of decline in muscular functional capacities and for improving muscular functional status in patients with muscular dystrophy.

In certain embodiments, sirtuin-modulating compounds may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, sirtuin-modulating compounds may be useful for treating patients suffering from toxic damage to mitochondria, such as, toxic damage due to calcium accumulation, excitotoxicity, nitric oxide exposure, drug induced toxic damage, or hypoxia.

In certain embodiments, sirtuin-modulating compounds may be useful for treating diseases or disorders associated with mitochondrial deregulation.

Muscle Performance

In other embodiments, the invention provides methods for enhancing muscle performance by administering a therapeutically effective amount of a sirtuin-modulating compound. For example, sirtuin-modulating compounds may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of a sirtuin-modulating compound that increase mitochondrial activity, increase mitochondrial biogenesis, and/or increase mitochondrial mass.

Sports performance refers to the ability of the athlete's muscles to perform when participating in sports activities Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc Enhanced sports performance is manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time.

It is contemplated that the methods of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides novel dietary compositions comprising sirtuin modulators, a method for their preparation, and a method of using the compositions for improvement of sports performance. Accordingly, provided are therapeutic compositions, foods and beverages that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

Sirtuin-modulating compounds that increase the level and/or activity of a sirtuin protein may be used for treating or preventing viral infections (such as infections by influenza, herpes or papilloma virus) or as antifungal agents. In certain embodiments, sirtuin-modulating compounds that increase the level and/or activity of a sirtuin protein may be administered as part of a combination drug therapy with another therapeutic agent for the treatment of viral diseases. In another embodiment, sirtuin-modulating compounds that increase the level and/or activity of a sirtuin protein may be administered as part of a combination drug therapy with another anti-fungal agent.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

Sirtuin-modulating compounds that increase the level and/or activity of a sirtuin protein may also be used to increase lifespan, stress resistance, and resistance to apoptosis in plants. In certain embodiments, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preserve them.

In other embodiments, sirtuin-modulating compounds that increase the level and/or activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin-modulating compounds that increase the level and/or activity of a sirtuin protein may also be used to increase lifespan, stress resistance and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods described herein may be applied to any organism, e.g., eukaryote, which may have commercial importance. For example, they can be applied to fish (aquaculture) and birds (e.g., chicken and fowl).

Higher doses of sirtuin-modulating compounds that increase the level and/or activity of a sirtuin protein may also be used as a pesticide by interfering with the regulation of silenced genes and the regulation of apoptosis during development. In this embodiment, a compound may be applied to plants using a method known in the art that ensures the compound is bio-available to insect larvae, and not to plants.

At least in view of the link between reproduction and longevity, sirtuin-modulating compounds that increase the level and/or activity of a sirtuin protein can be applied to affect the reproduction of organisms such as insects, animals and microorganisms.

4. Assays

Yet other methods contemplated herein include screening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be modulated by an agent known to modulate the sirtuin, and monitoring or determining the level of modulation of the sirtuin in the presence of the test agent relative to the absence of the test agent. The level of modulation of a sirtuin can be determined by determining its ability to deacetylate a substrate. Exemplary substrates are acetylated peptides which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys. Other substrates are peptides from human histones H3 and H4 or an acetylated amino acid. Substrates may be fluorogenic. The sirtuin may be SIRT1, Sir2, SIRT3, or a portion thereof. For example, recombinant SIRT1 can be obtained from BIOMOL. The reaction may be conducted for about 30 minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277:45099. The level of modulation of the sirtuin in an assay may be compared to the level of modulation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In certain embodiments, a screening assay comprises (i) contacting a sirtuin with a test agent and an acetylated substrate under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

In another embodiment, the screening assay may detect the formation of a 2'/3'-O-acetyl-ADP-ribose product of sirtuin-mediated NAD-dependent deacetylation. This O-acetyl-ADP-ribose product is formed in equimolar quantities with the deacetylated peptide product of the sirtuin deacetylation reaction. Accordingly, the screening assay may include (i) contacting a sirtuin with a test agent and an acetylated substrate under conditions appropriate for the sirtuin to deacetylate the substrate in the absence of the test agent; and (ii) determining the amount of O-acetyl-ADP-ribose formation, wherein an increase in O-acetyl-ADP-ribose formation in the presence of the test agent relative to the absence of the test agent indicates that the test agent stimulates deacetylation by the sirtuin, while a decrease in O-acetyl-ADP-ribose formation in the presence of the test agent relative to the absence of the test agent indicates that the test agent inhibits deacetylation by the sirtuin.

Methods for identifying an agent that modulates, e.g., stimulates, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also preferably fluorogenic, as further described herein. The method may further comprise lysing the cells to determine the level of acetylation of the substrate. Substrates may be added to cells at a concentration ranging from about 1 µM to about 10 mM, preferably from about 10 µM to 1 mM, even more preferably from about 100 µM to 1 mM, such as about 200 µM. A preferred substrate is an acetylated lysine, e.g., ε-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 µM, preferably from about 0.1 to 10 µM, such as 1 µM. Incubation of cells with the test compound and the substrate may be conducted for about 10 minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo.

5. Pharmaceutical Compositions

The compounds described herein may be formulated in a conventional manner using one or more physiologically or pharmaceutically acceptable carriers or excipients. For example, compounds and their pharmaceutically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, a compound may be administered locally, at the site where the target cells are present, i.e., in a specific tissue, organ, or fluid (e.g., blood, cerebrospinal fluid, etc.).

The compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, compounds may also be formulated as a depot preparation. Such long acting formulations may be administered by implantation (for example subcutaneously or intramuscularly) or by intramuscular injection. Thus, for example, compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Liposomes are a further drug delivery system which is easily injectable. Accordingly, in the method of invention the active compounds can also be administered in the form of a liposome delivery system. Liposomes are well known by those skilled in the art. Liposomes can be formed from a variety of phospholipids, such as cholesterol, stearylamine of phosphatidylcholines. Liposomes usable for the method of invention encompass all types of liposomes including, but not limited to, small unilamellar vesicles, large unilamellar vesicles and multilamellar vesicles.

Another way to produce a formulation, particularly a solution, of a compound described herein, is through the use of cyclodextrin. By cyclodextrin is meant α-, β-, or γ-cyclodextrin. Cyclodextrins are described in detail in Pitha et al., U.S. Pat. No. 4,727,064, which is incorporated herein by reference. Cyclodextrins are cyclic oligomers of glucose; these compounds form inclusion complexes with any drug whose molecule can fit into the lipophile-seeking cavities of the cyclodextrin molecule.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets.

Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

Pharmaceutical compositions (including cosmetic preparations) may comprise from about 0.00001 to 100% such as from 0.001 to 10% or from 0.1% to 5% by weight of one or more compounds described herein. In other embodiments, the pharmaceutical composition comprises: (i) 0.05 to 1000 mg of the compounds of the invention, or a pharmaceutically acceptable salt thereof, and (ii) 0.1 to 2 grams of one or more pharmaceutically acceptable excipients.

In some embodiments, a compound described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

The compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing.

The compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type.

The compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

The compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9).

The compounds may be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ aqueous carrier liquid, alcohols and oils can be used as the carrier liquid as well.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of a compound, or by insertion of a sustained release device that releases a compound. A compound may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

The compounds described herein may be stored in oxygen free environment. For example, a composition can be prepared in an airtight capsule for oral administration, such as Capsugel from Pfizer, Inc.

Cells, e.g., treated ex vivo with a compound as described herein, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of compounds can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6. Kits

Also provided herein are kits, e.g., kits for therapeutic purposes or kits for modulating the lifespan of cells or modulating apoptosis. A kit may comprise one or more compounds as described herein, e.g., in premeasured doses. A kit may optionally comprise devices for contacting cells with the compounds and instructions for use. Devices include syringes, stents and other devices for introducing a compound into a subject (e.g., the blood vessel of a subject) or applying it to the skin of a subject.

In yet another embodiment, the invention provides a composition of matter comprising a compound of this invention and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The compound and the other agent are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a compound of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The invention now being generally described, it will be more readily understood by reference to the following examples which are included merely for purposes of illustration of certain aspects and embodiments of the present invention, and are not intended to limit the invention in any way.

Example 1. Preparation of N-(pyridin-2-yl)-6-(3-(trifluoromethyl)phenyl)imidazo[1,2-b]pyridazine-3-carboxamide (Compound 4)

Step 1. Synthesis of 6-chloropyridazin-3-amine

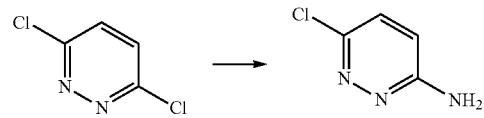 [SMILES: Clc1ccc(Cl)nn1 ; Nc1ccc(Cl)nn1]

A suspension of 3,6-dichloropyridazine (23.8 g, 155 mmol) in 25% aqueous ammonia (50 mL) was heated at 100° C. for about 12 h in a PTFE-lined pressure reactor. Upon cooling to room temp, the resulting crystalline solids were collected by filtration, washed with water and dried to afford to 6-chloropyridazin-3-amine (20.0 g, 96%). MS (ESI) calcd for $C_4H_4ClN_3$: 129.0.

Step 2. Synthesis of potassium salt of ethyl 2-chloro-3-oxopropanoate

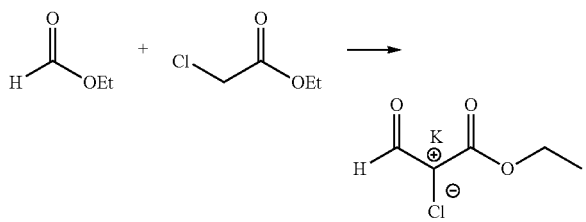

To a mixture containing ethyl formate (6.0 g, 81 mmol) and ethyl chloroacetate (9.89 g, 81 mmol) in 2-isopropoxypropane (200 mL) was added potassium tert-butoxide (t-BuOK) (9.07 g, 81 mmol) at 0° C. The mixture was stirred at room temp for 24 h. The mixture was filtered and the resulting yellow solids were washed with ethoxyethane to afford the potassium salt of ethyl 2-chloro-3-oxopropanoate (8.88 g, 58%).

Step 3. Synthesis of ethyl 6-chloroimidazo[1,2-b]pyridazine-3-carboxylate

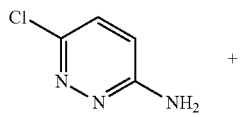 +

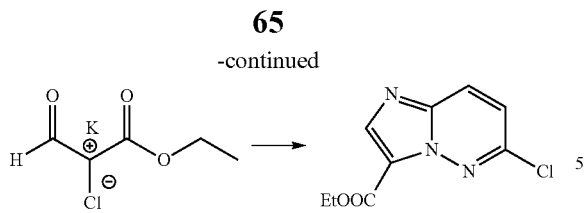

A mixture containing 6-chloropyridazin-3-amine (1.55 g, 119 mmol) and the potassium salt of ethyl 2-chloro-3-oxopropanoate (6.76 g, 357 mmol) in EtOH (100 mL) was stirred under reflux for 10 h. Upon cooling to room temp, the reaction mixture was concentrated under reduced pressure. Purification by chromatography afforded ethyl 6-chloroimidazo[1,2-b]pyridazine-3-carboxylate (1.5 g, 56%). MS (ESI) calcd for $C_9H_8ClN_3O_2$: 225.03. found: 226 [M+H].

Step 4. Synthesis of ethyl 6-(3-(trifluoromethyl)phenyl)imidazo[1,2-b]pyridazine-3-carboxylate

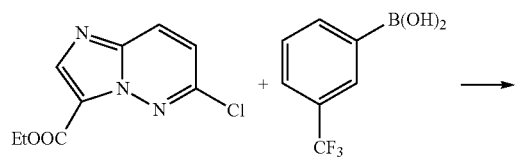

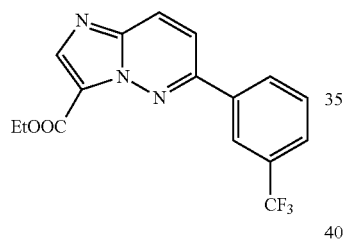

A mixture containing ethyl 6-chloroimidazo[1,2-b]pyridazine-3-carboxylate (1.25 g, 5.55 mmol), 3-(trifluoromethyl)phenylboronic acid (5.55 mmol), $Cs_2CO_3$ (3.62 g, 11.1 mmol) and $Pd(PPh_3)_4$ (0.32 g, 0.277 mmol) in 4:1:1 dioxane/water/ethanol (10 mL) was stirred at 100° C. for 2 h. Upon cooling to room temp, the reaction mixture was concentrated under reduced pressure. Purification by chromatography afforded ethyl 6-(3-(trifluoromethyl)phenyl)imidazo[1,2-b]pyridazine-3-carboxylate (1.5 g, 80%). MS (ESI) calcd for $C_{16}H_{12}F_3N_3O_2$: 335.09. found: 336 [M+H].

Step 5. Synthesis of 6-(3-(trifluoromethyl)phenyl)imidazo[1,2-b]pyridazine-3-carboxylic acid

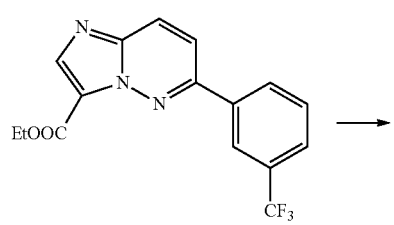

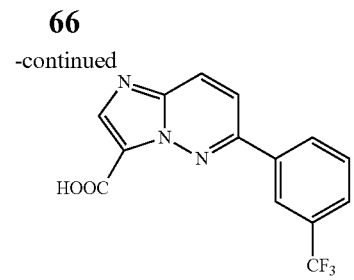

A mixture containing NaOH (0.36 g, 89.5 mmol) and ethyl 6-(3-(trifluoromethyl)phenyl)imidazo[1,2-b]pyridazine-3-carboxylate (1.5 g, 4.47 mmol) 1:1 dioxane: $H_2O$ (5 mL) was stirred at 0° C. for 4 h. The reaction mixture was concentrated under reduced pressure and enough 2% aqueous HCl was added to adjust the pH=5. The resulting solids were collected by filtration, washed with water and dried to afford 6-(3-(trifluoromethyl)phenyl)imidazo[1,2-b]pyridazine-3-carboxylic acid (1.1 g, 81%). MS (ESI) calcd for $C_{14}H_8F_3N_3O_2$: 307.06. found: 308 [M+H].

This general coupling procedure followed by ester hydrolysis could be used to prepare a variety of 6-(3-substituted phenyl) and 6-(2,6-disubstituted phenyl) imidazo[1,2-b]pyridazine-3-carboxylates by substituting the appropriate boronic acid or boronic ester moiety for 3-(trifluoromethyl)phenylboronic acid.

Step 6. Synthesis of N-(pyridin-2-yl)-6-(3-(trifluoromethyl)phenyl) imidazo[1,2-b]pyridazine-3-carboxamide

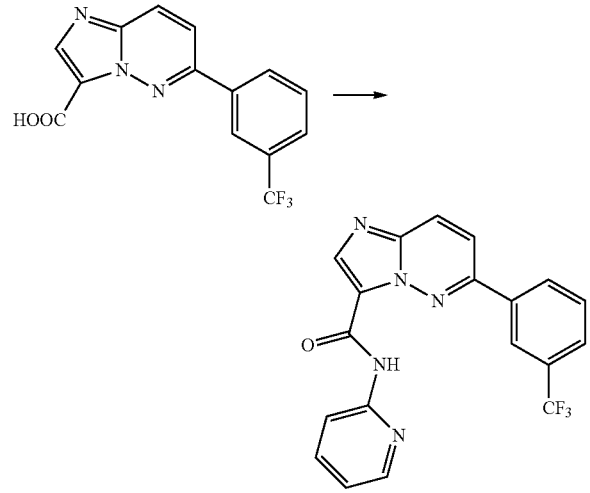

Compound 4

The following general amide coupling procedure was used:

A mixture containing 6-(3-(trifluoromethyl)phenyl)imidazo[1,2-b]pyridazine-3-carboxylic acid (200.0 mg, 0.65 mmol), 2-(7-Aza-1H-benzotriazole-1-yl)-1,1,3,3-tetramethyluronium hexafluorophosphate (HATU) (495.0 mg, 1.3 mmol), pyridin-2-amine (73.0 mg, 0.78 mmol) and N,N-Diisopropylethylamine (DIEA) (336.0 mg, 1.3 mmol) in DMF (5 mL) was stirred at 80° C. for 12 h. After cooling to room temp, the reaction mixture was concentrated and water was added. After extraction with $CH_2Cl_2$, the organic layer was dried ($Na_2SO_4$) and concentrated under reduced pressure. Purification by chromatography afforded N-(pyridin-2-yl)-6-(3-(trifluoromethyl)phenyl)imidazo[1,2-b]pyridazine-3-carboxamide (30.0 mg, 12%). MS (ESI) calcd for $C_{19}H_{12}F_3N_5O$: 383.10. found: 384 [M+H].

This general coupling procedure could be used to prepare a variety of 6-(3-trifluoromethylphenyl), 6-(3-trifluoromethoxyphenyl), 6-(3-morpholine), 6-(3-(methylsulfonyl)phenyl and 6-(2-fluoro-6-fluorophenyl)imidazo[1,2-b]pyridazine-3-carboxyamides by substituting the appropriate amine moiety for pyridine-2-amine.

Example 2. Preparation of N-(6-(morpholinomethyl)pyridin-2-yl)-6-(2-(trifluoromethyl)phenyl)imidazo[1,2-b]pyridazine-3-carboxamide (Compound 19)

Step 1. Synthesis of ethyl 6-(2-(trifluoromethyl)phenyl)imidazo[1,2-b]pyridazine-3-carboxylate

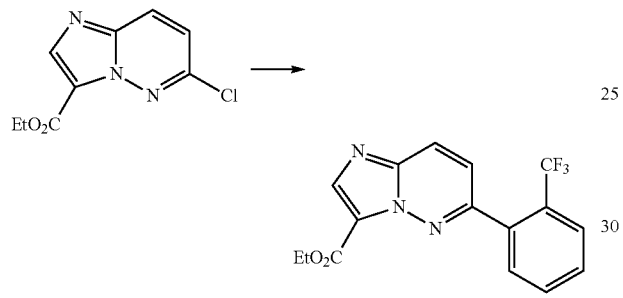

Dioxane (anhydrous, 30 mL) and $Cs_2CO_3$ (21.4 g, 65.6 mmol) were added to a mixture of ethyl 6-chloroimidazo[1,2-b]pyridazine-3-carboxylate (7.4 g, 32.8 mmol) and 2-(trifluoromethyl)phenylboronic acid (8.1 g, 42.6 mmol). The mixture was then added to $Pd(Ph_3P)_4$ (1.9 g, 1.64 mmol), and the reaction was heated to 130° C. in microwave. The mixture was filtered. After cooling to room temp, the filtrate was concentrated, and the residue was purified by column chromatography to give ethyl 6-(2-(trifluoromethyl)phenyl)imidazo[1,2-b]pyridazine-3-carboxylate (4.3 g, yield: 58%). MS (ESI) calcd for $C_{16}H_{12}F_3N_3O_2$: 335.1.

Step 2. Synthesis of 6-(2-(trifluoromethyl)phenyl)imidazo[1,2-b]pyridazine-3-carboxylic acid

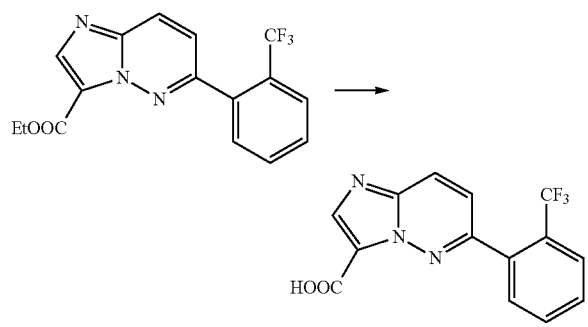

To a solution of compound ethyl 6-(2-(trifluoromethyl)phenyl)imidazo[1,2-b]pyridazine-3-carboxylate (2.25 g, 6.71 mmol) in water (25 mL) was added NaOH (4.29 g, 107 mmol). The solution was stirred for 20 min at 70° C. and pH was adjusted to 3 using concentrated HCl. After cooling to room temp, filtration gave 6-(2-(trifluoromethyl)phenyl)imidazo[1,2-b]pyridazine-3-carboxylic acid (1.84 g, 89%). MS (ESI) calcd for $C_{14}H_8F_3N_3O_2$: 335.1.

This general coupling procedure followed by ester hydrolysis could be used to prepare a variety of 6-(2-substituted phenyl), 6-(3-substituted phenyl), 6-(2,5-disubstituted phenyl), 6-(2,4-disubstituted phenyl), 6-(3,4-disubstituted phenyl), 6-(3,5-disubstituted phenyl), 6-(2,3-disubstituted phenyl) imidazo[1,2-b]pyridazine-3-carboxylic acids by substituting the appropriate boronic acid or boronic ester for 2-(trifluoromethyl)phenylboronic acid.

Step 3. Synthesis of N-(6-(morpholinomethyl)pyridin-2-yl)-6-(2-(trifluoromethyl)phenyl)imidazo[1,2-b]pyridazine-3-carboxamide

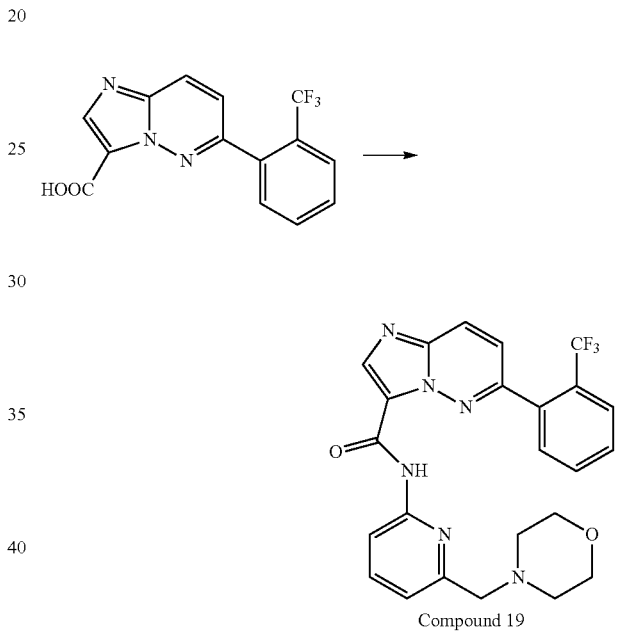

Compound 19

To 2 mL of DMF were added 6-(morpholinomethyl)pyridin-2-amine (24.4 mg, 0.24 mmol), 6-(2-(trifluoromethyl)phenyl)imidazo[1,2-b]pyridazine-3-carboxylic acid (50.0 mg, 0.16 mmol), HATU (119.0 mg, 0.32 mmol) and DIEA (41.0 mg, 0.32 mmol). The resulting mixture was stirred at 70° C. overnight. Water (20 mL) was added and the product was collected by filtration, washed with $H_2O$ and dried to afford N-(6-(morpholinomethyl)pyridin-2-yl)-6-(2-(trifluoromethyl)phenyl) imidazo[1,2-b]pyridazine-3-carboxamide (62.0 mg, 78.9%). MS (ESI) calcd for $C_{24}H_{21}F_3N_6O_2$: 482.1. found: 483.01 [M+H].

This general coupling procedure could be used to prepare a variety of 6-(2-trifluoromethyl)phenyl), 6-(2-trifluoromethoxyphenyl), 6-(3-trifluoromethylphenyl), 6-(3-chlorophenyl), 6-(3-fluorophenyl), 6-(2,5-difluorophenyl), 6-(2,4-difluorophenyl), 6-(3,4-difluorophenyl), 6-(3,5-difluorophenyl), 6-(2,3-difluorophenyl), 6-(2-chloro-3-fluorophenyl), 6-(2-(methylsulfonyl)phenyl and 6-(2-cyanophenyl)imidazo[1,2-b]pyridazine-3-carboxamides by substituting the appropriate amine moiety for 6-(morpholinomethyl)pyridin-2-amine.

Example 3. Preparation of N-(6-(2-oxa-6-azaspiro[3.3]heptan-6-yl)pyridin-2-yl)-6-(2-(trifluoromethyl)phenyl)imidazo[1,2-b]pyridazine-3-carboxamide

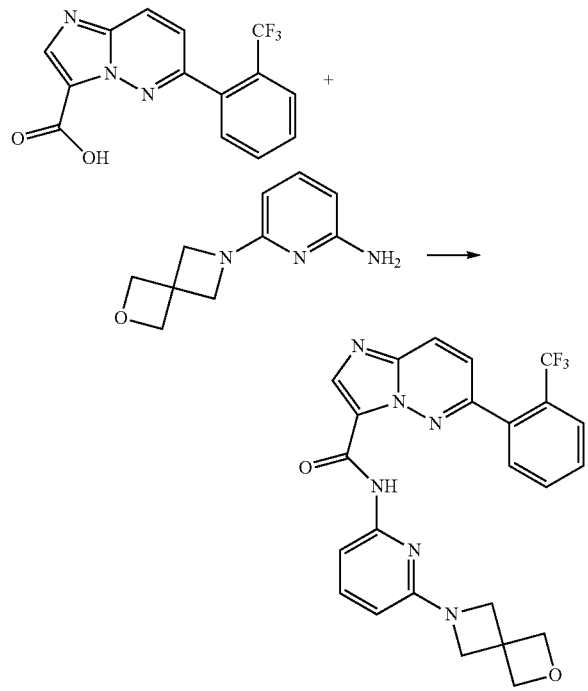

To a mixture of 6-(2-(trifluoromethyl)phenyl)imidazo[1,2-b]pyridazine-3-carboxylic acid (100.0 mg, 0.33 mmol) and HATU (245.0 mg, 0.64 mmol) DMF (2 mL) was added and stirred for 5 min. To this suspension, 6-(2-oxa-6-azaspiro[3.3]heptan-6-yl)pyridin-2-amine (93.0 mg, 0.49 mmol) and DIEA (0.12 mL) were added and the reaction was stirred at 60° C. for 18 h. After cooling to room temp, MeOH (0.3 mL) was added. The crude product was purified by reverse phase preparative HPLC to afford 53.0 mg (33%) of N-(6-(2-oxa-6-azaspiro[3.3]heptan-6-yl)pyridin-2-yl)-6-(2 (trifluoromethyl)phenyl)imidazo[1,2-b]pyridazine-3-carboxamide. MS (ESI) calcd for $C_{24}H_{19}F_3N_6O_2$: 480.1. found: 481.2 [M+H].

This general coupling procedure could also be used to prepare N-(2-(1-oxa-6-azaspiro[3.3]heptan-6-yl)pyrimidin-4-yl)-6-(2-(trifluoromethyl)phenyl) imidazo[1,2-b]pyridazine-3-carboxamide.

Example 4. Preparation of N-(2-(3-hydroxy-2-(hydroxymethyl)-2-methylpropoxy)pyrimidin-4-yl)-6-(2-(trifluoromethyl)phenyl)imidazo[1,2-b]pyridazine-3-carboxamide (Compound 278)

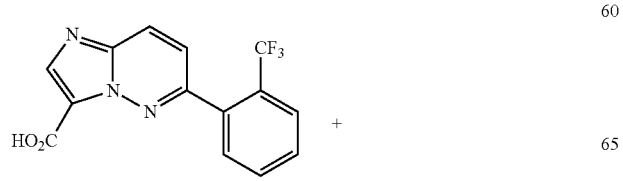

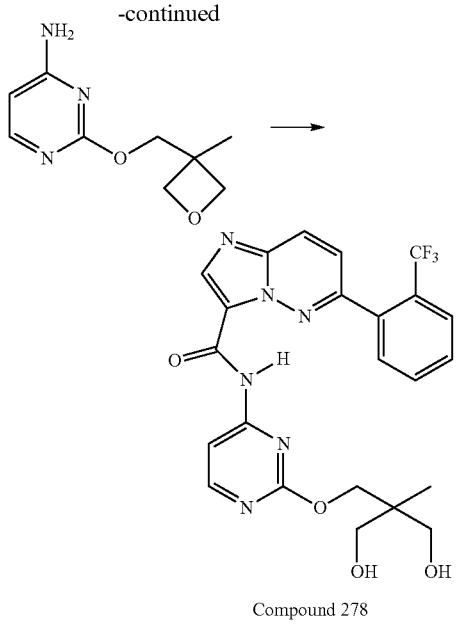

Compound 278

N-(2-(3-hydroxy-2-(hydroxymethyl)-2-methylpropoxy)pyrimidin-4-yl)-6-(2-(trifluoromethyl)phenyl)imidazo[1,2-b]pyridazine-3-carboxamide was prepared using the general coupling method above. The ring opening of the oxetane in the final product (N-(2-(3-hydroxy-2-(hydroxymethyl)-2-methylpropoxy)pyrimidin-4-yl)-6-(2-(trifluoromethyl)phenyl)imidazo[1,2-b]pyridazine-3-carboxamide) occurred during preparative HPLC purification. MS (ESI) calcd for $C_{23}H_{21}F_3N_6O_4$: 502.1.

Example 5. Preparation of N-(6-((1,3-dihydroxypropan-2-yl)oxy)pyridin-2-yl)-6-(2-(trifluoromethyl)phenyl)imidazo[1,2-b]pyridazine-3-carboxamide (Compound 423)

Step 1. Synthesis of N-(6-((2-phenyl-1,3-dioxan-5-yl)oxy)pyridin-2-yl)-6-(2-(trifluoromethyl)phenyl)imidazo[1,2-b]pyridazine-3-carboxamide N-(6-((2-phenyl-1,3-dioxan-5-yl)oxy)pyridin-2-yl)-6-(2-(trifluoromethyl)phenyl)imidazo[1,2-b]pyridazine-3-carboxamide was obtained (40.0 mg, 22%) from HATU mediated coupling of 6-chloroimidazo[1,2-b]pyridazine-3-carboxylate (100.0 mg, 0.32 mmol) and 6-((2-phenyl-1,3-dioxan-5-yl)oxy)pyridin-2-amine following the same procedure as described for the preparation of Compound 19. MS (ESI) calcd for $C_{28}H_{21}F_3N_5O_4$: 561.1.

Step 2. Synthesis of N-(6-((1,3-dihydroxypropan-2-yl)oxy)pyridin-2-yl)-6-(2-(trifluoromethyl)phenyl)imidazo[1,2-b]pyridazine-3-carboxamide

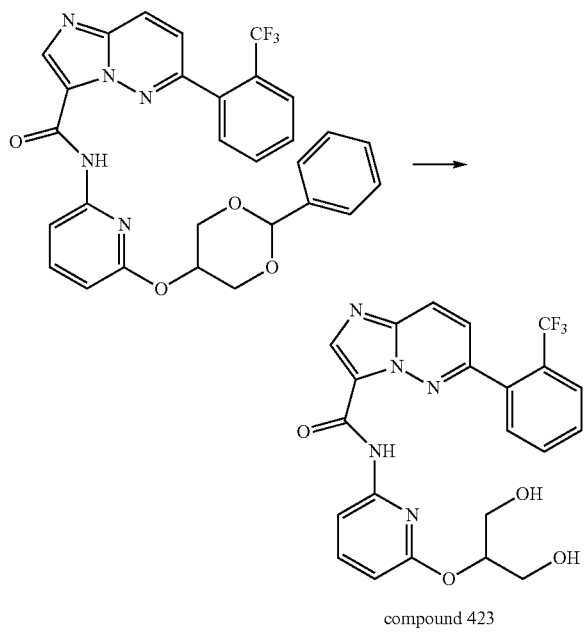

compound 423

N-(6-((2-phenyl-1,3-dioxan-5-yl)oxy)pyridin-2-yl)-6-(2-(trifluoromethyl)phenyl)imidazo[1,2-b]pyridazine-3-carboxamide (40.0 mg, 0.07 mmol) was taken up in EtOH:3N HCl (3:1, 7 mL) and heated to 80° C. for 2 h. After cooling to room temp and evaporating the solvent, the crude product was purified by preparative HPLC to afford N-(6-((1,3-dihydroxypropan-2-yl)oxy)pyridin-2-yl)-6-(2-(trifluoromethyl)phenyl)imidazo[1,2-b]pyridazine-3-carboxamide (12.0 mg, 35%). MS (ESI) calcd for $C_{22}H_{18}F_3N_5O_4$: 473.1. found 474.2.

Example 6. Preparation of N-(6-(2,3-dihydroxypropoxy)pyridin-2-yl)-6-(2-(trifluoromethyl)phenyl)imidazo[1,2-b]pyridazine-3-carboxamide (Compound 212)

Step 1. Preparation of 6-((2,2-dimethyl-1,3-dioxolan-4-yl)methoxy)pyridin-2-amine

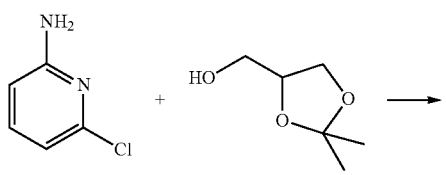

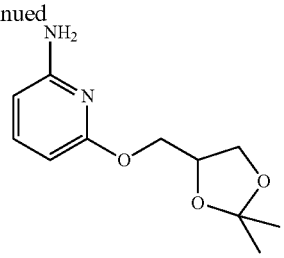

NaH (2.3 g, 60% in mineral oil, 57.5 mmol) was added the mixture of 6-chloropyridin-2-amine (2 g, 15.6 mmol) and solketal (6.0 g, 45.4 mmol) in Dioxane (25 mL) solution at 0° C. The temp was elevated to 120° C. for overnight, filtered the solid and concentrated, purified by column chromatography to give 6-((2,2-dimethyl-1,3-dioxolan-4-yl)methoxy)pyridin-2-amine (1.3 g, yield: 37.4%). MS (ESI) calcd for $C_{11}H_{16}N_2O_3$: 224.12.

This general coupling procedure could be used to prepare 6-((2,2-dimethyl-1,3-dioxolan-4-yl)methoxy)pyrazin-2-amine, 2-((2,2-dimethyl-1,3-dioxolan-4-yl)methoxy)pyrimidin-4-amine, 4-((2,2-dimethyl-1,3-dioxolan-4-yl)methoxy)pyrimidin-2-amine, 6-((2,2-dimethyl-1,3-dioxolan-4-yl)methoxy)pyridin-3-amine, 5-((2,2-dimethyl-1,3-dioxolan-4-yl)methoxy)pyrazin-2-amine, 2-((2,2-dimethyl-1,3-dioxolan-4-yl)methoxy)pyridin-4-amine, 4-((2,2-dimethyl-1,3-dioxolan-4-yl)methoxy)-6-methylpyrimidin-2-amine and 2-((2,2-dimethyl-1,3-dioxolan-4-yl)methoxy)-6-methylpyridin-4-amine moieties.

Step 2. Preparation of N-(6-(2,3-dihydroxypropoxy)pyridin-2-yl)-6-(2-(trifluoromethyl)phenyl)imidazo[1,2-b]pyridazine-3-carboxamide

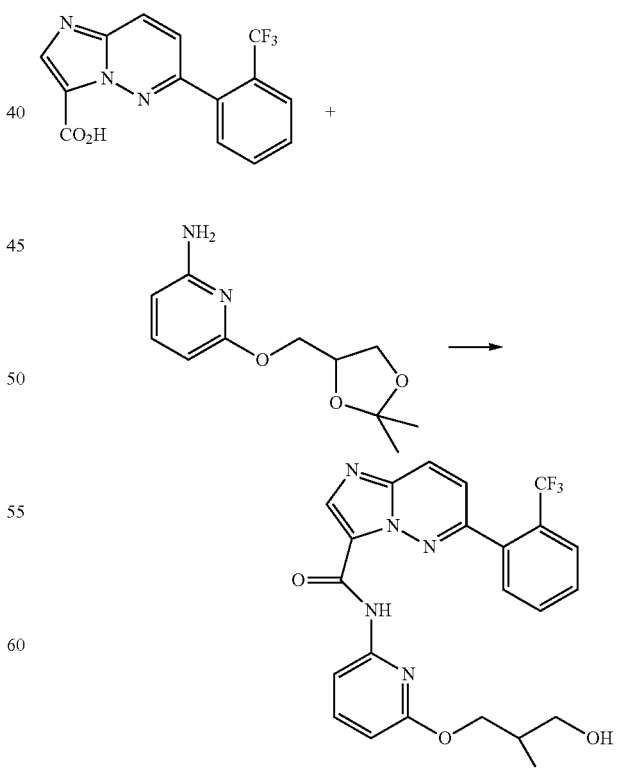

Compound 212

6-((2,2-dimethyl-1,3-dioxolan-4-yl)methoxy)pyridin-2-amine (110.0 mg, 0.49 mmol) was taken up in DMF (1 mL) along with 6-(2-(trifluoromethyl)phenyl)imidazo[1,2-b]pyridazine-3-carboxylic acid (100.0 mg, 0.33 mmol), HATU (247.0 mg, 0.65 mmol) and DIEA (84.0 mg, 0.65 mmol). The resulting reaction mixture was stirred at 65° C. for 24 h. Water (25 mL) was added and the solid was filtered, purified by flash chromatography to afford the intermediate N-(6-((2,2-dimethyl-1,3-dioxolan-4-yl)methoxy)pyridin-2-yl)-6-(2-(trifluoromethyl)phenyl)imidazo[1,2-b]pyridazine-3-carboxamide as a brown solid (80.0 mg). The solid was taken up in MeOH (10 mL), conc. HCl (0.1 mL) was added, and the mixture was stirred for 1 h at room temp. The solvents were evaporated to give a solid which was stirred with saturated $Na_2CO_3$ to neutralize the acid. The resulting solid was filtered to afford N-(6-(2,3-dihydroxypropoxy)pyridin-2-yl)-6-(2-(trifluoromethyl)phenyl)imidazo[1,2-b]pyridazine-3-carboxamide (101.0 mg, 65.6%). MS (ESI) calcd for $C_{22}H_{18}F_3N_5O_4$: 473.1. found: 473.8 [M+H].

This general coupling procedure could be used to prepare a variety of N-(2-(2,3-dihydroxypropoxy)pyrimidin-4-yl), N-(6-(2,3-dihydroxypropoxy)pyrazin-2-yl), N-(4-(2,3-dihydroxypropoxy)pyrimidin-2-yl), N-(6-(2,3-dihydroxypropoxy)pyridin-3-yl), N-(5-(2,3-dihydroxypropoxy)pyrazin-2-yl)-6-(2-(substituted)phenyl)imidazo[1,2-b]pyridazine-3-carboxamides, 6-(2-substituted)-N-(2-(2,3-dihydroxypropoxy)pyridin-4-yl)imidazo[1,2-b]pyridazine-3-carboxamides, 6-(2-substituted)-N-(4-(2,3-dihydroxypropoxy)-6-methylpyrimidin-2-yl)imidazo[1,2-b]pyridazine-3-carboxamides and N-(2-(2,3-dihydroxypropoxy)-6-methylpyridin-4-yl)-6-(2-substituted)phenyl) imidazo[1,2-b]pyridazine-3-carboxamides by starting from the appropriate 6-(2-(substituted)phenyl)imidazo[1,2-b]pyridazine-3-carboxylic acid.

Example 7. Preparation of N-(4-(2,3-dihydroxypropoxy)pyridin-2-yl)-6-(2-(trifluoromethyl)phenyl) imidazo[1,2-b]pyridazine-3-carboxamide (Compound 75)

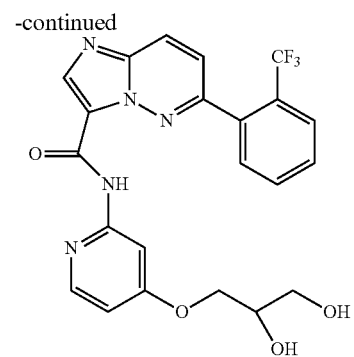

Compound 75

A mixture of 6-(2-(trifluoromethyl)phenyl)imidazo[1,2-b]pyridazine-3-carboxylic acid (154.0 mg, 0.5 mmol) and carboxydiimidazole (162.0 mg, 1.0 mmol) in dioxane (4 mL) was heated to 70° C. for 1 h. 4-((2,2-dimethyl-1,3-dioxolan-4-yl)methoxy)pyridin-2-amine (337.0 mg, 1.5 mmol) was then added and heating was continued at 100° C. for 17 h. After cooling to room temp, the solvent was evaporated and the residue was taken up in EtOH: 3 N HCl (3:1). The mixture was stirred at room temp for 1 h, then refluxed for 1 h. After evaporating the solvent and purification by preparative HPLC N-(4-(2,3-dihydroxypropoxy)pyridin-2-yl)-6-(2-(trifluoromethyl)phenyl)imidazo[1,2-b]pyridazine-3-carboxamide was obtained (118.0 mg, 50%). MS (ESI) calcd for $C_{22}H_{18}F_3N_5O_4$: 473.1. found: 473.8 [M+H].

This general procedure could also be used to prepare N-(4-(2,3-dihydroxypropoxy)-6-methylpyrimidin-2-yl)-6-(2-(trifluoromethyl)phenyl)imidazo[1,2-b]pyridazine-3-carboxamide and N-(2-(2,3-dihydroxypropoxy)pyridin-4-yl)-6-(2-(trifluoromethyl)phenyl) imidazo[1,2-b]pyridazine-3-carboxamide.

Example 8. Preparation of (S)-N-(6-(2,3-dihydroxypropoxy)pyrazin-2-yl)-6-(2-(trifluoromethyl)phenyl) imidazo[1,2-b]pyridazine-3-carboxamide (Compound 556)

Step 1. Synthesis of (R)-N-(6-((2,2-dimethyl-1,3-dioxolan-4-yl)methoxy)pyrazin-2-yl)-6-(2-(trifluoromethyl)phenyl)imidazo[1,2-b]pyridazine-3-carboxamide

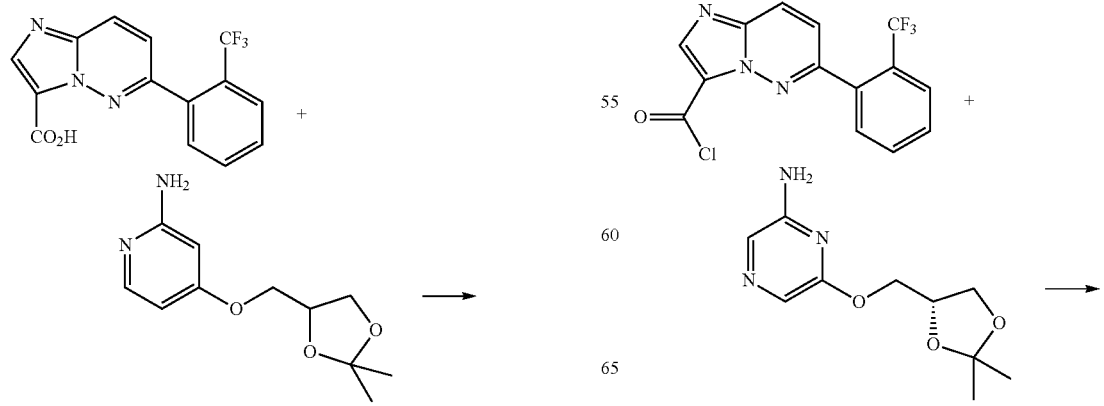

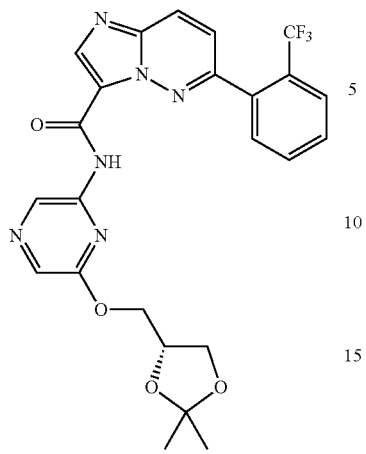

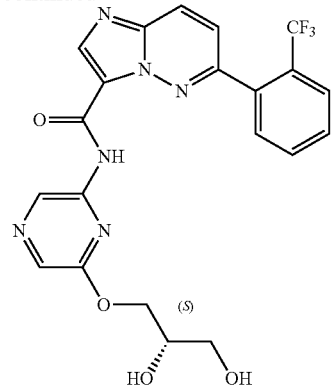

Compound 556

To a solution of (R)-6-((2,2-dimethyl-1,3-dioxolan-4-yl)methoxy)pyrazin-2-amine (200.0 mg, 0.89 mmol) in pyridine (10 mL), 6-(2-(trifluoromethyl)phenyl)imidazo[1,2-b]pyridazine-3-carbonyl chloride (320.0 mg, 0.98 mmol) was added and the reaction was heated to 60° C. for 10 min. After cooling to room temp, H$_2$O (50 mL) was added and the mixture was stirred. The white solid was collected by filtration, washed and dried to afford (R)-N-(6-((2,2-dimethyl-1,3-dioxolan-4-yl)methoxy)pyrazin-2-yl)-6-(2-(trifluoromethyl)phenyl)imidazo[1,2-b]pyridazine-3-carboxamide (250.0 mg, yield 54.6%). MS (ESI) calcd for C$_{24}$H$_{21}$F$_3$N$_6$O$_4$: 514.4.

To a solution of (R)-N-(6-((2,2-dimethyl-1,3-dioxolan-4-yl)methoxy)pyrazin-2-yl)-6-(2-(trifluoromethyl)phenyl)imidazo[1,2-b]pyridazine-3-carboxamide (250.0 mg, 0.49 mmol) in MeOH (10 mL) was added conc. HCl (1 mL) at room temp. After stirring for 1 h, 50 mL of cold aqueous NaHCO$_3$ solution was added. White solid separated after stirring and was collected by filtration, washed with water and dried to afford (S)-N-(6-(2,3-dihydroxypropoxy)pyrazin-2-yl)-6-(2-(trifluoromethyl)phenyl)imidazo[1,2-b]pyridazine-3-carboxamide (200.0 mg, yield 87%). MS (ESI) calcd for C$_{21}$H$_{17}$F$_3$N$_6$O$_4$: 474.1.

This general procedure could be used to prepare (R)-N-(6-(2,3-dihydroxypropoxy)pyrazin-2-yl)-6-(2-(trifluoromethyl)phenyl)imidazo[1,2-b]pyridazine-3-carboxamide, (R)-N-(6-(2,3-dihydroxypropoxy)pyridin-2-yl)-6-(2-(trifluoromethyl)phenyl)imidazo[1,2-b]pyridazine-3-carboxamide, (S)-N-(6-(2,3-dihydroxypropoxy)pyridin-2-yl)-6-(2-(trifluoromethyl)phenyl)imidazo[1,2-b]pyridazine-3-carboxamide, (R)-N-(2-(2,3-dihydroxypropoxy)-6-methylpyridin-4-yl)-6-(2-(trifluoromethyl)phenyl)imidazo[1,2-b]pyridazine-3-carboxamide and (S)-N-(2-(2,3-dihydroxypropoxy)-6-methylpyridin-4-yl)-6-(2-(trifluoromethyl)phenyl)imidazo[1,2-b]pyridazine-3-carboxamide.

Example 9. Preparation of 6-(2-(difluoromethyl)phenyl)-N-(thiazol-2-yl)imidazo[1,2-b]pyridazine-3-carboxamide (Compound 33)

Step 1. Synthesis of ethyl 6-(2-formylphenyl)imidazo[1,2-b]pyridazine-3-carboxylate Step 2. Synthesis of (S)-N-(6-(2,3-dihydroxypropoxy)pyrazin-2-yl)-6-(2-(trifluoromethyl)phenyl)imidazo[1,2-b]pyridazine-3-carboxamide

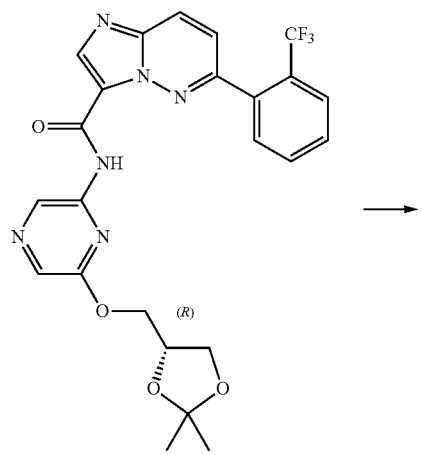

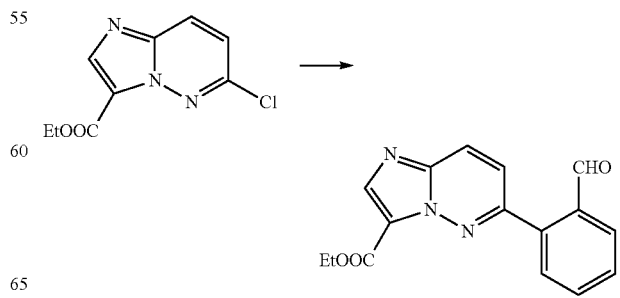

Ethyl 6-chloroimidazo[1,2-b]pyridazine-3-carboxylate (903.0 mg, 4 mmol) was taken up in 5 mL of dioxane/water (4:1) along with 2-formylphenylboronic acid (720.0 mg, 4.8 mmol), Pd(PPh$_3$)$_4$ (231.0 mg, 0.2 mmol) and Na$_2$CO$_3$ (1.02 g, 9.6 mmol). The resulting reaction mixture was stirred at 120° C. for 20 min in a microwave reactor. Upon cooling to room temp, the mixture was diluted with methylene chloride (DCM) (20 mL) and filtered. The filtrate was dried (Na$_2$SO$_4$) and concentrated under reduced pressure. The resulting residue was purified by chromatography to afford 6-(2-formyl-phenyl)-imidazo[1,2-b]pyridazine-3-carboxylic acid ethyl ester (700.0 mg, 59%). MS (ESI) calcd for C$_{18}$H$_{13}$N$_3$O$_3$: 295.10. found: 296 [M+H].

Step 2. Synthesis of ethyl 6-(2-(difluoromethyl)phenyl)imidazo[1,2-b]pyridazine-3-carboxylate

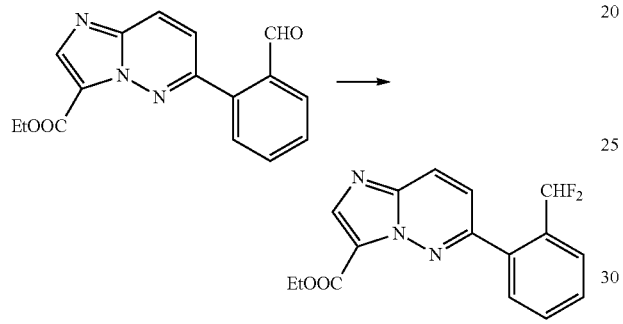

To a solution of 6-(2-formyl-phenyl)-imidazo[1,2-b]pyridazine-3-carboxylic acid ethyl ester (7.40 g, 25 mmol) in CH$_2$Cl$_2$ (160 mL) was added a solution of diethylaminosulfur trifluoride (DAST) (6.05 g, 37.6 mmol) in CH$_2$Cl$_2$ (20 mL) at 0° C. The resulting reaction mixture was stirred under a gentle reflux for 48 h. The mixture was then poured into a saturated aqueous NaHCO$_3$ solution and further extracted with DCM. The combined organic layers were dried (Na$_2$SO$_4$) and concentrated under reduced pressure. Purification by chromatography afforded 6-(2-difluoromethyl-phenyl)-imidazo[1,2-b]pyridazine-3-carboxylic acid ethyl ester (1.0 g, 13%). MS (ESI) calcd for C$_{16}$H$_{13}$F$_2$N$_3$O$_2$: 317.10. found: 318 [M+H].

Step 3. 6-(2-(difluoromethyl)phenyl)imidazo[1,2-b]pyridazine-3-carboxylic acid

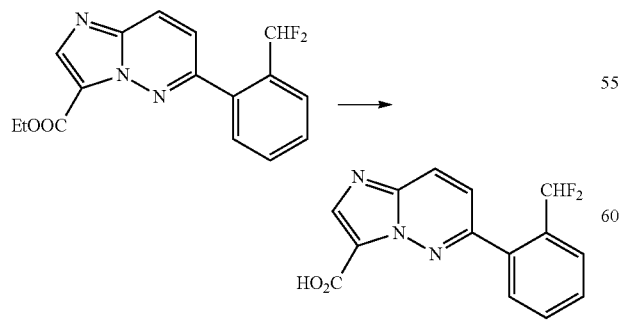

To a solution of 6-(2-difluoromethyl-phenyl)-imidazo[1,2-b]pyridazine-3-carboxylic acid ethyl ester (1.17 g, 3.69 mmol) in MeOH (50 mL) was added a solution of sodium hydroxide (6.0 N, 15 mL). The resulting reaction mixture was stirred under reflux for 90 min. Upon cooling to room temp, the mixture was acidified to pH=4 and then concentrated under reduced pressure. The resulting residue was purified by chromatography to afford 6-(2-difluoromethyl-phenyl)-imidazo[1,2-b]pyridazine-3-carboxylic acid (970.0 mg, 90%). MS (ESI) calcd for C$_{14}$H$_9$F$_2$N$_3$O$_2$: 289.07. found: 290 [M+H].

Step 4. Synthesis of 6-(2-(difluoromethyl)phenyl)-N-(thiazol-2-yl)imidazo[1,2-b]pyridazine-3-carboxamide

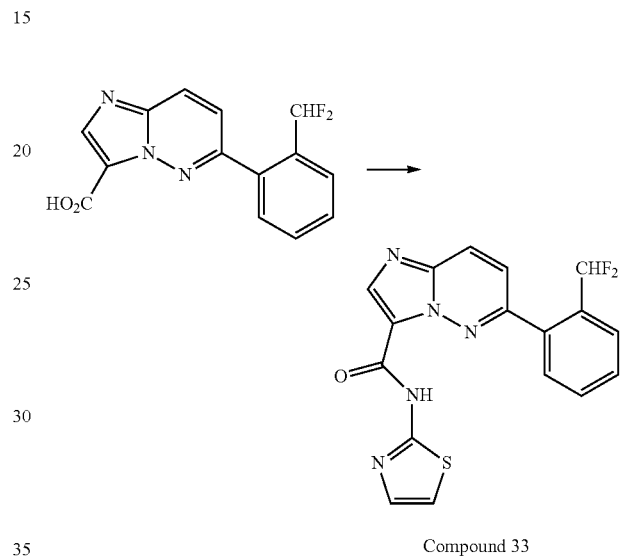

Compound 33

6-(2-Difluoromethyl-phenyl)-imidazo[1,2-b]pyridazine-3-carboxylic acid (0.3 mmol) and thiazol-2-amine (0.36 mmol) were subjected to the same general amide coupling procedure described above to prepare 6-(2-difluoromethyl-phenyl)-imidazo[1,2-b]pyridazine-3-carboxylic acid thiazol-2-ylamide (yield 61.3%). MS (ESI) calcd for C$_{17}$H$_{11}$F$_2$N$_3$OS: 371.07. found: 372 [M+H].

This general coupling procedure could be used to prepare a variety of 6-(2-(difluoromethyl)phenyl) imidazo[1,2-b]pyridazine-3-carboxamides by substituting the appropriate amine moiety for thiazol-2-amine.

Example 10. Preparation of 6-(3,5-dimethylisoxazol-4-yl)-N-(2-(pyrrolidin-1-yl)pyridin-4-yl)imidazo[1,2-b]pyridazine-3-carboxamide (Compound 54)

Step 1. Synthesis of 6-(3,5-dimethylisoxazol-4-yl)imidazo[1,2-b]pyridazine-3-carboxylic acid

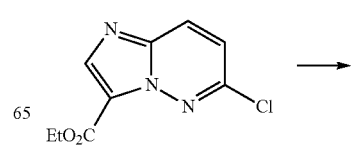

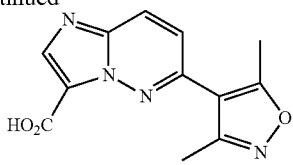

To a solution of ethyl 6-chloroimidazo[1,2-b]pyridazine-3-carboxylate (500.0 mg, 2.21 mmol) in dioxane:EtOH:H₂O (4:1:3, 9 mL), (3,5-dimethylisoxazol-4-yl)boronic acid (404 mg, 2.87 mmol), Cs₂CO₃ (1.45 g, 4.42 mmol) and Pd(PPh₃)₄ (127.0 mg, 0.11 mmol) were added and the reaction was refluxed for 15 h. After cooling to room temp, the solvents were evaporated and the solid was taken up in THF (6 mL). A solution of LiOH (106.0 mg, 4.42 mmol) in H₂O (3 mL) was added, the mixture was stirred for 15 h. The solvent was removed under reduced pressure and the residue was acidified to pH 4 with 3N HCl. The volatiles were evaporated under reduced pressure and the solid was triturated with MeOH:H₂O (1:1). Upon filtration 6-(3,5-dimethylisoxazol-4-yl)imidazo[1,2-b]pyridazine-3-carboxylic acid was obtained (331.0 mg, 58%). MS (ESI) calcd for C₁₂H₁₀N₄O₃: 258.1. found: 258.9 [M+H].

This general coupling procedure followed by ester hydrolysis could be used to prepare 6-(1-methyl-1H-pyrazol-4-yl), 6-(2-methylpyridin-3-yl), 6-(5-(difluoromethyl)pyridin-3-yl), 6-(2-methylpyridin-3-yl), 6-(2,4-dimethylthiazole), 6-(2,3,4-trifluoromethyl phenyl), 6-(2-fluorophenyl), 6-(2-chlorophenyl) 6-(2-fluoro-3-chlorophenyl) and 6-(2-chloro-6-fluorophenyl) imidazo[1,2-b]pyridazine-3-carboxylic acids by substituting the appropriate boronic acid or boronic ester moiety for (3,5-dimethylisoxazol-4-yl)boronic acid.

Step 2. Synthesis of 6-(3,5-dimethylisoxazol-4-yl)-N-(2-(pyrrolidin-1-yl)pyridin-4-yl)imidazo[1,2-b]pyridazine-3-carboxamide

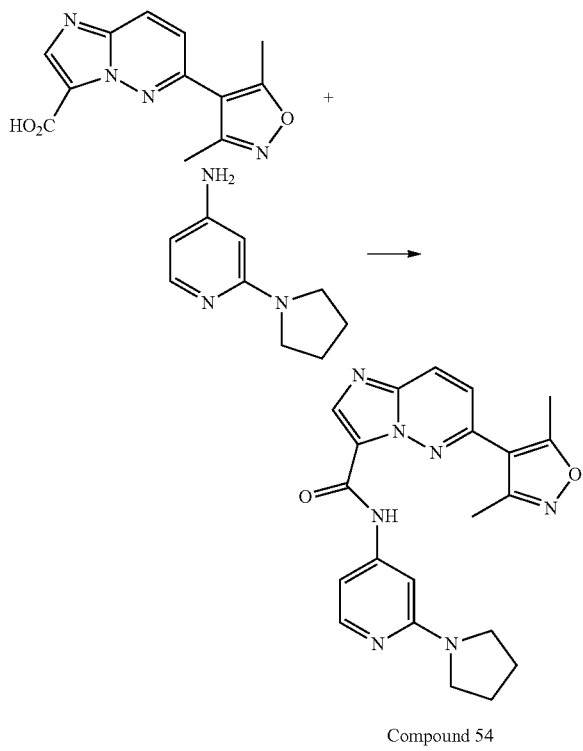

Compound 54

A solution of 6-(3,5-dimethylisoxazol-4-yl)imidazo[1,2-b]pyridazine-3-carboxylic acid (75.0 mg, 0.29 mmol), HATU (228.0 mg, 0.6 mmol), 2-(pyrrolidin-1-yl)pyridin-4-amine (72.0 mg, 0.44 mmol) and DIEA (0.11 mL) in DMF (2 mL) was stirred at room temp for 15 h. H₂O was added until solid precipitated out, which was collected by filtration, washed with H₂O and dried to afford 6-(3,5-dimethylisoxazol-4-yl)-N-(2-(pyrrolidin-1-yl)pyridin-4-yl)imidazo[1,2-b]pyridazine-3-carboxamide (44.0 mg, 38%). MS (ESI) calcd for C₂₁H₂₁N₇O₂: 403.1. found: 404 [M+H].

This general coupling procedure could be used to prepare 6-(3,5-dimethylisoxazol-4-yl), 6-(1-methyl-1H-pyrazol-4-yl), 6-(2-methylpyridin-3-yl), 6-(5-(difluoromethyl)pyridin-3-yl), 6-(2,4-dimethylthiazole), 6-(2,3,4-trifluoromethyl phenyl), 6-(2-fluorophenyl), 6-(2-chlorophenyl), 6-(2-fluoro-3-chlorophenyl) and 6-(2-chloro-6-fluorophenyl)imidazo[1,2-b]pyridazine-3-carboxamides by substituting the appropriate amine moiety for 2-(pyrrolidin-1-yl)pyridin-4-amine.

Example 11. Preparation of 6-(thiazol-2-yl)imidazo[1,2-b]pyridazine-3-carboxylic acid

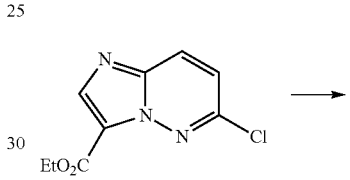

To a solution of ethyl 6-chloroimidazo[1,2-b]pyridazine-3-carboxylate (250.0 mg, 1.1 mmol) and 2-(tributylstannyl)thiazole (619.0 mg, 1.65 mmol) in dioxane (5 mL), Pd(PPh₃)₄ (150.0 mg, 0.17 mmol) was added and the reaction was heated to 80° C. for 17 h. After cooling to room temp, LiOH (53.0 mg, 2.3 mmol) in THF:H₂O (3:1) was added and stirred vigorously for 4 h. The solvents were evaporated and 6-(thiazol-2-yl)imidazo[1,2-b]pyridazine-3-carboxylic acid was precipitated out from MeOH:H₂O (164.0 mg, yield 66%). MS (ESI) calcd for C₁₀H₆N₄O₂S: 246.02.

The general amide coupling procedure described above for 6-(3,5-dimethylisoxazol-4-yl)-N-(2-(pyrrolidin-1-yl)pyridin-4-yl)imidazo[1,2-b]pyridazine-3-carboxamide could be used to prepare N-(6-morpholinopyridin-2-yl)-6-(thiazol-2-yl)imidazo[1,2-b]pyridazine-3-carboxamide (Compound 64).

Example 12. Preparation of 6-(2-(2,3-dihydroxy-propoxy)phenyl)-N-(6-morpholinopyridin-2-yl)imidazo[1,2-b]pyridazine-3-carboxamide (Compound 367)

Step 1. Synthesis of ethyl 6-(2-hydroxyphenyl)imidazo[1,2-b]pyridazine-3-carboxylate

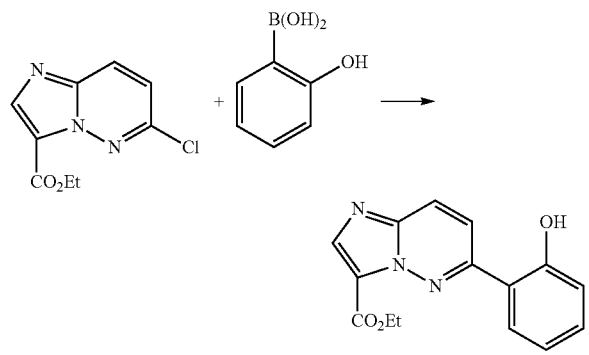

A mixture of ethyl 6-chloroimidazo[1,2-b]pyridazine-3-carboxylate (200.0 mg, 0.89 mmol), 2-hydroxyphenylboronic acid (183.0 mg, 1.33 mmol) $Cs_2CO_3$ (342.0 mg, 1.77 mmol), and $Pd(PPh_3)_4$ (102.0 mg, 0.09 mmol) was taken up in dioxane (4 mL) and refluxed for 2 h. After cooling to room temp, the reaction was diluted with EtOAc and extracted with $H_2O$. The organic layer was dried over $Na_2SO_4$, filtered and evaporated to dryness under reduced pressure. The crude material was purified by vacuum distillation to afford ethyl 6-(2-hydroxyphenyl)imidazo[1,2-b]pyridazine-3-carboxylate (120.0 mg, 47.8%). MS (ESI) calcd for $C_{14}H_{13}N_3O_3$: 283.1.

Step 2. Synthesis of ethyl 6-(2-((2,2-dimethyl-1,3-dioxolan-4-yl)methoxy)phenyl)imidazo[1,2-b]pyridazine-3-carboxylate

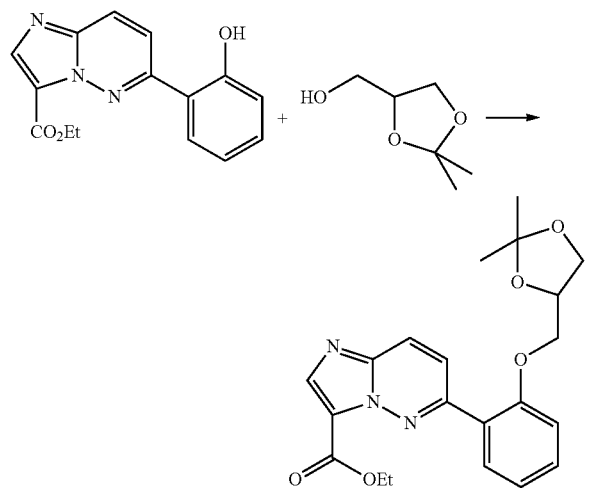

To a solution of ethyl 6-(2-hydroxyphenyl)imidazo[1,2-b]pyridazine-3-carboxylate (50.0 mg, 0.18 mmol), and triphenylphosphine (55.6 mg, 0.21 mmol), (2,2-dimethyl-1,3-dioxolan-4-yl)methanol (25.7 mg, 0.19 mmol) and DIAD (27.7 mg, 0.21 mmol) were added. The mixture was stirred in THF (2 mL) at 60° C. for 2 h. After cooling to room temp, the crude material was purified by column chromatography to give ethyl 6-(2-((2,2-dimethyl-1,3-dioxolan-4-yl)methoxy)phenyl)imidazo[1,2-b]pyridazine-3-carboxylate. MS (ESI) calcd for $C_{21}H_{23}N_3O_5$: 397.2.

Step 3. Synthesis of 6-(2-((2,2-dimethyl-1,3-dioxolan-4-yl)methoxy)phenyl)imidazo[1,2-b]pyridazine-3-carboxylic acid

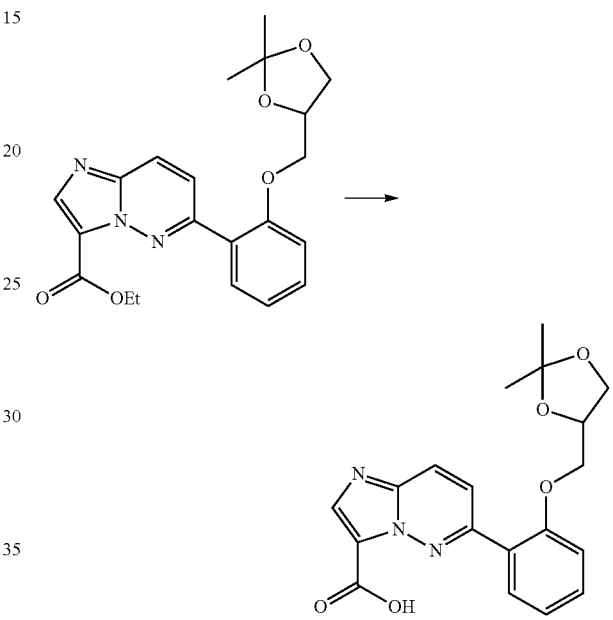

Ethyl 6-(2-((2,2-dimethyl-1,3-dioxolan-4-yl)methoxy)phenyl)imidazo[1,2-b]pyridazine-3-carboxylate (2.0 g, 5.03 mmol) was hydrolyzed to 6-(2-((2,2-dimethyl-1,3-dioxolan-4-yl)methoxy)phenyl)imidazo[1,2-b]pyridazine-3-carboxylic acid following the general procedure described above (1.3 g, 69.9%). MS (ESI) calcd for $C_{19}H_{19}N_3O_5$: 369.37.

Step 4. Synthesis of 6-(2-((2,2-dimethyl-1,3-dioxolan-4-yl)methoxy)phenyl)-N-(6-morpholinopyridin-2-yl)imidazo[1,2-b]pyridazine-3-carboxamide

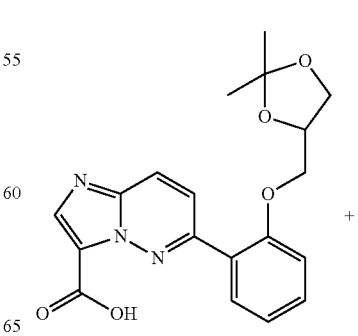

83

-continued

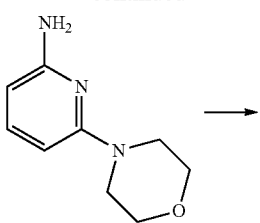

84

Step 5. Synthesis of 6-(2-(2,3-dihydroxypropoxy)phenyl)-N-(6-morpholinopyridin-2-yl)imidazo[1,2-b]pyridazine-3-carboxamide Compound 367

6-(2-((2,2-dimethyl-1,3-dioxolan-4-yl)methoxy)phenyl)imidazo[1,2-b]pyridazine-3-carboxylic acid (80.0 mg, 0.22 mmol) and 6-morpholinopyridin-2-amine were coupled using the HATU mediated general amide coupling procedure described above for preparation of Compound 19 to afford 6-(2-((2,2-dimethyl-1,3-dioxolan-4-yl)methoxy)phenyl)-N-(6-morpholinopyridin-2-yl)imidazo[1,2-b]pyridazine-3-carboxamide (50.0 mg, 43%). MS (ESI) calcd for $C_{28}H_{30}N_6O_5$: 530.2.

This general procedure could be used to prepare (S)-6-(2-((2,2-dimethyl-1,3-dioxolan-4-yl)methoxy)phenyl), (R)-6-(2-((2,2-dimethyl-1,3-dioxolan-4-yl)methoxy)phenyl), 6-(3-((2,2-dimethyl-1,3-dioxolan-4-yl)methoxy)phenyl) and 6-(2-(2,3-dihydroxypropoxy)phenyl)N-(substituted) imidazo[1,2-b]pyridazine-3-carboxylic acids by substituting the appropriate boronic acid for 2-hydroxyphenylboronic acid in step 1, and substituting the appropriate alcohol for (2,2-dimethyl-1,3-dioxolan-4-yl)methanol in step 2.

6-(2-((2,2-dimethyl-1,3-dioxolan-4-yl)methoxy)phenyl)-N-(6-morpholinopyridin-2-yl)imidazo[1,2-b]pyridazine-3-carboxamide (50.0 mg, 0.09 mmol) was dissolved in MeOH (2 mL), HCl (0.5 mL) was added and the reaction stirred at room temp for 15 h. The solvents were evaporated, the mixture was washed taken up in $Na_2CO_3$ solution and the resultant solids were filtered to give 6-(2-(2,3-dihydroxypropoxy)phenyl)-N-(6-morpholinopyridin-2-yl)imidazo[1,2-b]pyridazine-3-carboxamide (40.0 mg, 90%). MS (ESI) calcd for $C_{25}H_{26}N_6O_5$: 490.2. found 491.1 [M+H].

This general procedure could be used to prepare a variety of 6-(2-(2,3-dihydroxypropoxy)phenyl)-N-(substituted), 6-(3-(2,3-dihydroxypropoxy)phenyl)-N-(substituted) and 6-(2-(2,3-dihydroxypropoxy)phenyl)-N-(substituted) imidazo[1,2-b]pyridazine-3-carboxamides.

Example 13. Preparation of (S)-6-(3-fluoropyrrolidin-1-yl)-N-(6-morpholinopyridin-2-yl)imidazo[1,2-b]pyridazine-3-carboxamide (Compound 487)

Step 1. Synthesis of (S)-ethyl 6-(3-fluoropyrrolidin-1-yl)imidazo[1,2-b]pyridazine-3-carboxylate

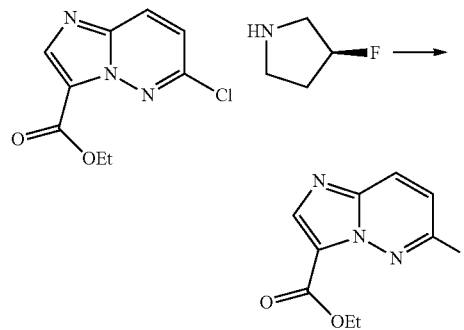

A mixture of ethyl 6-chloroimidazo[1,2-b]pyridazine-3-carboxylate (500.0 mg, 2.22 mmol), (S)-3-fluoropyrrolidine hydrochloride (557.0 mg, 4.43 mmol), and $K_2CO_3$ (1.53 g, 11.08 mmol) in DMSO (50 mL) was heated at 120° C. for 12 h. The mixture was portioned between $H_2O$ and EtOAc and the organic layer was separated and concentrated. The crude residue was purified by flash chromatography to give (S)-ethyl 6-(3-fluoropyrrolidin-1-yl)imidazo[1,2-b]pyridazine-3-carboxylate (300.0 mg, 49% yield). MS (ESI) calcd for $C_{13}H_{15}FN_4O_2$ (m/z): 278.12.

Step 2. Synthesis of (S)-6-(3-fluoropyrrolidin-1-yl)imidazo[1,2-b]pyridazine-3-carboxylic acid

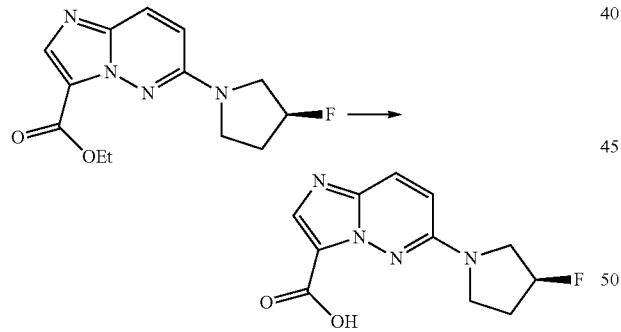

A mixture of (S)-ethyl 6-(3-fluoropyrrolidin-1-yl)imidazo[1,2-b]pyridazine-3-carboxylate (300.0 mg, 1.08 mmol) and NaOH (172.0 mg, 1.08 mmol) in MeOH/$H_2O$ (200 mL, 1:1) was heated at 70° C. for 2 h. The mixture was concentrated and the pH was adjusted to 3 by the addition of 2% aq HCl. The mixture was concentrated to give (S)-6-(3-fluoropyrrolidin-1-yl)imidazo[1,2-b]pyridazine-3-carboxylic acid (240.0 mg, 69% yield). MS (ESI) calcd for $C_{11}H_{11}FN_4O_2$ (m/z): 250.09.

This general coupling procedure followed by ester hydrolysis could be used to prepare a variety of 6-(3-fluoropyrrolidin-1-yl), 6-(3,3-difluoropyrrolidin-1-yl), 6-(3-(trifluoromethyl)piperidin-1-yl), 6-(3-dimethylpyrrolidin-3-amine), difluoroazetidin-1-yl), 6-(4,4-difluoropiperidin-1-yl), 6-(3-methylpyrrolidin-1-yl), 6-(3-hydroxypyrrolidin-1-yl), 6-(3-methoxypyrrolidin-1-yl), 6-(3-fluoropiperidin-1-yl), 6-(morpolin-1-yl), 6-(3-methylmorpolin-1-yl), 6-(3,5-dimethylmorpolin-1-yl) and 6-(N-methylpiperazin-1-yl), 6-(3-fluoropiperidin-1-yl)imidazo[1,2-b]pyridazine-3-carboxylates by substituting the appropriate amine moiety for (S)-3-fluoropyrrolidine hydrochloride in step 1. This general procedure could also be used to prepare (S)-6-(3-fluoropyrrolidin-1-yl)-2-methylimidazo[1,2-b]pyridazine-3-carboxylic acid by substituting ethyl 6-chloro-2-methylimidazo[1,2-b]pyridazine-3-carboxylate for ethyl 6-chloroimidazo[1,2-b]pyridazine-3-carboxylate in step 1.

Step 3. Synthesis of (S)-6-(3-fluoropyrrolidin-1-yl)-N-(6-morpholinopyridin-2-yl)imidazo[1,2-b]pyridazine-3-carboxamide

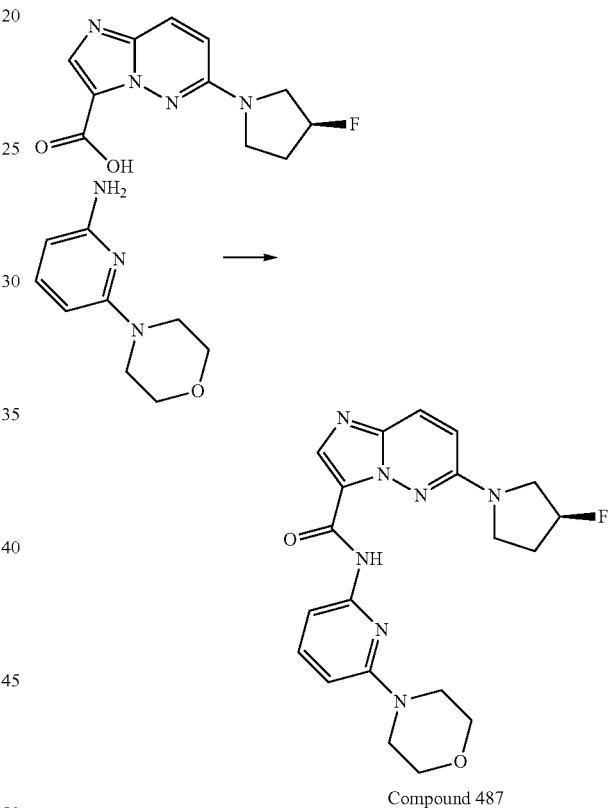

Compound 487

A solution of (S)-6-(3-fluoropyrrolidin-1-yl)imidazo[1,2-b]pyridazine-3-carboxylic acid (100.0 mg, 0.40 mmol), 6-morpholinopyridin-2-amine (107.0 mg, 0.60 mmol), DIPEA (103.0 mg, 0.80 mmol) and HATU (304.0 mg, 0.80 mmol) in DMF (5 mL) was heated at 70° C. for 16 h. $H_2O$ was added and the resulting ppt was purified by flash chromatography to give (S)-6-(3-fluoropyrrolidin-1-yl)-N-(6-morpholinopyridin-2-yl)imidazo[1,2-b]pyridazine-3-carboxamide (45.0 mg, 27% yield). MS (ESI) calcd for $C_{20}H_{22}FN_7O_2$ (m/z): 411.18. found: 412 [M+H].

This general coupling procedure could be used to prepare a variety of 6-(3-fluoropyrrolidin-1-yl), 6-(3,3-difluoropyrrolidin-1-yl), 6-(3-dimethylpyrrolidin-3-amine), 6-(pyrrolidin-1-yl), 6-(3,3-difluoroazetidin-1-yl), 6-(4,4-difluoropiperidin-1-yl), 6-(3-methylpyrrolidin-1-yl), 6-(3-hydroxypyrrolidin-1-yl), 6-(3-methoxypyrrolidin-1-yl), 6-(3-fluoropiperidin-1-yl), 6-(morpolin-1-yl), 6-(3-methyl-morpolin-1-yl), dimethylmorpolin-1-yl), 6-(N-methylpiperazin-1-yl) and 6-(3-fluoropiperidin-1-yl) imidazo[1,2-b]pyridazine-3-carboxamides, as well as 6-(substituted)-2-methylimidazo[1,2-b]pyridazine-3-carboxamides by substituting the appropriate amine moiety for 6-morpholinopyridin-2-amine and substituting the appropriate carboxylic acid moiety for (S)-6-(3-fluoropyrrolidin-1-yl)imidazo[1,2-b]pyridazine-3-carboxylic acid. In cases where the carboxylic acid moiety contains a protected glycerol group, and extra deprotection step is used as in previous examples.

Example 14. Preparation of N-(pyridin-3-yl)-6-(3,3,3-trifluoropropoxy)imidazo[1,2-b]pyridazine-3-carboxamide Step 1. Synthesis of ethyl 6-(3,3,3-trifluoropropoxy)imidazo[1,2-b]pyridazine-3-carboxylate

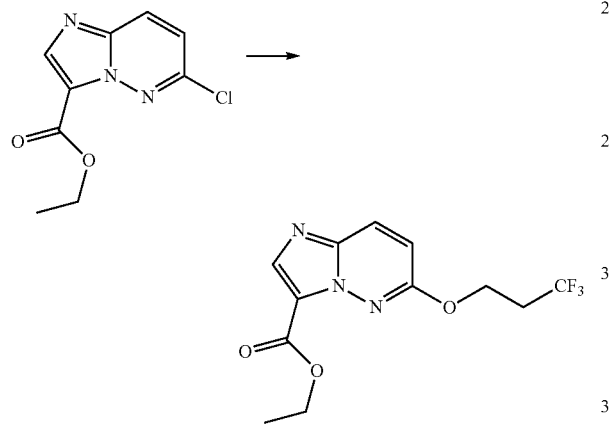

To 3,3,3-trifluoropropan-1-ol (19.9 mmol) in DMSO was added NaH (19.9 mmol). The mixture was allowed to stir at room temp under inert atmosphere for 1 h. Ethyl 6-chloroimidazo[1,2-b]pyridazine-3-carboxylate (3.0 g, 13.3 mmol) was added and the reaction was warmed to 100° C. until coupling was complete. After purification ethyl 6-(3,3,3-trifluoropropoxy)imidazo[1,2-b]pyridazine-3-carboxylate was obtained (1.2 g, 45%). MS (ESI) calcd for $C_{12}H_{12}F_3N_3O_3$: 303.08.

Step 2. Synthesis of 6-(3,3,3-trifluoropropoxy)imidazo[1,2-b]pyridazine-3-carboxylic acid

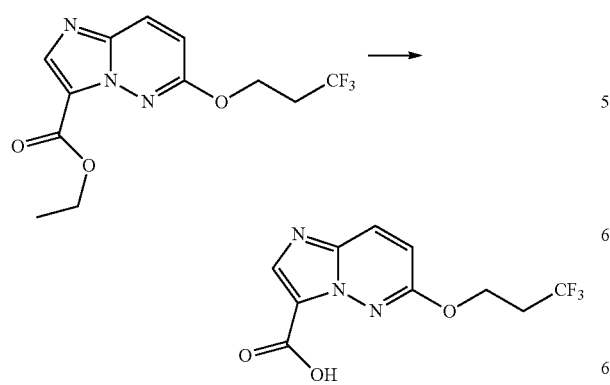

To a solution of ethyl 6-(3,3,3-trifluoropropoxy)imidazo[1,2-b]pyridazine-3-carboxylate (1.2 g, 3.96 mmol) in water/THF (1:1) was added LiOH (474.0 mg, 19.79 mmol). The reaction was allowed to stir at room temp until hydrolysis was complete. After purification 6-(3,3,3-trifluoropropoxy)imidazo[1,2-b]pyridazine-3-carboxylic acid was obtained (0.9 g, 83%). MS (ESI) calcd for $C_{10}H_8F_3N_3O_3$: 275.05.

Step 3. Synthesis of N-(pyridin-3-yl)-6-(3,3,3-trifluoropropoxy)imidazo[1,2-b]pyridazine-3-carboxamide

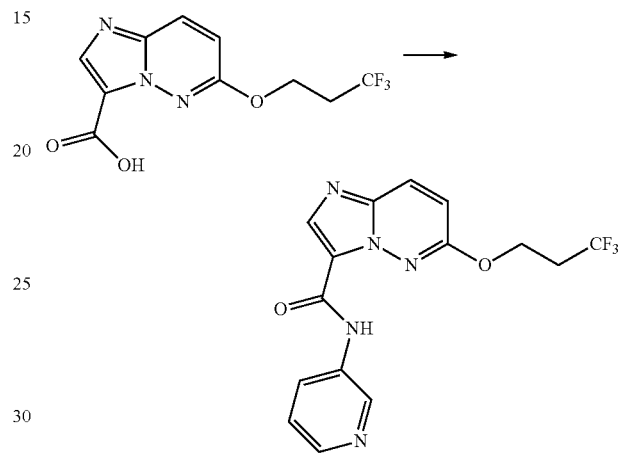

6-(3,3,3-trifluoropropoxy)imidazo[1,2-b]pyridazine-3-carboxylic acid (100.0 mg, 0.36 mmol) was dissolved in DCM. DMF (1 drop) and oxalyl chloride were added and the mixture was allowed to stir 1 h or more. 3-aminopyridine and DIEA were added and after coupling was complete, purification gave N-(pyridin-3-yl)-6-(3,3,3-trifluoropropoxy)imidazo[1,2-b]pyridazine-3-carboxamide (60.0 mg, 47%). MS (ESI) calcd for $C_{15}H_{12}F_3N_5O_2$: 351.09.

This general coupling procedure could be used to prepare a variety of 6-(3,3,3-trifluoropropoxy)imidazo[1,2-b]pyridazine-3-carboxamides by substituting the appropriate amine for 3-aminopyridine.

Example 15. Preparation of 2-methyl-N-(pyridazin-3-yl)-6-(2-(trifluoromethyl)phenyl)imidazo[1,2-b]pyridazine-3-carboxamide (Compound 462)

Step 1. Synthesis of Ethyl 6-chloro-2-methylimidazo[1,2-b]pyridazine-3-carboxylate

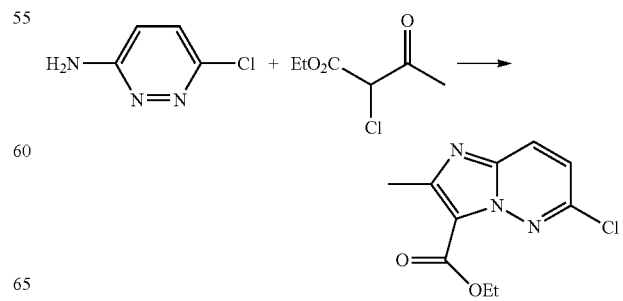

6-chloropyridazin-3-amine (1.0 g, 7.72 mmol), ethyl 2-chloro-3-oxobutanoate (2.53 g, 15.4 mmol) and EtOH (15 mL) was refluxed for 24 h. Upon cooling the mixture to room temp, the reaction was concentrated under reduced pressure. Crude material was adsorbed onto silica gel and purified by column chromatography to give ethyl 6-chloro-2-methylimidazo[1,2-b]pyridazine-3-carboxylate (480.0 mg, 26%). MS (ESI) calcd for $C_{10}H_{10}ClN_3O_2$: 239.05.

Step 2. 2-methyl-6-(2-(trifluoromethyl)phenyl)imidazo[1,2-b]pyridazine-3-carboxylic acid

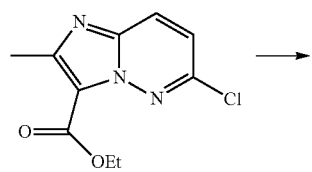

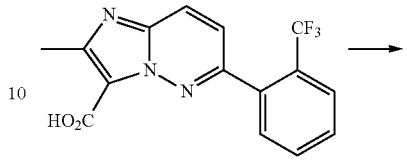

To a mixture of 6-chloro-2-methylimidazo[1,2-b]pyridazine-3-carboxylate (5.26 g, 22 mmol) and 2-(trifluoromethyl)phenyl-boronic acid (6.26 g, 32.5 mmol) in dioxane:EtOH:H$_2$O (8:1:1, 100 mL) was added Pd(PPh$_3$)$_4$ (2.4 g, 2.1 mmol) and Cs$_2$CO$_3$ (13.7 g, 42 mmol). The reaction was refluxed for 2 h. After cooling to room temp, the reaction was diluted with EtOAc (400 mL) and extracted with H$_2$O. The organic layer was dried, concentrated and the crude product was purified by column chromatography (0-10% CH$_2$Cl$_2$+MeOH). This material was taken up in THF, LiOH (1.58 g, 66 mmol) in H$_2$O was added and the mixture was stirred for 17 h. The solvents were evaporated and the residue was acidified with 3N HCl to pH 3. This aqueous suspension was extracted with EtOAc (2×300 mL). Combined organic layers were evaporated to dryness, the residue was purified by column chromatography (0-10% CH$_2$Cl$_2$+MeOH) to afford 2-methyl-6-(2-(trifluoromethyl)phenyl)imidazo[1,2-b]pyridazine-3-carboxylic acid (4.5 g, 64%). MS (ESI) calcd for $C_{15}H_{10}F_3N_3O_2$: 321.1. found 322.1 [M+H].

This general coupling procedure followed by ester hydrolysis could be used to prepare a variety of 2-methyl-6-(3-trifluoromethylphenyl), 2-methyl-6-(3-trifluoromethoxyphenyl), 2-methyl-6-(2-trifluoromethoxyphenyl), 2-methyl-6-(2-difluoromethylphenyl), 2-methyl-6-(2-methylphenyl), 2-methyl-6-(3-methylphenyl), 2-methyl-6-(3-fluorophenyl), 2-methyl-6-(2-fluorophenyl), 2-methyl-6-(2-bromophenyl), and 2-methyl-6-(3-cyanophenyl) imidazo[1,2-b]pyridazine-3-carboxylates by substituting the appropriate boronic acid or boronic ester moiety for 2-(trifluoromethyl)phenylboronic acid.

Step 3. Synthesis of 2-methyl-N-(pyridazin-3-yl)-6-(2-(trifluoromethyl)phenyl)imidazo[1,2-b]pyridazine-3-carboxamide

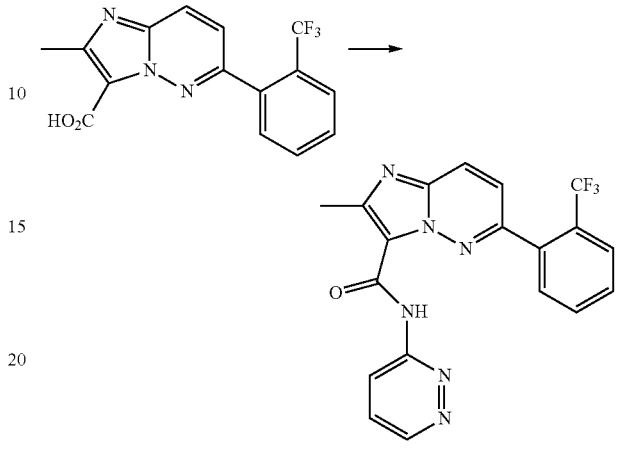

Compound 462

2-methyl-6-(2-(trifluoromethyl)phenyl)imidazo[1,2-b]pyridazine-3-carboxylic acid (1.1 g, 3.43 mmol), and HATU (2.6 g, 6.8 mmol) were taken up in DMF (12 mL). Pyridazine-3-amine (530.0 mg, 5.57 mmol) and DIEA (1.3 mL) were added and the resulting reaction mixture was stirred at 60° C. for overnight. After cooling to room temp, water (12 mL) was added and the solid was separated by filtration. The solid was taken up in EtOAc and washed with saturated NaHCO$_3$ solution. The organic layer was dried, evaporated and the crude product was purified by column chromatography (DCM+MeOH 0-5%) to afford 2-methyl-N-(pyridazin-3-yl)-6-(2-(trifluoromethyl)phenyl)imidazo[1,2-b]pyridazine-3-carboxamide (570.0 mg, 42%). MS (ESI) calcd for $C_{19}H_{13}F_3N_6O$: 398.1. found: 399.1 [M+H].

This general coupling procedure could be used to prepare a variety of 2-methyl-6-(3-trifluoromethylphenyl), 2-methyl-6-(3-trifluoromethoxyphenyl), 2-methyl-6-(2-trifluoromethoxyphenyl), 2-methyl-6-(2-difluoromethylphenyl), 2-methyl-6-(2-methylphenyl), 2-methyl-6-(3-methylphenyl), 2-methyl-6-(3-fluorophenyl), 2-methyl-6-(2-fluorophenyl), 2-methyl-6-(2-chlorophenyl), 2-methyl-6-(2-bromophenyl), and 2-methyl-6-(3-cyanophenyl) imidazo[1,2-b]pyridazine-3-carboxamides by substituting the appropriate amine moiety for pyridazine-3-amine.

Example 16. Preparation of N-(2-methoxypyrimidin-4-yl)-2-methyl-6-(2-(trifluoromethyl)phenyl)imidazo[1,2-b]pyridazine-3-carboxamide (Compound 602)

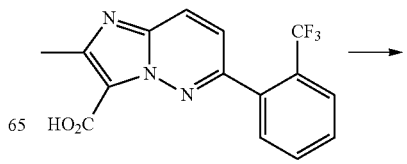

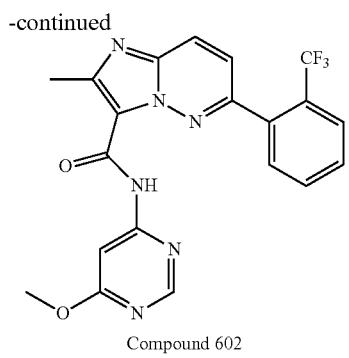
Compound 602

A pressure tube was charged with a solution of CDI (75.5 mg, 0.47 mmol) in dioxane (2 mL). A solution of 2-methyl-6-(2-(trifluoromethyl)phenyl)imidazo[1,2-b]pyridazine-3-carboxylic acid (100.0 mg, 0.31 mmol) in dioxane:DMA (1:1, 2 mL) was added and the mixture was heated to 100° C. for 15 h. 6-methoxypyrimidin-4-amine (117.0 mg, 0.93 mmol) was then added and the heating was continued for 3 d. After cooling to room temp, H$_2$O was added and suspension was extracted with CH$_2$Cl$_2$. The crude material was purified by column chromatography (0-5% CH$_2$Cl$_2$+MeOH) to afford N-(2-methoxypyrimidin-4-yl)-2-methyl-6-(2-(trifluoromethyl)phenyl) imidazo[1,2-b]pyridazine-3-carboxamide (71.0 mg, 53%). MS (ESI) calcd for C$_{20}$H$_{15}$F$_3$N$_6$O$_2$: 428.1. found: 429.1 [M+H].

This general procedure could be used to prepare N-(2-methoxypyrimidin-4-yl)-2-methyl-6-(2-(trifluoromethyl)phenyl)imidazo[1,2-b]pyridazine-3-carboxamide and N-(2-methoxypyrimidin-4-yl)-2-methyl-6-(2-(trifluoromethoxy)phenyl)imidazo[1,2-b]pyridazine-3-carboxamide.

Example 17. Preparation of N-(5-chloropyridin-2-yl)-2-methyl-6-(2-(trifluoromethyl)phenyl)imidazo[1,2-b]pyridazine-3-carboxamide (Compound 433)

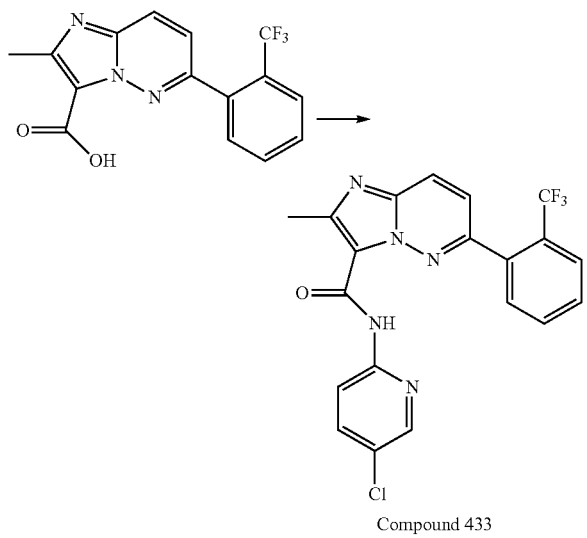
Compound 433

2-methyl-6-(2-(trifluoromethyl)phenyl)imidazo[1,2-b]pyridazine-3-carboxylic acid (97.0 mg, 0.3 mmol) and HATU (228.0 mg, 0.6 mmol) were taken up in ACN (2 mL) in a pressure tube. 5-Chloropyridine-2-amine (57.4 mg, 0.45 mmol) and pyridine (0.1 mL) were added and the reaction was heated to 100° C. for 15 h. After cooling to room temp, H$_2$O was added and the solid was separated by filtration to afford N-(5-chloropyridin-2-yl)-2-methyl-6-(2-(trifluoromethyl)phenyl)imidazo[1,2-b]pyridazine-3-carboxamide (80.0 mg, 43%). MS (ESI) calcd for C$_{20}$H$_{13}$ClF$_3$N$_5$O: 431.08. found: 432.1 [M+H].

This general procedure could be used to prepare N-(1-ethyl-1H-pyrazol-5-yl)-2-methyl-6-(2-(trifluoromethyl)phenyl)imidazo[1,2-b]pyridazine-3-carboxamide, 2-methyl-N-(1-methyl-1H-pyrazol-5-yl)-6-(2-(trifluoromethyl)phenyl)imidazo[1,2-b]pyridazine-3-carboxamide and N-(1-isopropyl-1H-pyrazol-5-yl)-2-methyl-6-(2-(trifluoromethyl)phenyl)imidazo[1,2-b]pyridazine-3-carboxamide.

Example 18. Preparation of (R)-6-(3-(2,3-dihydroxypropoxy)phenyl)-2-methyl-N-(pyridin-2-yl) imidazo[1,2-b]pyridazine-3-carboxamide (Compound 772)

Step 1. Synthesis of (S)-6-(3-((2,2-dimethyl-1,3-dioxolan-4-yl)methoxy)phenyl)-2-methyl-N-(pyridin-2-yl)imidazo[1,2-b]pyridazine-3-carboxamide

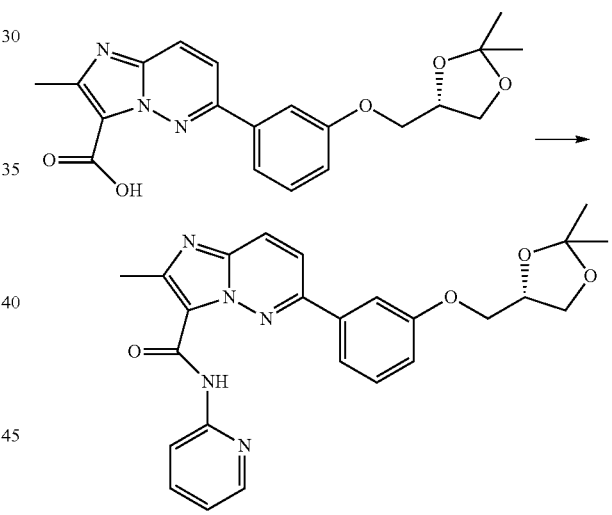

(S)-6-(3-((2,2-dimethyl-1,3-dioxolan-4-yl)methoxy)phenyl)-2-methylimidazo[1,2-b]pyridazine-3-carboxylic acid (100.0 mg, 0.261 mmol) and 2-aminopyridine (37.0 mg, 0.392 mmol) were coupled using the HATU mediated general amide coupling procedure described above for preparation of Compound 19 to afford (S)-6-(3-((2,2-dimethyl-1,3-dioxolan-4-yl)methoxy)phenyl)-2-methyl-N-(pyridin-2-yl)imidazo[1,2-b]pyridazine-3-carboxamide (50.0 mg, 43%). MS (ESI) calcd for C$_{25}$H$_{25}$N$_5$O$_4$: 459.2.

This procedure could be used to prepare (S)-6-(3-((2,2-dimethyl-1,3-dioxolan-4-yl)methoxy)phenyl)-2-methylimidazo[1,2-b]pyridazine-3-carboxylic acid and (R)-6-(3-((2,2-dimethyl-1,3-dioxolan-4-yl)methoxy)phenyl)-2-methylimidazo[1,2-b]pyridazine-3-carboxylic acid by reacting 6-chloro-2-methylimidazo[1,2-b]pyridazine-3-carboxylate with 3-hydroxyphenylboronic acid. MS (ESI) calculated for C$_{20}$H$_{21}$N$_3$O$_5$ 383.15.

Step 2. Synthesis of (R)-6-(3-(2,3-dihydroxypropoxy)phenyl)-2-methyl-N-(pyridin-2-yl)imidazo[1,2-b]pyridazine-3-carboxamide

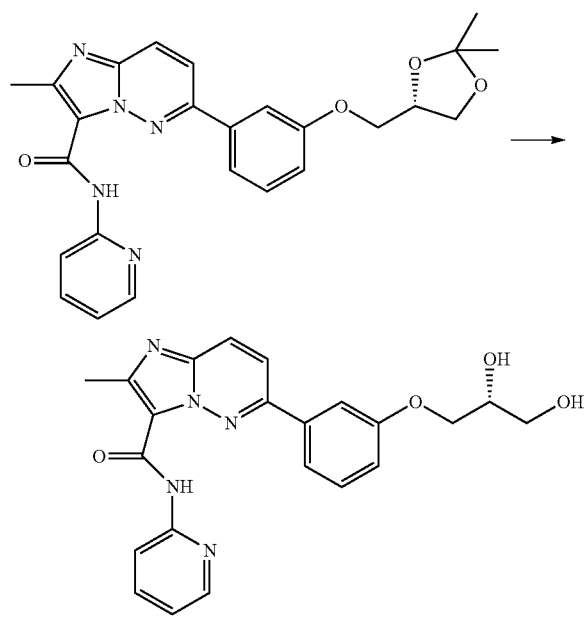

Compound 772

(S)-6-(3-((2,2-dimethyl-1,3-dioxolan-4-yl)methoxy)phenyl)-2-methyl-N-(pyridin-2-yl)imidazo[1,2-b]pyridazine-3-carboxamide (50.0 mg, 0.108 mmol) was taken up in EtOH: 3N HCl (3:1, 4 mL). This clear solution was stirred at room temp for 3 h. The solvent was removed under reduced pressure and the product was purified by reverse phase preparative HPLC to afford (R)-6-(3-(2,3-dihydroxypropoxy)phenyl)-2-methyl-N-(pyridin-2-yl)imidazo[1,2-b]pyridazine-3-carboxamide (20.0 mg, 50%). MS (ESI) calcd for $C_{22}H_{21}N_5O_4$: 419.1. found: 420.2 [M+H].

This general procedure could be used to prepare a variety of 6-(3-(2,3-dihydroxypropoxy)phenyl)-2-methyl-N-(substituted)imidazo[1,2-b]pyridazine-3-carboxamides by substituting the appropriate amine for 2-aminopyridine.

Example 19. Preparation of (R)-6-(2-(2,3-dihydroxypropoxy)phenyl)-2-methyl-N-(pyridin-2-yl)imidazo[1,2-b]pyridazine-3-carboxamide (Compound 815)

Step 1. Synthesis of ethyl 6-(2-hydroxyphenyl)-2-methylimidazo[1,2-b]pyridazine-3-carboxylate

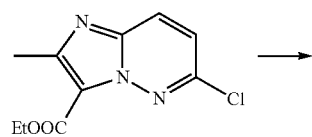

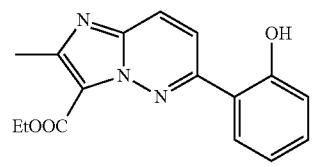

To the degassed dimethoxyethane (DME) (150 mL) were added ethyl 6-chloro-2-methylimidazo[1,2-b]pyridazine-3-carboxylate (3.8 g, 15.9 mmol), 2-hydroxyphenylboronic acid (3.28 g, 23.8 mmol), Pd(dppf)Cl$_2$ (697.0 mg, 0.95 mmol), and K$_2$CO$_3$ (4.38 g, 31.7 mmol). The mixture was stirred at 100° C. for 12 h. The mixture was concentrated and purified by column chromatography (pet ether:ethyl acetate=4:1) to give ethyl 6-(2-hydroxyphenyl)-2-methylimidazo[1,2-b]pyridazine-3-carboxylate (2.0 g, 40% yield). MS (ESI) calcd for $C_{16}H_{15}N_3O_3$: 297.1.

Step 2. Synthesis of (S)-ethyl 6-(2-((2,2-dimethyl-1,3-dioxolan-4-yl)methoxy)phenyl)-2-methylimidazo[1,2-b]pyridazine-3-carboxylate

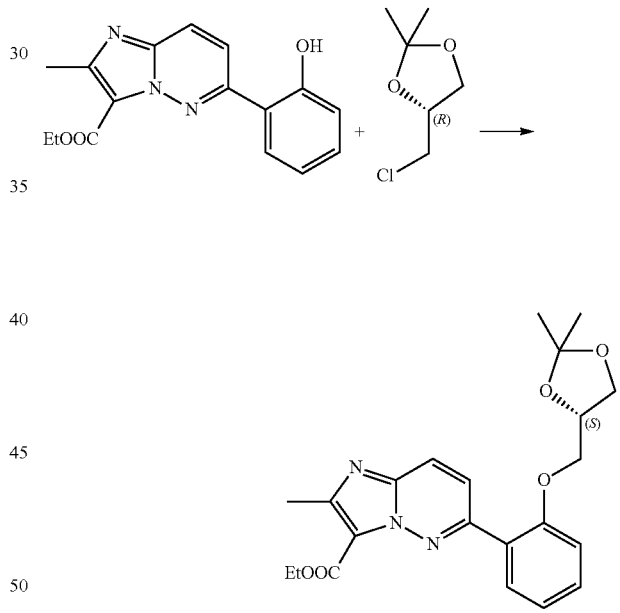

To a solution of ethyl 6-(2-hydroxyphenyl)-2-methylimidazo[1,2-b]pyridazine-3-carboxylate (2.0 g, 6.7 mmol) and (R)-4-Chloromethyl-2,2-dimethyl-1,3-dioxolane (1.5 g, 10 mmol) in DMF (80 mL) was added K$_2$CO$_3$ (3.7 g, 27 mmol). The mixture was heated to 100° C. for 12 h. After cooling to room temp, the solvent was removed in vacuo and ethyl acetate:H$_2$O (60 mL, 1:1) was added to the mixture. The resulting mixture was extracted with ethyl acetate (30 mL×3), combined organic layers were dried, and crude product was purified by column chromatography (petroleum ether:ethyl acetate=8:1) to give (S)-ethyl 6-(2-((2,2-dimethyl-1,3-dioxolan-4-yl)methoxy)phenyl)-2-methylimidazo[1,2-b]pyridazine-3-carboxylate (2.0 g, 72% yield). MS (ESI) calcd for $C_{22}H_{25}N_3O_5$: 411.2.

Step 3. Synthesis of (S)-6-(2-((2,2-dimethyl-1,3-dioxolan-4-yl)methoxy)phenyl)-2-methylimidazo[1,2-b]pyridazine-3-carboxylic acid

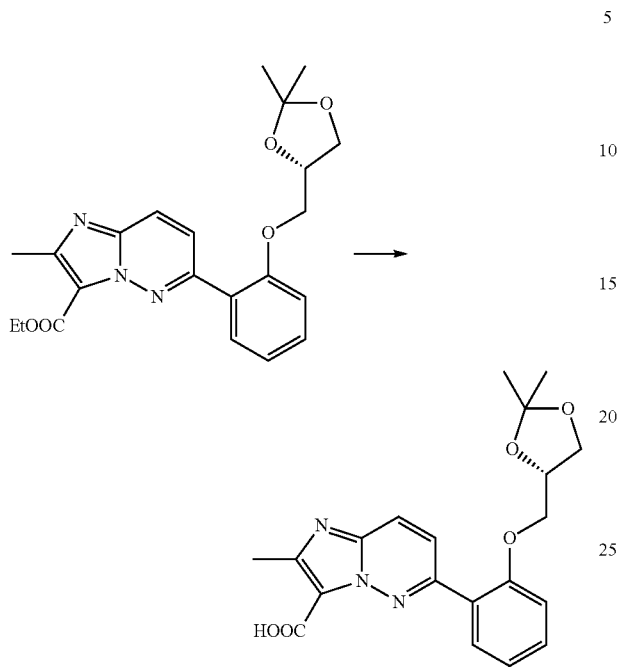

A solution of (S)-ethyl 6-(2-((2,2-dimethyl-1,3-dioxolan-4-yl)methoxy)phenyl)-2-methylimidazo[1,2-b]pyridazine-3-carboxylate (1.9 g, 4.6 mmol) and LiOH H$_2$O (0.97 g, 23 mmol) in THF:H$_2$O (60 mL, 5:1) was stirred at 50° C. overnight. The THF was removed in vacuo and the pH was adjusted to 4 using 1N aq HCl. The resulting precipitate was collected by filtration, rinsed with H$_2$O and dried to give (S)-6-(2-((2,2-dimethyl-1,3-dioxolan-4-yl)methoxy)phenyl)-2-methylimidazo[1,2-b]pyridazine-3-carboxylic acid (1.4 g, 80% yield). MS (ESI) calcd for C$_{20}$H$_{21}$N$_3$O$_5$: 383.1.

This general procedure could be used to prepare 6-(3-((2,2-dimethyl-1,3-dioxolan-4-yl)methoxy)phenyl)-2-methylimidazo[1,2-b]pyridazine-3-carboxylic acid by substituting 3-hydroxyphenylboronic acid for 2-hydroxyphenylboronic acid.

Step 4. Synthesis of (R)-6-(2-(2,3-dihydroxypropoxy)phenyl)-2-methyl-N-(pyridin-2-yl)imidazo[1,2-b]pyridazine-3-carboxamide

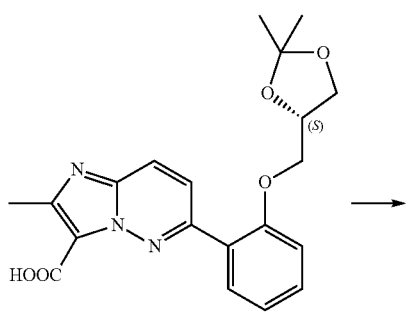

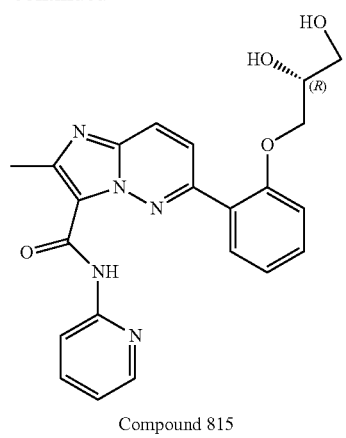

Compound 815

To a solution of (S)-6-(2-((2,2-dimethyl-1,3-dioxolan-4-yl)methoxy)phenyl)-2-methylimidazo[1,2-b]pyridazine-3-carboxylic acid (100.0 mg, 0.26 mmol), 2-aminopyridine (49.0 mg, 0.52 mmol) and HATU (198.0 mg, 0.52 mmol) in DMF (1.5 mL) was added DIEA (0.2 mL), the mixture was stirred at 60° C. overnight. H$_2$O was added and the resulting precipitate was filtered to give the crude product. The crude product was taken up in EtOH:3N HCl (3:1) and stirred overnight. The solvents were evaporated and further purification by using reverse phase preparative HPLC afforded (R)-6-(2-(2,3-dihydroxypropoxy)phenyl)-2-methyl-N-(pyridin-2-yl)imidazo[1,2-b]pyridazine-3-carboxamide as a white solid (16.4 mg, yield 15% over two steps). MS (ESI) calcd for C$_{22}$H$_{21}$N$_5$O$_4$: 419.1. found 420.0 [M+H].

Example 20. Preparation of (S)-6-(2-((2,2-dimethyl-1,3-dioxolan-4-yl)methoxy)phenyl)-2-methyl-N-(pyrimidin-4-yl)imidazo[1,2-b]pyridazine-3-carboxamide (Compound 774)

Step 1. Synthesis of (S)-4-nitrophenyl 6-(2-((2,2-dimethyl-1,3-dioxolan-4-yl)methoxy)phenyl)-2-methylimidazo[1,2-b]pyridazine-3-carboxylate

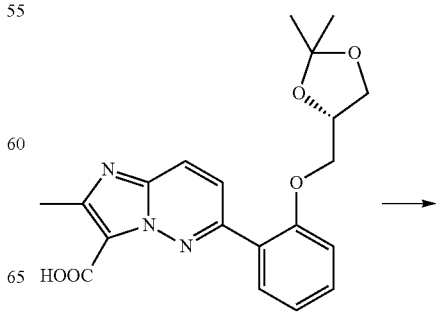

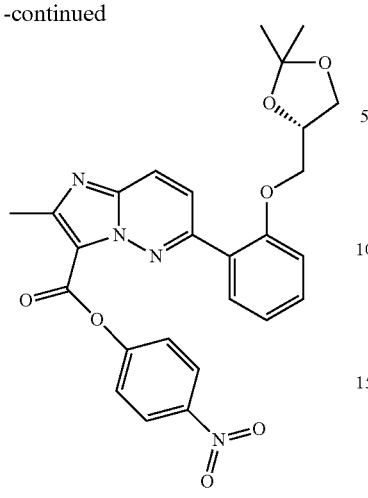

Step 2. Synthesis of (S)-6-(2-((2,2-dimethyl-1,3-dioxolan-4-yl)methoxy)phenyl)-2-methyl-N-(pyrimidin-4-yl)imidazo[1,2-b]pyridazine-3-carboxamide

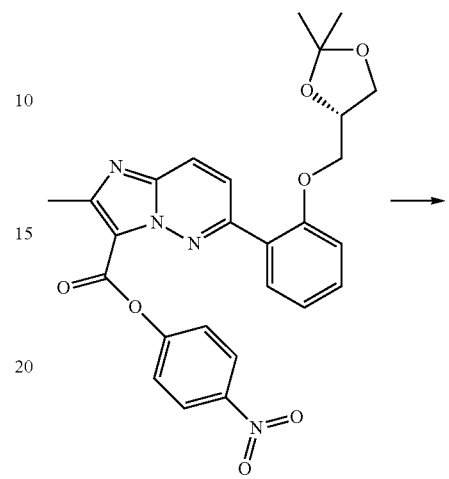

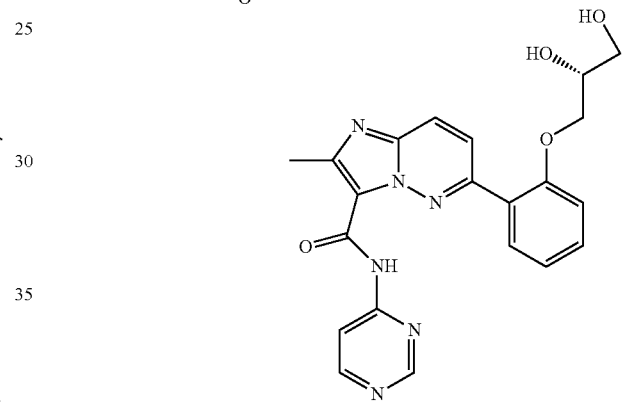

To a solution of (S)-6-(2-((2,2-dimethyl-1,3-dioxolan-4-yl)methoxy)phenyl)-2-methylimidazo[1,2-b]pyridazine-3-carboxylic acid (800.0 mg, 2.09 mmol) and 4-dimethylaminopyridine (DMAP) (382.0 mg, 3.13 mmol) in 10 mL of DMF was added 1-ethyl-3-(3-dimethylaminopropyl) carbodiimide) (EDCI) (600.0 mg, 3.13 mmol) under nitrogen. After stirring at room temp for 2 h, 4-nitrophenol (294.0 mg, 2.09 mmol) was added to the reaction and stirred at room temp for 18 h. Sodium carbonate solution (50 mL) was added to the mixture and aqueous layer was extracted with ethyl acetate (2×30 mL). The combined organic layers were washed with aqueous $Na_2CO_3$ (3×20 mL, until the aqueous layer was colorless), brine and then concentrated in vacuo to give a crude solid, which was triturated in pet ether: ethyl acetate (4:1) to give (S)-4-nitrophenyl 6-(2-((2,2-dimethyl-1,3-dioxolan-4-yl)methoxy)phenyl)-2-methylimidazo[1,2-b]pyridazine-3-carboxylate as a white solid (0.15 g, 14% yield). MS (ESI) calcd for $C_{26}H_{24}N_4O_7$: 504.2.

This general procedure could be used to prepare (S)-4-nitrophenyl 6-(3-((2,2-dimethyl-1,3-dioxolan-4-yl)methoxy)phenyl)-2-methylimidazo[1,2-b]pyridazine-3-carboxylate by starting from 6-(3-((2,2-dimethyl-1,3-dioxolan-4-yl)methoxy)phenyl)-2-methylimidazo[1,2-b]pyridazine-3-carboxylic acid.

To a solution of 4-aminopyrimidine (17.5 mg, 0.14 mmol) in THF (2 mL) at 0° C. was added NaH (8.4 mg, 0.21 mmol) and the reaction stirred for 10 min. (S)-4-nitrophenyl 6-(2-((2,2-dimethyl-1,3-dioxolan-4-yl)methoxy)phenyl)-2-methylimidazo[1,2-b]pyridazine-3-carboxylate (35.0 mg, 0.07 mmol) was added to the reaction mixture and stirred at room temp for 30 min. Saturated $NH_4Cl$ aqueous solution was added and the mixture was extracted with ethyl acetate. The organic layer was washed with aq. $Na_2CO_3$, brine, dried over $Na_2SO_4$ to give the crude product. Further purification by preparation TLC to give (S)-4-nitrophenyl 6-(2-((2,2-dimethyl-1,3-dioxolan-4-yl)methoxy)phenyl)-2-methylimidazo[1,2-b]pyridazine-3-carboxylate (30.2 mg, yield 87%). This material was taken up in EtOH:3N HCl (3:1) and stirred overnight. The solvents were evaporated and washed with aq. $Na_2CO_3$, brine to afford as a white solid (S)-6-(2-((2,2-dimethyl-1,3-dioxolan-4-yl)methoxy)phenyl)-2-methyl-N-(pyrimidin-4-yl)imidazo[1,2-b]pyridazine-3-carboxamide (15.0 mg, two steps yield 50%). MS (ESI) calcd for $C_{21}H_{20}N_6O_4$: 420.1. found: 421.2 [M+H].

This general procedure could be used to prepare a variety of 6-(2-((2,2-dimethyl-1,3-dioxolan-4-yl)methoxy)phenyl) and 6-(3-(2,3-dihydroxypropoxy)phenyl)-2-methyl-N-(substituted)imidazo[1,2-b]pyridazine-3-carboxamides by substituting the appropriate amine for 4-aminopyrimidine.

Example 21. Preparation of 8-methyl-N-(pyridin-4-yl)-6-(2-(trifluoromethyl)phenyl)imidazo[1,2-b]pyridazine-3-carboxamide (Compound 193)

Step 1. Synthesis of 6-chloro-5-methylpyridazin-3-amine (and 6-chloro-4-methylpyridazin-3-amine)

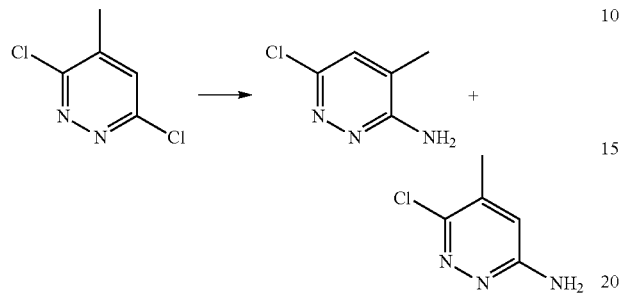

A solution of compound 3,6-dichloro-4-methylpyridazine (20.0 g, 122.7 mmol) and ammonium hydroxide in water (86.60 g, 245 mmol) was refluxed for about 30 h. The mixture was concentrated and used in the next step without purification.

Step 2. Synthesis of ethyl 6-chloro-8-methylimidazo[1,2-b]pyridazine-3-carboxylate (and ethyl 6-chloro-7-methylimidazo[1,2-b]pyridazine-3-carboxylate)

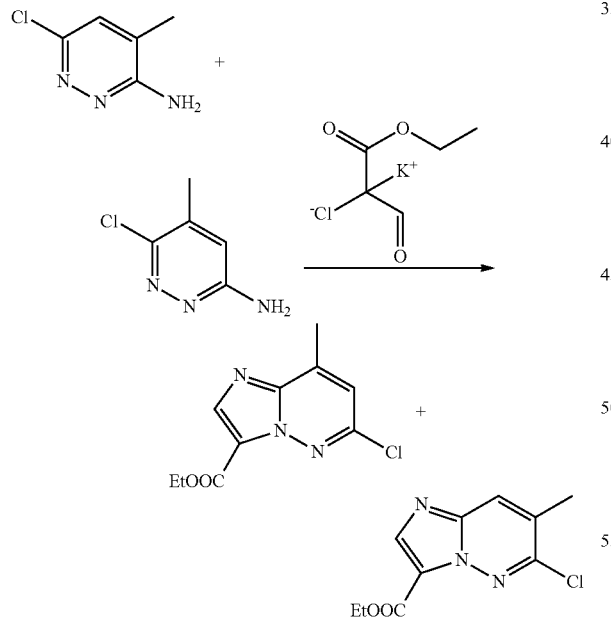

A mixture of potassium salt of ethyl 2-chloro-3-oxopropanoate prepared using the procedure above (13.14 g, 69.7 mmol), 6-chloro-5-methylpyridazin-3-amine and 6-chloro-4-methylpyridazin-3-amine (5.0 g, 34.8 mmol) was taken up in conc. sulfuric acid (3.42 g, 34.8 mmol) and EtOH (600 mL). The mixture was refluxed for about 30 h after which it was cooled to room temp, concentrated and purified by column chromatography to separate the regioisomeric ethyl 6-chloro-8-methylimidazo[1,2-b]pyridazine-3-carboxylate and ethyl 6-chloro-7-methylimidazo[1,2-b]pyridazine-3-carboxylate which were carried forward as single regioisomers.

Step 3. Synthesis of ethyl 8-methyl-6-(2-(trifluoromethyl)phenyl)imidazo[1,2-b]pyridazine-3-carboxylate

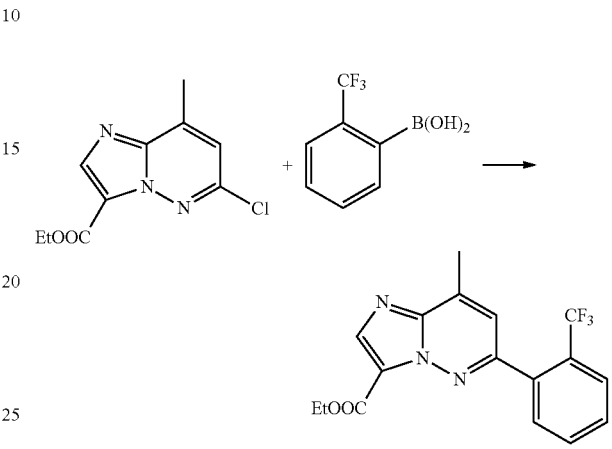

A solution of ethyl 6-chloro-8-methylimidazo[1,2-b]pyridazine-3-carboxylate (1.5 g, 6.26 mmol), 2-(trifluoromethyl)phenylboronic acid (2.38 g, 12.52 mmol), Pd(PPh$_3$)$_4$ (0.362 g, 0.313 mmol), Cs$_2$CO$_3$ (4.08 g, 12.52 mmol) in a mixture solvents (dioxane:EtOH:H$_2$O) was heated at 100° C. for about 30 h. Water was added and the solid was purified by column chromatography to afford ethyl 8-methyl-6-(2-(trifluoromethyl)phenyl) imidazo[1,2-b]pyridazine-3-carboxylate. MS (ESI) calcd for C$_{12}$H$_{14}$F$_3$N$_3$O$_2$: 349.10.

Step 4. Synthesis of 8-methyl-6-(2-(trifluoromethyl)phenyl)imidazo[1,2-b]pyridazine-3-carboxylic acid

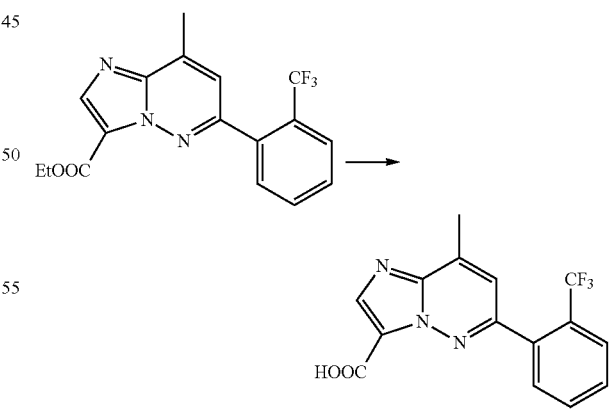

To a solution of ethyl 8-methyl-6-(2-(trifluoromethyl)phenyl)imidazo[1,2-b]pyridazine-3-carboxylate (0.1 g, 0.29 mmol) in THF (5 mL) and H$_2$O (5.00 mL) was added NaOH (0.18 g, 4.58 mmol) and the reaction mixture was stirred at 70° C. for 2 h. Solvents were removed under reduced pressure and 2% HCl aqueous was added to make pH=3.

The solid was separated by filtration to yield 8-methyl-6-(2-(trifluoromethyl)phenyl)imidazo[1,2-b]pyridazine-3-carboxylic acid. MS (ESI) calcd for $C_{15}H_{10}F_3N_3O_2$: 321.1.

Step 5. Synthesis of 8-methyl-N-(pyridin-4-yl)-6-(2-(trifluoromethyl)phenyl)imidazo[1,2-b]pyridazine-3-carboxamide

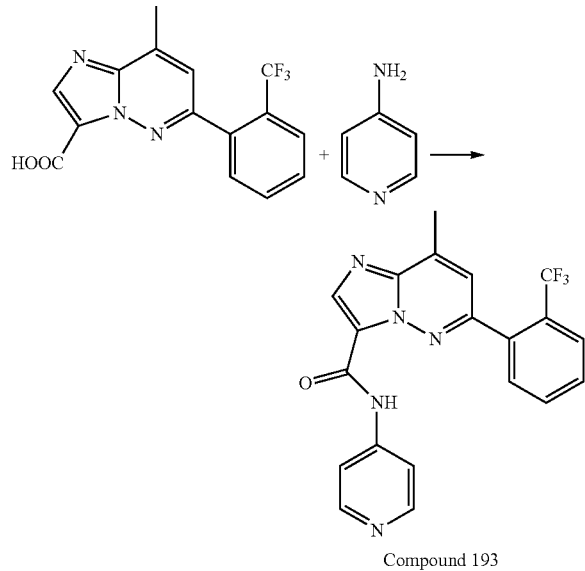

Compound 193

8-methyl-6-(2-(trifluoromethyl)phenyl)imidazo[1,2-b]pyridazine-3-carboxylic acid (40.0 mg, 0.13 mmol) and 4-amino pyridine (16.0 mg, 0.16 mmol) were coupled using the general amide coupling reaction described above for Compound 19 to afford 8-methyl-N-(pyridine-4-yl)-6-(2-(trifluoromethyl)phenyl)imidazo[1,2-b]pyridazine-3-carboxamide (18 mg, 36% yield). MS (ESI) calcd for $C_{20}H_{14}F_3N_3O$: 397.1. found: 397.9 [M+H].

This general procedure could be used to prepare a variety of 8-methyl-N-(pyridine-4-yl)-6-(2-(trifluoromethyl)phenyl)imidazo[1,2-b]pyridazine-3-carboxamides by substituting the appropriate amine for 4-amino pyridine.

Example 22. Preparation of 7-methyl-N-(pyridin-4-yl)-6-(2-(trifluoromethyl)phenyl)imidazo[1,2-b]pyridazine-3-carboxamide (Compound 223)

Step 1. Synthesis of ethyl 7-methyl-6-(2-(trifluoromethyl)phenyl)imidazo[1,2-b]pyridazine-3-carboxylate

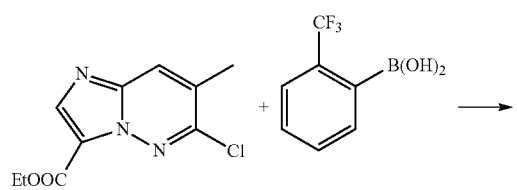

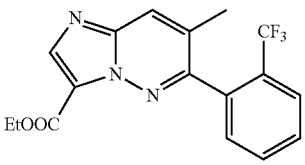

To a mixture of ethyl 6-chloro-7-methylimidazo[1,2-b]pyridazine-3-carboxylate (1.0 g, 4.17 mmol) prepared above, 2-(trifluoromethyl)phenylboronic acid (0.95 g, 5.01 mmol), $K_3PO_4$ (2.66 g, 12.52 mmol), $Pd_2(dba)_3$ (0.19 g, 0.21 mmol) and X-Phos (0.2 g, 0.42 mmol) was added dioxane (4 mL) and the mixture was heated at 120° C. for about 12 h. After cooling to room temp and concentrating under reduced pressure, the crude product was purified by column chromatography to afford ethyl 7-methyl-6-(2-(trifluoromethyl)phenyl)imidazo[1,2-b]pyridazine-3-carboxylate. MS (ESI) calcd for $C_{17}H_{14}F_3N_3O_2$: 349.10.

Step 2. Synthesis of 7-methyl-6-(2-(trifluoromethyl)phenyl)imidazo[1,2-b]pyridazine-3-carboxylic acid

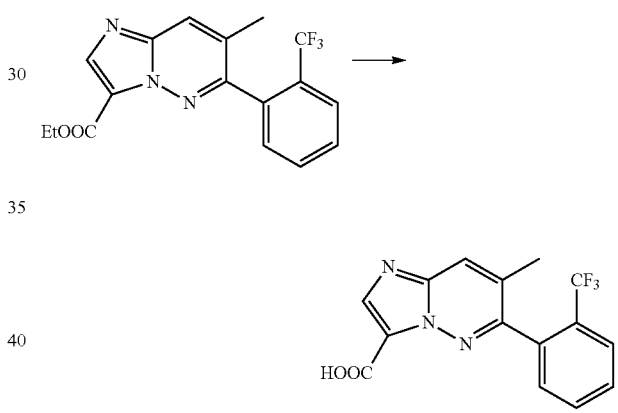

Ethyl 7-methyl-6-(2-(trifluoromethyl)phenyl) imidazo[1,2-b]pyridazine-3-carboxylate (0.15 g, 0.429 mmol) was hydrolyzed using the general procedure described above for the preparation of 8-methyl-6-(2-(trifluoromethyl)phenyl)imidazo[1,2-b]pyridazine-3-carboxylic acid to afford 7-methyl-6-(2-(trifluoromethyl)phenyl)imidazo[1,2-b]pyridazine-3-carboxylic acid. MS (ESI) calcd for $C_{15}H_{10}F_3N_3O_2$: 321.1.

Step 3. Synthesis of 7-methyl-N-(pyridin-4-yl)-6-(2-(trifluoromethyl)phenyl)imidazo[1,2-b]pyridazine-3-carboxamide

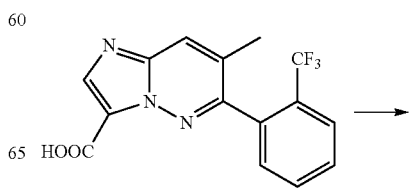

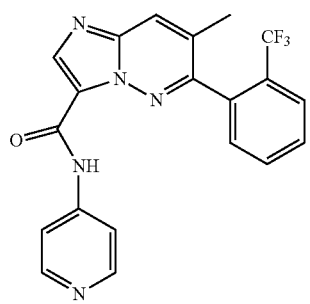

Compound 223

7-methyl-6-(2-(trifluoromethyl)phenyl)imidazo[1,2-b]pyridazine-3-carboxylic acid (50.0 mg, 0.16 mmol) and 4-amino pyridine (23.0 mg, 0.24 mmol) were coupled using the general amide coupling reaction described above to afford 7-methyl-N-(pyridin-4-yl)-6-(2-(trifluoromethyl)phenyl)imidazo[1,2-b]pyridazine-3-carboxamide (45.0 mg, 73% yield). MS (ESI) calcd for $C_{20}H_{14}F_3N_5O$: 397.1. found: 397.9 [M+H].

This general procedure could be used to prepare a variety of 7-methyl-N-(substituted)-6-(2-(trifluoromethyl)phenyl)imidazo[1,2-b]pyridazine-3-carboxamides by substituting the appropriate amine for 4-amino pyridine.

Example 23. Preparation of (R)-N-(6-(2,3-dihydroxypropoxy)pyridin-2-yl)-7,8-dimethyl-6-(2-(trifluoromethyl)phenyl)imidazo[1,2-b]pyridazine-3-carboxamide (Compound 387)

Step 1. Synthesis of ethyl 6-chloro-7,8-dimethylimidazo[1,2-b]pyridazine-3-carboxylate

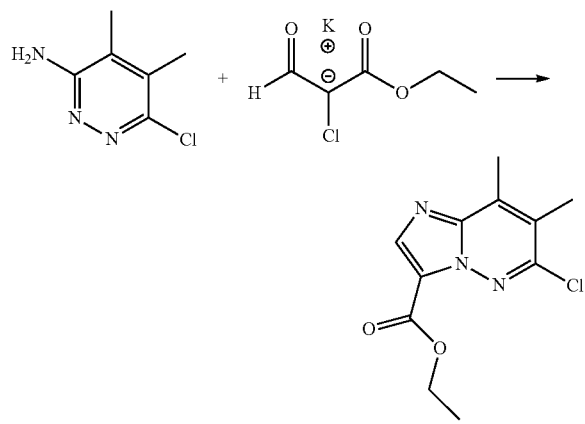

Concentrated sulfuric acid (1.14 mL, 21.4 mmol) was added to EtOH (39 mL) and cooled to 0° C. The potassium salt of ethyl 2-chloro-3-oxopropanoate (7.81 g, 41.4 mmol) was added, followed by 6-chloro-4,5-dimethylpyridazin-3-amine (2.11 g, 13.4 mmol). The reaction was allowed to stir at 0° C. for 5 min, then warmed to room temp for 5 min, then heated to reflux for 4 h. The mixture was cooled and concentrated in vacuo. Water was added (50 mL) and the aqueous layer was extracted with EtOAc (3×50 mL). The combined organics were washed with brine, dried with $Na_2SO_4$, filtered and concentrated. Purification by silica gel chromatography (0-100% EtOAc in pentane) gave ethyl 6-chloro-7,8-dimethylimidazo[1,2-b]pyridazine-3-carboxylate (1.41 g, 42%). MS (ESI) calcd for $C_{11}H_{12}ClN_3O_2$: 253.06. found: 254 [M+H].

Step 2. Synthesis of ethyl 7,8-dimethyl-6-(2-(trifluoromethyl)phenyl)imidazo[1,2-b]pyridazine-3-carboxylate

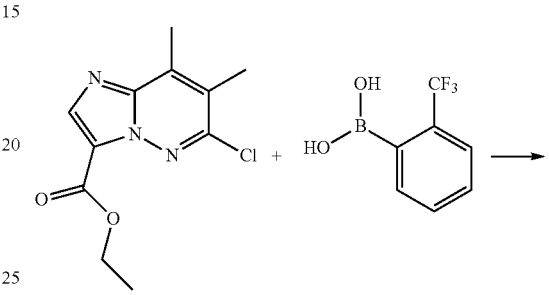

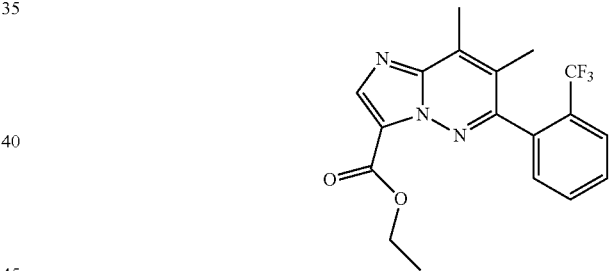

Ethyl 6-chloro-7,8-dimethylimidazo[1,2-b]pyridazine-3-carboxylate (750.0 mg, 2.96 mmol) and 2-(trifluoromethyl)phenylboronic acid (562.0 mg, 2.96 mmol) were weighed into a 5 mL microwave vial. Dicyclohexyl(2',6'-dimethoxybiphenyl-2-yl)phosphine (97.0 mg, 0.236 mmol) and $K_3PO_4$ (1.88 g, 8.87 mmol) were added, and the mixture was suspended in dioxane (3.6 mL) and water (0.36 mL). The mixture was purged with nitrogen for 5 min., tris(dibenzylideneacetone)dipalladium(0) (108.0 mg, 0.118 mmol) was added, and the mixture purged 5 min more with nitrogen. The vial was sealed and the reaction heated to 120° C. in the microwave for 1.5 h. Saturated aqueous $NaHCO_3$ (5 mL) was added and the mixture was allowed to stir 10 min, then it was extracted with EtOAc (3×20 mL). The combined organics were washed with brine, dried with $Na_2SO_4$, filtered and concentrated. Purification by silica gel chromatography (0-100% EtOAc in pentane) gave ethyl 7,8-dimethyl-6-(2-(trifluoromethyl)phenyl)imidazo[1,2-b]pyridazine-3-carboxylate (726.0 mg, 68%). MS (ESI) calcd for $C_{18}H_{16}F_3N_3O_2$: 363.12. found: 364 [M+H].

Step 3. Synthesis of 7,8-dimethyl-6-(2-(trifluoromethyl)phenyl)imidazo[1,2-b]pyridazine-3-carboxylic acid

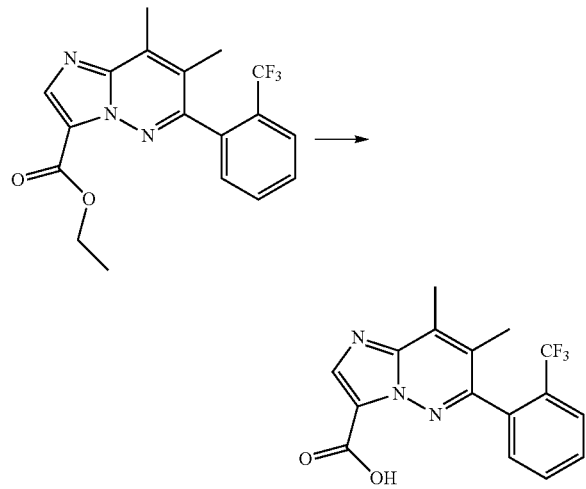

Ethyl 7,8-dimethyl-6-(2-(trifluoromethyl)phenyl)imidazo[1,2-b]pyridazine-3-carboxylate (726.0 mg, 2.0 mmol) was dissolved in THF (38 mL). Water was added (47 mL), followed by LiOH (239.0 mg, 9.98 mmol). The reaction was allowed to stir at room temp for 2 h. 1.0 N aqueous HCl (10.1 mL) was added and the mixture was extracted with EtOAc (3×100 mL). The combined organics were washed with brine, dried with $Na_2SO_4$, filtered and concentrated to give 7,8-dimethyl-6-(2-(trifluoromethyl)phenyl)imidazo[1,2-b]pyridazine-3-carboxylic acid (700.0 mg, quant.). MS (ESI) calcd for $C_{16}H_{12}F_3N_3O_2$: 335.09. found: 336 [M+H].

Step 4. Synthesis of (S)-N-(6-((2,2-dimethyl-1,3-dioxolan-4-yl)methoxy)pyridin-2-yl)-7,8-dimethyl-6-(2-(trifluoromethyl)phenyl) imidazo[1,2-b]pyridazine-3-carboxamide

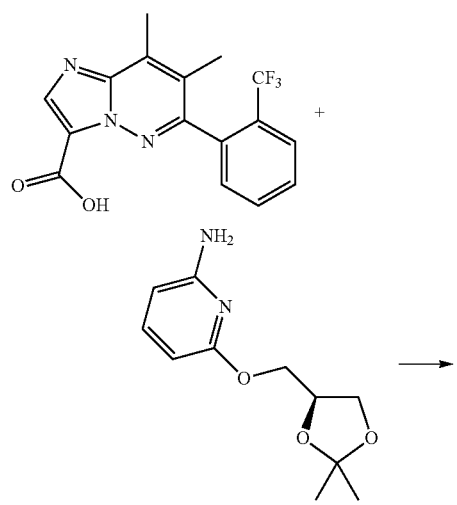

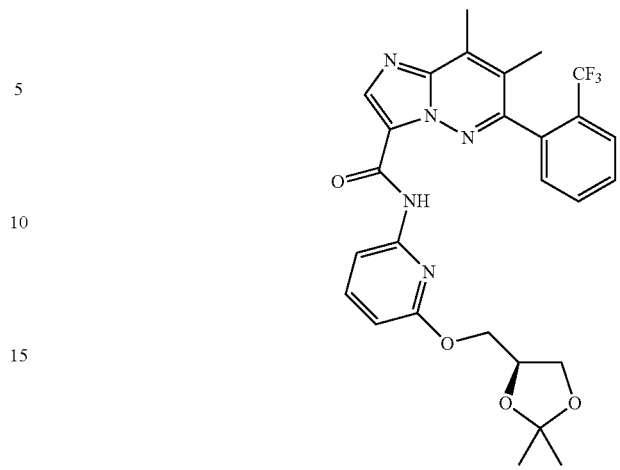

7,8-dimethyl-6-(2-(trifluoromethyl)phenyl)imidazo[1,2-b]pyridazine-3-carboxylic acid (150.0 mg, 0.445 mmol) and (S)-6-((2,2-dimethyl-1,3-dioxolan-4-yl)methoxy)pyridin-2-amine (82.0 mg, 0.45 mmol) were coupled according to the general amide coupling procedure above to give (S)-N-(6-((2,2-dimethyl-1,3-dioxolan-4-yl)methoxy)pyridin-2-yl)-7,8-dimethyl-6-(2-(trifluoromethyl)phenyl)imidazo[1,2-b]pyridazine-3-carboxamide (197.0 mg, 81%). MS (ESI) calcd for $C_{27}H_{26}F_3N_5O_4$: 541.19. found: 542 [M+H].

This general procedure could be used to prepare a variety N-(substituted)-7,8-dimethyl-6-(2-(trifluoromethyl)phenyl)imidazo[1,2-b]pyridazine-3-carboxamides by substituting the appropriate amine for (S)-6-((2,2-dimethyl-1,3-dioxolan-4-yl)methoxy)pyridin-2-amine.

Step 5. Synthesis of (R)-N-(6-(2,3-dihydroxypropoxy)pyridin-2-yl)-7,8-dimethyl-6-(2-(trifluoromethyl)phenyl) imidazo[1,2-b]pyridazine-3-carboxamide

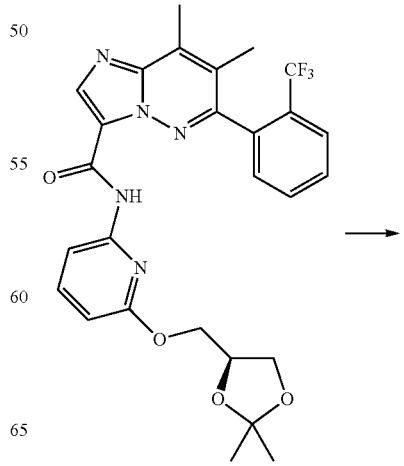

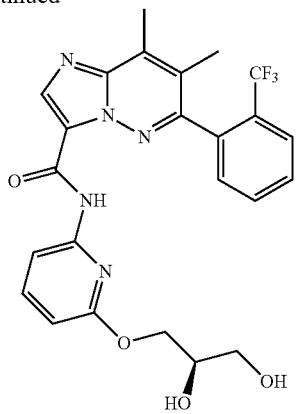

Compound 387

(S)-N-(6-((2,2-dimethyl-1,3-dioxolan-4-yl)methoxy)pyridin-2-yl)-7,8-dimethyl-6-(2-(trifluoromethyl)phenyl)imidazo[1,2-b]pyridazine-3-carboxamide (197.0 mg, 0.36 mmol) was dissolved in THF (7.8 mL). Concentrated HCl (aq.) was added (0.12 mL) and the reaction was allowed to stir at room temp for 5 h. Water (5 mL) and saturated aqueous NaHCO$_3$ (5 mL) were added, and the mixture was extracted with EtOAc (3×20 mL). The combined organics were washed with brine, dried with Na$_2$SO$_4$, filtered and concentrated. The crude material was purified by silica gel column chromatography (0-10% MeOH/CH$_2$Cl$_2$) to give (R)-N-(6-(2,3-dihydroxypropoxy)pyridin-2-yl)-7,8-dimethyl-6-(2-(trifluoromethyl)phenyl) imidazo[1,2-b]pyridazine-3-carboxamide (53.0 mg, 29%). MS (ESI) calcd for C$_{24}$H$_{22}$F$_3$N$_5$O$_4$: 501.16. found: 502 [M+H].

Example 24. First preparation of 2,8-dimethyl-N-(pyridazin-3-yl)-6-(2-(trifluoromethyl)phenyl)imidazo[1,2-b]pyridazine-3-carboxamide (Compound 428)

Step 1. Synthesis of ethyl 6-chloro-2,8-dimethylimidazo[1,2-b]pyridazine-3-carboxylate (and ethyl 6-chloro-2,7-dimethylimidazo[1,2-b]pyridazine-3-carboxylate)

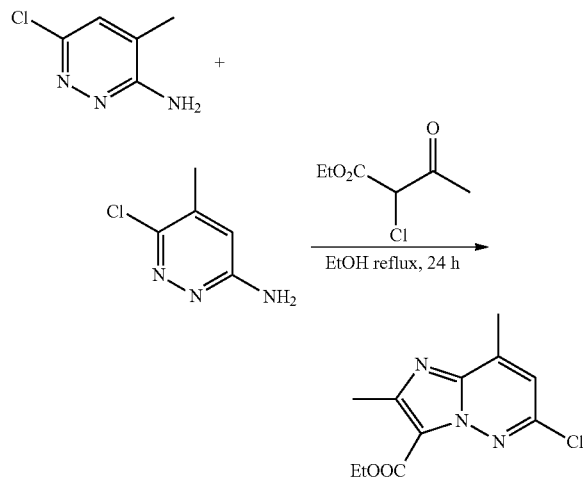

A mixture (50.0 g, 349 mmol) of 6-chloro-5-methylpyridazin-3-amine and 6-chloro-4-methylpyridazin-3 amine was dissolved in EtOH (600 mL). Ethyl 2-chloro-3-oxobutanoate (114.0 g, 680 mmol) was added. The mixture was refluxed for 48 h, followed by concentration. Water (500 mL) and CH$_2$Cl$_2$ (500 mL) were added. The organic layer was separated and dried over anhydrous Na$_2$SO$_4$, concentrated and purified by silica gel column chromatography to separate the methyl isomers, giving pure ethyl 6-chloro-2,8-dimethylimidazo[1,2-b]pyridazine-3-carboxylate (9.4 g, 10%). MS (ESI) calcd for C$_{11}$H$_{12}$ClN$_3$O$_2$: 253.06. found: 253.96 [M+H].

Step 2. Synthesis of ethyl 2,8-dimethyl-6-(2-(trifluoromethyl)phenyl)imidazo[1,2-b]pyridazine-3-carboxylate

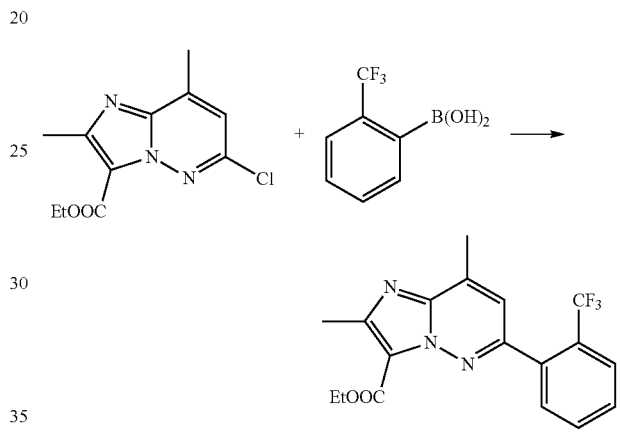

Ethyl 6-chloro-2,8-dimethylimidazo[1,2-b]pyridazine-3-carboxylate (7.4 g, 29 mmol), 2-(trifluoromethyl)phenylboronic acid (6.6 g, 35 mmol), cesium carbonate (19.0 g, 58 mmol), Pd(PPh$_3$)$_4$ (3.3 g, 3 mmol) were dissolved in a mixture of dioxane:water (4:1) plus 10 drops of EtOH. The mixture was heated to 75° C. for 5 h, then concentrated. Water (200 mL) was added and this was extracted with CH$_2$Cl$_2$ (300 mL). The organic layer was concentrated and purified on silica gel to give ethyl 2,8-dimethyl-6-(2-(trifluoromethyl)phenyl)imidazo[1,2-b]pyridazine-3-carboxylate (8.0 g, 75%). MS (ESI) calcd for C$_{18}$H$_{16}$F$_3$N$_3$O$_2$: 363.12.

Step 3. Synthesis of 2,8-dimethyl-6-(2-(trifluoromethyl)phenyl)imidazo[1,2-b]pyridazine-3-carboxylic acid

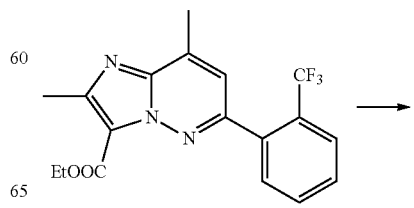

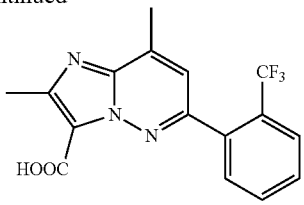

Ethyl 2,8-dimethyl-6-(2-(trifluoromethyl)phenyl) imidazo[1,2-b]pyridazine-3-carboxylate (8.0 g, 22 mmol) was dissolved in dioxane (100 mL). NaOH (1.76 g, 44 mmol) in water (100 mL) was added. The mixture was heated to 60° C. for 2 h, then concentrated. Water (100 mL) was added and the mixture was filtered. The pH was adjusted to 5 with aqueous HCl. The mixture was filtered again and the solid was dried under vacuum to give 2,8-dimethyl-6-(2-(trifluoromethyl)phenyl)imidazo[1,2-b]pyridazine-3-carboxylic acid (6.2 g, 75%). MS (ESI) calcd for $C_{16}H_{12}F_3N_3O_2$: 335.09. found: 335.98 [M+H].

This general coupling procedure followed by ester hydrolysis could be used to prepare a variety of carboxylates, including 2,8-dimethyl-6-(2-trifluoromethyl)phenyl) and 2,8-dimethyl-6-(2-trifluoromethoxy)phenyl) imidazo[1,2-b]pyridazine-3-carboxylates, by substituting the appropriate boronic acid or boronic ester moiety for 2-(trifluoromethyl)phenylboronic acid.

Step 4. Synthesis of 2,8-dimethyl-N-(pyridazin-3-yl)-6-(2-(trifluoromethyl)phenyl)imidazo[1,2-b]pyridazine-3-carboxamide

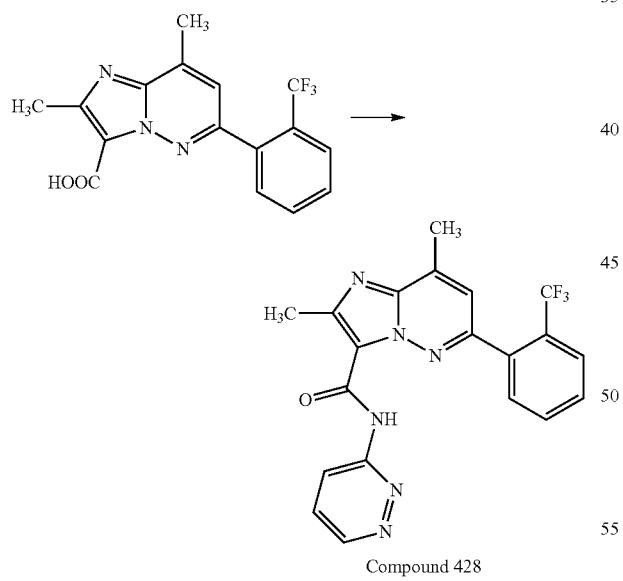

Compound 428

2,8-dimethyl-6-(2-(trifluoromethyl)phenyl)imidazo[1,2-b]pyridazine-3-carboxylic acid (150.0 mg, 0.45 mmol) was dissolved in DMF (2.4 mL). HATU (255.0 mg, 0.67 mmol) was added, followed by diisopropylethylamine (0.312 mL, 1.79 mmol). 3-aminopyridazine·HCl (59.0 mg, 0.45 mmol) was slurried in DMF (2.4 mL) and diisopropylethylamine (0.078 mL, 0.45 mmol) and added to the reaction mixture. This was warmed to 60° C. and allowed to stir under nitrogen atmosphere for 3.5 h. The mixture was cooled to room temp, and saturated aqueous NaHCO₃ was added (6 mL), then water was added (10 mL). This was extracted with EtOAc (3×20 mL) and the combined organics were washed with brine, dried with anhydrous Na₂SO₄, filtered, and concentrated. The crude product was purified by silica gel column chromatography using a gradient of 0-10% MeOH in CH₂Cl₂ to give 2,8-dimethyl-N-(pyridazin-3-yl)-6-(2-(trifluoromethyl)phenyl) imidazo[1,2-b]pyridazine-3-carboxamide (19.6 mg, 11%). MS (ESI) calcd for $C_{20}H_{15}F_3N_6O$: 412.13. found: 413.2 [M+H].

This general coupling procedure could be used to prepare a variety of 2,8-dimethyl-6-(2-trifluoromethyl)phenyl) and 2,8-dimethyl-6-(2-trifluoromethoxy)phenyl) imidazo[1,2-b]pyridazine-3-carboxamides by substituting the appropriate amine moiety for 3-aminopyridazine.

Example 25. Preparation of (R)-8-(2,3-dihydroxypropoxy)-2-methyl-N-(pyridazin-3-yl)-6-(2-(trifluoromethyl)phenyl)imidazo[1,2-b]pyridazine-3-carboxamide (Compound 773)

Step 1. Synthesis of 6-(2-(trifluoromethyl)phenyl)pyridazin-3-amine

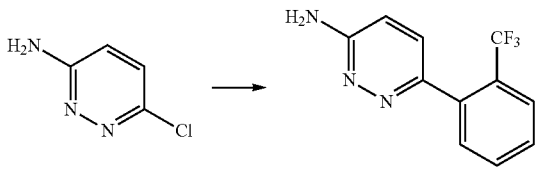 [SMILES: Nc1ccc(Cl)nn1 ; Nc1ccc(-c2ccccc2C(F)(F)F)nn1]

6-chloropyridazin-3-amine (10.0 g, 77.2 mmol) and 2-(trifluoromethyl)phenylboronic acid (29.3 g, 154.4 mmol) were added to a 250 mL flask. Cs₂CO₃ (50.3 g, 154.4 mol), Pd₂(dba)₃ (3.5 g, 3.82 mmol), and XPhos (1.8 g, 3.82 mmol) were added, followed by dioxane (100 mL) and water (20 mL). The reaction was heated to 100° C. for 3 h, followed by cooling to room temp. The mixture was concentrated in vacuo, and the residue was resuspended in DCM (500 mL). The organic layer was washed with bicarb (150 mL), then brine (150 mL), dried with Na₂SO₄, filtered and concentrated in vacuo. The crude product was purified via silica gel column chromatography (EtOAc:PE 2:1) to give 6-(2-(trifluoromethyl)phenyl)pyridazin-3-amine (14.0 g, 76%). MS (ESI) calcd for $C_{11}H_8F_3N_3$: 239.07.

Step 2. Synthesis of 4-bromo-6-(2-(trifluoromethyl)phenyl)pyridazin-3-amine

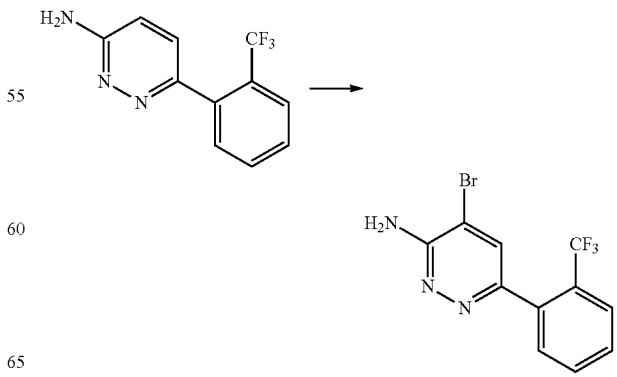

6-(2-(trifluoromethyl)phenyl)pyridazin-3-amine (3.0 g, 12.55 mmol) and NaHCO₃ (2.1 g, 25.1 mmol) were suspended in MeOH (30 mL). Br₂ was added (3.0 g, 0.96 mL, 18.8 mmol) dropwise at room temp. The reaction was allowed to stir for 1 h at room temp, then poured into bicarb (300 mL) after which a precipitate formed. The solid was collected by filtration, washed with water, and dried in vacuo to give 4-bromo-6-(2-(trifluoromethyl)phenyl)pyridazin-3-amine (3.8 g, 95%). MS (ESI) calcd for C₁₁H₂BrF₃N₃: 316.98.

Step 3. Synthesis of ethyl 8-bromo-2-methyl-6-(2-(trifluoromethyl)phenyl) imidazo[1,2-b]pyridazine-3-carboxylate

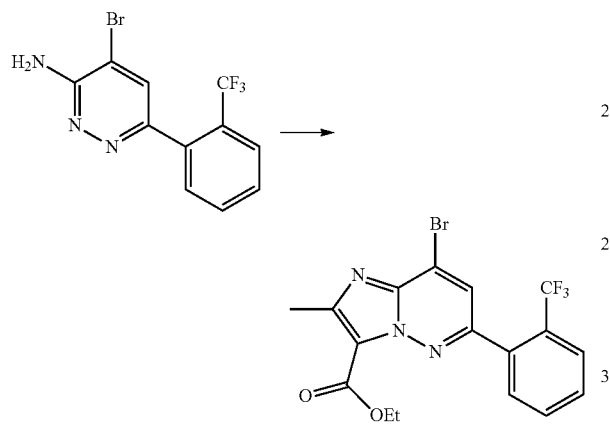

4-bromo-6-(2-(trifluoromethyl)phenyl)pyridazin-3-amine (500.0 mg, 1.57 mmol) was dissolved in EtOH (3.0 mL). Ethyl 2-chloro-3-oxobutanoate (285.0 mg, 1.73 mmol) was added and the reaction was heated to reflux under nitrogen atmosphere for 22 h. The mixture was cooled to room temp, concentrated in vacuo and purified via silica gel column chromatography (0-100% EtOAc/pentane) to give ethyl 8-bromo-2-methyl-6-(2-(trifluoromethyl)phenyl) imidazo[1,2-b]pyridazine-3-carboxylate (246.0 mg, 36%). MS (ESI) calcd for C₁₇H₁₃BrF₃N₃O₂: 427.01. found: 428 [M+H].

Step 4. Synthesis of 8-bromo-2-methyl-6-(2-(trifluoromethyl)phenyl)imidazo[1,2-b]pyridazine-3-carboxylic acid

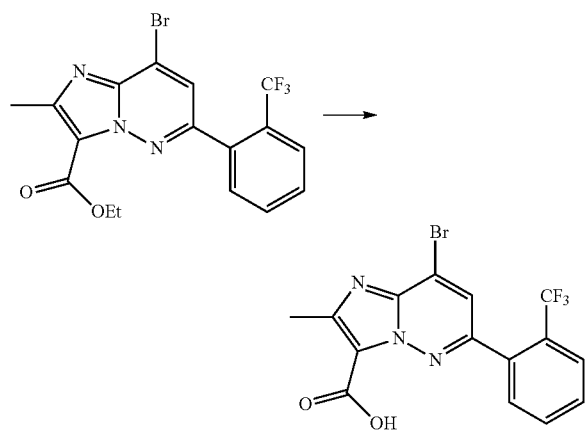

Ethyl 8-bromo-2-methyl-6-(2-(trifluoromethyl)phenyl) imidazo[1,2-b]pyridazine-3-carboxylate (246.0 mg, 0.573 mmol) was dissolved in THF (11.0 mL). Water was added (13.0 mL), followed by lithium hydroxide (55.0 mg, 2.29 mmol). The reaction was allowed to stir at room temp for 3.5 h. Aqueous HCl (1.0 N, 2.4 mL) was added, and the mixture was extracted with EtOAc (3×20 mL). The combined organics were washed with brine, dried with Na₂SO₄, filtered and concentrated in vacuo to give 8-bromo-2-methyl-6-(2-(trifluoromethyl)phenyl)imidazo[1,2-b]pyridazine-3-carboxylic acid (242.0 mg, quant.). MS (ESI) calcd for C₁₅H₉BrF₃N₃O₂: 398.98.

Step 5. Synthesis of 8-bromo-2-methyl-N-(pyridazin-3-yl)-6-(2-(trifluoromethyl)phenyl)imidazo[1,2-b]pyridazine-3-carboxamide

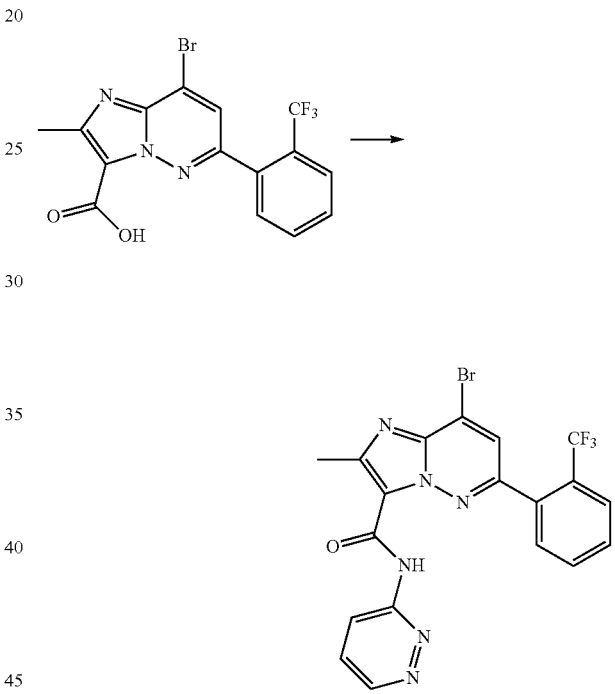

8-bromo-2-methyl-6-(2-(trifluoromethyl)phenyl)imidazo[1,2-b]pyridazine-3-carboxylic acid (75.0 mg, 0.187 mmol) was dissolved in MeCN (2.0 mL) in a vial. HATU (107.0 mg, 0.281 mmol), pyridine (44.0 mg, 0.562 mmol), and 3-aminopyridazine (54.0 mg, 0.562 mmol) were added. The vial was sealed and heated to 50° C. for 1 h, then to 80° C. for 2 h. The reaction was cooled to room temp and bicarb was added (4 mL). The mixture was extracted with EtOAc (3×15 mL). The combined organics were washed with brine, dried with Na₂SO₄, filtered and concentrated in vacuo. The residue was purified via silica gel column chromatography (0-10% MeOH/DCM) to give 8-bromo-2-methyl-N-(pyridazin-3-yl)-6-(2-(trifluoromethyl)phenyl)imidazo[1,2-b]pyridazine-3-carboxamide (53.0 mg, 60%). MS (ESI) calcd for C₁₉H₁₂BrF₃N₆O: 476.02. found: 477 [M+H].

This general procedure could be used to prepare a variety of 8-bromo-2-methyl-N-(pyridazin-3-yl)-6-(substituted) imidazo[1,2-b]pyridazine-3-carboxamides by substituting the appropriate amine for 3-aminopyridazine.

Step 6. Synthesis of (S)-8-((2,2-dimethyl-1,3-dioxo-lan-4-yl)methoxy)-2-methyl-N-(pyridazin-3-yl)-6-(2-(trifluoromethyl)phenyl)imidazo[1,2-b]pyridazine-3-carboxamide Step 7. Synthesis of (R)-8-(2,3-dihydroxypropoxy)-2-methyl-N-(pyridazin-3-yl)-6-(2-(trifluoromethyl)phenyl)imidazo[1,2-b]pyridazine-3-carboxamide

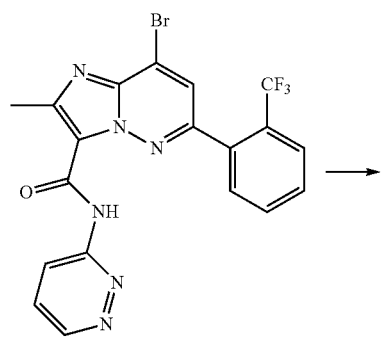

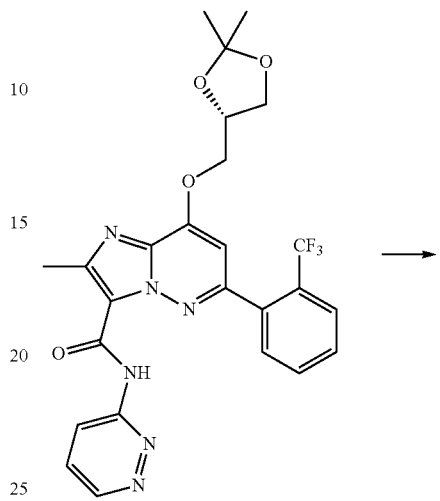

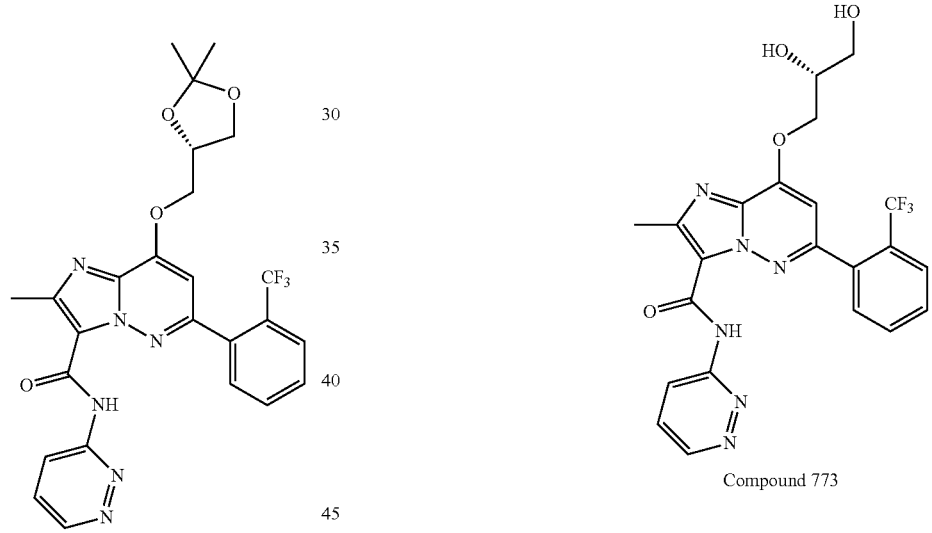

Compound 773

Sodium hydride (60% in oil, 14.0 mg, 350 mmol) was suspended in THF (2.0 mL). (S)-(2,2-dimethyl-1,3-dioxo-lan-4-yl)methanol (46.0 mg, 0.350 mmol) was added dropwise over 5 min. The mixture was allowed to stir at room temp for 30 min. 8-bromo-2-methyl-N-(pyridazin-3-yl)-6-(2-(trifluoromethyl)phenyl)imidazo[1,2-b]pyridazine-3-carboxamide (53.0 mg, 0.111 mmol) was added in THF (2.0 mL). The reaction was allowed to stir for 30 min at room temp, then was heated to reflux for 1.5 h, followed by cooling to room temp. Water was added (10 mL), and the mixture was extracted with EtOAc (3×10 mL). The combined organics were washed with brine, dried with $Na_2SO_4$, filtered and concentrated in vacuo. The residue was purified via silica gel column chromatography (0-10% MeOH/DCM) to give (S)-8-((2,2-dimethyl-1,3-dioxolan-4-yl)methoxy)-2-methyl-N-(pyridazin-3-yl)-6-(2-(trifluoromethyl)phenyl)imidazo[1,2-b]pyridazine-3-carboxamide (50.0 mg, 84%). MS (ESI) calcd for $C_{25}H_{23}F_3N_6O_4$: 528.17. found: 529 [M+H].

(S)-8-((2,2-dimethyl-1,3-dioxolan-4-yl)methoxy)-2-methyl-N-(pyridazin-3-yl)-6-(2-(trifluoromethyl)phenyl)imidazo[1,2-b]pyridazine-3-carboxamide (50.0 mg, 0.09 mmol) was dissolved in THF (2.1 mL). Concentrated HCl (0.031 mL) was added, and the reaction was allowed to stir at room temp for 2.5 h, during which time an orange precipitate formed. Bicarb and water were added (5 mL each), and the precipitate dissolved, followed by formation of a new precipitate (white). More water was added (35 mL) and the mixture was allowed to stand 10 min. The solid was collected by filtration, washed with water, and dried in vacuo. The solid was then further purified by trituration with EtOH, filtered and washed with EtOH and then diethyl ether, and dried in vacuo to give (R)-8-(2,3-dihydroxypropoxy)-2-methyl-N-(pyridazin-3-yl)-6-(2-(trifluoromethyl)phenyl)imidazo[1,2-b]pyridazine-3-carboxamide (6.5 mg, 14%). MS (ESI) calcd for $C_{22}H_{19}F_3N_6O_4$: 488.14. found: 489 [M+H].

This general procedure could be used to prepare a variety of 8-(2,3-dihydroxypropoxy)-2-methyl-N-(pyridazin-3-yl)-

6-(substituted)imidazo[1,2-b]pyridazine-3-carboxamides by substituting the appropriate amine for 3-aminopyridazine in step 5 described above.

Example 26. Preparation of 2-methyl-8-morpholino-N-(pyridazin-3-yl)-6-(2-(trifluoromethyl)phenyl)imidazo[1,2-b]pyridazine-3-carboxamide (Compound 738)

Step 1. Synthesis of 4-morpholino-6-(2-(trifluoromethyl)phenyl)pyridazin-3-amine

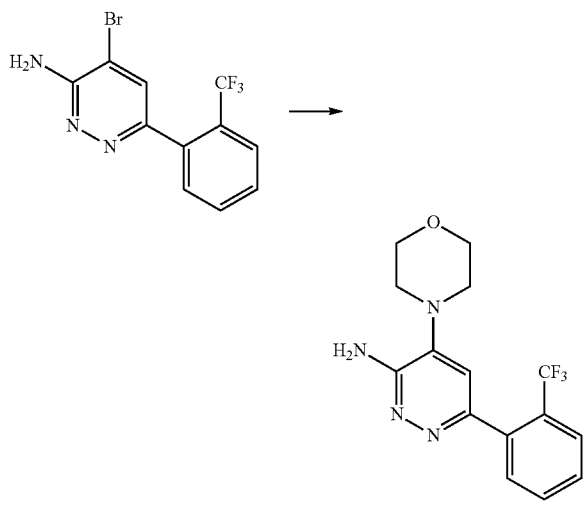

4-bromo-6-(2-(trifluoromethyl)phenyl)pyridazin-3-amine (100.0 mg, 0.314 mmol) was dissolved in DMSO (2.7 mL). Morpholine was added (0.27 mL, 3.14 mmol). The reaction was sealed and allowed to stir at room temp for 1 h, followed by heating to 110° C. for 18 h. The mixture was cooled to room temp and water was added (15 mL). The mixture was extracted with EtOAc (3×20 mL), and the combined organics were washed with brine, dried with $Na_2SO_4$, filtered and concentrated in vacuo to give 4-morpholino-6-(2-(trifluoromethyl)phenyl)pyridazin-3-amine (119.0 mg, quant.) which was used without further purification. MS (ESI) calcd for $C_{15}H_{15}F_3N_4O$: 324.12. found: 325 [M+H].

Step 2. Synthesis of ethyl 2-methyl-8-morpholino-6-(2-(trifluoromethyl)phenyl) imidazo[1,2-b]pyridazine-3-carboxylate

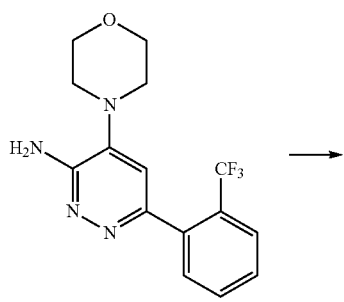

4-morpholino-6-(2-(trifluoromethyl)phenyl)pyridazin-3-amine (59.0 mg, 0.183 mmol) and ethyl-2-chloroacetoacetate (33.0 mg, 0.201 mmol) were dissolved in EtOH (1.0 mL) and heated to reflux under nitrogen atmosphere for 26 h. The reaction was cooled to room temp, causing a precipitate to form. The solid was collected by filtration, washed with cold EtOH, then diethyl ether, and dried in vacuo to give ethyl 2-methyl-8-morpholino-6-(2-(trifluoromethyl)phenyl)imidazo[1,2-b]pyridazine-3-carboxylate (26.0 mg, 33%). MS (ESI) calcd for $C_{21}H_{21}F_3N_4O_3$: 434.16. found: 435 [M+H].

Step 3. Synthesis of 2-methyl-8-morpholino-6-(2-(trifluoromethyl)phenyl)imidazo[1,2-b]pyridazine-3-carboxylic acid Ethyl 2-methyl-8-morpholino-6-(2-(trifluoromethyl)phenyl)imidazo[1,2-b]pyridazine-3-carboxylate (26.0 mg, 0.060 mmol) was suspended in THF (1.2 mL) water (2.4 mL) and MeOH (1 mL). Lithium hydroxide was added (7.0 mg, 0.300 mmol) and the mixture was heated to reflux for 3 h, followed by cooling to room temp. HCl was added (1.0 N, 0.35 mL), and the mixture was extracted with EtOAc (3×10 mL). The combined organics were washed with brine, dried with $Na_2SO_4$, filtered and concentrated to give 2-methyl-8-morpholino-6-(2-(trifluoromethyl)phenyl) imidazo[1,2-b]pyridazine-3-carboxylic acid (23.0 mg, 95%). MS (ESI) calcd for $C_{19}H_{17}F_3N_4O_3$: 406.13. found: 407 [M+H].

Step 4. Synthesis of 2-methyl-8-morpholino-N-(pyridazin-3-yl)-6-(2-(trifluoromethyl)phenyl)imidazo[1,2-b]pyridazine-3-carboxamide

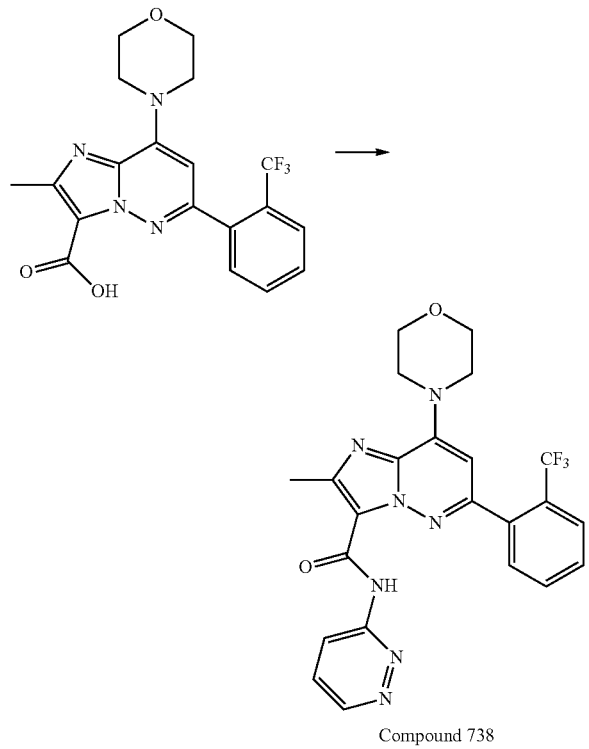

Compound 738

2-methyl-8-morpholino-6-(2-(trifluoromethyl)phenyl) imidazo[1,2-b]pyridazine-3-carboxylic acid (23.0 mg, 0.057 mmol) and 3-aminopyridazine (16.0 mg, 0.170 mmol) were dissolved in MeCN (1.2 mL). HATU (32.0 mg, 0.085 mmol) and pyridine (0.014 mL, 0.170 mmol) were added and the vial was sealed and heated to 50° C. for 1 h, then to 80° C. for 2 h. The reaction was cooled to room temp and bicarb (2 mL) and water (1 mL) were added. The mixture was extracted with EtOAc (3×5 mL) but there was precipitate in the organic layer. The solid was collected by filtration and washed with diethyl ether, and dried in vacuo to give 2-methyl-8-morpholino-N-(pyridazin-3-yl)-6-(2-(trifluoromethyl)phenyl)imidazo[1,2-b]pyridazine-3-carboxamide (8.0 mg, 29%). MS (ESI) calcd for $C_{23}H_{20}F_3N_7O_2$: 483.16. found: 484 [M+H].

Example 27. Preparation of 2-hydroxy-N-(pyridin-2-yl)-6-(2-(trifluoromethyl)phenyl) imidazo[1,2-b] pyridazine-3-carboxamide

Step 1. Synthesis of Ethyl 6-chloro-2-hydroxyimidazo[1,2-b]pyridazine-3-carboxylate

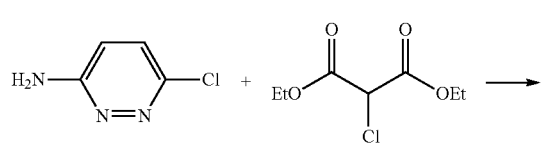

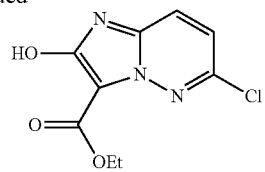

A mixture of 6-chloropyridazin-3-amine (2.0 g, 15.44 mmol) and diethyl 2-chloromalonate (4.51 g, 23.16 mmol) in EtOH (30 mL) was refluxed for 48 h. After cooling to room temp, the mixture was concentrated and purified by column chromatography to afford a 2:1 mixture of 6-chloropyridazin-3-amine and ethyl 6-chloro-2-hydroxyimidazo[1,2-b]pyridazine-3-carboxylate which was used without further purification. MS (ESI) calcd for $C_9H_8ClN_3O_3$: 241.03.

Step 2. Synthesis of ethyl 2-hydroxy-6-(2-(trifluoromethyl)phenyl)imidazo[1,2-b]pyridazine-3-carboxylate

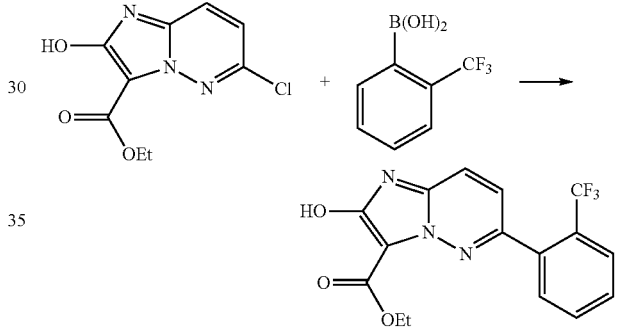

A mixture of ethyl 6-chloro-2-hydroxyimidazo[1,2-b]pyridazine-3-carboxylate (500.0 mg, 2.069 mmol), 2-(trifluoromethyl)phenylboronic acid (786.0 mg, 4.14 mmol), $K_3PO_4$ (878.0 mg, 4.14 mmol), $Pd_2dba_3$ (189.0 mg, 0.21 mmol), and X-Phos (197.0 mg, 0.41 mmol) was taken up in dioxane (30 mL), $H_2O$ (8 mL), EtOH (4 mL). The mixture was heated to 130° C. for 24 h. The solids were filtered, the filtrate was concentrated and purified by column chromatography to give ethyl 2-hydroxy-6-(2-(trifluoromethyl)phenyl)imidazo[1,2-b]pyridazine-3-carboxylate. MS (ESI) calcd for $C_{16}H_{12}F_3N_3O_3$: 351.1.

Step 3. Synthesis of 2-hydroxy-N-(pyridin-2-yl)-6-(2-(trifluoromethyl)phenyl)imidazo[1,2-b]pyridazine-3-carboxamide

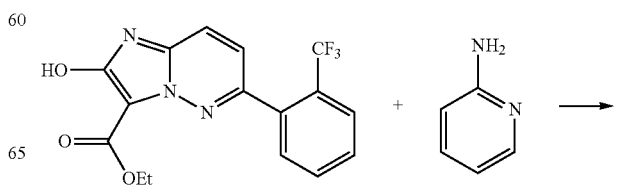

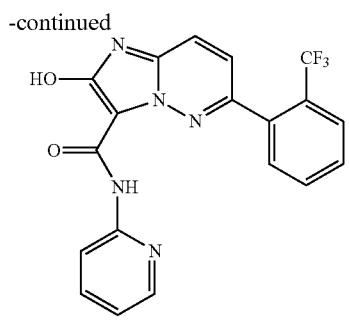

A mixture of Ethyl 2-hydroxy-6-(2-(trifluoromethyl)phenyl)imidazo[1,2-b]pyridazine-3-carboxylate (100.0 mg, 0.285 mmol), and pyridin-2-amine (54 mg, 0.57 mmol) was refluxed in toluene (10 mL) for 24 h. NaH (14 mg, 0.57 mmol) was then added and reflux was continued for another 2 h. The mixture was cooled to room temp, concentrated in vacuo and purified by column chromatography to give 2-hydroxy-N-(pyridin-2-yl)-6-(2-(trifluoromethyl)phenyl)imidazo[1,2-b]pyridazine-3-carboxamide (55 mg, 48%). MS (ESI) calcd for $C_{19}H_{12}F_3N_3O_2$: 399.1. found 399.9 [M+H].

This general coupling method could be used to prepare a variety of 2-hydroxy-N-(substituted)-6-(2-(trifluoromethyl)phenyl)imidazo[1,2-b]pyridazine-3-carboxamides by substituting the appropriate amine for pyridine-2-amine.

Example 28. Preparation of 6-morpholino-N-(6-(2-(trifluoromethyl)phenyl)imidazo[1,2-b]pyridazin-3-yl) pyrazine-2-carboxamide Step 1. Synthesis of benzyl 6-(2-(trifluoromethyl)phenyl)imidazo[1,2-b]pyridazin-3-ylcarbamate

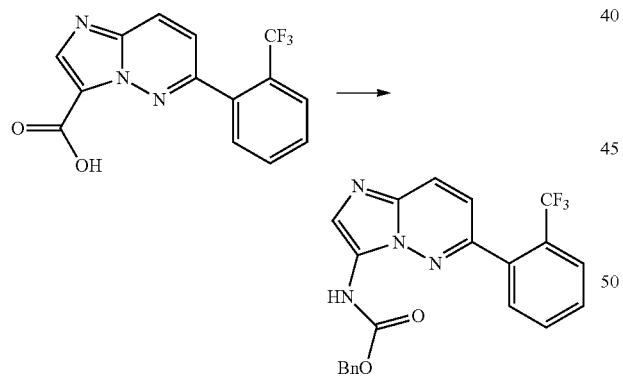

To a solution of 6-(2-(trifluoromethyl)phenyl)imidazo[1,2-b]pyridazine-3-carboxylic acid (1.70 g, 5.53 mmol) in toluene (22 mL) was added diphenylphosphorylamide (1.20 mL, 5.53 mmol), and triethylamine (1.20 mL, 8.29 mmol). The reaction mixture was stirred at 25° C. for 1 h then heated at reflux for 2 h. Benzyl alcohol (630 µl, 6.08 mmol) was added and heating continued for 16 h. The mixture was poured into citric acid (5% aq) and extracted with EtOAc. The combined organic layers were washed with sat. aq $NaHCO_3$, brine, dried ($MgSO_4$) and concentrated. The crude residue was purified by MPLC eluting with pentane/EtOAc (0-100%) to give 6-(2-(trifluoromethyl)phenyl)imidazo[1,2-b]pyridazin-3-amine. (1.07 g, 47% yield). MS (ESI) calcd for $C_{21}H_{15}F_3N_4O_2$ (m/z): 412.11. found: 413 [M+H].

Step 2. Synthesis of 6-(2-(trifluoromethyl)phenyl)imidazo[1,2-b]pyridazin-3-amine

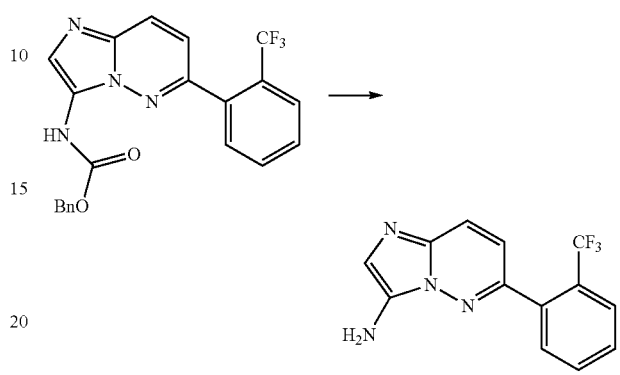

Pd/C 10 wt % (200 mg) was added to a degassed solution of benzyl 6-(2-(trifluoromethyl)phenyl)imidazo[1,2-b]pyridazin-3-ylcarbamate (1.07 g, 2.59 mmol) in THF/MeOH (40 mL, 1:1). The mixture was hydrogenated under balloon pressure at 25° C. for 16 h. The catalyst was removed by filtration and the mixture concentrated. The crude residue was purified by MPLC eluting with $CH_2Cl_2$/MeOH (0-5%) to give 6-(2-(trifluoromethyl)phenyl)imidazo[1,2-b]pyridazin-3-amine (651 mg, 90% yield). MS (ESI) calcd for $C_{13}H_9F_3N_4$ (m/z): 278.08. found: 279 [M+H].

Step 3. Synthesis of 5-methyl-N-(6-(2-(trifluoromethyl)phenyl)imidazo[1,2-b]pyridazin-3-yl)pyrazine-2-carboxamide (Compound 219)

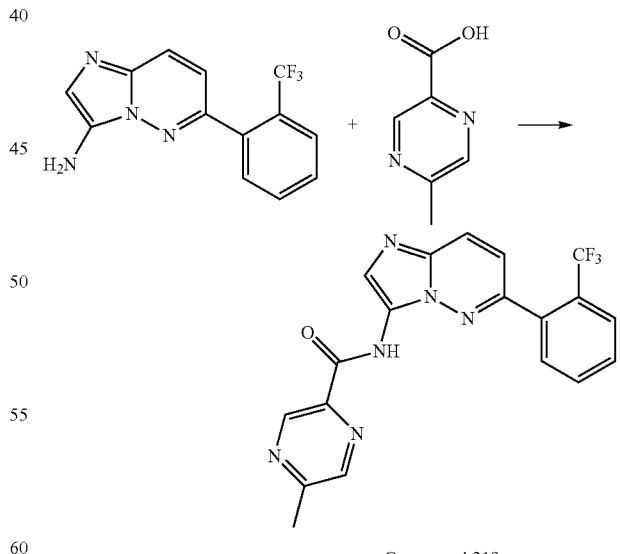

Compound 219

HATU (109 mg, 0.0.29 mmol) was added to a solution of 6-(2-(trifluoromethyl)phenyl)imidazo[1,2-b]pyridazin-3-amine (50.0 mg, 0.18 mmol), 5-methylpyrazine-2-carboxylic acid (37.0 mg, 0.27 mmol), and DIEA (78 µl, 0.44 mmol) in DMAC (7 mL) The mixture was stirred at 60° C.

for 3 h. H₂O (45 mL) was added and the resulting ppt was collected by filtration, rinsed with H₂O, and dried under vacuum. The crude residue was purified by MPLC eluting with CH₂Cl₂/MeOH (0-5%). The product was further purified by recrystallization from CH₃CN to give 5-methyl-N-(6-(2-(trifluoromethyl)phenyl)imidazo[1,2-b]pyridazin-3-yl)pyrazine-2-carboxamide (55.0 mg, 77% yield). MS (ESI) calcd for $C_{19}H_{13}F_3N_6O$ (m/z): 398.11. found: 399 [M+H].

This general coupling procedure could be used to prepare a variety of 6-(2-trifluoromethyl)phenyl)imidazo[1,2-b]pyridazin-3-yl)pyrazine-2-carboxamides by substituting the appropriate carboxylic acid moiety for 5-methylpyrazine-2-carboxylic acid.

Example 29. Preparation of 6-hydroxy-N-(6-(2-(trifluoromethyl)phenyl) imidazo[1,2-b]pyridazin-3-yl)pyrimidine-4-carboxamide

Example 30. Preparation of (S)-6-(2,3-dihydroxypropoxy)-N-(6-(2-(trifluoromethyl)phenyl)imidazo[1,2-b]pyridazin-3-yl) pyrazine-2-carboxamide hydrochloride Step 1. Synthesis of (R)-6-((2,2-dimethyl-1,3-dioxolan-4-yl)methoxy)-N-(6-(2-(trifluoromethyl)phenyl)imidazo[1,2-b]pyridazin-3-yl) pyrazine-2-carboxamide

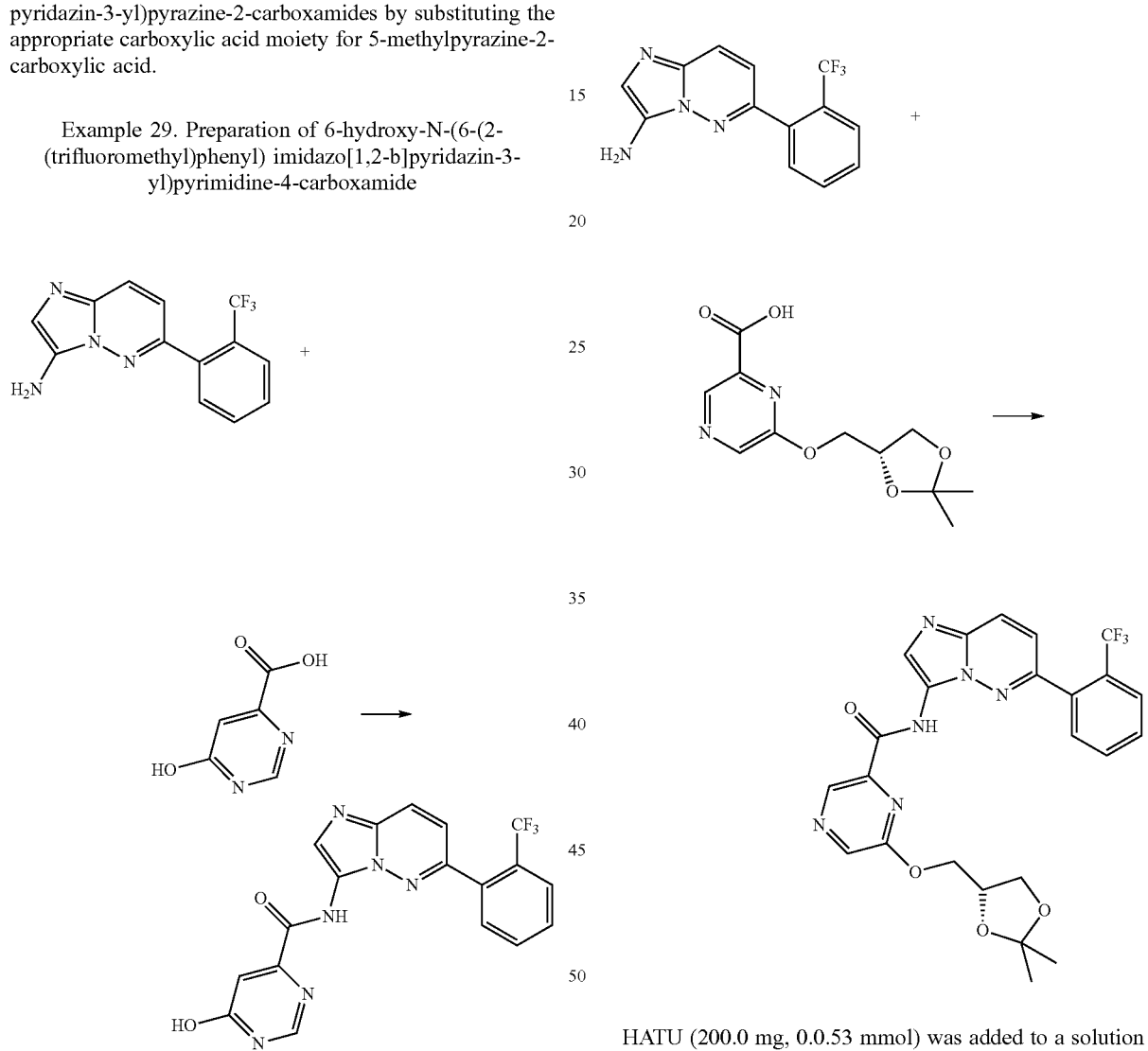

HATU (203.0 mg, 0.53 mmol) was added to a solution of 6-(2-(trifluoromethyl)phenyl)imidazo[1,2-b]pyridazin-3-amine (93.0 mg, 0.33 mmol), 6-hydroxypyrimidine-4-carboxylic acid (70.0 mg, 0.50 mmol), and pyridine (81 μl, 1.00 mmol) in CH₃CN (15 mL). The reaction mixture was heated at reflux for 72 h. H₂O was added and the resulting ppt was collected by filtration rinsed with H₂O and dried under vacuum. The crude residue was recrystallized from CH₃CN to give 6-hydroxy-N-(6-(2-(trifluoromethyl)phenyl) imidazo[1,2-b]pyridazin-3-yl)pyrimidine-4-carboxamide (73.0 mg, 55% yield). MS (ESI) calcd for $C_{18}H_{11}F_3N_6O_2$ (m/z): 400.09. found: 401 [M+H].

HATU (200.0 mg, 0.0.53 mmol) was added to a solution of 6-(2-(trifluoromethyl)phenyl)imidazo[1,2-b]pyridazin-3-amine (91.0 mg, 0.33 mmol), (R)-6-((2,2-dimethyl-1,3-dioxolan-4-yl)methoxy)pyrazine-2-carboxylic acid (125.0 mg, 0.49 mmol), and N,N-diisopropylethylamine (DIPEA) (150 μl, 0.82 mmol) in dimethylacetamide (DMAC) (6 mL). The mixture was stirred at 80° C. for 16 h. H₂O was added and the resulting ppt was collected by filtration, rinsed with H₂O, and dried under vacuum. The crude residue was purified by MPLC eluting with CH₂Cl₂/MeOH (0-5%) to give (R)-6-((2,2-dimethyl-1,3-dioxolan-4-yl)methoxy)-N-(6-(2-(trifluoromethyl)phenyl) imidazo[1,2-b]pyridazin-3-yl)pyrazine-2-carboxamide (113.0 mg, 67% yield). MS (ESI) calcd for $C_{24}H_{21}F_3N_6O_4$ (m/z): 514.16. found: 515 [M+H].

Step 2. Synthesis of (S)-6-(2,3-dihydroxypropoxy)-N-(6-(2-(trifluoromethyl)phenyl)imidazo[1,2-b]pyridazin-3-yl) pyrazine-2-carboxamide hydrochloride Example 31. Preparation of N-(2-methyl-6-(2-(trifluoromethyl)phenyl)imidazo[1,2-b]pyridazin-3-yl) picolinamide Step 1. Synthesis of 2-methyl-6-(2-(trifluoromethyl)phenyl)imidazo[1,2-b]pyridazin-3-amine

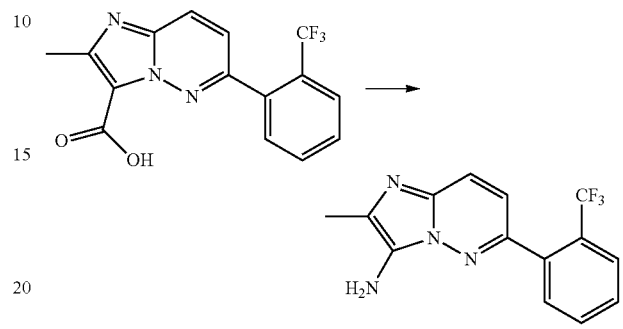

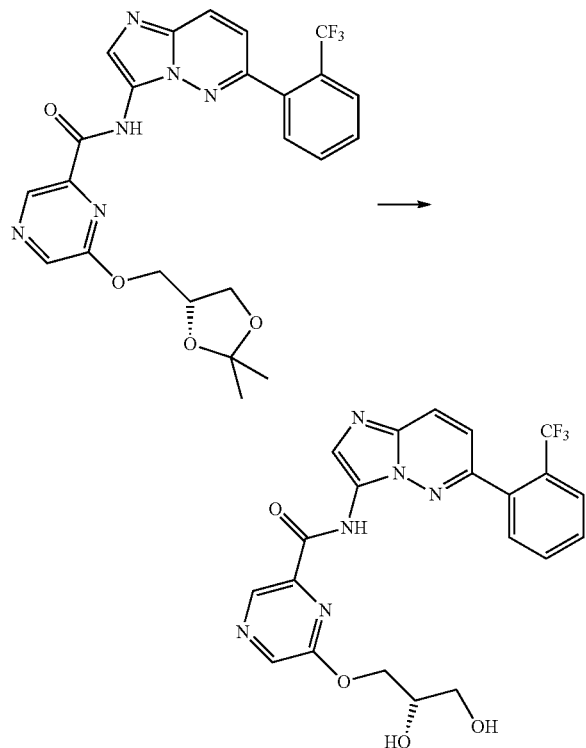

To a solution of 2-methyl-6-(2-(trifluoromethyl)phenyl)imidazo[1,2-b]pyridazine-3-carboxylic acid (3.50 g, 10.89 mmol) in DMF (100 mL) was added diphenylphosphorylamide (4.50 g, 16.34 mmol), and triethylamine (2.20 g, 21.79 mmol). The reaction mixture was stirred at 25° C. for 1.5 h. H$_2$O (2 mL) was added and the mixture was heated to 100° C. for 1 h. The mixture was poured into cold H$_2$O (250 mL) and the resulting ppt was collected by filtration to afford 2-methyl-6-(2-(trifluoromethyl)phenyl)imidazo[1,2-b]pyridazin-3-amine. (2.0 g, 63% yield). MS (ESI) calcd for C$_{14}$H$_{11}$F$_3$N$_4$ (m/z): 292.09.

This general procedure could be used to prepare a variety of N-(2-methyl-6-(2-(trifluoromethyl)phenyl) and N-(2-methyl-6-(2-chlorophenyl) imidazo[1,2-b]pyridazine-3-amines by starting with the appropriately substituted carboxylic acid moiety.

Step 2. Synthesis of N-(2-methyl-6-(2-(trifluoromethyl)phenyl)imidazo[1,2-b]pyridazin-3-yl)picolinamide

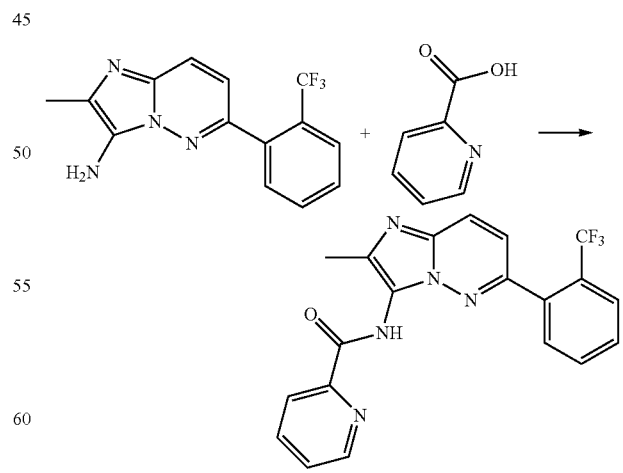

3N HCl (100 mL, 0.30 mmol) was added to a suspension of (R)-6-((2,2-dimethyl-1,3-dioxolan-4-yl)methoxy)-N-(6-(2-(trifluoromethyl)phenyl) imidazo[1,2-b]pyridazin-3-yl) pyrazine-2-carboxamide (113.0 mg, 0.22 mmol) in EtOH (10 mL). The mixture was heated at 60° C. until the mixture became homogenous then stirred at room temp for 16 h. The mixture was concentrated and the crude residue was recrystallized from CH$_3$CN to give (S)-6-(2,3-dihydroxypropoxy)-N-(6-(2-(trifluoromethyl)phenyl)imidazo[1,2-b]pyridazin-3-yl)pyrazine-2-carboxamide hydrochloride (87.0 mg, 78% yield). MS (ESI) calcd for C$_{21}$H$_{17}$F$_3$N$_6$O$_4$ (m/z): 474.13. found: 475 [M+H].

This general coupling procedure followed by acid deprotection could be used to prepare a variety of (6-(2-(trifluoromethyl)phenyl)imidazo[1,2-b]pyridazin-3-yl) substituted carboxamides by substituting the appropriate acid moiety for (R)-6-((2,2-dimethyl-1,3-dioxolan-4-yl)methoxy)pyrazine-2-carboxylic acid in step 1.

A solution of 2-methyl-6-(2-(trifluoromethyl)phenyl)imidazo[1,2-b]pyridazin-3-amine (75.0 mg, 0.26 mmol), picolinic acid (32.0 mg, 0.26 mmol), DIPEA (99.0 mg, 0.77 mmol) and HATU (124.0 mg, 0.51 mmol) in DMF (8 mL)

was stirred at 60° C. for 12 h. H$_2$O was added (30 mL) and the resulting ppt was collected by filtration and washed with MeOH to give N-(2-methyl-6-(2-(trifluoromethyl)phenyl) imidazo[1,2-b]pyridazin-3-yl)picolinamide (38.0 mg, 37%). MS (ESI) calcd for C$_{20}$H$_{14}$F$_3$N$_5$O (m/z): 397.12. found: 398 [M+H].

This general procedure could be used to prepare a variety of N-(2-methyl-6-(2-(trifluoromethyl)phenyl), N-(2-methyl-6-(2-chlorophenyl) imidazo[1,2-b]substituted amides by substituting the appropriate carboxylic acid for picolinic acid. In the case which includes a glycerol moiety, an extra deprotection step is required (see step 2 of the previous preparation).

Example 32. Preparation of N-(8-methyl-6-(2-(trifluoromethyl)phenyl)imidazo[1,2-b]pyridazin-3-yl) picolinamide (Compound 407)

Step 1. Synthesis of 8-methyl-6-(2-(trifluoromethyl) phenyl)imidazo[1,2-b]pyridazin-3-amine

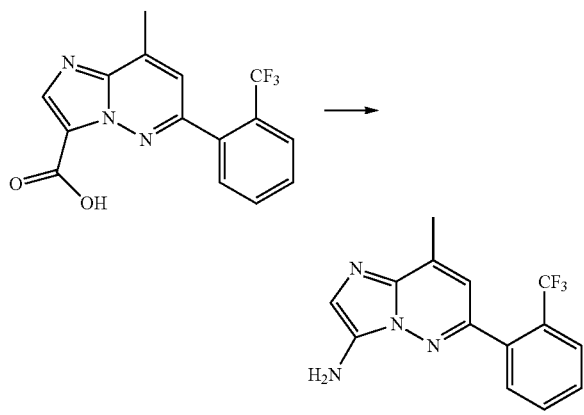

To a solution of 8-methyl-6-(2-(trifluoromethyl)phenyl) imidazo[1,2-b]pyridazine-3-carboxylic acid (3.0 g, 9.34 mmol) in DMF (10 mL) was added diphenylphosphorylamide (3.85 g, 14.01 mmol), and triethylamine (1.42 g, 14.01 mmol). The reaction mixture was stirred at 25° C. for 10 h. H$_2$O (0.2 mL) was added and stirring continued 24 h. The mixture was poured into 25% aq NaOH, and the resulting ppt was collected by filtration.

The crude residue was purified by flash chromatography to afford 8-methyl-6-(2-(trifluoromethyl)phenyl)imidazo[1,2-b]pyridazin-3-amine. (1.50 g, 55% yield). MS (ESI) calcd for C$_{14}$H$_{11}$F$_3$N$_4$ (m/z): 292.09.

Step 2. Synthesis of N-(8-methyl-6-(2-(trifluoromethyl)phenyl)imidazo[1,2-b]pyridazin-3-yl)picolinamide

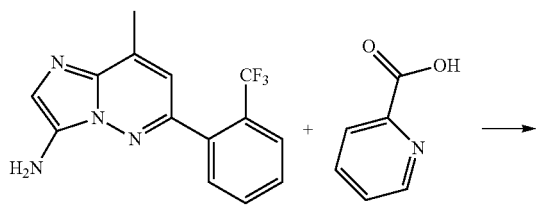

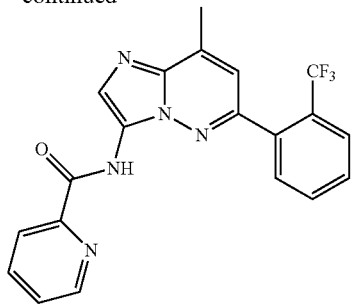

Compound 407

A solution of 8-methyl-6-(2-(trifluoromethyl)phenyl)imidazo[1,2-b]pyridazin-3-amine (100.0 mg, 0.34 mmol), picolinic acid (63.0 mg, 0.51 mmol), DIPEA (88.0 mg, 0.68 mmol) and HATU (260.0 mg, 0.68 mmol) in DMF (5 mL) was stirred at 70° C. for 16 h and H$_2$O was added. The crude residue was purified by flash chromatography to give N-(8-methyl-6-(2-(trifluoromethyl)phenyl) imidazo[1,2-b] pyridazin-3-yl)picolinamide (55.0 mg, 41%). MS (ESI) calcd for C$_{20}$H$_{14}$F$_3$N$_5$O (m/z): 397.12. found: 398 [M+H].

This general procedure could be used to prepare a variety of N-substituted-(2-(trifluoromethyl)phenyl) imidazo[1,2-b] pyridazin-3-yl)amides by substituting the appropriate carboxylic acid for picolinic acid. In cases where this carboxylic acid contains a glycerol moiety, an extra deprotection step is required (as previously shown).

Example 33. Preparation of N-(7-methyl-6-(2-(trifluoromethyl)phenyl)imidazo[1,2-b]pyridazin-3-yl) picolinamide (Compound 441)

Step 1. Synthesis of 7-methyl-6-(2-(trifluoromethyl) phenyl)imidazo[1,2-b]pyridazin-3-amine

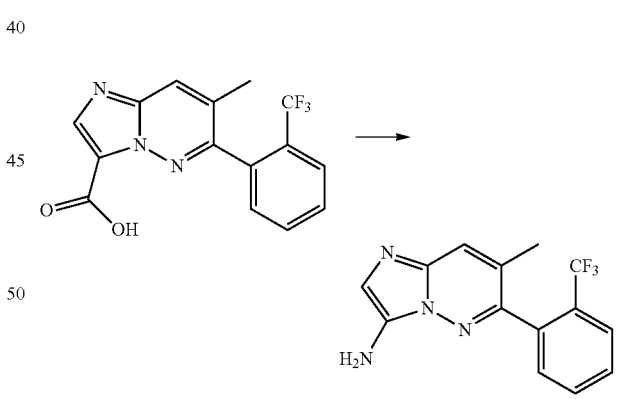

To a solution of 7-methyl-6-(2-(trifluoromethyl)phenyl) imidazo[1,2-b]pyridazine-3-carboxylic acid (1.5 g, 4.67 mmol) in DMF (10 mL) was added diphenylphosphorylamide (1.93 g, 7.00 mmol), and triethylamine (709.0 mg, 7.00 mmol). The reaction mixture was stirred at 25° C. for 10 h. H$_2$O (0.15 mL) was added and the mixture was stirred at room temp for 24 h. The mixture was poured into 25% aq NaOH, and the resulting ppt was collected by filtration. The crude residue was purified by flash chromatography to afford 7-methyl-6-(2-(trifluoromethyl)phenyl)imidazo[1,2-b] pyridazin-3-amine (650.0 mg, 48% yield). MS (ESI) calcd for C$_{14}$H$_{11}$F$_3$N$_4$ (m/z): 292.09.

Step 2. Synthesis of N-(7-methyl-6-(2-(trifluoromethyl)phenyl)imidazo[1,2-b]pyridazin-3-yl)picolinamide

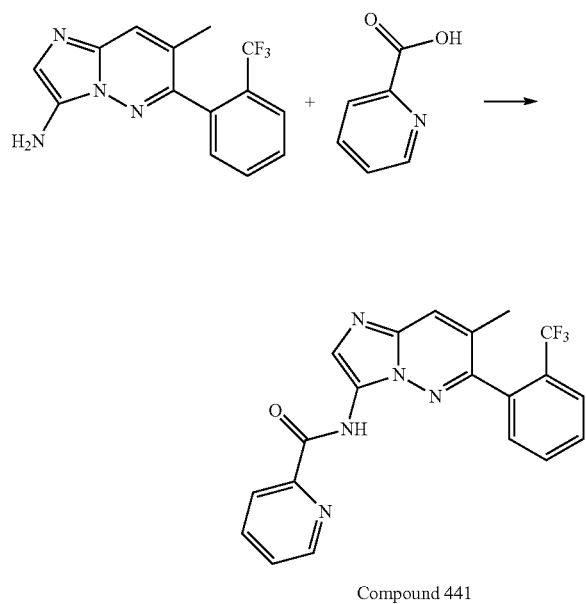

Compound 441

A solution of 7-methyl-6-(2-(trifluoromethyl)phenyl)imidazo[1,2-b]pyridazin-3-amine (50.0 mg, 0.17 mmol), picolinic acid (32.0 mg, 0.26 mmol), DIPEA (44.0 mg, 0.34 mmol) and HATU (130.0 mg, 0.34 mmol) in DMF (5 mL) was stirred at 70° C. for 16 h. H$_2$O was added and the resulting ppt was purified by flash chromatography to give N-(7-methyl-6-(2-(trifluoromethyl)phenyl) imidazo[1,2-b]pyridazin-3-yl)picolinamide (45.0 mg, 66%). MS (ESI) calcd for C$_2$H$_{14}$F$_3$N$_5$O (m/z): 397.12. found: 398 [M+H].

This general procedure could be used to prepare a variety N-(7-methyl-6-(2-(trifluoromethyl)phenyl)imidazo[1,2-b]pyridazin-3-yl)amides by substituting the appropriate carboxylic acid for picolinic acid.

Example 34. Preparation of 6-(2,3-dihydroxypropoxy)-N-(7,8-dimethyl-6-(2-(trifluoromethyl)phenyl) imidazo[1,2-b]pyridazin-3-yl)picolinamide (Compound 422)

Step 1. Synthesis of tert-butyl 7,8-dimethyl-6-(2-(trifluoromethyl)phenyl) imidazo[1,2-b]pyridazin-3-ylcarbamate

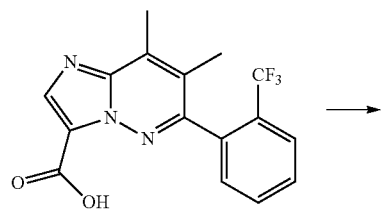

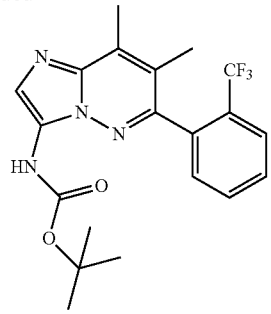

7,8-dimethyl-6-(2-(trifluoromethyl)phenyl)imidazo[1,2-b]pyridazine-3-carboxylic acid (420.0 mg, 1.25 mmol) was suspended in t-BuOH (2.6 mL) and toluene (2.6 mL). Triethylamine (0.58 mL, 4.13 mmol) was added, followed by dropwise addition of diphenylphosphorylamide (0.45 mL, 2.09 mmol). The mixture was warmed to 65° C. for 1 h, then heated to reflux for 17 h. The reaction was cooled and concentrated, and the residue suspended in EtOAc (50 mL). The organic layer was washed with saturated aqueous NaHCO$_3$ (25 mL) and brine (25 mL), dried with Na$_2$SO$_4$, filtered and concentrated. Purification by silica gel column chromatography (0-100% EtOAc/pentane) gave tert-butyl 7,8-dimethyl-6-(2-(trifluoromethyl)phenyl) imidazo[1,2-b]pyridazin-3-ylcarbamate (280.0 mg, 55%). MS (ESI) calcd for C$_{20}$H$_{21}$F$_3$N$_4$O$_2$: 406.16. found: 407 [M+H].

Step 2. Synthesis of 7,8-dimethyl-6-(2-(trifluoromethyl)phenyl)imidazo[1,2-b]pyridazin-3-amine

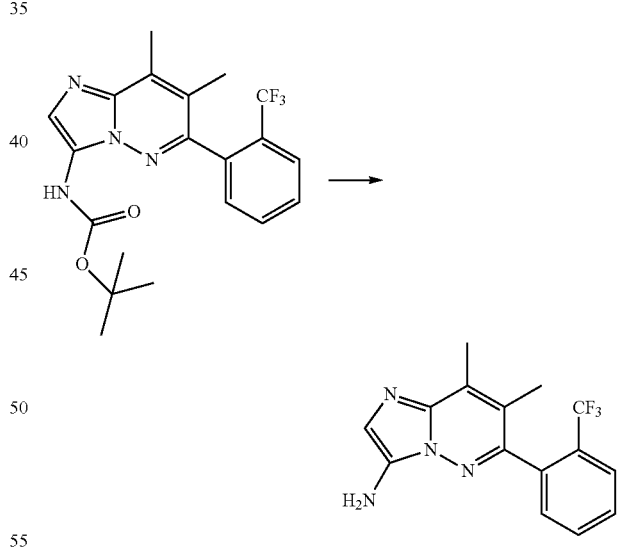

Tert-butyl 7,8-dimethyl-6-(2-(trifluoromethyl)phenyl) imidazo[1,2-b]pyridazin-3-ylcarbamate (280.0 mg, 0.69 mmol) was dissolved in CH$_2$Cl$_2$ (2.0 mL). Trifluoroacetic acid (1.0 mL) was added, and the reaction was allowed to stir for 2 h. The mixture was concentrated and water (5 mL) and saturated aqueous NaHCO$_3$ (5 mL) were added. The aqueous mixture was extracted with EtOAc (3×20 mL), and the combined organics were washed with brine, dried with Na$_2$SO$_4$, filtered and concentrated. The residue was triturated with pentane, and the solid was dried under vacuum to give 7,8-dimethyl-6-(2-(trifluoromethyl)phenyl)imidazo[1, 2-b]pyridazin-3-amine (182.0 mg, 86%). MS (ESI) calcd for C$_{15}$H$_{13}$F$_3$N$_4$: 306.11. found: 307 [M+H].

Step 3. Synthesis of 6-((2,2-dimethyl-1,3-dioxolan-4-yl)methoxy)-N-(7,8-dimethyl-6-(2-(trifluoromethyl)phenyl)imidazo[1,2-b]pyridazin-3-yl)picolinamide

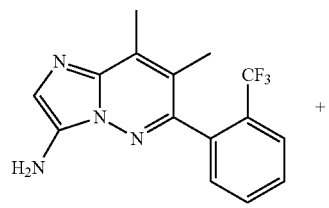

+

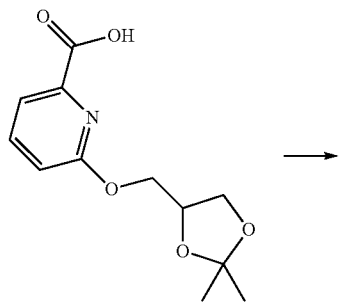

→

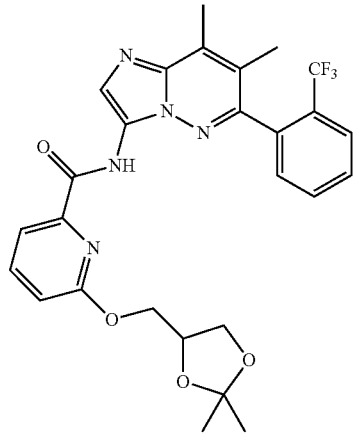

7,8-dimethyl-6-(2-(trifluoromethyl)phenyl)imidazo[1,2-b]pyridazin-3-amine (45.0 mg, 0.15 mmol) and 6-((2,2-dimethyl-1,3-dioxolan-4-yl) methoxy)picolinic acid (38.0 mg, 0.15 mmol) were coupled according to the general amide coupling procedure to give 6-((2,2-dimethyl-1,3-dioxolan-4-yl)methoxy)-N-(7,8-dimethyl-6-(2-(trifluoromethyl)phenyl)imidazo[1,2-b]pyridazin-3-yl)picolinamide (60.0 mg, 75%). MS (ESI) calcd for C$_{27}$H$_{26}$F$_3$N$_5$O$_4$: 541.19. found: 542 [M+H].

This general procedure could be used to prepare a variety of substituted-(7,8-dimethyl-6-(2-(trifluoromethyl)phenyl)imidazo[1,2-b]pyridazin-3-yl)amides by substituting the appropriate carboxylic acid for 6-((2,2-dimethyl-1,3-dioxolan-4-yl)methoxy)picolinic acid.

Step 4. Synthesis of 6-(2,3-dihydroxypropoxy)-N-(7,8-dimethyl-6-(2-(trifluoromethyl)phenyl)imidazo[1,2-b]pyridazin-3-yl)picolinamide

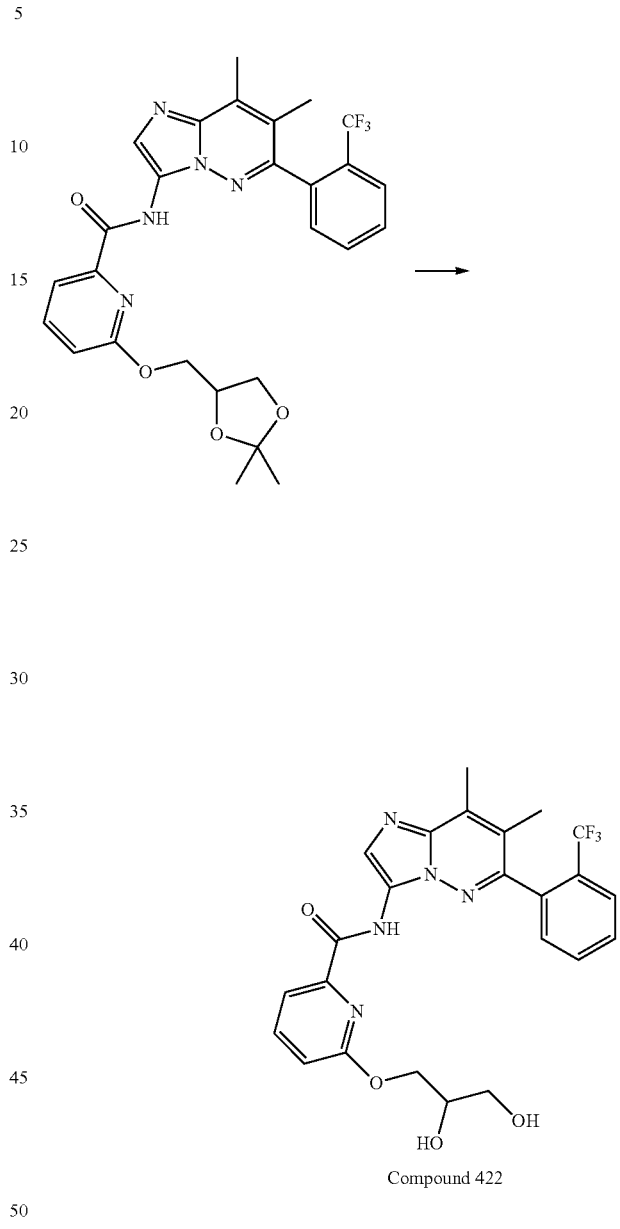

Compound 422

6-((2,2-dimethyl-1,3-dioxolan-4-yl)methoxy)-N-(7,8-dimethyl-6-(2-(trifluoromethyl)phenyl)imidazo[1,2-b]pyridazin-3-yl)picolinamide (60.0 mg, 0.11 mmol) was dissolved in THF (2.4 mL). Concentrated HCl (aq.) (0.04 mL, 0.44 mmol) was added and the reaction was allowed to stir at room temp for 6 h. Water (5 mL) and saturated aqueous NaHCO$_3$ (5 mL) were added and the mixture was extracted with EtOAc (3×20 mL). The combined organics were washed with brine, dried with Na$_2$SO$_4$, filtered and concentrated. The crude product was triturated with minimal CH$_2$Cl$_2$ in Et$_2$O, the suspension filtered and the solid washed with Et$_2$O. The solid was dried under vacuum to give 6-(2,3-dihydroxypropoxy)-N-(7,8-dimethyl-6-(2-(trifluoromethyl)phenyl) imidazo[1,2-b]pyridazin-3-yl)picolinamide (30.0 mg, 54%). MS (ESI) calcd for C$_{24}$H$_{22}$F$_3$N$_5$O$_4$: 501.16. found: 502 [M+H].

131

Example 35. Preparation of N-(2,8-dimethyl-6-(2-(trifluoromethyl)phenyl)imidazo[1,2-b]pyridazin-3-yl)-6-methoxypicolinamide (Compound 589)

Step 1. Synthesis of tert-butyl 2,8-dimethyl-6-(2-(trifluoromethyl)phenyl) imidazo[1,2-b]pyridazin-3-ylcarbamate

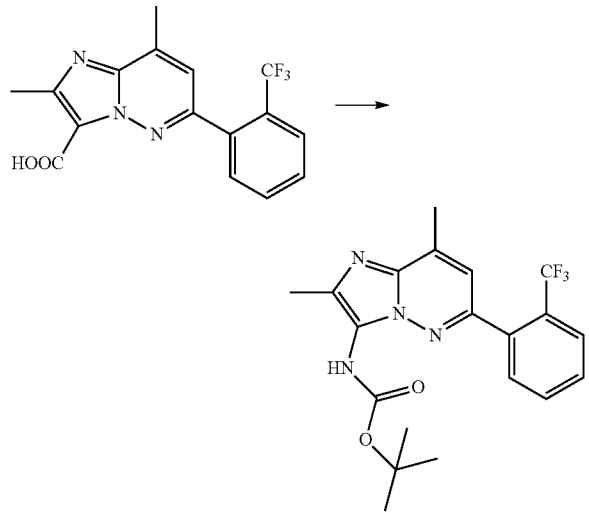

To 2,8-dimethyl-6-(2-(trifluoromethyl)phenyl)imidazo[1,2-b]pyridazine-3-carboxylic acid (500.0 mg, 1.49 mmol) suspended in 1:1 t-BuOH/toluene (6.4 mL) was added triethylamine (0.686 mL, 4.92 mmol), followed by dropwise addition of diphenylphosphorylamide (0.537 mL, 2.49 mmol) over 15 min. The mixture was warmed to 55° C. for 2 h, then heated to reflux for 19 h, followed by cooling and concentration, resuspension in EtOAc and saturated aqueous NaHCO$_3$. The layers were separated and the aqueous layer was washed with EtOAc (3×50 mL). The combined organics were washed with brine, dried with anhydrous Na$_2$SO$_4$, filtered and concentrated. Purification by silica gel column chromatography (0-100% gradient EtOAc in pentane) gave tert-butyl 2,8-dimethyl-6-(2-(trifluoromethyl)phenyl) imidazo[1,2-b]pyridazin-3-ylcarbamate (0.22 g, 36%). MS (ESI) calcd for C$_{20}$H$_{21}$F$_3$N$_4$O$_2$: 406.16.

Step 2. Synthesis of 2,8-dimethyl-6-(2-(trifluoromethyl)phenyl)imidazo[1,2-b]pyridazin-3-amine

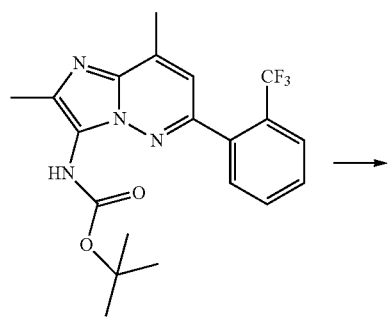

132

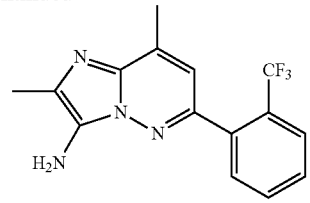

Tert-butyl 2,8-dimethyl-6-(2-(trifluoromethyl)phenyl)imidazo[1,2-b]pyridazin-3-ylcarbamate (220.0 mg, 0.54 mmol) was dissolved in CH$_2$Cl$_2$ (1.6 mL). Trifluoroacetic acid (0.784 mL) was added and the mixture was allowed to stir at room temp for 2.5 h. The mixture was concentrated and water (10 mL) was added, as well as saturated aqueous NaHCO$_3$ (10 mL). Extraction with EtOAc (3×20 mL), washing with brine, drying with anhydrous Na$_2$SO$_4$, filtration and concentration gave crude product. Trituration with pentane (5×10 mL) and vacuum drying gave 2,8-dimethyl-6-(2-(trifluoromethyl)phenyl)imidazo[1,2-b]pyridazin-3-amine (0.158 g, 95%). MS (ESI) calcd for C$_{15}$H$_{13}$F$_3$N$_4$: 306.11. found: 307.1 [M+H].

Step 3. Synthesis of N-(2,8-dimethyl-6-(2-(trifluoromethyl)phenyl)imidazo[1,2-b]pyridazin-3-yl)-6-methoxypicolinamide

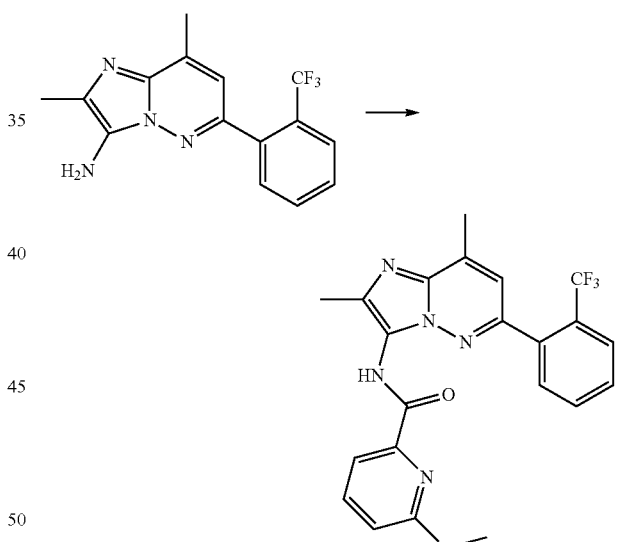

Compound 589

6-methoxypicolinic acid (40.0 mg, 0.26 mmol) was dissolved in dimethylformamide (1.0 mL). HATU (147.0 mg, 0.39 mmol) was added, followed by diisopropylethylamine (0.18 mL, 1.03 mmol). 2,8-dimethyl-6-(2-(trifluoromethyl)phenyl)imidazo[1,2-b]pyridazin-3-amine (79.0 mg, 0.26 mmol) was dissolved in 2.1 mL dimethylformamide and added to the reaction mixture, which was then warmed to 50° C. for 4 h. The mixture was cooled to room temp and saturated aqueous NaHCO$_3$ (4 mL) and water (4 mL) were added. An orange precipitate formed, and the mixture was filtered through a glass frit. The solid was washed with water and dried under vacuum, followed by purification by silica gel column chromatography (0-10% gradient MeOH in CH₂Cl₂) to give N-(2,8-dimethyl-6-(2-(trifluoromethyl)phenyl)imidazo[1,2-b]pyridazin-3-yl)-6-methoxypicolinamide (24.0 mg, 21%). MS (ESI) calcd for C₂₂H₁₈F₃N₄O₂: 441.14. found: 442.1 [M+H].

This general coupling procedure could be used to prepare N-(2,8-dimethyl-6-(2-(trifluoromethyl)phenyl)imidazo[1,2-b]pyridazin-3-yl)-6-hydroxypicolinamide.

Example 36. Preparation of (S)-N-(6-(3-fluoropyrrolidin-1-yl)imidazo[1,2-b]pyridazin-3-yl)-6-methylpicolinamide (Compound 565)

Step 1. Synthesis of (S)-6-(3-fluoropyrrolidin-1-yl)imidazo[1,2-b]pyridazin-3-amine

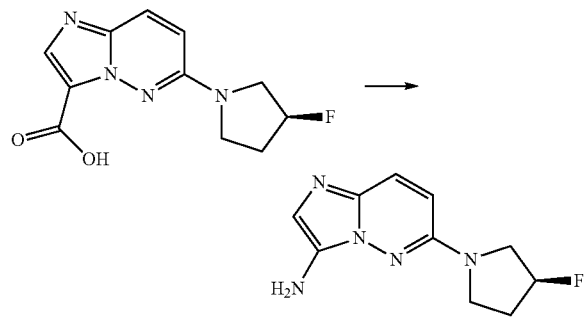

To a solution of (S)-6-(3-fluoropyrrolidin-1-yl)imidazo[1,2-b]pyridazine-3-carboxylic acid (600.0 mg, 1.71 mmol) in DMF (20 mL) was added diphenylphosphorylamide (707.0 mg, 2.57 mmol), and triethylamine (346.0 mg, 3.42 mmol). The reaction mixture was stirred at 25° C. for 1 h. H₂O (1 mL) was added and the mixture was heated at 70° C. for 1 h. The mixture was poured into 25% aq NaOH, and the resulting ppt was collected by filtration. The crude residue was purified by flash chromatography to afford (S)-6-(3-fluoropyrrolidin-1-yl)imidazo[1,2-b]pyridazin-3-amine (250.0 mg, 66% yield). MS (ESI) calcd for C₁₀H₁₂FN₄ (m/z): 221.11.

Step 2. Synthesis of (S)-N-(6-(3-fluoropyrrolidin-1-yl)imidazo[1,2-b]pyridazin-3-yl)-6-methylpicolinamide

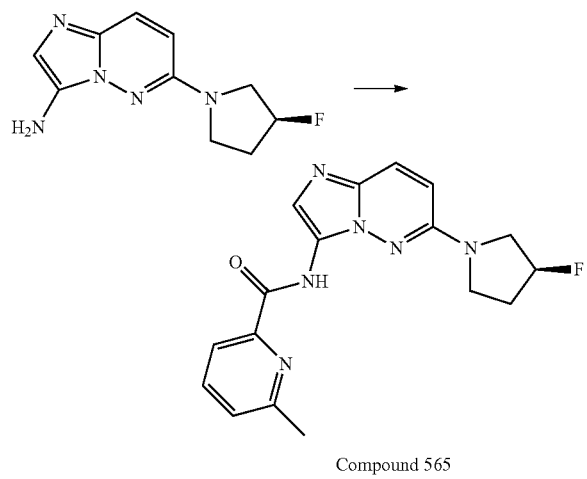

Compound 565

A solution of (S)-6-(3-fluoropyrrolidin-1-yl)imidazo[1,2-b]pyridazin-3-amine (44.0 mg, 0.20 mmol), 6-methylpicolinic acid (33.0 mg, 0.24 mmol), DIPEA (51.0 mg, 0.40 mmol), and HATU in DMF (8 mL) was heated at 60° C. for 3 h. The crude residue was purified by flash chromatography to afford (S)-N-(6-(3-fluoropyrrolidin-1-yl)imidazo[1,2-b]pyridazin-3-yl)-6-methylpicolinamide (30 mg, 44% yield). MS (ESI) calcd for C₁₇H₁₇FN₆O (m/z): 340.14. found: 341 [M+H].

This general procedure could be used to prepare a variety of N-(6-(3-fluoropyrrolidin-1-yl)imidazo[1,2-b]pyridazin-3-yl) amides by substituting the appropriate carboxylic acid moiety for 6-methylpicolinic acid.

Example 37. Preparation of N-(pyridin-4-yl)-5-(2-(trifluoromethyl)phenyl)pyrazolo[1,5-a]pyrimidine-3-carboxamide (Compound 240)

Step 1. Synthesis of ethyl 5-oxo-4,5-dihydropyrazolo[1,5-a]pyrimidine-3-carboxylate

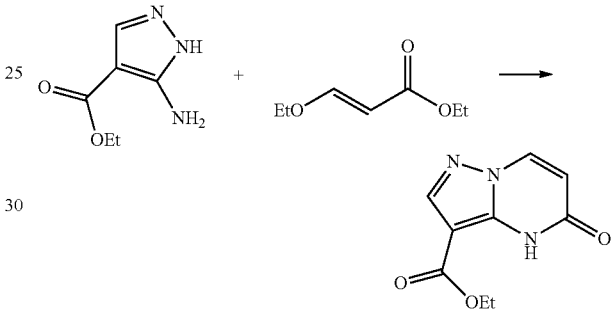

Cs₂CO₃ (64.20 g, 197.20 mmol) was added to a solution of ethyl 5-amino-1H-pyrazole-4-carboxylate (20.40 g, 131.40 mmol) and ethyl-3-ethoxyacrylate (28.6 mL, 197.20 mmol) in DMF (250 mL). The reaction mixture was stirred at 110° C. for 16 h. The mixture was cooled to room temp and the pH was adjusted to 4 by the addition of AcOH (80 mL). The mixture was concentrated in vacuo and the residue partitioned between CH₂Cl₂/H₂O (1000 mL, 1:1). The organic layer was separated and the aqueous layer was extracted with CH₂Cl₂ (3×500 mL). The combined organics were washed with brine, dried (MgSO₄) and concentrated. The crude residue was suspended in EtOH (300 mL) and heated to boiling. After cooling to room temperature the solid was collected by filtration, rinsed with EtOH, then Et₂O and dried under vacuum to give ethyl 5-oxo-4,5-dihydropyrazolo[1,5-a]pyrimidine-3-carboxylate (25.16 g, 92%). MS (ESI) calcd for C₉H₉N₃O₃ (m/z): 207.06. found: 208 [M+H].

Step 2. Synthesis of ethyl 5-chloropyrazolo[1,5-a]pyrimidine-3-carboxylate

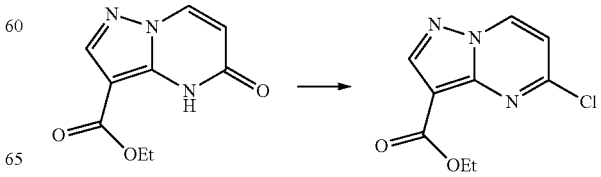

A mixture of ethyl 5-oxo-4,5-dihydropyrazolo[1,5-a]pyrimidine-3-carboxylate (5.70 g, 27.52 mmol) in phosphoryl trichloride (50 mL) was heated at 120° C. for 4 h. The reaction mixture was concentrated in vacuo. The crude residue was partitioned between CH$_2$Cl$_2$ and iced, sat. aq NaHCO$_3$. The organic phase was separated and washed with brine, dried and concentrated to give ethyl 5-chloropyrazolo[1,5-a]pyrimidine-3-carboxylate (5.40 g, 94% yield). MS (ESI) calcd for C$_9$H$_8$ClN$_3$O$_2$ (m/z): 225.03.

Step 3. Synthesis of ethyl 5-(2-(trifluoromethyl)phenyl)pyrazolo[1,5-a]pyrimidine-3-carboxylate

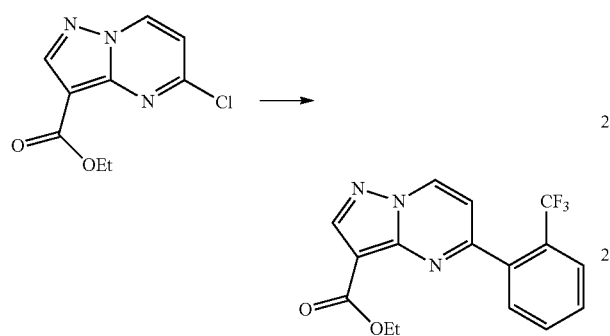

Nitrogen was bubbled through a solution of ethyl 5-chloropyrazolo[1,5-a]pyrimidine-3-carboxylate (5.40 g, 23.94 mmol) in dioxane/EtOH/H$_2$O (130 mL, 20:3:3). 2-(trifluoromethyl)phenylboronic acid (6.80 g, 35.90 mmol), Pd(PPh$_3$)$_4$ (2.80 g, 2.39 mmol), and Cs$_2$CO$_3$ (15.60 g, 47.88 mmol) were added and the reaction mixture was heated at reflux for 2 h. The mixture was cooled to room temp, poured into EtOAc (300 mL) washed with brine, dried (MgSO$_4$), and concentrated. The crude residue was purified by MPLC eluting with pentane/EtOAc (0-100%) to give ethyl 5-(2-(trifluoromethyl)phenyl)pyrazolo[1,5-a]pyrimidine-3-carboxylate (6.30 g, 78% yield). MS (ESI) calcd for C$_{16}$H$_{12}$F$_3$N$_3$O$_2$ (m/z): 335.09. found: 336 [M+H].

Step 4. Synthesis of 5-(2-(trifluoromethyl)phenyl)pyrazolo[1,5-a]pyrimidine-3-carboxylic acid

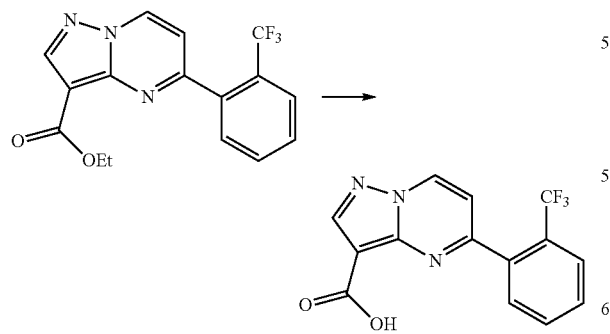

A solution of LiOH (902.0 mg, 37.60 mmol) in H$_2$O (30 mL) was added to a solution of ethyl 5-(2-(trifluoromethyl)phenyl)pyrazolo[1,5-a]pyrimidine-3-carboxylate (6.30 g, 18.80 mmol) in THF (75 mL) and MeOH (20 mL). The reaction mixture was stirred at 25° C. for 16 h. The pH was adjusted to 3 by the addition of 3N HCl (13 mL). The mixture was poured into brine, extracted with EtOAc, dried and concentrated. The crude residue was recrystallized from EtOH (70 mL) to give 5-(2-(trifluoromethyl)phenyl)pyrazolo[1,5-a]pyrimidine-3-carboxylic acid (4.20 g, 73% yield). MS (ESI) calcd for C$_{14}$H$_8$F$_3$N$_3$O$_2$ (m/z): 307.06. found: 308 [M+H].

Step 5. Synthesis of N-(pyridin-4-yl)-5-(2-(trifluoromethyl)phenyl)pyrazolo[1,5-a]pyrimidine-3-carboxamide

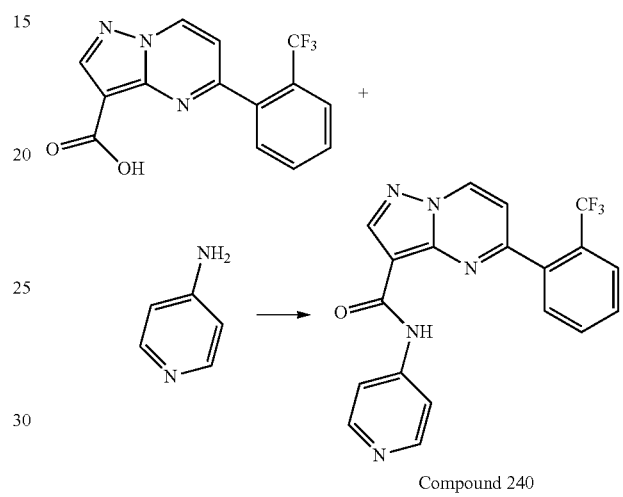

Compound 240

4-aminopyridine (122 mg, 1.30 mmol) was added to a solution of 5-(2-(trifluoromethyl)phenyl)pyrazolo[1,5-a]pyrimidine-3-carboxylic acid (100.0 mg, 0.33 mmol), pyridine (105 µl, 1.30 mmol) and HATU (149.0 mg, 0.39 mmol) in CH$_3$CN (15 mL), and the reaction was heated at reflux for 72 h. H$_2$O was added and the resulting precipitate was collected by filtration, rinsed with H$_2$O, and dried under vacuum. The crude residue was purified by recrystallization from CH$_3$CN to give N-(pyridin-4-yl)-5-(2-(trifluoromethyl)phenyl)pyrazolo[1,5-a]pyrimidine-3-carboxamide (91.0 mg, 73% yield). MS (ESI) calcd for C$_{19}$H$_{12}$F$_3$N$_5$O (m/z): 383.10. found: 384 [M+H].

This general coupling procedure could be used to prepare N-(pyrazin-2-yl)-5-(2-(trifluoromethyl)phenyl)pyrazolo[1,5-a]pyrimidine-3-carboxamide, N-(pyridazin-3-yl)-5-(2-(trifluoromethyl)phenyl)pyrazolo[1,5-a]pyrimidine-3-carboxamide and N-(2-methylpyridin-4-yl)-5-(2-(trifluoromethoxy)phenyl)pyrazolo[1,5-a]pyrimidine-3-carboxamide.

Example 38. Preparation of N-(pyridin-2-yl)-5-(2-(trifluoromethyl)phenyl)pyrazolo[1,5-a]pyrimidine-3-carboxamide (Compound 265)

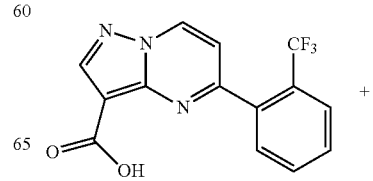

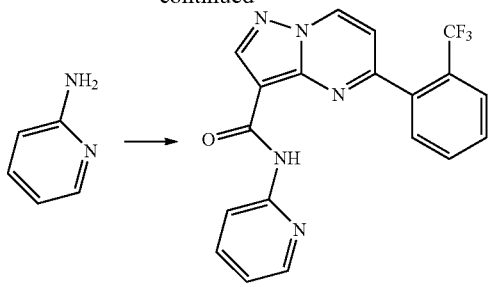

Compound 265

A solution of 5-(2-(trifluoromethyl)phenyl)pyrazolo[1,5-a]pyrimidine-3-carboxylic acid (60.0 mg, 0.33 mmol), 2-aminopyridine (40.0 mg, 0.42 mmol), DIEA (84.0 mg, 0.65 mmol) and HATU (186.0 mg, 0.49 mmol) in DMF (5 mL) was stirred at 60° C. for 16 h. $H_2O$ was added and the resulting ppt was collected by filtration, rinsed with $H_2O$, and dried under vacuum. The crude residue was purified by flash chromatography to give N-(pyridin-2-yl)-5-(2-(trifluoromethyl)phenyl)pyrazolo[1,5-a]pyrimidine-3-carboxamide (65.0 mg, 52%). MS (ESI) calcd for $C_{19}H_{12}F_3N_5O$ (m/z): 383.10. found: 384 [M+H].

This general coupling procedure could be used to prepare a variety of N-(substituted)-5-(2-(trifluoromethyl)phenyl) and N-(substituted)-5-(2-(trifluoromethoxy)phenyl)pyrazolo[1,5-a]pyrimidine-3-carboxamides by starting with the appropriate carboxylic acid and substituting the appropriate amine for 2-aminopyridine.

Example 39. Preparation of N-(pyrimidin-4-yl)-5-(2-(trifluoromethoxy)phenyl)pyrazolo[1,5-a]pyrimidine-3-carboxamide (Compound 533)

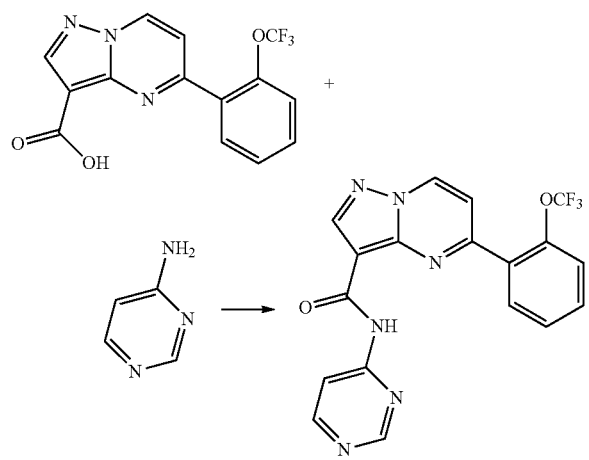

A solution of 5-(2-(trifluoromethoxy)phenyl)pyrazolo[1,5-a]pyrimidine-3-carboxylic (200.0 mg, 0.62 mmol), 4-aminopyrimidine (71.0 mg, 0.74 mmol), NaH (15.0 mg, 0.62 mmol) and HATU (235.0 mg, 0.62 mmol) in DMF (5 mL) was stirred at 70° C. for 16 h. $H_2O$ was added and the crude residue was purified by flash chromatography to give N-(pyrimidin-4-yl)-5-(2-(trifluoromethoxy)phenyl)pyrazolo[1,5-a]pyrimidine-3-carboxamide (20.0 mg, 8% yield). MS (ESI) calcd for $C_{19}H_{11}F_3N_6O_2$ (m/z): 400.09. found: 401 [M+H].

Example 40. Preparation of N-(5-methylpyrazin-2-yl)-5-(2-(trifluoromethyl)phenyl)pyrazolo[1,5-a]pyrimidine-3-carboxamide (Compound 723)

Compound 723

A solution of 5-(2-(trifluoromethyl)phenyl)pyrazolo[1,5-a]pyrimidine-3-carboxylic acid (60.0 mg, 0.20 mmol), 5-methylpyrazin-2-amine (36.0 mg, 0.24 mmol), $B(OH)_3$ (36.0 mg, 0.60 mmol) in 1,3,5-trimethylbenzene (3 mL) was stirred at 200° C. for 48 h. The reaction mixture was concentrated and the residue was purified by preparative TLC eluting with pentane/EtOAc (2:3) to give N-(5-methylpyrazin-2-yl)-5-(2-(trifluoromethyl)phenyl)pyrazolo[1,5-a]pyrimidine-3-carboxamide. (13.0 mg, 17% yield). MS (ESI) calcd for $C_{19}H_{13}F_3N_6O$ (m/z): 398.11. found: 399 [M+H].

This general coupling procedure could be used to prepare N-(3,5-difluoropyridin-2-yl)-5-(2-(trifluoromethyl)phenyl)pyrazolo[1,5-a]pyrimidine-3-carboxamide, N-(2,6-dimethylpyrimidin-4-yl)-5-(2-(trifluoromethoxy)phenyl)pyrazolo[1,5-a]pyrimidine-3-carboxamide, N-(5-fluoropyridin-3-yl)-5-(2-(trifluoromethoxy)phenyl)pyrazolo[1,5-a]pyrimidine-3-carboxamide, N-(4,6-dimethylpyrimidin-2-yl)-5-(2-(trifluoromethoxy)phenyl)pyrazolo[1,5-a]pyrimidine-3-carboxamide, N-(3,5-dimethylpyrazin-2-yl)-5-(2-(trifluoromethoxy)phenyl)pyrazolo[1,5-a]pyrimidine-3-carboxamide, N-(3,5-difluoropyridin-2-yl)-5-(2-(trifluoromethoxy)phenyl)pyrazolo[1,5-a]pyrimidine-3-carboxamide, N-(6-methoxypyrimidin-4-yl)-5-(2-(trifluoromethyl)phenyl)pyrazolo[1,5-a]pyrimidine-3-carboxamide, N-(3,5-dimethylpyrazin-2-yl)-5-(2-(trifluoromethyl)phenyl)pyrazolo[1,5-a]pyrimidine-3-carboxamide and N-(3-methylpyridin-2-yl)-5-(2-(trifluoromethyl)phenyl)pyrazolo[1,5-a]pyrimidine-3-carboxamide.

Example 41. Preparation of N-(pyrimidin-2-yl)-5-(2-(trifluoromethyl)phenyl)pyrazolo[1,5-a]pyrimidine-3-carboxamide (Compound 266)

Step 1. Synthesis of 5-(2-(trifluoromethyl)phenyl)pyrazolo[1,5-a]pyrimidine-3-carbonyl chloride

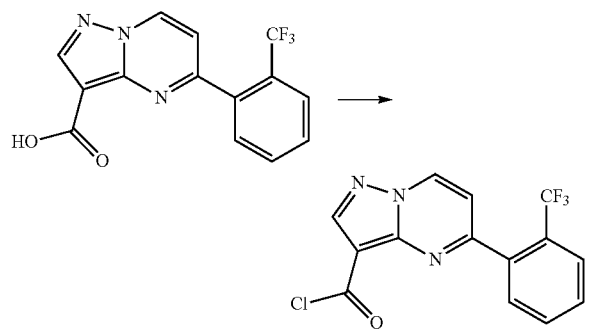

Oxalyl chloride (186.0 mg, 1.47 mmol) was added to a solution of 5-(2-(trifluoromethyl)phenyl)pyrazolo[1,5-a]pyrimidine-3-carboxylic acid (150.0 mg, 0.49 mmol) in $CH_2CL_2$ (5 mL) followed by DMF (3 drops). The reaction mixture was stirred at 25° C. for 8 h then concentrated to dryness to give crude 5-(2-(trifluoromethyl)phenyl)pyrazolo[1,5-a]pyrimidine-3-carbonyl chloride used without further purification. MS (ESI) calcd for $C_{14}H_2ClF_3N_3O$ (m/z): 325.02.

Step 2. Synthesis of N-(pyrimidin-2-yl)-5-(2-(trifluoromethyl)phenyl)pyrazolo[1,5-a]pyrimidine-3-carboxamide

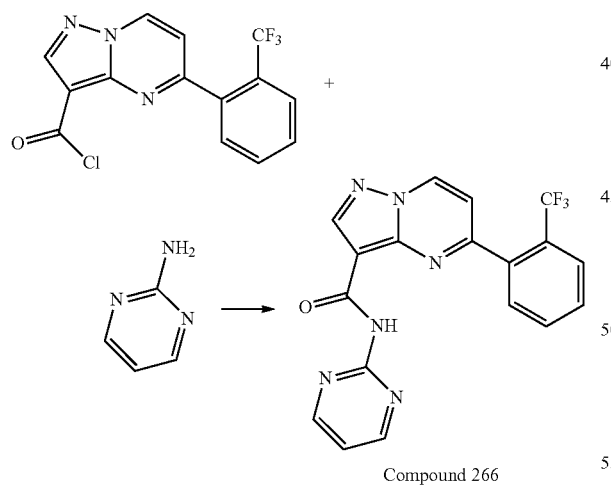

Compound 266

A solution of 5-(2-(trifluoromethyl)phenyl)pyrazolo[1,5-a]pyrimidine-3-carbonyl chloride (160.0 mg, 0.49 mmol) and 2-aminopyrimidine (60.0 mg, 0.64 mmol) in pyridine (5 mL) was stirred for 16 h at 25° C. The reaction mixture was poured into $H_2O$ and the mixture was concentrated. The crude residue was purified by flash chromatography to give N-(pyrimidin-2-yl)-5-(2-(trifluoromethyl)phenyl)pyrazolo[1,5-a]pyrimidine-3-carboxamide (40.0 mg, 21% yield). MS (ESI) calcd for $C_{18}H_{11}F_3N_6O$ (m/z): 384.09. found: 385 [M+H].

This general coupling procedure could be used to prepare N-(pyrazin-2-yl)-5-(2-(trifluoromethyl)phenyl)pyrazolo[1,5-a]pyrimidine-3-carboxamide, N-(pyrimidin-4-yl)-5-(2-(trifluoromethyl)phenyl)pyrazolo[1,5-a]pyrimidine-3-carboxamide, N-(6-hydroxypyridin-2-yl)-5-(2-(trifluoromethyl)phenyl)pyrazolo[1,5-a]pyrimidine-3-carboxamide, N-(6-methoxypyridin-2-yl)-5-(2-(trifluoromethyl)phenyl)pyrazolo[1,5-a]pyrimidine-3-carboxamide, N-(6-methylpyridin-2-yl)-5-(2-(trifluoromethyl)phenyl)pyrazolo[1,5-a]pyrimidine-3-carboxamide, N-(4-methylpyridin-2-yl)-5-(2-(trifluoromethyl)phenyl)pyrazolo[1,5-a]pyrimidine-3-carboxamide, N-(4,6-dimethylpyridin-2-yl)-5-(2-(trifluoromethyl)phenyl)pyrazolo[1,5-a]pyrimidine-3-carboxamide, N-(2,6-dimethylpyrimidin-4-yl)-5-(2-(trifluoromethyl)phenyl)pyrazolo[1,5-a]pyrimidine-3-carboxamide, N-(2,6-dimethylpyrimidin-4-yl)-5-(2-(trifluoromethyl)phenyl)pyrazolo[1,5-a]pyrimidine-3-carboxamide, N-(thiazol-2-yl)-5-(2-(trifluoromethyl)phenyl)pyrazolo[1,5-a]pyrimidine-3-carboxamide, N-(5-methylthiazol-2-yl)-5-(2-(trifluoromethyl)phenyl)pyrazolo[1,5-a]pyrimidine-3-carboxamide, N-(4-methylthiazol-2-yl)-5-(2-(trifluoromethyl)phenyl)pyrazolo[1,5-a]pyrimidine-3-carboxamide, N-(4,5-dimethylthiazol-2-yl)-5-(2-(trifluoromethyl)phenyl)pyrazolo[1,5-a]pyrimidine-3-carboxamide, N-(3-fluoropyridin-4-yl)-5-(2-(trifluoromethyl)phenyl)pyrazolo[1,5-a]pyrimidine-3-carboxamide, N-(5-fluoropyridin-2-yl)-5-(2-(trifluoromethyl)phenyl)pyrazolo[1,5-a]pyrimidine-3-carboxamide, N-(2-methoxypyrimidin-4-yl)-5-(2-(trifluoromethyl)phenyl)pyrazolo[1,5-a]pyrimidine-3-carboxamide, N-(pyrazin-2-yl)-5-(2-(trifluoromethoxy)phenyl)pyrazolo[1,5-a]pyrimidine-3-carboxamide and N-(pyrimidin-2-yl)-5-(2-(trifluoromethoxy)phenyl)pyrazolo[1,5-a]pyrimidine-3-carboxamide.

Example 42. Preparation of N-(6-hydroxypyridin-2-yl)-5-(2-(trifluoromethyl)phenyl)pyrazolo[1,5-a]pyrimidine-3-carboxamide (Compound 485)

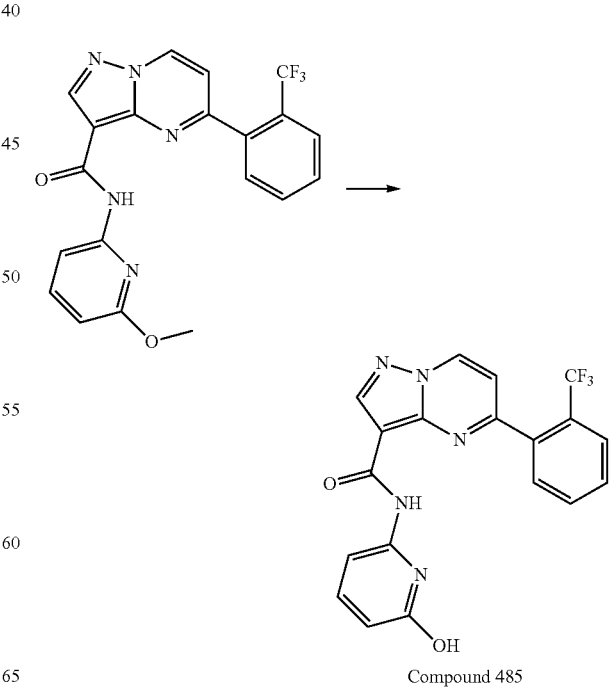

Compound 485

Chlorotrimethylsilane (32.0 mg, 0.29 mmol) was added to a solution of N-(6-methoxypyridin-2-yl)-5-(2-(trifluoromethyl)phenyl)pyrazolo[1,5-a]pyrimidine-3-carboxamide (60.0 mg, 0.15 mmol) and potassium iodide (48.0 mg, 0.29 mmol) in CH$_3$CN (10 mL) at room temp. The mixture was heated at 80° C. for 2 h. Sat. aq NaHCO$_3$ (50 mL) was added and the resulting ppt was collected by filtration, rinsed with EtOH and dried to give N-(pyrimidin-2-yl)-5-(2-(trifluoromethyl)phenyl)pyrazolo[1,5-a]pyrimidine-3-carboxamide (35.0 mg, 48% yield). MS (ESI) calcd for C$_{19}$H$_{12}$F$_3$N$_5$O$_2$ (m/z): 399.09. found: 400 [M+H].

This general coupling procedure could be used to prepare N-(6-hydroxypyridin-2-yl)-5-(2-(trifluoromethoxy)phenyl)pyrazolo[1,5-a]pyrimidine-3-carboxamide, N-(6-hydroxypyridin-2-yl)-2-methyl-5-(2-(trifluoromethyl)phenyl)pyrazolo[1,5-a]pyrimidine-3-carboxamide, N-(6-hydroxypyridin-2-yl)-2-methyl-5-(2-(trifluoromethyl)phenyl)pyrazolo[1,5-a]pyrimidine-3-carboxamide, N-(6-hydroxypyrimidin-4-yl)-5-(2-(trifluoromethoxy)phenyl)pyrazolo[1,5-a]pyrimidine-3-carboxamide, 5-hydroxy-N-(5-(2-(trifluoromethyl)phenyl)pyrazolo[1,5-a]pyrimidin-3-yl)pyrazine-2-carboxamide and N-(2-hydroxypyridin-4-yl)-5-(2-(trifluoromethoxy)phenyl)pyrazolo[1,5-a]pyrimidine-3-carboxamide.

Example 43. Preparation of N-(5-(2-(trifluoromethyl)phenyl)pyrazolo[1,5-a]pyrimidin-3-yl) picolinamide Step 1. Synthesis of tert-butyl 5-(2-(trifluoromethyl)phenyl)pyrazolo[1,5-a]pyrimidin-3-ylcarbamate

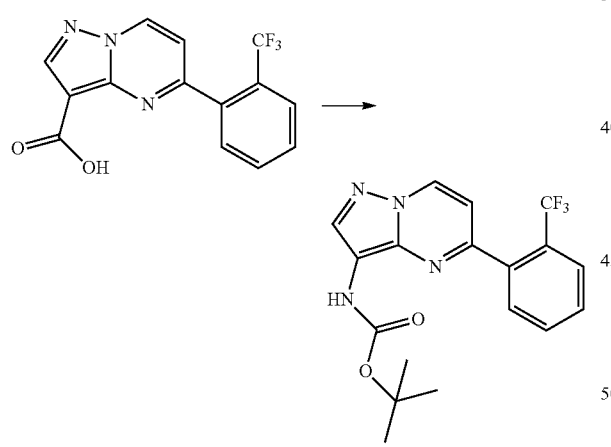

Diphenylphosphoryl azide (674.0 mg, 2.45 mmol) was added to a solution of 5-(2-(trifluoromethyl)phenyl)pyrazolo[1,5-a]pyrimidine-3-carboxylic acid (500.0 mg, 1.63 mmol) and triethylamine (329.0 mg, 3.26 mmol) in toluene (10 mL). The mixture was stirred for 1 h at 25° C. then heated at reflux for 2 h. tert-Butyl alcohol (1.22 g, 16.30 mmol) was added and the mixture was heated at reflux for 3 h. After cooling to room temp, the reaction mixture was poured into H$_2$O. The resulting ppt was collected by filtration, rinsed with H$_2$O and dried. The crude residue was purified by flash chromatography eluting with pentane/EtOAc (10%) to give tert-butyl 5-(2-(trifluoromethyl)phenyl)pyrazolo[1,5-a]pyrimidin-3-ylcarbamate (270.0 mg, 44% yield). MS (ESI) calcd for C$_{18}$H$_{17}$F$_3$N$_4$O$_2$ (m/z): 378.13.

Step 2. Synthesis of 5-(2-(trifluoromethyl)phenyl)pyrazolo[1,5-a]pyrimidin-3-amine hydrochloride

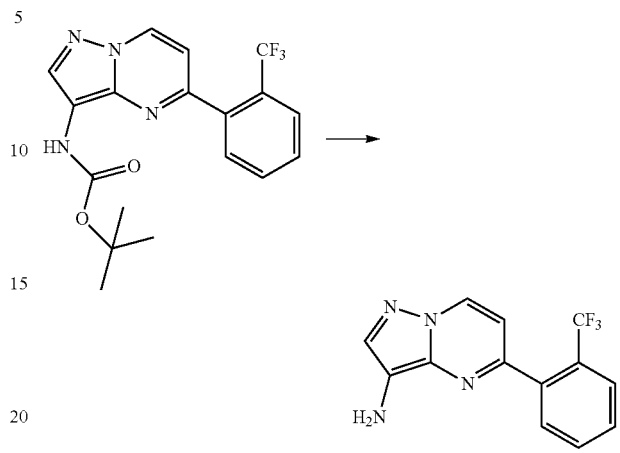

Tert-butyl 5-(2-(trifluoromethyl)phenyl)pyrazolo[1,5-a]pyrimidin-3-ylcarbamate (100.0 mg, 0.26 mmol) was dissolved in 3M HCl/dioxane (2 mL, 6.0 mmol). The reaction mixture was stirred at room temp for 16 h. The mixture was concentrated to give 5-(2-(trifluoromethyl)phenyl)pyrazolo[1,5-a]pyrimidin-3-amine hydrochloride (90.0 mg, 100% yield). MS (ESI) calcd for C$_{13}$H$_9$F$_3$N$_4$ (m/z): 278.08.

Step 3. Synthesis of N-(5-(2-(trifluoromethyl)phenyl)pyrazolo[1,5-a]pyrimidin-3-yl)picolinamide

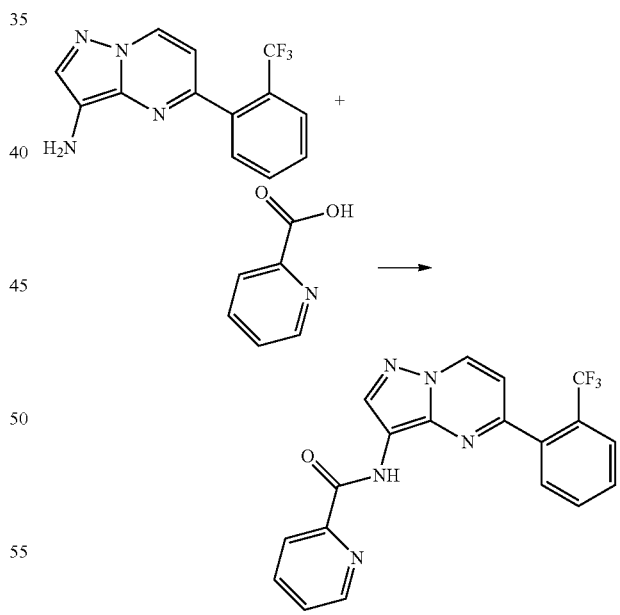

A solution of 5-(2-(trifluoromethyl)phenyl)pyrazolo[1,5-a]pyrimidin-3-amine (60.0 mg, 0.22 mmol), picolinic acid (27.0 mg, 0.22 mmol), DIPEA (83.0 mg, 0.65 mmol) and HATU (164.0 mg, 0.43 mmol) in DMF (8 mL) was stirred at 60° C. for 16 h. H$_2$O (30 mL) was added and the resulting ppt was collected by filtration and rinsed with MeOH to give N-(5-(2-(trifluoromethyl)phenyl)pyrazolo[1,5-a]pyrimidin-3-yl)picolinamide (60.0 mg, 73%). MS (ESI) calcd for C$_{19}$H$_{12}$F$_3$N$_5$O (m/z): 383.10. found: 384 [M+H].

This general coupling procedure could be used to prepare a variety of N-(5-(2-(trifluoromethyl)phenyl) and N-(5-(2-(trifluoromethoxy)phenyl)pyrazolo[1,5-a]pyrimidin-3-yl) amides by substituting the appropriate carboxylic acid for picolinic acid.

Example 44. Preparation of N-(6-methoxypyridin-2-yl)-2-methyl-5-(2-(trifluoromethyl)phenyl)pyrazolo[1,5-a]pyrimidine-3-carboxamide (Compound 551)

Step 1. Synthesis of ethyl 2-methyl-5-oxo-4,5-dihydropyrazolo[1,5-a]pyrimidine-3-carboxylate

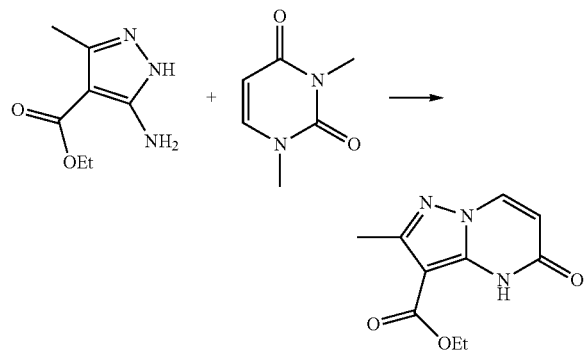

Sodium ethoxide (4.02 g, 59.10 mmol) was added to a solution of ethyl 5-amino-3-methyl-1H-pyrazole-4-carboxylate (10.0 g, 59.10 mmol) and 1,3-dimethyluracil (8.28 g, 59.10 mmol) in EtOH (50 mL). The reaction mixture was stirred at 140° C. for 2 h. After cooling to room temp the solid was collected by filtration. The solid was dissolved in H$_2$O (100 mL) and the pH was adjusted to 7. The resulting precipitate was collected by filtration and dried under vacuum to give ethyl 2-methyl-5-oxo-4,5-dihydropyrazolo[1,5-a]pyrimidine-3-carboxylate (10.0 g, 76% yield). MS (ESI) calcd for C$_{10}$H$_{11}$N$_3$O$_3$ (m/z): 221.08.

Step 2. Synthesis of ethyl 2-methyl-5-chloropyrazolo[1,5-a]pyrimidine-3-carboxylate

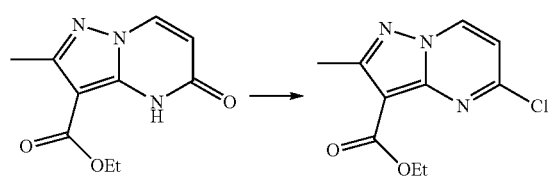 [SMILES: CCOC(=O)c1c(C)nn2ccc(=O)[nH]c12 ; CCOC(=O)c1c(C)nn2ccc(Cl)nc12]

A mixture of ethyl 2-methyl-5-oxo-4,5-dihydropyrazolo[1,5-a]pyrimidine-3-carboxylate (10.0 g, 45.20 mmol) in phosphoryl trichloride (50 mL) was heated at reflux for 3 h. The reaction mixture was concentrated in vacuo. The crude residue was dissolved in H$_2$O and the pH was adjusted to 7. The resulting precipitate was collected by filtration and dried under vacuum to give ethyl 2-methyl-5-chloropyrazolo[1,5-a]pyrimidine-3-carboxylate (10.00 g, 92% yield). MS (ESI) calcd for C$_{10}$H$_{10}$ClN$_3$O$_2$ (m/z): 239.05.

Step 3. Synthesis of ethyl 2-methyl-5-(2-(trifluoromethyl)phenyl)pyrazolo[1,5-a]pyrimidine-3-carboxylate

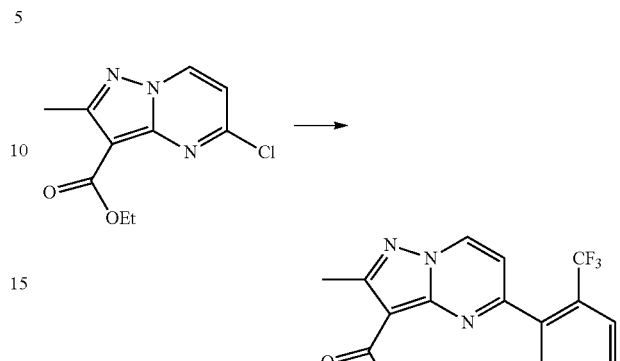

A solution of ethyl 2-methyl-5-chloropyrazolo[1,5-a]pyrimidine-3-carboxylate (9.06 g, 37.70 mmol) 2-(trifluoromethyl)phenylboronic acid (14.25 g, 75.00 mmol), Pd(dppf)Cl$_2$ (1.51 g, 2.10 mmol), and K$_2$CO$_3$ (10.35 g, 75.00 mmol) in degassed dimethoxyethane (120 mL) was heated at 100° C. for 12 h. The mixture was concentrated and purified by flash chromatography to give ethyl 2-methyl-5-(2-(trifluoromethyl)phenyl)pyrazolo[1,5-a]pyrimidine-3-carboxylate (11.70 g, 90% yield). MS (ESI) calcd for C$_{17}$H$_{14}$F$_3$N$_3$O$_2$ (m/z): 349.10.

Step 4. Synthesis of 2-methyl-5-(2-(trifluoromethyl)phenyl)pyrazolo[1,5-a]pyrimidine-3-carboxylic acid

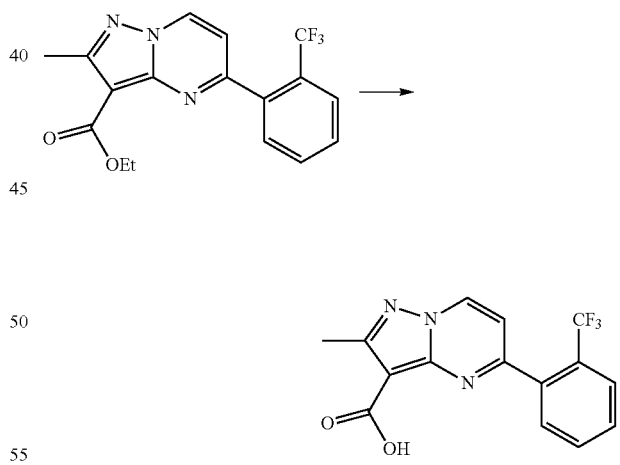

LiOH (14.30 mg, 340.0 mmol) was added to a solution of ethyl 5-(2-(trifluoromethyl)phenyl)pyrazolo[1,5-a]pyrimidine-3-carboxylate (11.70 g, 34.00 mmol) in THF/H$_2$O (100 mL, 1:1). The reaction mixture was stirred at 25° C. for 60 h. The mixture was concentrated and the pH was adjusted to 3 by the addition of 1N HCl. The resulting ppt was collected by filtration, rinsed with H$_2$O and dried to give 5-(2-(trifluoromethyl)phenyl)pyrazolo[1,5-a]pyrimidine-3-carboxylic acid (5.00 g, 46% yield). MS (ESI) calcd for C$_{15}$H$_{10}$F$_3$N$_3$O$_2$ (m/z): 321.07.

145

Step 5. Synthesis of 2-methyl-5-(2-(trifluoromethyl) phenyl)pyrazolo[1,5-a]pyrimidine-3-carbonyl chloride

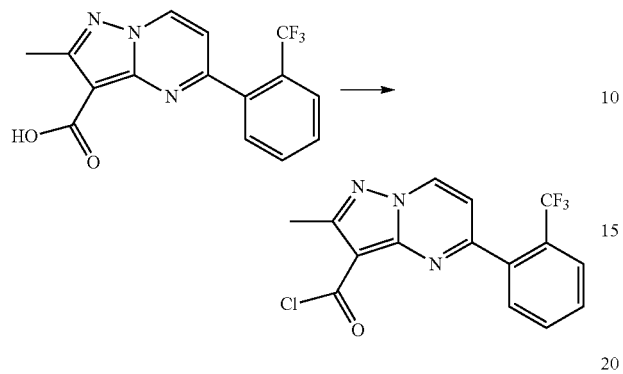

Oxalyl chloride (814 μl, 9.34 mmol) was added to a suspension of 2-methyl-5-(2-(trifluoromethyl)phenyl)pyrazolo[1,5-a]pyrimidine-3-carboxylic acid (1.0 g, 3.11 mmol) in $CH_2CL_2$ (20 mL) followed by DMF (3 drops). The reaction mixture was stirred at 25° C. for 2 h then concentrated to dryness to give crude 2-methyl-5-(2-(trifluoromethyl)phenyl)pyrazolo[1,5-a]pyrimidine-3-carbonyl chloride used without further purification (1.10 g, 100% yield). MS (ESI) calcd for $C_{15}H_9ClF_3N_3O$ (m/z): 339.04.

Step 6. Synthesis of N-(6-methoxypyridin-2-yl)-2-methyl-5-(2-(trifluoromethyl)phenyl)pyrazolo[1,5-a] pyrimidine-3-carboxamide

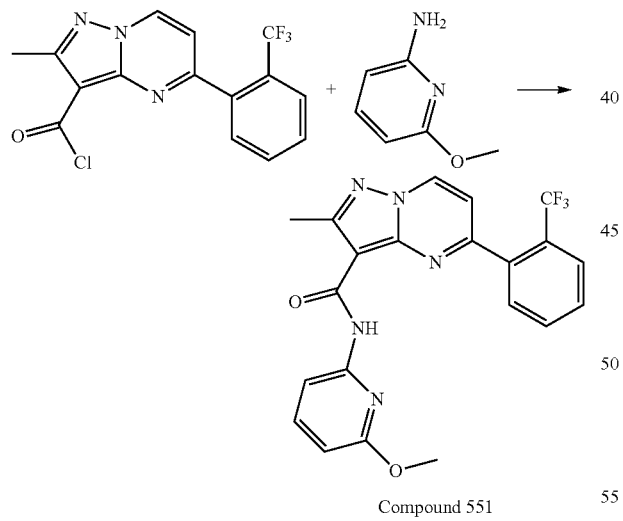

Compound 551

A solution of 5-(2-(trifluoromethyl)phenyl)pyrazolo[1,5-a]pyrimidine-3-carbonyl chloride (254.0 mg, 0.75 mmol) and 6-methoxypyridine-2-amine (136.0 mg, 1.10 mmol) in pyridine (10 mL) was stirred for 2 h at 50° C. The reaction mixture was poured into $H_2O$ and the solid was collected by filtration. The crude residue was purified by flash chromatography to give N-(6-methoxypyridin-2-yl)-2-methyl-5-(2-(trifluoromethyl)phenyl)pyrazolo[1,5-a]pyrimidine-3-carboxamide (85.0 mg, 27% yield). MS (ESI) calcd for $C_{21}H_{16}F_3N_5O_2$ (m/z): 427.13. found: 428 [M+H].

146

This general coupling procedure could be used to prepare 2-methyl-N-(pyrimidin-4-yl)-5-(2-(trifluoromethyl)phenyl)pyrazolo[1,5-a]pyrimidine-3-carboxamide, 2-methyl-N-(pyridin-2-yl)-5-(2-(trifluoromethyl)phenyl)pyrazolo[1,5-a]pyrimidine-3-carboxamide, 2-methyl-N-(pyridin-3-yl)-5-(2-(trifluoromethyl)phenyl)pyrazolo[1,5-a]pyrimidine-3-carboxamide, 2-methyl-N-(6-(morpholinomethyl)pyridin-2-yl)-5-(2-(trifluoromethyl)phenyl)pyrazolo[1,5-a]pyrimidine-3-carboxamide, 2-methyl-N-(6-morpholinopyridin-2-yl)-5-(2-(trifluoromethyl)phenyl)pyrazolo[1,5-a]pyrimidine-3-carboxamide and 2-methyl-N-(pyridin-4-yl)-5-(2-(trifluoromethyl)phenyl)pyrazolo[1,5-a]pyrimidine-3-carboxamide.

Example 45. Preparation of N-(2-methoxypyrimidin-4-yl)-2-methyl-5-(2-(trifluoromethyl)phenyl)pyrazolo[1,5-a]pyrimidine-3-carboxamide (Compound 793)

Step 1. Synthesis of 4-nitrophenyl 2-methyl-5-(2-(trifluoromethyl)phenyl)pyrazolo[1,5-a]pyrimidine-3-carboxylate

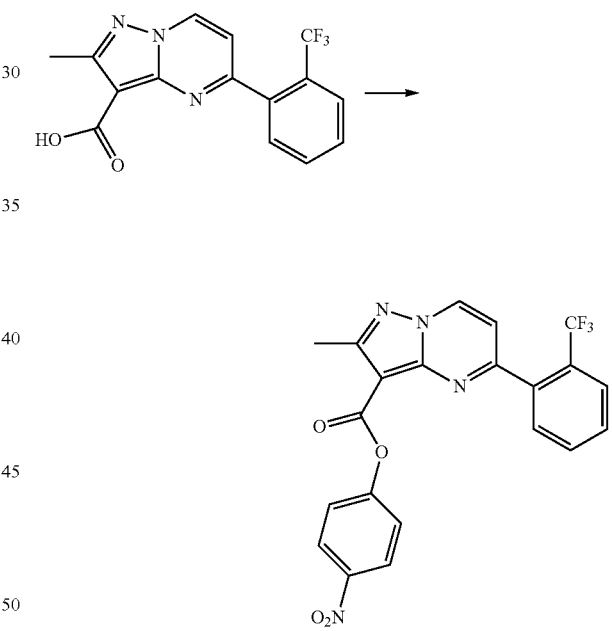

EDCI (720.0 mg, 3.75 mmol) was added to a solution of 2-methyl-5-(2-(trifluoromethyl)phenyl)pyrazolo[1,5-a]pyrimidine-3-carboxylic acid (800.0 mg, 2.50 mmol) and DMAP (460.0 mg, 3.75 mmol) in DMF (10 mL). The reaction mixture was stirred at 25° C. for 2 h then 4-nitrophenol (350.0 mg, 2.50 mmol) was added and stirring continued for 18 h. The mixture was diluted with sat. aq $Na_2CO_3$ (50 mL) and extracted with EtOAc (2×30 mL). The combined organic layers were washed with sat. aq $Na_2CO_3$ (3×20 mL), brine, and concentrated. The crude residue was triturated with pentane/EtOAc (5:1) to give 4-nitrophenyl 2-methyl-5-(2-(trifluoromethyl)phenyl)pyrazolo[1,5-a]pyrimidine-3-carboxylate which (960.0 mg, 87% yield). MS (ESI) calcd for $C_{21}H_{13}F_3N_4O_4$ (m/z): 442.09.

Step 2. Synthesis of N-(2-methoxypyrimidin-4-yl)-2-methyl-5-(2-(trifluoromethyl)phenyl)pyrazolo[1,5-a]pyrimidine-3-carboxamide

Example 46. Preparation of 2-methyl-N-(6-methyl-pyridin-2-yl)-5-(2-(trifluoromethyl)phenyl)pyrazolo[1,5-a]pyrimidine-3-carboxamide (Compound 628)

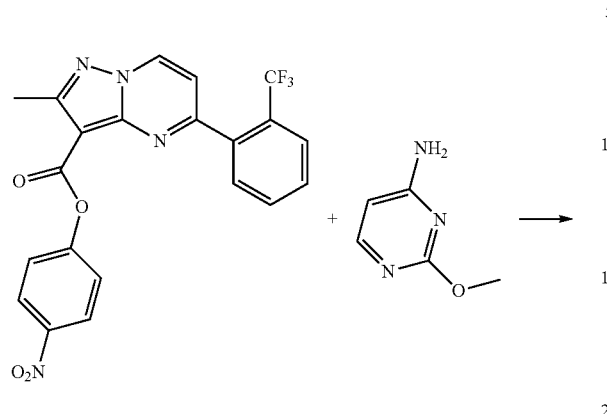

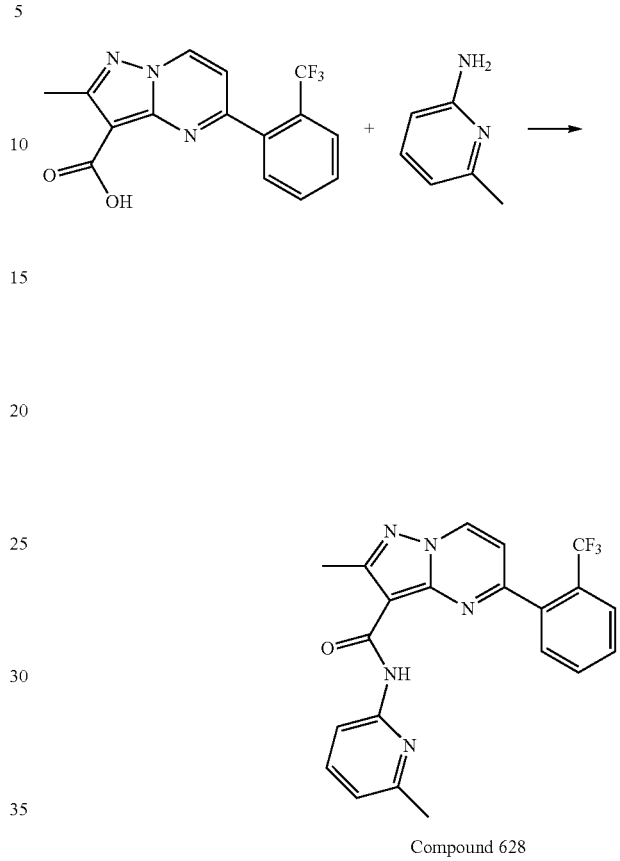

Compound 793

Compound 628

Sodium hydride (11.0 mg, 0.42 mmol) was added to a solution of 2-methoxypyrimidine-4-amine (35.0 mg, 0.28 mmol) in THF (3 mL) at 0° C. The reaction mixture was stirred for 10 min and 4-nitrophenyl 2-methyl-5-(2-(trifluoromethyl)phenyl)pyrazolo[1,5-a]pyrimidine-3-carboxylate (60.0 mg, 0.14 mmol) was added and stirring continued for 30 min. The reaction was quenched by the addition of at. aq NH$_4$Cl. The mixture was extracted with EtOAc. The organic layer was washed with sat. aq Na$_2$CO$_3$, brine, dried and concentrated. The crude product was triturated with pentane/EtOAc (4:1) to give N-(2-methoxypyrimidin-4-yl)-2-methyl-5-(2-(trifluoromethyl)phenyl)pyrazolo[1,5-a]pyrimidine-3-carboxamide (21.0 mg, 36% yield). MS (ESI) calcd for C$_{20}$H$_{15}$F$_3$N$_6$O$_2$ (m/z): 428.12. found: 429 [M+H].

This general coupling procedure could be used to prepare N-(3,5-difluoropyridin-2-yl)-2-methyl-5-(2-(trifluoromethyl)phenyl)pyrazolo[1,5-a]pyrimidine-3-carboxamide, N-(2-hydroxypyridin-4-yl)-2-methyl-5-(2-(trifluoromethyl)phenyl)pyrazolo[1,5-a]pyrimidine-3-carboxamide, N-(2,6-dimethylpyrimidin-4-yl)-2-methyl-5-(2-(trifluoromethyl)phenyl)pyrazolo[1,5-a]pyrimidine-3-carboxamide, N-(6-methoxypyrimidin-4-yl)-2-methyl-5-(2-(trifluoromethyl)phenyl)pyrazolo[1,5-a]pyrimidine-3-carboxamide, N-(2-ethoxypyrimidin-4-yl)-2-methyl-5-(2-(trifluoromethyl)phenyl)pyrazolo[1,5-a]pyrimidine-3-carboxamide and N-(4,6-dimethylpyrimidin-2-yl)-2-methyl-5-(2-(trifluoromethyl)phenyl)pyrazolo[1,5-a]pyrimidine-3-carboxamide.

A solution of 2-methyl-5-(2-(trifluoromethyl)phenyl)pyrazolo[1,5-a]pyrimidine-3-carboxylic (80.0 mg, 0.25 mmol), 6-methyl-2-aminopyridine (54.0 mg, 0.50 mmol), DIEA (223.0 mg, 1.72 mmol) and HATU (189.0 mg, 0.498 mmol) in DMF (3 mL) was stirred at 60° C. for 16 h. H$_2$O was added. The resulting ppt was collected by filtration, rinsed with H$_2$O, and dried to give 2-methyl-N-(6-methyl-pyridin-2-yl)-5-(2-(trifluoromethyl)phenyl)pyrazolo[1,5-a]pyrimidine-3-carboxamide (26.0 mg, 25% yield). MS (ESI) calcd for C$_{21}$H$_{16}$F$_3$N$_5$O (m/z): 411.13. found: 412 [M+H].

This general coupling procedure could be used to prepare a variety of 2-methyl-N-(substituted)-5-(2-(trifluoromethyl)phenyl)pyrazolo[1,5-a]pyrimidine-3-carboxamides by substituting the appropriate amine for 6-methyl-2-aminopyridine.

Example 47. Preparation of 2-methyl-N-(3-methyl-pyridin-2-yl)-5-(2-(trifluoromethyl)phenyl)pyrazolo[1,5-a]pyrimidine-3-carboxamide (Compound 722)

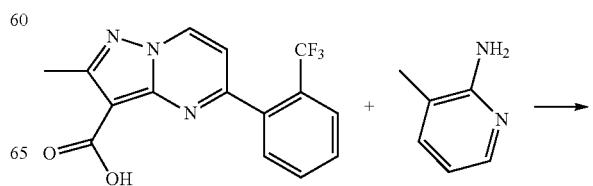

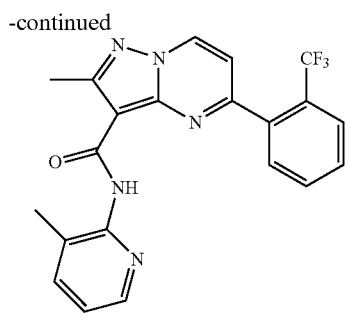

Compound 722

B(OH)₃ (46.0 mg, 0.74 mmol) was added to a solution of 2-methyl-5-(2-(trifluoromethyl)phenyl)pyrazolo[1,5-a]pyrimidine-3-carboxylic (80.0 mg, 0.25 mmol), and 3-methyl-2-aminopyridine (33.0 mg, 0.30 mmol) in 1,3,5-trimethylbenzene (10 mL). The reaction mixture was heated at 200° C. for 24 h. The reaction mixture was concentrated to dryness and purified by preparative TLC eluting with CH₂Cl₂/EtOAc (1:1) to give 2-methyl-N-(3-methylpyridin-2-yl)-5-(2-(trifluoromethyl)phenyl)pyrazolo[1,5-a]pyrimidine-3-carboxamide (12.0 mg, 11% yield). MS (ESI) calcd for C₂₁H₁₆F₃N₅O (m/z): 411.13. found: 412 [M+H].

This general coupling procedure could be used to prepare 2-methyl-N-(6-methylpyrazin-2-yl)-5-(2-(trifluoromethyl)phenyl)pyrazolo[1,5-a]pyrimidine-3-carboxamide, N-(3,5-dimethylpyrazin-2-yl)-2-methyl-5-(2-(trifluoromethyl)phenyl)pyrazolo[1,5-a]pyrimidine-3-carboxamide and N-(5-fluoropyridin-3-yl)-2-methyl-5-(2-(trifluoromethyl)phenyl)pyrazolo[1,5-a]pyrimidine-3-carboxamide.

Example 48. Preparation of N-(2-methyl-5-(2-(trifluoromethyl)phenyl)pyrazolo[1,5-a]pyrimidin-3-yl) picolinamide (Compound 567)

Step 1. Synthesis of benzyl 2-methyl-5-(2-(trifluoromethyl)phenyl)pyrazolo[1,5-a]pyrimidin-3-ylcarbamate

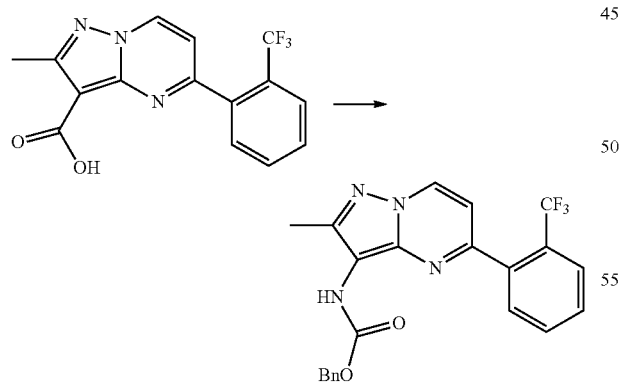

Diphenylphosphoryl azide (1 mL, 4.67 mmol) was added to a solution of 2-methyl-5-(2-(trifluoromethyl)phenyl)pyrazolo[1,5-a]pyrimidine-3-carboxylic acid (1.5 g, 4.67 mmol) and triethylamine (967 μl, 7.01 mmol) in toluene (25 mL). The mixture was stirred for 1 h at 25° C. then heated at reflux for 3 h. Benzyl alcohol (532 μl, 5.14 mmol) was added and the mixture was heated at reflux for 16 h. After cooling to room temp, the reaction mixture was poured into sat. aq NH₄Cl and extracted with EtOAc. The combined organics were washed with brine, dried (MgSO₄) and concentrated. The crude residue was purified by MPLC eluting with pentane/EtOAc (20-100%) to give benzyl 2-methyl-5-(2-(trifluoromethyl)phenyl)pyrazolo[1,5-a]pyrimidin-3-ylcarbamate (1.49 g, 75% yield). MS (ESI) calcd for C₂₂H₁₇F₃N₄O₂ (m/z): 426.13. found: 427 [M+H].

Step 2. Synthesis of 2-methyl-5-(2-(trifluoromethyl)phenyl)pyrazolo[1,5-a]pyrimidin-3-amine hydrochloride

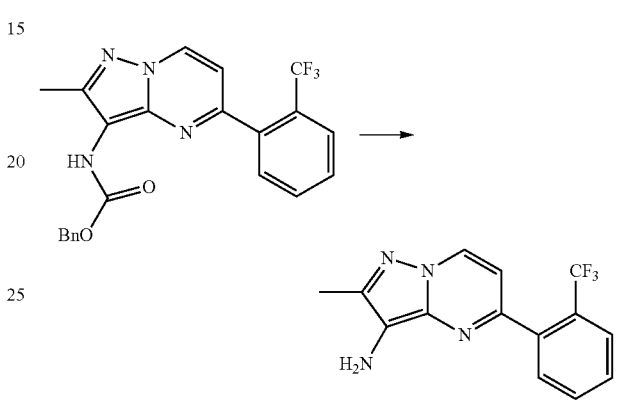

Conc. HCl (15 mL) was added to a solution of benzyl 2-methyl-5-(2-(trifluoromethyl)phenyl)pyrazolo[1,5-a]pyrimidin-3-ylcarbamate (1.49 g, 3.49 mmol) in EtOH (25 mL). The reaction mixture was heated at reflux for 2.5 h. After cooling to room temp, the mixture was concentrated to dryness and chased with toluene to give 2-methyl-5-(2-(trifluoromethyl)phenyl)pyrazolo[1,5-a]pyrimidin-3-amine hydrochloride (1.15 g, 100% yield). MS (ESI) calcd for C₁₄H₁₁F₃N₄ (m/z): 292.09. found: 293 [M+H].

Step 3. Synthesis of N-(2-methyl-5-(2-(trifluoromethyl)phenyl)pyrazolo[1,5-a]pyrimidin-3-yl) picolinamide

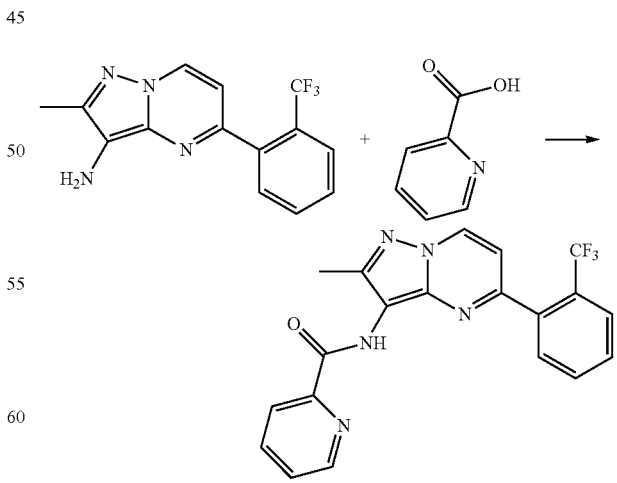

Compound 567

A solution of 5-(2-(trifluoromethyl)phenyl)pyrazolo[1,5-a]pyrimidin-3-amine (50.0 mg, 0.16 mmol), picolinic acid (32.0 mg, 0.26 mmol), DIPEA (44.0 mg, 0.34 mmol) and HATU (129.0 mg, 0.34 mmol) in DMF (20 mL) was stirred at 50° C. for 2 h. H₂O was added and the resulting ppt was collected by filtration. The crude residue was purified by flash chromatography to give N-(2-methyl-5-(2-(trifluoromethyl)phenyl)pyrazolo[1,5-a]pyrimidin-3-yl)picolinamide (19.0 mg, 30% yield). MS (ESI) calcd for $C_{20}H_{14}F_3N_5O$ (m/z): 397.12. found: 398 [M+H].

This general coupling procedure could be used to prepare a variety of N-(2-methyl-5-(2-(trifluoromethyl)phenyl)pyrazolo[1,5-a]pyrimidin-3-yl)amides by substituting the appropriate carboxylic acid for picolinic acid.

Example 49. Preparation of N-(pyridin-3-yl)-2-(2-(trifluoromethyl)phenyl)imidazo[1,5-a]pyrimidine-8-carboxamide (Compound 451)

Step 1. Synthesis of ethyl 5-amino-1H-imidazole-4-carboxylate

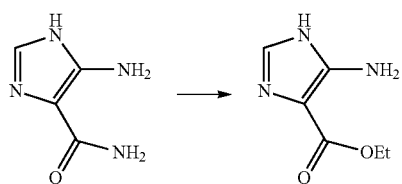 [SMILES: NC(=O)c1nc[nH]c1N ; CCOC(=O)c1nc[nH]c1N]

A mixture of 5-amino-1H-imidazole-4-carboxamide (30.0 g, 238 mmol) and sulfuric acid (70.0 g, 714 mmol) in ethanol (300 mL) was heated to 120° C. in a sealed tube for 24 h. The reaction mixture was cooled to room temp, and the solvent was removed in vacuo. The residue was purified via silica gel column chromatography to give ethyl 5-amino-1H-imidazole-4-carboxylate (20.0 g, 54%). MS (ESI) calcd for $C_6H_9N_3O_2$: 155.07.

Step 2. Synthesis of ethyl 2-oxo-1,2-dihydroimidazo[1,5-a]pyrimidine-8-carboxylate

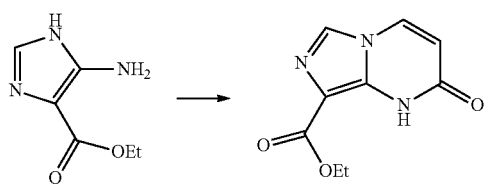 [SMILES: CCOC(=O)c1nc[nH]c1N ; CCOC(=O)c1ncn2ccc(=O)[nH]c12]

A solution of ethyl 5-amino-1H-imidazole-4-carboxylate (10.0 g, 64.5 mmol), 2,5-dioxopyrrolidin-1-yl 3-(2,5-dioxopyrrolidin-1-yloxy)acrylate (20.01 g, 70.9 mmol), and triethylamine (13.02 g, 129 mmol) in anhydrous acetonitrile (200 mL) was heated to 50° C. for 16 h. After concentration in vacuo, the residue was treated with MeOH (100 mL), and the mixture was stirred at 60° C. for 30 min. The mixture was filtered, and the filtrate was concentrated and purified via silica gel column chromatography (MeOH/CHCl₃, 4:96 v/v) to give ethyl 2-oxo-1,2-dihydroimidazo[1,5-a]pyrimidine-8-carboxylate (5.0 g, 37.4%) as a white solid. MS (ESI) calcd for $C_9H_9N_3O_2$: 207.06.

Step 3. Synthesis of ethyl 2-chloroimidazo[1,5-a]pyrimidine-8-carboxylate

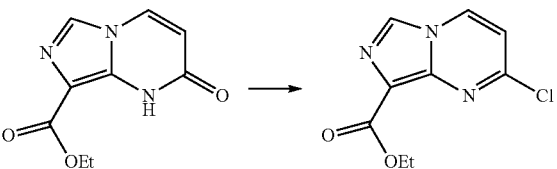 [SMILES: CCOC(=O)c1ncn2ccc(=O)[nH]c12 ; CCOC(=O)c1ncn2ccc(Cl)nc12]

A mixture of ethyl 2-oxo-1,2-dihydroimidazo[1,5-a]pyrimidine-8-carboxylate (8.0 g, 38.6 mmol) and phosphoryl trichloride (5.92 g, 38.6 mmol) were heated to 120° C. for 1 h, then cooled to room temp. After concentration in vacuo, water was added (300 mL) and the mixture was extracted with EtOAc. The mixture was concentrated and purified to give ethyl 2-chloroimidazo[1,5-a]pyrimidine-8-carboxylate (4.5 g, 52%). MS (ESI) calcd for $C_9H_8ClN_3O_2$: 225.03.

Step 4. Synthesis of ethyl 2-(2-(trifluoromethyl)phenyl)imidazo[1,5-a]pyrimidine-8-carboxylate

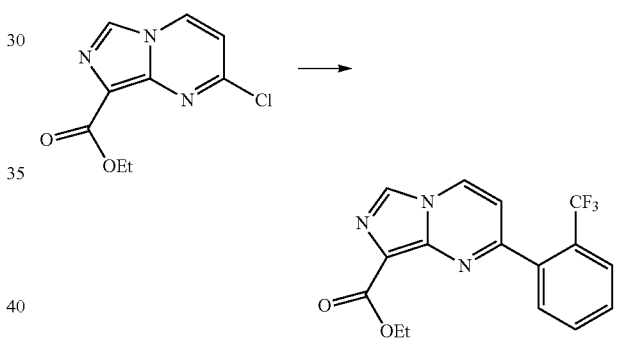

A mixture of ethyl 2-chloroimidazo[1,5-a]pyrimidine-8-carboxylate (2.0 g, 8.86 mmol), 2-(trifluoromethyl)phenylboronic acid (3.03 g, 15.96 mmol), Pd(PPh₃)₄ (1.02 g, 0.89 mmol) and Cs₂CO₃ (5.78 g, 17.73 mmol) in dioxane (50 mL), was heated at 100° C. for 1 h, then cooled to room temp. The mixture was poured into cold water (200 mL) and stirred. The precipitate was collected by filtration to give ethyl 2-(2-(trifluoromethyl)phenyl) imidazo[1,5-a]pyrimidine-8-carboxylate (0.8 g, 27%). MS (ESI) calcd for $C_{16}H_{12}F_3N_3O_2$: 335.09.

Step 5. Synthesis of 2-(2-(trifluoromethyl)phenyl) imidazo[1,5-a]pyrimidine-8-carboxylic acid

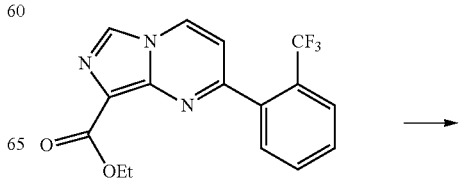

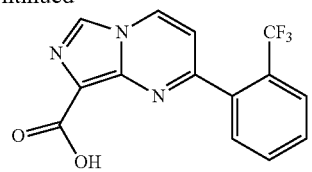

To a mixture of ethyl 2-(2-(trifluoromethyl)phenyl)imidazo[1,5-a]pyrimidine-8-carboxylate (1.5 g, 4.47 mmol) and potassium hydroxide (2.51 g, 44.7 mmol) in water (50 mL) was added MeOH (20 mL). The reaction was heated to reflux for 1 h, then cooled to room temp. The mixture was washed with EtOAc (2×50 mL) and the organics discarded. The aqueous phase was adjusted to pH 4, after which precipitation occurred. The precipitate was collected by filtration to give 2-(2-(trifluoromethyl)phenyl)imidazo[1,5-a]pyrimidine-8-carboxylic acid (1.0 g, 73%). MS (ESI) calcd for $C_{14}H_8F_3N_3O_2$: 307.06.

Step 6. Synthesis of N-(pyridin-3-yl)-2-(2-(trifluoromethyl)phenyl)imidazo[1,5-a]pyrimidine-8-carboxamide

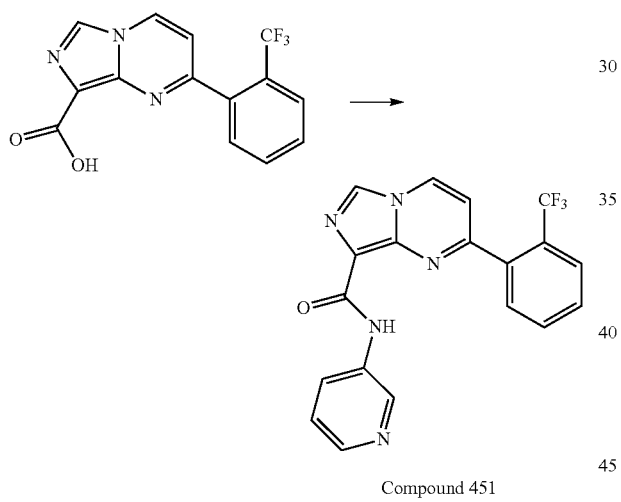

Compound 451

To a solution of 2-(2-(trifluoromethyl)phenyl)imidazo[1,5-a]pyrimidine-8-carboxylic acid (70.0 mg, 0.228 mmol) in DCM (5 mL) was added DMF (1 drop) and oxalyl dichloride (87.0 mg, 0.684 mmol). The mixture was stirred for 0.5 h and concentrated in vacuo. To the residue was added pyridine (8 mL) and pyridin-3-amine (32.2 mg, 0.342 mmol) at room temp. After 2 h, water was added (20 mL) and the mixture stirred for 1 h. The solid was collected by filtration, washed and dried to give N-(pyridin-3-yl)-2-(2-(trifluoromethyl)phenyl)imidazo[1,5-a]pyrimidine-8-carboxamide (24.0 mg, 28%). MS (ESI) calcd for $C_{19}H_{12}F_3N_5O$: 383.10.

This general procedure could be used to prepare N-(pyridin-2-yl)-2-(2-(trifluoromethyl)phenyl)imidazo[1,5-a]pyrimidine-8-carboxamide, N-(pyrimidin-4-yl)-2-(2-(trifluoromethyl)phenyl)imidazo[1,5-a]pyrimidine-8-carboxamide, N-(pyrimidin-2-yl)-2-(2-(trifluoromethyl)phenyl)imidazo[1,5-a]pyrimidine-8-carboxamide and N-(6-morpholinopyridin-2-yl)-2-(2-(trifluoromethyl)phenyl)imidazo[1,5-a]pyrimidine-8-carboxamide.

Example 50. Preparation of N-(2-(2-(trifluoromethyl)phenyl)imidazo[1,5-a]pyrimidin-8-yl)picolinamide (Compound 455)

Step 1. Synthesis of 2-(2-(trifluoromethyl)phenyl)imidazo[1,5-a]pyrimidin-8-amine

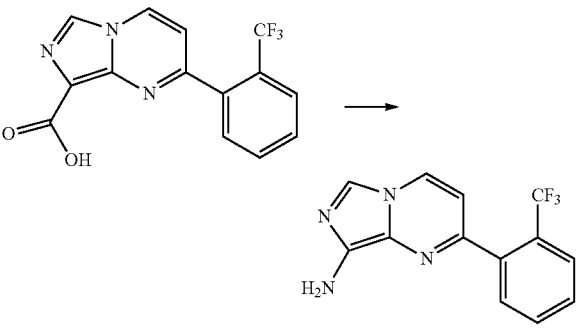

To a mixture of 2-(2-(trifluoromethyl)phenyl)imidazo[1,5-a]pyrimidine-8-carboxylic acid (300.0 mg, 0.976 mmol) and triethylamine (197.0 mg, 1.953 mmol) in DMF (30 mL) was added diphenylphosphoryl azide (DPPA) (537.0 mg, 1.953 mmol) at room temp. The mixture was stirred for 1 h, then water (1 mL) was added and the mixture was heated to 100° C. followed by cooling. The reaction mixture was poured into cold water (250 mL) and stirred. The precipitate that formed was collected by filtration, washed with water, and dried in vacuo to give 2-(2-(trifluoromethyl)phenyl)imidazo[1,5-a]pyrimidin-8-amine (50.0 mg, 18%). MS (ESI) calcd for $C_{13}H_9F_3N_4$: 278.08.

Step 2. Synthesis of N-(2-(2-(trifluoromethyl)phenyl)imidazo yl)picolinamide

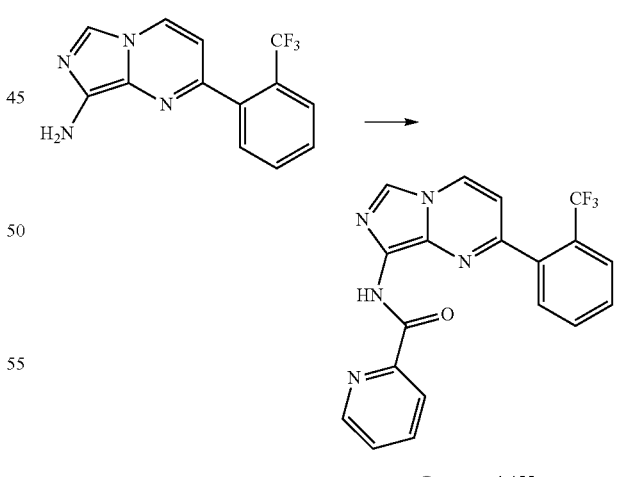

Compound 455

A mixture of 2-(2-(trifluoromethyl)phenyl)imidazo[1,5-a]pyrimidin-8-amine (25.0 mg, 0.90 mmol), picolinic acid (16.6 mg, 0.135 mmol), HATU (43.3 mg, 0.180 mmol) and DIEA (34.8 mg, 0.270 mmol) in DMF (5 mL) was heated to 60° C. for 12 h. The mixture was poured into cold water (30 mL) and stirred. The precipitate that formed was collected by filtration, washed with methanol, and dried in vacuo to give N-(2-(2-(trifluoromethyl)phenyl)imidazo[1,5-a]pyrimidin-8-yl)picolinamide (19.0 mg, 55%). MS (ESI) calcd for $C_{19}H_{12}F_3N_5O$: 383.10. found: 383.98 [M+H].

This general coupling procedure could be utilized to prepare 6-morpholino-N-(2-(2-(trifluoromethyl)phenyl)imidazo[1,5-a]pyrimidin-8-yl)picolinamide, N-(2-(2-(trifluoromethyl)phenyl)imidazo[1,5-a]pyrimidin-8-yl)nicotinamide and N-(2-(2-(trifluoromethyl)phenyl)imidazo[1,5-a]pyrimidin-8-yl)pyrimidine-4-carboxamide.

Example 51. Synthesis of N-(6-(azetidin-1-yl)pyridin-2-yl)-6-(2-(trifluoromethyl)phenyl)-[1,2,4]-triazolo[4,3-b]pyridazine-3-carboxamide (Compound 73)

Step 1. Synthesis of 3-chloro-6-(2-(trifluoromethyl)phenyl)pyridazine

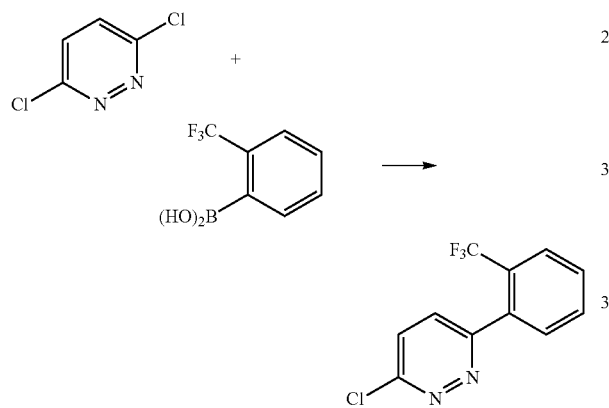

To a mixture of 3,6-dichloropyridazine (6.0 g, 40.3 mmol) and 2-(trifluoromethyl)phenyl-boronic acid (9.18 g, 48.3 mmol) were added $K_2CO_3$ (8.35 g, 60.4 mmol) and $Pd(PPh_3)_4$ (2.33 g, 2.01 mmol). The mixture was stirred in dioxane:$H_2O$ (4:1) at 120° C. in a microwave for about 0.5 h. After cooling to room temp, the reaction was diluted with EtOAc and washed with $H_2O$. The combined organic layers were dried over $Na_2SO_4$, filtered and evaporated to dryness under reduced pressure. The crude material was purified by vacuum distillation to afford 3-chloro-6-(2-(trifluoromethyl)phenyl)pyridazine (2.8 g, 26.9%). MS (ESI) calcd for $C_{11}H_6ClF_3N_2$: 258.02.

Step 2. Synthesis of 3-hydrazinyl-6-(2-(trifluoromethyl)phenyl)pyridazine

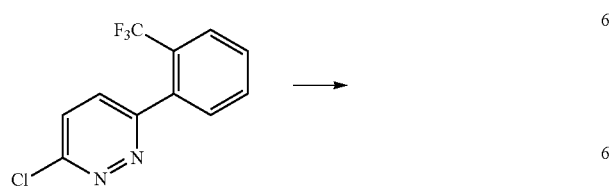

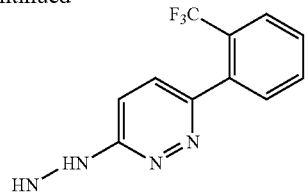

To a solution of 3-chloro-6-(2-(trifluoromethyl)phenyl)pyridazine (3.0 g, 11.60 mmol) in EtOH was added hydrazine hydrate (13.66 g, 232 mmol). The mixture was stirred at 90° C. for about 24 h. Upon cooling to room temp, the reaction was quenched with $H_2O$ and extracted with $CH_2Cl_2$. The combined organic layers were dried over $Na_2SO_4$, filtered and evaporated to dryness under reduced pressure. The crude material was purified by vacuum distillation to afford 3-hydrazinyl-6-(2-(trifluoromethyl)phenyl)pyridazine (2.5 g, 85%). MS (ESI) calcd for $C_{11}H_9F_3N_4$: 254.1.

Step 3. Synthesis of 2-(6-(azetidin-1-yl)pyridin-2-ylamino)-2-oxoacetyl chloride

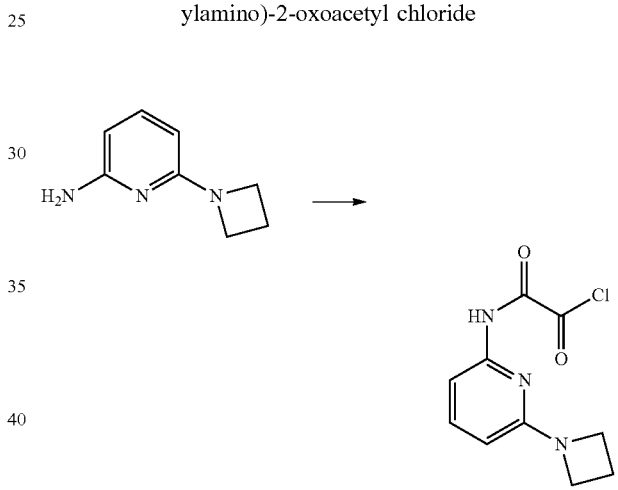

6-(Azetidin-1-yl)pyridin-2-amine (0.1 g, 0.67 mmol) was dissolved in $(COCl)_2$ (2.55 g, 20.11 mmol). The reaction was heated to 50° C. for 1 h, and then cooled to room temp and the volatiles were removed under reduced pressure. Remaining solid was dried under vacuum to provide 2-(6-(azetidin-1-yl)pyridin-2-ylamino)-2-oxoacetyl chloride (0.26 g, 81%). MS (ESI) calcd for $C_{10}H_{10}ClN_3O_2$: 239.1.

Step 4. Synthesis of N-(6-(azetidin-1-yl)pyridin-2-yl)-2-oxo-2-(2-(6-(2-(trifluoromethyl)phenyl)pyridazin-3-yl)hydrazinyl)acetamide

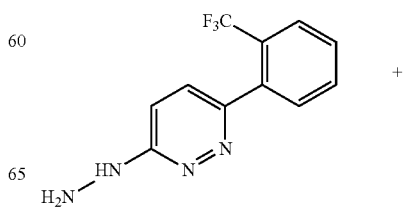

-continued

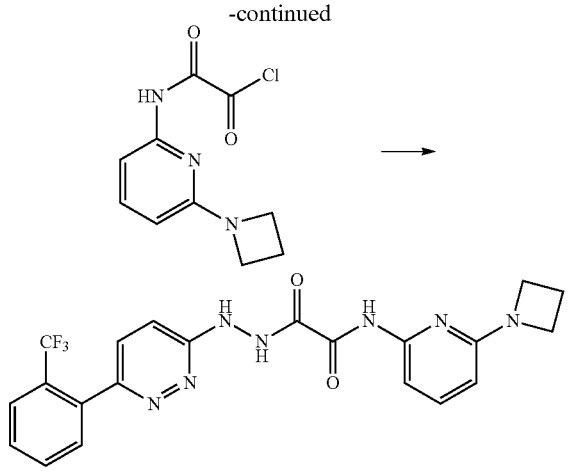

2-(6-(Azetidin-1-yl)pyridin-2-ylamino)-2-oxoacetyl chloride (140.0 mg, 0.58 mmol) was dissolved in methylene chloride (15 mL). 3-hydrazinyl-6-(2-(trifluoromethyl)phenyl)pyridazine (149.0 mg, 0.58 mmol), and triethylamine (70.9 mg, 0.701 mmol) were then added. The reaction was stirred at 25° C. for 16 h. Upon completion, the reaction was poured into NaHCO$_3$ solution, and extracted with CH$_2$Cl$_2$. The combined organic layers were dried with Na$_2$SO$_4$, concentrated, and purified by chromatography to give N-(6-(azetidin-1-yl)pyridin-2-yl)-2-oxo-2-(2-(6-(2-(trifluoromethyl)phenyl)pyridazin-3-yl)hydrazinyl)acetamide (180.0 mg, 67.4%). MS (ESI) calcd for $C_{21}H_{18}F_3N_7O_2$: 457.2.

Step 5. Synthesis of N-(6-(azetidin-1-yl)pyridin-2-yl)-6-(2-(trifluoromethyl)phenyl)-1,2,41-triazolo[4,3-b]pyridazine-3-carboxamide

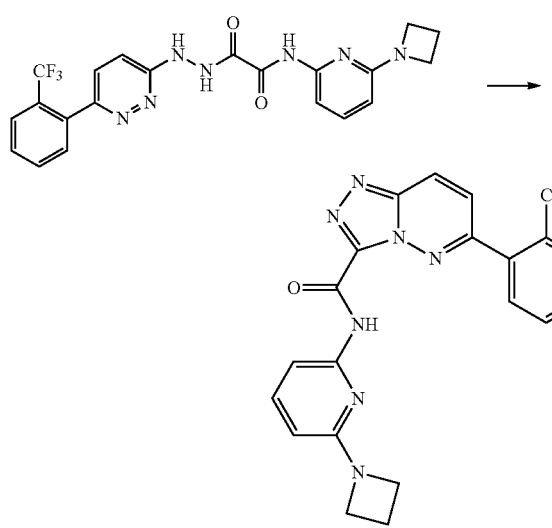

Compound 73

N-(6-(azetidin-1-yl)pyridin-2-yl)-2-oxo-2-(2-(6-(2-(trifluoromethyl)phenyl)pyridazin-3-yl)hydrazinyl)acetamide (100.0 mg, 0.22 mmol) was dissolved in xylene (15 mL), and the reaction was heated in a microwave at 150° C. for 6 h. Upon cooling to room temp, the reaction was poured into H$_2$O, and extracted with DCM. The combined organic layers were dried with Na$_2$SO$_4$, the solvent was removed in vacuo and residue was purified by chromatography to give N-(6-(azetidin-1-yl)pyridin-2-yl)-6-(2-(trifluoromethyl)phenyl)-[1,2,4]triazolo[4,3-b]pyridazine-3-carboxamide (6.0 mg, 6.25%). MS (ESI) calcd for $C_{21}H_{16}F_3N_7O$: 439.1. found: 440.0 [M+H].

This general procedure could be used to prepare N-(6-(pyrrolidin-1-yl)pyridin-2-yl)-6-(2-(trifluoromethyl)phenyl)-[1,2,4]triazolo[4,3-b]pyridazine-3-carboxamide, N-(6-morpholinopyridin-2-yl)-6-(2-(trifluoromethyl)phenyl)-[1,2,4]triazolo[4,3-b]pyridazine-3-carboxamide and 6-(2-(difluoromethyl)phenyl)-N-(2-morpholinopyridin-4-yl)-[1,2,4]triazolo[4,3-b]pyridazine-3-carboxamide.

Example 52. Preparation of 6-((2,2-dimethyl-1,3-dioxolan-4-yl)methoxy)pyrazine-2-carbaldehyde

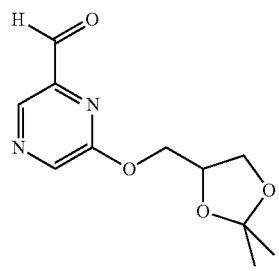 [SMILES: CC1(C)OCC(COc2cncc(C=O)n2)O1]

6-((2,2-dimethyl-1,3-dioxolan-4-yl)methoxy)pyrazine-2-carbaldehyde was prepared using the same method described above as for the preparation of 6-((2,2-dimethyl-1,3-dioxolan-4-yl)methoxy)picolinaldehyde.

Example 53. Preparation of 6-(morpholinomethyl)pyridin-3-amine

Step 1. Synthesis of ethyl 5-(tert-butoxycarbonylamino)picolinate)

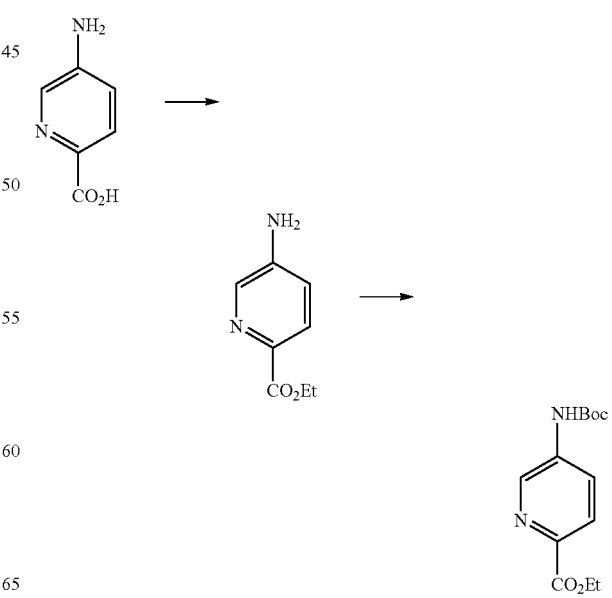

To a solution of 5-aminopyridiencarboxylic acid (8.4 g, 60.8 mmol) in ethanol (100 mL) was added SOCl₂ (14.5 g, 120 mmol) at 0° C. The mixture was refluxed for 12 h. The solvent was removed and saturated Na₂CO₃ solution was added to adjust pH=9 and filtrated to give a solid. The solid was dried in vacuo to give ethyl 5-aminopicolinate (7.5 g, 75%). MS (ESI) calcd for $C_8H_{10}N_2O_2$ (m/z): 166.18.

To a solution of ethyl 5-aminopicolinate (7.5 g, 45 mmol) in t-BuOH (60 mL) and acetone (20 mL) was added DMAP (0.10 g, 0.9 mmol) and di-t-butyl dicarbonate (19.6 g, 90 mmol). The reaction was stirred at room temp overnight. The solvent was removed and hexane (150 mL) was added and cooled to −20° C. for 2 h. The mixture was filtered and the solid was dried in vacuo to give ethyl 5-(tert-butoxycarbonylamino)picolinate (8.9 g, 53%). MS (ESI) calcd for $C_{13}H_{18}N_2O_4$: (m/z) 266.29.

Step 2. Synthesis of tert-butyl 6-(hydroxymethyl)pyridin-3-ylcarbamate

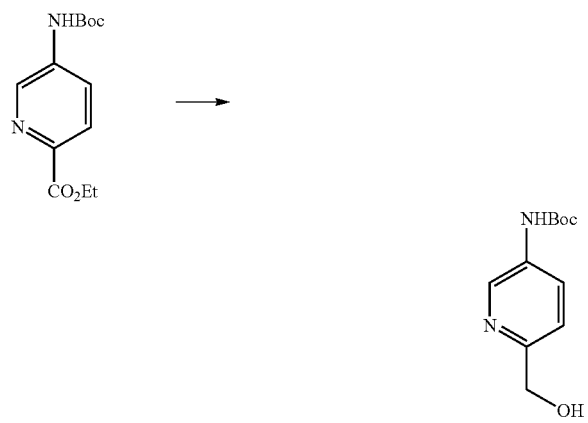

To a stirred solution of ethyl 5-(tert-butoxycarbonylamino)picolinate (8.9 g, 24 mmol) in ethyl ether (200 mL) under nitrogen was added LAH (1.8 g, 48 mmol) in ethyl ether (100 mL) over a period of 30 min at 0° C. The reaction mixture was stirred for 3 h, water (1 mL) and 10% NaOH solution (2 mL) was added and the mixture was filtered and the filtrate was dried over Na₂SO₄ and concentrated under reduced pressure to give compound tert-butyl 6-(hydroxymethyl)pyridin-3-ylcarbamate (4.2 g, 78%). MS (ESI) calcd for $C_{11}H_{16}N_2O_3$ (m/z): 224.26.

Step 3. Synthesis of tert-butyl 6-(morpholinomethyl)pyridin-3-ylcarbamate

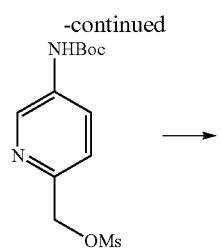

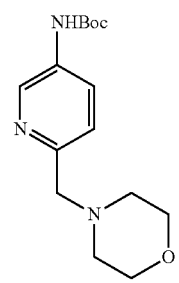

To a solution of tert-butyl 6-(hydroxymethyl)pyridin-3-ylcarbamate (4.2 g, 18.8 mmol) and DIPEA (7.0 g, 56.4 mmol) in THF (20 mL) was added MsCl (2.8 g, 24.4 mmol) over a period of 30 min at 0° C. and the mixture was stirred for 1 h. The reaction was quenched by adding saturated aqueous NaHCO₃ and extracted with EtOAc (3×60 mL). The combined organic layer was washed with brine and dried over Na₂SO₄. The organic solvent was removed to give compound (5-(tert-butoxycarbonylamino)pyridin-2-yl)methyl methanesulfonate (5.5 g) without further purification for next step.

A mixture of (5-(tert-butoxycarbonylamino)pyridin-2-yl)methyl methanesulfonate (1.70 g), morpholine (1.0 g, 11.3 mmol) and K₂CO₃ (2.30 g, 16.9 mmol) acetonitrile (30 mL) was stirred at room temperature for 12 h. Water (30 mL) was added and the mixture was extracted with ethyl acetate (3×30 mL) and dried over MgSO₄, concentrated in vacuo and purified by chromatography on silica gel (petroleum ether:ethyl acetate=1:1 to 1:3) to give tert-butyl 6-(morpholinomethyl)pyridin-3-ylcarbamate (1.20 g, 71% for two steps). MS (ESI) calcd for $C_{15}H_{23}N_3O_3$ (m/z): 293.36.

Step 4. Synthesis of 6-(morpholinomethyl)pyridin-3-amine

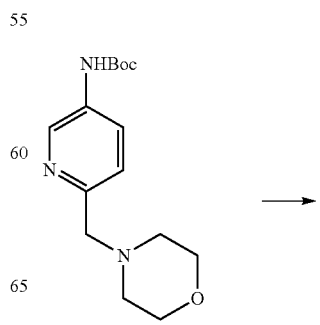

-continued

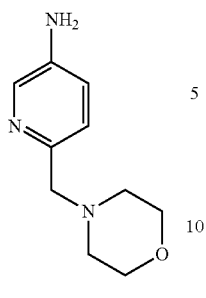

To a solution of tert-butyl 6-(morpholinomethyl)pyridin-3-ylcarbamate (1.20 g, 4.1 mmol) in $CH_2Cl_2$ (20 mL) was added TFA (6 mL). The mixture was stirred for 12 h at room temp. The solvent was removed in vacuo and the solid was basified to pH=9 with saturated $Na_2CO_3$. The mixture was concentrated to dryness and acidified to pH=1, basified to pH=9 and concentrated to dryness. The residue was washed with ethyl acetate (3×25 mL), the combined organic layers were concentrated to give 6-(morpholinomethyl)pyridin-3-amine (450.0 mg, 56%). MS (ESI) calcd for $C_{10}H_{13}N_3O$ (m/z): 193.25. found 194[M+11].

6-(morpholinomethyl)pyridin-2-amine

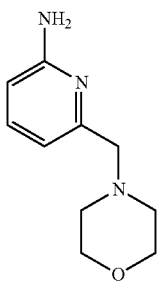 [SMILES: Nc1cccc(CN2CCOCC2)n1]

and
2-(morpholinomethyl)pyridin-4-amine

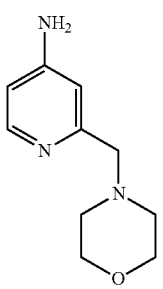 [SMILES: Nc1ccnc(CN2CCOCC2)c1]

were prepared by the same sequence above, starting from 6-aminopicolinic acid and 2-aminopicolinic acid respectively.

5-(pyrrolidin-1-ylmethyl)pyridin-2-amine

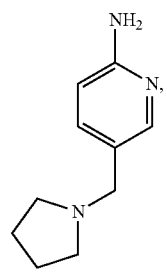 [SMILES: Nc1ccc(CN2CCCC2)cn1]

6-(pyrrolidin-1-ylmethyl)pyridin-2-amine

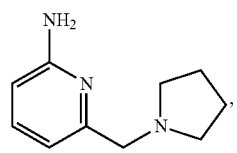 [SMILES: Nc1cccc(CN2CCCC2)n1]

6-(pyrrolidin-1-ylmethyl)pyridin-3-amine

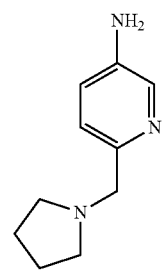 [SMILES: Nc1ccc(CN2CCCC2)nc1]

and 2-(pyrrolidin-1-ylmethyl)pyridin-4-amine

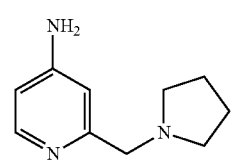 [SMILES: Nc1ccnc(CN2CCCC2)c1]

were prepared by the same sequence above, starting from 6-aminonicotinic acid, 6-aminopicolinic acid, 5-aminopicolinic acid and 4-aminopicolinic acid and reacting the resulting mesylate intermediates with pyrrolidine.

Example 54. Preparation of
6-morpholinopyridin-2-amine

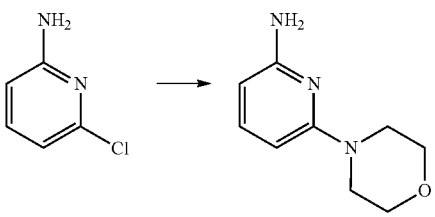 [SMILES: Nc1cccc(Cl)n1 ; Nc1cccc(N2CCOCC2)n1]

A mixture of 6-chloropyridin-2-amine (19.3 g, 150 mmol), K₂CO₃ (41.7 g, 0.30 mol) and morpholine (38.9 mL, 450 mmol) in DMSO (150 mL) was stirred at 190° C. (oil bath) for 10 h. After cooling to room temp, water (300 mL) was added and extracted with ethyl acetate (4×150 mL). The combined organic layers were washed with water (3×25 mL), dried over Na₂SO₄ and concentrated in vacuo. The residue was purified by silica gel chromatography (10:1 petroleum ether: ethyl acetate) to give 6-morpholinopyridin-2-amine as a white solid (9.0 g, 54.8 mmol). MS (ESI) calcd for C₉H₁₃N₃O (m/z): 179.11. found 180 [M+H].

4-morpholinopyridin-2-amine

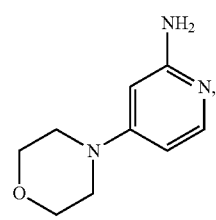 [SMILES: Nc1cc(N2CCOCC2)ccn1]

5-morpholinopyridin-2-amine

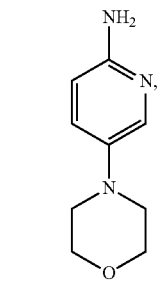 [SMILES: Nc1ccc(N2CCOCC2)cn1]

2-morpholinopyridin-3-amine

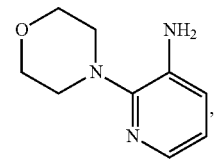

5-morpholinopyridin-3-amine

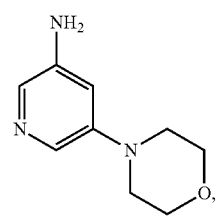 [SMILES: Nc1cncc(N2CCOCC2)c1]

6-morpholinopyridin-3-amine

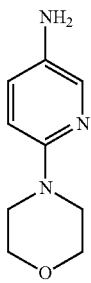 [SMILES: Nc1ccc(N2CCOCC2)nc1]

and 2-morpholinopyridin-4-amine

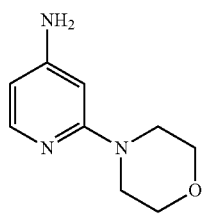 [SMILES: Nc1ccnc(N2CCOCC2)c1]

were prepared by the same sequence above, starting from 4-chloropyridin-2-amine, 5-chloropyridin-2-amine, 2-chloropyridin-3-amine, 5-chloropyridin-3-amine, 6-chloropyridin-3-amine and 2-chloropyridin-4-amine respectively.

2-(pyrrolidin-1-yl)pyridin-4-amine

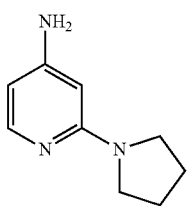 [SMILES: Nc1ccnc(N2CCCC2)c1]

and 6-(pyrrolidin-1-yl)pyridin-2-amine

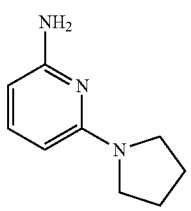 [SMILES: Nc1cccc(N2CCCC2)n1]

were prepared by the same sequence above, starting from 2-chloropyridin-4-amine and 6-chloropyridin-2-amine respectively and reacting with pyrrolidine.

Example 55. Preparation of 6-(2,2,2-trifluoroethoxy)pyridin-2-amine

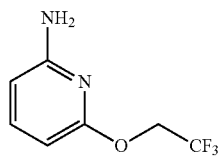

6-(2,2,2-trifluoroethoxy)pyridin-2-amine was prepared similarly to 2-(2,2,2-trifluoroethoxy)pyridin-4-amine above, using 6-chloropyridin-2-amine. MS (ESI) calcd for $C_7H_7F_3N_2O$: 192.05.

Example 56. Preparation of 4-(2,2,2-trifluoroethoxy)pyrimidin-2-amine

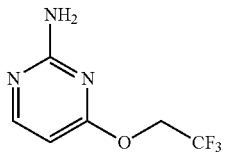

4-(2,2,2-trifluoroethoxy)pyrimidin-2-amine was prepared the same as above, using 4-chloropyrimidin-2 amine. MS (ESI) calcd for $C_6H_6F_3N_3O$: 193.05.

Example 57. Preparation of 4-methyl-6-(2,2,2-trifluoroethoxy)pyrimidin-2-amine

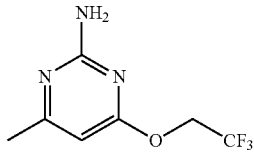

4-methyl-6-(2,2,2-trifluoromethoxy)pyrimidin-2-amine was prepared the same as above, using 4-chloro-6-methylpyrimidin-2-amine. MS (ESI) calcd for $C_7H_8F_3N_3O$: 207.06.

Example 58. Preparation of 2-(2,2,2-trifluoroethoxy)pyrimidin-4-amine

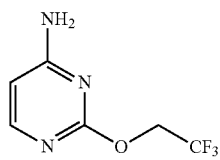

2-(2,2,2-trifluoroethoxy)pyrimidin-4-amine was prepared the same as above, using 2-chloropyrimidin-4-amine. MS (ESI) calcd for $C_6H_6F_3N_3O$: 193.05.

Example 59. Preparation of 6-(2,2,2-trifluoroethoxy)pyridin-2-amine

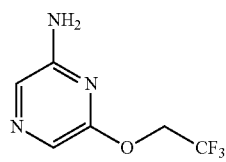 [SMILES: Nc1cncc(OCC(F)(F)F)n1]

Prepared using the same method as that for 2-(2,2,2-trifluoroethoxy)pyridin-4-amine. MS (ESI) calcd for $C_6H_6F_3N_3O$: 193.05.

Example 60. Preparation of 4-((2,2-dimethyl-1,3-dioxolan-4-yl)methoxy)pyrimidin-2-amine

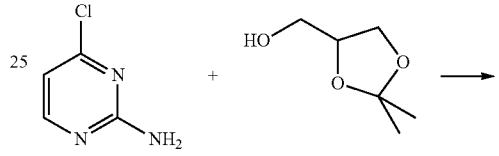

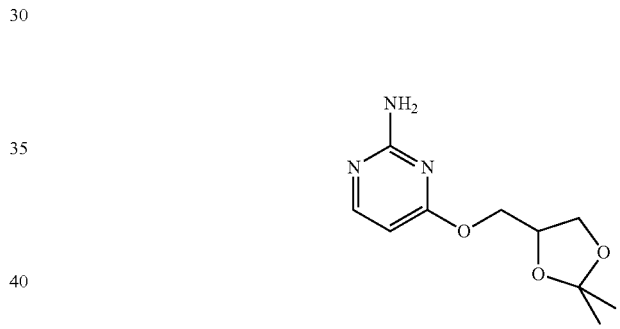

NaH (1.15 g, 60% in mineral oil, 28.7 mmol) was added the mixture of 4-chloropyrimidin-2-amine (1.0 g, 7.75 mmol) and solketal (3.07 g, 23.25 mmol) in dioxane (12 mL) solution at 0° C. The temperature was elevated to 120° C. for 15 h. After cooling to room temp, the solids were filtered, filtrate was concentrated and residue purified by column chromatography to give 4-((2,2-dimethyl-1,3-dioxolan-4-yl)methoxy)pyrimidin-2-amine (1.2 g, 69%). MS (ESI) calcd for $C_{10}H_{15}N_3O_3$: 225.11.

Example 61. Preparation of 6-((2,2-dimethyl-1,3-dioxolan-4-yl)methoxy)pyridin-3-amine

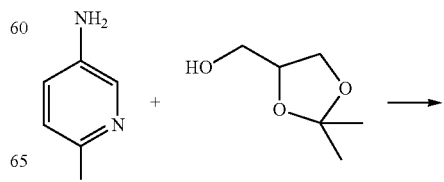

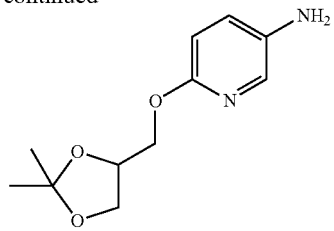

The 2-bromopyridin-4-amine (650.0 mg, 3.76 mmol) was taken up in dioxane (25 mL) along with (2,2-dimethyl-1,3-dioxolan-4-yl) methanol (3.97 g, 30.1 mmol) and NaH (451.0 mg, 18.78 mmol). The resulting reaction mixture was stirred at reflux for 48 h, concentrated in vacuo and purified by chromatography to give 6-((2,2-dimethyl-1,3-dioxolan-4-yl)methoxy)pyridin-3-amine as a pale yellow solid (260.0 mg, 40%). MS (ESI) calcd for $C_{11}H_{16}N_2O_3$: 224.12. found 224.87 [M+H].

Example 62. Preparation of 2-((2,2-dimethyl-1,3-dioxolan-4-yl)methoxy)pyridin-4-amine

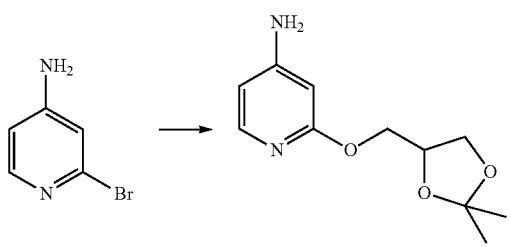 [SMILES: Nc1ccnc(Br)c1 ; CC1(C)OCC(COc2cc(N)ccn2)O1]

2-((2,2-dimethyl-1,3-dioxolan-4-yl)methoxy)pyridin-4-amine was prepared using the same method described above using 2-bromopyridin-4-amine. MS (ESI) calcd for $C_{11}H_{16}N_2O_3$: 224.12.

Example 63. Preparation of 5-((2,2-dimethyl-1,3-dioxolan-4-yl)methoxy)pyrazin-2-amine

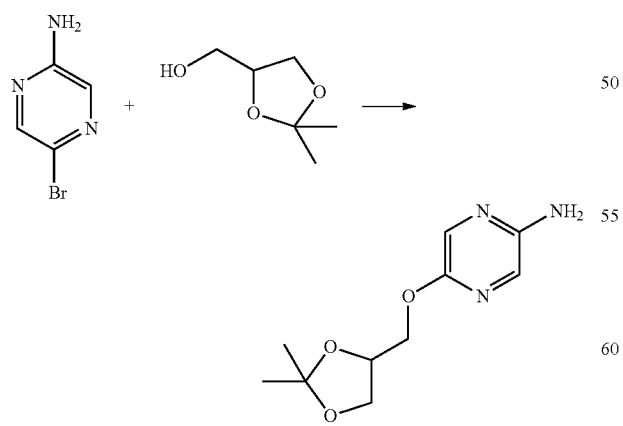

5-((2,2-dimethyl-1,3-dioxolan-4-yl)methoxy)pyrazin-2-amine was prepared the same as above, using 5-bromopyrazin-2-amine. MS (ESI) calcd for $C_{10}H_{15}N_3O_3$: 225.11.

Example 64. Preparation of 2-((2,2-dimethyl-1,3-dioxolan-4-yl)methoxy)-6-methylpyridin-4-amine Step 1. Synthesis 2-bromo-6-methylpyridine 1-oxide

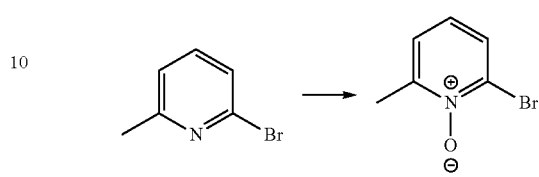

To a solution of 2-bromo-6-methylpyridine (40.0 g, 233 mmol) in acetic acid (50 mL) was added $CH_3CO_3H$ (175 mL, 233 mmol) maintaining temperature below 50° C. After completion of addition the mixture was stirred at 50° C. for 15 h and then cooled to room temp. Crushed ice was added and the pH was adjusted to 12 with 40% aqueous KOH solution. After extraction with $CHCl_3$, the combined organic layers were dried over $Na_2SO_4$, concentrated in vacuo and crude product was purified by silica-gel using EtOAc:Pentane=1:1, then DCM:MeOH=10:1 to give 2-bromo-6-methylpyridine 1-oxide. MS (ESI) calcd for $C_6H_6BrNO$: 188.96.

Step 2. Synthesis of 2-bromo-6-methyl-4-nitropyridine 1-oxide

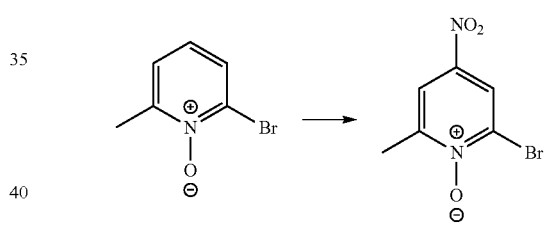

Flask charged with solid 2-bromo-6-methylpyridine 1-oxide (16.0 g, 85 mmol) was cooled to 0° C. To this fuming nitric acid (80 mL) was added followed by $H_2SO_4$ (98%, 30 mL). The mixture was stirred at 90° C. for 90 min and then cooled to room temp. Crushed ice was added and the pH was adjusted to 12 with 30% aqueous NaOH solution. The solid was filtered to give 2-bromo-6-methyl-4-nitropyridine 1-oxide (16.0 g, 81%) as a pale yellow solid. MS (ESI) calcd for $C_6H_5BrN_2O_3$: 232.0.

Step 3. Synthesis of 2-bromo-6-methylpyridin-4-amine

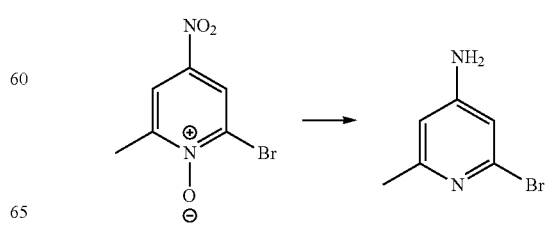

A solution of 2-bromo-6-methyl-4-nitropyridine 1-oxide (16.0 g, 68.7 mmol) in acetic acid (300 mL) was treated with powdered iron (25.8 g, 460 mmol), the mixture was slowly heated to 100° C., kept for 2 h at this temperature, then cooled to room temp and filtered. After evaporation of the solvent, the residue was purified by silica-gel using EtOAc:Pet ether=1:1 to give 2-bromo-6-methylpyridin-4-amine. MS (ESI) calcd for $C_6H_7BrN_2$: 185.98. found: 186.96 [M+H].

Step 4. 2-((2,2-dimethyl-1,3-dioxolan-4-yl)methoxy)-6-methylpyridin-4-amine

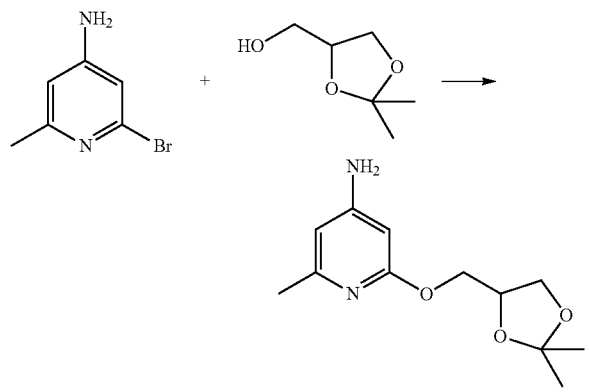

2-((2,2-dimethyl-1,3-dioxolan-4-yl)methoxy)-6-methyl-pyridin-4-amine was prepared the same as above, using 2-bromo-6-methylpyridin-4-amine. MS (ESI) calcd for $C_{12}H_{18}N_2O_3$: 238.13.

Each individual enantiomer was also prepared the same as above.

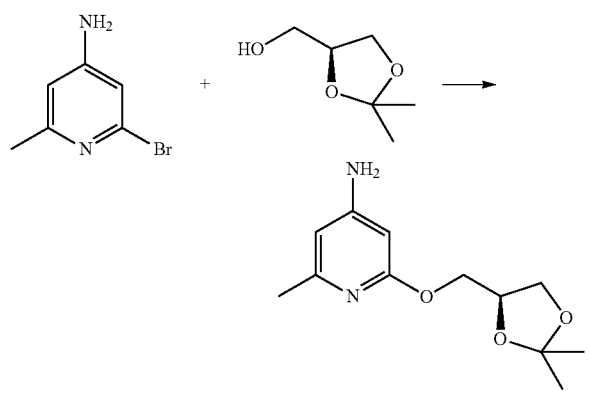

To make (S)-2-((2,2-dimethyl-1,3-dioxolan-4-yl)methoxy)-6-methylpyridin-4-amine, (S)-(2,2-dimethyl-1,3-dioxolan-4-yl)methanol was used.

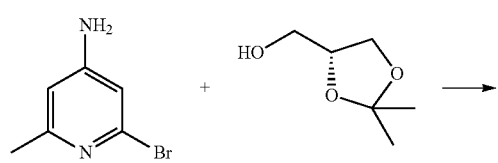

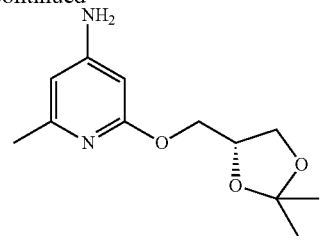

To make (R)-2-(2,2-dimethyl-1,3-dioxolan-4-yl)methoxy)-6-methylpyridin-4-amine, (R)-(2,2-dimethyl-1,3-dioxolan-4-yl)methanol was used.

Example 65. Preparation of 4-((2,2-dimethyl-1,3-dioxolan-4-yl)methoxy)-6-methylpyrimidin-2-amine

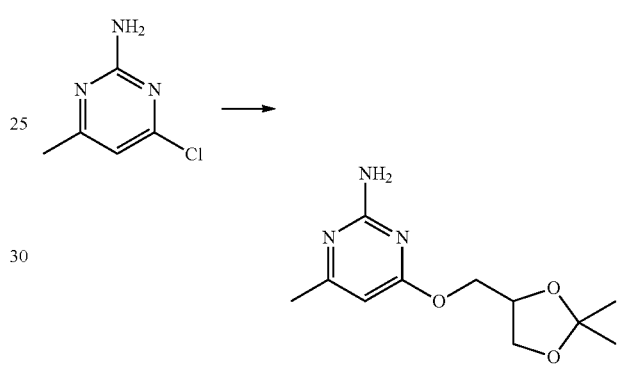

Solketal (49.5 g, 0.38 mol) was added to a suspension of NaH (15.0 g, 0.38 mol) in THF at 0° C. The resulting mixture was stirred at room temp for 2 h. 4-chloro-6-methylpyrimidin-2-amine (18.0 g, 0.125 mol) was added. The reaction was heated at 70° C. for 17 h. After cooling to room temp, $H_2O$ (100 mL) was added. The aqueous layer was extracted with ethyl acetate. Combined organic layers were dried, concentrated and the product was washed with diethyl ether/hexanes (10:1) to afford 4-((2,2-dimethyl-1,3-dioxolan-4-yl)methoxy)-6-methylpyrimidin-2-amine (19.0 g, 63% yield). MS (ESI) calcd for $C_{11}H_{17}N_3O_3$: 239.1.

Example 66. Preparation of 4-((2,2-dimethyl-1,3-dioxolan-4-yl)methoxy)pyridin-2-amine

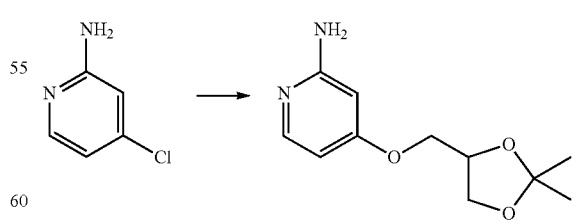

This was prepared using the same method as that for 4-((2,2-dimethyl-1,3-dioxolan-4-yl)methoxy)-6-methylpyrimidin-2-amine except that no solvent was used and heating was at 110° C. for 3 d. MS (ESI) calcd for $C_{11}H_{16}N_2O_3$: 224.1.

Example 67. Preparation of 2-((2,2-dimethyl-1,3-dioxolan-4-yl)methoxy)pyrimidin-4-amine

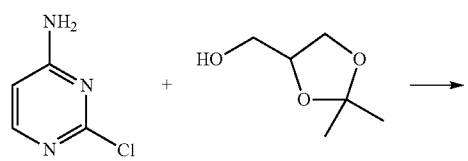

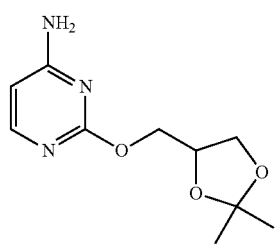

To a solution of solketal (34.4 g, 260 mmol) in THF (150 mL) was added NaH (10.4 g, 260 mmol) at room temp and the mixture stirred for 1 h. 2-chloro-4-aminopyrimidine (15.0 g, 115 mmol) was then added, and the mixture was stirred at 70° C. for 48 h. The reaction mixture was concentrated and the crude residue was purified by flash chromatography (CH$_2$Cl$_2$:MeOH=15:1-10:1) to give 2-((2,2-dimethyl-1,3-dioxolan-4-yl)methoxy)pyrimidin-4-amine (18.2 g, 70% yield) as an oil. MS (ESI) calcd for C$_{10}$H$_{15}$N$_3$O$_3$: 225.11.

Example 68. Preparation of (S)-6-((2,2-dimethyl-1,3-dioxolan-4-yl)methoxy)pyrazin-2-amine

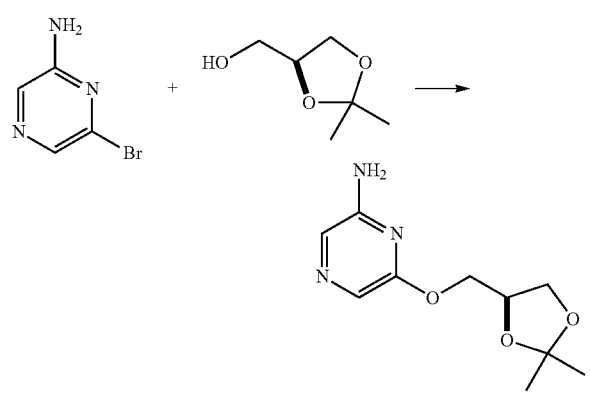

(S)-6-((2,2-dimethyl-1,3-dioxolan-4-yl)methoxy)pyrazin-2-amine was prepared the same as above, using 6-chloropyrazin-2-amine and (S)-(2,2-dimethyl-1,3-dioxolan-4-yl)methanol. MS (ESI) calcd for C$_{10}$H$_{15}$N$_3$O$_3$: 225.11.

Example 69. Preparation of 5-morpholinopyridin-2-amine

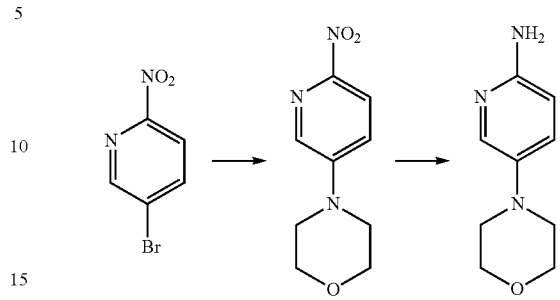

5-bromo-2-nitropyridine (1.0 g, 4.93 mmol), morpholine (0.47 g, 5.42 mmol), Bu$_4$NI (0.09 g, 0.25 mmol), K$_2$CO$_3$ (0.75 g, 5.42 mmol) were stirred in DMSO (10 mL) at 80° C. for 30 h. Water was added and the solid separated by filtration was purified by column chromatography to give (4-(6-nitropyridin-3-yl)morpholine).

To a solution of 4-(6-nitropyridin-3-yl)morpholine (0.7 g, 3.35 mmol) in CH$_3$OH (10 mL) Raney nickel (0.20 g, 3.35 mmol) was added at 25° C. and the mixture was stirred under H$_2$ balloon for about 12 h. After filtration and concentration of the solvent, 5-morpholinopyridin-3-amine was obtained and was used without further purification. MS (ESI) calcd for C$_9$H$_{13}$N$_3$O: 179.11.

Example 70. Preparation of 3-morpholinopyridin-2-amine

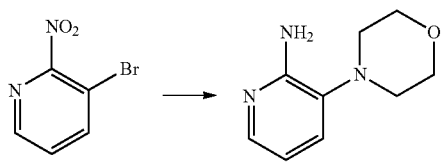 [SMILES: O=[N+]([O-])c1ncccc1Br ; Nc1ncccc1N1CCOCC1]

3-morpholinopyridin-2-amine was prepared from 3-bromo-2-nitropyridine using the same two-step procedure described above.

Example 71. Preparation of 4-morpholinopyridin-3-amine

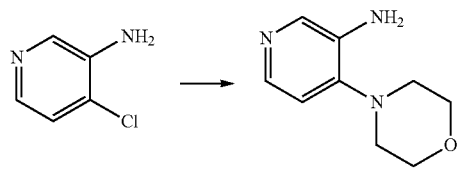 [SMILES: Nc1cnccc1Cl ; Nc1cnccc1N1CCOCC1]

A solution of 4-chloropyridin-3-amine (0.5 g, 3.89 mmol) and morpholine (0.68 g, 7.78 mmol) in DMAC (10 mL) was heated at 200° C. for 30 h. After cooling to room temp, water was added and the solid was purified by column chromatography to give 4-morpholinopyridin-3-amine. MS (ESI) calcd for C$_9$H$_{13}$N$_3$O: 179.11.

Example 72. Preparation of 2-(2-oxa-6-azaspiro[3.3]heptan-6-yl)pyrimidin-4-amine

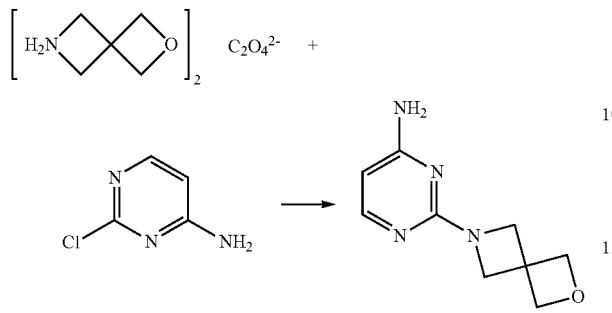

To a mixture of 4-amino-2-chloropyrimidine (300.0 mg, 2.3 mmol) in THF (4 mL), DIEA (0.8 mL) was added. The reaction was refluxed for 15 h. After cooling to room temperature, the solvent was evaporated and the solid was taken up in $CH_2Cl_2$. After filtration, the solid was dissolved in $CH_2Cl_2$+MeOH (1:1) and adsorbed onto silica gel for purification by column chromatography to afford 2-(2-oxa-6-azaspiro[3.3]heptan-6-yl)pyrimidin-4-amine (160.0 mg, 36%). MS (ESI) calcd for $C_9H_{12}N_4O$: 192.1.

Example 73. Preparation of 6-(ethylamino)pyridin-2-aminium 2,2,2-trifluoroacetate

Step 1. Synthesis of tert-butyl (6-(ethylamino)pyridin-2-yl)carbamate

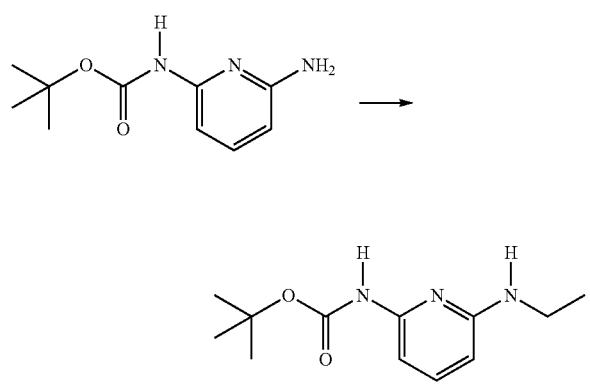

To a solution of tert-butyl (6-aminopyridin-2-yl)carbamate (209.0 mg, 1.0 mmol) in dichloroethane (3 mL), a solution of acetaldehyde (0.06 mL, 1.0 mmol) in dichloroethane (0.5 mL) was added. After 1 h at room temp the reaction was quenched with saturated $NaHCO_3$ solution. The aqueous mixture was extracted with dichloromethane (2×50 mL). After concentrating the combined organic layers, the crude product was purified by flash column chromatography (pentane:ethyl acetate=10-30%) to afford tert-butyl (6-(ethylamino)pyridin-2-yl)carbamate (100.0 mg, 42%). MS (ESI) calcd for $C_{12}H_{19}N_3O_2$: 237.2.

Step 2. Synthesis of 6-(ethylamino)pyridin-2-aminium 2,2,2-trifluoroacetate

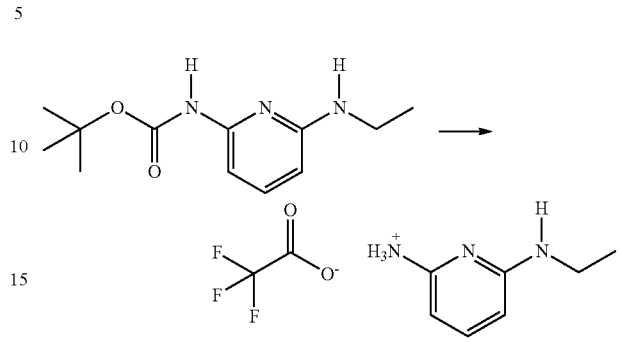

Tert-butyl (6-(ethylamino)pyridin-2-yl)carbamate (200 mg, 0.84 mmol) was taken up in TFA:$CH_2Cl_2$ (1:1, 4 mL) and stirred at room temperature for 2 h. Solvents were evaporated under reduced pressure, the residue was dried on the high vacuum pump upon which 6-(ethylamino)pyridin-2-aminium 2,2,2-trifluoroacetate was obtained as solid (220.0 mg, yield quant.). MS (ESI) calcd for $C_9H_{12}F_3N_3O_2$: 251.1.

Example 74. Preparation of 2-((3-methyloxetan-3-yl)methoxy)pyrimidin-4-amine

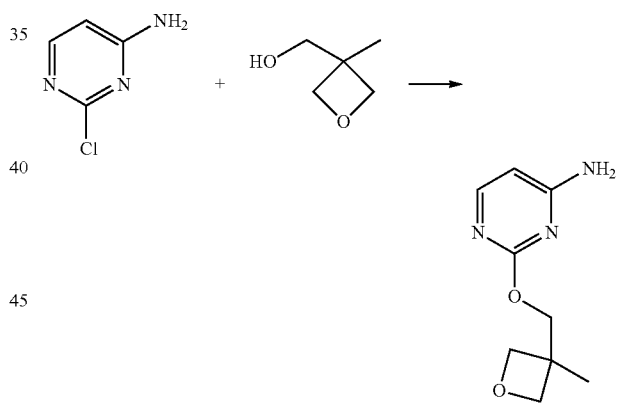

NaH (60% in oil, 2.47 g, 61.8 mmol) was washed twice with pentane and dried under vacuum. THF (25 mL) was added, followed by (3-methyloxetan-3-yl)methanol (6.1 mL, 61.8 mmol) dropwise. This was allowed to stir 1 h at room temp before addition of 15 mL more TNF and 4-amino-2-chloropyrimidine (4.0 g, 30.9 mmol). The reaction was heated to reflux for 17 h, cooled and concentrated. Water was added (50 mL), and enough saturated $NH_4Cl$ to bring the pH down to 8. The mixture extracted with EtOAc (3×75 mL), and the combined organics were washed with saturated aqueous $NaHCO_3$ and brine, dried with $Na_2SO_4$, filtered and concentrated. The crude product was purified by silica gel column chromatography (0-10% MeOH/$CH_2Cl_2$) to give 2-((3-methyloxetan-3-yl)methoxy)pyrimidin-4-amine (1.84 g, 30%). MS (ESI) calcd for $C_9H_{13}N_3O_2$: 195.10. found: 196 [M+H].

Example 75. Preparation of 4-methyl-6-((3-methyloxetan-3-yl)methoxy)pyrimidin-2-amine

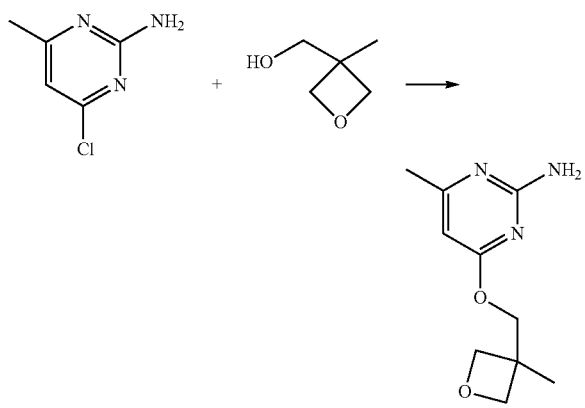

NaH (60% in oil, 2.23 g, 55.7 mmol) was washed twice with pentane and dried under vacuum. THF (35 mL) was added, followed by (3-methyloxetan-3-yl)methanol (5.5 mL, 55.7 mmol) dropwise. This was allowed to stir 1 h at room temp before addition of 5 mL more THF and 4-chloro-6-methylpyrimidin-2-amine (4.0 g, 27.9 mmol). The reaction was heated to reflux for 17 h, cooled and concentrated. Water was added (50 mL), and the mixture was extracted with EtOAc (3×75 mL), and the combined organics were washed with saturated aqueous NaHCO$_3$ and brine, dried with Na$_2$SO$_4$, filtered and concentrated. The crude product was triturated with Et$_2$O and the white solid was dried under vacuum to give 4-methyl-6-((3-methyloxetan-3-yl)methoxy)pyrimidin-2-amine (2.42 g, 41%). MS (ESI) calcd for C$_{10}$H$_{15}$N$_3$O$_2$: 209.12. found: 210 [M+H].

Example 76. Preparation of 6-((3-methyloxetan-3-yl)methoxy)pyrazin-2-amine

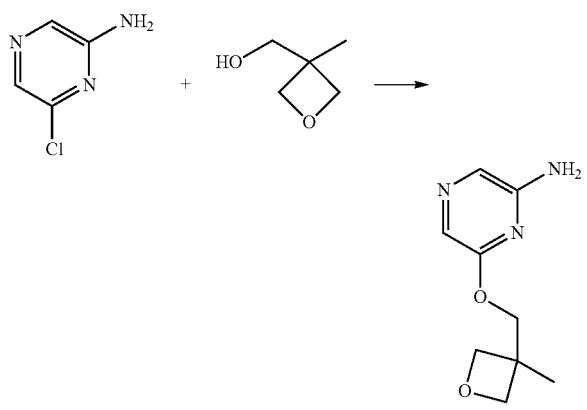

NaH (60% in oil, 1.24 g, 30.9 mmol) was washed twice with pentane and dried under vacuum. Dioxane (50 mL) was added, followed by (3-methyloxetan-3-yl)methanol (3.0 mL, 30.9 mmol) dropwise. This was allowed to stir 2 h at room temp before addition of 6-chloropyrazin-2-amine (2.0 g, 15.4 mmol). The reaction was heated to reflux for 16 h, cooled and concentrated. Water was added (50 mL), and the mixture was extracted with EtOAc (3×75 mL), and the combined organics were washed with water and brine, dried with Na$_2$SO$_4$, filtered and concentrated. The crude product was purified by silica gel column chromatography (0-10% MeOH/CH$_2$Cl$_2$) to give 6-((3-methyloxetan-3-yl)methoxy)pyrazin-2-amine (3.02 g, quant.). MS (ESI) calcd for C$_9$H$_{13}$N$_3$O$_2$: 195.10. found: 196 [M+H].

Example 77. Preparation of 2-(tetrahydro-2H-pyran-4-yloxy)pyrimidin-4-amine

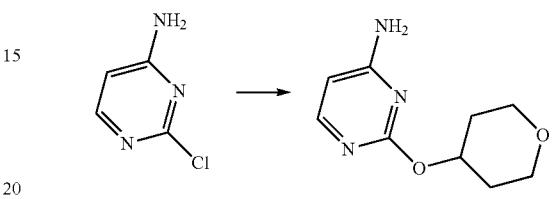

NaH (60% in oil, 126.0 mg, 3.15 mmol) was washed twice with pentane and dried under vacuum. THF (3.0 mL) was added, followed by tetrahydro-2H-pyran-4-ol (0.3 mL, 3.15 mmol) dropwise over 5 min. The mixture was allowed to stir at room temp for 1 h. 2-chloro-4-aminopyrimidine (314.0 mg, 2.43 mmol) was added and the reaction was heated to reflux for 18 h. The mixture was cooled to room temp and water was added (5 mL), along with enough saturated aqueous NH$_4$Cl to bring the pH down to 8. Minimal EtOAc was added (2 mL), but there was a precipitate between layers so the entire mixture was filtered and the solid was washed with water. The solid was dried under vacuum to give clean 2-(tetrahydro-2H-pyran-4-yloxy)pyrimidin-4-amine (220.0 mg, 46%). MS (ESI) calcd for C$_9$H$_{13}$N$_3$O$_2$: 195.10. found: 196 [M+H].

Example 78. Preparation of (R)-2-(tetrahydrofuran-3-yloxy)pyrimidin-4-amine

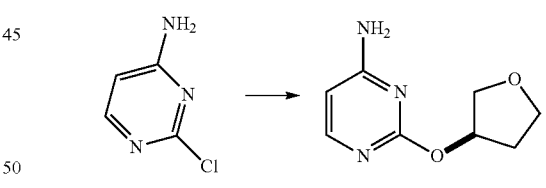

The reaction was run similarly to the above, with NaH (60% in oil, 227.0 mg, 5.67 mmol), THF (5.4 mL), (R)-tetrahydrofuran-3-ol (0.456 mL, 5.67 mmol), and 2-chloro-4-aminopyrimidine (566.0 mg, 4.36 mmol) for 19 h. Water and EtOAc were added (10 mL each), along with enough saturated aqueous NH$_4$Cl to bring the pH down to 8 (about 2 mL). The layers were separated and the aqueous layer was washed twice more with EtOAc (2×10 mL). The combined organics were washed with brine, dried with Na$_2$SO$_4$, filtered and concentrated to give 748.0 mg of crude product. This was triturated with Et$_{2O}$ and filtered. The solid was washed with Et$_2$O and dried under vacuum to give (R)-2-(tetrahydrofuran-3-yloxy)pyrimidin-4-amine (419 mg, 53%). MS (ESI) calcd for C$_8$H$_{11}$N$_3$O$_2$: 181.09. found: 182 [M+H].

Example 79. Preparation of (S)-2-(tetrahydrofuran-3-yloxy)pyrimidin-4-amine

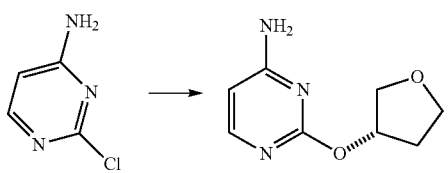

(S)-2-(tetrahydrofuran-3-yloxy)pyrimidin-4-amine was prepared the same as above, using (S)-tetrahydrofuran-3-ol. 53% yield. MS (ESI) calcd for $C_8H_{11}N_3O_2$: 181.09. found: 182 [M+H].

Example 80. Preparation of 2-isopropoxypyrimidin-4-amine

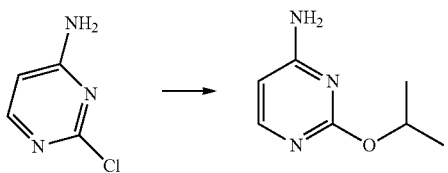

2-isopropoxypyrimidin-4-amine was prepared the same as above, using isopropanol. 23% yield. MS (ESI) calcd for $C_7H_{11}N_3O$: 153.09. found: 154 [M+H].

Example 81. Preparation of 2-(2-methoxyethoxy)pyrimidin-4-amine

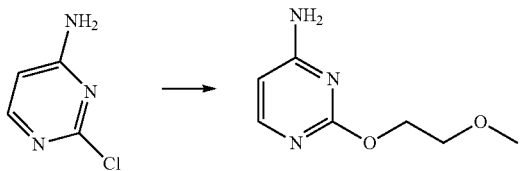

2-(2-methoxyethoxy)pyrimidin-4-amine was prepared the same as above, using 2-methoxyethanol. 73% yield. MS (ESI) calcd for $C_7H_{11}N_3O_2$: 169.09. found: 170 [M+H].

Example 82. Preparation of 6-(2-methoxyethoxy)pyrimidin-4-amine

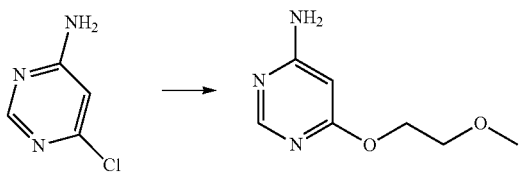

6-(2-methoxyethoxy)pyrimidin-4-amine was prepared the same as above, using 4-amino-6-chloropyrimidine. 82% yield. MS (ESI) calcd for $C_7H_{11}N_3O_2$: 169.09. found: 170 [M+H].

Example 83. Preparation of (R)-6-(tetrahydrofuran-3-yloxy)pyrimidin-4-amine

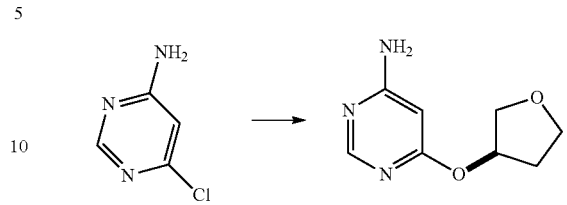

(R)-6-(tetrahydrofuran-3-yloxy)pyrimidin-4-amine was prepared the same as above, using (R)-tetrahydrofuran-3-ol. 45% yield. MS (ESI) calcd for $C_8H_1N_3O_2$: 181.09. found: 182 [M+H].

Example 84. Preparation of (S)-6-(tetrahydrofuran-3-yloxy)pyrimidin-4-amine

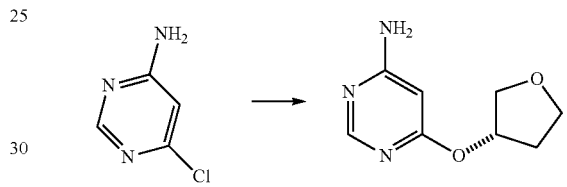

(S)-6-(tetrahydrofuran-3-yloxy)pyrimidin-4-amine was prepared the same as above, using (S)-tetrahydrofuran-3-ol. 68% yield. MS (ESI) calcd for $C_8H_{11}N_3O_2$: 181.09. found: 182 [M+H].

Example 85. Preparation of 6-(pyrrolidin-1-yl)pyrimidin-4-amine

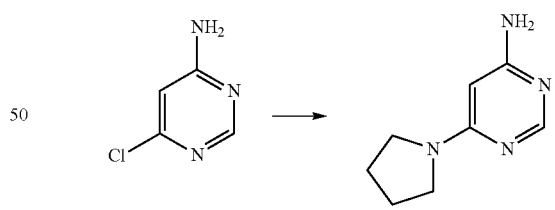

A microwave vial was charged with 4-amino-6-chloropyrimidine (1.0 g, 7.72 mmol), and pyrrolidine (10 mL) was added. The vial was sealed, and heated in the microwave at 180° C. for 1 h. After cooling, the reaction was diluted with methanol (30 mL), and silica (15.0 g) was added. All solvents were removed in vacuo, and the remaining silica slurry loaded on a 40.0 g silica column. Elution with a 0% to 10% methanol in dichloromethane gradient yielded 6-(pyrrolidin-1-yl)pyrimidin-4-amine (1.22 g, 96% yield). MS (ESI) calcd for $C_8H_{14}N_4$: 164.11.

Example 86. Preparation of 4-(pyrrolidin-1-yl)pyrimidin-2-amine

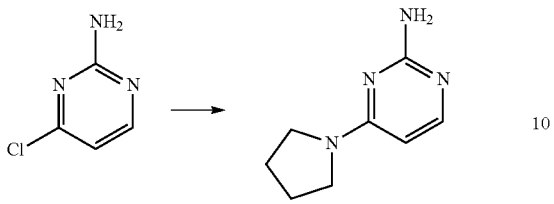

A microwave vial was charged with 2-amino-4-chloropyrimidine (2.0 g, 15.4 mmol), and pyrrolidine (10 mL) was added. The vial was sealed, and heated in the microwave at 150° C. for 1 h. After cooling, the reaction was diluted with methanol (30 mL), and silica (15 g) was added. All solvents were removed in vacuo, and the remaining silica slurry loaded on a 40.0 g silica column. Elution with a 0% to 10% methanol in dichloromethane gradient yielded 4-(pyrrolidin-1-yl)pyrimidin-2-amine (1.70 g, 67% yield). MS (ESI) calcd for $C_8H_{14}N_4$: 164.11.

Example 87. Preparation of 2-(1-(dioxothia)-6-azaspiro[3.3]heptan-6-yl)pyrimidin-4-amine

Step 1. Synthesis of tert-butyl 3-(2-oxoethylidene)azetidine-1-carboxylate

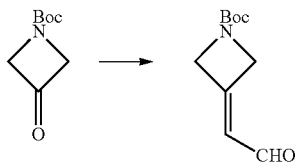 [SMILES: CC(C)(C)OC(=O)N1CC(=O)C1 ; CC(C)(C)OC(=O)N1CC(=CC=O)C1]

To a solution of tert-butyl 3-oxoazetidine-1-carboxylate (20.0 g, 117 mmol) in DCM (400 mL) was added (formylmethylene)triphenylphosphorane (40 g, 129 mmol) at room temp, and the reaction mixture was stirred at 40° C. for 6 h, followed by concentration in vacuo. The residue was purified by silica gel column chromatography (hexanes:EtOAc 5:1) to give tert-butyl 3-(2-oxoethylidene)azetidine-1-carboxylate as a yellow oil (23.0 g, quant.). MS (ESI) calcd for $C_{10}H_{15}NO_3$: 197.11.

Step 2. Synthesis of tert-butyl 3-(acetylthio)-3-(2-oxoethyl)azetidine-1-carboxylate

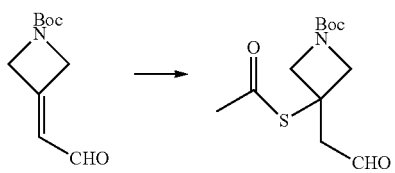 [SMILES: CC(C)(C)OC(=O)N1CC(=CC=O)C1 ; CC(=O)SC1(CC=O)CN(C(=O)OC(C)(C)C)C1]

To a solution of tert-butyl 3-(2-oxoethylidene)azetidine-1-carboxylate (985.0 mg, 5 mmol) in THF (4 mL) was added piperidine (0.035 mL, 0.35 mmol). Thioacetic acid (0.535 mL, 7.5 mmol) was added and the mixture was stirred at room temp for 6 h. The mixture was then directly purified by silica gel column chromatography (hexanes:EtOAc 2:1) to give tert-butyl 3-(acetylthio)-3-(2-oxoethyl)azetidine-1-carboxylate as a yellow oil (1.2 g, 88%). MS (ESI) calcd for $C_{12}H_9NO_4S$: 273.10.

Step 3. Synthesis of tert-butyl 3-(2-hydroxyethyl)-3-mercaptoazetidine-1-carboxylate

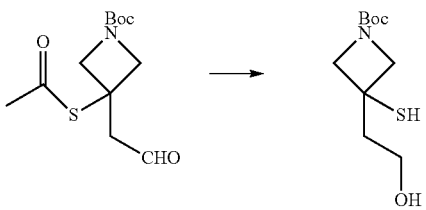 [SMILES: CC(=O)SC1(CC=O)CN(C(=O)OC(C)(C)C)C1 ; CC(C)(C)OC(=O)N1CC(S)(CCO)C1]

To a solution of tert-butyl 3-(acetylthio)-3-(2-oxoethyl)azetidine-1-carboxylate (2.0 g, 7.3 mmol) in $Et_2O$ (8 mL) was added dropwise $LiAlH_4$ (4 M in $Et_2O$; 8.4 mL, 8.4 mmol), upon which the mixture immediately turned to a colorless suspension. The mixture was stirred at room temp for 25 min, then it was diluted with $Et_2O$ (20 mL) and quenched by addition of saturated aqueous $NaHCO_3$ (40 mL). The organic phase was diluted with EtOAc (40 mL) and to the aqueous phase was added a saturated aqueous solution of Rochelle's salt (40 mL), and the phases were separated. The aqueous phase was saturated with NaCl and extracted with EtOAc (50 mL). The combined organic phases were dried with $Na_2SO_4$, filtered, and concentrated in vacuo to afford tert-butyl 3-(2-hydroxyethyl)-3-mercaptoazetidine-1-carboxylate as a yellow oil (1.1 g, 65%). MS (ESI) calcd for $C_{10}H_{19}NO_3S$: 233.11.

Step 4. Synthesis of tert-butyl 1-thia-6-azaspiro[3.3]heptane-6-carboxylate

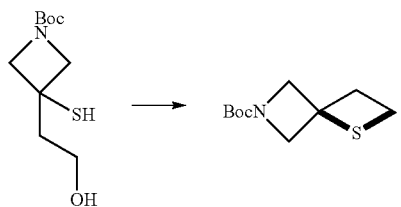

To a solution of diethoxytriphenylphosphorane (3.1 g, 5.2 mmol) in toluene (10 mL) was added at −30° C. a solution of tert-butyl 3-(2-hydroxyethyl)-3-mercaptoazetidine-1-carboxylate (1.0 g, 4.3 mmol) in toluene (8 mL), and the mixture was stirred at −30° C. for 1 h, then it was allowed to slowly warm to room temp overnight. After stirring for 13 h, the mixture was diluted with EtOAc (30 mL) and quenched with brine (20 mL). The phases were separated and the organic phase was dried with $MgSO_4$, filtered, and concentrated in vacuo. Purification via silica gel column chromatography (hexanes:EtOAc 6:1) gave tert-butyl 1-thia-6-azaspiro[3.3]heptane-6-carboxylate as a yellow oil (420.0 mg, 46%). MS (ESI) calcd for $C_{10}H_{17}NO_2S$: 215.10.

Step 5. Synthesis of tert-butyl 1-(dioxothia)-6-azaspiro[3.3]heptane-6-carboxylate

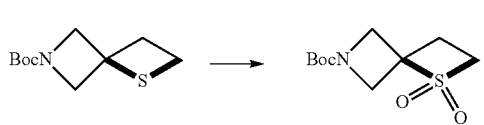

To a solution of tert-butyl 1-thia-6-azaspiro[3.3]heptane-6-carboxylate (420.0 mg, 1.96 mmol) in DCM (5 mL) was added at 0° C. m-CPBA (85%, 836.0 mg, 4.12 mmol), and the mixture was stirred at 0° C. for 15 min, followed by warming to room temp, and stirring was continued for 3.5 h. The reaction mixture was diluted with DCM (30 mL) and bicarb (30 mL) was added. The phases were separated, and the organic phase was dried with MgSO$_4$, filtered, and concentrated in vacuo. The product was purified via silica gel column chromatography (hexanes:EtOAc 2:1) to give tert-butyl 1-(dioxothia)-6-azaspiro[3.3]heptane-6-carboxylate as a colorless solid (500.0 mg, 100%). MS (ESI) calcd for $C_{10}H_{17}NO_4S$: 247.09.

Step 6. Synthesis of 1-(dioxothia)-6-azaspiro[3.3]heptane

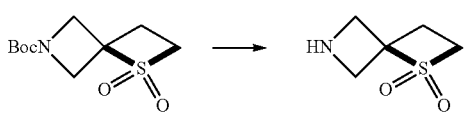

To tert-butyl 1-(dioxothia)-6-azaspiro[3.3]heptane-6-carboxylate (500.0 mg, 1.96 mmol) was added HCl/dioxane (4 M, 8 mL), and the mixture was stirred at room temp for 18 h. The mixture was concentrated in vacuo to give 1-(dioxothia)-6-azaspiro[3.3]heptane as a white solid (424.0 mg, ~100%). MS (ESI) calcd for $C_5H_9NO_2S$: 147.04. found: 148.0 [M+H].

Step 7. Synthesis of 2-(1-(dioxothia)-6-azaspiro[3.3]heptan-6-yl)pyrimidin-4-amine

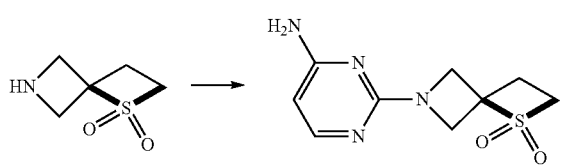

To a solution of 1-(dioxothia)-6-azaspiro[3.3]heptane (1.7 g, 8.6 mmol) in DMF (20 mL) was added 2-chloropyrimidine-4-ylamine (1.5 g, 11.2 mmol) and CsCO$_3$ (11.2 g, 34.4 mmol), and the mixture stirred at 70° C. for 18 h. The mixture was concentrated in vacuo and the residue dissolved with DCM/MeOH 2:1. This solution was filtered and the filtrate concentrated in vacuo. Purification with prep. TLC (DCM/MeOH 15:1) gave 2-O-(dioxothia)-6-azaspiro[3.3]heptan-6-yl)pyrimidin-4-amine as a white solid (903.0 mg, 43%). MS (ESI) calcd for $C_9H_{12}N_4O_2S$: 240.07. found: 241.0 [M+H].

Example 88. Preparation of 5-morpholinothiazol-2-amine

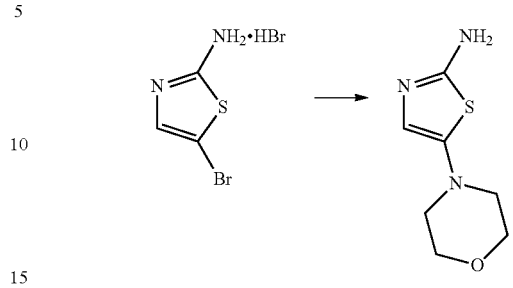

A mixture of 5-bromothiazol-2-amine hydrobromide (7.8 g, 30.0 mmol), morpholine (10.5 g, 120 mmol), and Cs$_2$CO$_3$ (48.9 g, 150 mmol) in CH$_3$CN (100 mL) was stirred at room temperature for 1 h. The mixture was poured into H$_2$O (100 mL), extracted with EtOAc, dried (Na$_2$SO$_4$), and concentrated. The crude product was purified by column chromatography to give 5-morpholinothiazol-2-amine (2.0 g, 36% yield). MS (ESI) calcd for $C_7H_{11}N_3OS$ (m/z): 185.06.

Example 89. Preparation of 6-((4,4-difluoropiperidin-1-yl)methyl)pyridin-2-amine

Step 1. Synthesis of tert-butyl 6-(chloromethyl)pyridin-2-ylcarbamate

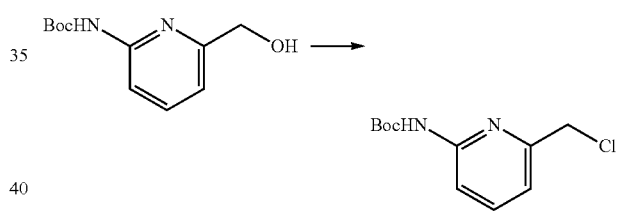

Methanesulfonyl chloride (19.0 g, 165.9 mmol) was added dropwise to a solution of tert-butyl 6-(hydroxymethyl)pyridin-2-ylcarbamate (30.0 g, 133.4 mmol) and diisopropylethylamine (50.0 g, 387.6 mmol) in CH$_2$Cl$_2$ (300 mL) at 0° C. The mixture was stirred for 24 h at room temp. The reaction mixture was concentrated and H$_2$O (300 mL) was added. The mixture was extracted with ethyl acetate (3×200 mL), dried (Na$_2$SO$_4$) and concentrated under reduced pressure. The crude product was purified by column chromatography eluting with pentane/EtOAc to give tert-butyl 6-(chloromethyl)pyridin-2-ylcarbamate (29.5 g, 91% yield). MS (ESI) calcd for $C_{11}H_{15}ClN_2O_2$ (m/z): 242.08.

Step 2. Synthesis of tert-butyl 6-((4,4-difluoropiperidin-1-yl)methyl)pyridin-2-ylcarbamate

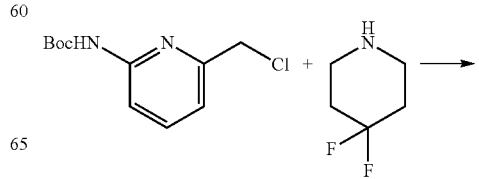

-continued

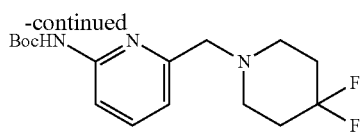

A mixture of tert-butyl 6-(chloromethyl)pyridin-2-ylcarbamate (7.0 g, 28.9 mmol), 4,4-difluoropiperidine hydrochloride (5.2 g, 43.1 mmol), K$_2$CO$_3$ (10.4 g, 75.4 mmol) and potassium iodide (800.0 mg, 4.8 mmol) in DMF (70 mL) was stirred at 60° C. for 16 h. H$_2$O (200 mL) was added and the mixture was extracted with EtOAc then washed with H$_2$O. The crude product was purified by column chromatography eluting with EtOAc/pentane (1:2) to give tert-butyl 6-((4,4-difluoropiperidin-1-yl)methyl)pyridin-2-ylcarbamate (8.0 g, 85% yield). MS (ESI) calcd for C$_{16}$H$_{23}$F$_2$N$_3$O$_2$ (m/z): 327.18.

Step 3. Synthesis of 6-((4,4-difluoropiperidin-1-yl)methyl)pyridin-2-amine

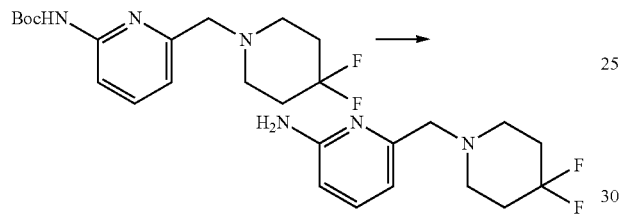

HCl (g) was bubbled through a solution of tert-butyl 6-((4,4-difluoropiperidin-1-yl)methyl)pyridin-2-ylcarbamate (8.0 g, 24.4 mmol) in MeOH (100 mL) at room temperature for 2 h. The reaction mixture was concentrated under reduced pressure. The crude residue was dissolved in MeOH (5 mL) and a mixture of CH$_2$Cl$_2$/acetone was added to form a ppt which was collected by filtration and rinsed with CH$_2$Cl$_2$. Repeated three times to give 6-((4,4-difluoropiperidin-1-yl)methyl)pyridin-2-amine hydrochloride (6.0 g, 93% yield). MS (ESI) calcd for C$_{11}$H$_{15}$F$_2$N$_3$ (m/z): 227.12.

Example 90. Preparation of (R)-6-((2,2-dimethyl-1,3-dioxolan-4-yl)methoxy)pyrazine-2-carboxylic acid

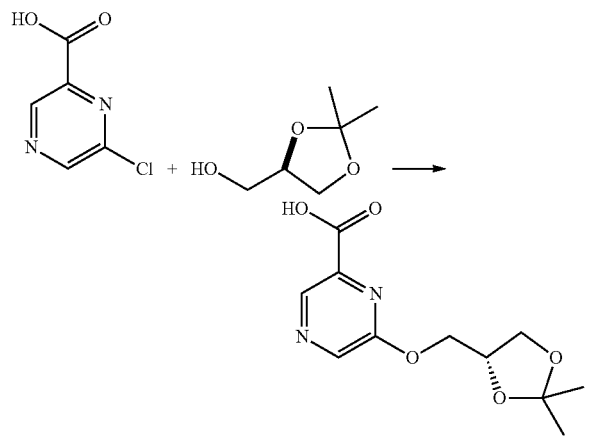

(R)-(2,2-dimethyl-1,3-dioxolan-4-yl) methanol (2.50 g, 18.93 mmol) was added to a room temperature suspension of NaH 60 wt % (833.0 mg, 20.82 mmol) in THF (50 mL). The reaction mixture was stirred at room temp for 30 min and a solution of 6-chloropyrazine-2-carboxylic acid (1.0 g, 6.31 mmol) in THF (20 mL) was added. The reaction mixture was stirred at room temp for 30 min then heated at reflux for 2 h. After cooling to room temp, the pH was adjusted to 3 by the addition of 3 N HCl (4 mL). The mixture was poured into brine and extracted with EtOAc. The combined organics were dried and concentrated. The crude product was recrystallized from pentane/EtOAc to give (R)-6-((2,2-dimethyl-1,3-dioxolan-4-yl)methoxy)pyrazine-2-carboxylic acid (764.0 mg, 48% yield). MS (ESI) calcd for C$_{11}$H$_{14}$N$_2$O$_6$ (m/z): 254.09. found: 255 [M+H].

Example 91. Preparation of (S)-6-((2,2-dimethyl-1,3-dioxolan-4-yl)methoxy)picolinic acid

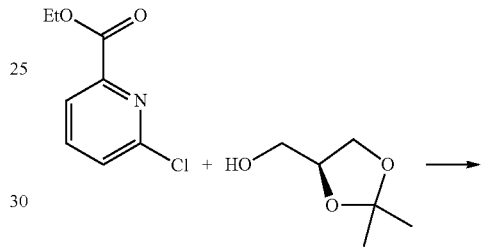

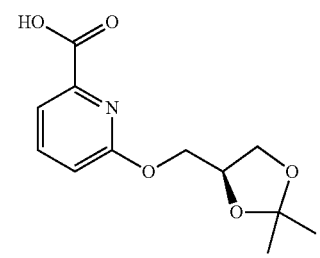

(S)-(2,2-dimethyl-1,3-dioxolan-4-yl) methanol (4.98 g, 37.72 mmol) was added to a room temperature suspension of NaH 60 wt % (1.7 g, 41.5 mmol) in THF. The reaction mixture was stirred at room temp for 30 min and a solution of ethyl 6-chloropicolinate (1.40 g, 7.54 mmol) in THF was added. The reaction mixture was heated at reflux for 16 h. After cooling to room temp, the pH was adjusted to 4 by the addition of 3 N HCl. The mixture was poured into brine and extracted with EtOAc. The combined organics were dried and concentrated. The crude product was recrystallized from pentane/EtOAc to give (S)-6-((2,2-dimethyl-1,3-dioxolan-4-yl)methoxy)pyrazine-2-carboxylic acid (1.30 g, 68% yield). MS (ESI) calcd for C$_{12}$H$_{15}$NO$_5$ (m/z): 253.10.

Example 92. Preparation of (R)-6-((2,2-dimethyl-1,3-dioxolan-4-yl)methoxy)picolinic acid

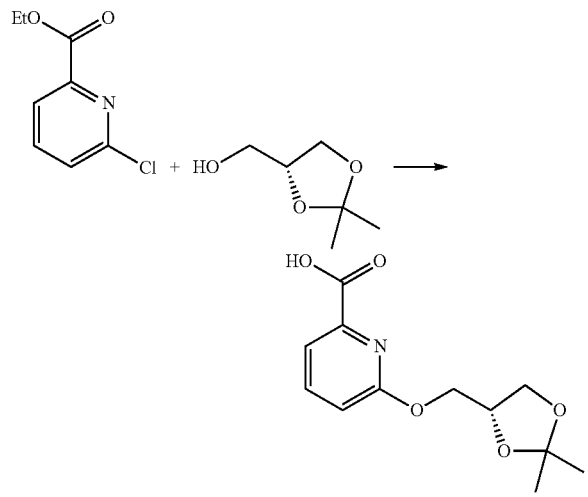

(R)-(2,2-dimethyl-1,3-dioxolan-4-yl) methanol (1.07 g, 8.07 mmol) was added to a room temperature suspension of NaH 60 wt % (385.0 mg, 8.89 mmol) in THF. The reaction mixture was stirred at room temp for 30 min and a solution of ethyl 6-chloropicolinate (500.0 mg, 2.69 mmol) in THF was added. The reaction mixture was heated at reflux for 16 h. After cooling to room temp, the pH was adjusted to 4 by the addition of 3 N HCl. The mixture was poured into brine and extracted with EtOAc. The combined organics were dried and concentrated. The crude product was recrystallized from pentane/EtOAc to give (R)-6-((2,2-dimethyl-1,3-dioxolan-4-yl)methoxy)pyrazine-2-carboxylic acid (500.0 mg, 74% yield). MS (ESI) calcd for $C_{12}H_{15}NO_5$ (m/z): 253.10.

Example 93. Preparation of (R)-2-((2,2-dimethyl-1,3-dioxolan-4-yl)methoxy)nicotinic acid

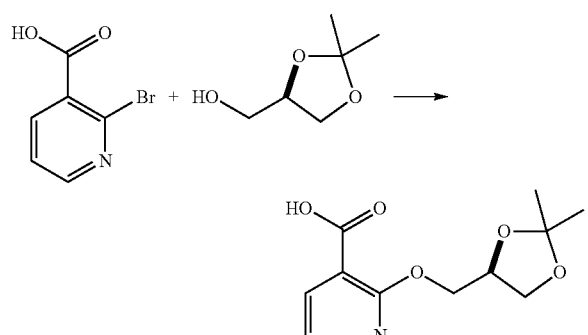

(R)-(2,2-dimethyl-1,3-dioxolan-4-yl) methanol (1.80 mL, 14.95 mmol) was added to a room temperature suspension of NaH 60 wt % (653.0 mg, 16.34 mmol) in THF (30 mL). The reaction mixture was stirred at room temp for 30 min and 2-bromo-nicotinic acid (1.0 g, 4.95 mmol) was added. The reaction mixture was heated at reflux for 16 h. After cooling to room temp, the pH was adjusted to 3 by the addition of 3 N HCl. The mixture was poured into brine and extracted with EtOAc. The combined organics were dried and concentrated. The crude product was recrystallized from pentane/EtOAc to give (R)-2-((2,2-dimethyl-1,3-dioxolan-4-yl)methoxy)nicotinic acid (1.16 g, 92% yield). MS (ESI) calcd for $C_{12}H_{15}NO_5$ (m/z): 253.10.

Example 94. Preparation of 6-((2,2-dimethyl-1,3-dioxolan-4-yl)methoxy)picolinic acid

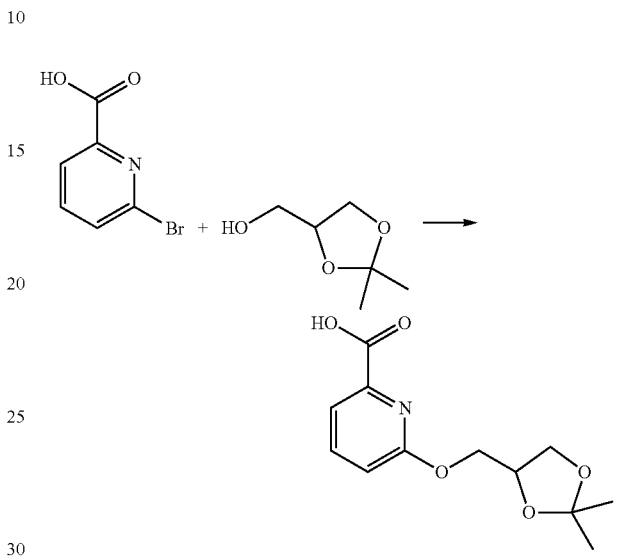

Solketal (23.5 g, 178 mmol) was added dropwise to a suspension of NaH 60 wt % (7.1 g, 178 mmol) in THF (400 mL) at 0° C. The reaction mixture was stirred for 1 h at 25° C. and 6-bromopicolinic acid (12.0 g, 59.4 mmol) was added. The reaction mixture was heated at reflux for 1.5 h. After cooling to room temp, $H_2O$ was added and the pH was adjusted to 2-3. The mixture extracted with EtOAc. The combined organics were washed with $H_2O$, dried and concentrated. The crude product was recrystallized from pentane/EtOAc to give 6-((2,2-dimethyl-1,3-dioxolan-4-yl)methoxy)picolinic acid (10.0 g, 66% yield). MS (ESI) calcd for $C_{12}H_{15}NO_5$ (m/z): 253.10. found: 254 [M+H].

Example 95. Preparation of 2-((2,2-dimethyl-1,3-dioxolan-4-yl)methoxy)nicotinic acid

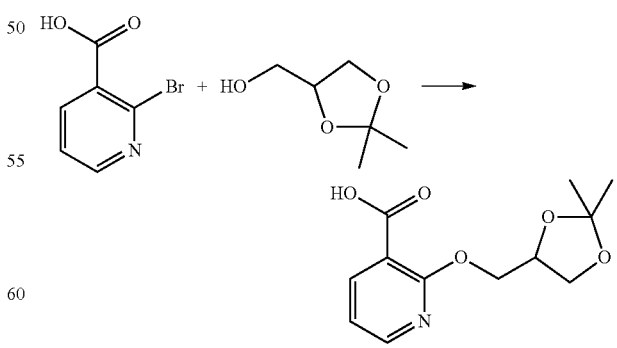

Solketal (39.1 g, 300 mmol) was added to a suspension of NaH 60 wt % (12.0 g, 300 mmol) at 0° C. in 1,4-dioxane (1.5 L) at 0° C. The reaction mixture was stirred for 1 h at 25° C. and 2-bromonicotinic acid (20.0 g, 100 mmol) was added.

The reaction mixture was heated at reflux. After cooling to room temp, H₂O was added and the pH was adjusted to 2-3. The mixture extracted with EtOAc. The combined organics were dried and concentrated. The crude product was purified by column chromatography eluting with MeOH/DCM/AcOH (300:60:1) to give 2-((2,2-dimethyl-1,3-dioxolan-4-yl)methoxy)nicotinic acid (6.1 g, 24% yield). MS (ESI) calcd for $C_{12}H_{13}NO_3$ (m/z): 253.10. found: 254 [M+H].

Example 96. Preparation of 6-(azetidin-1-yl)picolinic acid

Step 1. Synthesis of methyl 6-(azetidin-1-yl)picolinate

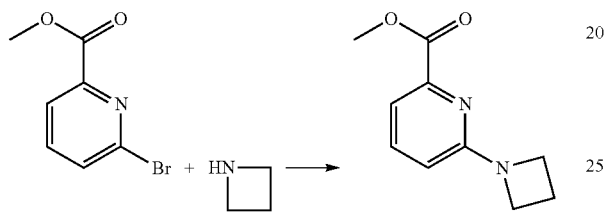

A mixture of methyl 6-bromopicolinate (5.0 g, 23.00 mmol), azetidine hydrochloride (4.40 g, 46.0 mmol), K₂CO₃ (9.70 g, 70.0 mmol), CuI (880.0 mg, 4.60 mmol) and L-proline (1.06 g, 9.20 mmol) in DMSO (50 mL) was stirred at 80° C. 16 h. The mixture was cooled to room temp and the solids were removed by filtration. The filtrate was diluted with CH₂Cl₂ (800 mL), washed with water, brine, dried and concentrated. The crude residue was purified by flash chromatography to give methyl 6-(azetidin-1-yl)picolinate (2.84 g, 64% yield). MS (ESI) calcd for $C_{10}H_{12}N_2O_2$ (m/z): 192.09.

Step 2. Synthesis of 6-(azetidin-1-yl)picolinic acid

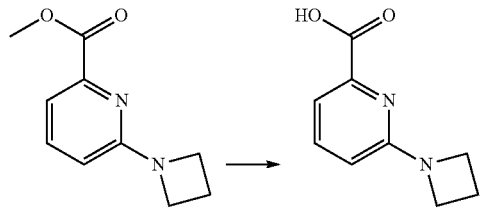

A mixture of methyl 6-(azetidine-1-yl)picolinate (5.67 g, 29.50 mmol) and KOH (3.36 g, 60.0 mmol) in MeOH (100 mL) was stirred at room temp for 16 h. Conc. HCl (5.00 mL) was added. The resulting ppt was removed by filtration and the filtrate was concentrated. The residue was dissolved in CH₂Cl₂ and the solids removed by filtration. The CH₂Cl₂ was concentrated and the residue was recrystallized from iPrOH to give 6-(azetidine-1-yl)picolinic acid (4.01 g, 76% yield). MS (ESI) calcd for $C_9H_{10}N_2O_2$ (m/z): 178.07. found: 179 [M+H].

Example 97. Preparation of (R)-3-(2,2-dimethyl-1,3-dioxolan-4-yl)methoxy)benzoic acid Step 1. Synthesis of (R)-methyl 3-((2,2-dimethyl-1,3-dioxolan-4-yl)methoxy)benzoate

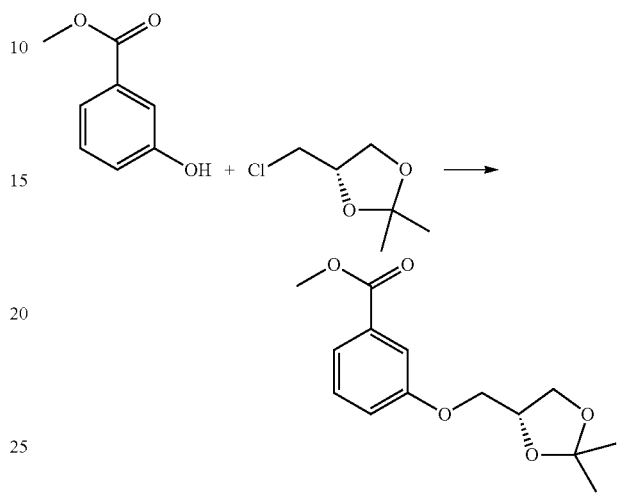

A mixture of methyl 3-hydroxybenzoate (3.0 g, 19.7 mmol), (S)-4-(chloromethyl)-2,2-dimethyl-1,3-dioxolane (4.5 g, 29.6 mmol) and K₂CO₃ (5.5 g, 39.4 mmol) in DMF (50 mL) was stirred for 18 h at 160° C. The mixture was diluted with water (150 mL) and the pH was adjusted to 6 by addition of 3N HCl. The mixture was extracted with ethyl acetate (3×200 mL) and the combined organic layers were dried over anhydrous MgSO₄, concentrated under reduced pressure to give (R)-methyl 3-((2,2-dimethyl-1,3-dioxolan-4-yl)methoxy)benzoate (3.0 g, 57% yield). MS (ESI) calcd for $C_{14}H_{18}O_5$ (m/z): 266.12.

Step 2. Synthesis of (R)-3-((2,2-dimethyl-1,3-dioxolan-4-yl)methoxy)benzoic acid

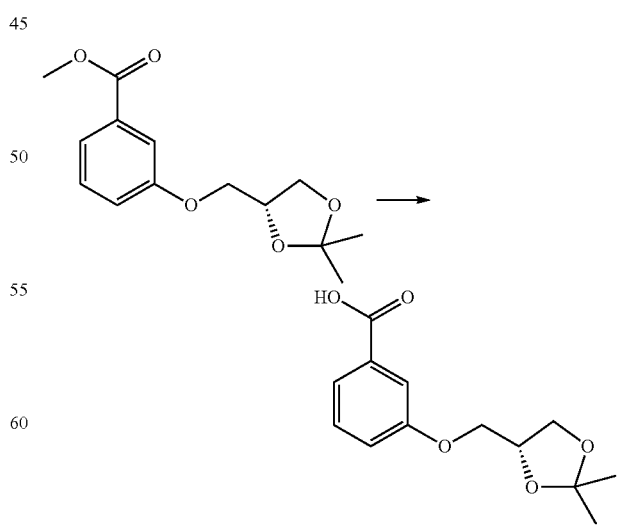

A solution of (R)-methyl 3-((2,2-dimethyl-1,3-dioxolan-4-yl)methoxy)benzoate (5.5 g, 20.7 mmol) in THF/H₂O (2:1, 60 mL) was added dropwise to a solution of LiOH (2.3 g, 95.8 mmol) in H₂O. The mixture was stirred for 8 h at 40° C. then concentrated and diluted with H₂O (20 mL). The mixture was washed with EtOAc (2×50 mL) and the aqueous layer was brought to pH 4 by the addition of 3N HCl. The resulting ppt was collected by filtration and dried. The crude residue was purified by column chromatography eluting with CH₂Cl₂/MeOH (5%) to give (R)-3-((2,2-dimethyl-1,3-dioxolan-4-yl)methoxy)benzoic acid (3.0 g, 57% yield). MS (ESI) calcd for C₁₃H₁₆O₅ (m/z): 252.10. found 251 [M−H].

Example 98. Preparation of (S)-3-((2,2-dimethyl-1,3-dioxolan-4-yl)methoxy)benzoic acid Step 1. Synthesis of (S)-methyl 3-((2,2-dimethyl-1,3-dioxolan-4-yl)methoxy)benzoate

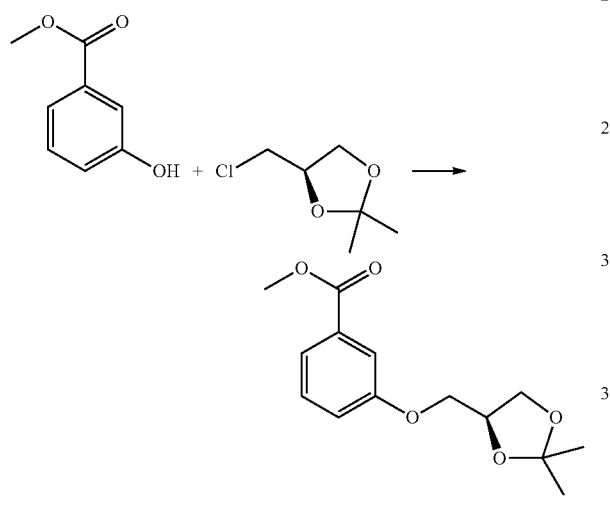

A mixture of methyl 3-hydroxybenzoate (6.7 g, 44.3 mmol), (R)-4-(chloromethyl)-2,2-dimethyl-1,3-dioxolane (10.0 g, 66.4 mmol) and K₂CO₃ (12.2 g, 88.6 mmol) in DMF (100 mL) was stirred for 18 h at 160° C. The mixture was diluted with water (500 mL) and the pH was adjusted to 5 by addition of 3N HCl. The mixture was extracted with ethyl acetate (3×200 mL) and the combined organic layers were dried over anhydrous MgSO₄, concentrated under reduced pressure to give (S)-methyl 3-((2,2-dimethyl-1,3-dioxolan-4-yl)methoxy)benzoate (10.0 g, 85% yield). MS (ESI) calcd for C₁₄H₁₈O₅ (m/z): 266.12.

Step 2. Synthesis of (S)-3-((2,2-dimethyl-1,3-dioxolan-4-yl)methoxy)benzoic acid

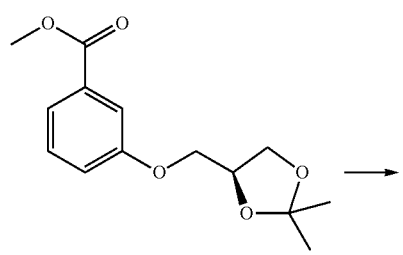

LiOH (5.0 g, 208 mmol) in H₂O was added to a solution of (S)-methyl 3-((2,2-dimethyl-1,3-dioxolan-4-yl)methoxy)benzoate (10.0 g, 37.6 mmol) in THF/H₂O (5:1, 120 mL). The mixture was stirred for 15 h at 40° C. then concentrated and diluted with sat. aq Na₂CO₃ (100 mL). The mixture was washed with EtOAc (2×100 mL) and the aqueous layer was brought to pH 4 by the addition of 3N HCl. The resulting ppt was collected by filtration and dried. The crude residue was purified by column chromatography eluting with pentane/EtOAc (2:1) to give (S)-3-((2,2-dimethyl-1,3-dioxolan-4-yl)methoxy)benzoic acid (4.9 g, 52% yield). MS (ESI) calcd for C₁₃H₁₆O₅ (m/z): 252.10. found 251 [M−H].

Example 99. Preparation of 6-(morpholinomethyl)picolinic acid

Step 1. Synthesis of 4-((6-bromopyridin-2-yl)methyl)morpholine

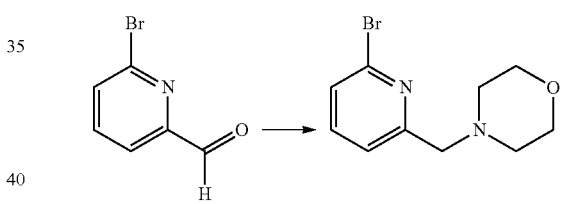

NaBH(OAc)₃ (68.5 g, 0.323 mol) was added to a solution of 6-bromopicolinaldehyde (40 g, 0.22 mol) and morpholine (20.9 g, 0.24 mol) in 1,2-dichloroethane (500 mL). The mixture was stirred at room temp for 16 h. Saturated NaHCO₃ (500 mL) was added and the mixture was extracted with EtOAc, washed with brine, dried (Na₂SO₄) and concentrated in vacuo. The residue was purified by column chromatography on silica gel eluting with petroleum ether: ethyl acetate (10:1) to give 4-((6-bromopyridin-2-yl)methyl)morpholine (38.0 g, 68% yield). MS (ESI) calcd for C₁₀H₁₃BrN₂O (m/z): 256.02.

Step 2. Synthesis of 6-(morpholinomethyl)picolinic acid

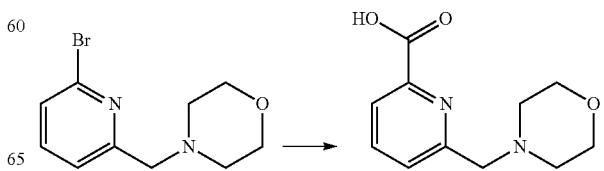

n-BuLi (3.7 mL, 9.30 mmol) in THF was added to a solution of 4-((6-bromopyridin-2-yl)methyl)morpholine (2.0 g, 7.78 mol) in THF (20 mL) at −78° C. The mixture was stirred for 30 min and $CO_2$ (gas) was bubbled through the reaction mixture for 30 min. The volatiles were removed in vacuo and the residue was dissolved in $H_2O$. The pH was adjusted to 5 with 3N HCl then to 7 with sat. aq $NaHCO_3$. The mixture was concentrated to dryness and the residue was taken up in $CH_2Cl_2$/MeOH (1:1), passed through a filter and the filtrate was concentrated. The residue was dissolved in $CH_2Cl_2$, passed through a filter, concentrated and dried under vacuum to give 6-(morpholinomethyl)picolinic acid (1.0 g, 67% yield). MS (ESI) calcd for $C_{11}H_{14}N_2O_3$ (m/z): 222.10. found 223 [M+H].

Example 100. Preparation of 6-(pyrrolidin-1-ylmethyl)picolinic acid

Step 1. Synthesis of methyl 6-(chloromethyl)picolinate

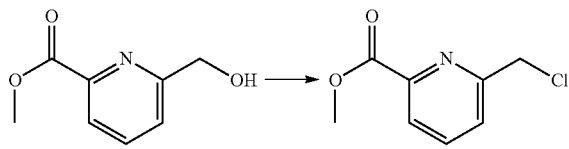

$SOCl_2$ (1.4 g, 12.0 mmol) was added to a solution of methyl 6-(hydroxymethyl)picolinate (1.0 g, 6.0 mmol) in $CH_2Cl_2$ (30 mL) at 25° C. The mixture was stirred at 40° C. for 1 h and sat. aq $Na_2CO_3$ was added to adjust the pH to 9. The mixture was extracted with $CH_2Cl_2$ and the combined organics were washed with brine, dried ($Na_2SO_4$), and concentrated. The crude residue was purified by column chromatography eluting with pentane/EtOAc (3:1) to give methyl 6-(chloromethyl)picolinate (600.0 mg, 55% yield). MS (ESI) calcd for $C_8H_8ClNO_2$ (m/z): 185.02.

Step 2. Synthesis of methyl 6-(pyrrolidin-1-ylmethyl)picolinate

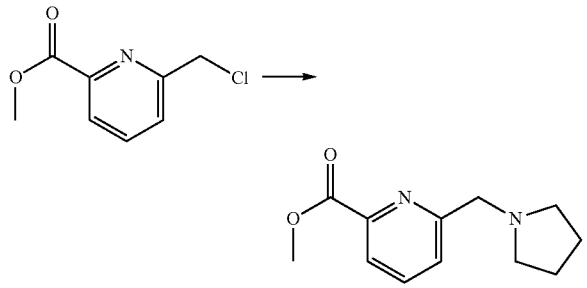

$K_2CO_3$ (746.0 mg, 5.40 mmol) was added to a solution of methyl 6-(chloromethyl)picolinate (500.0 mg, 2.70 mmol) and pyrrolidine (288.0 mg, 4.05 mmol) in DMF (20 mL). The reaction mixture was heated at 45° C. for 16 h. Water (20 mL) was added and the mixture was extracted with EtOAc. The combined organic layers were washed with brine, dried ($Na_2SO_4$) and concentrated. The crude residue was purified by column chromatography eluting with $CH_2Cl_2$/MeOH (10-20%) to give methyl 6-(pyrrolidin-1-ylmethyl)picolinate (330.0 mg, 56% yield). MS (ESI) calcd for $C_{12}H_{16}N_2O_2$ (m/z): 220.12.

Step 3. Synthesis of 6-(pyrrolidin-1-ylmethyl)picolinic acid

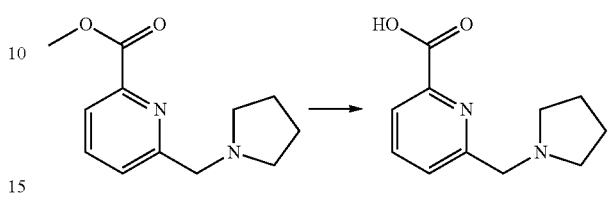

A mixture of methyl 6-(pyrrolidin-1-ylmethyl)picolinate (200.0 mg, 0.91 mmol) and NaOH (200.0 mg, 4.55 mmol) in ethanol/water (2:1, 30 mL) was stirred at 70° C. for 16 h. The pH was adjusted to 7 with 3N HCl and the mixture was concentrated. The residue was dissolved in $CH_2Cl_2$/MeOH (5:1), passed through a filter and concentrated to dryness to give 6-(pyrrolidin-1-ylmethyl)picolinic acid (187.0 mg, 99% yield). MS (ESI) calcd for $C_{11}H_{14}N_2O_2$ (m/z): 206.11. found 207 [M+H].

Example 101. Preparation of 5-(pyrrolidin-1-ylmethyl)thiazol-2-amine

Step 1. Synthesis of tert-butyl 5-(hydroxymethyl)thiazol-2-ylcarbamate (10)

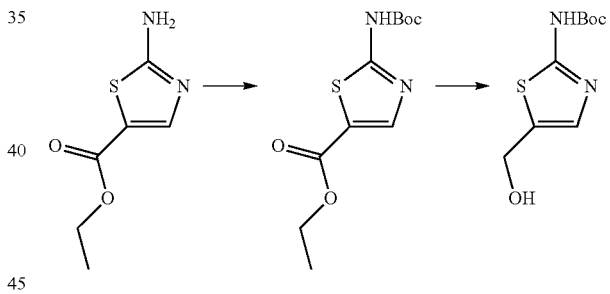

A slurry of ethyl 2-aminothiazole-5-carboxylate (8; 145.0 g, 840 mmol), di-tert-butyl dicarbonate (275.0 g, 1260 mmol) and DMAP (5.0 mg, catalytic) in THF (2175 mL) was stirred at 30° C. for 5.5 h. The reaction mixture was concentrated to dryness and EtOAc (1450 mL) was added. The organic solvent was washed with water (2×435 mL) and brine (2×145 mL), dried over $MgSO_4$ and concentrated to give ethyl 2-(tert-butoxycarbonylamino)thiazole-5-carboxylate (227.0 g, 99.23%) as a crude product, which was used for the next step without any further purification. MS (ESI) calcd for $C_{11}H_{16}N_2O_4S$ (m/z): 272.32.

A stirred solution of ethyl 2-(tert-butoxycarbonylamino)thiazole-5-carboxylate (227.0 g, 830 mmol) in anhydrous THF (1512 mL) was cooled to −45° C. A solution of superhydride in THF (1.0 M, 1877 mL) was added over 1 hr, and then the reaction mixture was stirred at −45° C. for 2 h, warmed to room temp for 20 h. The reaction was quenched was brine, and warmed to room temp. The mixture was concentrated, taken up in EtOAc and washed with brine, dried over $Na_2SO_4$, concentrated and purified by column chromatography on silica gel (petroleum ether/ethyl acetate=1:1) to give tert-butyl 5-(hydroxymethyl)thiazol-2-ylcarbamate (10; 95 g, 49%). MS (ESI) calcd for $C_9H_{14}N_2O_3S$ (m/z): 230.28.

Step 2. Synthesis of 5-(pyrrolidin-1-ylmethyl)thiazol-2-amine-hydrochloride salt (12)

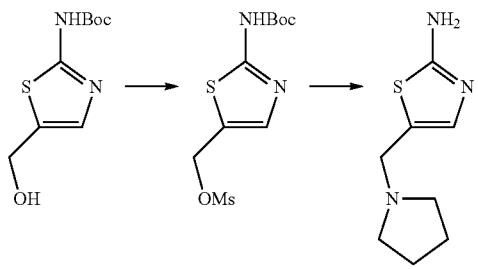 [SMILES: CC(C)(C)OC(=O)Nc1ncc(CO)s1 ; CC(C)(C)OC(=O)Nc1ncc(COS(C)(=O)=O)s1 ; Nc1ncc(CN2CCCC2)s1]

A solution of tert-butyl 5-(hydroxymethyl)thiazol-2-ylcarbamate (37.0 g, 160 mmol), triethylamine (24.2 g, 240 mmol) in $CH_2Cl_2$ (231 mL) was cooled to 0° C. Mesyl chloride (23.16 g, 200 mmol) was added and the mixture was extracted with $CH_2Cl_2$ (2×93 mL). The combined organic layers were dried over $Na_2SO_4$ and concentrated in vacuo to give 2-(tert-butoxycarbonylamino)thiazol-5-yl) methyl methanesulfonate (40.0 g, 75%). MS (ESI) calcd for $C_{10}H_{16}N_2O_3S_2$ (m/z): 308.37.

To a stirred solution of 2-(tert-butoxycarbonylamino) thiazol-5-yl) methyl methanesulfonate (40.0 g, 0.13 mol) in $CH_2Cl_2$ (140 mL) was added pyrrolidine (37.69 g, 530 mmol) at 0° C. and warmed to room temp. The mixture was washed with saturated $NaHCO_3$, and brine (93 mL). The organic solvent was dried over $Na_2SO_4$, concentrated and purified by column chromatography on silica gel (petroleum ether:ethyl acetate=1:1) to give 5-(pyrrolidin-1-ylmethyl) thiazol-2-amine (as the free amine)(34.0 g, 75%). MS (ESI) calcd for $C_8H_{13}N_3S$ (m/z): 183.27.

A stirred solution of 5-(pyrrolidin-1-ylmethyl)thiazol-2-amine (34.0 g, 190 mmol) in methanol (121 mL) was bubbled with HCl (gas) and monitored by TLC until all material consumed. The solvent was removed and EtOAc (121 mL) was added to form a precipitate. The mixture was filtered and the filter cake was washed successively with EtOAc to give 5-(pyrrolidin-1-ylmethyl)thiazol-2-amine (as the HCl salt) (20.6 g, 67%) as a white solid. MS (ESI) calcd for $C_8H_{13}N_3S$ HCl (m/z): 219.73. found 184 [M+H].

5-(morpholinomethyl)thiazol-2-amine

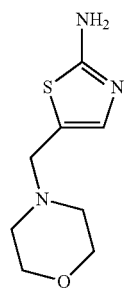 [SMILES: Nc1ncc(CN2CCOCC2)s1]

was prepared by the same procedure above, by substituting morpholine for pyrrolidine.

Example 102. Preparation of 2-(difluoromethyl)benzaldehyde 92

Step 1. Synthesis of 1-bromo-2-(difluoromethyl)benzene

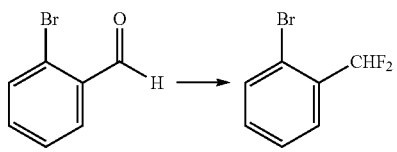 [SMILES: O=Cc1ccccc1Br ; FC(F)c1ccccc1Br]

DAST (8.7 g, 54.1 mmol) was added to a mixture of 2-bromobenzaldehyde (5.0 g, 27.0 mmol) in dichloromethane (100 mL) at 0° C. The reaction mixture was stirred at room temperature for 12 h, poured into sat. aq $NaHCO_3$, and extracted with EtOAc. The organic layer was concentrated to give 1-bromo-2-(difluoromethyl)benzene (5.4 g, 96% yield), which was used in next step with no further purification.

Step 2. Synthesis of 2-(difluoromethyl)benzaldehyde

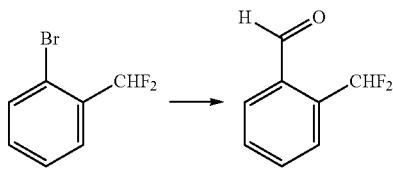 [SMILES: FC(F)c1ccccc1Br ; O=Cc1ccccc1C(F)F]

A solution of n-BuLi (4.2 mL, 10.6 mmol) in THF was added to a solution of 1-bromo-2-(difluoromethyl)benzene (2.0 g, 9.7 mmol) in THF (50 mL) at −78° C. The reaction mixture was stirred for 30 min and DMF (1.4 g, 19.3 mmol) was added. Stirring was continued for 1 h at −40° C. and the reaction was quenched by the addition of sat. aq $NH_4Cl$. The crude mixture was extracted with $Et_2O$, dried ($MgSO_4$) and concentrated to give 2-(difluoromethyl)benzaldehyde (1.7 g, 94% yield).

Example 103. Preparation of 2-(difluoromethyl)benzoyl chloride 96

Step 1. Synthesis of methyl 2-(difluoromethyl)benzoate

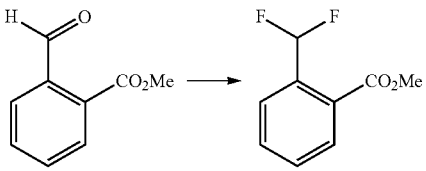 [SMILES: COC(=O)c1ccccc1C=O ; COC(=O)c1ccccc1C(F)F]

A solution of methyl 2-formylbenzoate (10.0 g, 61 mmol) and bis-(2-methoxyethyl)amino-sulfur trifluoride (40.4 g, 183 mmol) in $CH_2Cl_2$ was heated at reflux for 12 h. The reaction mixture was cooled to room temp, concentrated and partitioned between EtOAc (500 mL)/$H_2O$ (300 mL).

NaHCO$_3$ was added to adjust the pH to 8. The organic phase was separated, washed with brine, dried and concentrated. The residue was purified by flash chromatography to give methyl 2-(difluoromethyl)benzoate (7.0 g, 62% yield).

Step 2. Synthesis of 2-(difluoromethyl)benzoic acid

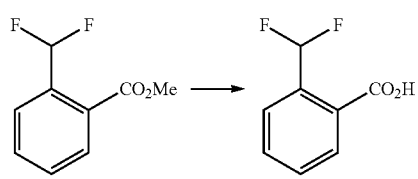 [SMILES: COC(=O)c1ccccc1C(F)F ; O=C(O)c1ccccc1C(F)F]

A mixture of methyl 2-(difluoromethyl)benzoate (7.0 g, 38 mmol) and 10% aq. NaOH (100 mL) in MeOH (50 mL) was heated at reflux for 30 min. The pH was adjusted to 4 by the addition of 3N HCl. The resulting solid was collected by filtration, rinsed with H$_2$O and dried to give 2-(difluoromethyl)benzoic acid (6.0 g, 93% yield).

Step 3. Synthesis of 2-(difluoromethyl)benzoyl chloride

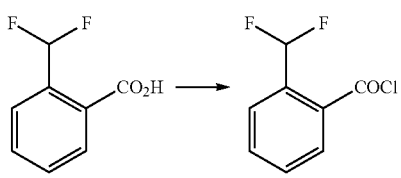 [SMILES: O=C(O)c1ccccc1C(F)F ; O=C(Cl)c1ccccc1C(F)F]

A solution of 2-(difluoromethyl)benzoic acid (1.8 g, 10 mmol) in thionyl chloride (25 mL) was heated at reflux for 3 h. The reaction mixture was concentrated and dried under vacuum to give 2-(difluoromethyl)benzoyl chloride. The crude acid chloride was used without further purification.

Example 104. Preparation of 3-(difluoromethyl)benzoyl chloride

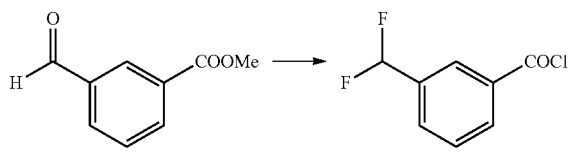 [SMILES: COC(=O)c1cccc(C=O)c1 ; O=C(Cl)c1cccc(C(F)F)c1]

3-(difluoromethyl)benzoyl chloride was prepared by a procedure similar to that reported for 2-(difluoromethyl)benzoyl chloride in 32% yield.

Example 105. Preparation of (R)-2-((2,2-dimethyl-1,3-dioxolan-4-yl)methoxy)nicotinic acid

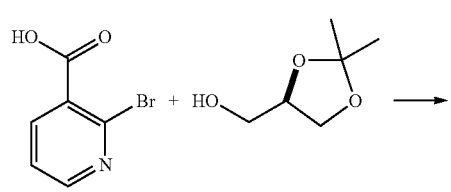

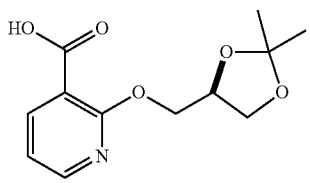

(R)-(2,2-dimethyl-1,3-dioxolan-4-yl) methanol (1.8 mL, 14.9 mmol) was added to a room temperature suspension of NaH (392.0 mg, 16.3 mmol) in THF (30 mL). The reaction mixture was stirred at room temp for 30 min and 2-bromonicotinic acid (1.0 g, 4.95 mmol) was added. The reaction mixture was heated at reflux for 12 h. After cooling to room temp, the pH was adjusted to 3 by the addition of 3 N HCl. The mixture was poured into brine and extracted with EtOAc. The combined organics were dried and concentrated. The crude product was recrystallized from pentane/EtOAc to give (R)-2-((2,2-dimethyl-1,3-dioxolan-4-yl)methoxy)nicotinic acid (1.2 g, 92% yield).

Example 106. Preparation of (R)-6-((2,2-dimethyl-1,3-dioxolan-4-yl)methoxy)picolinic acid

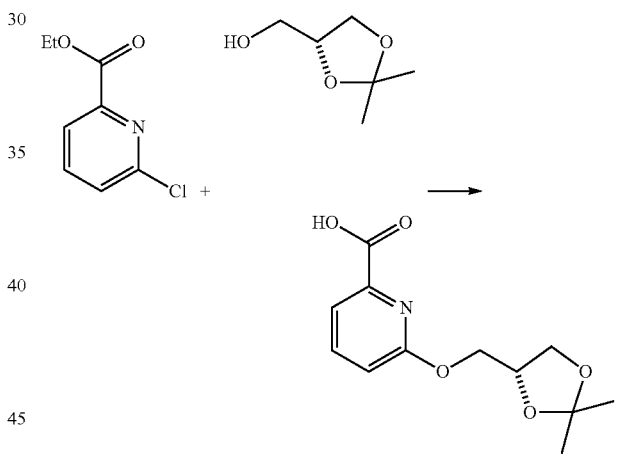

(R)-6-((2,2-dimethyl-1,3-dioxolan-4-yl)methoxy)picolinic acid was prepared by a procedure similar to that reported for (R)-6-((2,2-dimethyl-1,3-dioxolan-4-yl)methoxy)picolinic acid in 74% yield.

Example 107. Preparation of (R)-2-(2,2-dimethyl-1,3-dioxolan-4-yl)methoxy) isonicotinic acid

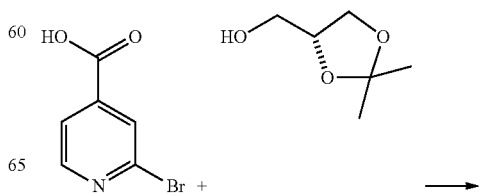

-continued

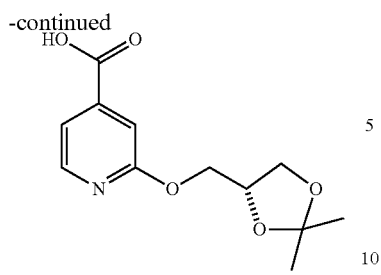

(R)-2-((2,2-dimethyl-1,3-dioxolan-4-yl)methoxy)isonicotinic acid was prepared by a procedure similar to that reported for (R)-6-((2,2-dimethyl-1,3-dioxolan-4-yl)methoxy)picolinic acid in 72% yield.

Example 108. Preparation of (R)-6-((2,2-dimethyl-1,3-dioxolan-4-yl)methoxy)nicotinic acid

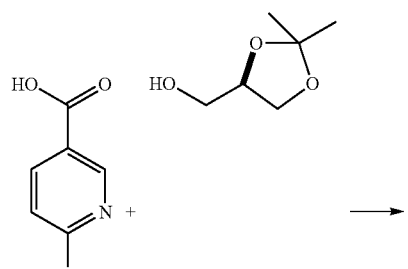

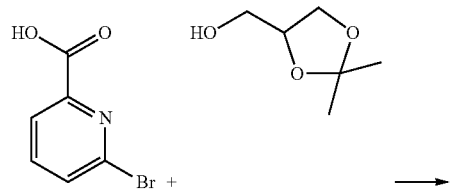

(R)-6-((2,2-dimethyl-1,3-dioxolan-4-yl)methoxy)nicotinic acid was prepared by a procedure similar to that reported for (R)-6-((2,2-dimethyl-1,3-dioxolan-4-yl)methoxy)picolinic acid in 60% yield.

Example 109. Preparation of 6-((2,2-dimethyl-1,3-dioxolan-4-yl)methoxy)picolinic acid -continued

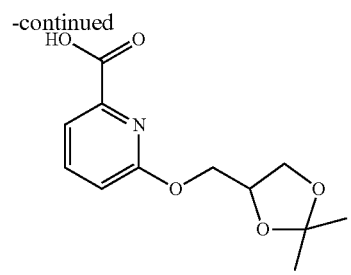

6-((2,2-dimethyl-1,3-dioxolan-4-yl)methoxy)picolinic acid was prepared by a procedure similar to that reported for (R)-6-((2,2-dimethyl-1,3-dioxolan-4-yl)methoxy)picolinic acid in 66% yield.

Example 110. Preparation of 2-((2,2-dimethyl-1,3-dioxolan-4-yl)methoxy)nicotinic acid

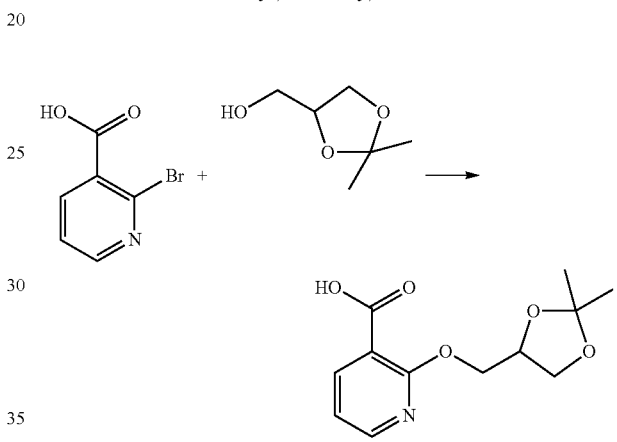

2-((2,2-dimethyl-1,3-dioxolan-4-yl)methoxy)nicotinic acid was prepared by a procedure similar to that reported for (R)-6-((2,2-dimethyl-1,3-dioxolan-4-yl)methoxy)picolinic acid in 23% yield.

Example 111. Preparation 6-(morpholinomethyl)picolinic acid

Step 1. Synthesis of 4-((6-bromopyridin-2-yl)methyl)morpholine

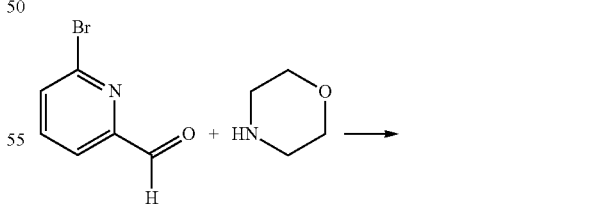

NaBH(OAc)$_3$ (68.5 g, 0.323 mol) was added to a solution of 6-bromopicolinaldehyde (40.0 g, 0.22 mol) and morpholine (20.9 g, 0.24 mol) in 1,2-dichloroethane (500 mL). The mixture was stirred at room temperature for 16 h. Saturated NaHCO₃ (500 mL) was added and the mixture was extracted with EtOAc, washed with brine, dried (Na₂SO₄) and concentrated in vacuo. The residue was purified by flash chromatography on silica gel eluting with petroleum ether: ethyl acetate (10:1) to give 4-((6-bromopyridin-2-yl)methyl)morpholine (38.0 g, 68% yield).

Step 2. Synthesis of 6-(morpholinomethyl)picolinic acid

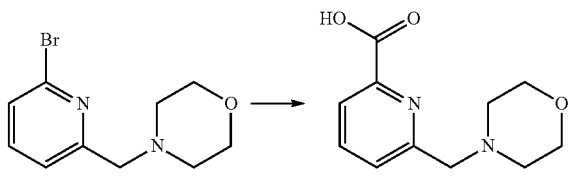 [SMILES: Brc1cccc(CN2CCOCC2)n1 ; O=C(O)c1cccc(CN2CCOCC2)n1]

n-BuLi (56 mL, 0.140 mol) in THF was added to a solution of 4-((6-bromopyridin-2-yl)methyl)morpholine (30.0 g, 0.12 mol) in THF (500 mL) at −78° C. The mixture was stirred for 30 min and CO₂ (gas) was bubbled through the reaction mixture for 30 min. The volatiles were removed in vacuo and the residue was extracted with CH₂Cl₂/MeOH (1:1). The solvent was evaporated and the residue was washed with CH₂Cl₂ to give 6-(morpholinomethyl)picolinic acid (11.0 g, 42% yield).

Example 112. Preparation of 6-(pyrrolidin-1-ylmethyl)picolinic acid

Step 1. Synthesis of methyl 6-(chloromethyl)picolinate

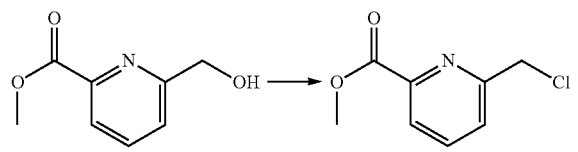

SOCl₂ (57.0 g, 0.48 mol) was added to a solution of methyl 6-(hydroxymethyl)picolinate (40.0 g, 0.239 mol) in dichloromethane (500 mL) at room temp. The mixture was stirred at 40° C. for 1 h and sat. aq K₂CO₃ was added to adjust the pH to 9. The mixture was extracted with CH₂Cl₂ and the combined organics were washed with brine, dried (Na₂SO₄), and concentrated in vacuo to give methyl 6-(chloromethyl)picolinate (45.0 g).

Step 2. Synthesis of methyl 6-(pyrrolidin-1-ylmethyl)picolinate

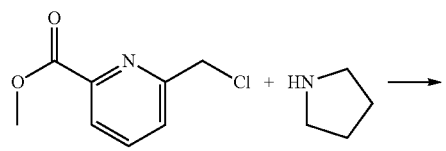

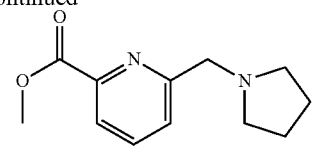

K₂CO₃ (66.0 g, 0.48 mol) was added to a solution of methyl 6-(chloromethyl)picolinate (45.0 g) and pyrrolidine (34.0 g, 0.48 mol) in DMF (300 mL). The reaction mixture was heated at 80° C. for 12 h. H₂O (300 mL) was added and the mixture was extracted with EtOAc. The combined organic layers were washed with brine, dried (Na₂SO₄) and concentrated in vacuo to give methyl 6-(pyrrolidin-1-ylmethyl)picolinate (36.0 g).

Step 3. Synthesis of 6-(pyrrolidin-1-ylmethyl)picolinic acid

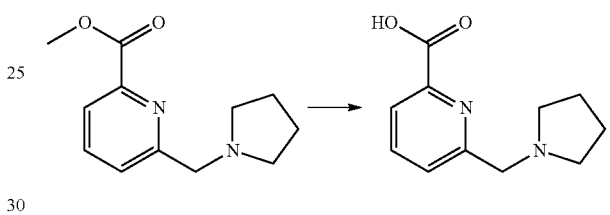

A mixture of methyl 6-(pyrrolidin-1-ylmethyl)picolinate (36.0 g) and NaOH (40.0 g, 1.0 mol) in ethanol/H₂O (320 mL) was stirred at 75° C. for 16 h. The pH was adjusted to 7 with 3N HCl and extracted with EtOAc. The aqueous layer was concentrated to dryness and extracted with dichloromethane/methanol (v:v=3:1), The organic layer was dried to give 6-(pyrrolidin-1-ylmethyl)picolinic acid (27.0 g, 55% yield).

Example 113. Preparation of N-methyl proline

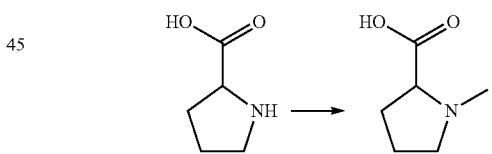

N-methyl proline was prepared by a procedure similar to that reported in J. Org. Chem. 2003, 66, 2652.

Example 114. Preparation of 1-methyl-5-oxopyrrolidine-2-carboxylic acid

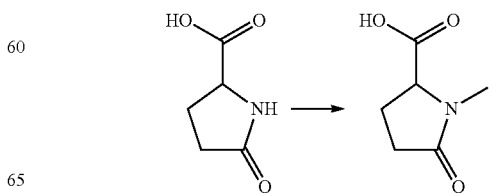

1-methyl-5-oxopyrrolidine-2-carboxylic acid was prepared by a procedure similar to that reported in J. Heterocyclic. Chem. 1991, 28, 1143.

Example 115. Preparation of 3-(morpholinomethyl)aniline

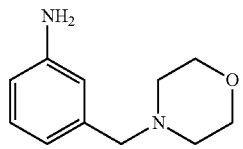 [SMILES: Nc1cccc(CN2CCOCC2)c1]

3-(morpholinomethyl)aniline was prepared by a procedure similar to that reported in J. Med. Chem. 1990, 33(1), 327-36.

Example 116. Preparation of 6-(pyrrolidin-1-ylmethyl)pyridin-2-amine

Step 1. Synthesis of ethyl 6-aminopicolinate

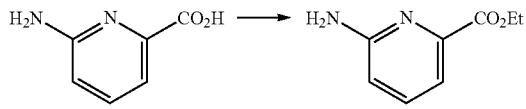 [SMILES: Nc1cccc(C(=O)O)n1 ; CCOC(=O)c1cccc(N)n1]

To a solution of 2-amino-6-pyridinecarboxylic acid (6.0 g, 43.5 mmol) in ethanol (150 mL) was added thionyl chloride (12.0 g, 101 mmol) at 0° C. The resulting reaction mixture was stirred at reflux for 12 h. Upon cooling to room temp, the reaction mixture was concentrated under reduced pressure. Saturated aqueous $Na_2CO_3$ solution was added until the pH of the solution reached 9. The mixture was concentrated under reduced pressure and dichloromethane (150 mL) was added to the resulting residue. The mixture was stirred vigorously at room temp for 30 min and then filtered. The filtrate was concentrated under reduced pressure to afford ethyl 6-aminopicolinate (5.5 g, 76% yield).

Step 2. Synthesis of ethyl 6-(tert-butoxycarbonylamino)picolinate

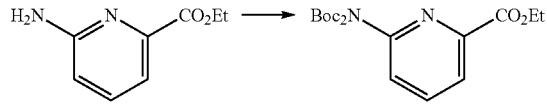

To a solution of ethyl 6-aminopicolinate (5.5 g, 33 mmol) in t-BuOH (120 mL) and acetone (40 mL) was added 4-dimethylaminopyridine (0.08 g, 0.66 mmol) and di-tert-butyl dicarbonate (10.8 g, 49.5 mmol). The reaction mixture was stirred at room temp for 18 h. The solvent was removed by concentration under reduced pressure and a mixture of hexane/dichloromethane (180 mL, 3:1) was added. The resulting mixture was cooled to −20° C. for 2 h. The resulting solids were collected by filtration and dried to afford ethyl 6-(tert-butoxycarbonylamino)picolinate (11.0 g, 91% yield).

Step 3. Synthesis of tert-butyl 6-(hydroxymethyl)pyridin-2-ylcarbamate

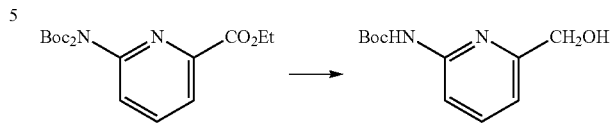

To a stirred solution of ethyl 6-(bis(tert-butoxycarbonyl)amino)picolinate (11.0 g, 33 mmol) in THF (120 mL) under nitrogen was added $LiAlH_4$ (3.80 g, 100 mmol) in THF (60 mL) over a period of 30 min at 0° C. The reaction mixture was stirred at 0° C. for 6 h and carefully quenched by the addition of $H_2O$ (2.0 mL) and 10% NaOH solution (4.0 mL) at 0° C. The reaction mixture was filtered and the filtrate was dried ($Na_2SO_4$) and concentrated under reduced pressure. The resulting residue purified by chromatography (1:1 petroleum ether: ethyl acetate) to afford tert-butyl 6-(hydroxymethyl)pyridin-2-ylcarbamate (3.0 g, 41% yield).

Step 4. Synthesis of (6-(tert-butoxycarbonylamino)pyridin-2-yl)methyl methanesulfonate

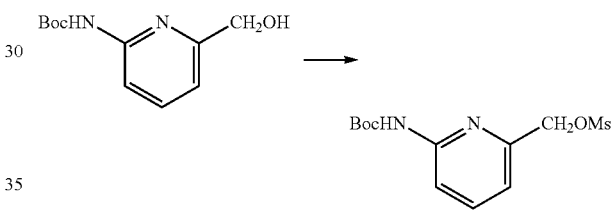

To a solution of tert-butyl 6-(hydroxymethyl)pyridin-2-ylcarbamate (3.0 g, 13.4 mmol) and diisopropylethylamine (5.0 g, 40 mmol) in acetonitrile (30 mL) was added methanesulfonyl chloride (2.0 g, 17.4 mmol) over a period of 30 min at 0° C. and the mixture was stirred for 2 h at room temp. The reaction was quenched by adding saturated aqueous $NaHCO_3$ and extracted with ethyl acetate (3×60 mL). The combined organic layers were washed with brine, dried ($Na_2SO_4$) and concentrated under reduced pressure to afford (6-(tert-butoxycarbonylamino)pyridin-2-yl)methyl methanesulfonate in quantitative yield of crude.

Step 5. Synthesis of tert-butyl 6-(pyrrolidin-1-ylmethyl)pyridin-2-ylcarbamate

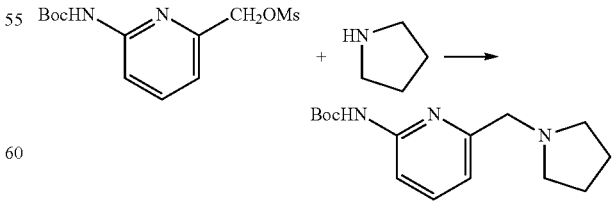

A mixture containing (6-(tert-butoxycarbonylamino)pyridin-2-yl)methyl methanesulfonate (1.30 g, 3.2 mmol), pyrrolidine (0.46 g, 6.4 mmol) and $K_2CO_3$ (1.30 g, 9.6 mmol) in acetonitrile (15 mL) was stirred at room temp for 12 h.

Saturated aqueous NaHCO₃ was added and the mixture was concentrated under reduced pressure. The resulting aqueous layer was extracted with EtOAc. The combined organic layers were dried (Na₂SO₄) and concentrated under reduced pressure to afford tert-butyl 6-(pyrrolidin-1-ylmethyl)pyridin-2-ylcarbamate (0.75 g, 62% yield).

Step 6. Synthesis of 6-(pyrrolidin-1-ylmethyl)pyridin-2-amine

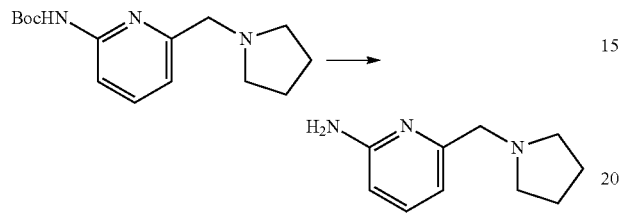

To a solution of tert-butyl 6-(pyrrolidin-1-ylmethyl)pyridin-2-ylcarbamate (750.0 mg, 2.71 mmol) in dichloromethane (10 mL) was added trifluoroacetic acid (4.0 mL) at room temp. The resulting reaction mixture was stirred at room temp for 6 h and then concentrated under reduced pressure. Saturated aqueous Na₂CO₃ was added to the resulting residue until the solution pH reached 9. The mixture was then extracted with ethyl acetate (3×25 mL). The combined organic layers were dried with Na₂SO₄ and concentrated under reduced pressure to afford 6-(pyrrolidin-1-ylmethyl)pyridin-2-amine (440.0 mg, 92% yield).

Example 117. Preparation of 6-(morpholinomethyl)pyridin-2-amine

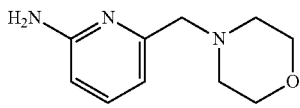 [SMILES: Nc1cccc(CN2CCOCC2)n1]

6-(morpholinomethyl)pyridin-2-amine was prepared by a method similar to that reported for 6-(pyrrolidin-1-ylmethyl)pyridin-2-amine.

Example 118. Preparation of (R)-6-(3-fluoropyrrolidin-1-yl)methyl)pyridin-2-amine

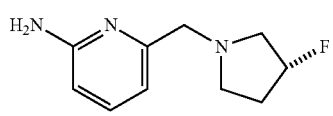 [SMILES: Nc1cccc(CN2CC[C@@H](F)C2)n1]

(R)-6-((3-fluoropyrrolidin-1-yl)methyl)pyridin-2-amine was prepared by a method similar to that reported for 6-(pyrrolidin-1-ylmethyl)pyridin-2-amine.

Example 119. Preparation of (S)-6-((3-fluoropyrrolidin-1-yl)methyl)pyridin-2-amine

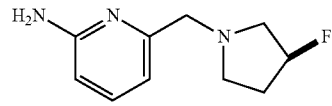 [SMILES: Nc1cccc(CN2CC[C@H](F)C2)n1]

(S)-6-((3-fluoropyrrolidin-1-yl)methyl)pyridin-2-amine was prepared by a method similar to that reported for 6-(pyrrolidin-1-ylmethyl)pyridin-2-amine.

Example 120. Preparation of 6-(piperazin-1-ylmethyl)pyridin-2-amine

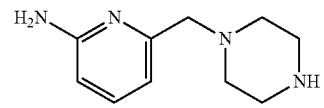

6-(piperazin-1-ylmethyl)pyridin-2-amine was prepared by a method similar to that reported for 6-(pyrrolidin-1-ylmethyl)pyridin-2-amine.

Example 121. Preparation of tert-butyl 4-((6-aminopyridin-2-yl)methyl)piperazine-1-carboxylate

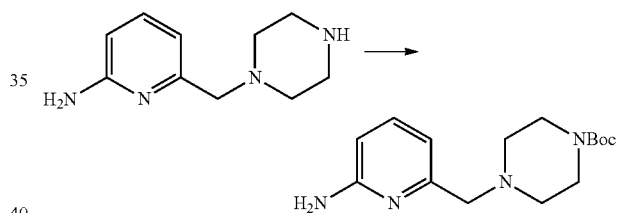

To a solution of 6-(piperazin-1-ylmethyl)198yridine-2-amine in THF was added di-tert-butyl carbonate (1 eq) and 4-(dimethyl)aminopyridine (catalytic). The reaction mixture was stirred at room temp for 18 h. It was then concentrated under reduced pressure. Pentane was added and the resulting solid was collected by filtration and dried to afford tert-butyl 4-((6-aminopyridin-2-yl)methyl)piperazine-1-carboxylate.

Example 122. Preparation of 4-(morpholinomethyl)thiazol-2-amine trifluoroacetate Step 1. Synthesis of ethyl 2-(tert-butoxycarbonylamino)thiazole-4-carboxylate

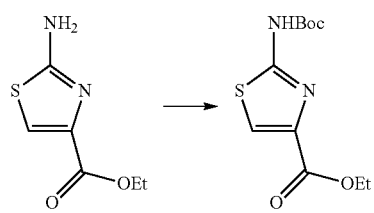 [SMILES: CCOC(=O)c1csc(N)n1 ; CCOC(=O)c1csc(NC(=O)OC(C)(C)C)n1]

Ethyl 2-aminothiazole-4-carboxylate (10.0 g, 58.1 mmol) was taken up in 150 mL of anhydrous THF along with di-tert-butyl carbonate (12.67 g, 58.1 mmol) and 4-(dimethyl)aminopyridine (DMAP) (10.0 mg, 0.082 mmol). The reaction mixture was stirred at 50° C. for 4 h and then at room temp for 18 h. It was then concentrated under reduced pressure to obtain a thick oil. Pentane was added and the resulting crystalline materials were collected by filtration and dried to afford ethyl 2-(tert-butoxycarbonylamino)thiazole-4-carboxylate (10.5 g, 66% yield).

Step 2. Synthesis of tert-butyl 4-(hydroxymethyl)thiazol-2-ylcarbamate

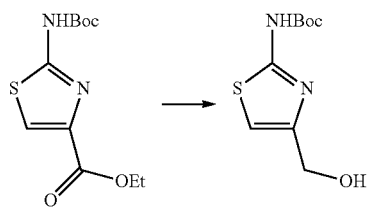 [SMILES: CCOC(=O)c1csc(NC(=O)OC(C)(C)C)n1 ; CC(C)(C)OC(=O)Nc1nc(CO)cs1]

Ethyl 2-(tert-butoxycarbonylamino)thiazole-4-carboxylate (10.5 g, 38.6 mmol) was dissolved in 300 mL of anhydrous THF and cooled in dry ice-acetonitrile bath. A solution of 1 M Super Hydride™ in THF (85 mL) was then added over a period of 10 min. The resulting reaction mixture was stirred at −45° C. for 2 h. Another portion of 1 M Super Hydride™ in THF (35 mL) was then added and the reaction mixture was stirred for an additional 2 h at −45° C. The reaction was quenched at −45° C. by the addition of 50 mL of brine. Upon warming to room temp, the reaction mixture was concentrated under reduced pressure. The resulting mixture was extracted with EtOAc. The combined organic layers were washed with brine, dried with $Na_2SO_4$, and concentrated under reduced pressure. The resulting residue was purified by chromatography to afford tert-butyl 4-(hydroxymethyl)thiazol-2-ylcarbamate (6.39 g, 72% yield).

Step 3. Synthesis of tert-butyl 4-(morpholinomethyl)thiazol-2-ylcarbamate

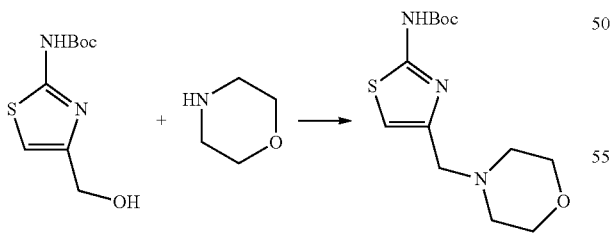

tert-Butyl 4-(hydroxymethyl)thiazol-2-ylcarbamate (2.0 g, 8.68 mmol) was taken up in 25 mL of $CH_2Cl_2$ along with $Et_3N$ (1.82 mL, 13.05 mmol) and cooled to 0° C. Methanesulfonyl chloride (0.85 mL, 10.88 mmol) was added and the resulting reaction mixture was stirred at 0° C. for 60 min. Morpholine (3.0 mL, 35 mmol) was then added and the reaction mixture stirred at room temp for 18 h. The reaction mixture was concentrated under reduced pressure. The resulting residue was taken up in EtOAc and washed with dilute aqueous $NaHCO_3$, brine, dried with $Na_2SO_4$, and concentrated under reduced pressure. This material was purified by filtering through a short column of silica gel. The filtrate was concentrated to afford tert-butyl 4-(morpholinomethyl)thiazol-2-ylcarbamate (1.88 g, 69% yield).

Step 4. Synthesis of 4-(morpholinomethyl)thiazol-2-amine trifluoroacetate

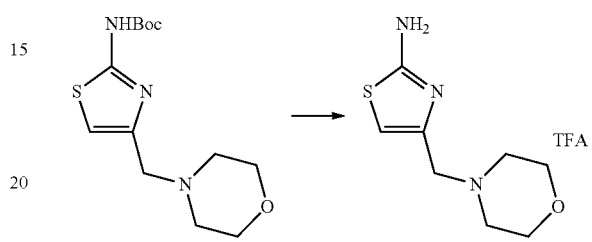

Tert-butyl 4-(morpholinomethyl)thiazol-2-ylcarbamate 1.88 g, 6.28 mmol) was treated with 20 mL of 25% trifluoroacetic acid in $CH_2Cl_2$ for 18 h at room temp. After all the solvent had been removed by concentrating and drying under high vacuum, the resulting residue was treated with a mixture of pentane/EtOAc to afford 4-(morpholinomethyl)thiazol-2-amine trifluoroacetate (1.96 g, 100% yield) as a white solid.

Example 123. Preparation of 4-(pyrrolidin-1-ylmethyl)thiazol-2-amine trifluoroacetate

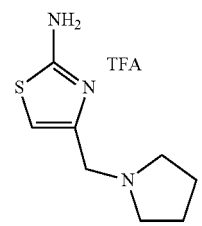 [SMILES: Nc1nc(CN2CCCC2)cs1]

4-(pyrrolidin-1-ylmethyl)thiazol-2-amine trifluoroacetate was prepared by a procedure similar to that reported for 4-(morpholinomethyl)thiazol-2-amine trifluoroacetate.

Example 124. Preparation of 5-(morpholinomethyl)thiazol-2-amine trifluoroacetate

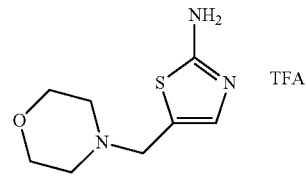 [SMILES: Nc1ncc(CN2CCOCC2)s1]

5-(morpholinomethyl)thiazol-2-amine trifluoroacetate was prepared by a procedure similar to that reported for 4-(morpholinomethyl)thiazol-2-amine trifluoroacetate.

Example 125. Preparation 5-(pyrrolidin-1-ylmethyl)thiazol-2-amine trifluoroacetate

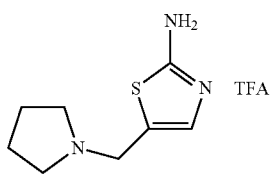 [SMILES: Nc1ncc(CN2CCCC2)s1 ; "TFA"]

5-(pyrrolidin-1-ylmethyl)thiazol-2-amine trifluoroacetate was prepared by a procedure similar to that reported for 4-(morpholinomethyl)thiazol-2-amine trifluoroacetate.

Example 126. Preparation 4-(piperazin-1-ylmethyl)thiazol-2-amine trifluoroacetate

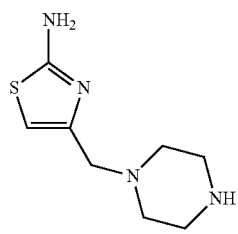 [SMILES: Nc1nc(CN2CCNCC2)cs1]

4-(piperazin-1-ylmethyl)thiazol-2-amine trifluoroacetate was prepared by a procedure similar to that reported for 4-(morpholinomethyl)thiazol-2-amine trifluoroacetate.

Example 127. Preparation of tert-butyl 4-((2-aminothiazol-4-yl)methyl)piperazine-1-carboxylate

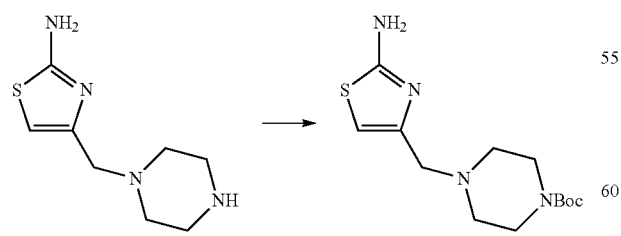

tert-butyl 4-((2-aminothiazol-4-yl)methyl)piperazine-1-carboxylate was prepared by a procedure similar to that reported for tert-butyl 4-(((6-aminopyridin-2-yl)methyl)piperazine-1-carboxylate.

Example 128. Preparation of 2-((2,2-dimethyl-1,3-dioxolan-4-yl)methoxy)pyrimidin-4-amine

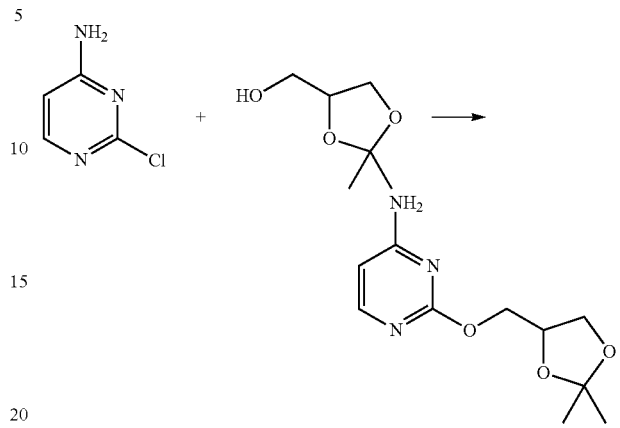

To a solution of solketal (34.4 g, 260 mmol) in THF (150 mL) was added NaH (10.4 g, 260 mmol) at room temp and the mixture stirred for 1 h. 2-chloro-4-aminopyrimidine (15.0 g, 115 mmol) was then added, and the mixture was stirred at 70° C. for 48 h. The reaction mixture was concentrated and the crude residue was purified by flash chromatography (DCM:MeOH=15:1-10:1) to give 2-((2,2-dimethyl-1,3-dioxolan-4-yl)methoxy)pyrimidin-4-amine (18.2 g, 70% yield) as an oil.

Example 129. Preparation of 6-((2,2-dimethyl-1,3-dioxolan-4-yl)methoxy)pyrazin-2-amine

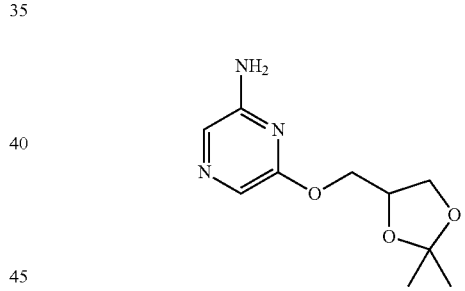

6-((2,2-dimethyl-1,3-dioxolan-4-yl)methoxy)pyrazin-2-amine was prepared by a method similar to that reported for 2-((2,2-dimethyl-1,3-dioxolan-4-yl)methoxy)pyrimidin-4-amine.

Example 130. Preparation of (S)-6-(2,2-dimethyl-1,3-dioxolan-4-yl)methoxy)-2-aminopyridine

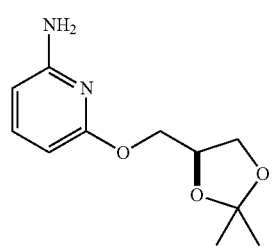 [SMILES: CC1(C)OC[C@H](COc2cccc(N)n2)O1]

(S)-6-((2,2-dimethyl-1,3-dioxolan-4-yl)methoxy)-2-aminopyridine was prepared by a method similar to that reported for 2-((2,2-dimethyl-1,3-dioxolan-4-yl)methoxy)pyrimidin-4-amine, using (S)-(2,2-dimethyl-1,3-dioxolan-4-yl)methanol.

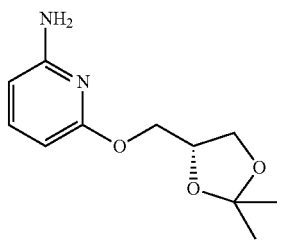 [SMILES: CC1(C)OC[C@@H](COc2cccc(N)n2)O1]

The enantiomer was prepared the same as above, using (R)-(2,2-dimethyl-1,3-dioxolan-4-yl)methanol.

Example 131. Preparation of (R)-6-((2,2-dimethyl-1,3-dioxolan-4-yl)methoxy)-2-aminopyridine

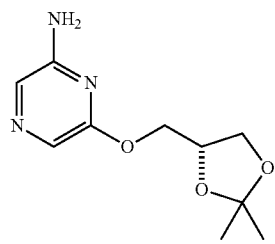

(R)-6-((2,2-dimethyl-1,3-dioxolan-4-yl)methoxy)-2-aminopyridine was prepared by a method similar to that reported for 2-((2,2-dimethyl-1,3-dioxolan-4-yl)methoxy)pyrimidin-4-amine.

Example 132. Preparation of (R)-3-((2,2-dimethyl-1,3-dioxolan-4-yl)methoxy)aniline Step 1. Synthesis of (R)-2,2-dimethyl-4-((3-nitrophenoxy)methyl)-1,3-dioxolane

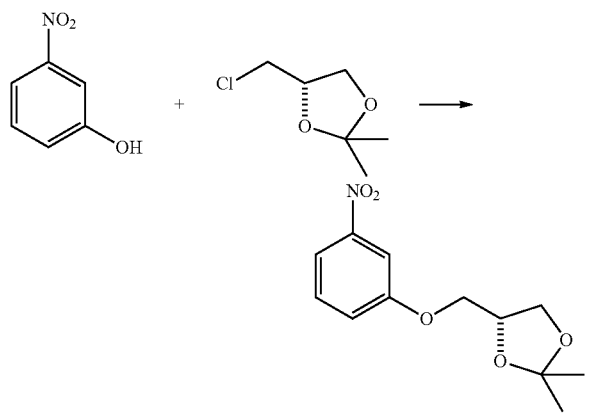

A mixture of 3-nitrophenol (2.0 g, 14.4 mmol), potassium carbonate (4.96 g, 35.9 mmol) and (S)-4-(chloromethyl)-2,2-dimethyl-1,3-dioxolane (2.55 mL, 18.7 mmol) in DMF (20 mL) was heated in a microwave reactor at 160° C. for 4 h. The crude reaction mixture was poured into H₂O and extracted with dichloromethane (3×15 mL). The combined organic layers were dried (Na₂SO₄) and concentrated under reduced pressure. The crude residue was purified by chromatography using ethyl acetate: pentane to obtain (R)-2,2-dimethyl-4-((3-nitrophenoxy)methyl)-1,3-dioxolane (1.90 g, 52% yield) as an amber-colored oil.

Step 2. Synthesis of (R)-3-((2,2-dimethyl-1,3-dioxolan-4-yl)methoxy)aniline

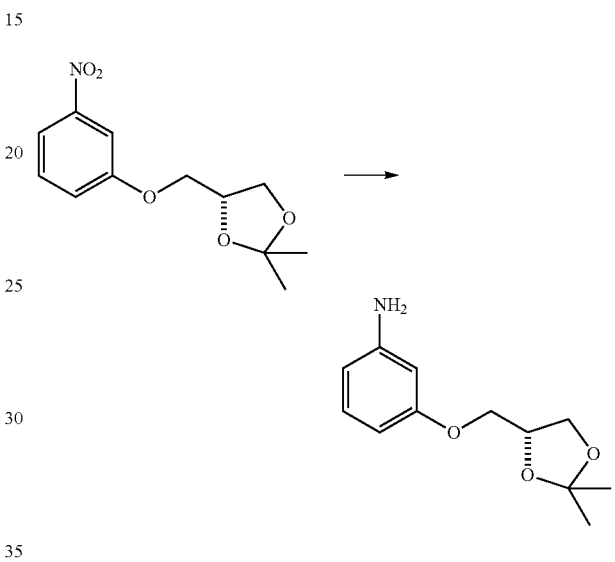

A mixture of Fe powder (2.38 g, 42.5 mmol), NH₄Cl (2.27 g, 42.5 mmol) and (R)-2,2-dimethyl-4-((3-nitrophenoxy)methyl)-1,3-dioxolane (1.80 g, 7.09 mmol) in isopropanol (30 mL)/H₂O (10 mL) was heated at reflux for 18 h. The crude material was filtered through a pad of Celite and the filtrate was concentrated under reduced pressure. The resulting aqueous layer was extracted with dichloromethane (3×15 mL). The combined organic layers were dried with Na₂SO₄, and concentrated under reduced pressure to afford (R)-3-((2,2-dimethyl-1,3-dioxolan-4-yl) methoxy)aniline (1.25 g, 76% yield).

Example 133. Preparation of 3-((2,2-dimethyl-1,3-dioxolan-4-yl)methoxy)aniline

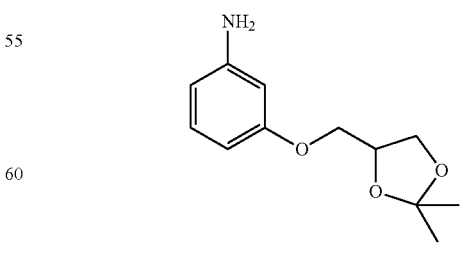

3-((2,2-dimethyl-1,3-dioxolan-4-yl) methoxy)aniline was prepared by a method similar to that reported for (R)-3-((2,2-dimethyl-1,3-dioxolan-4-yl)methoxy)aniline.

Example 134. Preparation of (S)-3-((2,2-dimethyl-1,3-dioxolan-4-yl)methoxy)aniline

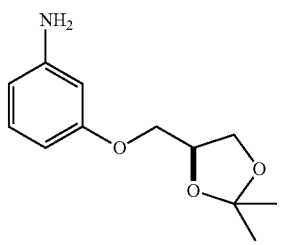 [SMILES: CC1(C)OC[C@H](COc2cccc(N)c2)O1]

(S)-3-((2,2-dimethyl-1,3-dioxolan-4-yl) methoxy)aniline was prepared by a method similar to that reported for (R)-3-((2,2-dimethyl-1,3-dioxolan-4-yl)methoxy)aniline.

Example 135. Preparation of 4-((2,2-dimethyl-1,3-dioxolan-4-yl)methoxy)aniline

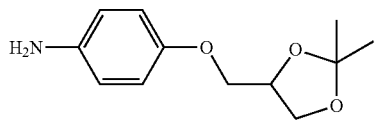 [SMILES: CC1(C)OCC(COc2ccc(N)cc2)O1]

4-((2,2-dimethyl-1,3-dioxolan-4-yl) methoxy)aniline was prepared by a method similar to that reported for (R)-3-((2,2-dimethyl-1,3-dioxolan-4-yl)methoxy)aniline.

Example 136. Preparation of 2-(pyrrolidin-1-yl)pyridin-4-amine

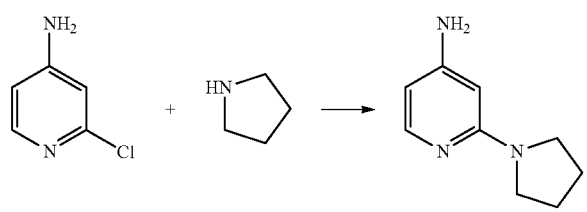 [SMILES: Nc1ccnc(Cl)c1 ; C1CCNC1 ; Nc1ccnc(N2CCCC2)c1]

A mixture of 2-chloro-4-aminopyridine (2.29 g, 17.8 mmol) and pyrrolidine (5.0 mL) was heated at 200° C. in a microwave reactor for 10 min. After cooling to room temp, the solid was filtered and washed with dichloromethane (10 mL×3). The filter cake was dissolved in aqueous $K_2CO_3$ and extracted with $CH_2Cl_2$ (40 mL×3). The combined organic layers were dried over $Na_2SO_4$ and concentrated to obtain (2-(pyrrolidin-1-yl)pyridin-4-amine (2.30 g, 79% yield).

Example 137. Preparation of 2-morpholinopyridin-4-amine 2-morpholinopyridin-4-amine was prepared by a method similar to that reported for 2-(pyrrolidin-1-yl)pyridin-4-amine.

Example 138. Preparation of 6-morpholinopyridin-2-amine 6-morpholinopyridin-2-amine was prepared by a method similar to that reported for 2-(pyrrolidin-1-yl)pyridin-4-amine.

Example 139. Preparation of 6-(pyrrolidin-1-yl)pyridin-2-amine 6-(pyrrolidin-1-yl)pyridin-2-amine was prepared by a method similar to that reported for 2-(pyrrolidin-1-yl)pyridin-4-amine.

Example 140. Preparation of (S)-5-((3-fluoropyrrolidin-1-yl)methyl)pyridin-2-amine Step 1. Synthesis of ethyl 6-aminonicotinate

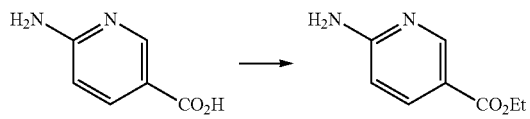 [SMILES: Nc1ccc(C(=O)O)cn1 ; CCOC(=O)c1ccc(N)nc1]

To a solution of 2-amino-5-pyridinecarboxylic acid (150.0 g, 1.09 mol) in ethanol (2 L) was added thionyl chloride (259.0 g, 2.18 mol) at 0° C. The mixture was heated at reflux for 12 h. The solvent was removed under reduced pressure. Saturated aq Na₂CO₃ was added to adjust the pH to 9 and the resulting solid was collected by filtration, rinsed with H₂O, and dried to give ethyl 6-aminonicotinate (160.0 g, 88% yield).

Step 2. Synthesis of ethyl 6-(bis(tert-butoxycarbonyl)amino)nicotinate

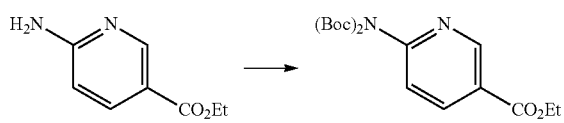

To a solution of ethyl 6-aminonicotinate (160.0 g, 963 mmol) in t-BuOH (1.7 L) and acetone (560 mL) was added DMAP (2.38 g, 19.1 mmol) and di-t-butyl dicarbonate (420.0 g, 1.92 mol). The reaction was stirred at room temp overnight. The solvent was removed and hexane/dichloromethane (2.5 L, 3:1) was added. The mixture was cooled to −20° C. for 2 h. The solid was collected by filtration and dried in vacuo to give ethyl 6-(bis(tert-butoxycarbonyl)amino)nicotinate (300.0 g, 85% yield).

Step 3. Synthesis of tert-butyl 5-(hydroxymethyl)pyridin-2-ylcarbamate

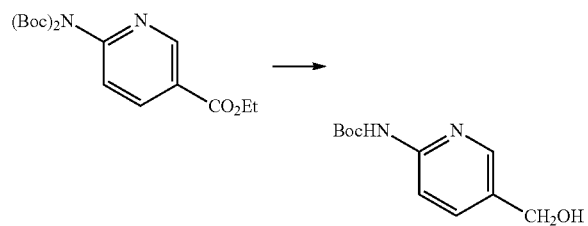

To a stirred solution of ethyl 6-(bis(tert-butoxycarbonyl)amino)nicotinate (300.0 g, 819 mmol) in THF (1.2 L) was added LiAlH₄ (57.6 g, 1.51 mol) in THF (3 L) over a period of 30 min at 0° C. The reaction mixture was stirred for 6 h, and H₂O (30.0 mL) and 10% NaOH solution (60.0 mL) were added. The solids were removed by filtration and the filtrate was dried (Na₂SO₄) and concentrated. The crude residue was purified by flash chromatography (DCM:MeOH=40:1) to give tert-butyl 5-(hydroxymethyl)pyridin-2-ylcarbamate (85.0 g, 46% yield).

Step 4. Synthesis of tert-butyl 5-(chloromethyl)pyridin-2-ylcarbamate

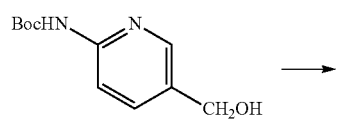

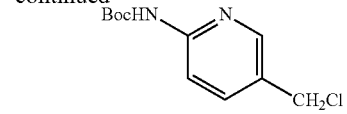

To a solution of tert-butyl 5-(hydroxymethyl)pyridin-2-ylcarbamate (85.0 g, 379 mmol) and diisopropylethylamine (296.0 g, 2.27 mol) in THF (850 mL) was added methanesulfonyl chloride (130.0 g, 1.14 mol) over a period of 30 min at 0° C. The mixture was stirred for 12 h at room temp then washed with H₂O (2×100 mL) and dried over Na₂SO₄. The mixture was concentrated and the crude residue was purified by flash chromatography (petroleum ether: ethyl acetate=10:1) to give tert-butyl 5-(chloromethyl)pyridin-2-ylcarbamate (30.0 g, 63% yield).

Step 5. Synthesis of (S)-tert-butyl 5-((3-fluoropyrrolidin-1-yl)methyl)pyridin-2-ylcarbamate

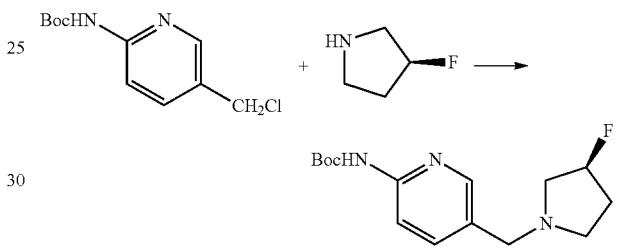

A mixture of tert-butyl 5-(chloromethyl)pyridin-2-ylcarbamate (9.5 g, 39.1 mmol), (S)-3-fluoropyrrolidine (4.19 g, 47.0 mmol), potassium carbonate (16.2 g, 117 mmol) and sodium iodide (0.59 g, 3.91 mmol) in DMF (150 mL) was stirred at 60° C. for 2 h. The reaction mixture was filtered, and the filtrate was concentrated in vacuo. H₂O (250 mL) was added and the resulting solid was collected by filtration, rinsed with H₂O and dried to give (S)-tert-butyl 5-((3-fluoropyrrolidin-1-yl)methyl)pyridin-2-ylcarbamate (7.0 g, 61% yield).

Step 6. Synthesis of (S)-5-((3-fluoropyrrolidin-1-yl)methyl)pyridin-2-amine

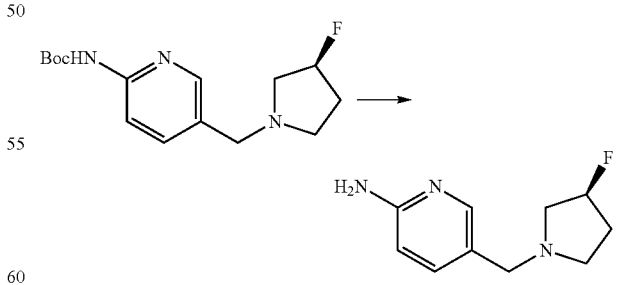

To a solution of (S)-tert-butyl 5-((3-fluoropyrrolidin-1-yl)methyl)pyridin-2-ylcarbamate (7.0 g, 23.7 mmol) in dichloromethane (70 mL) was added trifluoroacetic acid (TFA) (15.5 g, 142 mmol). The mixture was stirred for 12 h at room temp. The solvent was removed in vacuo and sat. aq Na₂CO₃ was added. The mixture was extracted with dichloromethane, dried (MgSO₄) and concentrated to give (S)-5-((3-fluoropyrrolidin-1-yl)methyl)pyridin-2-amine (4.50 g, 97% yield).

Example 141. Preparation of 5-(morpholinomethyl)pyridin-3-amine

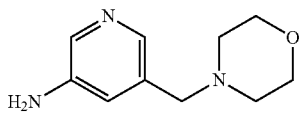

5-(morpholinomethyl)pyridin-3-amine was prepared by a method similar to that reported for (S)-5-((3-fluoropyrrolidin-1-yl)methyl)pyridin-2-amine.

Example 142. Preparation of 6-(morpholinomethyl)pyridin-3-amine

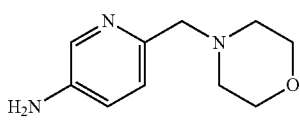

6-(morpholinomethyl)pyridin-3-amine was prepared by a method similar to that reported for (S)-5-((3-fluoropyrrolidin-1-yl)methyl)pyridin-2-amine.

Example 143. Preparation of (R)-5-((3-fluoropyrrolidin-1-yl)methyl)pyridin-2-amine

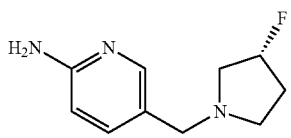 [SMILES: Nc1ccc(CN2CC[C@@H](F)C2)cn1]

(R)-5-((3-fluoropyrrolidin-1-yl)methyl)pyridin-2-amine was prepared by a method similar to that reported for (S)-5-((3-fluoropyrrolidin-1-yl)methyl)pyridin-2-amine.

Example 144. Preparation of 2-(morpholinomethyl)pyrimidin-4-amine

Step 1. Synthesis of 2-chloroacetimidamide dihydrochloride

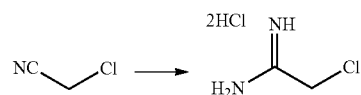

2-chloroacetonitrile (300.0 g, 4.0 mol) was added to a solution of sodium (10.0 g, 0.43 mol) in methanol (1000 mL) keeping the temperature below 20° C. The mixture was stirred at room temp for 2 h. NH₄Cl (234.0 g, 4.37 mol) was added in 5 batches and stirring continued for another 2 h. The solvent was removed to give 2-chloroacetimidamide dihydrochloride (525.0 g, 79% yield) which was used directly for next step without further purification.

Step 2. Synthesis of 2-(chloromethyl)pyrimidin-4-amine

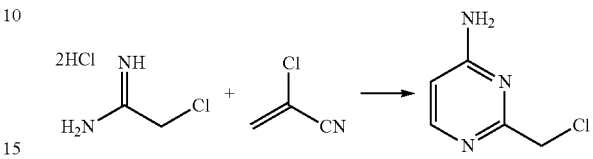

A solution of 2-chloroacetimidamide dihydrochloride (250.0 g, 1.51 mol), 2-chloroacrylonitrile (171.0 g, 1.95 mol) and triethylamine (490.0 g, 4.8 mol) in anhydrous ethanol (600 mL) was heated at reflux for 30 min. The solvent was removed in vacuo and the residue was purified by flash chromatography (DCM MeOH=30:1) to give 2-(chloromethyl)pyrimidin-4-amine (39.0 g, 18% yield).

Step 3. Synthesis of 2-(morpholinomethyl)pyrimidin-4-amine

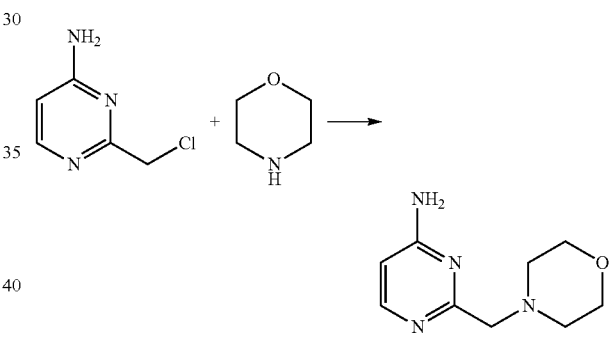

A solution of 2-(chloromethyl)pyrimidin-4-amine (30.0 g, 209 mmol), morpholine (23.7 g, 272 mmol) and triethylamine (42.3 g, 418 mmol) in anhydrous ethanol (250 mL) was heated at reflux for 16 h. The solvent was removed in vacuo and methanol (400 mL), H₂O (100 mL) and sodium bicarbonate (25.0 g) were added. Stirring was continued for 30 min. The mixture was concentrated and purified by flash chromatography (dichloromethane:methanol:triethylamine=100:8:0.5) to give 2-(morpholinomethyl)pyrimidin-4-amine (25.0 g, 62% yield).

Example 145. Preparation of tert-butyl 4-((4-aminopyrimidin-2-yl)methyl)piperazine-1-carboxylate

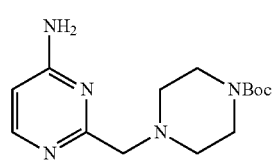 [SMILES: CC(C)(C)OC(=O)N1CCN(Cc2nccc(N)n2)CC1]

tert-butyl 4-((4-aminopyrimidin-2-yl)methyl)piperazine-1-carboxylate was prepared by a method similar to that reported for 2-(morpholinomethyl)pyrimidin-4-amine.

Example 146. Preparation of 2-(pyrrolidin-1-ylmethyl)pyrimidin-4-amine

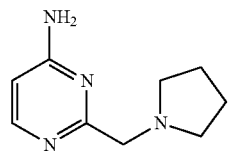 [SMILES: Nc1ccnc(CN2CCCC2)n1]

2-(pyrrolidin-1-ylmethyl)pyrimidin-4-amine was prepared by a method similar to that reported for 2-(morpholinomethyl)pyrimidin-4-amine.

Example 147. Preparation of 4-((3-methyloxetan-3-yl)methoxy)pyrimidin-2-amine

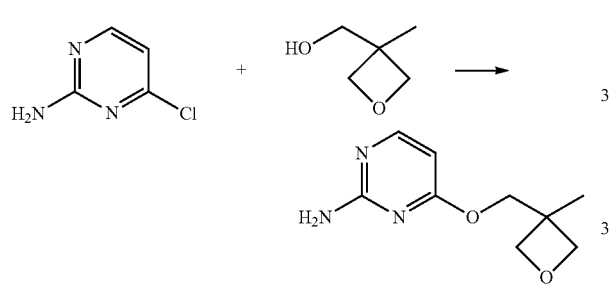

NaH (1.23 g, 0.03 mol) was washed with pentane and dried under vacuum for 15 min. THF (10 mL) was added to the flask under $N_2$ and the mixture was stirred. To this, (3-methyloxetan-3-yl)methanol (3.15 g, 0.03 mmol) was added dropwise. 10 mL of THF was added at room temp and solids were scraped to facilitate stirring. The dense mixture was stirred at room temp for 1 h. A slurry of 4-chloropyrimidin-2-amine (2.0 g, 0.02 mol) in THF was added to the reaction and it was refluxed for 15 h. After cooling to room temp, $H_2O$ (100 mL) was added and the aqueous layer was extracted with EtOAc. The crude product was purified by flash chromatography (0-100% EtOAc+pentane). The recovered material was taken up in diethyl ether and the solid that separated was isolated by filtration to afford 4-((3-methyloxetan-3-yl)methoxy)pyrimidin-2-amine (1.9 g, 65%). MS (ESI) calcd for $C_9H_{13}N_3O_2$ 195.1. found 196.0 [M+H].

Example 148. Preparation of 6-((3-methyloxetan-3-yl)methoxy)pyridin-2-amine

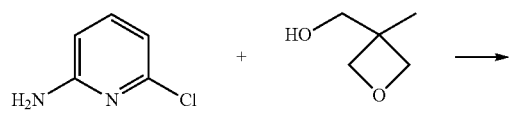

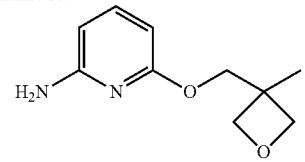

To 6-chloropyridin-2-amine (2.57 g, 20 mmol), (3-methyloxetan-3-yl)methanol (2.04 g, 20.0 mmol) and NaOH (8.0 g, 0.3 mol) was added 30 mL toluene. The mixture was heated at reflux under $N_2$ for 48 h. After cooling to room temp, $H_2O$ (40 mL) was added, the layers were separated and the organic layer was washed with $H_2O$ (15 mL), brine (30 mL) and dried over $Na_2SO_4$. After removing the solvent in vacuo, the crude product was purified by column chromatography to give 6-((3-methyloxetan-3-yl)methoxy)pyridin-2-amine (2.1 g, 54%). MS (ESI) calcd for $C_{10}H_{14}N_2O_2$ 194.11. found 195.2 [M+H].

Example 149. Preparation of 2-(2,2,2-trifluoroethoxy)pyridin-4-amine

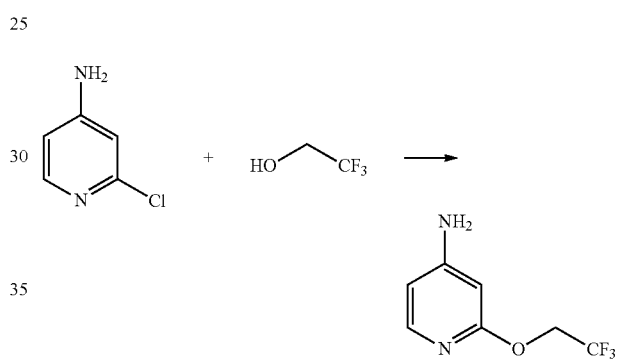

2-bromopyridin-4-amine (680.0 mg, 3.94 mmol) was taken up in 10 mL of dioxane along with 2,2,2-trifluoroethanol (1.56 g, 15.6 mmol), sodium hydride (373.0 mg, 15.6 mmol). The resulting reaction mixture was stirred refluxed for 15 h, cooled to room temp, concentrated in vacuo and purified by chromatography (EtOAc: Pet ether (1:10)) to afford 2-(2,2,2-trifluoroethoxy)pyridin-4-amine (500.0 mg, 66.2%). MS (ESI) calcd for $C_7H_7F_3N_2O$ 192.05.

Example 150. Preparation of 5-morpholinopyridin-3-amine

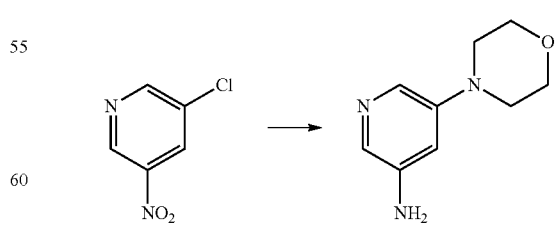

5-morpholinopyridin-3-amine was prepared from 3-chloro-5-nitropyridine using the same two-step procedure described above for the synthesis of 5-morpholinopyridin-2-amine.

Example 151. Preparation of 6-(2-oxa-6-azaspiro[3.3]heptan-6-yl)pyridin-2-amine

Step 1. Synthesis of 6-tosyl-2-oxa-6-azaspiro[3.3]heptane

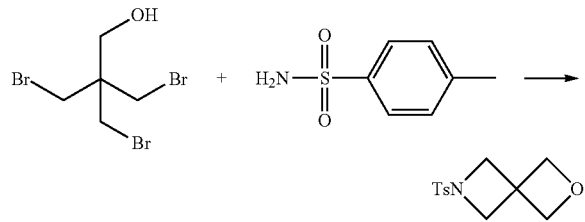

To a solution of KOH (33.2 g, 0.59 mol) and p-tosylamide (37.9 g, 0.22 mol) in 600 mL ethanol, 3-Bromo-2,2-bis(bromomethyl)propan-1-ol (60.1 g, 0.19 mol) was added at room temp and the reaction mixture was heated to reflux for 90 h. The solvent was removed by evaporation, 500 mL 1M KOH was added and the white suspension was left to stir for another 2 h at room temp. The mixture was filtered and the white filter cake was rinsed with water until the washing water was neutral. The filter cake was dried under high vacuum to give 30.55 g of product containing 10 mol % of tosylamide as a white solid. The overall yield of pure 6-tosyl-2-oxa-6-azaspiro[3.3]heptane was calculated to be 27.4 g (58%). MS (ESI) calcd for $C_{12}H_{15}NO_3S$: 253.3.

Step 2. Synthesis of 2-oxa-6-azaspiro[3.3]heptane oxalate

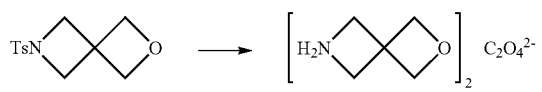

6-tosyl-2-oxa-6-azaspiro[3.3]heptanes (7.30 g, 28.8 mol) and magnesium (4.9 g, 0.2 mol) were sonicated for one h in methanol (500 mL). Almost all solvent was removed from the grey reaction mixture on a rotary evaporator to give a viscous grey residue. Diethyl ether (500 mL) and sodium sulfate (15.0 g) were added and the resulting light grey mixture was stirred vigorously for 30 min before filtration. The filtrate was dried over anhydrous sodium sulfate and anhydrous oxalic acid (1.3 g, 14.4 mol) dissolved in ethanol (~1 mL) was added to the organic phase. A thick white precipitate formed instantly. It was filtered off and dried under vacuum to give 2-oxa-6-azaspiro[3.3]heptane oxalate 3.37 g (81%) as amorphous white solid.

Step 3. Synthesis of ethyl 6-(2-oxa-6-azaspiro[3.3]heptan-6-yl)picolinate

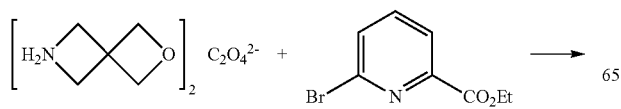

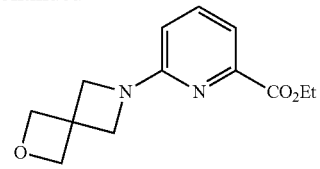

2-oxa-6-azaspiro[3.3]heptane oxalate (20 g, 0.23 mol), ethyl 6-bromopicolinate (56.9 g, 0.25 mol) and $K_2CO_3$ (62 g, 0.454 mol) were dissolved in DMSO (100 mL). The suspension was heated to 140° C. After cooling to room temp, the reaction was poured into water and extracted with methylene chloride. The organic layer was evaporated to dryness and product was purified on a gel silica to afford ethyl 6-(2-oxa-6-azaspiro[3.3]heptan-6-yl)picolinate (7.2 g, 30%). MS (ESI) calcd for $C_{13}H_{16}N_2O_3$: 248.1.

Step 4. Synthesis of 6-(2-oxa-6-azaspiro[3.3]heptan-6-yl)picolinic acid

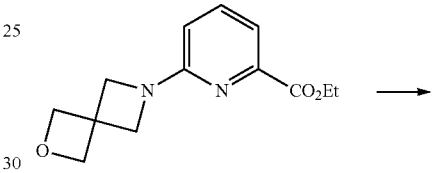

Ethyl 6-(2-oxa-6-azaspiro[3.3]heptan-6-yl)picolinate (7.2 g, 0.03 mol) was dissolved in dioxane (50 mL), and NaOH (2.3 g, 0.06 mol) in water (50 mL) was added. The suspension was stirred at 50° C. for about 2 h. The solvent was removed and water (50 mL) was added. The pH was adjusted 5 to afford 6-(2-oxa-6-azaspiro[3.3]heptan-6-yl)picolinic acid (4.5 g, 70%). MS (ESI) calcd for $C_{11}H_{12}N_2O_3$: 220.1. found: 221.2 [M+H].

Step 5. Synthesis of tert-butyl (6-(2-oxa-6-azaspiro[3.3]heptan-6-yl)pyridin-2-yl)carbamate

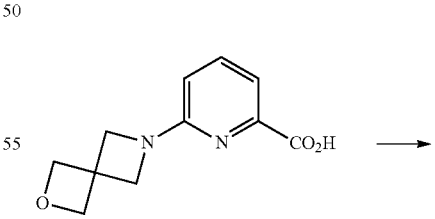

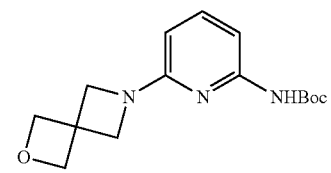

To a solution of 6-(2-oxa-6-azaspiro[3.3]heptan-6-yl)picolinic acid (4.4 g, 0.02 mol) in t-BuOH (50 mL) was added Et₃N (2.4 g, 0.02 mol) and DPPA (6.6 g, 0.024 mol). The mixture was refluxed overnight. After cooling to room temp, the solvent was evaporated and crude product was purified column chromatography to afford tert-butyl (6-(2-oxa-6-azaspiro[3.3]heptan-6-yl)pyridin-2-yl)carbamate (4.0 g, 70%).

Step 6. Synthesis of 6-(2-oxa-6-azaspiro[3.3]heptan-6-yl)pyridin-2-amine

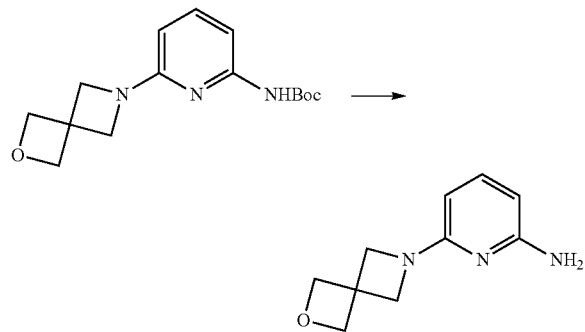

To a solution of tert-butyl (6-(2-oxa-6-azaspiro[3.3]heptan-6-yl)pyridin-2-yl)carbamate (4.4 g, 0.015 mol) in DCM (50 mL) was added CF₃COOH (20 mL). The mixture was stirred at room temp for about 4 h. The solvent was removed and CH₃CN (50 mL) was added. The pH was adjusted to 7. After evaporating the volatiles, 6-(2-oxa-6-azaspiro[3.3]heptan-6-yl)pyridin-2-amine was as obtained by purification on a silica gel column (2.05 g, 70%). MS (ESI) calcd for $C_{10}H_{13}N_3O$: 191.1. found 192.2 [M+H].

Example 152. Preparation of N-(6-(1-oxa-6-azaspiro[3.3]heptan-6-yl)pyridin-2-yl)-6-(2-(trifluoromethyl)phenyl)imidazo[1,2-b]pyridazine-3-carboxamide

Step 1. Synthesis of tert-butyl 1-oxa-6-azaspiro[3.3]heptane-6-carboxylate

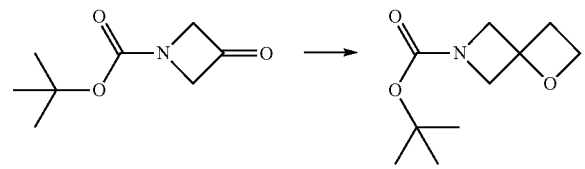

To a suspension of trimethylsulfoxonium iodide (80 g, 0.37 mol) in dry tert-BuOH (1.4 L) was added at 50° C. potassium tert-butoxide (41.3 g, 0.37 mmol), upon which the mixture turned to a cloudy suspension. The mixture was stirred at that temperature for 1.5 h, after which was added tert-butyl 3-oxoazetidine-1-carboxylate (25.0 g, 0.15 mmol). The suspension was stirred at 50° C. for 48 h. It was cooled to room temp and the mixture was partitioned between saturated aqueous NH₄Cl (30 mL) and EtOAc (50 mL). The phases were separated and the aqueous phase was extracted with EtOAc (50 mL). The combined organic phases were dried (Na₂SO₄), filtered, and concentrated in vacuo. tert-Butyl 1-oxa-6-azaspiro[3.3]heptane-6-carboxylate was obtained (8.0 g, 28%) after purification by flash chromatography on silica gel hexanes:EtOAc 2:1→0:1 gradient). MS (ESI) calcd for $C_{24}H_{19}F_3N_6O_2$: 199.1.

Step 2. Synthesis of 1-oxa-6-azaspiro[3.3]heptanes TFA salt

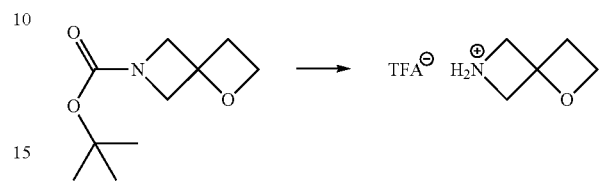

To a solution of tert-butyl 1-oxa-6-azaspiro[3.3]heptane-6-carboxylate (3.0 g, 15.06 mmol) in CH₂Cl₂ (10 mL) was added 2,2,2-trifluoroacetic acid (34.3 g, 301 mmol) and the mixture was stirred at 20° C. for 30 min. The volatiles were removed in vacuo. The residue 1-oxa-6-azaspiro[3.3]heptanes TFA salt was used without further purification (2.5 g, 85%).

Step 3. Synthesis of tert-butyl (6-(1-oxa-6-azaspiro[3.3]heptan-6-yl)pyridin-2-yl)carbamate

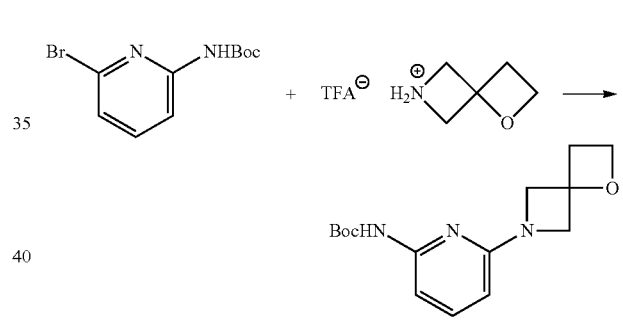

A mixture of tert-butyl 6-bromopyridin-2-ylcarbamate (8.18 g, 30.0 mmol), 1-oxa-6-azoniaspiro[3.3]heptane (3.0 g, 30.0 mmol), DPPF (1.66 g, 3.00 mmol), Pd(OAc)₂ (0.34 g, 1.5 mmol), and Cs₂CO₃ (19.5 g, 59.9 mmol) in 50 mL of toluene was heated to 120° C. for 5 h in a sealed tube and cooled. After evaporation of the solvent tert-butyl (6-O-oxa-6-azaspiro[3.3]heptan-6-yl)pyridin-2-yl)carbamate was obtained by flash column chromatography (2.7 g, 23%). MS (ESI) calcd for $C_{15}H_{21}N_3O_3$: 291.2.

Step 4. Synthesis 6-(1-oxa-6-azaspiro[3.3]heptan-6-yl)pyridin-2-amine

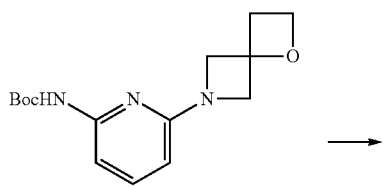

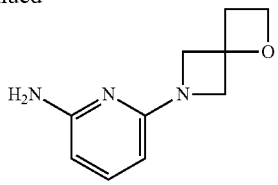

To a solution of tert-butyl 6-(1-oxa-6-azaspiro[3.3]heptan-6-yl)pyridin-2-ylcarbamate (2.0 g, 6.86 mmol) in 20 mL of methylene chloride was added 2,2,2-trifluoroacetic acid (7.83 g, 68.6 mmol) at room temp. The mixture was stirred for further 1 h and 50 ml of saturated aq. $Na_2CO_3$ was added. The organic phase was separated and concentrated. 6-(1-oxa-6-azaspiro[3.3]heptan-6-yl)pyridin-2-amine was obtained by flash column chromatography (900.0 mg, 69%). MS (ESI) calcd for $C_{10}H_{13}N_3O$: 191.1. found: 192.2.

Example 153. Preparation of 6-(oxazol-5-yl)pyridin-2-amine

Step 1: Synthesis of 6-amino-N-methoxy-N-methylpicolinamide

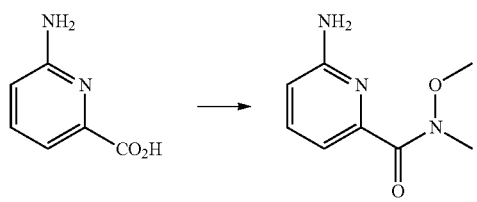

To a slurry of 6-aminopicolinic acid (10.0 g, 72.5 mmol) in acetonitrile (150 mL) was added N,O-dimethylhydroxylamine hydrochloride (8.52 g, 87.0 mmol), 1-hydroxybenzotriazole (11.8 g, 87.0 mmol), N-(3-dimethylamino)-N'-ethylcarbodiimide hydrochloride (16.7 g, 87.0 mmol), and N,N-diisopropylethylamine (37.7 mL, 217 mmol). The mixture was stirred at room temperature overnight, and the solvent removed in vacuo. The residue was partitioned between 1N NaOH and ethyl acetate, and the aqueous layer was extracted three times with ethyl acetate. The combined organic layers were washed with brine, dried with sodium sulfate, and the solvent removed in vacuo. The remaining residue was purified by flash chromatography (ethyl acetate with 0.1% triethylamine) to give 6-amino-N-methoxy-N-methylpicolinamide (4.30 g, 23.7 mmol, 33% yield). MS (ESI) calcd for $C_8H_7N_3O$: 181.1

Step 2: Synthesis of 6-(oxazol-5-yl)pyridin-2-amine

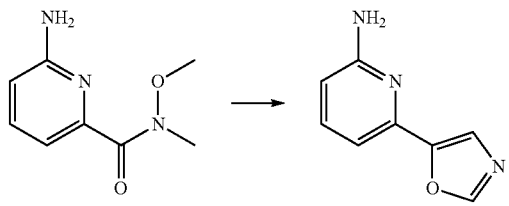

Lithium aluminum hydride (1.08 g, 28.5 mmol) was added to a solution of 6-amino-N-methoxy-N-methylpicolinamide (4.30 g, 23.7 mmol) in THF (30 mL). The reaction was stirred at room temperature for 90 min. Ethyl acetate (30 mL) was added slowly, the reaction was filtered, and the filtrate taken and all the solvent removed in vacuo to give 6-aminopicolinaldehyde, which was taken on crude to the next step.

To a solution of the above aldehyde in methanol (20 mL) was added p-toluenesulfonylmethyl isocyanide (13.9 g, 71.2 mmol) and potassium carbonate (19.4 g, 140 mmol). The reaction was stirred at reflux for 2 h, then all solvent removed in vacuo. The residue was partitioned between ethyl acetate (150 mL) and water (70 mL). The organic layer was washed with brine, dried with sodium sulfate, and the solvent removed in vacuo. The remaining residue was purified by flash chromatography (10% methanol in dichloromethane) to give 6-(oxazol-5-yl)pyridin-2-amine (2.00 g, 12.4 mmol, 52% yield over two steps). MS (ESI) calcd for $C_8H_{11}N_3O_2$: 161.06

4-(oxazol-5-yl)pyridin-2-amine was made according to the same procedure described above for 6-(oxazol-5-yl)pyridin-2-amine, by substituting 6-amino-N-methoxy-N-methylpicolinamide with 2-aminoisonicotinic acid.

Example 154. Preparation of (S)-6-(3-methoxypyrrolidin-1-yl)-N-(pyrimidin-4-yl)imidazo[1,2-b]pyridazine-3-carboxamide (Compound 973)

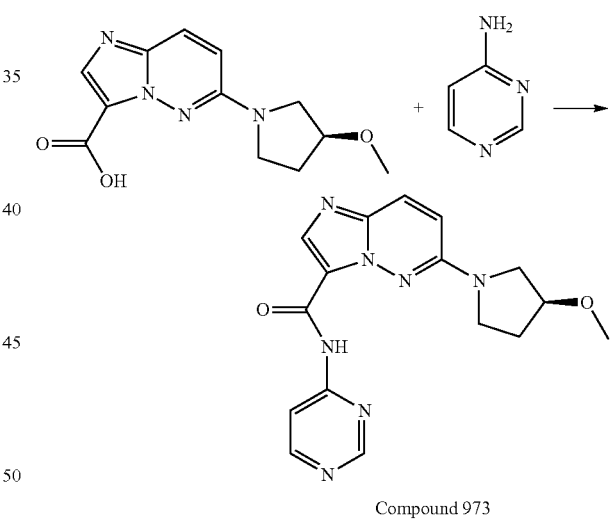

Compound 973

A mixture of (S)-6-(3-methoxypyrrolidin-1-yl)imidazo[1,2-b]pyridazine-3-carboxylic acid (100 mg, 0.38 mmol), HATU (290 mg, 0.76 mmol) and DIEA (0.12 mL, 0.82 mmol) in dry DCM (5 mL) was stirred at rt for 2 h, then evaporated to dryness under reduced pressure, the resulting residue was used directly for the next step. In another flask, pyrimidin-4-amine (40 mg, 0.42 mmol) was treated with NaH (64 mg, 2.6 mmol) in dry THF (5 mL) for 30 min, the crude active ester prepared above was added, stirred for another 2 h, cold water was added carefully, then extracted with ethyl acetate. The combined organic phase was dried over $Na_2SO_4$, concentrated. The crude product was purified by prep-TLC (DCM:MeOH=25:1) to give (S)-6-(3-methoxypyrrolidin-1-yl)-N-(pyrimidin-4-yl)imidazo[1,2-b]

pyridazine-3-carboxamide (12.6 mg, yield 10%) MS (ESI) calcd for $C_{16}H_{17}N_7O_2$ (m/z): 339.14.

This general coupling procedure could be used to prepare a variety of (S)-6-(3-methoxypyrrolidin-1-yl)-N-(substituted)imidazo[1,2-b]pyridazine-3-carboxamides by substituting the appropriate amine moiety for pyrimidin-4-amine.

Example 155. Preparation of 6-(3,3-difluoropyrrolidin-1-yl)-2-methyl-N-(pyridin-3-yl)imidazo[1,2-b]pyridazine-3-carboxamide (Compound 980)

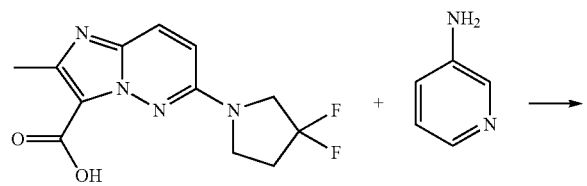

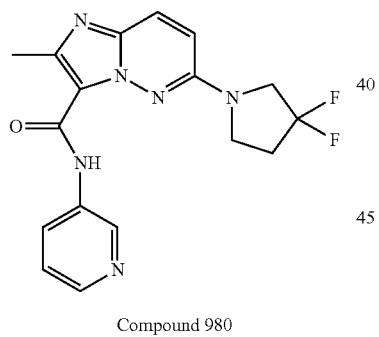

Compound 980

6-(3,3-difluoropyrrolidin-1-yl)-2-methylimidazo[1,2-b]pyridazine-3-carboxylic acid (100 mg, 0.35 mmol) was taken up in acetonitrile (2 mL). HATU (269 mg, 0.7 mmol) was added. After stirring for 2 min. 3-aminopyridine (66 mg, 0.7 mmol) and pyridine (0.5 mL) were added. The reaction was heated in a pressure tube at 100° C. for 17 h. After cooling to room temperature, water was added. The aqueous layer was extracted with dichloromethane. Combined organic layers were dried, concentrated and the crude product was purified by HPLC or silica gel column chromatography (yield 35 mg, 25%) MS (ESI) calcd for $C_{17}H_{16}F_2N_6O$ (m/z): 358.14. found 359.1 [M+H].

This general coupling procedure could be used to prepare a variety of 6-(3,3-difluoropyrrolidin-1-yl)-2-methyl-N-(substituted)imidazo[1,2-b]pyridazine-3 carboxamides by substituting the appropriate amine moiety for 3-aminopyridine.

Example 156. Preparation of N-(pyridin-3-yl)-6-(2-(trifluoromethyl)pyrrolidin-1-yl)imidazo[1,2-b]pyridazine-3-carboxamide (Compound 966)

Step 1: Synthesis of ethyl 6-(2-(trifluoromethyl)pyrrolidin-1-yl)imidazo[1,2-b]pyridazine-3-carboxylate

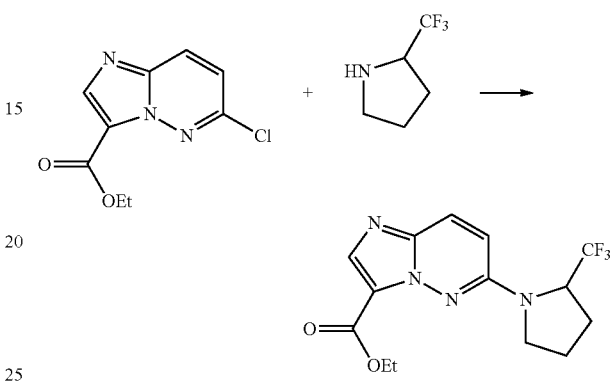

Ethyl 6-chloroimidazo[1,2-b]pyridazine-3-carboxylate (600 mg, 2.66 mmol) and 2-(trifluoromethyl)pyrrolidine (1 g, 7.19 mmol) were heated in a sealed tube at 173° C. for 16 h. After cooling to room temperature, water (100 mL) was added. The aqueous layer was extracted with ethyl acetate (2×100 mL). Combined organic layers were dried, concentrated and product was purified by column chromatography to afford ethyl 6-(2-(trifluoromethyl)pyrrolidin-1-yl)imidazo[1,2-b]pyridazine-3-carboxylate (270 mg, 30%). MS (ESI) calcd for $C_{14}H_{15}F_3N_4O_2$ (m/z): 328.1.

Step 2: Synthesis of 6-(2-(trifluoromethyl)pyrrolidin-1-yl)imidazo[1,2-h]pyridazine-3-carboxylic acid

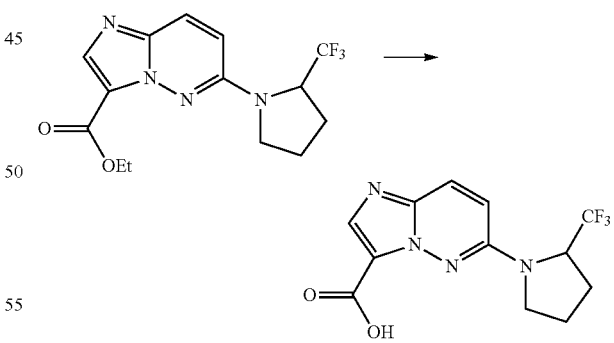

6-(2-(trifluoromethyl)pyrrolidin-1-yl)imidazo[1,2-b]pyridazine-3-carboxylic acid was prepared using the same procedure that was used to make (S)-6-(3-fluoropyrrolidin-1-yl)imidazo[1,2-b]pyridazine-3-carboxylic acid described above. (yield 85%) MS (ESI) calcd for $C_{12}H_{11}F_3N_4O_2$ (m/z): 300.08.

This general procedure, followed by standard ester hydrolysis could also be used to prepare (S)-6-(2-methylpyrrolidin-1-yl)imidazo[1,2-b]pyridazine-3-carboxylic acid.

Step 3: Synthesis of N-(pyridin-3-yl)-6-(2-(trifluoromethyl)pyrrolidin-1-yl)imidazo[1,2-b]pyridazine-3-carboxamide (Compound 966)

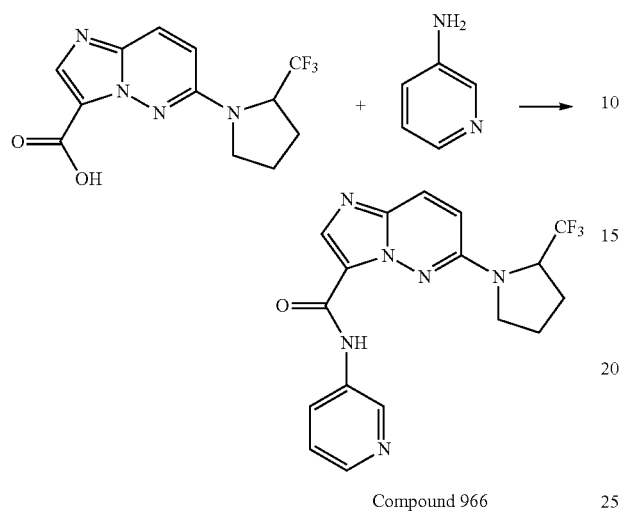

Compound 966

N-(pyridin-3-yl)-6-(2-(trifluoromethyl)pyrrolidin-1-yl)imidazo[1,2-b]pyridazine-3-carboxamide was prepared using the same procedure that was used to make (S)-6-(3-fluoropyrrolidin-1-yl)-N-(6-morpholinopyridin-2-yl)imidazo[1,2-b]pyridazine-3-carboxamide described above (yield 89%). MS (ESI) calcd for $C_{17}H_{15}F_3N_6O$ (m/z): 376.1. found 377.1 [M+H].

This general procedure could be used to prepare a variety of N-(substituted)-6-(2-(trifluoromethyl)pyrrolidin-1-yl)imidazo[1,2-b]pyridazine-3-carboxamide by substituting the appropriate amine for 3-amino pyridine.

Example 157. Preparation of N-(pyrimidin-4-yl)-6-(2-(trifluoromethyl)pyrrolidin-1-yl)imidazo[1,2-b]pyridazine-3-carboxamide (Compound 970)

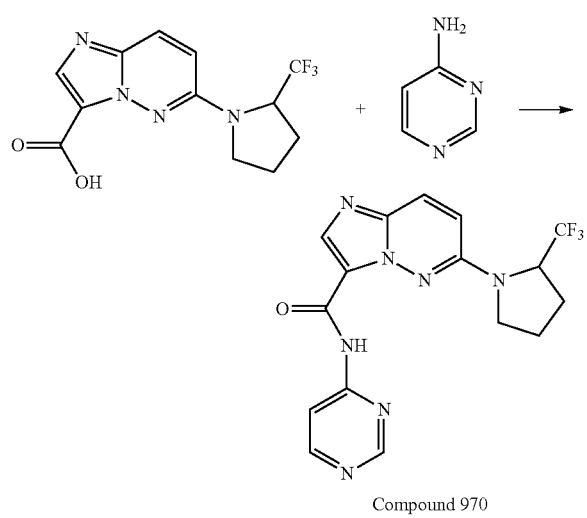

Compound 970

Carboxydiimidazole (33 mg, 0.2 mmol) was taken in a pressure tube and dissolved in dioxane (1 mL). A solution of 6-(2-(trifluoromethyl)pyrrolidin-1-yl)imidazo[1,2-b]pyridazine-3-carboxylic acid (50 mg, 0.167 mmol) in DMA (1 mL) was added and heated to 100° C. for 15 h. After cooling to room temperature 2-aminopyrimidine (48 mg, 0.501 mmol) was added. Heating was continued at 100° C. for 2 d. After cooling back to room temperature, water (20 mL) was added upon which a solid separated. The solid was separated by filtration, taken up in MeOH heated and filtered again to afford N-(pyrimidin-4-yl)-6-(2-(trifluoromethyl)pyrrolidin-1-yl)imidazo[1,2-b]pyridazine-3-carboxamide (29 mg, 46%). MS (ESI) calcd for $C_{16}H_{14}F_3N_7O$ (m/z): 377.1. found 378.1 [M+H].

Example 158. Preparation of N-(pyridin-3-yl)-5-(2-(trifluoromethyl)piperidin-1-yl)pyrazolo[1,5-a]pyrimidine-3-carboxamide (Compound 945)

Step 1) Synthesis of ethyl 5-(2-(trifluoromethyl)piperidin-1-yl)pyrazolo[1,5-a]pyrimidine-3-carboxylate

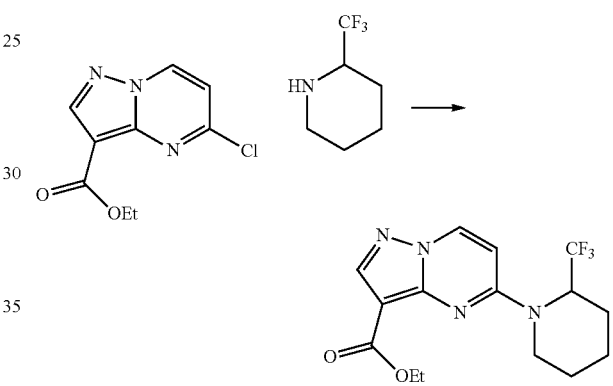

A suspension of ethyl 5-chloropyrazolo[1,5-a]pyrimidine-3-carboxylate (600 mg, 2.66 mmol) in 2-(trifluoromethyl)piperidine (2.5 mL) was heated at 125° C. for 12 h in a sealed tube. After cooling to room temperature the crude residue was purified by MPLC eluting with pentane/EtOAc (20-100%) to give ethyl 5-(2-(trifluoromethyl)piperidin-1-yl)pyrazolo[1,5-a]pyrimidine-3-carboxylate (575 mg, 63% yield). MS (ESI) calcd for $C_{15}H_{17}F_3N_4O_2$ (m/z): 342.13.

Step 2) Synthesis of 5-(2-(trifluoromethyl)piperidin-1-yl)pyrazolo[1,5-a]pyrimidine-3-carboxylic acid

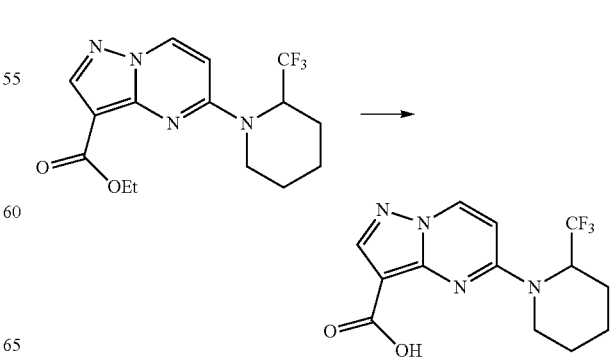

A solution of LiOH (81 mg, 3.36 mmol) in H₂O (1.5 mL) was added to a solution of ethyl 5-(2-(trifluoromethyl)piperidin-1-yl)pyrazolo[1,5-a]pyrimidine-3-carboxylate carboxylate (575 mg, 1.68 mmol) and LiOH (81 mg, 3.36 mmol) in THF/MeOH (9.5 mL, 1:1) was stirred at nom temperature for 12 h. H₂O (3 mL) was added and the mixture was heated at 65° C. for 3 h. The mixture was concentrated, H₂O added and the pH was adjusted to 2. The mixture was extracted with CH₂Cl₂, dried (MgSO₄) and concentrated. The crude product was recrystallized from heptane/EtOAc to give 5-(2-(trifluoromethyl)piperidin-1-yl)pyrazolo[1,5-a]pyrimidine-3-carboxylic acid. (429 mg, 81% yield). MS (ESI) calcd for C₁₃H₁₃F₃N₄O₂ (m/z): 314.10.

Step 3) Synthesis of N-(pyridin-3-yl)-5-(2-(trifluoromethyl)piperidin-1-yl)pyrazolo[1,5-a]pyrimidine-3-carboxamide (Compound 945)

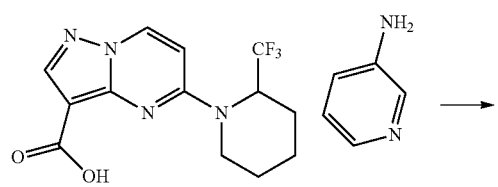

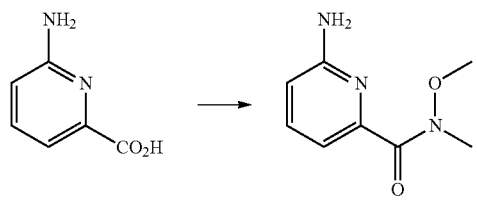

Compound 945

A mixture of 5-(2-(trifluoromethyl)piperidin-1-yl)pyrazolo[1,5-a]pyrimidine-3-carboxylic acid (50 mg, 0.16 mmol), 3-amino pyridine (30 mg, 0.32 mmol), pyridine (40 µL mg, 0.48 mmol), and HATU (73 mg, 0.19 mmol) in CH₃CN (10 mL) was heated at reflux for 16 h. The mixture was poured into brine, extracted with CH₂Cl₂, dried (MgSO₄) and concentrated. The crude product was purified on MPLC eluting with CH₂Cl₂/MeOH (0-5%) then recrystallized from heptane/EtOAc to give N-(pyridin-3-yl)-5-(2-(trifluoromethyl)piperidin-1-yl)pyrazolo[1,5-a]pyrimidine-3-carboxamide. (48 mg, 77% yield). MS (ESI) calcd for C₁₈H₁₇F₃N₆O (m/z): 390.14. found: 391.1 [M+H].

This general procedure could be used to prepare a variety of N-(substituted)-5-(2-(trifluoromethyl)piperidin-1-yl)pyrazolo[1,5-a]pyrimidine-3-carboxamide by substituting the appropriate amine for 3-amino pyridine.

Example 159. Preparation of (S)-N-(4,5-dimethylthiazol-2-yl)-5-(2-(trifluoromethyl)pyrrolidin-1-yl)pyrazolo[1,5-a]pyrimidine-3-carboxamide (Compound 1032)

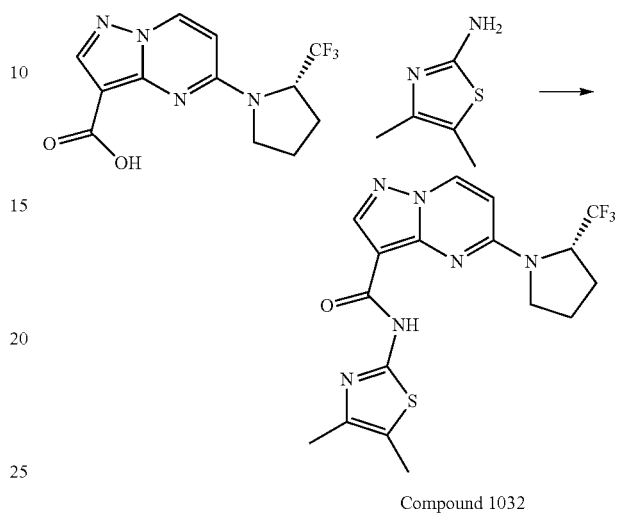

Compound 1032

A mixture of (S)-5-(2-(trifluoromethyl)pyrrolidin-1-yl)pyrazolo[1,5-a]pyrimidine-3-carboxylic acid (80 mg, 0.27 mmol), HATU (203 mg, 0.53 mmol) and DIEA (0.2 mL) in CH₂Cl₂ (15 mL) was stirred at room temperature for 0.5 h. The mixture was concentrated to dryness under reduced pressure at room temperature and used directly in the next step. In another flask, 4,5-dimethylthiazol-2-amine (88 mg, 0.53 mmol) was treated with NaH (>2 eq) in dry THF for 15 min, the crude activated ester from above was added. Stirring was continued for another 1 h, ice-water was added carefully, then extracted with CH₂Cl₂. The combined organic phase was dried (Na₂SO₄) and concentrated. The crude product was purified by prep-TLC(CH₂Cl₂/MeOH, 25:1) to give (S)-N-(4,5-dimethylthiazol-2-yl)-5-(2-(trifluoromethyl)pyrrolidin-1-yl)pyrazolo[1,5-a]pyrimidine-3-carboxamide (28 mg, 23% yield). MS (ESI) calcd for C₁₇H₁₇F₃N₆OS (m/z): 410.11. found: 411.0 [M+H].

This general procedure could be used to prepare a variety of N-(substituted)-5-(2-(trifluoromethyl)pyrrolidin-1-yl)pyrazolo[1,5-a]pyrimidine-3-carboxamides by substituting the appropriate amine for 4,5-dimethylthiazol-2-amine.

Example 160. Preparation of 6-(oxazol-5-yl)pyridin-2-amine

Step 1: Synthesis of 6-amino-N-methoxy-N-methylpicolinamide

To a slurry of 6-aminopicolinic acid (10.0 g, 72.5 mmol) in acetonitrile (150 mL) was added N,O-dimethylhydroxylamine hydrochloride (8.52 g, 87.0 mmol), 1-hydroxybenzotriazole (11.8 g, 87.0 mmol), N-(3-dimethylamino)-N'-ethylcarbodiimide hydrochloride (16.7 g, 87.0 mmol), and N,N-diisopropylethylamine (37.7 mL, 217 mmol). The mixture was stirred at room temperature overnight, and the solvent removed in vacuo. The residue was partitioned between 1N NaOH and ethyl acetate, and the aqueous layer was extracted three times with ethyl acetate. The combined organic layers were washed with brine, dried with sodium sulfate, and the solvent removed in vacuo. The remaining residue was purified by flash chromatography (ethyl acetate with 0.1% triethylamine) to give 6-amino-N-methoxy-N-methylpicolinamide (4.30 g, 23.7 mmol, 33% yield). MS (ESI) calcd for $C_8H_7N_3O$: 181.1

Step 2: Synthesis of 6-(oxazol-5-yl)pyridin-2-amine

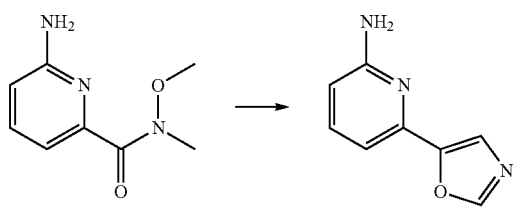

Lithium aluminum hydride (1.08 g, 28.5 mmol) was added to a solution of 6-amino-N-methoxy-N-methylpicolinamide (4.30 g, 23.7 mmol) in THF (30 mL). The reaction was stirred at room temperature for 90 min. Ethyl acetate (30 mL) was added slowly, the reaction was filtered, and the filtrate taken and all the solvent removed in vacuo to give 6-aminopicolinaldehyde, which was taken on crude to the next step. To a solution of the above aldehyde in methanol (20 mL) was added p-toluenesulfonylmethyl isocyanide (13.9 g, 71.2 mmol) and potassium carbonate (19.4 g, 140 mmol). The reaction was stirred at reflux for 2 h, then all solvent removed in vacuo. The residue was partitioned between ethyl acetate (150 mL) and water (70 mL). The organic layer was washed with brine, dried with sodium sulfate, and the solvent removed in vacuo. The remaining residue was purified by flash chromatography (10% methanol in dichloromethane) to give 6-(oxazol-5-yl)pyridin-2-amine (2.00 g, 12.4 mmol, 52% yield over two steps). MS (ESI) calcd for $C_8H_{11}N_3O_2$: 161.06

4-(oxazol-5-yl)pyridin-2-amine

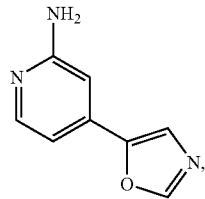 [SMILES: Nc1cc(-c2cnco2)ccn1]

was prepared according to the same procedure provided above,

Example 160. Biological Activity

Mass spectrometry based assays were used to identify modulators of SIRT1 activity. The TAMRA based assay utilized a peptide having 20 amino acid residues as follows: Ac-EE-K(biotin)-GQSTSSHSK(Ac)NleSTEG-K(5TMR)-EE-NH$_2$ (SEQ ID NO: 1), wherein K(Ac) is an acetylated lysine residue and Nle is a norleucine. The peptide was labeled with the fluorophore 5TMR (excitation 540 nm/emission 580 nm) at the C-terminus. The sequence of the peptide substrate was based on p53 with several modifications. In addition, the methionine residue naturally present in the sequence was replaced with the norleucine because the methionine may be susceptible to oxidation during synthesis and purification. The Trp based assay utilized a peptide having an amino acid residues as follows: Ac-R-H-K-K(Ac)-W-NH2 (SEQ ID NO: 2).

The TAMRA based mass spectrometry assay was conducted as follows: 0.5 μM peptide substrate and 120 μM βNAD$^+$ was incubated with 10 nM SIRT1 for 25 minutes at 25° C. in a reaction buffer (50 mM Tris-acetate pH 8, 137 mM NaCl, 2.7 mM KCl, 1 mM MgCl$_2$, 5 mM DTT, 0.05% BSA). The SIRT1 protein was obtained by cloning the SirT1 gene into a T7-promoter containing vector, which was then transformed and expressed in BL21(DE3) bacterial cells. Test compound was added at varying concentrations to this reaction mixture and the resulting reactions were monitored. After the 25 minute incubation with SIRT1, 10 μL of 10% formic acid was added to stop the reaction. The resulting reactions were sealed and frozen for later mass spec analysis. Determination of the amount of deacetylated substrate peptide formed (or, alternatively, the amount of O-acetyl-ADP-ribose (OAADPR) generated) by the sirtuin-mediated NAD-dependent deacetylation reaction allowed for the precise measurement of relative SIRT1 activity in the presence of varying concentrations of the test compound versus control reactions lacking the test compound.

The Trp mass spectrometry assay was conducted as follows. 0.5 μM peptide substrate and 120 μM βNAD$^+$ were incubated with 10 nM SIRT1 for 25 minutes at 25° C. in a reaction buffer (50 mM HEPES pH 7.5, 1500 mM NaCl, 1 mM DTT, 0.05% BSA). The SIRT1 protein was obtained by cloning the SirT1 gene into a T7-promoter containing vector, which was then expressed in BL21(DE3) bacterial cells and purified as described in further detail below. Test compound was added at varying concentrations to this reaction mixture and the resulting reactions were monitored. After the 25 minute incubation with SIRT1, 10 μL of 10% formic acid was added to stop the reaction. The resulting reactions were sealed and frozen for later mass spec analysis. The relative SIRT1 activity was then determined by measuring the amount of O-acetyl-ADP-ribose (OAADPR) formed (or, alternatively, the amount of deacetylated Trp peptide generated) by the NAD-dependent sirtuin deacetylation reaction in the presence of varying concentrations of the test compound versus control reactions lacking the test compound. The degree to which the test agent activated deacetylation by SIRT1 was expressed as EC$_{1.5}$ (i.e., the concentration of compound required to increase SIRT1 activity by 50% over the control lacking test compound), and Percent Maximum Activation (i.e., the maximum activity relative to control (100%) obtained for the test compound).

A control for inhibition of sirtuin activity was conducted by adding 1 μL of 500 mM nicotinamide as a negative control at the start of the reaction (e.g., permits determination of maximum sirtuin inhibition). A control for activation of sirtuin activity was conducted using 10 nM of sirtuin protein, with 1 μL of DMSO in place of compound, to determine the amount of deacetylation of the substrate at a given time point within the linear range of the assay. This time point was the same as that used for test compounds and, within the linear range, the endpoint represents a change in velocity.

For the above assay, SIRT1 protein was expressed and purified as follows. The SirT1 gene was cloned into a T7-promoter containing vector and transformed into BL21 (DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl]phosphine (TCEP), 10 µM $ZnCl_2$, 200 mM NaCl) and further treated with sonication for 10 mM for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Tris-HCl, 2 mM TCEP) overnight. The protein was aliquoted and frozen at −80° C. until further use.

Sirtuin-modulating compounds of Formula (I) that activated SIRT1 were identified using the assay described above and are shown below in Table 1. The $EC_{1.5}$ values represent the concentration of test compounds that result in 150% activation of SIRT1. The $EC_{1.5}$ values for the activating compounds of Formula (I) are represented by A ($EC_{1.5}$<1 µM), B ($EC_{1.5}$ 1-25 µM), C ($EC_{1.5}$>25 µM). The percent maximum fold activation is represented by A (Fold activation ≥350%) or B (Fold Activation <350%). "NT" means not tested; "ND" means not determinable.

TABLE 1

Compounds of Formula (I).

| Compound No | [M + H]+$_{[Calc]}$ | Structure | TAMRA EC1.5 (µM) | TAMRA % Fold Act | Trp EC1.5 (µM) | Trp % Fold Act |
|---|---|---|---|---|---|---|
| 1 | 398 | 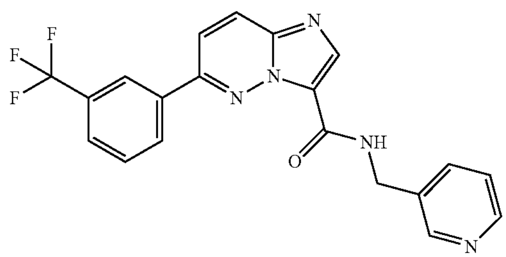 [SMILES: O=C(NCc1cccnc1)c1cnc2ccc(-c3cccc(C(F)(F)F)c3)nn12] | B | B | NT | NT |
| 2 | 384 | 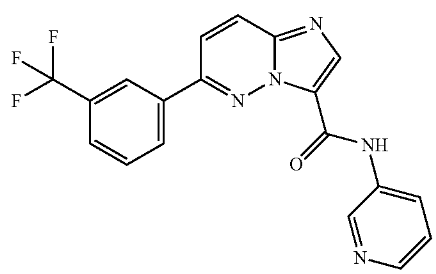 [SMILES: O=C(Nc1cccnc1)c1cnc2ccc(-c3cccc(C(F)(F)F)c3)nn12] | B | B | A | A |
| 3 | 390 | 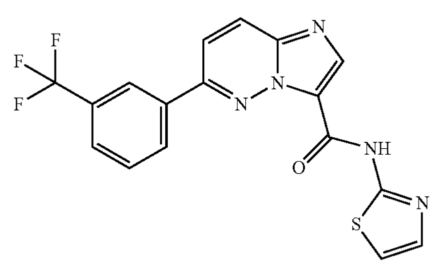 [SMILES: O=C(Nc1nccs1)c1cnc2ccc(-c3cccc(C(F)(F)F)c3)nn12] | B | B | NT | NT |
| 4 | 384 | 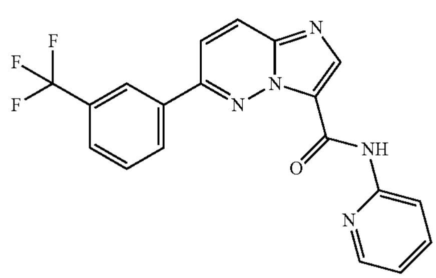 [SMILES: O=C(Nc1ccccn1)c1cnc2ccc(-c3cccc(C(F)(F)F)c3)nn12] | B | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 5 | 483 | 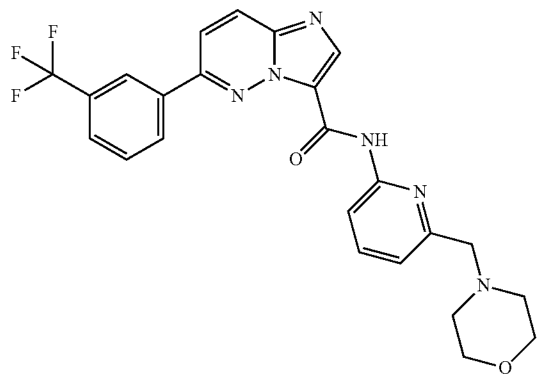 [SMILES: O=C(Nc1cccc(CN2CCOCC2)n1)c1cnc2ccc(-c3cccc(C(F)(F)F)c3)nn12] | A | A | B | B |
| 6 | 489 | 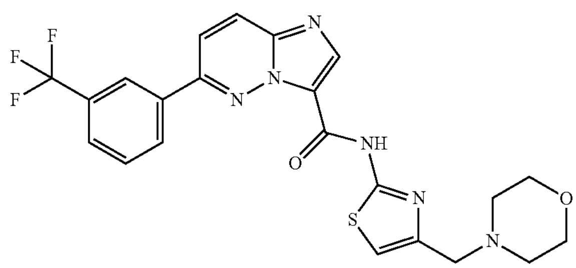 [SMILES: O=C(Nc1nc(CN2CCOCC2)cs1)c1cnc2ccc(-c3cccc(C(F)(F)F)c3)nn12] | A | A | NT | NT |
| 7 | 406 | 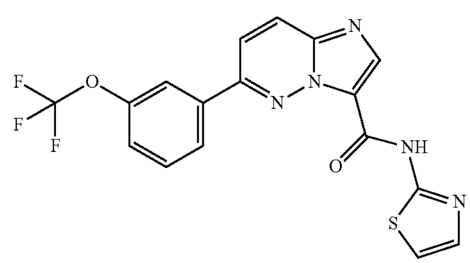 [SMILES: O=C(Nc1nccs1)c1cnc2ccc(-c3cccc(OC(F)(F)F)c3)nn12] | B | B | NT | NT |
| 8 | 400 | 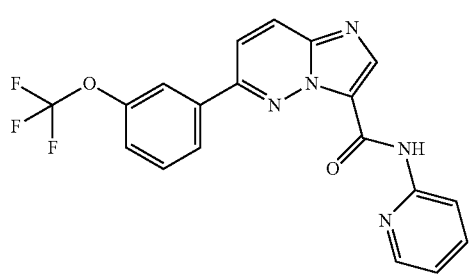 [SMILES: O=C(Nc1ccccn1)c1cnc2ccc(-c3cccc(OC(F)(F)F)c3)nn12] | B | B | B | B |
| 9 | 407 | 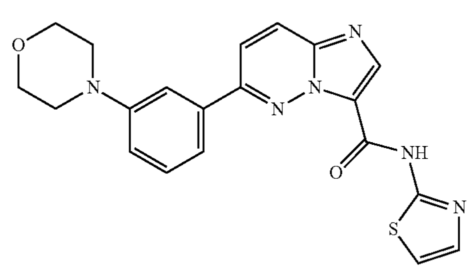 [SMILES: O=C(Nc1nccs1)c1cnc2ccc(-c3cccc(N4CCOCC4)c3)nn12] | C | B | NT | NT |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 10 | 401 | 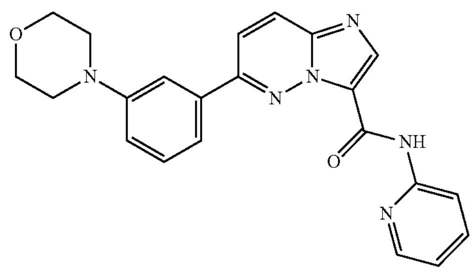 [SMILES: O=C(Nc1ccccn1)c1cnc2ccc(-c3cccc(N4CCOCC4)c3)nn12] | B | B | NT | NT |
| 11 | 400 | 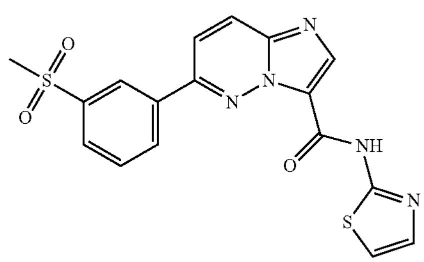 [SMILES: CS(=O)(=O)c1cccc(-c2ccc3ncc(C(=O)Nc4nccs4)n3n2)c1] | C | B | A | A |
| 12 | 394 | 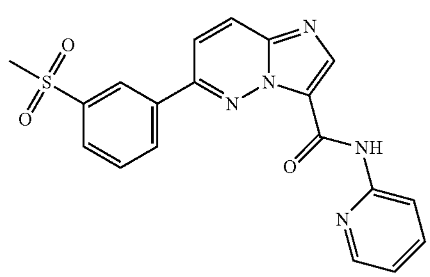 [SMILES: CS(=O)(=O)c1cccc(-c2ccc3ncc(C(=O)Nc4ccccn4)n3n2)c1] | C | B | NT | NT |
| 13 | 406 | 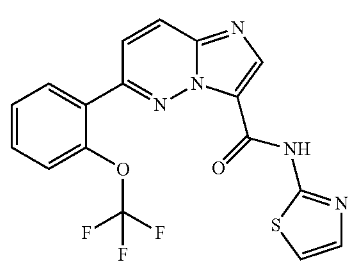 [SMILES: O=C(Nc1nccs1)c1cnc2ccc(-c3ccccc3OC(F)(F)F)nn12] | A | A | NT | NT |
| 14 | 400 | 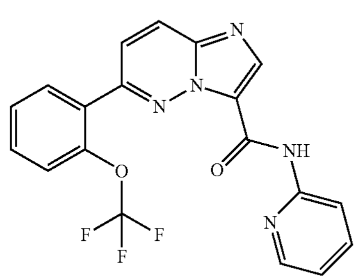 | A | A | B | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 15 | 390 | 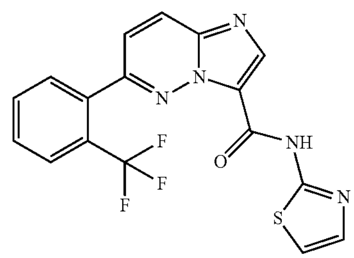 | B | A | NT | NT |
| 16 | 384 | 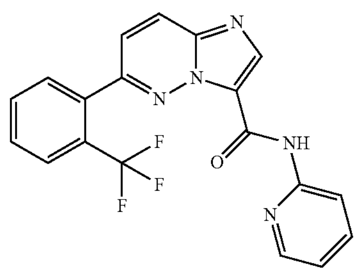 | A | A | NT | NT |
| 17 | 404 | 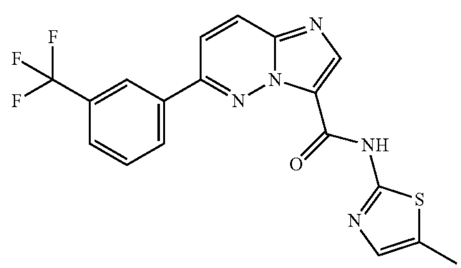 [SMILES: Cc1cnc(NC(=O)c2cnc3ccc(-c4cccc(C(F)(F)F)c4)nn23)s1] | B | B | B | B |
| 18 | 385 | 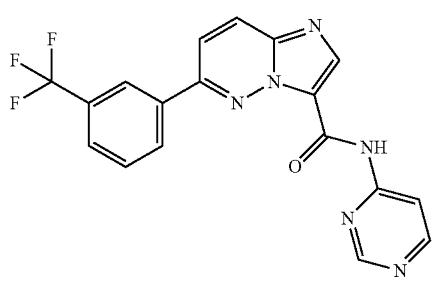 [SMILES: O=C(Nc1ccncn1)c1cnc2ccc(-c3cccc(C(F)(F)F)c3)nn12] | B | B | NT | NT |
| 19 | 483 | 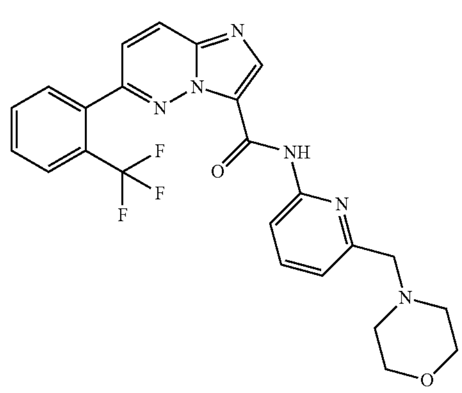 [SMILES: O=C(Nc1cccc(CN2CCOCC2)n1)c1cnc2ccc(-c3ccccc3C(F)(F)F)nn12] | A | A | NT | NT |

TABLE 1-continued

Compounds of Formula (I).

| Compound No | [M + H]+$_{[Calc]}$ | Structure | TAMRA | | Trp | |
|---|---|---|---|---|---|---|
| | | | EC1.5 (μM) | % Fold Act | EC1.5 (μM) | % Fold Act |
| 20 | 489 | | A | A | B | B |
| 21 | 469 | | A | A | NT | NT |
| 22 | 453 | | A | A | NT | NT |
| 23 | 484 | | B | A | B | B |

TABLE 1-continued

Compounds of Formula (I).

| Compound No | [M + H]+$_{[Calc]}$ | Structure | TAMRA EC1.5 (µM) | TAMRA % Fold Act | Trp EC1.5 (µM) | Trp % Fold Act |
|---|---|---|---|---|---|---|
| 24 | 469 | 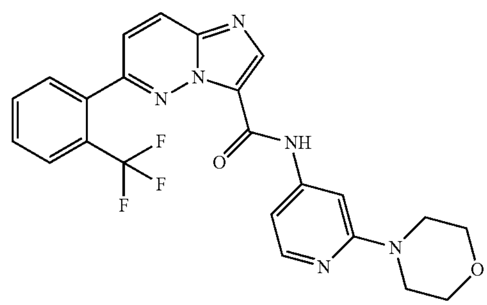 [SMILES: O=C(Nc1ccnc(N2CCOCC2)c1)c1cnc2ccc(-c3ccccc3C(F)(F)F)nn12] | B | A | NT | NT |
| 25 | 453 | 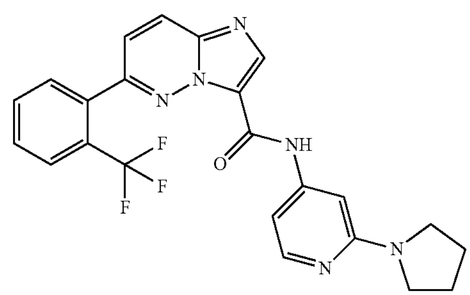 [SMILES: O=C(Nc1ccnc(N2CCCC2)c1)c1cnc2ccc(-c3ccccc3C(F)(F)F)nn12] | A | A | A | A |
| 26 | 449 | 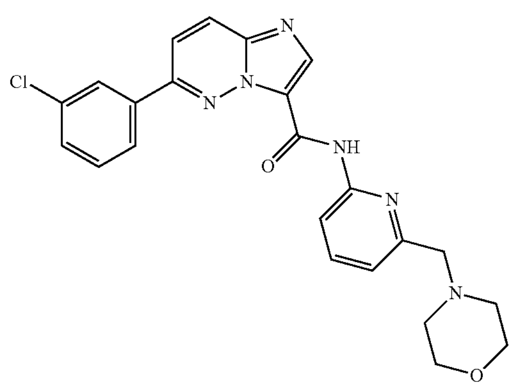 [SMILES: O=C(Nc1cccc(CN2CCOCC2)n1)c1cnc2ccc(-c3cccc(Cl)c3)nn12] | A | A | C | B |
| 27 | 455 | 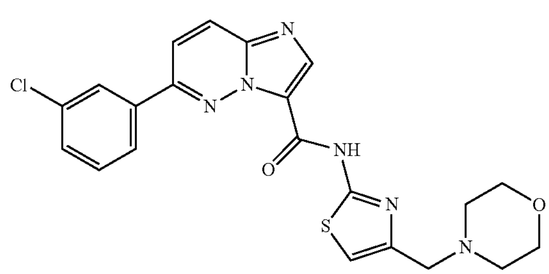 [SMILES: O=C(Nc1nc(CN2CCOCC2)cs1)c1cnc2ccc(-c3cccc(Cl)c3)nn12] | A | A | NT | NT |

TABLE 1-continued

Compounds of Formula (I).

| Compound No | [M + H]+$_{[Calc]}$ | Structure | TAMRA | | Trp | |
|---|---|---|---|---|---|---|
| | | | EC1.5 (μM) | % Fold Act | EC1.5 (μM) | % Fold Act |
| 28 | 433 | | A | B | NT | NT |
| 29 | 439 | | B | B | B | B |
| 30 | 451 | | B | B | NT | NT |
| 31 | 457 | | B | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 32 | 366 | 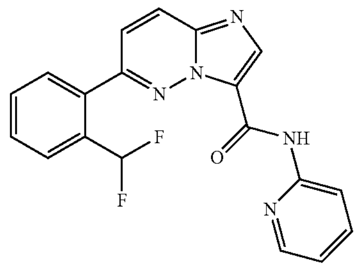 [SMILES: O=C(Nc1ccccn1)c1cnc2ccc(-c3ccccc3C(F)F)nn12] | B | B | B | B |
| 33 | 372 | 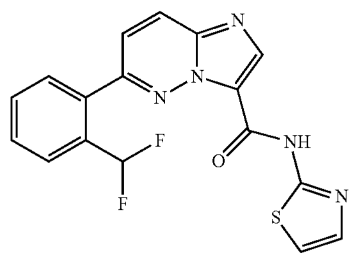 [SMILES: O=C(Nc1nccs1)c1cnc2ccc(-c3ccccc3C(F)F)nn12] | B | B | NT | NT |
| 34 | 465 | 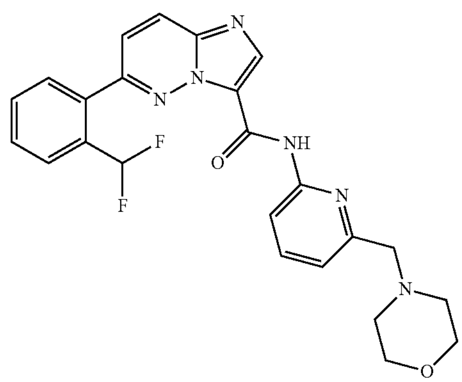 [SMILES: O=C(Nc1cccc(CN2CCOCC2)n1)c1cnc2ccc(-c3ccccc3C(F)F)nn12] | A | A | B | B |
| 35 | 471 | 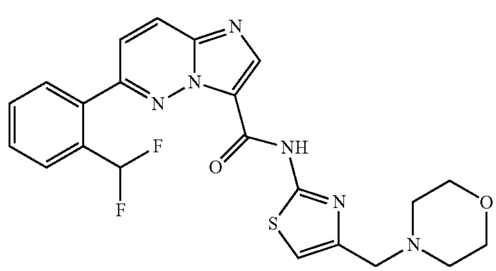 [SMILES: O=C(Nc1nc(CN2CCOCC2)cs1)c1cnc2ccc(-c3ccccc3C(F)F)nn12] | B | B | C | B |
| 36 | 451 | 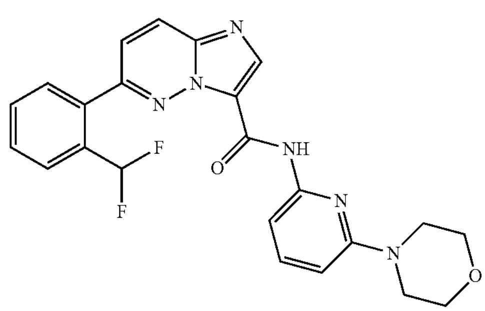 [SMILES: O=C(Nc1cccc(N2CCOCC2)n1)c1cnc2ccc(-c3ccccc3C(F)F)nn12] | A | A | NT | NT |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 37 | 435 | 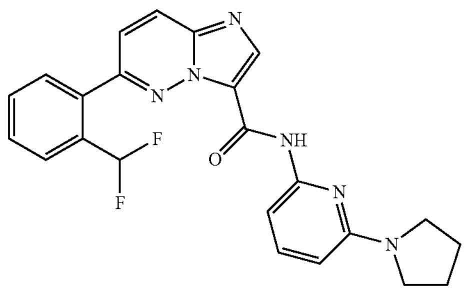 [SMILES: O=C(Nc1cccc(N2CCCC2)n1)c1cnc2ccc(-c3ccccc3C(F)F)nn12] | A | A | NT | NT |
| 38 | 466 | 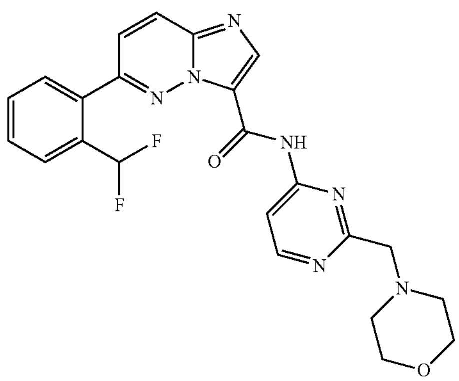 [SMILES: O=C(Nc1ccnc(CN2CCOCC2)n1)c1cnc2ccc(-c3ccccc3C(F)F)nn12] | B | B | C | B |
| 39 | 451 | 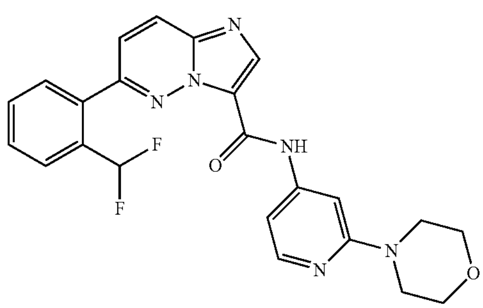 [SMILES: O=C(Nc1ccnc(N2CCOCC2)c1)c1cnc2ccc(-c3ccccc3C(F)F)nn12] | A | A | NT | NT |
| 40 | 435 | 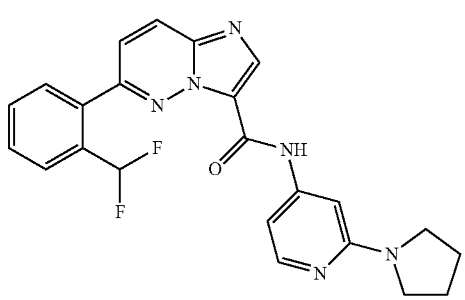 [SMILES: O=C(Nc1ccnc(N2CCCC2)c1)c1cnc2ccc(-c3ccccc3C(F)F)nn12] | A | A | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 41 | 451 | 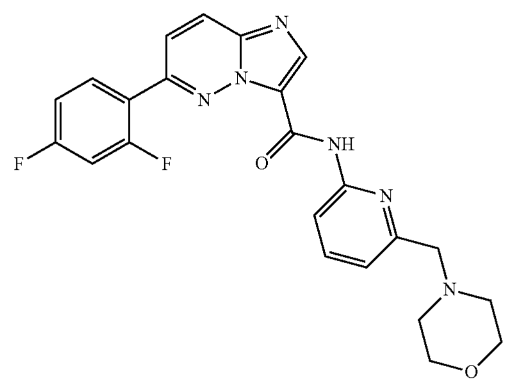 [SMILES: O=C(Nc1cccc(CN2CCOCC2)n1)c1cnc2ccc(-c3ccc(F)cc3F)nn12] | B | B | C | B |
| 42 | 457 | 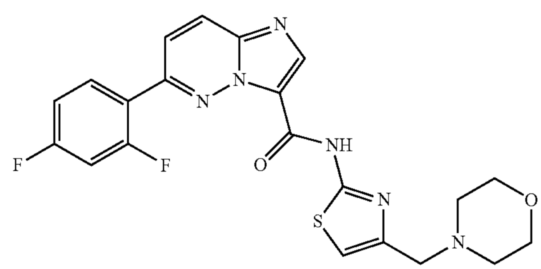 [SMILES: O=C(Nc1nc(CN2CCOCC2)cs1)c1cnc2ccc(-c3ccc(F)cc3F)nn12] | B | B | NT | NT |
| 43 | 451 | 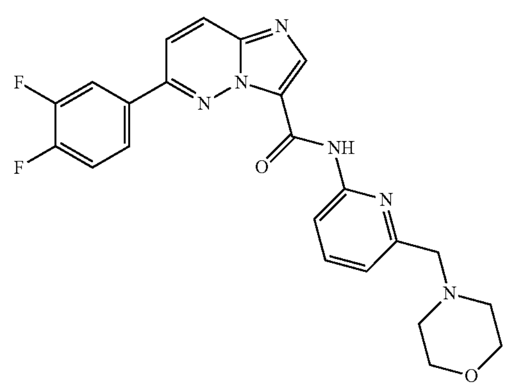 [SMILES: O=C(Nc1cccc(CN2CCOCC2)n1)c1cnc2ccc(-c3ccc(F)c(F)c3)nn12] | B | B | C | B |
| 44 | 457 | 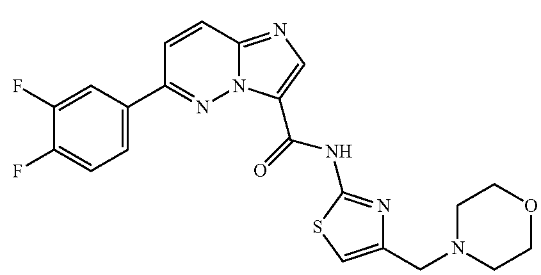 [SMILES: O=C(Nc1nc(CN2CCOCC2)cs1)c1cnc2ccc(-c3ccc(F)c(F)c3)nn12] | B | B | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 45 | 451 | | B | B | NT | NT |
| 46 | 457 | | B | B | NT | NT |
| 47 | 451 | | A | A | C | B |
| 48 | 457 | | B | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 49 | 439 | 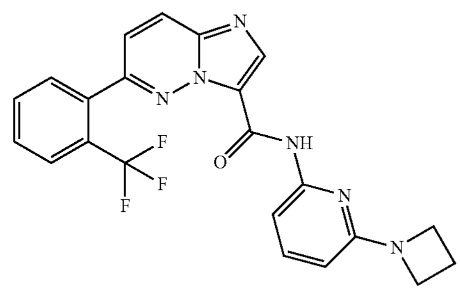 [SMILES: O=C(Nc1cccc(N2CCC2)n1)c1cnc2ccc(-c3ccccc3C(F)(F)F)nn12] | A | A | NT | NT |
| 50 | 439 | 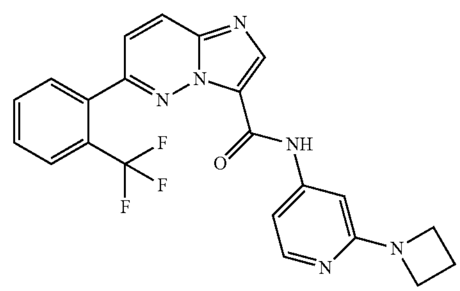 [SMILES: O=C(Nc1ccnc(N2CCC2)c1)c1cnc2ccc(-c3ccccc3C(F)(F)F)nn12] | A | A | A | A |
| 51 | 421 | 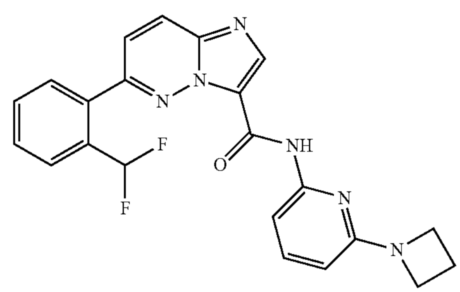 [SMILES: O=C(Nc1cccc(N2CCC2)n1)c1cnc2ccc(-c3ccccc3C(F)F)nn12] | A | A | B | A |
| 52 | 421 | 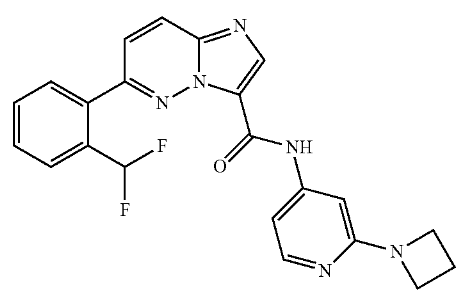 [SMILES: O=C(Nc1ccnc(N2CCC2)c1)c1cnc2ccc(-c3ccccc3C(F)F)nn12] | A | A | NT | NT |
| 53 | 420 | 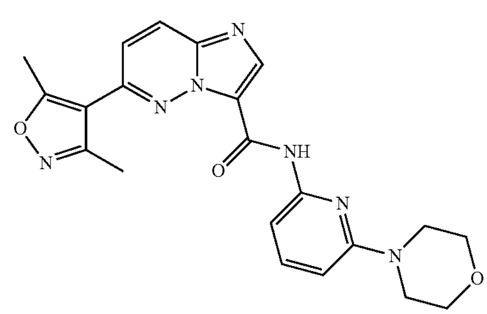 [SMILES: Cc1noc(C)c1-c1ccc2ncc(C(=O)Nc3cccc(N4CCOCC4)n3)n2n1] | B | B | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 54 | 404 | | C | B | NT | NT |
| 55 | 390 | | C | B | NT | NT |
| 56 | 405 | | B | B | B | B |
| 57 | 389 | | C | B | NT | NT |
| 58 | 416 | | B | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 59 | 400 | 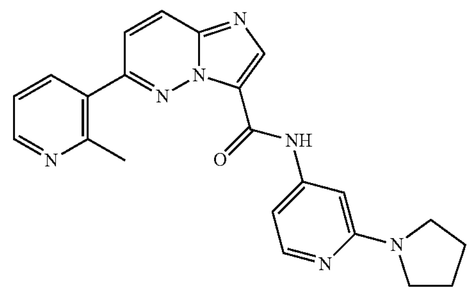 [SMILES: Cc1ncccc1-c1ccc2ncc(C(=O)Nc3ccnc(N4CCCC4)c3)n2n1] | B | B | C | B |
| 60 | 452 | 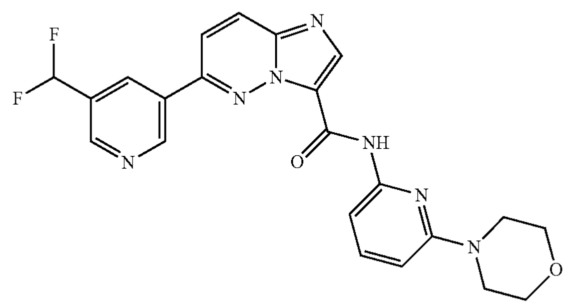 [SMILES: O=C(Nc1cccc(N2CCOCC2)n1)c1cnc2ccc(-c3cncc(C(F)F)c3)nn12] | A | B | NT | NT |
| 61 | 436 | 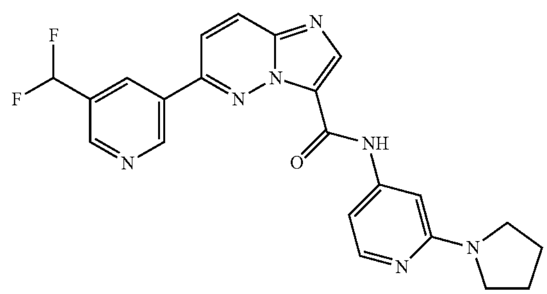 [SMILES: O=C(Nc1ccnc(N2CCCC2)c1)c1cnc2ccc(-c3cncc(C(F)F)c3)nn12] | B | B | NT | NT |
| 62 | 422 | 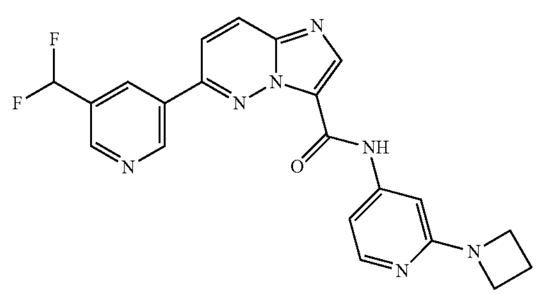 [SMILES: O=C(Nc1ccnc(N2CCC2)c1)c1cnc2ccc(-c3cncc(C(F)F)c3)nn12] | B | B | C | B |
| 63 | 386 | 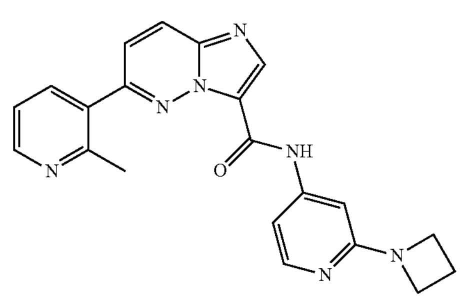 [SMILES: Cc1ncccc1-c1ccc2ncc(C(=O)Nc3ccnc(N4CCC4)c3)n2n1] | C | B | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 64 | 408 | | NT | NT | NT | NT |
| 65 | 436 | | A | B | ND | ND |
| 66 | 454 | | A | A | NT | NT |
| 67 | 470 | | A | A | NT | NT |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 68 | 452 | 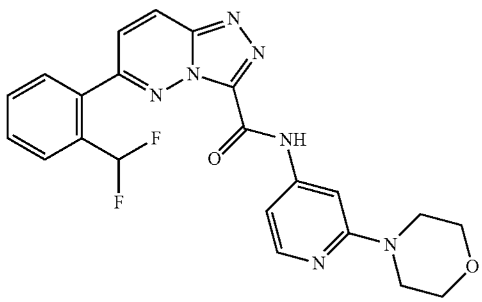 [SMILES: O=C(Nc1ccnc(N2CCOCC2)c1)c1nnc2ccc(-c3ccccc3C(F)F)nn12] | B | B | B | B |
| 69 | 453 | 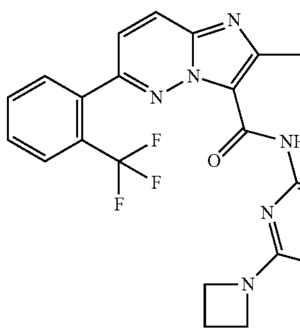 | A | A | B | A |
| 70 | 467 | 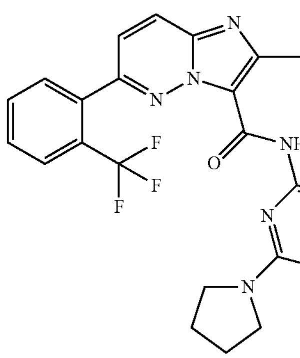 | A | A | NT | NT |
| 71 | 483 | 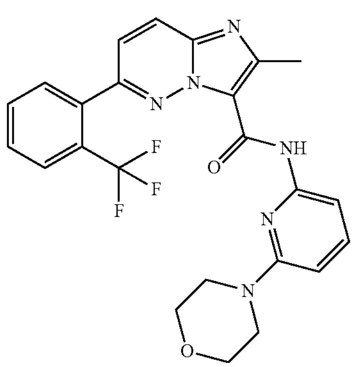 [SMILES: Cc1nc2ccc(-c3ccccc3C(F)(F)F)nn2c1C(=O)Nc1cccc(N2CCOCC2)n1] | A | A | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 72 | 465 | | A | A | NT | NT |
| 73 | 440 | | A | B | NT | NT |
| 74 | 475 | | A | A | A | A |
| 75 | 474 | | B | A | NT | NT |

TABLE 1-continued

Compounds of Formula (I).

| Compound No | [M + H]+$_{[Calc]}$ | Structure | TAMRA EC1.5 (µM) | % Fold Act | Trp EC1.5 (µM) | % Fold Act |
|---|---|---|---|---|---|---|
| 76 | 489 | | B | A | NT | NT |
| 77 | 384 | | B | A | B | B |
| 78 | 398 | | A | A | A | A |
| 79 | 385 | | B | A | NT | NT |
| 80 | 385 | | B | A | C | B |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 81 | 483 | | A | A | NT | NT |
| 82 | 469 | | A | A | NT | NT |
| 83 | 474 | | A | A | A | A |
| 84 | 385 | | B | A | B | A |
| 85 | 384 | | A | A | NT | NT |
| 86 | 384 | | C | B | C | B |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 87 | 384 | 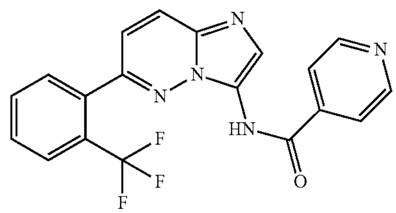 [SMILES: O=C(Nc1cnc2ccc(-c3ccccc3C(F)(F)F)nn12)c1ccncc1] | C | B | NT | NT |
| 88 | 385 | 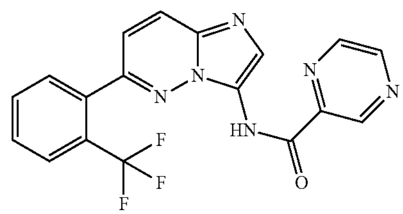 [SMILES: O=C(Nc1cnc2ccc(-c3ccccc3C(F)(F)F)nn12)c1cnccn1] | A | A | NT | NT |
| 89 | 474 | 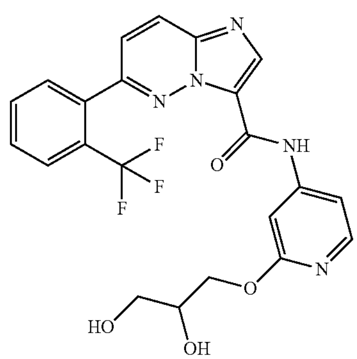 [SMILES: O=C(Nc1ccnc(OCC(O)CO)c1)c1cnc2ccc(-c3ccccc3C(F)(F)F)nn12] | A | A | ND | ND |
| 90 | 385 | 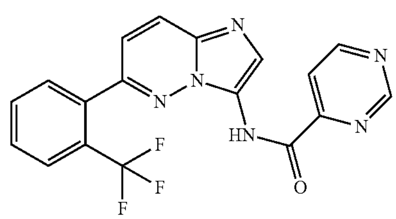 [SMILES: O=C(Nc1cnc2ccc(-c3ccccc3C(F)(F)F)nn12)c1ccncn1] | A | A | NT | NT |
| 91 | 387 | 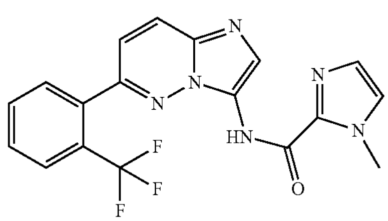 [SMILES: Cn1ccnc1C(=O)Nc1cnc2ccc(-c3ccccc3C(F)(F)F)nn12] | B | A | NT | NT |
| 92 | 387 | 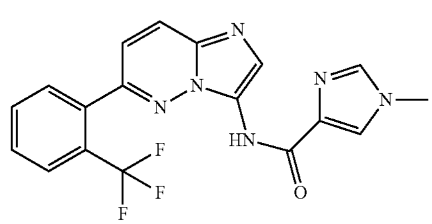 [SMILES: Cn1cnc(C(=O)Nc2cnc3ccc(-c4ccccc4C(F)(F)F)nn23)c1] | B | A | C | B |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 93 | 387 | 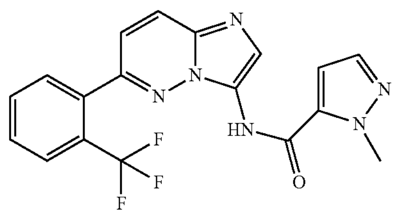 [SMILES: Cn1nccc1C(=O)Nc1cnc2ccc(-c3ccccc3C(F)(F)F)nn12] | C | B | C | B |
| 94 | 350 | 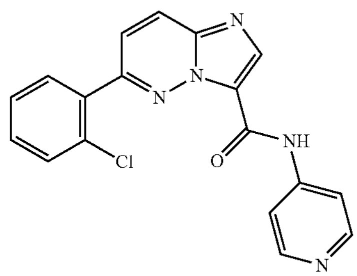 | B | B | NT | NT |
| 95 | 435 | 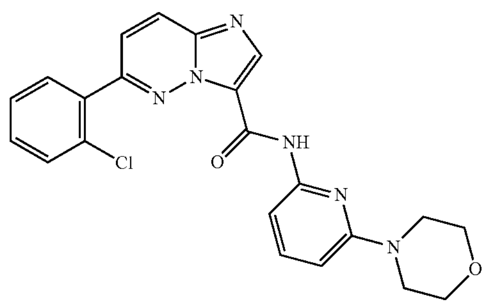 | A | A | A | B |
| 96 | 405 | 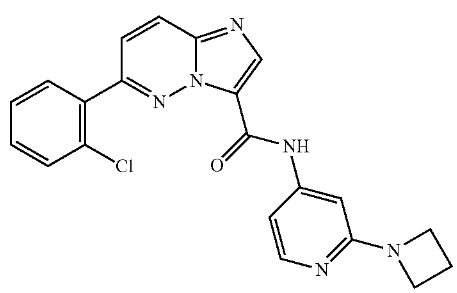 | A | A | NT | NT |
| 97 | 398 | 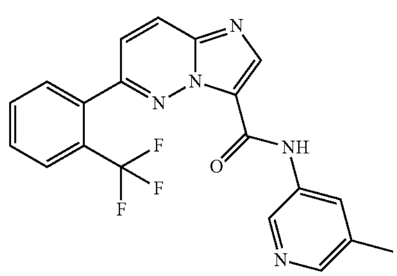 [SMILES: Cc1cncc(NC(=O)c2cnc3ccc(-c4ccccc4C(F)(F)F)nn23)c1] | B | A | NT | NT |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 98 | 398 | | B | A | B | A |
| 99 | 412 | | A | A | NT | NT |
| 100 | 402 | | A | A | NT | NT |
| 101 | 412 | | A | A | B | A |
| 102 | 398 | | A | A | B | A |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 103 | 414 | | A | A | NT | NT |
| 104 | 427 | | A | A | B | B |
| 105 | 385 | | NT | NT | NT | NT |
| 106 | 385 | | B | B | NT | NT |
| 107 | 402 | | B | A | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 108 | 384 | | B | B | NT | NT |
| 109 | 404 | | A | A | NT | NT |
| 110 | 402 | | A | A | B | B |
| 111 | 420 | | B | B | NT | NT |
| 112 | 387 | | B | A | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 113 | 398 | | B | B | B | B |
| 114 | 374 | | B | B | NT | NT |
| 115 | 387 | | C | B | NT | NT |
| 116 | 449 | | A | A | C | B |
| 117 | 350 | | B | B | NT | NT |

TABLE 1-continued
Compounds of Formula (I).
| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 118 | 350 | 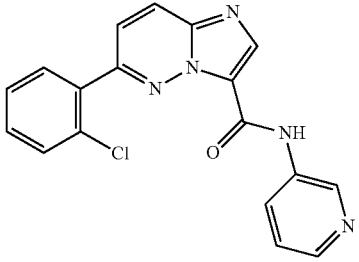 [SMILES: O=C(Nc1cccnc1)c1cnc2ccc(-c3ccccc3Cl)nn12] | B | B | NT | NT |
| 119 | 351 | 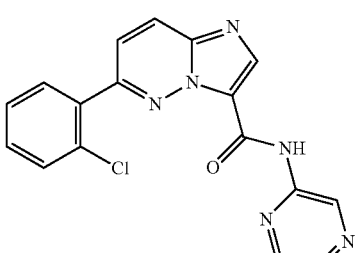 | B | B | C | B |
| 120 | 470 | 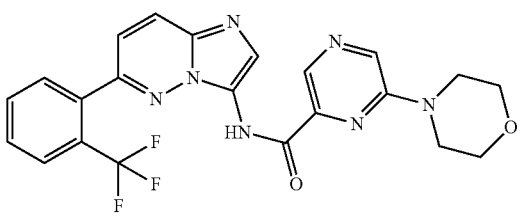 [SMILES: O=C(Nc1cnc2ccc(-c3ccccc3C(F)(F)F)nn12)c1cncc(N2CCOCC2)n1] | A | A | B | A |
| 121 | 385 | 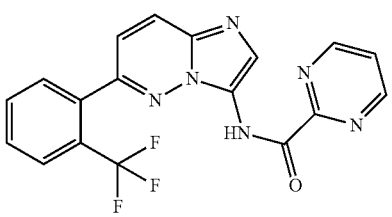 [SMILES: O=C(Nc1cnc2ccc(-c3ccccc3C(F)(F)F)nn12)c1ncccn1] | A | A | NT | NT |
| 122 | 390 | 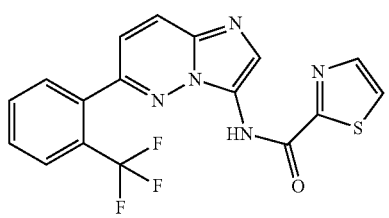 [SMILES: O=C(Nc1cnc2ccc(-c3ccccc3C(F)(F)F)nn12)c1nccs1] | A | A | B | B |
| 123 | 404 | 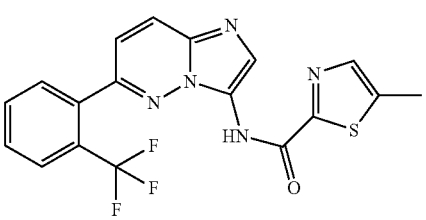 [SMILES: Cc1cnc(C(=O)Nc2cnc3ccc(-c4ccccc4C(F)(F)F)nn23)s1] | A | A | NT | NT |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 124 | 453 | 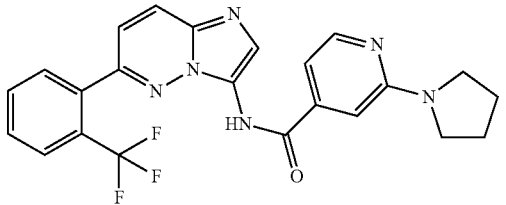 [SMILES: O=C(Nc1cnc2ccc(-c3ccccc3C(F)(F)F)nn12)c1ccnc(N2CCCC2)c1] | A | A | NT | NT |
| 125 | 412 | 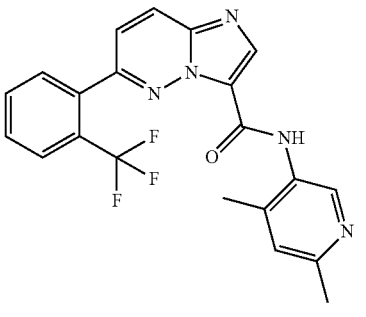 [SMILES: Cc1cc(C)c(NC(=O)c2cnc3ccc(-c4ccccc4C(F)(F)F)nn23)cn1] | B | B | B | B |
| 126 | 455 | 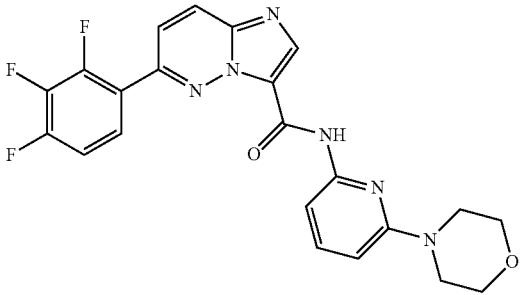 [SMILES: O=C(Nc1cccc(N2CCOCC2)n1)c1cnc2ccc(-c3ccc(F)c(F)c3F)nn12] | A | B | B | B |
| 127 | 469 | 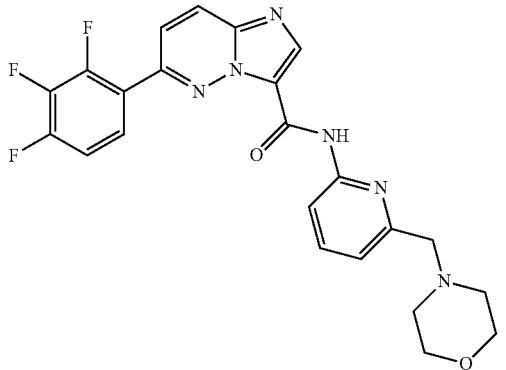 [SMILES: O=C(Nc1cccc(CN2CCOCC2)n1)c1cnc2ccc(-c3ccc(F)c(F)c3F)nn12] | B | B | NT | NT |
| 128 | 370 | 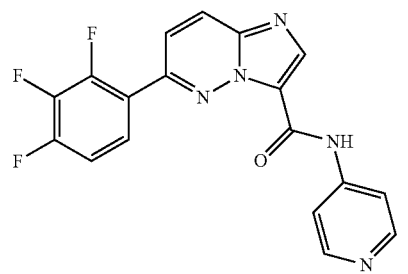 [SMILES: O=C(Nc1ccncc1)c1cnc2ccc(-c3ccc(F)c(F)c3F)nn12] | C | B | C | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 129 | 370 | 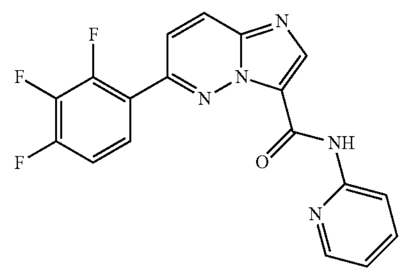 [SMILES: O=C(Nc1ccccn1)c1cnc2ccc(-c3ccc(F)c(F)c3F)nn12] | C | B | NT | NT |
| 130 | 371 | 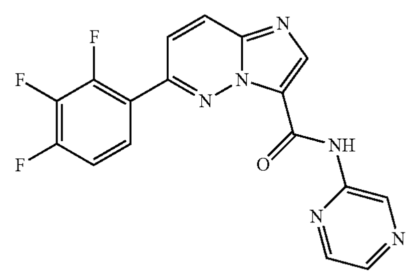 [SMILES: O=C(Nc1cnccn1)c1cnc2ccc(-c3ccc(F)c(F)c3F)nn12] | NT | NT | NT | NT |
| 131 | 370 | 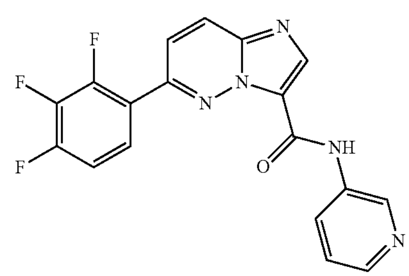 [SMILES: O=C(Nc1cccnc1)c1cnc2ccc(-c3ccc(F)c(F)c3F)nn12] | C | B | C | B |
| 132 | 425 | 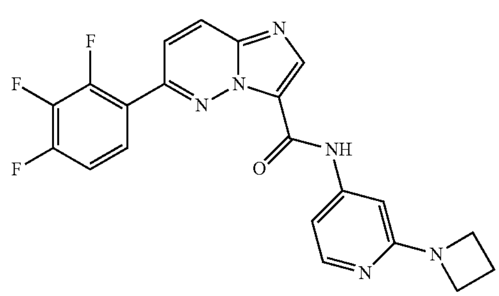 [SMILES: O=C(Nc1ccnc(N2CCC2)c1)c1cnc2ccc(-c3ccc(F)c(F)c3F)nn12] | C | B | NT | NT |
| 133 | 419 | 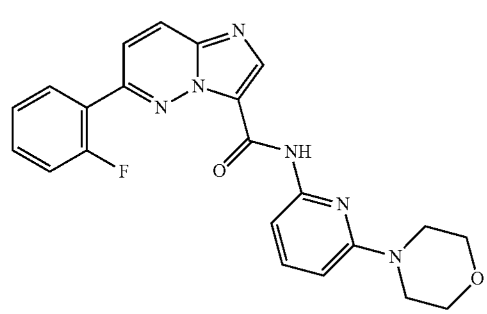 [SMILES: O=C(Nc1cccc(N2CCOCC2)n1)c1cnc2ccc(-c3ccccc3F)nn12] | A | A | A | B |

TABLE 1-continued

Compounds of Formula (I).

| Compound No | [M + H]+<sub>[Calc]</sub> | Structure | TAMRA EC1.5 (μM) | % Fold Act | Trp EC1.5 (μM) | % Fold Act |
|---|---|---|---|---|---|---|
| 134 | 389 | | A | A | C | B |
| 135 | 433 | | A | A | NT | NT |
| 136 | 334 | | B | B | NT | NT |
| 137 | 334 | | B | B | ND | ND |
| 138 | 334 | | B | B | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 139 | 335 | | B | B | NT | NT |
| 140 | 467 | | A | A | B | B |
| 141 | 368 | | C | B | C | B |
| 142 | 368 | | B | B | NT | NT |

TABLE 1-continued
Compounds of Formula (I).
| Compound No | [M + H]+_[Calc] | Structure | TAMRA EC1.5 (μM) | TAMRA % Fold Act | Trp EC1.5 (μM) | Trp % Fold Act |
|---|---|---|---|---|---|---|
| 143 | 368 | 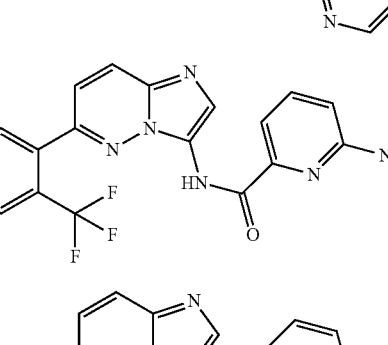 | C | B | A | B |
| 144 | 439 | 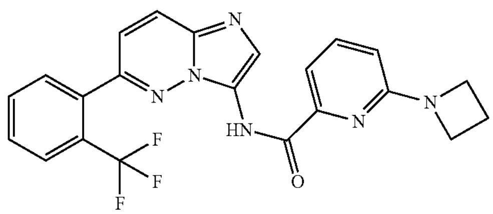 [SMILES: O=C(Nc1cnc2ccc(-c3ccccc3C(F)(F)F)nn12)c1cccc(N2CCC2)n1] | A | A | NT | NT |
| 145 | 467 | 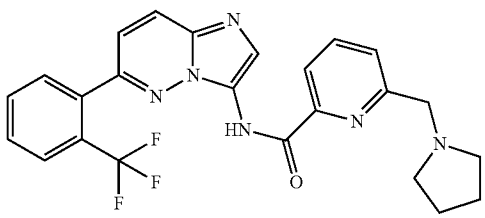 [SMILES: O=C(Nc1cnc2ccc(-c3ccccc3C(F)(F)F)nn12)c1cccc(CN2CCCC2)n1] | A | A | NT | NT |
| 146 | 474 | 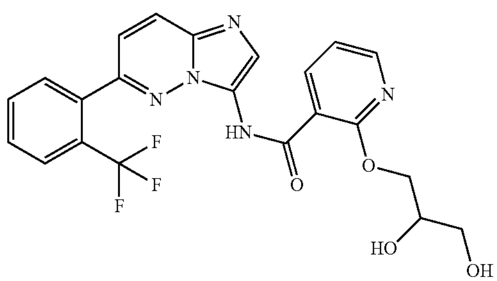 [SMILES: O=C(Nc1cnc2ccc(-c3ccccc3C(F)(F)F)nn12)c1cccnc1OCC(O)CO] | A | A | B | A |
| 147 | 483 | 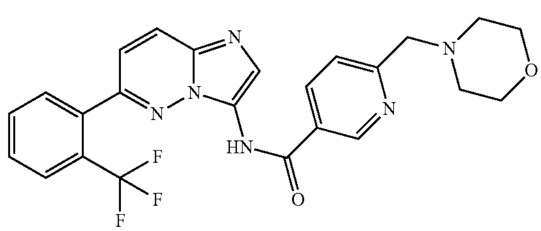 [SMILES: O=C(Nc1cnc2ccc(-c3ccccc3C(F)(F)F)nn12)c1ccc(CN2CCOCC2)nc1] | B | B | NT | NT |
| 148 | 483 | 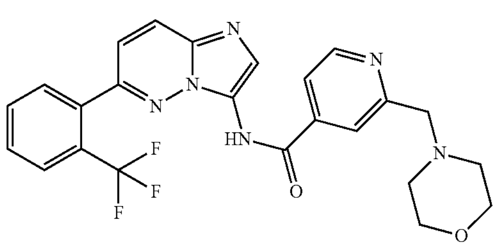 [SMILES: O=C(Nc1cnc2ccc(-c3ccccc3C(F)(F)F)nn12)c1ccnc(CN2CCOCC2)c1] | C | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 149 | 467 | 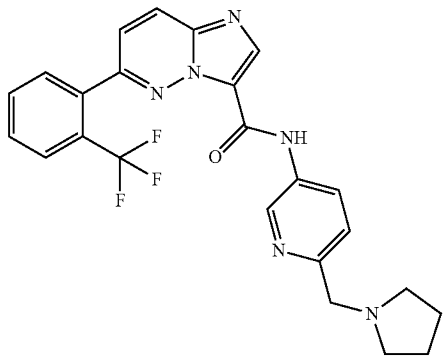 [SMILES: O=C(Nc1ccc(CN2CCCC2)nc1)c1cnc2ccc(-c3ccccc3C(F)(F)F)nn12] | B | B | B | B |
| 150 | 489 | 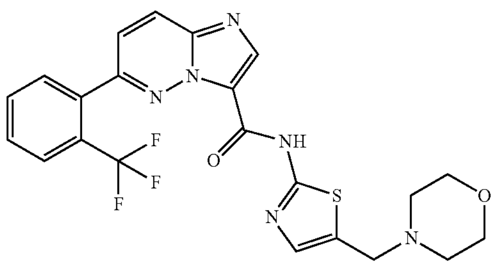 [SMILES: O=C(Nc1ncc(CN2CCOCC2)s1)c1cnc2ccc(-c3ccccc3C(F)(F)F)nn12] | B | B | B | B |
| 151 | 475 | 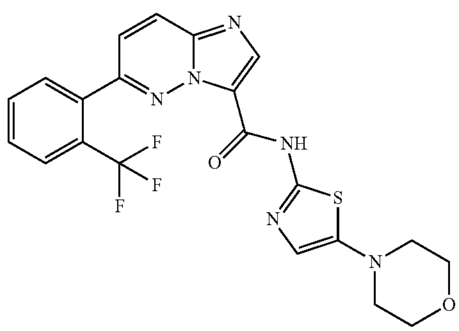 [SMILES: O=C(Nc1ncc(N2CCOCC2)s1)c1cnc2ccc(-c3ccccc3C(F)(F)F)nn12] | A | A | NT | NT |
| 152 | 404 | 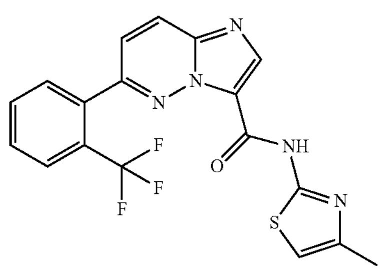 [SMILES: Cc1csc(NC(=O)c2cnc3ccc(-c4ccccc4C(F)(F)F)nn23)n1] | A | A | A | A |
| 153 | 387 | 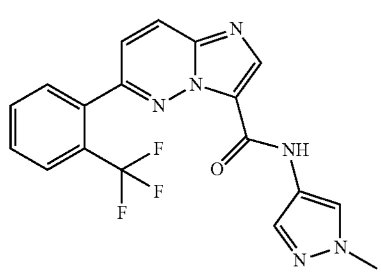 [SMILES: Cn1cc(NC(=O)c2cnc3ccc(-c4ccccc4C(F)(F)F)nn23)cn1] | B | A | NT | NT |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 154 | 431 | 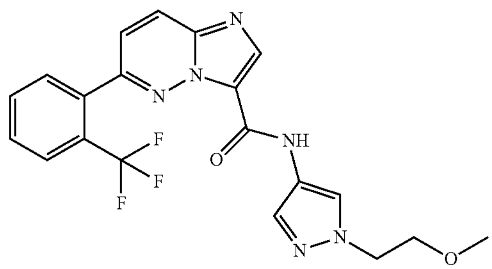 [SMILES: COCCn1cc(NC(=O)c2cnc3ccc(-c4ccccc4C(F)(F)F)nn23)cn1] | B | A | NT | NT |
| 155 | 444 | 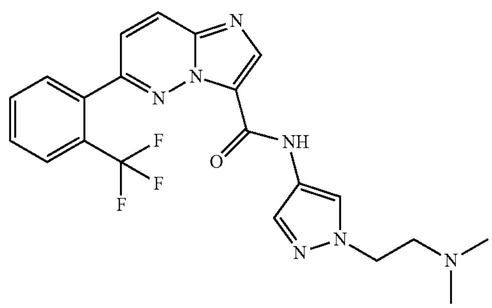 [SMILES: CN(C)CCn1cc(NC(=O)c2cnc3ccc(-c4ccccc4C(F)(F)F)nn23)cn1] | B | B | C | B |
| 156 | 458 | 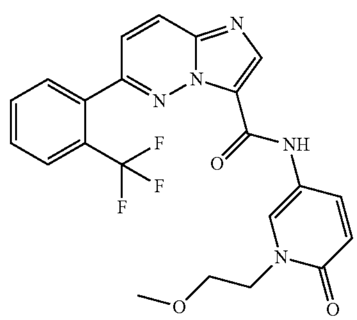 [SMILES: COCCn1cc(NC(=O)c2cnc3ccc(-c4ccccc4C(F)(F)F)nn23)ccc1=O] | B | B | NT | NT |
| 157 | 369 | 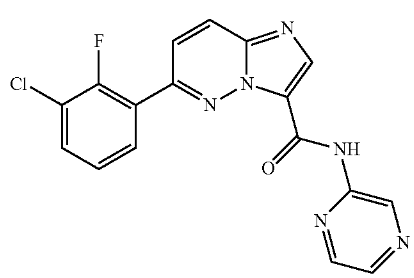 [SMILES: O=C(Nc1cnccn1)c1cnc2ccc(-c3cccc(Cl)c3F)nn12] | B | B | NT | NT |
| 158 | 453 | 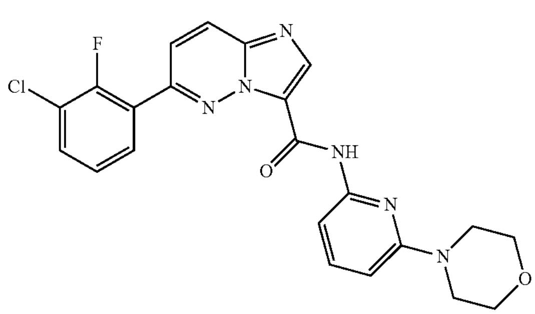 [SMILES: O=C(Nc1cccc(N2CCOCC2)n1)c1cnc2ccc(-c3cccc(Cl)c3F)nn12] | A | A | ND | ND |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 159 | 423 | 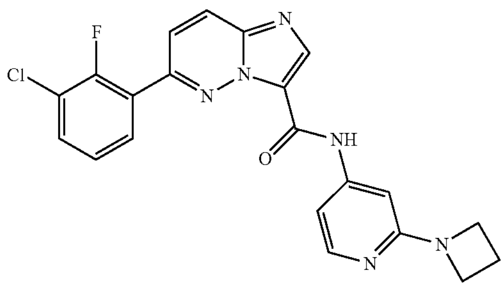 [SMILES: O=C(Nc1ccnc(N2CCC2)c1)c1cnc2ccc(-c3cccc(Cl)c3F)nn12] | A | B | B | B |
| 160 | 467 | 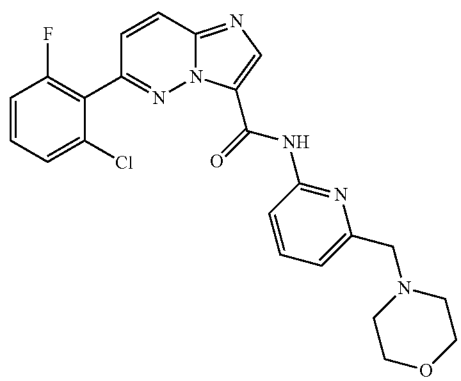 [SMILES: O=C(Nc1cccc(CN2CCOCC2)n1)c1cnc2ccc(-c3c(F)cccc3Cl)nn12] | B | A | NT | NT |
| 161 | 368 | 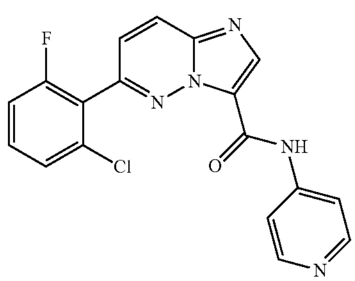 [SMILES: O=C(Nc1ccncc1)c1cnc2ccc(-c3c(F)cccc3Cl)nn12] | B | B | C | B |
| 162 | 368 | 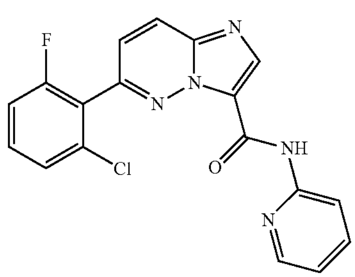 [SMILES: O=C(Nc1ccccn1)c1cnc2ccc(-c3c(F)cccc3Cl)nn12] | B | B | NT | NT |

TABLE 1-continued

Compounds of Formula (I).

| Compound No | [M + H]+$_{[Calc]}$ | Structure | TAMRA EC1.5 (µM) | TAMRA % Fold Act | Trp EC1.5 (µM) | Trp % Fold Act |
|---|---|---|---|---|---|---|
| 163 | 368 | | C | B | NT | NT |
| 164 | 453 | | A | A | B | B |
| 165 | 423 | | B | A | NT | NT |
| 166 | 352 | | C | B | NT | NT |
| 167 | 352 | | C | B | C | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 168 | 437 | 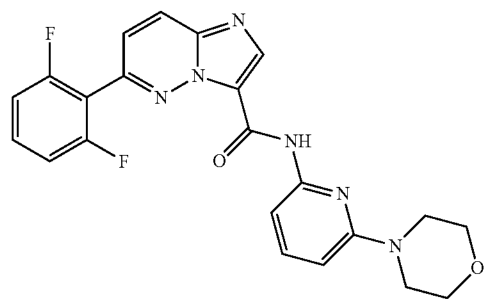 [SMILES: O=C(Nc1cccc(N2CCOCC2)n1)c1cnc2ccc(-c3c(F)cccc3F)nn12] | A | A | ND | ND |
| 169 | 352 | 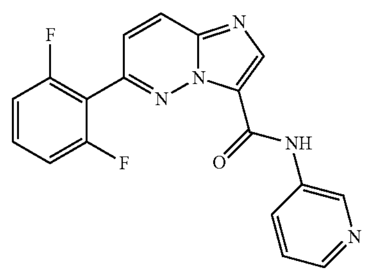 [SMILES: O=C(Nc1cccnc1)c1cnc2ccc(-c3c(F)cccc3F)nn12] | C | B | NT | NT |
| 170 | 407 | 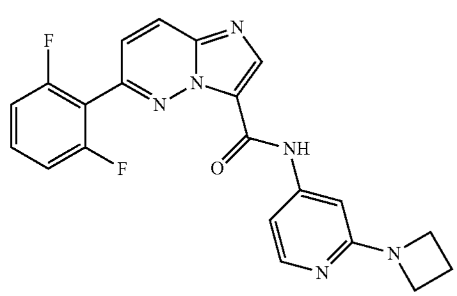 [SMILES: O=C(Nc1ccnc(N2CCC2)c1)c1cnc2ccc(-c3c(F)cccc3F)nn12] | A | B | B | B |
| 171 | 353 | 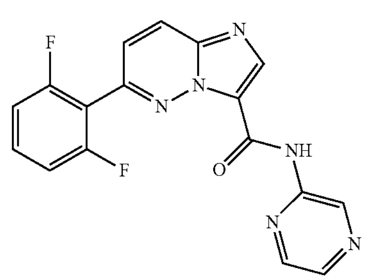 | C | B | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 172 | 451 | | B | A | C | B |
| 173 | 415 | | A | A | B | A |
| 174 | 429 | | A | A | NT | NT |
| 175 | 415 | | A | A | B | A |

TABLE 1-continued

Compounds of Formula (I).

| Compound No | [M + H]+<sub>[Calc]</sub> | Structure | TAMRA EC1.5 (µM) | % Fold Act | Trp EC1.5 (µM) | % Fold Act |
|---|---|---|---|---|---|---|
| 176 | 469 | | A | B | NT | NT |
| 177 | 469 | | C | B | C | B |
| 178 | 453 | | A | B | NT | NT |
| 179 | 423 | | A | B | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
| --- | --- | --- | --- | --- | --- | --- |
| 180 | 467 | 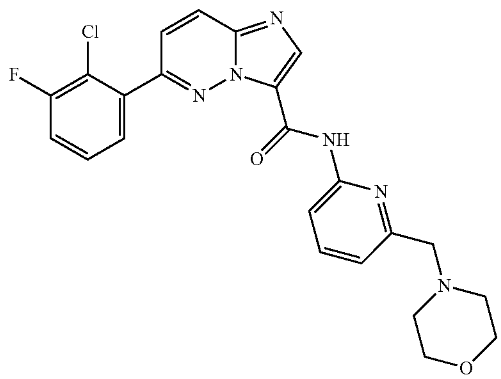 | B | A | ND | ND |
| 181 | 368 | 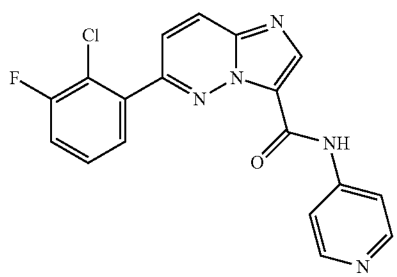 [SMILES: O=C(Nc1ccncc1)c1cnc2ccc(-c3cccc(F)c3Cl)nn12] | B | B | NT | NT |
| 182 | 368 | 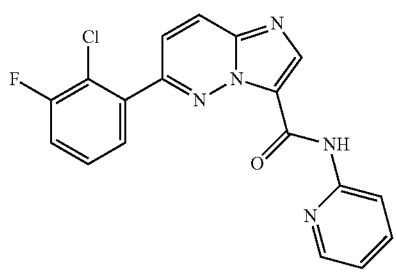 [SMILES: O=C(Nc1ccccn1)c1cnc2ccc(-c3cccc(F)c3Cl)nn12] | B | B | B | B |
| 183 | 368 | 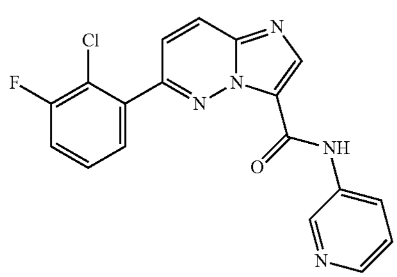 [SMILES: O=C(Nc1cccnc1)c1cnc2ccc(-c3cccc(F)c3Cl)nn12] | B | B | C | B |
| 184 | 369 | 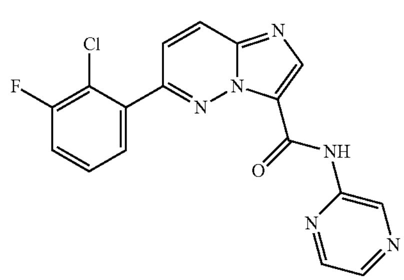 [SMILES: O=C(Nc1cnccn1)c1cnc2ccc(-c3cccc(F)c3Cl)nn12] | B | B | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 185 | 479 | 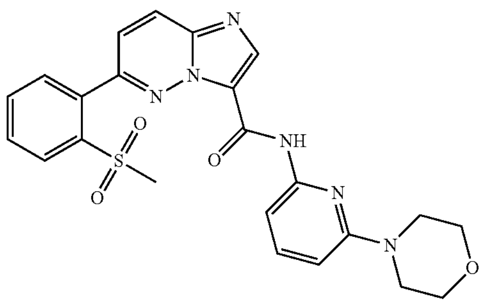 [SMILES: CS(=O)(=O)c1ccccc1-c1ccc2ncc(C(=O)Nc3cccc(N4CCOCC4)n3)n2n1] | B | B | NT | NT |
| 186 | 449 | 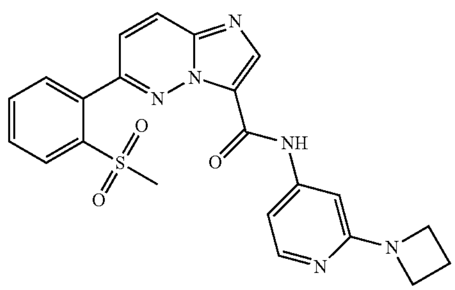 [SMILES: CS(=O)(=O)c1ccccc1-c1ccc2ncc(C(=O)Nc3ccnc(N4CCC4)c3)n2n1] | B | B | C | B |
| 187 | 394 | 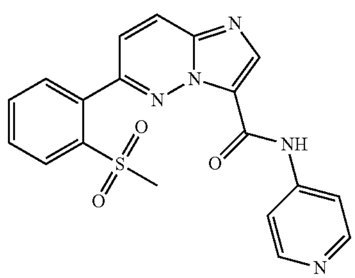 [SMILES: CS(=O)(=O)c1ccccc1-c1ccc2ncc(C(=O)Nc3ccncc3)n2n1] | C | B | NT | NT |
| 188 | 394 | 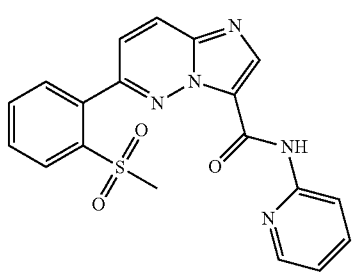 [SMILES: CS(=O)(=O)c1ccccc1-c1ccc2ncc(C(=O)Nc3ccccn3)n2n1] | C | B | NT | NT |
| 189 | 394 | 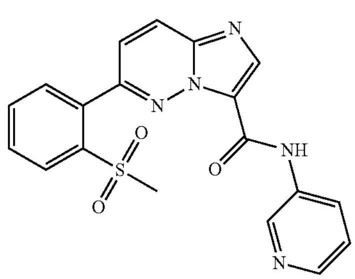 [SMILES: CS(=O)(=O)c1ccccc1-c1ccc2ncc(C(=O)Nc3cccnc3)n2n1] | C | B | C | B |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 190 | 395 | 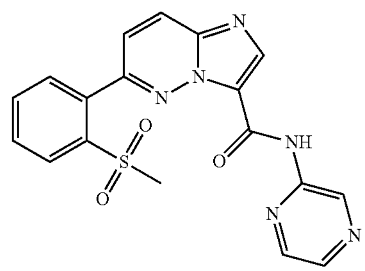 [SMILES: CS(=O)(=O)c1ccccc1-c1ccc2ncc(C(=O)Nc3cnccn3)n2n1] | NT | NT | NT | NT |
| 191 | 426 | 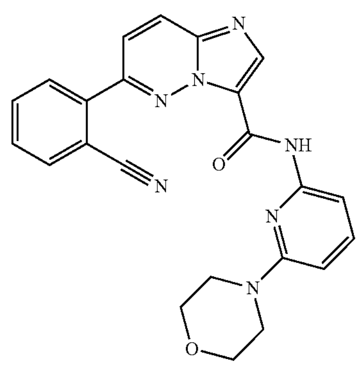 [SMILES: N#Cc1ccccc1-c1ccc2ncc(C(=O)Nc3cccc(N4CCOCC4)n3)n2n1] | A | B | NT | NT |
| 192 | 483 | 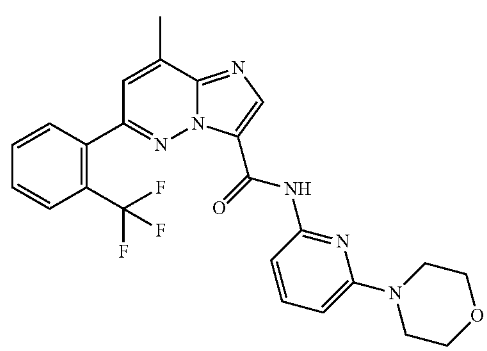 [SMILES: Cc1cc(-c2ccccc2C(F)(F)F)nn2c(C(=O)Nc3cccc(N4CCOCC4)n3)cnc12] | A | A | A | A |
| 193 | 398 | 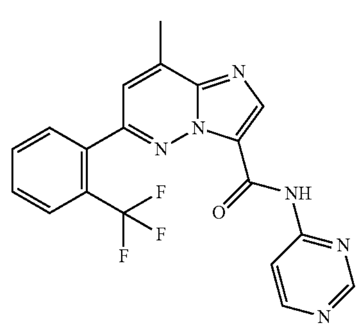 [SMILES: Cc1cc(-c2ccccc2C(F)(F)F)nn2c(C(=O)Nc3ccncn3)cnc12] | A | A | NT | NT |

TABLE 1-continued

Compounds of Formula (I).

| Compound No | [M + H]+$_{[Calc]}$ | Structure | TAMRA | | Trp | |
|---|---|---|---|---|---|---|
| | | | EC1.5 (μM) | % Fold Act | EC1.5 (μM) | % Fold Act |
| 194 | 398 | 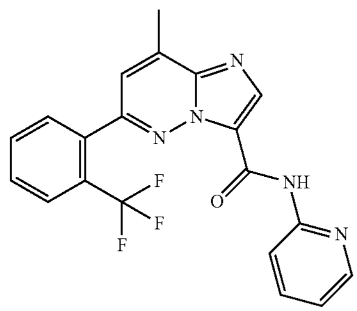 [SMILES: Cc1cc(-c2ccccc2C(F)(F)F)nn2c(C(=O)Nc3ccccn3)cnc12] | A | A | NT | NT |
| 195 | 497 | 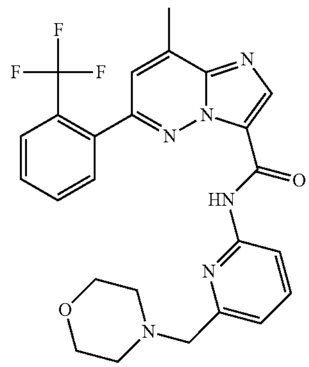 [SMILES: Cc1cc(-c2ccccc2C(F)(F)F)nn2c(C(=O)Nc3cccc(CN4CCOCC4)n3)cnc12] | A | A | ND | ND |
| 196 | 445 | 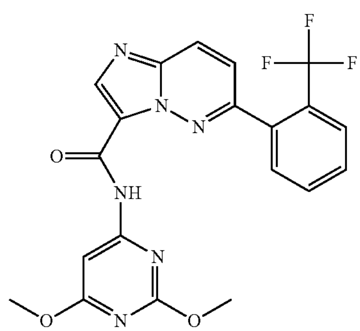 [SMILES: COc1cc(NC(=O)c2cnc3ccc(-c4ccccc4C(F)(F)F)nn23)nc(OC)n1] | A | A | NT | NT |
| 197 | 415 | 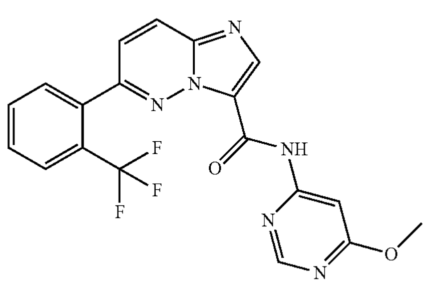 [SMILES: COc1cc(NC(=O)c2cnc3ccc(-c4ccccc4C(F)(F)F)nn23)ncn1] | A | A | B | B |

TABLE 1-continued

Compounds of Formula (I).

| Compound No | [M + H]+[Calc] | Structure | TAMRA | | Trp | |
| --- | --- | --- | --- | --- | --- | --- |
| | | | EC1.5 (μM) | % Fold Act | EC1.5 (μM) | % Fold Act |
| 198 | 445 | | A | A | B | B |
| 199 | 469 | | A | A | NT | NT |
| 200 | 341 | | B | B | NT | NT |
| 201 | 396 | | B | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 202 | 440 | 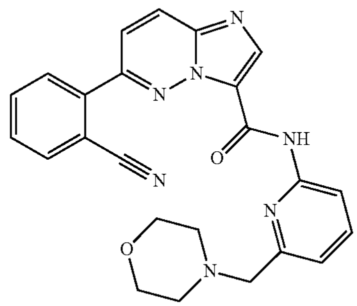 [SMILES: N#Cc1ccccc1-c1ccc2ncc(C(=O)Nc3cccc(CN4CCOCC4)n3)n2n1] | B | B | NT | NT |
| 203 | 341 | 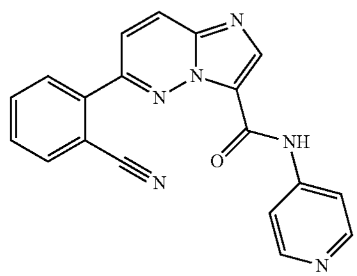 [SMILES: N#Cc1ccccc1-c1ccc2ncc(C(=O)Nc3ccncc3)n2n1] | B | B | NT | NT |
| 204 | 341 | 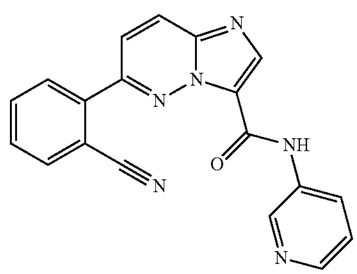 [SMILES: N#Cc1ccccc1-c1ccc2ncc(C(=O)Nc3cccnc3)n2n1] | NT | NT | NT | NT |
| 205 | 342 | 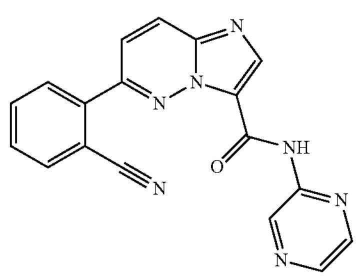 [SMILES: N#Cc1ccccc1-c1ccc2ncc(C(=O)Nc3cnccn3)n2n1] | B | B | NT | NT |
| 206 | 398 | 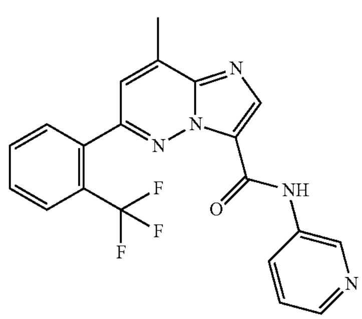 [SMILES: Cc1cc(-c2ccccc2C(F)(F)F)nn2c(C(=O)Nc3cccnc3)cnc12] | B | A | B | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 207 | 453 | 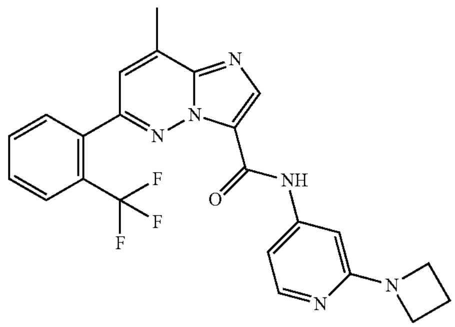 [SMILES: Cc1cc(-c2ccccc2C(F)(F)F)nn2c(C(=O)Nc3ccnc(N4CCC4)c3)cnc12] | A | A | A | A |
| 208 | 399 | 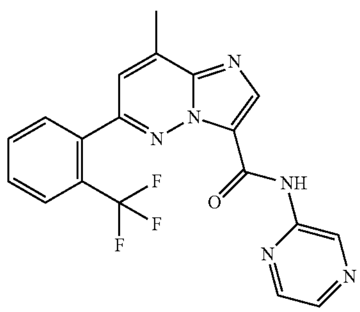 | A | A | NT | NT |
| 209 | 483 | 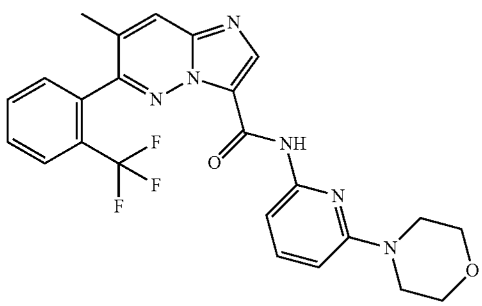 [SMILES: Cc1cc2ncc(C(=O)Nc3cccc(N4CCOCC4)n3)n2nc1-c1ccccc1C(F)(F)F] | A | A | NT | NT |
| 210 | 398 | 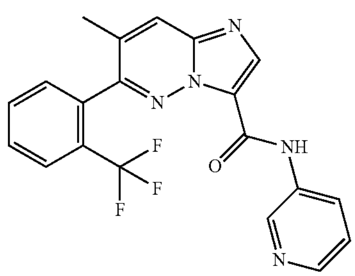 [SMILES: Cc1cc2ncc(C(=O)Nc3cccnc3)n2nc1-c1ccccc1C(F)(F)F] | B | A | B | A |
| 211 | 469 | 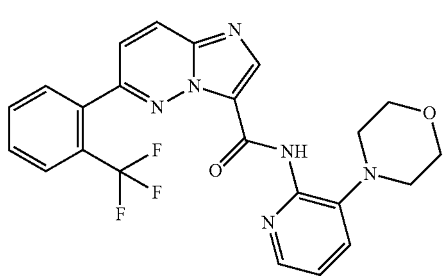 [SMILES: O=C(Nc1ncccc1N1CCOCC1)c1cnc2ccc(-c3ccccc3C(F)(F)F)nn12] | C | B | NT | NT |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 212 | 474 | 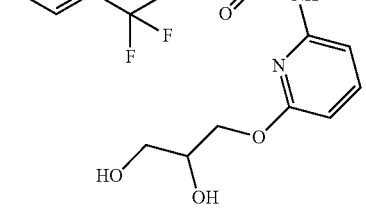 | A | A | NT | NT |
| 213 | 475 | 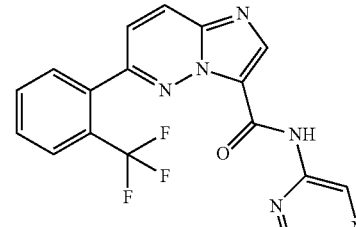 | A | A | A | A |
| 214 | 467 | 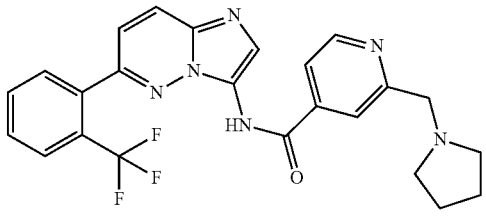 [SMILES: O=C(Nc1cnc2ccc(-c3ccccc3C(F)(F)F)nn12)c1ccnc(CN2CCCC2)c1] | C | B | C | B |
| 215 | 469 | 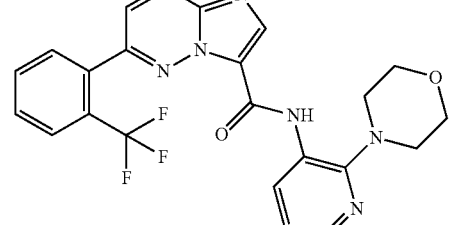 | C | B | C | B |

TABLE 1-continued
Compounds of Formula (I).
| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 216 | 469 | 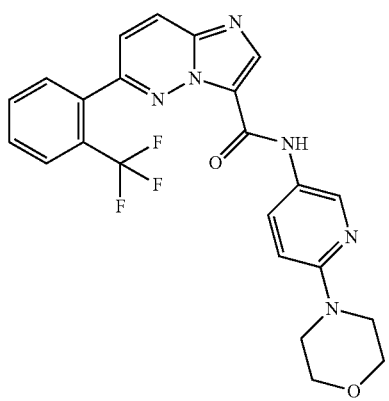 [SMILES: O=C(Nc1ccc(N2CCOCC2)nc1)c1cnc2ccc(-c3ccccc3C(F)(F)F)nn12] | B | A | NT | NT |
| 217 | 469 | 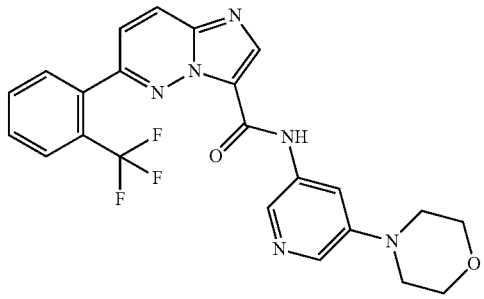 [SMILES: O=C(Nc1cncc(N2CCOCC2)c1)c1cnc2ccc(-c3ccccc3C(F)(F)F)nn12] | A | A | NT | NT |
| 218 | 390 | 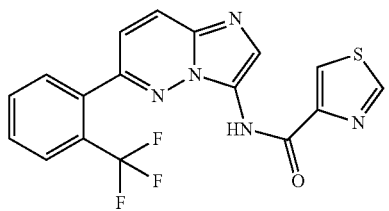 [SMILES: O=C(Nc1cnc2ccc(-c3ccccc3C(F)(F)F)nn12)c1cscn1] | A | A | B | B |
| 219 | 399 | 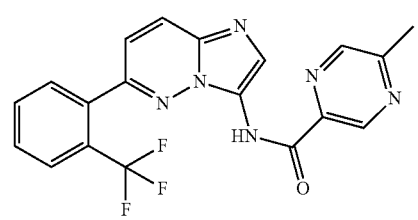 [SMILES: Cc1cnc(C(=O)Nc2cnc3ccc(-c4ccccc4C(F)(F)F)nn23)cn1] | A | A | NT | NT |
| 220 | 418 | 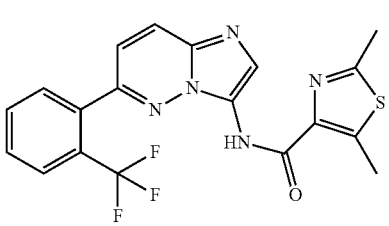 [SMILES: Cc1nc(C(=O)Nc2cnc3ccc(-c4ccccc4C(F)(F)F)nn23)c(C)s1] | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 221 | 413 | 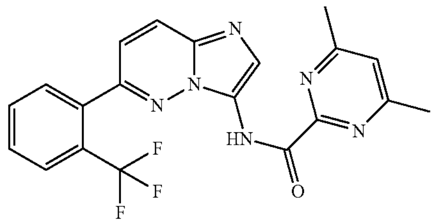 [SMILES: Cc1cc(C)nc(C(=O)Nc2cnc3ccc(-c4ccccc4C(F)(F)F)nn23)n1] | A | A | B | B |
| 222 | 497 | 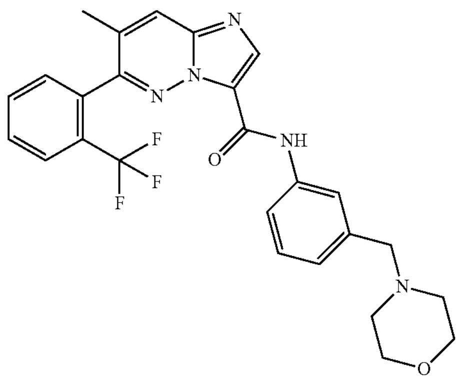 [SMILES: Cc1cc2ncc(C(=O)Nc3cccc(CN4CCOCC4)c3)n2nc1-c1ccccc1C(F)(F)F] | A | A | NT | NT |
| 223 | 398 | 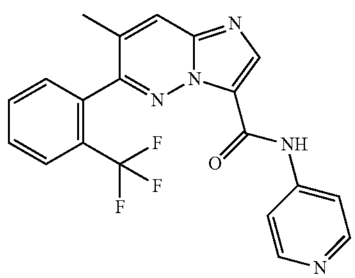 [SMILES: Cc1cc2ncc(C(=O)Nc3ccncc3)n2nc1-c1ccccc1C(F)(F)F] | B | A | B | A |
| 224 | 398 | 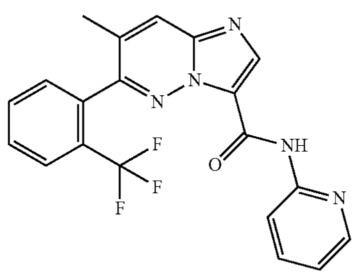 [SMILES: Cc1cc2ncc(C(=O)Nc3ccccn3)n2nc1-c1ccccc1C(F)(F)F] | B | A | B | A |
| 225 | 453 | 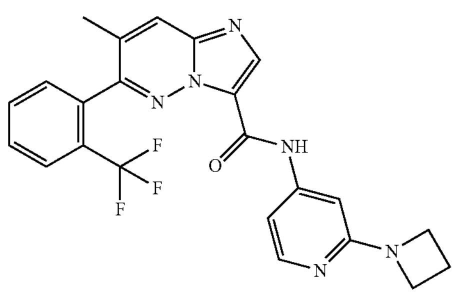 [SMILES: Cc1cc2ncc(C(=O)Nc3ccnc(N4CCC4)c3)n2nc1-c1ccccc1C(F)(F)F] | A | A | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 226 | 475 | 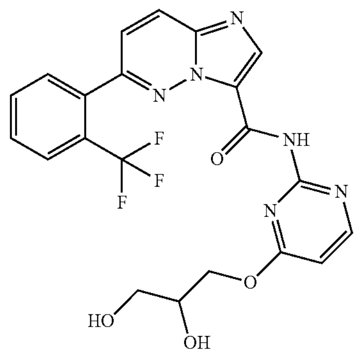 [SMILES: O=C(Nc1nccc(OCC(O)CO)n1)c1cnc2ccc(-c3ccccc3C(F)(F)F)nn12] | B | A | NT | NT |
| 227 | 497 | 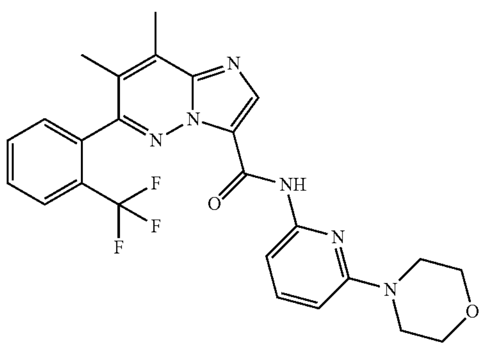 [SMILES: Cc1c(-c2ccccc2C(F)(F)F)nn2c(C(=O)Nc3cccc(N4CCOCC4)n3)cnc2c1C] | A | A | B | A |
| 228 | 440 | 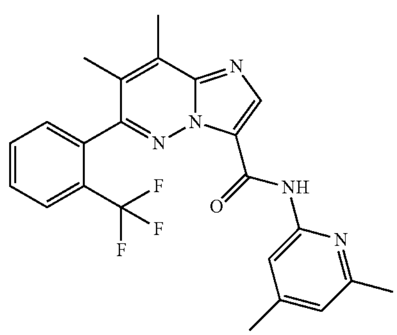 [SMILES: Cc1cc(C)nc(NC(=O)c2cnc3c(C)c(C)c(-c4ccccc4C(F)(F)F)nn23)c1] | A | A | NT | NT |
| 229 | 463 | 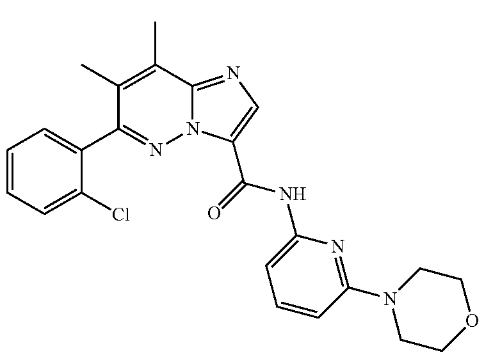 [SMILES: Cc1c(-c2ccccc2Cl)nn2c(C(=O)Nc3cccc(N4CCOCC4)n3)cnc2c1C] | A | A | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 230 | 406 | | A | A | C | B |
| 231 | 398 | | B | A | B | B |
| 232 | 398 | | A | A | NT | NT |
| 233 | 398 | | A | A | C | B |
| 234 | 398 | | A | A | NT | NT |
| 235 | 474 | | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 236 | 474 | | A | A | A | A |
| 237 | 418 | | A | A | NT | NT |
| 238 | 413 | | A | A | C | B |
| 239 | 384 | | B | A | B | A |
| 240 | 384 | | A | A | NT | NT |

TABLE 1-continued
Compounds of Formula (I).
| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 241 | 469 | 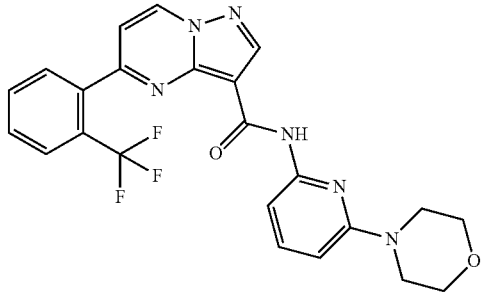 [SMILES: O=C(Nc1cccc(N2CCOCC2)n1)c1cnn2ccc(-c3ccccc3C(F)(F)F)nc12] | A | A | NT | NT |
| 242 | 348 | 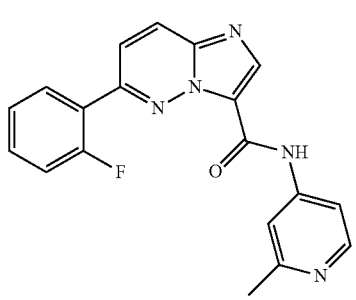 [SMILES: Cc1cc(NC(=O)c2cnc3ccc(-c4ccccc4F)nn23)ccn1] | B | B | B | B |
| 243 | 362 | 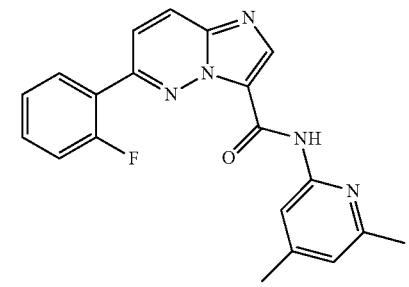 [SMILES: Cc1cc(C)nc(NC(=O)c2cnc3ccc(-c4ccccc4F)nn23)c1] | A | A | NT | NT |
| 244 | 364 | 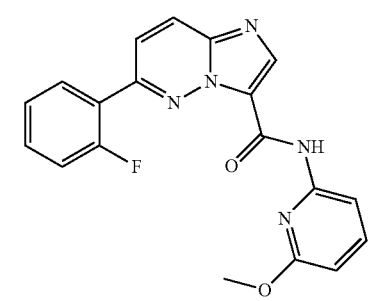 [SMILES: COc1cccc(NC(=O)c2cnc3ccc(-c4ccccc4F)nn23)n1] | B | B | A | B |
| 245 | 378 | 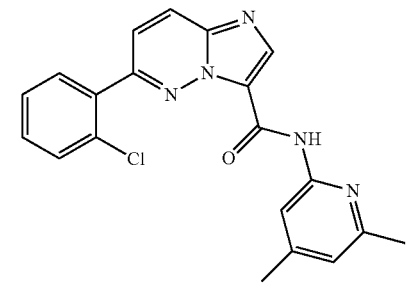 [SMILES: Cc1cc(C)nc(NC(=O)c2cnc3ccc(-c4ccccc4Cl)nn23)c1] | A | A | ND | ND |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 246 | 399 | 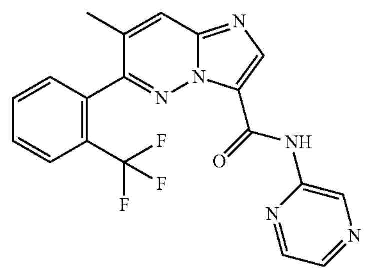 [SMILES: Cc1cc2ncc(C(=O)Nc3cnccn3)n2nc1-c1ccccc1C(F)(F)F] | B | A | NT | NT |
| 247 | 413 | 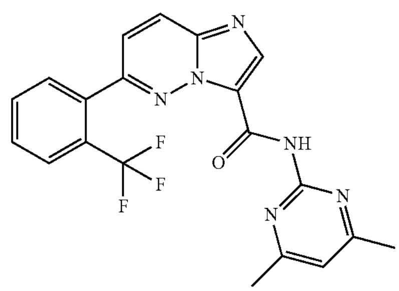 [SMILES: Cc1cc(C)nc(NC(=O)c2cnc3ccc(-c4ccccc4C(F)(F)F)nn23)n1] | A | A | NT | NT |
| 248 | 467 | 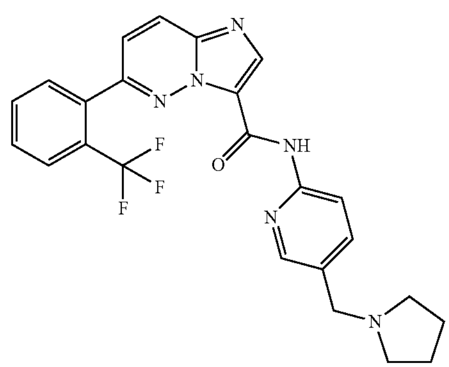 [SMILES: O=C(Nc1ccc(CN2CCCC2)cn1)c1cnc2ccc(-c3ccccc3C(F)(F)F)nn12] | B | A | B | B |
| 249 | 384 | 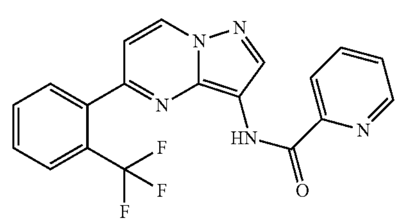 [SMILES: O=C(Nc1cnn2ccc(-c3ccccc3C(F)(F)F)nc12)c1ccccn1] | A | A | B | B |
| 250 | 384 | 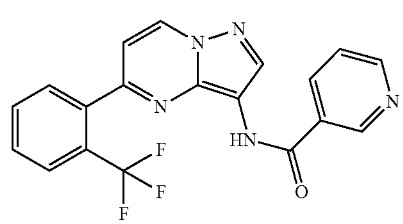 [SMILES: O=C(Nc1cnn2ccc(-c3ccccc3C(F)(F)F)nc12)c1cccnc1] | C | B | NT | NT |

TABLE 1-continued

Compounds of Formula (I).

| Compound No | [M + H]+$_{[Calc]}$ | Structure | TAMRA EC1.5 (µM) | TAMRA % Fold Act | Trp EC1.5 (µM) | Trp % Fold Act |
|---|---|---|---|---|---|---|
| 251 | 384 | | C | B | C | B |
| 252 | 385 | | B | A | NT | NT |
| 253 | 385 | | B | A | NT | NT |
| 254 | 385 | | B | A | C | B |
| 255 | 483 | | A | A | B | B |
| 256 | 469 | | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 257 | 362 | 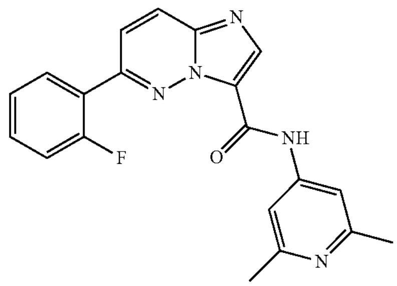 [SMILES: Cc1cc(NC(=O)c2cnc3ccc(-c4ccccc4F)nn23)cc(C)n1] | A | B | B | B |
| 258 | 432 | 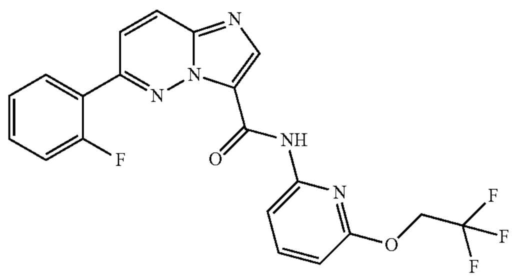 [SMILES: O=C(Nc1cccc(OCC(F)(F)F)n1)c1cnc2ccc(-c3ccccc3F)nn12] | C | B | NT | NT |
| 259 | 364 | 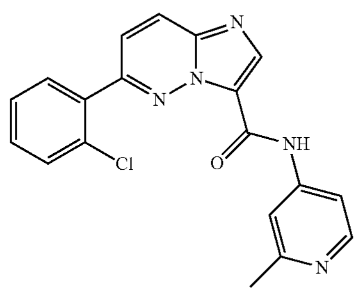 [SMILES: Cc1cc(NC(=O)c2cnc3ccc(-c4ccccc4Cl)nn23)ccn1] | B | A | NT | NT |
| 260 | 378 | 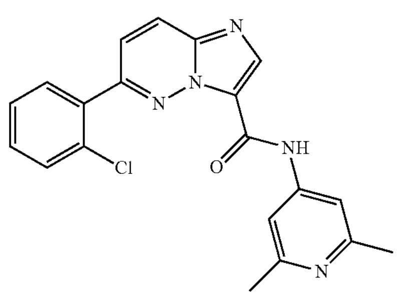 [SMILES: Cc1cc(NC(=O)c2cnc3ccc(-c4ccccc4Cl)nn23)cc(C)n1] | A | A | B | B |
| 261 | 380 | 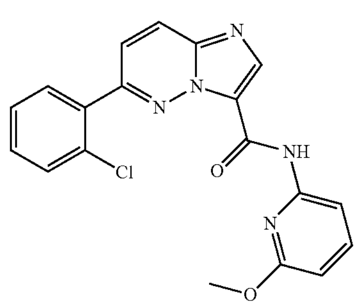 [SMILES: COc1cccc(NC(=O)c2cnc3ccc(-c4ccccc4Cl)nn23)n1] | A | B | A | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 262 | 448 | | C | B | NT | NT |
| 263 | 474 | | B | A | B | B |
| 264 | 482 | | B | A | NT | NT |
| 265 | 384 | | A | A | NT | NT |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 266 | 385 | | B | A | B | B |
| 267 | 385 | | A | A | B | B |
| 268 | 385 | | A | A | NT | NT |
| 269 | 483 | | A | A | B | A |
| 270 | 399 | | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 271 | 404 | 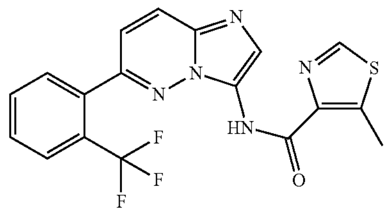 [SMILES: Cc1scnc1C(=O)Nc1cnc2ccc(-c3ccccc3C(F)(F)F)nn12] | A | A | NT | NT |
| 272 | 432 | 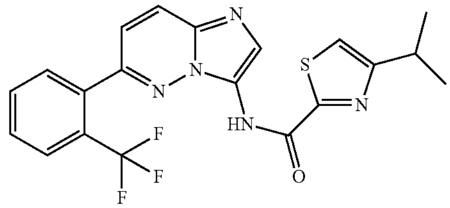 [SMILES: CC(C)c1csc(C(=O)Nc2cnc3ccc(-c4ccccc4C(F)(F)F)nn23)n1] | A | A | B | B |
| 273 | 404 | 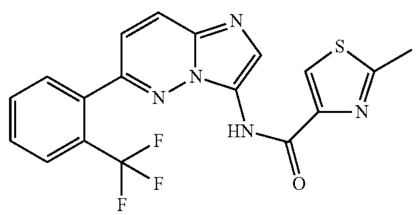 [SMILES: Cc1nc(C(=O)Nc2cnc3ccc(-c4ccccc4C(F)(F)F)nn23)cs1] | A | A | B | A |
| 274 | 427 | 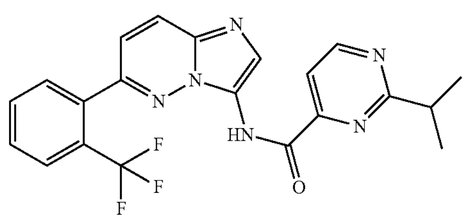 [SMILES: CC(C)c1nccc(C(=O)Nc2cnc3ccc(-c4ccccc4C(F)(F)F)nn23)n1] | A | A | NT | NT |
| 275 | 413 | 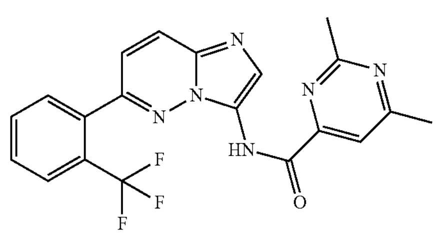 [SMILES: Cc1cc(C(=O)Nc2cnc3ccc(-c4ccccc4C(F)(F)F)nn23)nc(C)n1] | A | A | B | B |
| 276 | 399 | 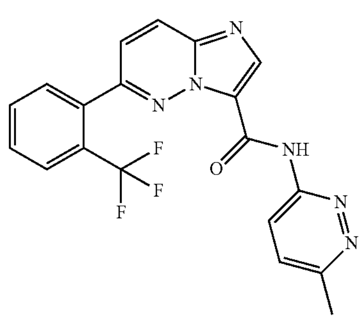 [SMILES: Cc1ccc(NC(=O)c2cnc3ccc(-c4ccccc4C(F)(F)F)nn23)nn1] | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 277 | 499 | | A | A | NT | NT |
| 278 | 489 | | B | B | NT | NT |
| 279 | 334 | | B | B | C | B |
| 280 | 335 | | B | B | NT | NT |
| 281 | 335 | | C | B | C | B |
| 282 | 335 | | B | B | NT | NT |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 283 | 440 | 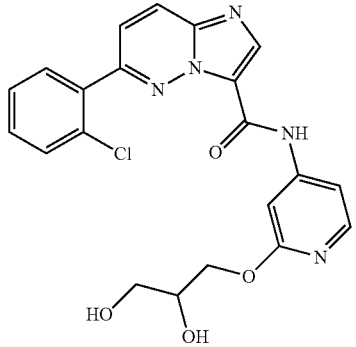 [SMILES: O=C(Nc1ccnc(OCC(O)CO)c1)c1cnc2ccc(-c3ccccc3Cl)nn12] | A | B | NT | NT |
| 284 | 424 | 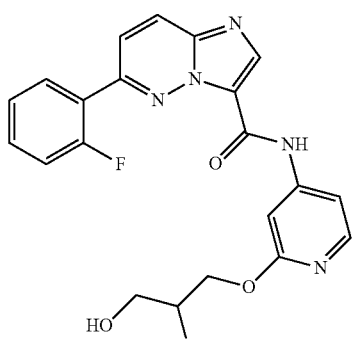 | C | B | C | B |
| 285 | 455 | 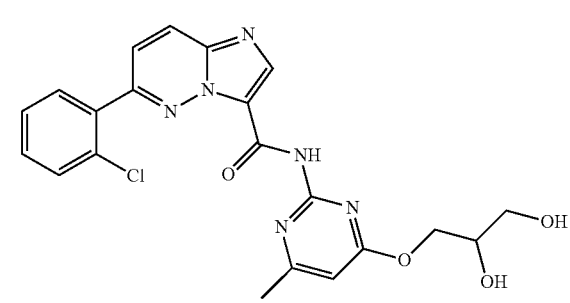 [SMILES: Cc1cc(OCC(O)CO)nc(NC(=O)c2cnc3ccc(-c4ccccc4Cl)nn23)n1] | B | B | B | B |
| 286 | 439 | 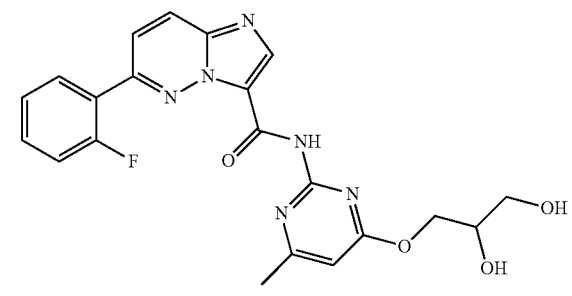 [SMILES: Cc1cc(OCC(O)CO)nc(NC(=O)c2cnc3ccc(-c4ccccc4F)nn23)n1] | B | B | NT | NT |
| 287 | 350 | 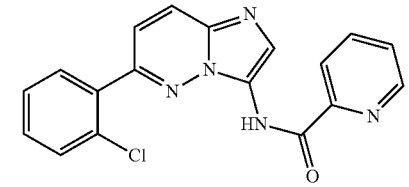 [SMILES: O=C(Nc1cnc2ccc(-c3ccccc3Cl)nn12)c1ccccn1] | A | A | C | B |

TABLE 1-continued

Compounds of Formula (I).

| Compound No | [M + H]+[Cale] | Structure | TAMRA EC1.5 (μM) | TAMRA % Fold Act | Trp EC1.5 (μM) | Trp % Fold Act |
|---|---|---|---|---|---|---|
| 288 | 351 | | B | B | NT | NT |
| 289 | 351 | | B | B | NT | NT |
| 290 | 351 | | B | A | C | B |
| 291 | 356 | | B | A | C | B |
| 292 | 370 | | A | A | NT | NT |
| 293 | 384 | | A | A | C | B |
| 294 | 356 | | B | B | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 295 | 484 | | A | A | NT | NT |
| 296 | 482 | | B | B | B | B |
| 297 | 475 | | A | A | B | B |
| 298 | 340 | | B | B | NT | NT |

TABLE 1-continued
Compounds of Formula (I).
| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 299 | 354 | 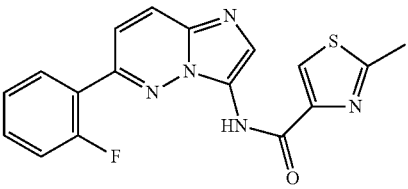 [SMILES: Cc1nc(C(=O)Nc2cnc3ccc(-c4ccccc4F)nn23)cs1] | B | B | ND | ND |
| 300 | 368 | 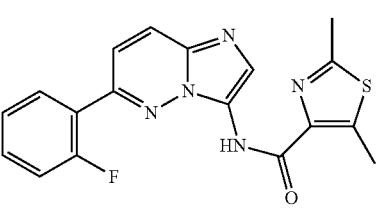 [SMILES: Cc1nc(C(=O)Nc2cnc3ccc(-c4ccccc4F)nn23)c(C)s1] | A | B | NT | NT |
| 301 | 419 | 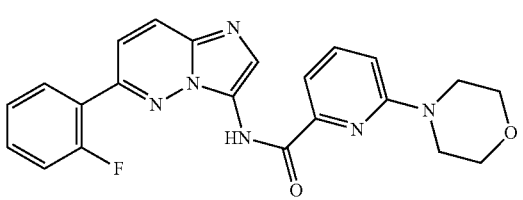 [SMILES: O=C(Nc1cnc2ccc(-c3ccccc3F)nn12)c1cccc(N2CCOCC2)n1] | A | A | NT | NT |
| 302 | 389 | 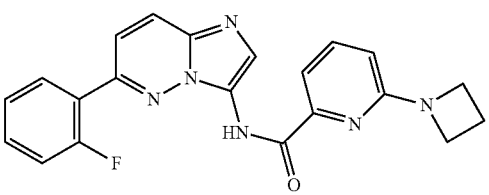 [SMILES: O=C(Nc1cnc2ccc(-c3ccccc3F)nn12)c1cccc(N2CCC2)n1] | A | A | ND | ND |
| 303 | 340 | 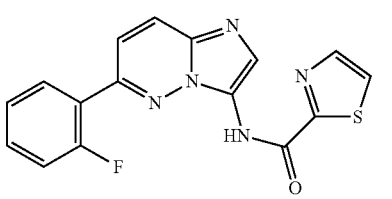 [SMILES: O=C(Nc1cnc2ccc(-c3ccccc3F)nn12)c1nccs1] | B | B | C | B |
| 304 | 354 | 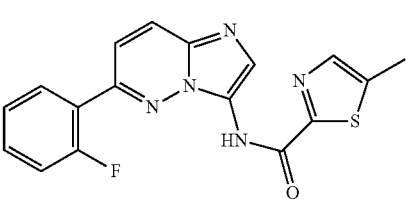 [SMILES: Cc1cnc(C(=O)Nc2cnc3ccc(-c4ccccc4F)nn23)s1] | B | B | NT | NT |
| 305 | 424 | 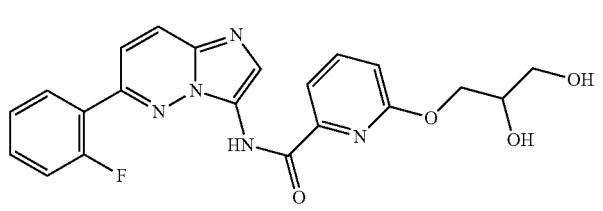 [SMILES: O=C(Nc1cnc2ccc(-c3ccccc3F)nn12)c1cccc(OCC(O)CO)n1] | B | B | A | B |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 306 | 370 | 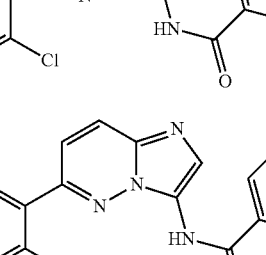 | B | A | NT | NT |
| 307 | 435 | 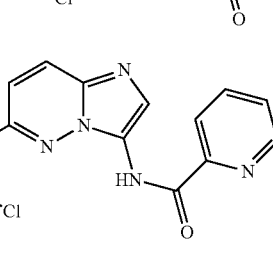 | A | A | NT | NT |
| 308 | 405 | 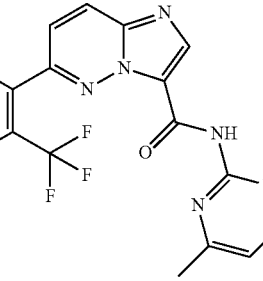 | A | A | A | B |
| 309 | 440 | 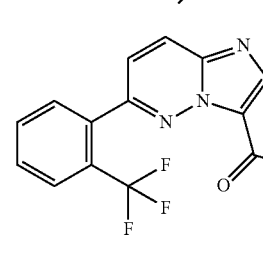 | A | A | A | B |
| 310 | 497 | 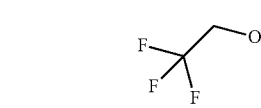 | A | A | NT | NT |
| 311 | 483 | 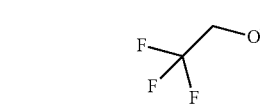 | A | A | A | A |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 312 | 400 | | A | A | NT | NT |
| 313 | 401 | | A | A | NT | NT |
| 314 | 401 | | A | A | B | B |
| 315 | 401 | | A | A | B | A |
| 316 | 406 | | A | A | NT | NT |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 317 | 420 | | A | A | C | B |
| 318 | 434 | | A | A | NT | NT |
| 319 | 406 | | A | A | NT | NT |
| 320 | 420 | | A | A | B | B |
| 321 | 485 | | A | A | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 322 | 455 | | A | A | NT | NT |
| 323 | 490 | | A | A | A | A |
| 324 | 400 | | B | B | NT | NT |
| 325 | 483 | | B | B | NT | NT |
| 326 | 393 | | A | A | A | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 327 | 377 | | A | A | A | B |
| 328 | 341 | | A | A | NT | NT |
| 329 | 342 | | B | B | C | B |
| 330 | 342 | | B | B | NT | NT |
| 331 | 342 | | B | A | NT | NT |
| 332 | 347 | | B | B | C | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 333 | 361 | | B | A | ND | ND |
| 334 | 375 | | A | A | NT | NT |
| 335 | 347 | | B | B | B | B |
| 336 | 361 | | B | A | NT | NT |
| 337 | 426 | | A | A | NT | NT |
| 338 | 396 | | A | A | A | B |
| 339 | 431 | | A | A | A | B |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 340 | 485 | 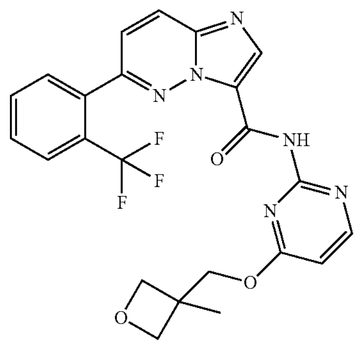 | A | A | A | A |
| 341 | 428 | 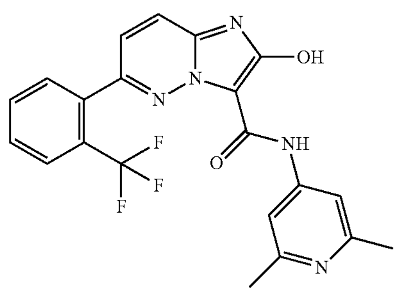 [SMILES: Cc1cc(NC(=O)c2c(O)nc3ccc(-c4ccccc4C(F)(F)F)nn23)cc(C)n1] | C | B | NT | NT |
| 342 | 401 | 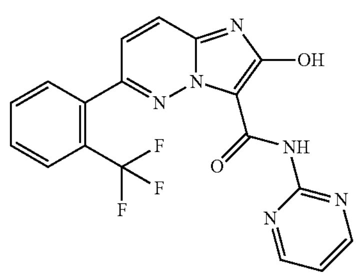 [SMILES: O=C(Nc1ncccn1)c1c(O)nc2ccc(-c3ccccc3C(F)(F)F)nn12] | C | ND | NT | NT |
| 343 | 414 | 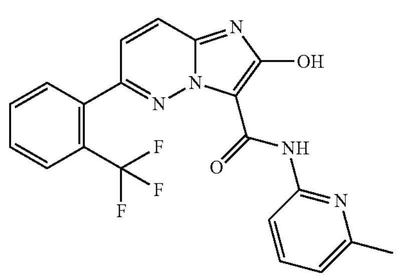 [SMILES: Cc1cccc(NC(=O)c2c(O)nc3ccc(-c4ccccc4C(F)(F)F)nn23)n1] | C | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 344 | 490 | | B | B | NT | NT |
| 345 | 491 | | B | A | NT | NT |
| 346 | 364 | | B | B | C | B |
| 347 | 365 | | C | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 348 | 365 | | C | B | C | B |
| 349 | 365 | | C | B | NT | NT |
| 350 | 370 | | C | B | NT | NT |
| 351 | 384 | | B | B | C | B |
| 352 | 398 | | B | B | C | B |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 353 | 370 | 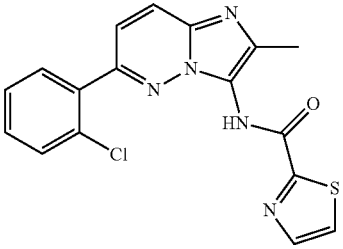 [SMILES: Cc1nc2ccc(-c3ccccc3Cl)nn2c1NC(=O)c1nccs1] | B | B | NT | NT |
| 354 | 384 | 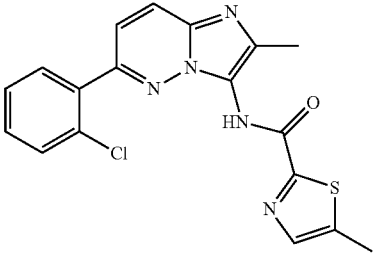 [SMILES: Cc1cnc(C(=O)Nc2c(C)nc3ccc(-c4ccccc4Cl)nn23)s1] | B | B | C | B |
| 355 | 449 | 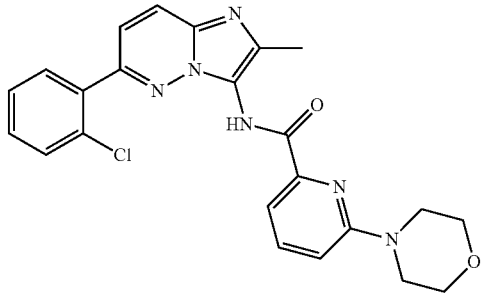 [SMILES: Cc1nc2ccc(-c3ccccc3Cl)nn2c1NC(=O)c1cccc(N2CCOCC2)n1] | A | A | NT | NT |
| 356 | 419 | 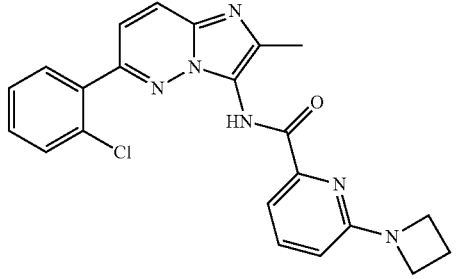 [SMILES: Cc1nc2ccc(-c3ccccc3Cl)nn2c1NC(=O)c1cccc(N2CCC2)n1] | A | B | NT | NT |
| 357 | 454 | 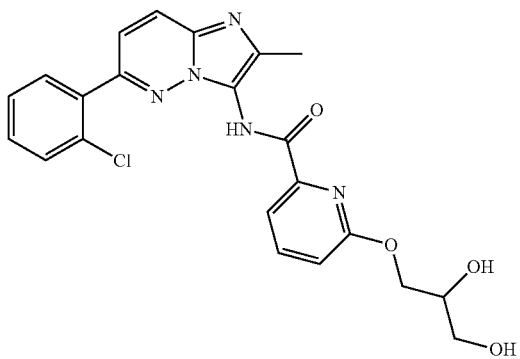 [SMILES: Cc1nc2ccc(-c3ccccc3Cl)nn2c1NC(=O)c1cccc(OCC(O)CO)n1] | C | B | C | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 358 | 401 | | A | A | B | A |
| 359 | 418 | | B | A | NT | NT |
| 360 | 418 | | B | B | A | B |
| 361 | 440 | | A | A | NT | NT |

TABLE 1-continued

Compounds of Formula (I).

| Compound No | [M + H]+$_{[Calc]}$ | Structure | TAMRA EC1.5 (µM) | % Fold Act | Trp EC1.5 (µM) | % Fold Act |
|---|---|---|---|---|---|---|
| 362 | 401 | | A | A | NT | NT |
| 363 | 428 | | A | A | A | B |
| 364 | 414 | | A | A | A | A |
| 365 | 428 | | B | B | NT | NT |
| 366 | 414 | | B | B | NT | NT |

TABLE 1-continued
Compounds of Formula (I).
| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 367 | 491 | 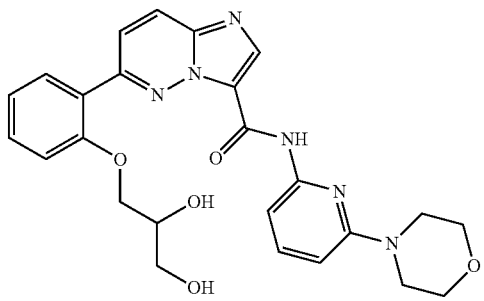 [SMILES: O=C(Nc1cccc(N2CCOCC2)n1)c1cnc2ccc(-c3ccccc3OCC(O)CO)nn12] | A | A | NT | NT |
| 368 | 406 | 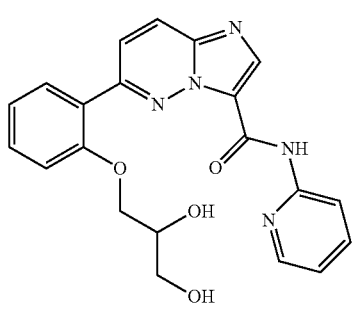 [SMILES: O=C(Nc1ccccn1)c1cnc2ccc(-c3ccccc3OCC(O)CO)nn12] | B | A | NT | NT |
| 369 | 420 | 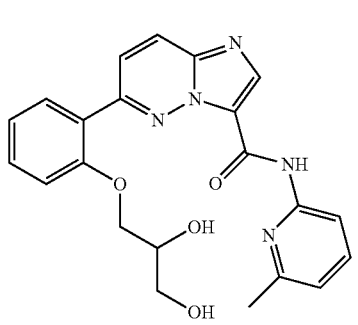 [SMILES: Cc1cccc(NC(=O)c2cnc3ccc(-c4ccccc4OCC(O)CO)nn23)n1] | A | A | B | A |
| 370 | 420 | 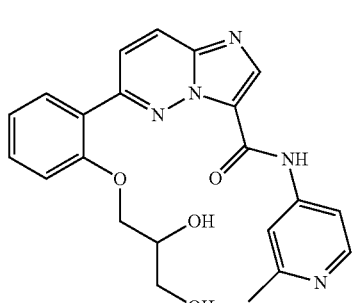 | B | A | ND | ND |

TABLE 1-continued
Compounds of Formula (I).
| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 371 | 434 | 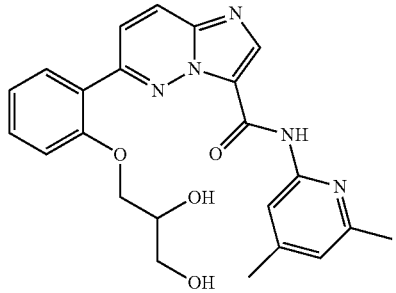 [SMILES: Cc1cc(C)nc(NC(=O)c2cnc3ccc(-c4ccccc4OCC(O)CO)nn23)c1] | A | A | NT | NT |
| 372 | 491 | 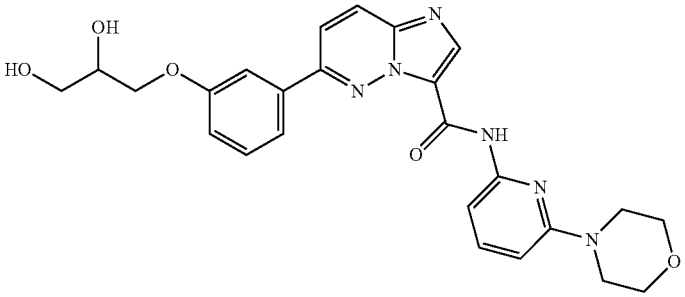 [SMILES: O=C(Nc1cccc(N2CCOCC2)n1)c1cnc2ccc(-c3cccc(OCC(O)CO)c3)nn12] | A | A | A | B |
| 373 | 406 | 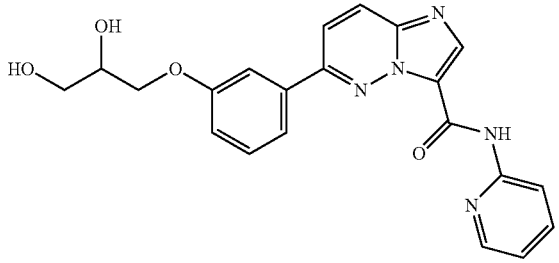 [SMILES: O=C(Nc1ccccn1)c1cnc2ccc(-c3cccc(OCC(O)CO)c3)nn12] | B | B | NT | NT |
| 374 | 420 | 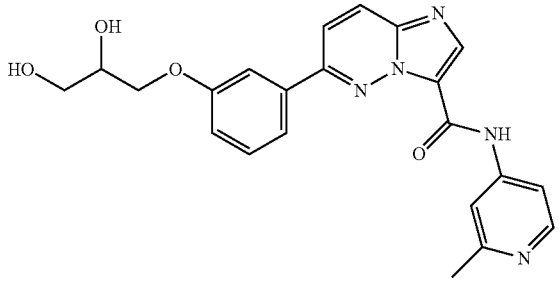 [SMILES: Cc1cc(NC(=O)c2cnc3ccc(-c4cccc(OCC(O)CO)c4)nn23)ccn1] | B | B | NT | NT |
| 375 | 398 | 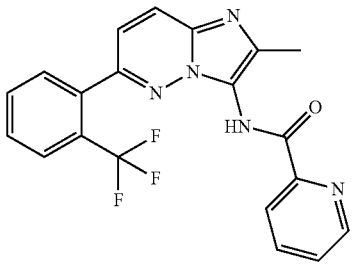 [SMILES: Cc1nc2ccc(-c3ccccc3C(F)(F)F)nn2c1NC(=O)c1ccccn1] | B | A | C | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 376 | 399 | | B | B | NT | NT |
| 377 | 399 | | B | B | C | B |
| 378 | 399 | | B | A | NT | NT |
| 379 | 432 | | B | A | NT | NT |
| 380 | 404 | | B | A | C | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 381 | 418 | 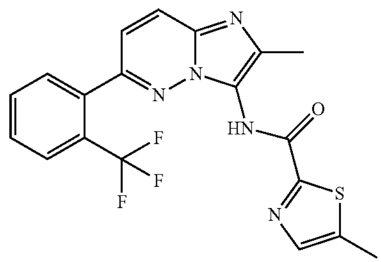 [SMILES: Cc1cnc(C(=O)Nc2c(C)nc3ccc(-c4ccccc4C(F)(F)F)nn23)s1] | B | A | C | B |
| 382 | 483 | 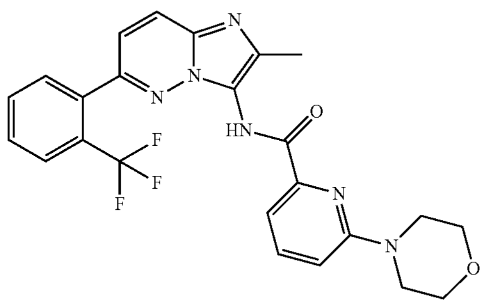 [SMILES: Cc1nc2ccc(-c3ccccc3C(F)(F)F)nn2c1NC(=O)c1cccc(N2CCOCC2)n1] | A | A | NT | NT |
| 383 | 453 | 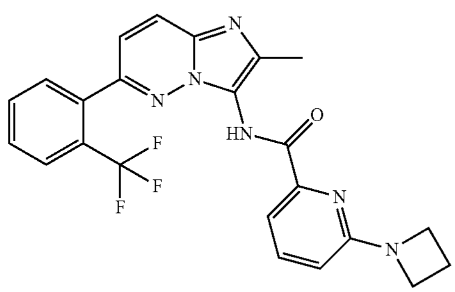 [SMILES: Cc1nc2ccc(-c3ccccc3C(F)(F)F)nn2c1NC(=O)c1cccc(N2CCC2)n1] | A | A | B | A |
| 384 | 488 | 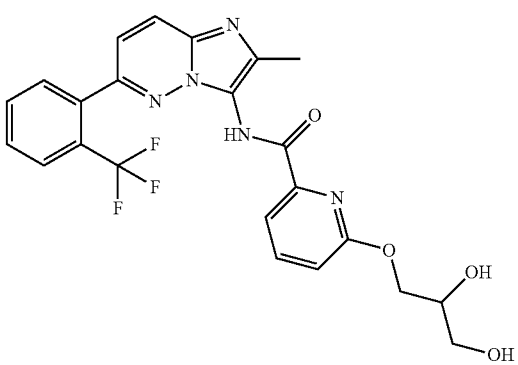 [SMILES: Cc1nc2ccc(-c3ccccc3C(F)(F)F)nn2c1NC(=O)c1cccc(OCC(O)CO)n1] | B | B | NT | NT |
| 385 | 398 | 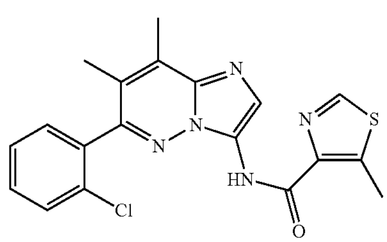 [SMILES: Cc1scnc1C(=O)Nc1cnc2c(C)c(C)c(-c3ccccc3Cl)nn12] | A | A | NT | NT |

TABLE 1-continued
Compounds of Formula (I).
| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 386 | 447 | 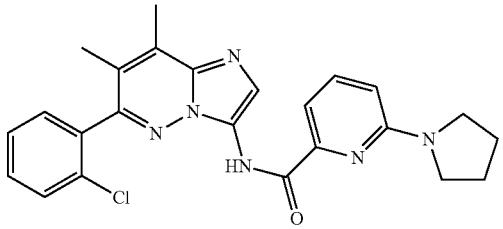 [SMILES: Cc1c(-c2ccccc2Cl)nn2c(NC(=O)c3cccc(N4CCCC4)n3)cnc2c1C] | A | A | B | B |
| 387 | 502 | 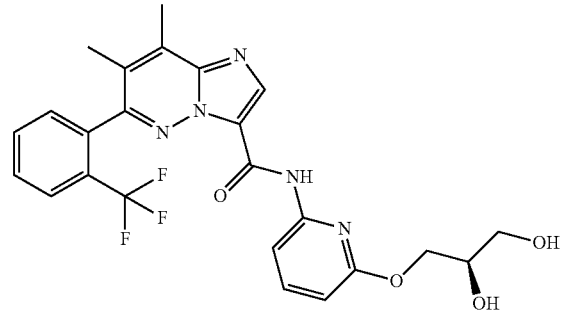 [SMILES: Cc1c(-c2ccccc2C(F)(F)F)nn2c(C(=O)Nc3cccc(OC[C@H](O)CO)n3)cnc2c1C] | A | A | A | A |
| 388 | 407 | 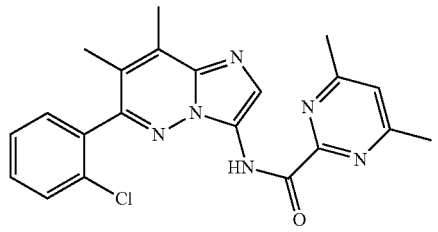 [SMILES: Cc1cc(C)nc(C(=O)Nc2cnc3c(C)c(C)c(-c4ccccc4Cl)nn23)n1] | A | A | NT | NT |
| 389 | 399 | 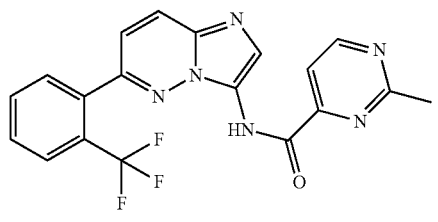 [SMILES: Cc1nccc(C(=O)Nc2cnc3ccc(-c4ccccc4C(F)(F)F)nn23)n1] | A | A | B | B |
| 390 | 485 | 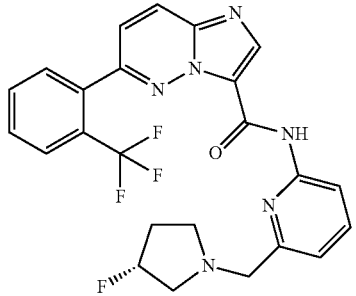 [SMILES: O=C(Nc1cccc(CN2CC[C@@H](F)C2)n1)c1cnc2ccc(-c3ccccc3C(F)(F)F)nn12] | A | A | NT | NT |

TABLE 1-continued
Compounds of Formula (I).
| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 391 | 517 | 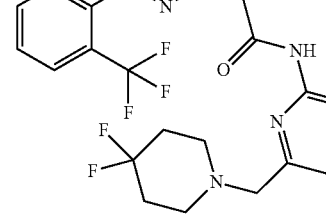 | A | A | NT | NT |
| 392 | 398 | 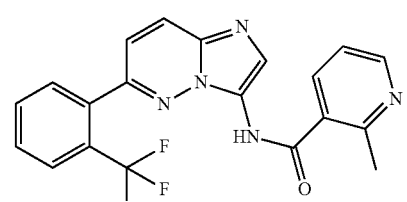 | C | B | C | B |
| 393 | 398 | 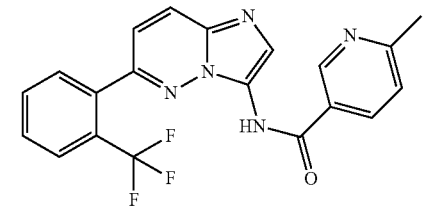 [SMILES: Cc1ccc(C(=O)Nc2cnc3ccc(-c4ccccc4C(F)(F)F)nn23)cn1] | B | B | C | B |
| 394 | 412 | 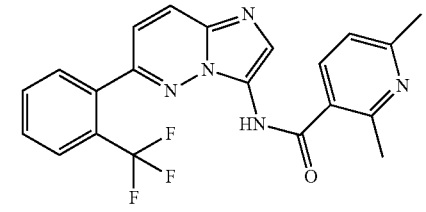 [SMILES: Cc1ccc(C(=O)Nc2cnc3ccc(-c4ccccc4C(F)(F)F)nn23)c(C)n1] | B | B | NT | NT |
| 395 | 401 | 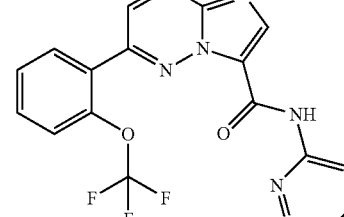 | A | A | A | A |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 396 | 415 | | A | A | NT | NT |
| 397 | 420 | | A | B | NT | NT |
| 398 | 429 | | A | A | B | B |
| 399 | 429 | | B | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 400 | 500 | | A | A | NT | NT |
| 401 | 415 | | A | A | A | A |
| 402 | 468 | | A | A | NT | NT |
| 403 | 432 | | A | A | NT | NT |
| 404 | 404 | | B | B | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 405 | 418 | | B | A | NT | NT |
| 406 | 488 | | A | A | A | A |
| 407 | 398 | | A | A | B | A |
| 408 | 399 | | A | A | NT | NT |
| 409 | 399 | | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 410 | 399 | 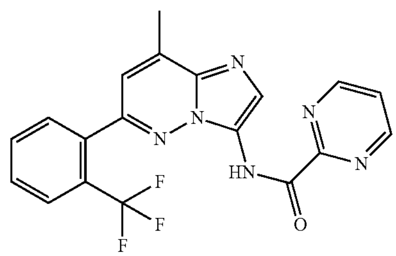 [SMILES: Cc1cc(-c2ccccc2C(F)(F)F)nn2c(NC(=O)c3ncccn3)cnc12] | A | A | NT | NT |
| 411 | 404 | 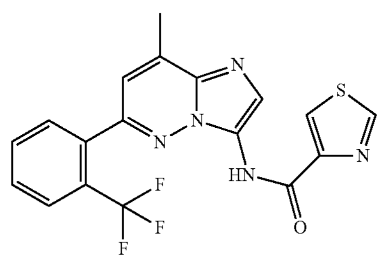 [SMILES: Cc1cc(-c2ccccc2C(F)(F)F)nn2c(NC(=O)c3cscn3)cnc12] | A | A | NT | NT |
| 412 | 418 | 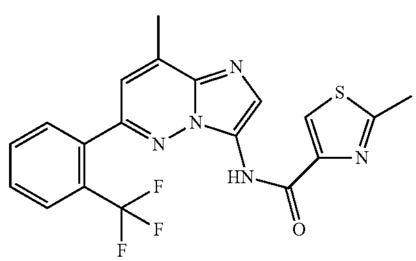 [SMILES: Cc1nc(C(=O)Nc2cnc3c(C)cc(-c4ccccc4C(F)(F)F)nn23)cs1] | A | A | A | A |
| 413 | 432 | 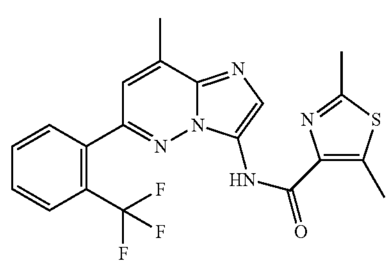 [SMILES: Cc1nc(C(=O)Nc2cnc3c(C)cc(-c4ccccc4C(F)(F)F)nn23)c(C)s1] | A | A | A | B |
| 414 | 404 | 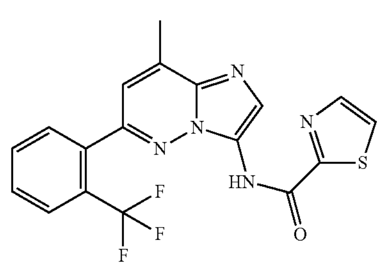 [SMILES: Cc1cc(-c2ccccc2C(F)(F)F)nn2c(NC(=O)c3nccs3)cnc12] | A | A | NT | NT |

TABLE 1-continued

Compounds of Formula (I).

| Compound No | [M + H]+$_{[Calc]}$ | Structure | TAMRA EC1.5 (µM) | TAMRA % Fold Act | Trp EC1.5 (µM) | Trp % Fold Act |
|---|---|---|---|---|---|---|
| 415 | 434 | 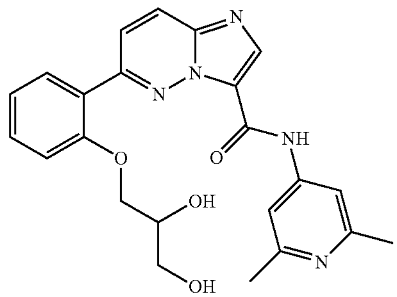 [SMILES: Cc1cc(NC(=O)c2cnc3ccc(-c4ccccc4OCC(O)CO)nn23)cc(C)n1] | A | A | B | A |
| 416 | 420 | 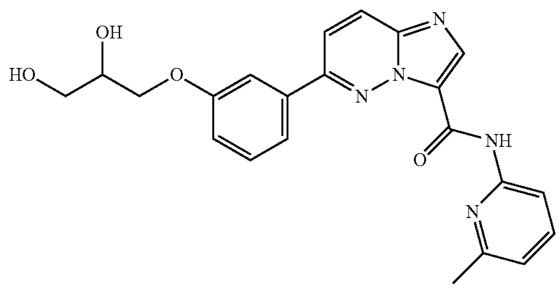 [SMILES: Cc1cccc(NC(=O)c2cnc3ccc(-c4cccc(OCC(O)CO)c4)nn23)n1] | A | A | NT | NT |
| 417 | 434 | 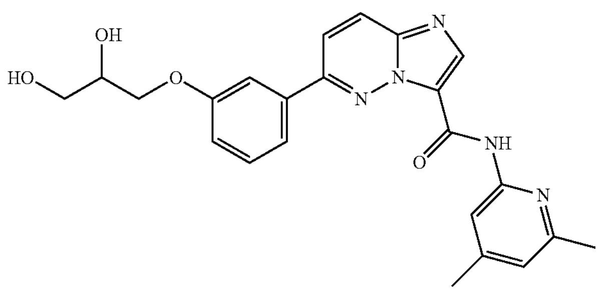 [SMILES: Cc1cc(C)nc(NC(=O)c2cnc3ccc(-c4cccc(OCC(O)CO)c4)nn23)c1] | A | A | NT | NT |
| 418 | 434 | 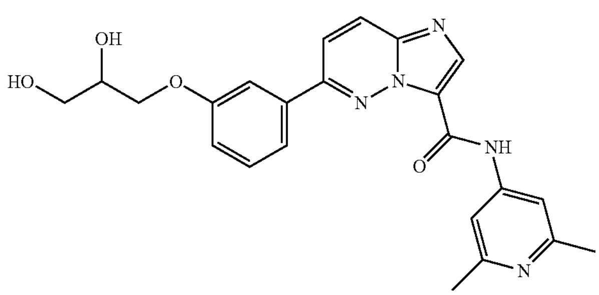 [SMILES: Cc1cc(NC(=O)c2cnc3ccc(-c4cccc(OCC(O)CO)c4)nn23)cc(C)n1] | B | B | C | B |
| 419 | 428 | 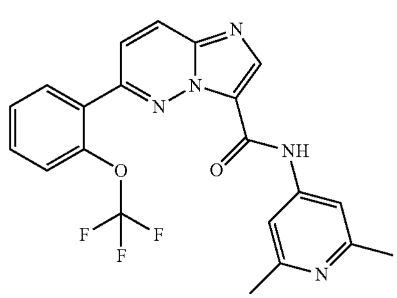 [SMILES: Cc1cc(NC(=O)c2cnc3ccc(-c4ccccc4OC(F)(F)F)nn23)cc(C)n1] | A | A | A | A |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 420 | 441 | 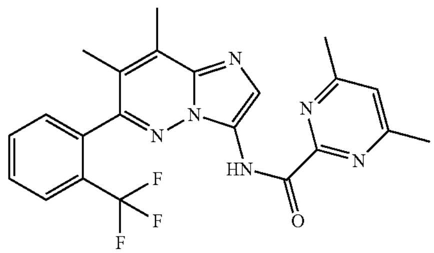 [SMILES: Cc1cc(C)nc(C(=O)Nc2cnc3c(C)c(C)c(-c4ccccc4C(F)(F)F)nn23)n1] | A | A | NT | NT |
| 421 | 481 | 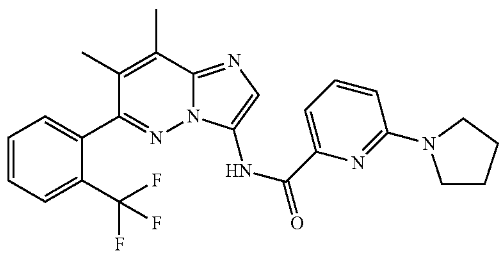 [SMILES: Cc1c(-c2ccccc2C(F)(F)F)nn2c(NC(=O)c3cccc(N4CCCC4)n3)cnc2c1C] | A | A | A | A |
| 422 | 502 | 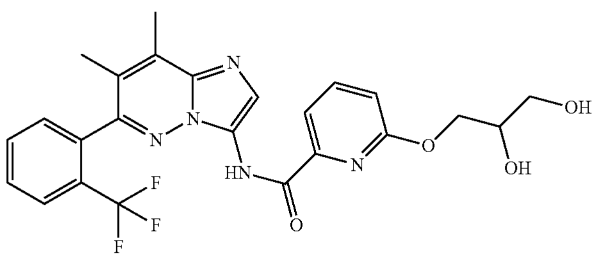 [SMILES: Cc1c(-c2ccccc2C(F)(F)F)nn2c(NC(=O)c3cccc(OCC(O)CO)n3)cnc2c1C] | A | A | NT | NT |
| 423 | 474 | 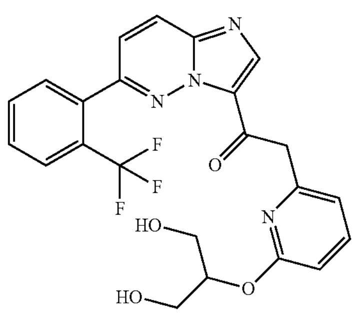 [SMILES: O=C(Cc1cccc(OC(CO)CO)n1)c1cnc2ccc(-c3ccccc3C(F)(F)F)nn12] | A | A | NT | NT |
| 424 | 418 | 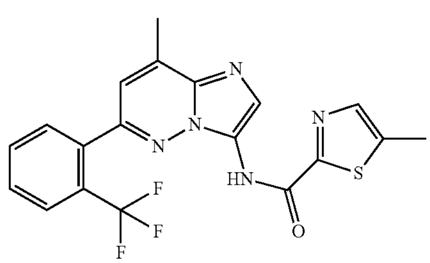 [SMILES: Cc1cnc(C(=O)Nc2cnc3c(C)cc(-c4ccccc4C(F)(F)F)nn23)s1] | A | A | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 425 | 483 | 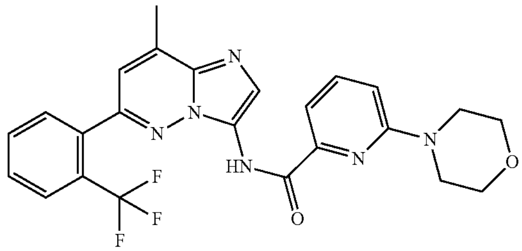 [SMILES: Cc1cc(-c2ccccc2C(F)(F)F)nn2c(NC(=O)c3cccc(N4CCOCC4)n3)cnc12] | A | A | A | A |
| 426 | 453 | 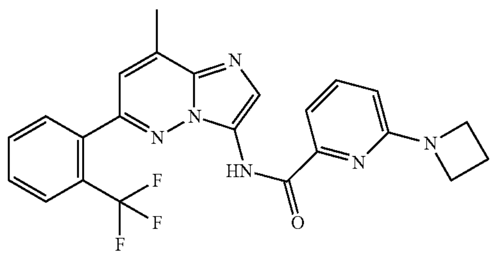 [SMILES: Cc1cc(-c2ccccc2C(F)(F)F)nn2c(NC(=O)c3cccc(N4CCC4)n3)cnc12] | A | A | NT | NT |
| 427 | 488 | 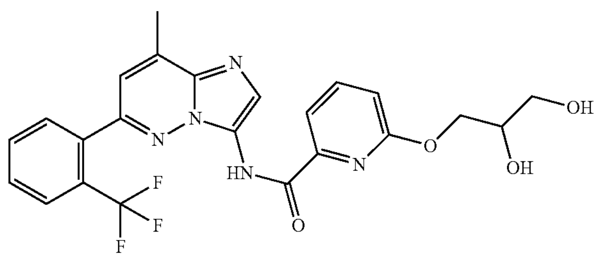 [SMILES: Cc1cc(-c2ccccc2C(F)(F)F)nn2c(NC(=O)c3cccc(OCC(O)CO)n3)cnc12] | A | A | A | A |
| 428 | 413 | 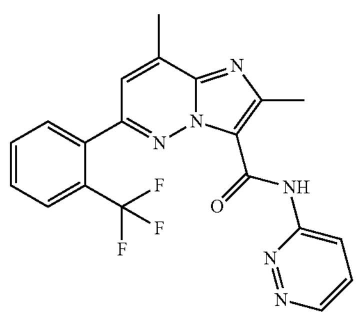 [SMILES: Cc1nc2c(C)cc(-c3ccccc3C(F)(F)F)nn2c1C(=O)Nc1cccnn1] | A | A | A | A |
| 429 | 440 | 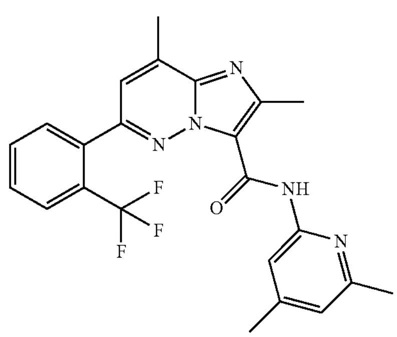 [SMILES: Cc1cc(C)nc(NC(=O)c2c(C)nc3c(C)cc(-c4ccccc4C(F)(F)F)nn23)c1] | A | A | NT | NT |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 430 | 431 | | A | A | A | A |
| 431 | 414 | | A | A | B | B |
| 432 | 440 | | A | A | NT | NT |
| 433 | 418 | | A | A | C | B |
| 434 | 404 | | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 435 | 483 | 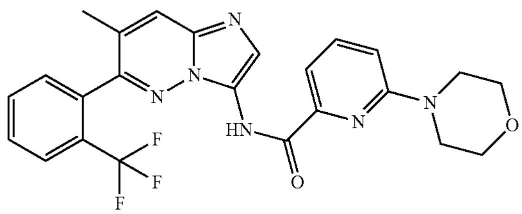 [SMILES: Cc1cc2ncc(NC(=O)c3cccc(N4CCOCC4)n3)n2nc1-c1ccccc1C(F)(F)F] | A | A | NT | NT |
| 436 | 412 | 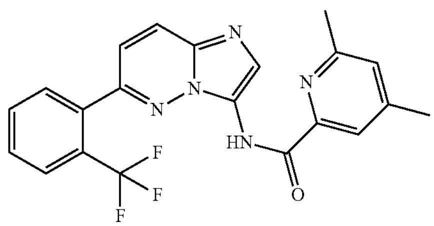 [SMILES: Cc1cc(C)nc(C(=O)Nc2cnc3ccc(-c4ccccc4C(F)(F)F)nn23)c1] | A | A | C | B |
| 437 | 414 | 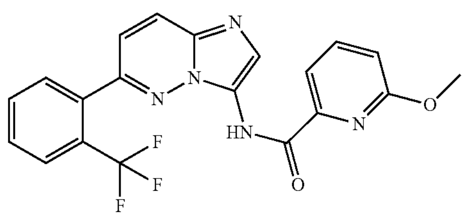 [SMILES: COc1cccc(C(=O)Nc2cnc3ccc(-c4ccccc4C(F)(F)F)nn23)n1] | A | A | A | A |
| 438 | 451 | 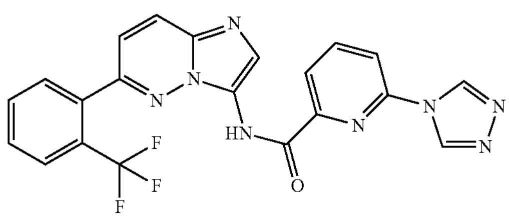 [SMILES: O=C(Nc1cnc2ccc(-c3ccccc3C(F)(F)F)nn12)c1cccc(-n2cnnc2)n1] | A | A | NT | NT |
| 439 | 402 | 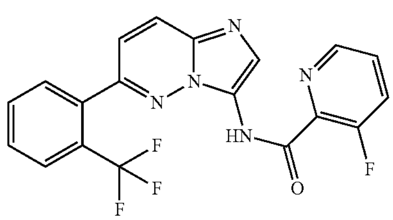 | A | A | A | B |
| 440 | 420 | 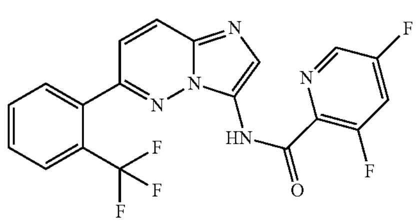 [SMILES: O=C(Nc1cnc2ccc(-c3ccccc3C(F)(F)F)nn12)c1ncc(F)cc1F] | A | A | NT | NT |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 441 | 398 | | A | A | NT | NT |
| 442 | 399 | | A | A | C | B |
| 443 | 399 | | A | A | C | B |
| 444 | 399 | | A | A | NT | NT |
| 445 | 432 | | A | A | B | B |
| 446 | 404 | | A | A | NT | NT |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 447 | 418 | | A | A | NT | NT |
| 448 | 453 | | A | A | B | A |
| 449 | 488 | | A | A | A | A |
| 450 | 384 | | B | A | NT | NT |
| 451 | 384 | | B | A | B | A |
| 452 | 385 | | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 453 | 385 | 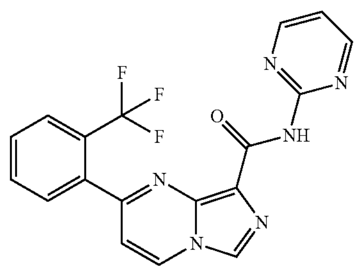 [SMILES: O=C(Nc1ncccn1)c1ncn2ccc(-c3ccccc3C(F)(F)F)nc12] | B | A | NT | NT |
| 454 | 469 | 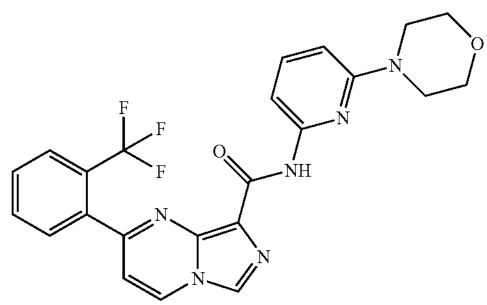 [SMILES: O=C(Nc1cccc(N2CCOCC2)n1)c1ncn2ccc(-c3ccccc3C(F)(F)F)nc12] | A | A | A | A |
| 455 | 384 | 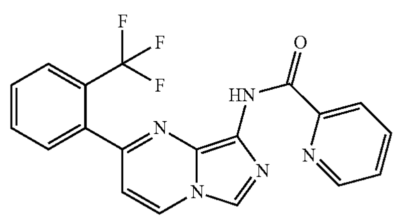 [SMILES: O=C(Nc1ncn2ccc(-c3ccccc3C(F)(F)F)nc12)c1ccccn1] | B | B | C | B |
| 456 | 469 | 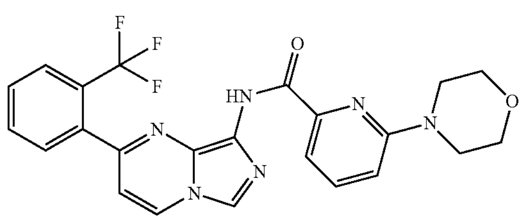 [SMILES: O=C(Nc1ncn2ccc(-c3ccccc3C(F)(F)F)nc12)c1cccc(N2CCOCC2)n1] | A | A | NT | NT |
| 457 | 446 | 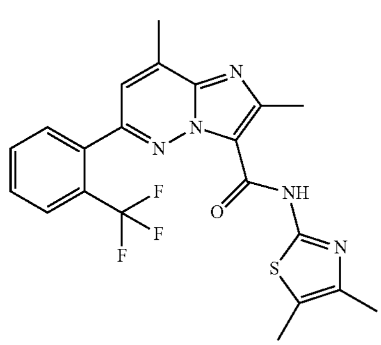 [SMILES: Cc1nc(NC(=O)c2c(C)nc3c(C)cc(-c4ccccc4C(F)(F)F)nn23)sc1C] | A | A | A | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 458 | 426 | 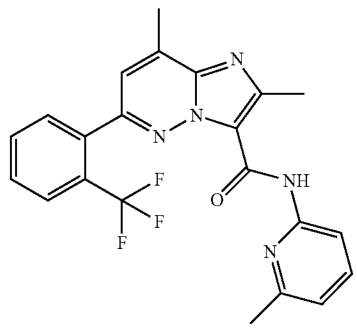 [SMILES: Cc1cccc(NC(=O)c2c(C)nc3c(C)cc(-c4ccccc4C(F)(F)F)nn23)n1] | A | A | NT | NT |
| 459 | 426 | 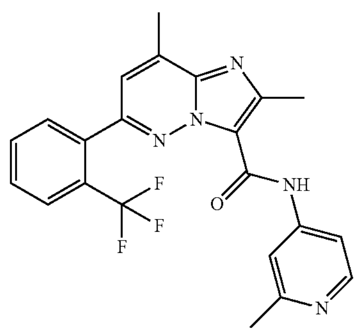 [SMILES: Cc1cc(NC(=O)c2c(C)nc3c(C)cc(-c4ccccc4C(F)(F)F)nn23)ccn1] | A | A | NT | NT |
| 460 | 413 | 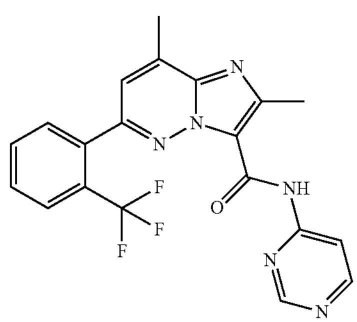 [SMILES: Cc1nc2c(C)cc(-c3ccccc3C(F)(F)F)nn2c1C(=O)Nc1ccncn1] | A | A | A | A |
| 461 | 399 | 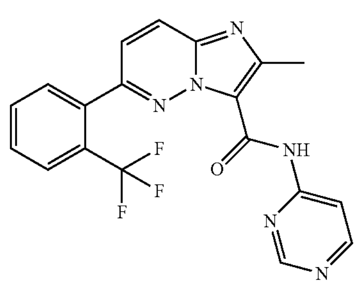 [SMILES: Cc1nc2ccc(-c3ccccc3C(F)(F)F)nn2c1C(=O)Nc1ccncn1] | A | A | B | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 462 | 399 | | A | A | NT | NT |
| 463 | 399 | | A | A | B | A |
| 464 | 416 | | A | A | NT | NT |
| 465 | 416 | | A | A | NT | NT |
| 466 | 432 | | A | A | A | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 467 | 400 | 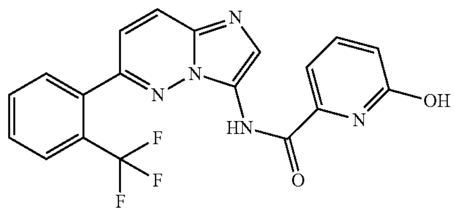 [SMILES: O=C(Nc1cnc2ccc(-c3ccccc3C(F)(F)F)nn12)c1cccc(O)n1] | B | A | B | B |
| 468 | 503 | 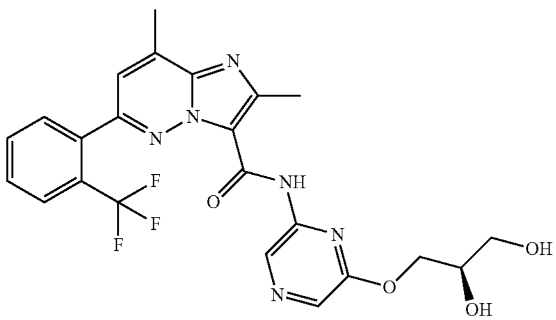 [SMILES: Cc1nc2c(C)cc(-c3ccccc3C(F)(F)F)nn2c1C(=O)Nc1cncc(OC[C@H](O)CO)n1] | A | A | NT | NT |
| 469 | 415 | 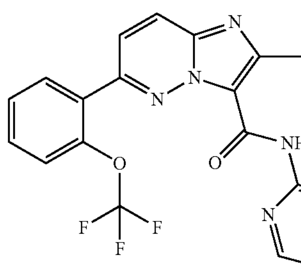 | A | A | B | A |
| 470 | 415 | 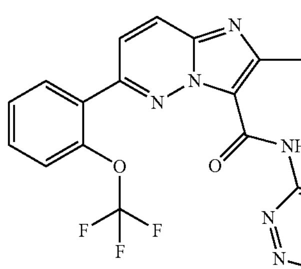 | A | A | NT | NT |
| 471 | 415 | 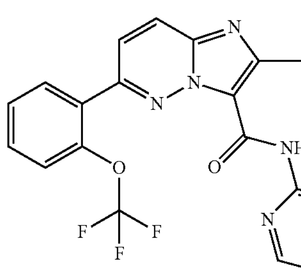 | A | A | NT | NT |

TABLE 1-continued

Compounds of Formula (I).

| Compound No | [M + H]+_[Calc] | Structure | TAMRA EC1.5 (μM) | TAMRA % Fold Act | Trp EC1.5 (μM) | Trp % Fold Act |
|---|---|---|---|---|---|---|
| 472 | 432 | 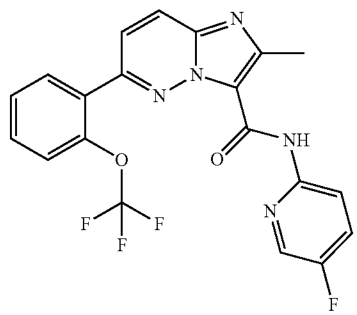 [SMILES: Cc1nc2ccc(-c3ccccc3OC(F)(F)F)nn2c1C(=O)Nc1ccc(F)cn1] | B | B | C | B |
| 473 | 430 | 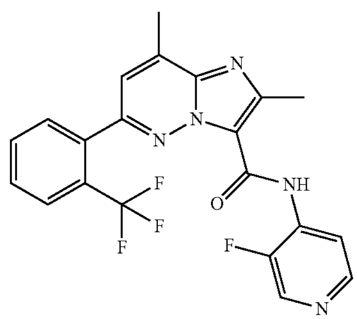 [SMILES: Cc1nc2c(C)cc(-c3ccccc3C(F)(F)F)nn2c1C(=O)Nc1ccncc1F] | A | A | A | A |
| 474 | 430 | 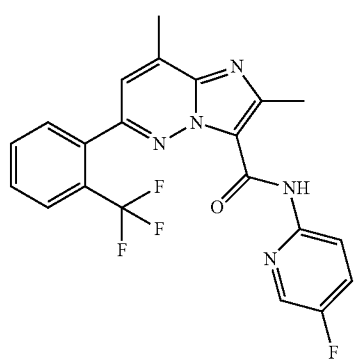 [SMILES: Cc1nc2c(C)cc(-c3ccccc3C(F)(F)F)nn2c1C(=O)Nc1ccc(F)cn1] | A | A | NT | NT |
| 475 | 441 | 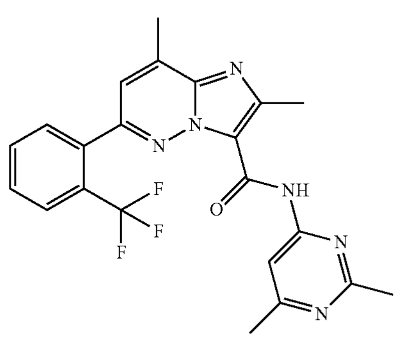 [SMILES: Cc1cc(NC(=O)c2c(C)nc3c(C)cc(-c4ccccc4C(F)(F)F)nn23)nc(C)n1] | A | A | B | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 476 | 429 | 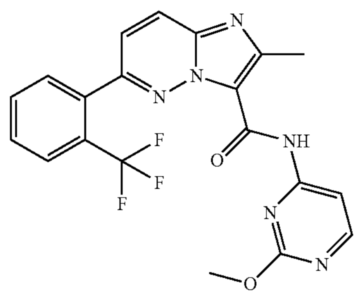 [SMILES: COc1nccc(NC(=O)c2c(C)nc3ccc(-c4ccccc4C(F)(F)F)nn23)n1] | A | A | NT | NT |
| 477 | 445 | 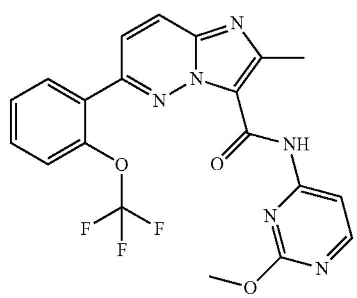 [SMILES: COc1nccc(NC(=O)c2c(C)nc3ccc(-c4ccccc4OC(F)(F)F)nn23)n1] | A | A | NT | NT |
| 478 | 429 | 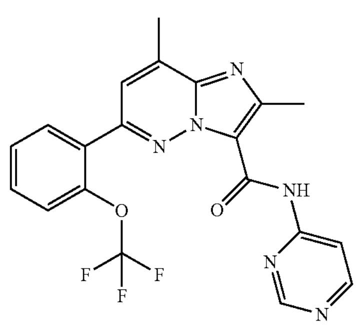 [SMILES: Cc1nc2c(C)cc(-c3ccccc3OC(F)(F)F)nn2c1C(=O)Nc1ccncn1] | A | A | A | A |
| 479 | 429 | 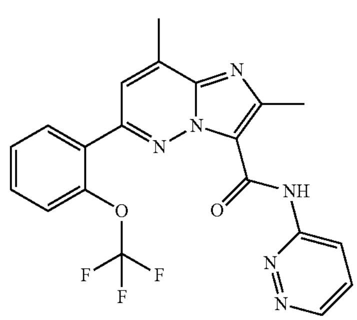 [SMILES: Cc1nc2c(C)cc(-c3ccccc3OC(F)(F)F)nn2c1C(=O)Nc1cccnn1] | A | A | NT | NT |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 480 | 442 | | A | A | B | B |
| 481 | 442 | | A | A | A | A |
| 482 | 462 | | A | A | NT | NT |
| 483 | 384 | | NT | NT | NT | NT |
| 484 | 385 | | B | B | C | B |

TABLE 1-continued
Compounds of Formula (I).
| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 485 | 400 | 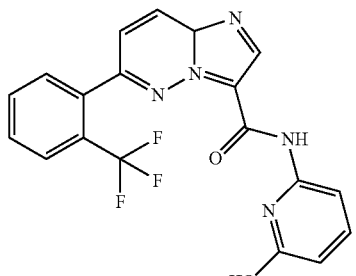 | B | B | NT | NT |
| 486 | 414 | 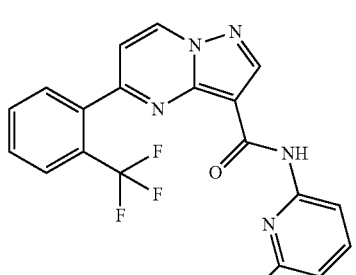 | A | A | A | A |
| 487 | 412 | 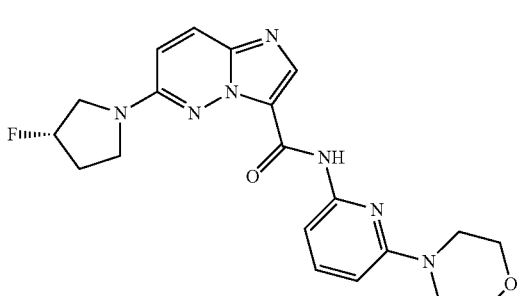 | B | B | A | A |
| 488 | 412 | 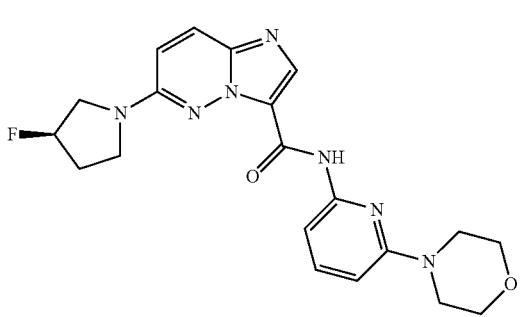 [SMILES: O=C(Nc1cccc(N2CCOCC2)n1)c1cnc2ccc(N3CC[C@@H](F)C3)nn12] | B | A | NT | NT |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 489 | 430 | 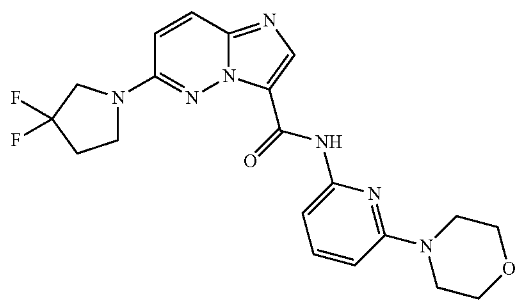 [SMILES: O=C(Nc1cccc(N2CCOCC2)n1)c1cnc2ccc(N3CCC(F)(F)C3)nn12] | B | B | A | A |
| 490 | 355 | 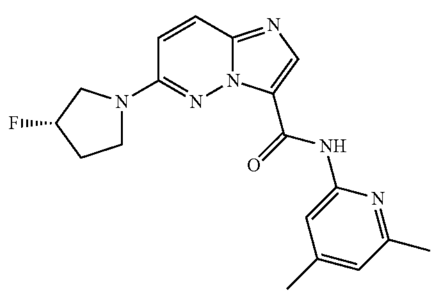 [SMILES: Cc1cc(C)nc(NC(=O)c2cnc3ccc(N4CC[C@H](F)C4)nn23)c1] | B | A | B | B |
| 491 | 355 | 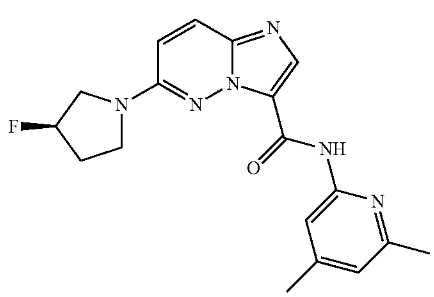 [SMILES: Cc1cc(C)nc(NC(=O)c2cnc3ccc(N4CC[C@@H](F)C4)nn23)c1] | B | B | NT | NT |
| 492 | 373 | 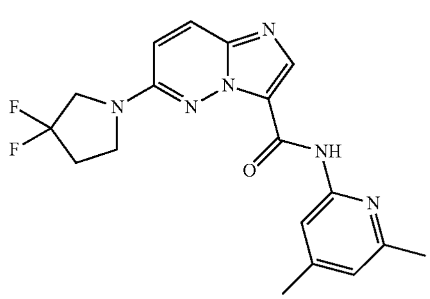 [SMILES: Cc1cc(C)nc(NC(=O)c2cnc3ccc(N4CCC(F)(F)C4)nn23)c1] | B | B | NT | NT |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 493 | 456 | 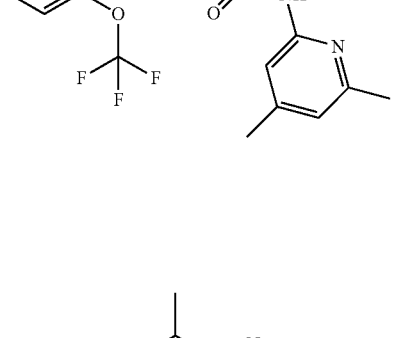 | A | A | ND | ND |
| 494 | 446 | 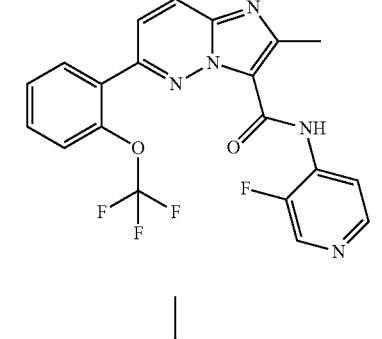 | A | A | NT | NT |
| 495 | 446 | 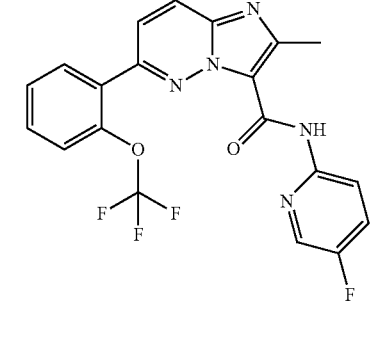 | A | B | ND | ND |
| 496 | 414 | 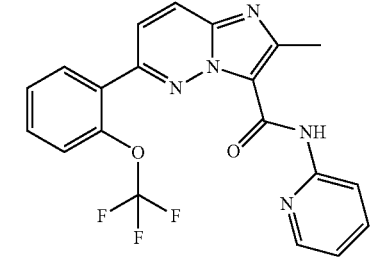 [SMILES: Cc1nc2ccc(-c3ccccc3OC(F)(F)F)nn2c1C(=O)Nc1ccccn1] | A | A | A | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 497 | 414 | | A | A | NT | NT |
| 498 | 398 | | A | A | NT | NT |
| 499 | 398 | | A | A | A | A |
| 500 | 398 | | A | A | NT | NT |
| 501 | 398 | | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 502 | 412 | 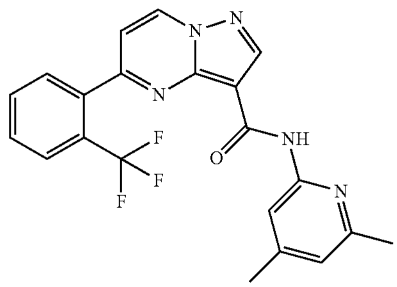 [SMILES: Cc1cc(C)nc(NC(=O)c2cnn3ccc(-c4ccccc4C(F)(F)F)nc23)c1] | A | A | ND | ND |
| 503 | 413 | 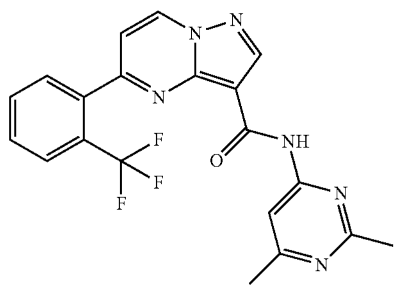 [SMILES: Cc1cc(NC(=O)c2cnn3ccc(-c4ccccc4C(F)(F)F)nc23)nc(C)n1] | A | A | NT | NT |
| 504 | 412 | 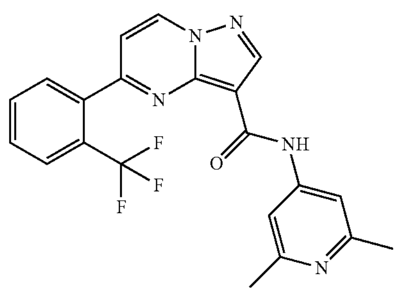 [SMILES: Cc1cc(NC(=O)c2cnn3ccc(-c4ccccc4C(F)(F)F)nc23)cc(C)n1] | A | A | NT | NT |
| 505 | 385 | 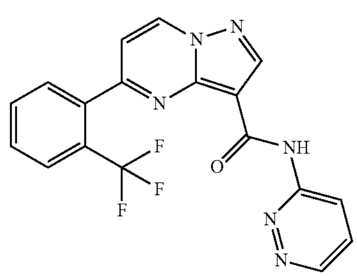 [SMILES: O=C(Nc1cccnn1)c1cnn2ccc(-c3ccccc3C(F)(F)F)nc12] | A | A | B | B |
| 506 | 390 | 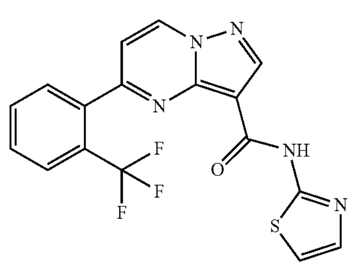 [SMILES: O=C(Nc1nccs1)c1cnn2ccc(-c3ccccc3C(F)(F)F)nc12] | A | A | NT | NT |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 507 | 404 | 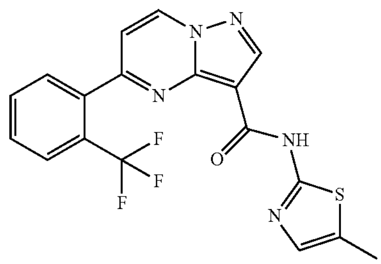 [SMILES: Cc1cnc(NC(=O)c2cnn3ccc(-c4ccccc4C(F)(F)F)nc23)s1] | A | A | B | B |
| 508 | 404 | 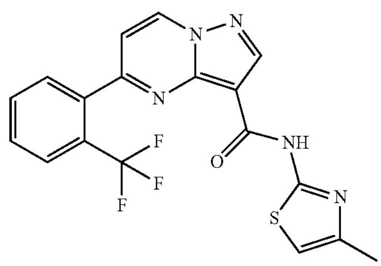 [SMILES: Cc1csc(NC(=O)c2cnn3ccc(-c4ccccc4C(F)(F)F)nc23)n1] | A | A | A | A |
| 509 | 418 | 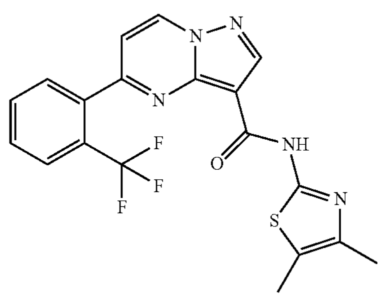 [SMILES: Cc1nc(NC(=O)c2cnn3ccc(-c4ccccc4C(F)(F)F)nc23)sc1C] | A | A | NT | NT |
| 510 | 437 | 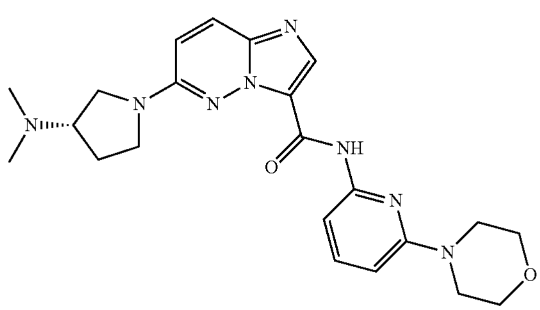 [SMILES: CN(C)[C@H]1CCN(c2ccc3ncc(C(=O)Nc4cccc(N5CCOCC5)n4)n3n2)C1] | B | B | NT | NT |
| 511 | 437 | 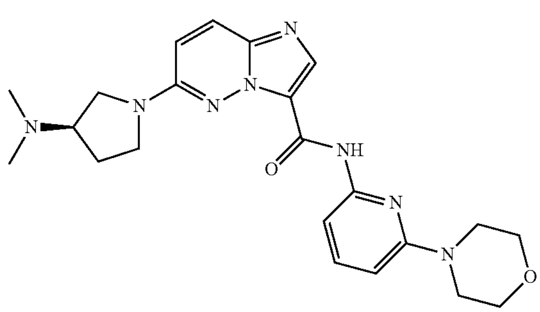 [SMILES: CN(C)[C@@H]1CCN(c2ccc3ncc(C(=O)Nc4cccc(N5CCOCC5)n4)n3n2)C1] | B | B | B | B |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 512 | 380 | 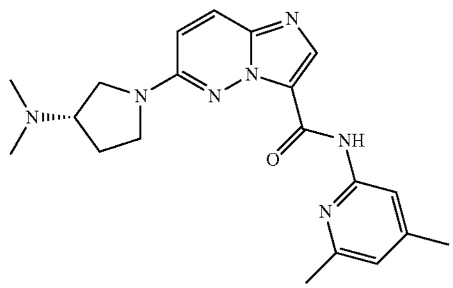 | B | B | NT | NT |
| 513 | 380 | 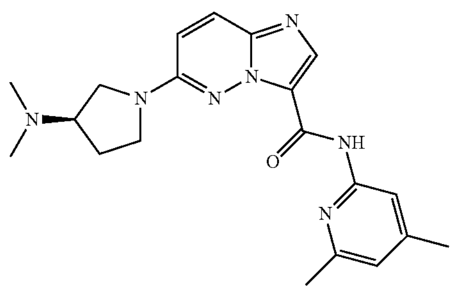 | B | B | C | B |
| 514 | 399 | 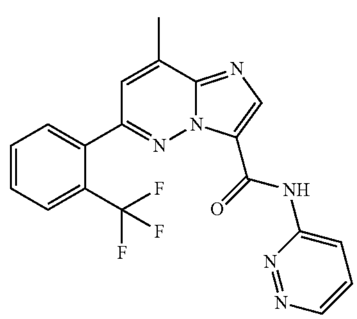 [SMILES: Cc1cc(-c2ccccc2C(F)(F)F)nn2c(C(=O)Nc3cccnn3)cnc12] | A | A | A | A |
| 515 | 399 | 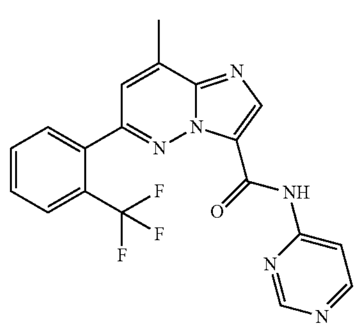 [SMILES: Cc1cc(-c2ccccc2C(F)(F)F)nn2c(C(=O)Nc3ccncn3)cnc12] | A | A | NT | NT |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 516 | 426 | 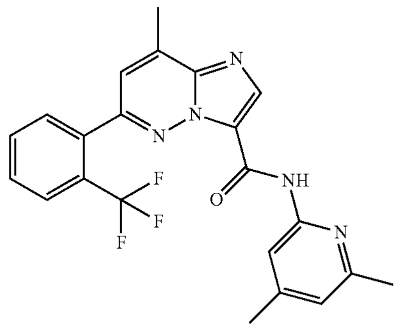 [SMILES: Cc1cc(C)nc(NC(=O)c2cnc3c(C)cc(-c4ccccc4C(F)(F)F)nn23)c1] | A | A | B | B |
| 517 | 402 | 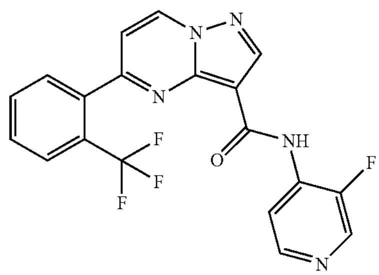 [SMILES: O=C(Nc1ccncc1F)c1cnn2ccc(-c3ccccc3C(F)(F)F)nc12] | B | A | B | B |
| 518 | 402 | 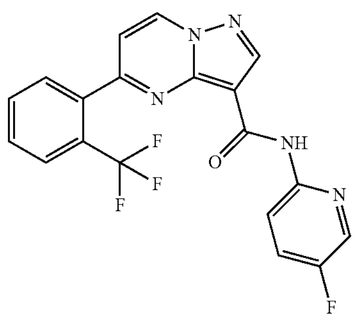 [SMILES: O=C(Nc1ccc(F)cn1)c1cnn2ccc(-c3ccccc3C(F)(F)F)nc12] | A | A | B | B |
| 519 | 415 | 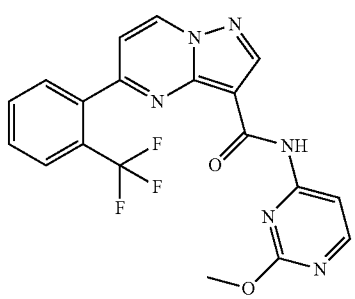 [SMILES: COc1nccc(NC(=O)c2cnn3ccc(-c4ccccc4C(F)(F)F)nc23)n1] | A | A | NT | NT |
| 520 | 400 | 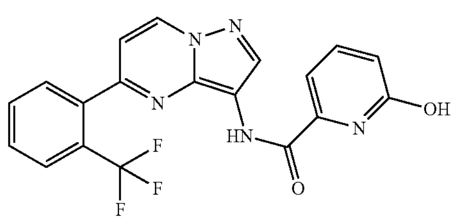 [SMILES: O=C(Nc1cnn2ccc(-c3ccccc3C(F)(F)F)nc12)c1cccc(O)n1] | B | B | NT | NT |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 521 | 414 | 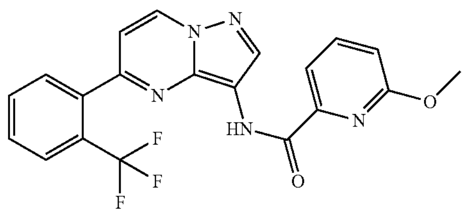 [SMILES: COc1cccc(C(=O)Nc2cnn3ccc(-c4ccccc4C(F)(F)F)nc23)n1] | A | A | A | B |
| 522 | 398 | 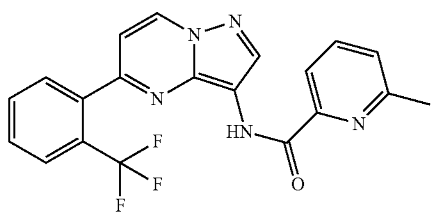 [SMILES: Cc1cccc(C(=O)Nc2cnn3ccc(-c4ccccc4C(F)(F)F)nc23)n1] | A | A | NT | NT |
| 523 | 398 | 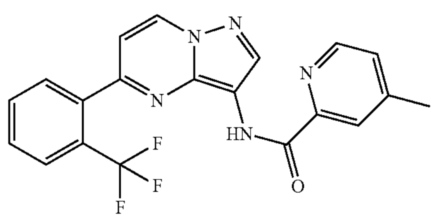 [SMILES: Cc1ccnc(C(=O)Nc2cnn3ccc(-c4ccccc4C(F)(F)F)nc23)c1] | A | A | C | B |
| 524 | 412 | 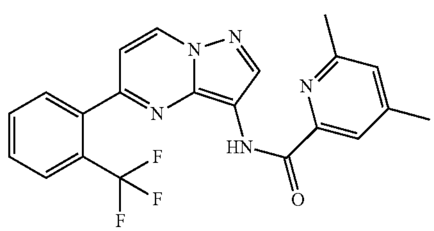 [SMILES: Cc1cc(C)nc(C(=O)Nc2cnn3ccc(-c4ccccc4C(F)(F)F)nc23)c1] | A | A | C | B |
| 525 | 404 | 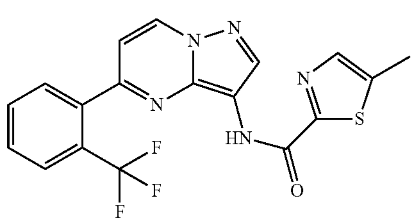 [SMILES: Cc1cnc(C(=O)Nc2cnn3ccc(-c4ccccc4C(F)(F)F)nc23)s1] | A | A | NT | NT |
| 526 | 418 | 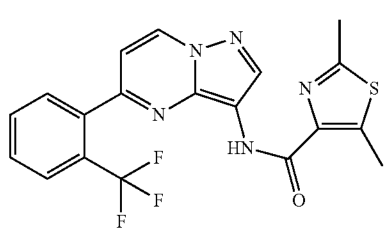 [SMILES: Cc1nc(C(=O)Nc2cnn3ccc(-c4ccccc4C(F)(F)F)nc23)c(C)s1] | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 527 | 404 | 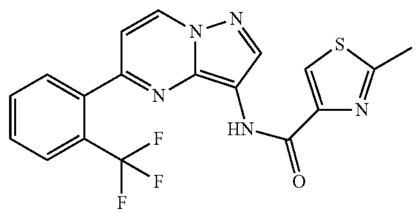 [SMILES: Cc1nc(C(=O)Nc2cnn3ccc(-c4ccccc4C(F)(F)F)nc23)cs1] | A | A | B | B |
| 528 | 426 | 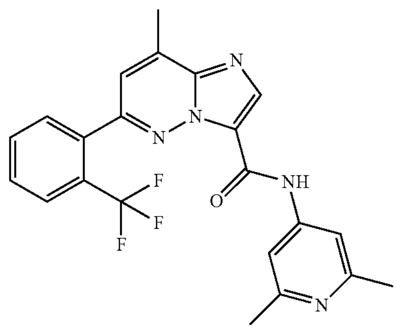 [SMILES: Cc1cc(NC(=O)c2cnc3c(C)cc(-c4ccccc4C(F)(F)F)nn23)cc(C)n1] | A | A | NT | NT |
| 529 | 400 | 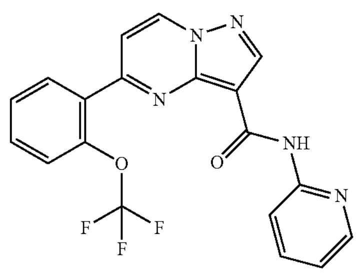 [SMILES: O=C(Nc1ccccn1)c1cnn2ccc(-c3ccccc3OC(F)(F)F)nc12] | A | A | A | B |
| 530 | 400 | 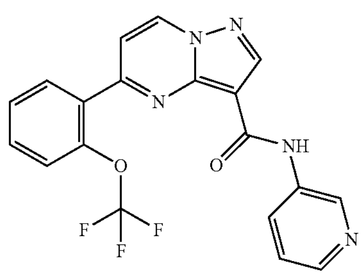 [SMILES: O=C(Nc1cccnc1)c1cnn2ccc(-c3ccccc3OC(F)(F)F)nc12] | A | A | A | A |
| 531 | 400 | 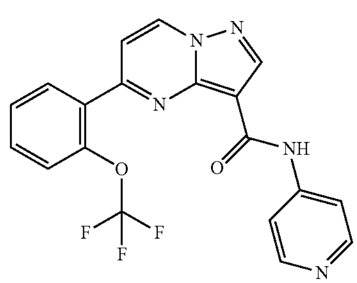 [SMILES: O=C(Nc1ccncc1)c1cnn2ccc(-c3ccccc3OC(F)(F)F)nc12] | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 532 | 401 | 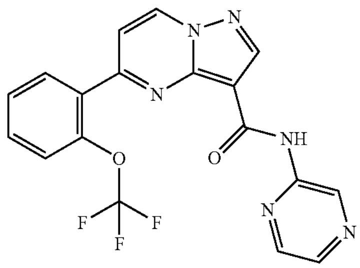 [SMILES: O=C(Nc1cnccn1)c1cnn2ccc(-c3ccccc3OC(F)(F)F)nc12] | A | A | NT | NT |
| 533 | 401 | 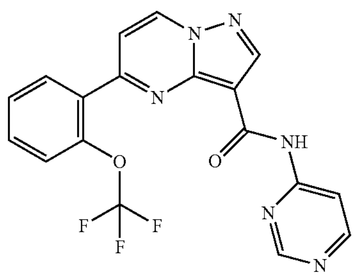 [SMILES: O=C(Nc1ccncn1)c1cnn2ccc(-c3ccccc3OC(F)(F)F)nc12] | A | A | B | B |
| 534 | 485 | 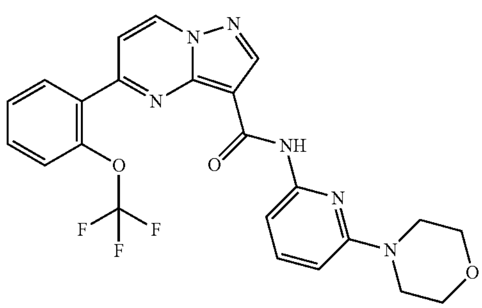 [SMILES: O=C(Nc1cccc(N2CCOCC2)n1)c1cnn2ccc(-c3ccccc3OC(F)(F)F)nc12] | A | A | NT | NT |
| 535 | 499 | 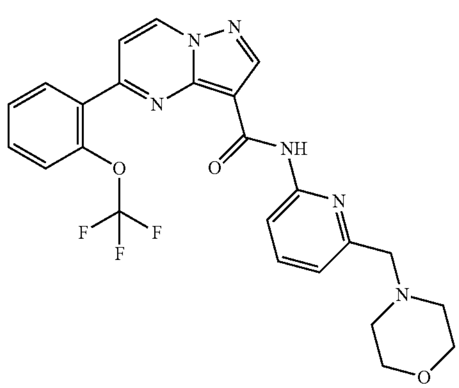 [SMILES: O=C(Nc1cccc(CN2CCOCC2)n1)c1cnn2ccc(-c3ccccc3OC(F)(F)F)nc12] | A | A | A | A |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 536 | 430 | | A | A | A | B |
| 537 | 481 | | A | A | NT | NT |
| 538 | 481 | | A | A | NT | NT |
| 539 | 412 | | A | A | ND | ND |

TABLE 1-continued

Compounds of Formula (I).

| Compound No | [M + H]+[Calc] | Structure | TAMRA | | Trp | |
|---|---|---|---|---|---|---|
| | | | EC1.5 (µM) | % Fold Act | EC1.5 (µM) | % Fold Act |
| 540 | 412 | 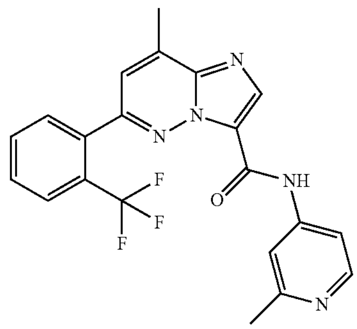 [SMILES: Cc1cc(NC(=O)c2cnc3c(C)cc(-c4ccccc4C(F)(F)F)nn23)ccn1] | A | A | NT | NT |
| 541 | 416 | 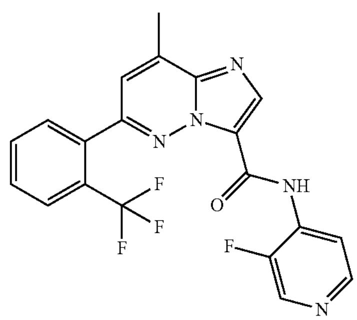 [SMILES: Cc1cc(-c2ccccc2C(F)(F)F)nn2c(C(=O)Nc3ccncc3F)cnc12] | A | A | B | A |
| 542 | 416 | 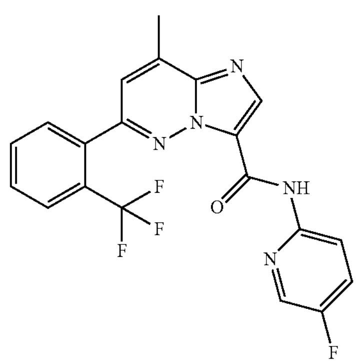 [SMILES: Cc1cc(-c2ccccc2C(F)(F)F)nn2c(C(=O)Nc3ccc(F)cn3)cnc12] | A | A | B | B |
| 543 | 443 | 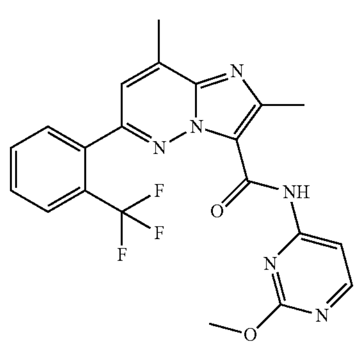 [SMILES: COc1nccc(NC(=O)c2c(C)nc3c(C)cc(-c4ccccc4C(F)(F)F)nn23)n1] | A | A | NT | NT |

TABLE 1-continued

Compounds of Formula (I).

| Compound No | [M + H]+_[Calc] | Structure | TAMRA EC1.5 (μM) | % Fold Act | Trp EC1.5 (μM) | % Fold Act |
|---|---|---|---|---|---|---|
| 544 | 509 | | A | A | NT | NT |
| 545 | 525 | | A | A | A | A |
| 546 | 495 | | A | A | NT | NT |
| 547 | 399 | | A | A | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 548 | 398 | | A | A | ND | ND |
| 549 | 398 | | A | A | B | A |
| 550 | 497 | | A | A | NT | NT |
| 551 | 428 | | A | A | A | A |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 552 | 483 | 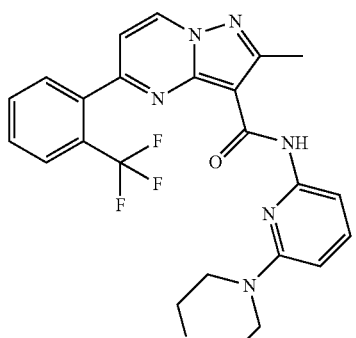 | A | A | A | A |
| 553 | 474 | 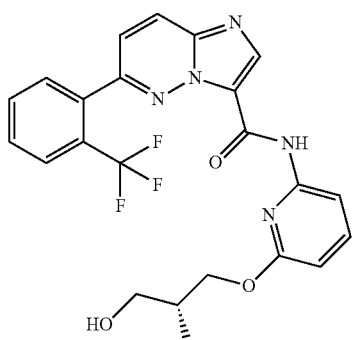 | A | A | NT | NT |
| 554 | 474 | 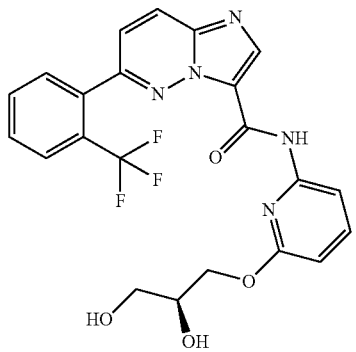 [SMILES: O=C(Nc1cccc(OC[C@@H](O)CO)n1)c1cnc2ccc(-c3ccccc3C(F)(F)F)nn12] | A | A | NT | NT |
| 555 | 475 | 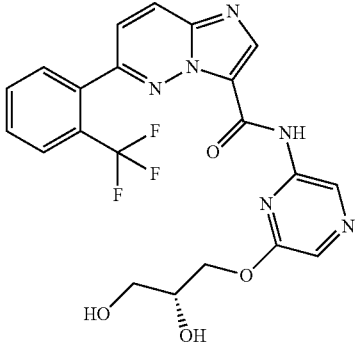 [SMILES: O=C(Nc1cncc(OC[C@H](O)CO)n1)c1cnc2ccc(-c3ccccc3C(F)(F)F)nn12] | A | A | A | A |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 556 | 475 | 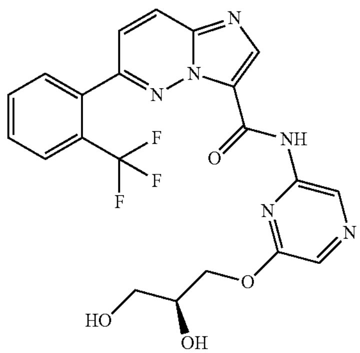 [SMILES: O=C(Nc1cncc(OC[C@@H](O)CO)n1)c1cnc2ccc(-c3ccccc3C(F)(F)F)nn12] | A | A | NT | NT |
| 557 | 488 | 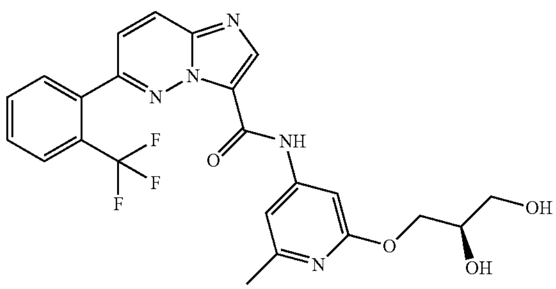 [SMILES: Cc1cc(NC(=O)c2cnc3ccc(-c4ccccc4C(F)(F)F)nn23)cc(OC[C@H](O)CO)n1] | A | A | NT | NT |
| 558 | 488 | 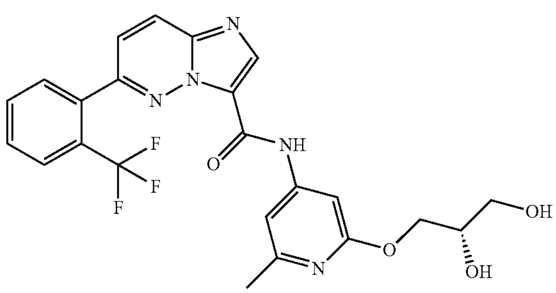 [SMILES: Cc1cc(NC(=O)c2cnc3ccc(-c4ccccc4C(F)(F)F)nn23)cc(OC[C@@H](O)CO)n1] | A | A | A | A |
| 559 | 401 | 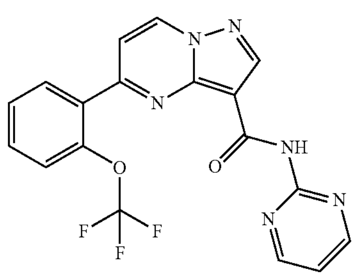 [SMILES: O=C(Nc1ncccn1)c1cnn2ccc(-c3ccccc3OC(F)(F)F)nc12] | B | B | B | A |
| 560 | 398 | 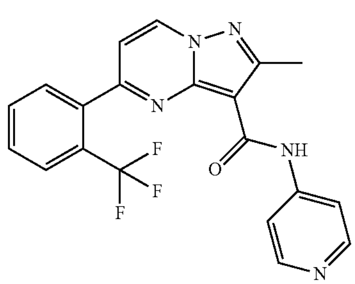 [SMILES: Cc1nn2ccc(-c3ccccc3C(F)(F)F)nc2c1C(=O)Nc1ccncc1] | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 561 | 426 | 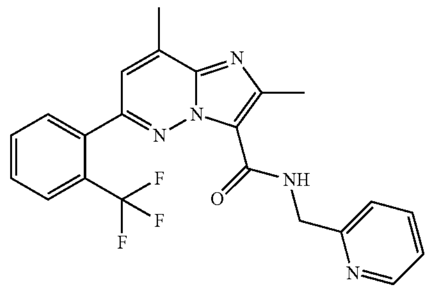 [SMILES: Cc1nc2c(C)cc(-c3ccccc3C(F)(F)F)nn2c1C(=O)NCc1ccccn1] | B | B | B | A |
| 562 | 509 | 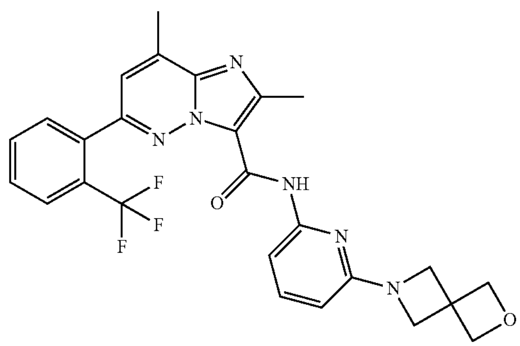 [SMILES: Cc1nc2c(C)cc(-c3ccccc3C(F)(F)F)nn2c1C(=O)Nc1cccc(N2CC3(COC3)C2)n1] | A | A | NT | NT |
| 563 | 390 | 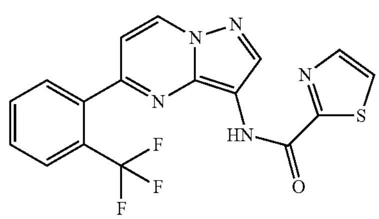 [SMILES: O=C(Nc1cnn2ccc(-c3ccccc3C(F)(F)F)nc12)c1nccs1] | A | A | NT | NT |
| 564 | 327 | 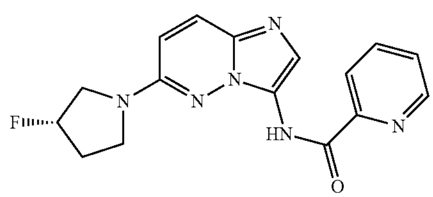 [SMILES: O=C(Nc1cnc2ccc(N3CC[C@H](F)C3)nn12)c1ccccn1] | B | B | NT | NT |
| 565 | 341 | 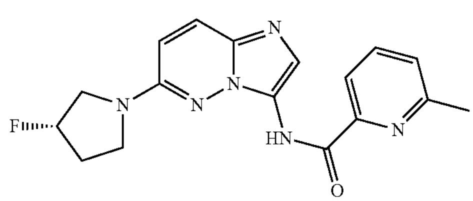 [SMILES: Cc1cccc(C(=O)Nc2cnc3ccc(N4CC[C@H](F)C4)nn23)n1] | B | A | B | B |
| 566 | 355 | 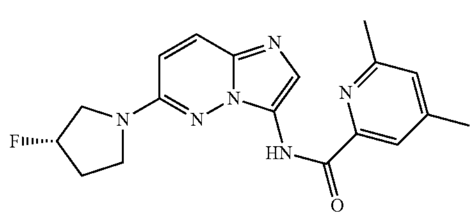 [SMILES: Cc1cc(C)nc(C(=O)Nc2cnc3ccc(N4CC[C@H](F)C4)nn23)c1] | B | A | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 567 | 398 | | B | B | NT | NT |
| 568 | 398 | | C | B | C | B |
| 569 | 398 | | C | B | NT | NT |
| 570 | 399 | | B | B | NT | NT |
| 571 | 399 | | C | B | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 572 | 399 | | C | B | C | B |
| 573 | 497 | | B | B | NT | NT |
| 574 | 483 | | A | A | B | B |
| 575 | 414 | | C | B | NT | NT |
| 576 | 428 | | C | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 577 | 414 | | B | B | A | B |
| 578 | 476 | | A | A | A | A |
| 579 | 419 | | B | B | NT | NT |
| 580 | 416 | | B | A | A | A |
| 581 | 400 | | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 582 | 400 | | B | B | NT | NT |
| 583 | 400 | | B | B | C | B |
| 584 | 401 | | B | A | C | B |
| 585 | 401 | | B | A | NT | NT |
| 586 | 413 | | A | A | A | A |

TABLE 1-continued
Compounds of Formula (I).
| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 587 | 499 | 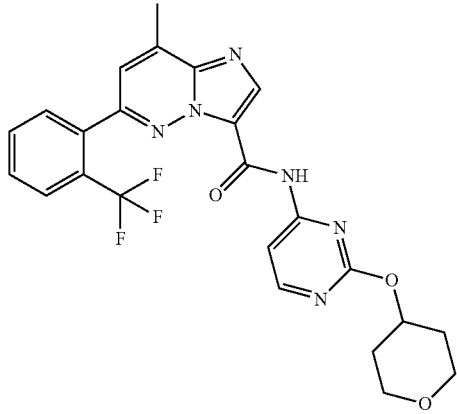 [SMILES: Cc1cc(-c2ccccc2C(F)(F)F)nn2c(C(=O)Nc3ccnc(OC4CCOCC4)n3)cnc12] | A | A | NT | NT |
| 588 | 432 | 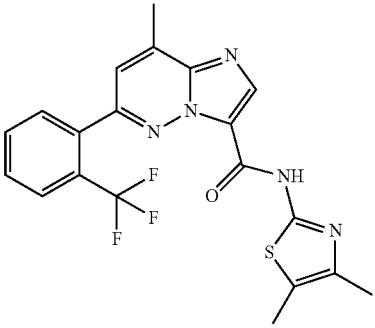 [SMILES: Cc1nc(NC(=O)c2cnc3c(C)cc(-c4ccccc4C(F)(F)F)nn23)sc1C] | B | B | NT | NT |
| 589 | 442 | 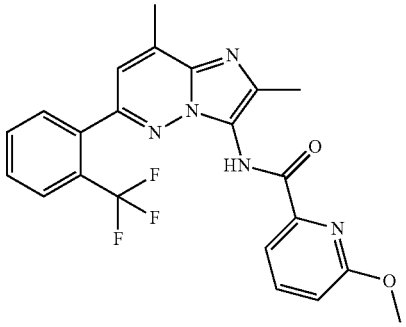 [SMILES: COc1cccc(C(=O)Nc2c(C)nc3c(C)cc(-c4ccccc4C(F)(F)F)nn23)n1] | B | A | B | B |
| 590 | 428 | 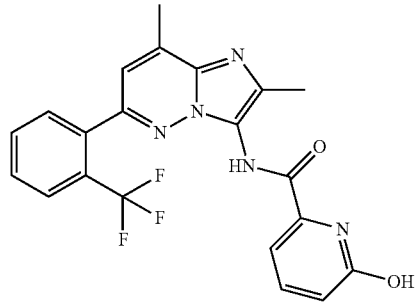 [SMILES: Cc1nc2c(C)cc(-c3ccccc3C(F)(F)F)nn2c1NC(=O)c1cccc(O)n1] | B | B | C | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 591 | 434 | 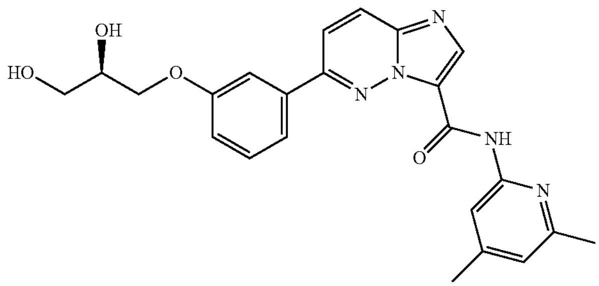 [SMILES: Cc1cc(C)nc(NC(=O)c2cnc3ccc(-c4cccc(OC[C@H](O)CO)c4)nn23)c1] | A | A | A | B |
| 592 | 482 | 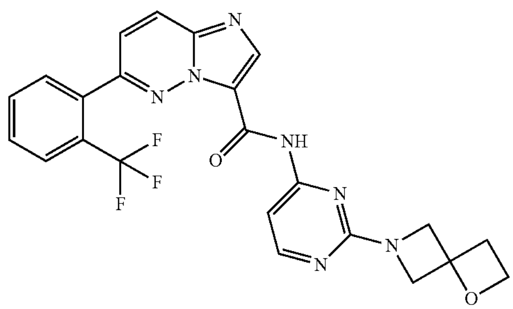 [SMILES: O=C(Nc1ccnc(N2CC3(CCO3)C2)n1)c1cnc2ccc(-c3ccccc3C(F)(F)F)nn12] | A | A | NT | NT |
| 593 | 513 | 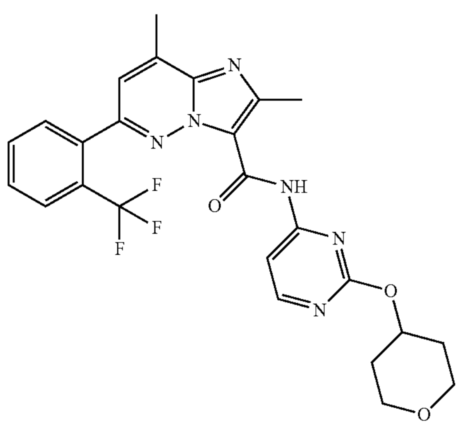 [SMILES: Cc1nc2c(C)cc(-c3ccccc3C(F)(F)F)nn2c1C(=O)Nc1ccnc(OC2CCOCC2)n1] | A | A | NT | NT |
| 594 | 421 | 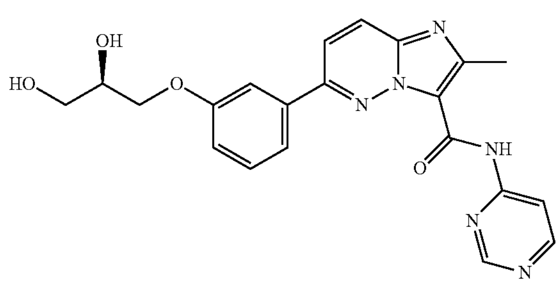 | B | B | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 595 | 429 | | A | B | NT | NT |
| 596 | 443 | | A | A | NT | NT |
| 597 | 421 | | B | B | A | B |
| 598 | 485 | | A | A | A | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 600 | 429 | | A | A | A | A |
| 601 | 485 | | A | A | NT | NT |
| 602 | 429 | | A | A | NT | NT |
| 603 | 420 | | B | A | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 604 | 414 | 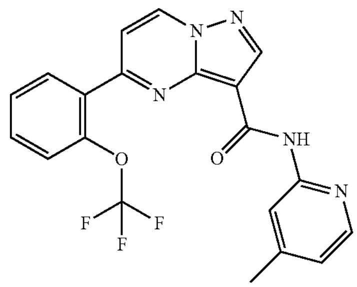 [SMILES: Cc1ccnc(NC(=O)c2cnn3ccc(-c4ccccc4OC(F)(F)F)nc23)c1] | A | A | B | B |
| 605 | 428 | 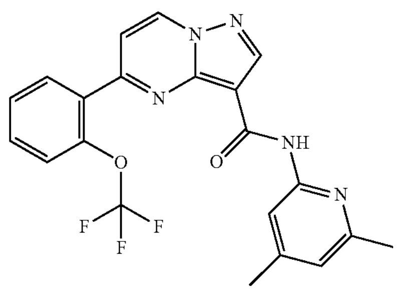 [SMILES: Cc1cc(C)nc(NC(=O)c2cnn3ccc(-c4ccccc4OC(F)(F)F)nc23)c1] | A | A | NT | NT |
| 606 | 418 | 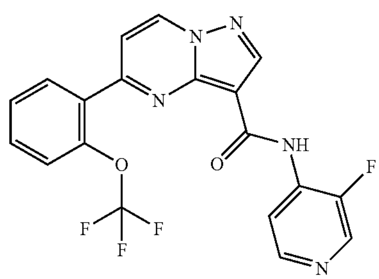 [SMILES: O=C(Nc1ccncc1F)c1cnn2ccc(-c3ccccc3OC(F)(F)F)nc12] | A | A | A | B |
| 607 | 406 | 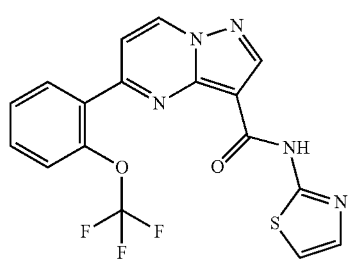 [SMILES: O=C(Nc1nccs1)c1cnn2ccc(-c3ccccc3OC(F)(F)F)nc12] | B | B | NT | NT |
| 608 | 414 | 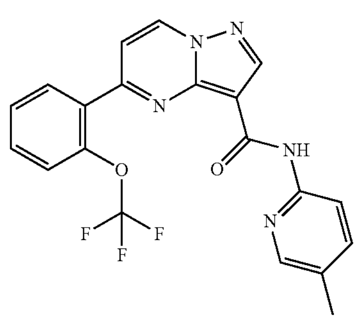 [SMILES: Cc1ccc(NC(=O)c2cnn3ccc(-c4ccccc4OC(F)(F)F)nc23)nc1] | C | B | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 609 | 418 | 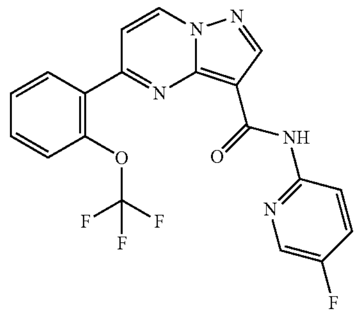 [SMILES: O=C(Nc1ccc(F)cn1)c1cnn2ccc(-c3ccccc3OC(F)(F)F)nc12] | C | B | C | B |
| 610 | 414 | 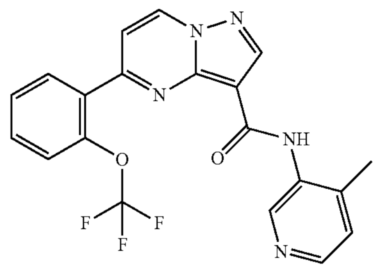 [SMILES: Cc1ccncc1NC(=O)c1cnn2ccc(-c3ccccc3OC(F)(F)F)nc12] | B | B | A | A |
| 611 | 428 | 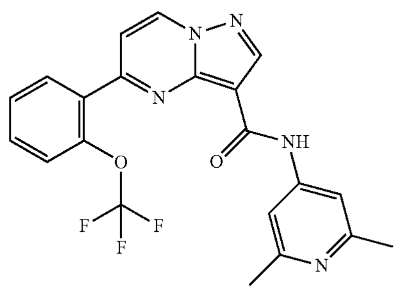 [SMILES: Cc1cc(NC(=O)c2cnn3ccc(-c4ccccc4OC(F)(F)F)nc23)cc(C)n1] | A | A | NT | NT |
| 612 | 414 | 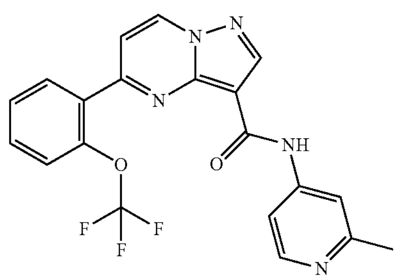 [SMILES: Cc1cc(NC(=O)c2cnn3ccc(-c4ccccc4OC(F)(F)F)nc23)ccn1] | A | A | A | A |
| 613 | 428 | 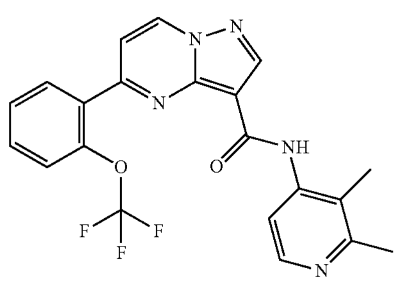 [SMILES: Cc1nccc(NC(=O)c2cnn3ccc(-c4ccccc4OC(F)(F)F)nc23)c1C] | A | B | NT | NT |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 614 | 434 | 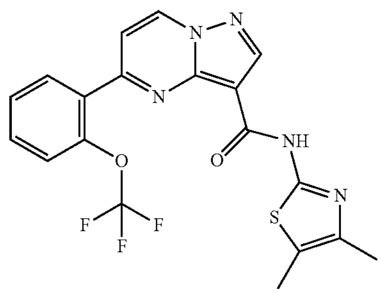 [SMILES: Cc1nc(NC(=O)c2cnn3ccc(-c4ccccc4OC(F)(F)F)nc23)sc1C] | A | A | NT | NT |
| 615 | 457 | 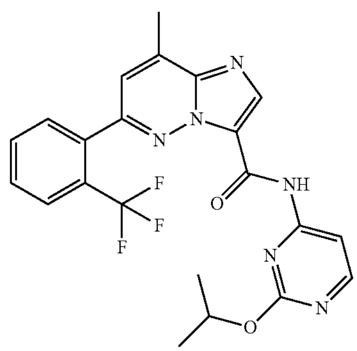 [SMILES: Cc1cc(-c2ccccc2C(F)(F)F)nn2c(C(=O)Nc3ccnc(OC(C)C)n3)cnc12] | A | A | A | A |
| 616 | 414 | 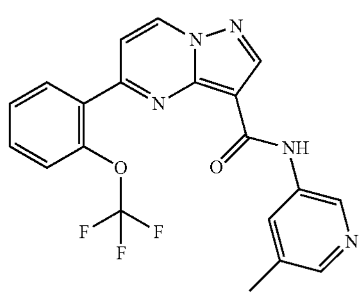 [SMILES: Cc1cncc(NC(=O)c2cnn3ccc(-c4ccccc4OC(F)(F)F)nc23)c1] | A | A | A | A |
| 617 | 414 | 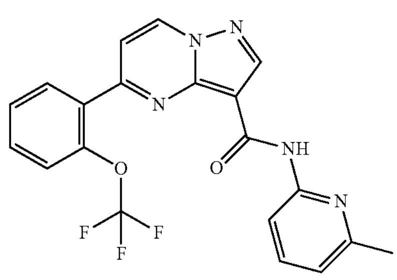 [SMILES: Cc1cccc(NC(=O)c2cnn3ccc(-c4ccccc4OC(F)(F)F)nc23)n1] | A | A | NT | NT |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 618 | 398 | 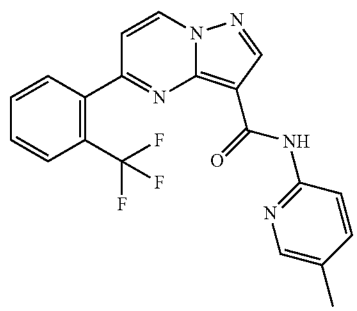 [SMILES: Cc1ccc(NC(=O)c2cnn3ccc(-c4ccccc4C(F)(F)F)nc23)nc1] | A | A | B | A |
| 619 | 398 | 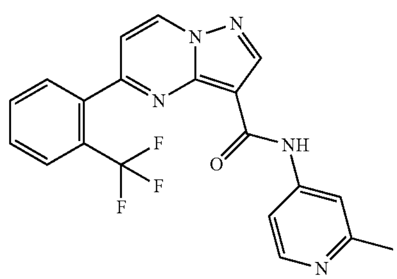 [SMILES: Cc1cc(NC(=O)c2cnn3ccc(-c4ccccc4C(F)(F)F)nc23)ccn1] | A | A | NT | NT |
| 620 | 412 | 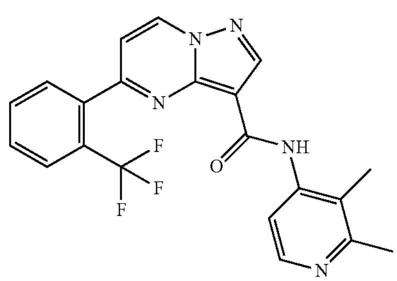 [SMILES: Cc1nccc(NC(=O)c2cnn3ccc(-c4ccccc4C(F)(F)F)nc23)c1C] | B | B | NT | NT |
| 621 | 414 | 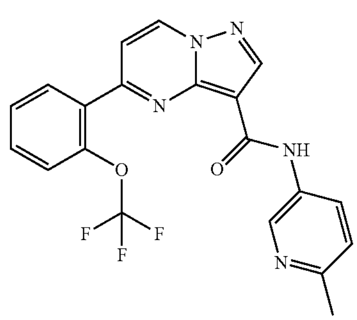 [SMILES: Cc1ccc(NC(=O)c2cnn3ccc(-c4ccccc4OC(F)(F)F)nc23)cn1] | A | A | A | A |
| 622 | 414 | 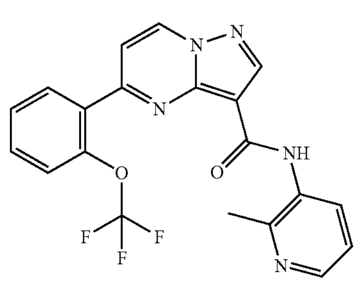 [SMILES: Cc1ncccc1NC(=O)c1cnn2ccc(-c3ccccc3OC(F)(F)F)nc12] | B | B | A | A |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 623 | 415 | 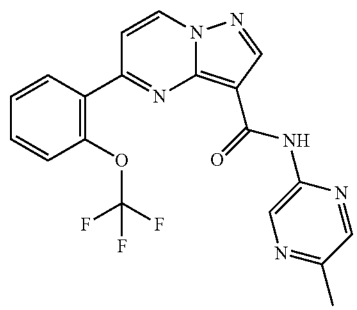 [SMILES: Cc1cnc(NC(=O)c2cnn3ccc(-c4ccccc4OC(F)(F)F)nc23)cn1] | A | A | NT | NT |
| 624 | 401 | 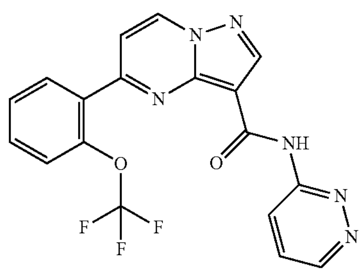 [SMILES: O=C(Nc1cccnn1)c1cnn2ccc(-c3ccccc3OC(F)(F)F)nc12] | A | A | A | A |
| 625 | 428 | 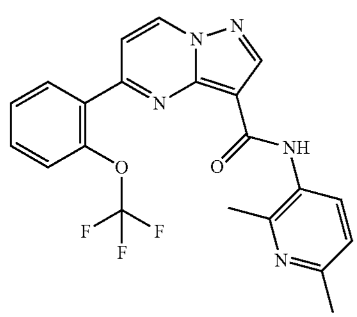 [SMILES: Cc1ccc(NC(=O)c2cnn3ccc(-c4ccccc4OC(F)(F)F)nc23)c(C)n1] | B | B | NT | NT |
| 626 | 444 | 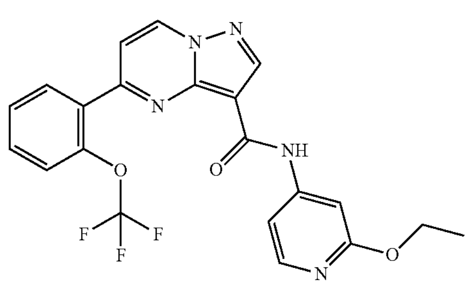 [SMILES: CCOc1cc(NC(=O)c2cnn3ccc(-c4ccccc4OC(F)(F)F)nc23)ccn1] | A | A | NT | NT |

TABLE 1-continued

Compounds of Formula (I).

| Compound No | [M + H]+[Calc] | Structure | TAMRA | | Trp | |
|---|---|---|---|---|---|---|
| | | | EC1.5 (µM) | % Fold Act | EC1.5 (µM) | % Fold Act |
| 627 | 473 | | A | A | A | A |
| 628 | 412 | | A | A | A | A |
| 629 | 412 | | A | A | NT | NT |
| 630 | 398 | | B | B | A | A |

TABLE 1-continued
Compounds of Formula (I).
| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 631 | 398 | 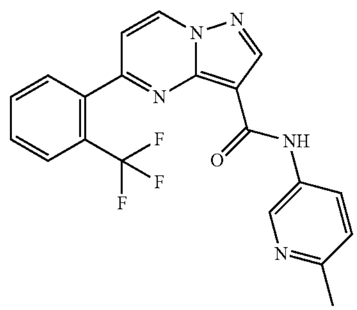 [SMILES: Cc1ccc(NC(=O)c2cnn3ccc(-c4ccccc4C(F)(F)F)nc23)cn1] | A | A | NT | NT |
| 632 | 398 | 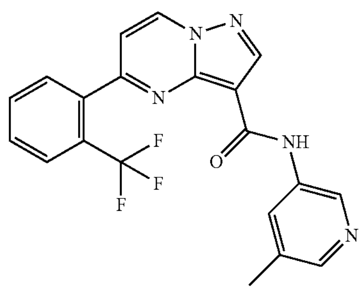 [SMILES: Cc1cncc(NC(=O)c2cnn3ccc(-c4ccccc4C(F)(F)F)nc23)c1] | A | A | NT | NT |
| 633 | 415 | 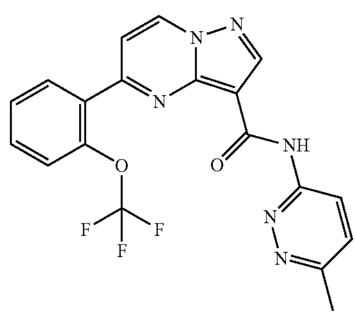 [SMILES: Cc1ccc(NC(=O)c2cnn3ccc(-c4ccccc4OC(F)(F)F)nc23)nn1] | A | A | B | B |
| 634 | 459 | 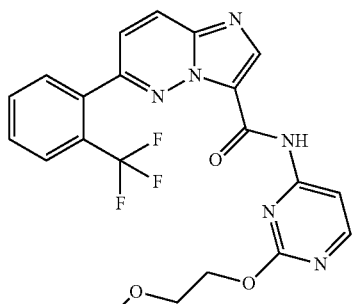 | A | A | A | A |

TABLE 1-continued

Compounds of Formula (I).

| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 635 | 431 | 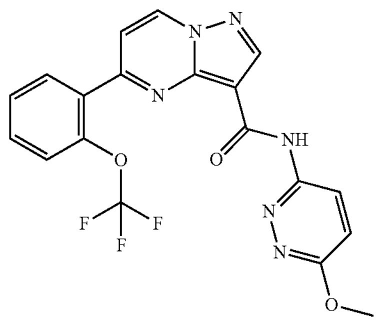 [SMILES: COc1ccc(NC(=O)c2cnn3ccc(-c4ccccc4OC(F)(F)F)nc23)nn1] | A | A | NT | NT |
| 636 | 445 | 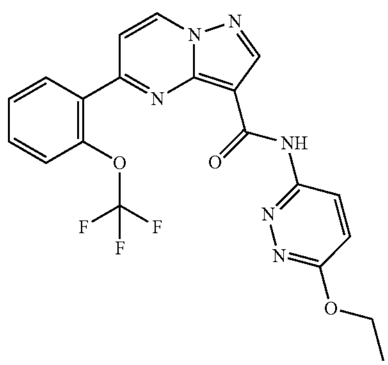 [SMILES: CCOc1ccc(NC(=O)c2cnn3ccc(-c4ccccc4OC(F)(F)F)nc23)nn1] | A | A | B | B |
| 637 | 412 | 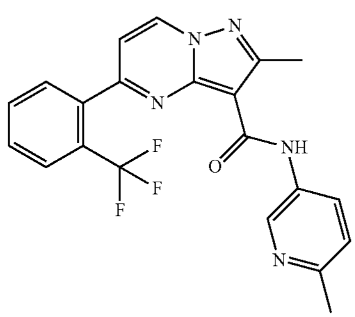 [SMILES: Cc1ccc(NC(=O)c2c(C)nn3ccc(-c4ccccc4C(F)(F)F)nc23)cn1] | A | A | NT | NT |
| 638 | 412 | 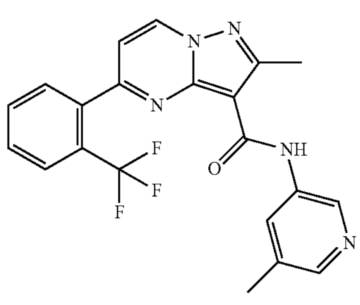 [SMILES: Cc1cncc(NC(=O)c2c(C)nn3ccc(-c4ccccc4C(F)(F)F)nc23)c1] | A | A | NT | NT |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 639 | 426 | 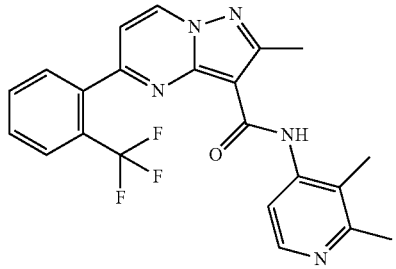 [SMILES: Cc1nccc(NC(=O)c2c(C)nn3ccc(-c4ccccc4C(F)(F)F)nc23)c1C] | A | A | A | A |
| 640 | 398 | 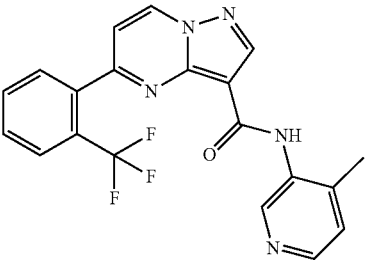 [SMILES: Cc1ccncc1NC(=O)c1cnn2ccc(-c3ccccc3C(F)(F)F)nc12] | B | B | B | B |
| 641 | 412 | 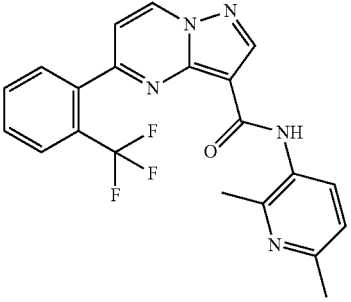 [SMILES: Cc1ccc(NC(=O)c2cnn3ccc(-c4ccccc4C(F)(F)F)nc23)c(C)n1] | B | A | NT | NT |
| 642 | 402 | 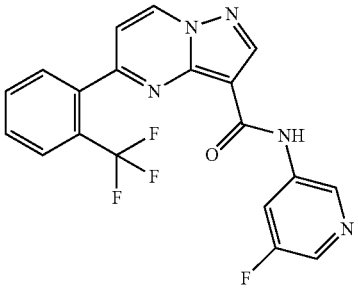 [SMILES: O=C(Nc1cncc(F)c1)c1cnn2ccc(-c3ccccc3C(F)(F)F)nc12] | A | A | B | A |
| 643 | 428 | 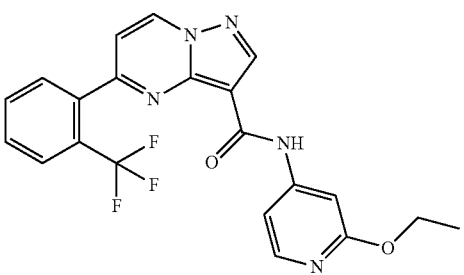 [SMILES: CCOc1cc(NC(=O)c2cnn3ccc(-c4ccccc4C(F)(F)F)nc23)ccn1] | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 644 | 415 | | A | A | B | B |
| 645 | 475 | | A | A | A | A |
| 646 | 468 | | A | A | NT | NT |
| 647 | 468 | | A | A | A | A |
| 648 | 426 | | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 649 | 412 | | A | B | NT | NT |
| 650 | 418 | | A | A | A | A |
| 651 | 432 | | A | A | NT | NT |
| 652 | 418 | | A | A | NT | NT |
| 653 | 398 | | C | B | B | A |

TABLE 1-continued

Compounds of Formula (I).

| Compound No | [M + H]+[Calc] | Structure | TAMRA | | Trp | |
|---|---|---|---|---|---|---|
| | | | EC1.5 (µM) | % Fold Act | EC1.5 (µM) | % Fold Act |
| 654 | 399 | | A | A | B | B |
| 655 | 399 | | A | A | NT | NT |
| 656 | 420 | | B | A | B | B |
| 657 | 415 | | NT | NT | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 658 | 429 | 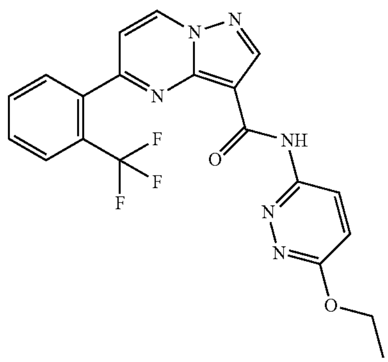 [SMILES: CCOc1ccc(NC(=O)c2cnn3ccc(-c4ccccc4C(F)(F)F)nc23)nn1] | A | A | NT | NT |
| 659 | 429 | 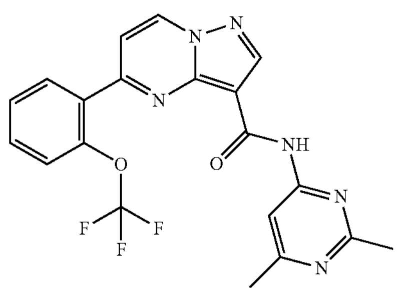 | A | A | B | B |
| 660 | 418 | 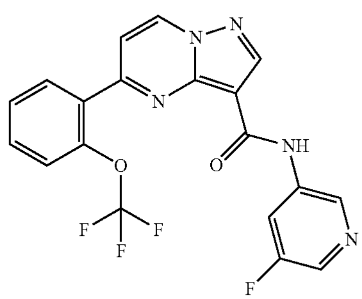 [SMILES: O=C(Nc1cncc(F)c1)c1cnn2ccc(-c3ccccc3OC(F)(F)F)nc12] | A | A | NT | NT |
| 661 | 428 | 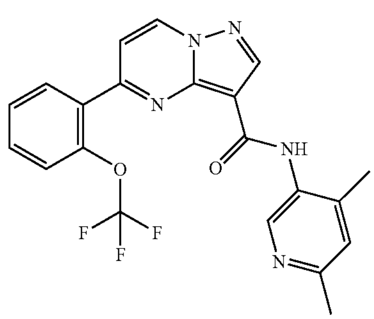 [SMILES: Cc1cc(C)c(NC(=O)c2cnn3ccc(-c4ccccc4OC(F)(F)F)nc23)cn1] | B | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 662 | 473 | 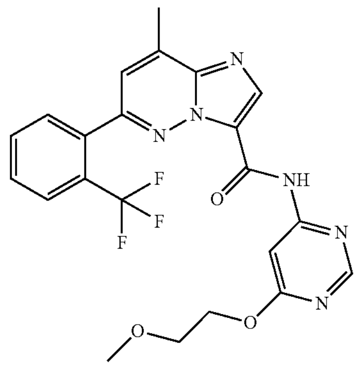 [SMILES: COCCOc1cc(NC(=O)c2cnc3c(C)cc(-c4ccccc4C(F)(F)F)nn23)ncn1] | A | B | NT | NT |
| 663 | 459 | 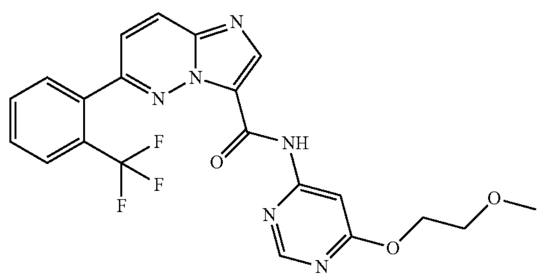 [SMILES: COCCOc1cc(NC(=O)c2cnc3ccc(-c4ccccc4C(F)(F)F)nn23)ncn1] | A | A | B | B |
| 664 | 413 | 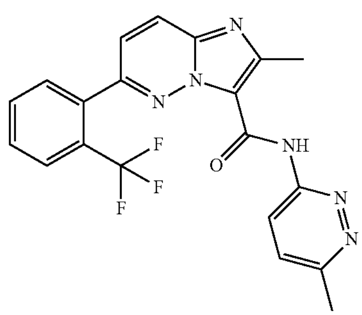 [SMILES: Cc1ccc(NC(=O)c2c(C)nc3ccc(-c4ccccc4C(F)(F)F)nn23)nn1] | A | A | NT | NT |
| 665 | 429 | 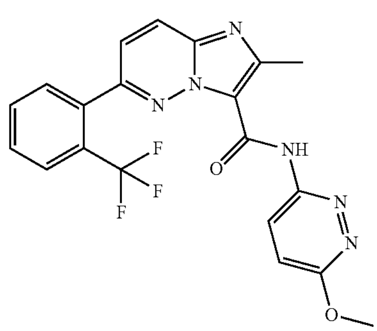 [SMILES: COc1ccc(NC(=O)c2c(C)nc3ccc(-c4ccccc4C(F)(F)F)nn23)nn1] | A | A | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 666 | 443 | 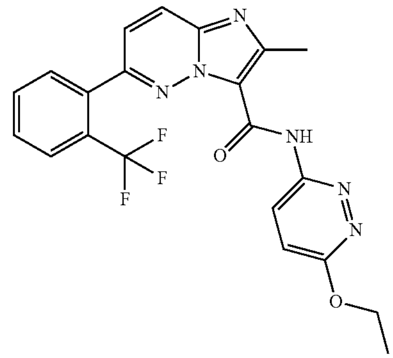 [SMILES: CCOc1ccc(NC(=O)c2c(C)nc3ccc(-c4ccccc4C(F)(F)F)nn23)nn1] | A | A | NT | NT |
| 667 | 400 | 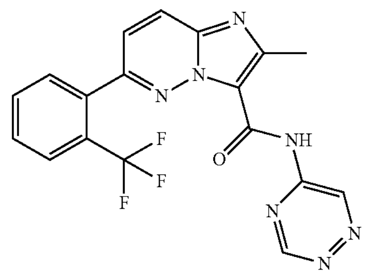 [SMILES: Cc1nc2ccc(-c3ccccc3C(F)(F)F)nn2c1C(=O)Nc1cnncn1] | A | A | NT | NT |
| 668 | 468 | 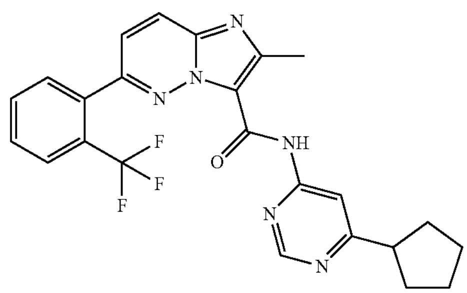 | A | A | A | B |
| 669 | 468 | 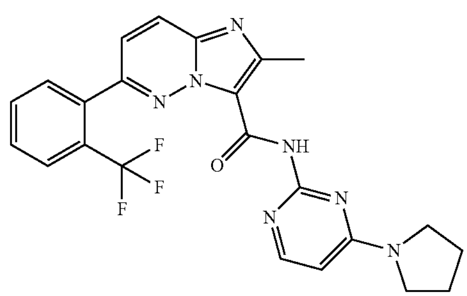 [SMILES: Cc1nc2ccc(-c3ccccc3C(F)(F)F)nn2c1C(=O)Nc1nccc(N2CCCC2)n1] | A | A | NT | NT |
| 670 | 429 | 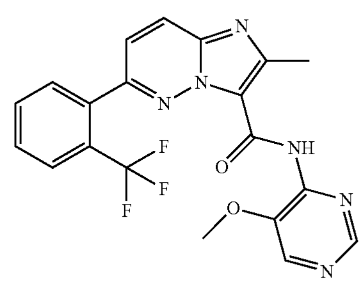 [SMILES: COc1cncnc1NC(=O)c1c(C)nc2ccc(-c3ccccc3C(F)(F)F)nn12] | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 671 | 428 | | A | A | A | A |
| 672 | 443 | | B | B | B | B |
| 673 | 432 | | A | A | NT | NT |
| 674 | 415 | | B | B | B | A |
| 675 | 401 | | C | B | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 676 | 432 | | A | A | NT | NT |
| 677 | 429 | | NT | NT | NT | NT |
| 678 | 445 | | NT | NT | NT | NT |
| 679 | 459 | | NT | NT | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 680 | 429 | 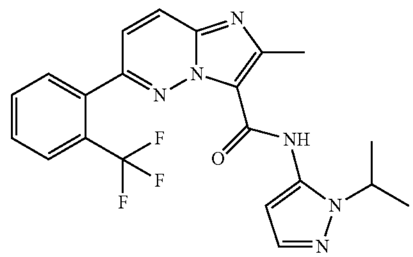 [SMILES: Cc1nc2ccc(-c3ccccc3C(F)(F)F)nn2c1C(=O)Nc1ccnn1C(C)C] | B | B | B | A |
| 681 | 413 | 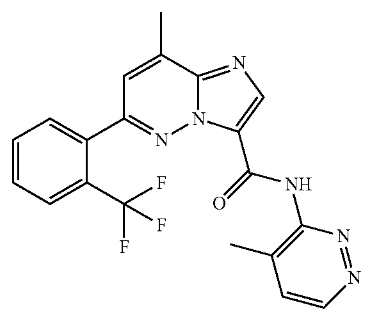 [SMILES: Cc1ccnnc1NC(=O)c1cnc2c(C)cc(-c3ccccc3C(F)(F)F)nn12] | C | B | B | A |
| 682 | 413 | 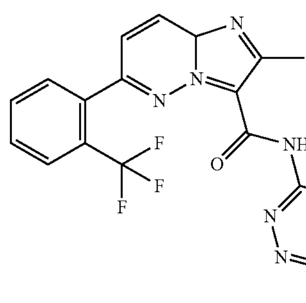 | A | A | NT | NT |
| 683 | 412 | 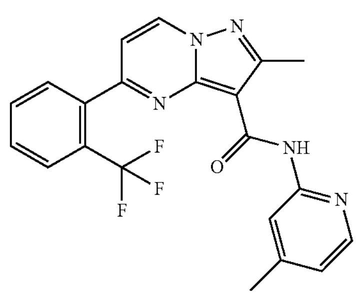 [SMILES: Cc1ccnc(NC(=O)c2c(C)nn3ccc(-c4ccccc4C(F)(F)F)nc23)c1] | A | A | A | A |
| 684 | 412 | 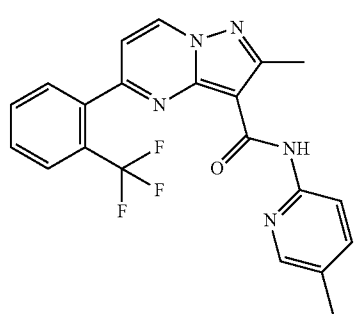 [SMILES: Cc1ccc(NC(=O)c2c(C)nn3ccc(-c4ccccc4C(F)(F)F)nc23)nc1] | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 685 | 426 | 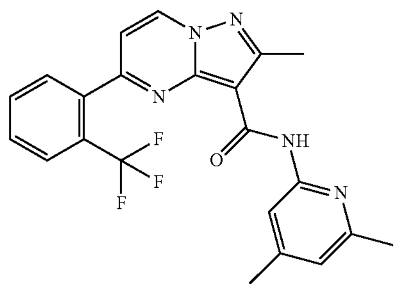 [SMILES: Cc1cc(C)nc(NC(=O)c2c(C)nn3ccc(-c4ccccc4C(F)(F)F)nc23)c1] | A | A | NT | NT |
| 686 | 416 | 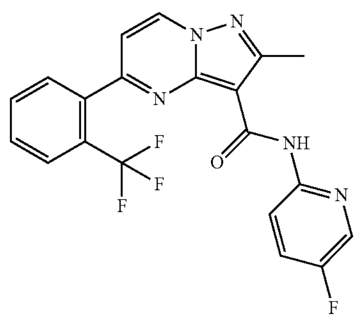 [SMILES: Cc1nn2ccc(-c3ccccc3C(F)(F)F)nc2c1C(=O)Nc1ccc(F)cn1] | A | A | A | B |
| 687 | 412 | 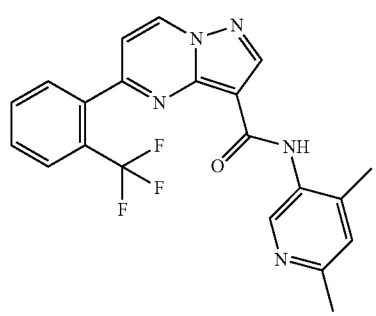 [SMILES: Cc1cc(C)c(NC(=O)c2cnn3ccc(-c4ccccc4C(F)(F)F)nc23)cn1] | B | B | NT | NT |
| 688 | 429 | 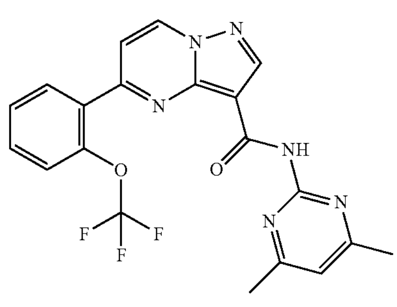 [SMILES: Cc1cc(C)nc(NC(=O)c2cnn3ccc(-c4ccccc4OC(F)(F)F)nc23)n1] | B | A | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 689 | 429 | 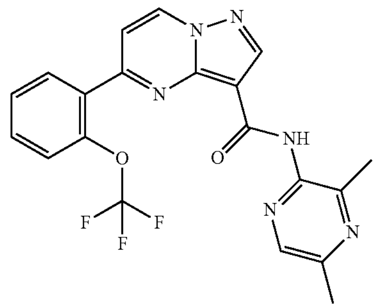 [SMILES: Cc1cnc(NC(=O)c2cnn3ccc(-c4ccccc4OC(F)(F)F)nc23)c(C)n1] | C | B | NT | NT |
| 690 | 436 | 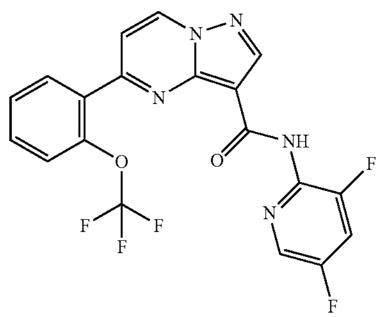 [SMILES: O=C(Nc1ncc(F)cc1F)c1cnn2ccc(-c3ccccc3OC(F)(F)F)nc12] | C | B | NT | NT |
| 691 | 544 | 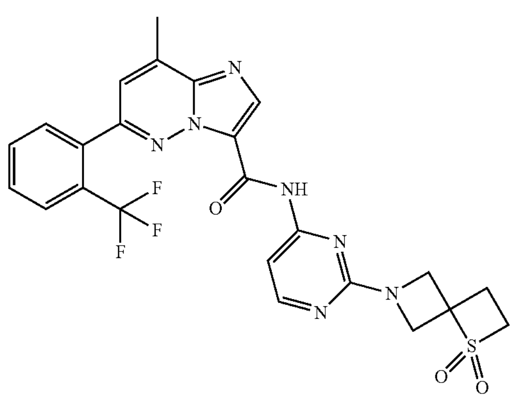 [SMILES: Cc1cc(-c2ccccc2C(F)(F)F)nn2c(C(=O)Nc3ccnc(N4CC5(CCS5(=O)=O)C4)n3)cnc12] | A | A | NT | NT |
| 692 | 359 | 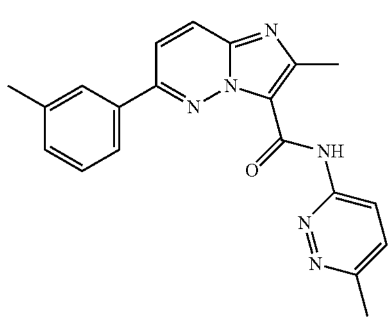 [SMILES: Cc1cccc(-c2ccc3nc(C)c(C(=O)Nc4ccc(C)nn4)n3n2)c1] | A | B | A | B |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 693 | 429 | 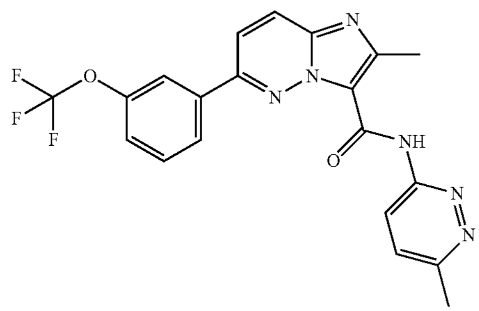 [SMILES: Cc1ccc(NC(=O)c2c(C)nc3ccc(-c4cccc(OC(F)(F)F)c4)nn23)nn1] | NT | NT | NT | NT |
| 694 | 359 | 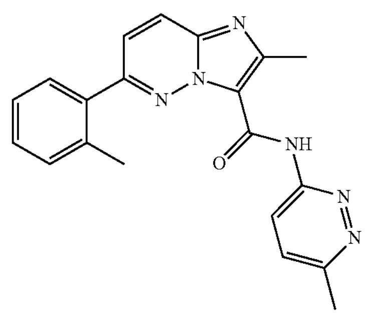 [SMILES: Cc1ccc(NC(=O)c2c(C)nc3ccc(-c4ccccc4C)nn23)nn1] | B | A | B | B |
| 695 | 399 | 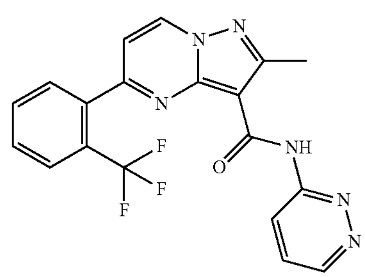 [SMILES: Cc1nn2ccc(-c3ccccc3C(F)(F)F)nc2c1C(=O)Nc1cccnn1] | A | A | A | A |
| 696 | 429 | 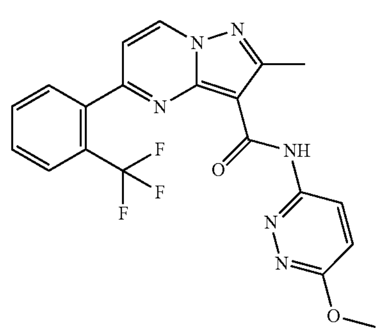 [SMILES: COc1ccc(NC(=O)c2c(C)nn3ccc(-c4ccccc4C(F)(F)F)nc23)nn1] | A | A | NT | NT |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 697 | 443 | 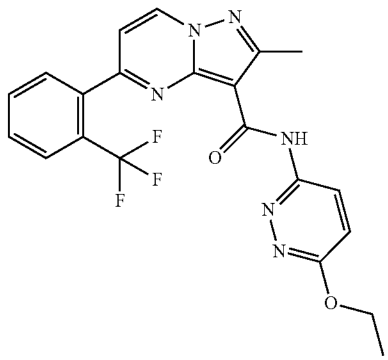 [SMILES: CCOc1ccc(NC(=O)c2c(C)nn3ccc(-c4ccccc4C(F)(F)F)nc23)nn1] | A | A | NT | NT |
| 698 | 426 | 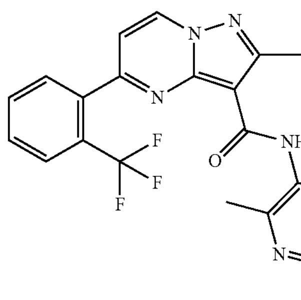 | A | A | A | A |
| 699 | 412 | 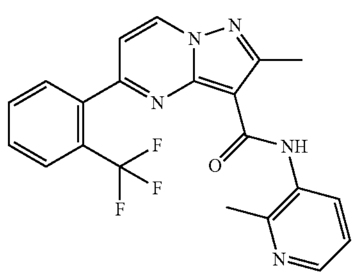 [SMILES: Cc1ncccc1NC(=O)c1c(C)nn2ccc(-c3ccccc3C(F)(F)F)nc12] | A | B | NT | NT |
| 700 | 415 | 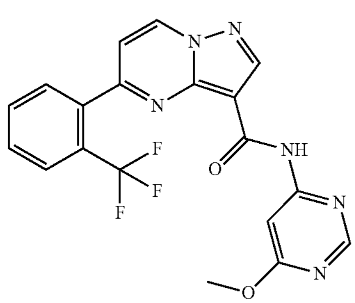 [SMILES: COc1cc(NC(=O)c2cnn3ccc(-c4ccccc4C(F)(F)F)nc23)ncn1] | NT | NT | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 701 | 414 | 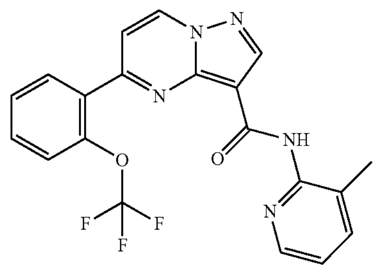 [SMILES: Cc1cccnc1NC(=O)c1cnn2ccc(-c3ccccc3OC(F)(F)F)nc12] | B | B | A | A |
| 702 | 420 | 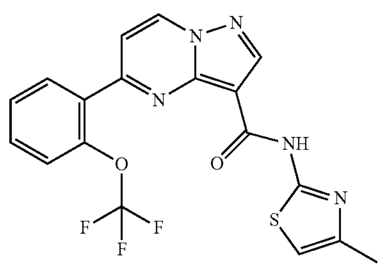 [SMILES: Cc1csc(NC(=O)c2cnn3ccc(-c4ccccc4OC(F)(F)F)nc23)n1] | A | A | NT | NT |
| 703 | 431 | 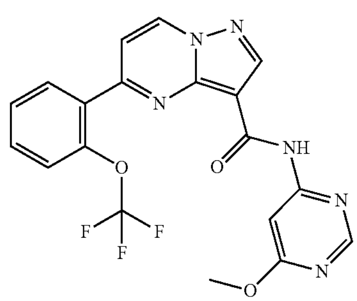 [SMILES: COc1cc(NC(=O)c2cnn3ccc(-c4ccccc4OC(F)(F)F)nc23)ncn1] | A | A | NT | NT |
| 704 | 401 | 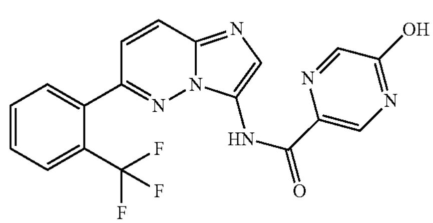 [SMILES: O=C(Nc1cnc2ccc(-c3ccccc3C(F)(F)F)nn12)c1cnc(O)cn1] | A | A | B | B |
| 705 | 401 | 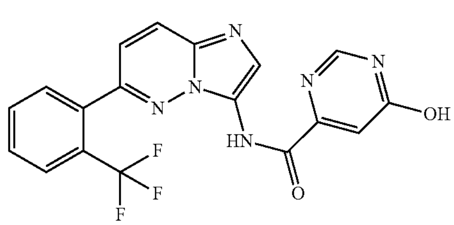 [SMILES: O=C(Nc1cnc2ccc(-c3ccccc3C(F)(F)F)nn12)c1cc(O)ncn1] | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 706 | 349 | 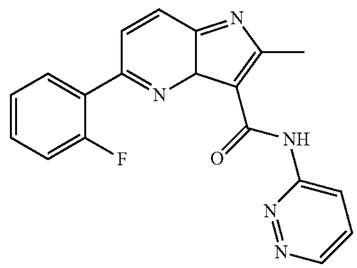 [SMILES: CC1=C(C(=O)Nc2cccnn2)C2N=C(c3ccccc3F)C=CC2=N1] | B | B | A | B |
| 707 | 442 | 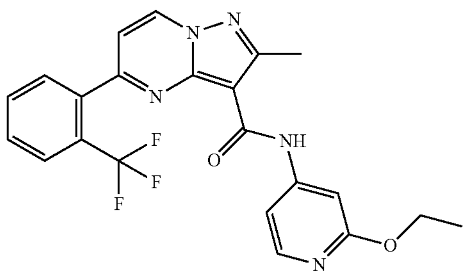 [SMILES: CCOc1cc(NC(=O)c2c(C)nn3ccc(-c4ccccc4C(F)(F)F)nc23)ccn1] | A | A | A | A |
| 708 | 426 | 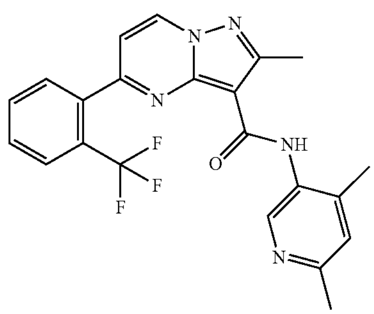 [SMILES: Cc1cc(C)c(NC(=O)c2c(C)nn3ccc(-c4ccccc4C(F)(F)F)nc23)cn1] | B | A | NT | NT |
| 709 | 404 | 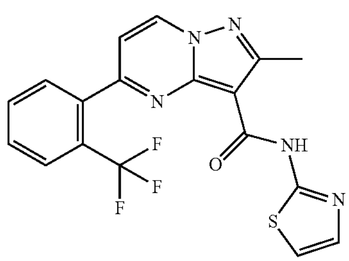 [SMILES: Cc1nn2ccc(-c3ccccc3C(F)(F)F)nc2c1C(=O)Nc1nccs1] | A | A | NT | NT |
| 710 | 413 | 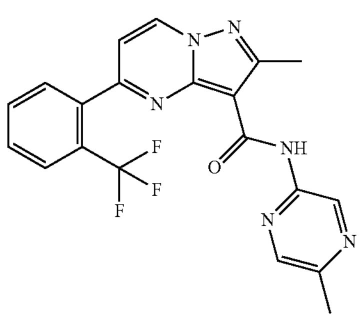 [SMILES: Cc1cnc(NC(=O)c2c(C)nn3ccc(-c4ccccc4C(F)(F)F)nc23)cn1] | A | A | A | A |

TABLE 1-continued
Compounds of Formula (I).
| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 711 | 417 | 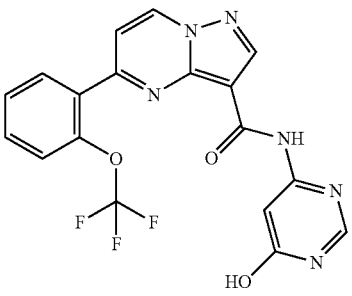 [SMILES: O=C(Nc1cc(O)ncn1)c1cnn2ccc(-c3ccccc3OC(F)(F)F)nc12] | A | A | NT | NT |
| 712 | 414 | 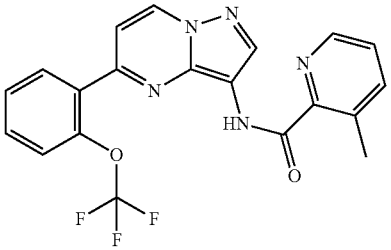 [SMILES: Cc1cccnc1C(=O)Nc1cnn2ccc(-c3ccccc3OC(F)(F)F)nc12] | NT | NT | NT | NT |
| 713 | 434 | 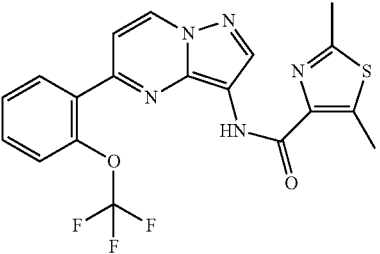 [SMILES: Cc1nc(C(=O)Nc2cnn3ccc(-c4ccccc4OC(F)(F)F)nc23)c(C)s1] | B | A | B | B |
| 714 | 414 | 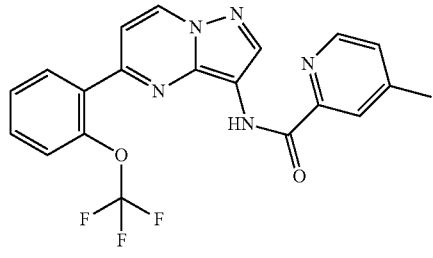 [SMILES: Cc1ccnc(C(=O)Nc2cnn3ccc(-c4ccccc4OC(F)(F)F)nc23)c1] | A | A | NT | NT |
| 715 | 365 | 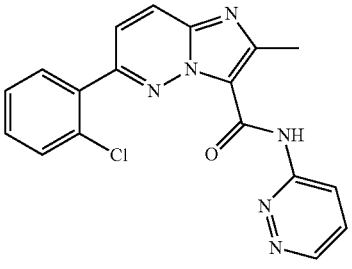 [SMILES: Cc1nc2ccc(-c3ccccc3Cl)nn2c1C(=O)Nc1cccnn1] | B | A | NT | NT |

TABLE 1-continued

Compounds of Formula (I).

| Compound No | [M + H]+$_{[Calc]}$ | Structure | TAMRA | | Trp | |
|---|---|---|---|---|---|---|
| | | | EC1.5 (μM) | % Fold Act | EC1.5 (μM) | % Fold Act |
| 716 | 363 | | B | B | A | B |
| 717 | 370 | | NT | NT | NT | NT |
| 718 | 445 | | A | B | C | B |
| 719 | 459 | | NT | NT | ND | ND |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 720 | 375 | | B | A | NT | NT |
| 721 | 389 | | B | B | NT | NT |
| 722 | 412 | | B | B | A | A |
| 723 | 399 | | A | A | NT | NT |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 724 | 413 | 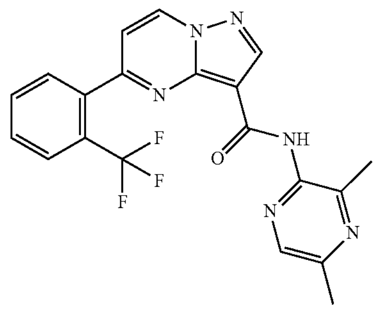 [SMILES: Cc1cnc(NC(=O)c2cnn3ccc(-c4ccccc4C(F)(F)F)nc23)c(C)n1] | C | B | B | B |
| 725 | 414 | 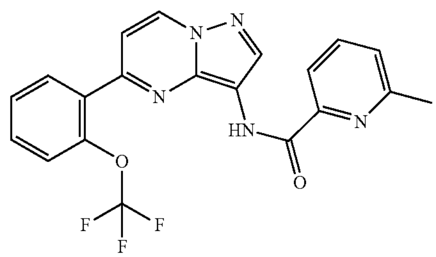 [SMILES: Cc1cccc(C(=O)Nc2cnn3ccc(-c4ccccc4OC(F)(F)F)nc23)n1] | A | A | B | B |
| 726 | 415 | 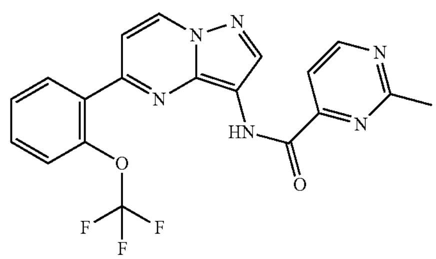 [SMILES: Cc1nccc(C(=O)Nc2cnn3ccc(-c4ccccc4OC(F)(F)F)nc23)n1] | A | A | NT | NT |
| 727 | 429 | 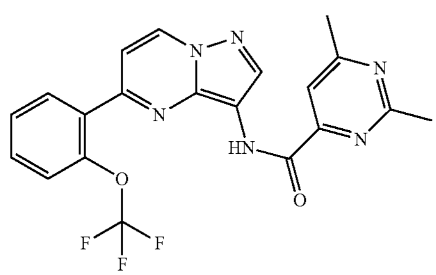 [SMILES: Cc1cc(C(=O)Nc2cnn3ccc(-c4ccccc4OC(F)(F)F)nc23)nc(C)n1] | A | A | NT | NT |
| 728 | 443 | 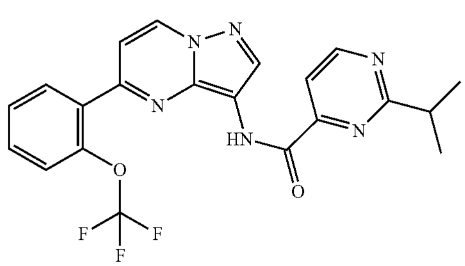 [SMILES: CC(C)c1nccc(C(=O)Nc2cnn3ccc(-c4ccccc4OC(F)(F)F)nc23)n1] | A | A | C | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 729 | 427 | | A | A | NT | NT |
| 730 | 455 | | A | A | A | A |
| 731 | 469 | | A | A | A | B |
| 732 | 453 | | A | A | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 733 | 457 | 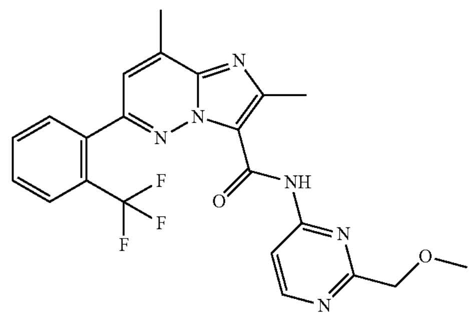 [SMILES: COCc1nccc(NC(=O)c2c(C)nc3c(C)cc(-c4ccccc4C(F)(F)F)nn23)n1] | A | A | NT | NT |
| 734 | 415 | 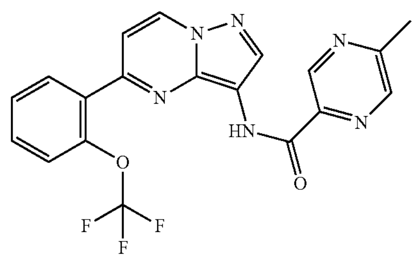 [SMILES: Cc1cnc(C(=O)Nc2cnn3ccc(-c4ccccc4OC(F)(F)F)nc23)cn1] | B | A | C | B |
| 735 | 417 | 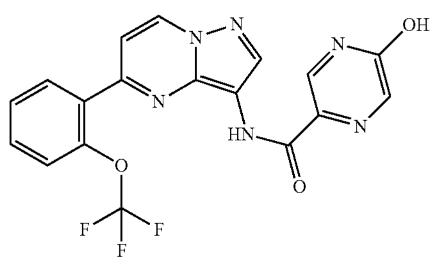 [SMILES: O=C(Nc1cnn2ccc(-c3ccccc3OC(F)(F)F)nc12)c1cnc(O)cn1] | B | A | NT | NT |
| 736 | 429 | 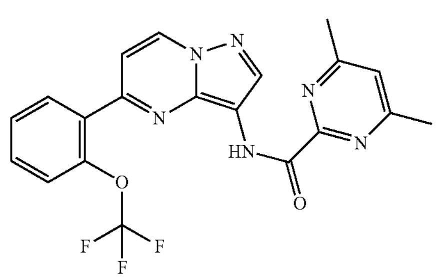 [SMILES: Cc1cc(C)nc(C(=O)Nc2cnn3ccc(-c4ccccc4OC(F)(F)F)nc23)n1] | A | A | C | B |
| 737 | 413 | 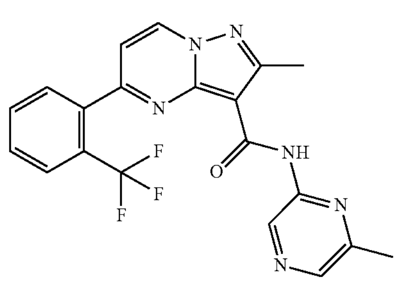 | A | A | A | A |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 738 | 484 | 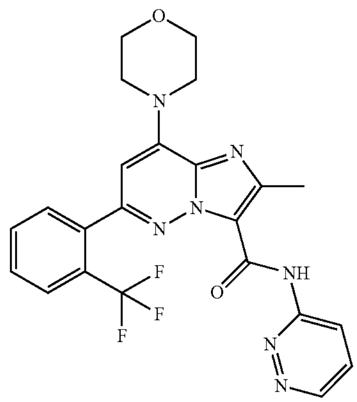 [SMILES: Cc1nc2c(N3CCOCC3)cc(-c3ccccc3C(F)(F)F)nn2c1C(=O)Nc1cccnn1] | A | A | NT | NT |
| 739 | 363 | 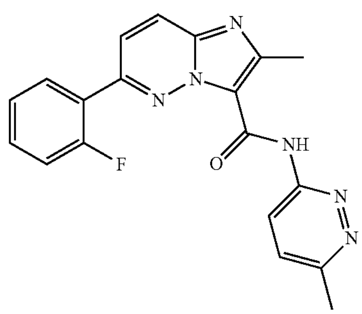 | NT | NT | NT | NT |
| 740 | 379 | 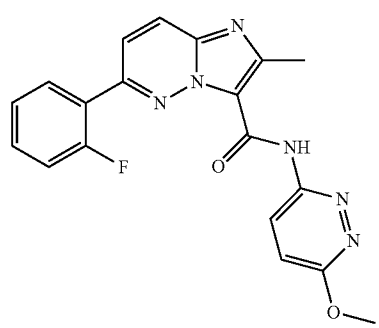 [SMILES: COc1ccc(NC(=O)c2c(C)nc3ccc(-c4ccccc4F)nn23)nn1] | NT | NT | ND | ND |
| 741 | 393 | 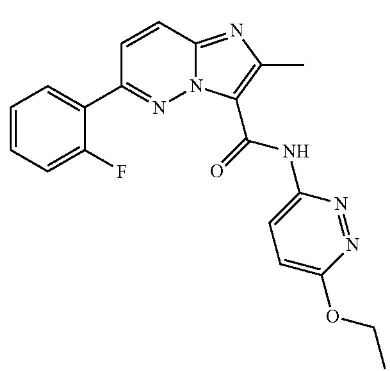 [SMILES: CCOc1ccc(NC(=O)c2c(C)nc3ccc(-c4ccccc4F)nn23)nn1] | B | B | NT | NT |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 742 | 379 | 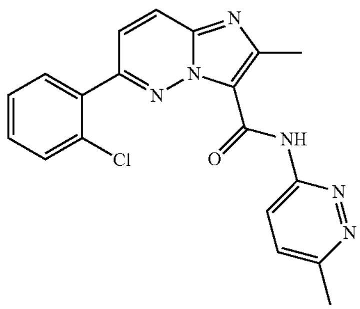 [SMILES: Cc1ccc(NC(=O)c2c(C)nc3ccc(-c4ccccc4Cl)nn23)nn1] | A | B | C | B |
| 743 | 395 | 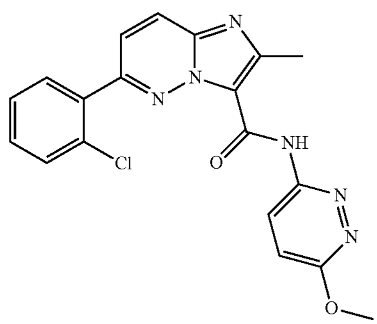 | B | B | C | B |
| 744 | 409 | 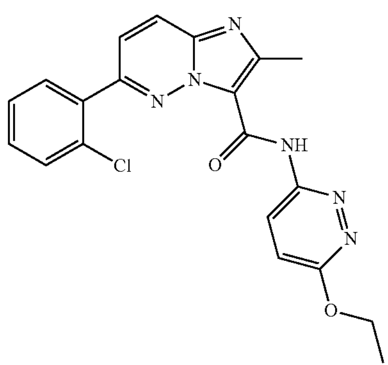 [SMILES: CCOc1ccc(NC(=O)c2c(C)nc3ccc(-c4ccccc4Cl)nn23)nn1] | A | B | NT | NT |
| 745 | 529 | 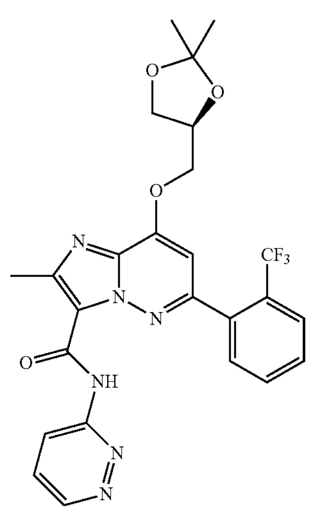 [SMILES: Cc1nc2c(OC[C@H]3COC(C)(C)O3)cc(-c3ccccc3C(F)(F)F)nn2c1C(=O)Nc1cccnn1] | A | A | NT | NT |

TABLE 1-continued

Compounds of Formula (I).

| Compound No | [M + H]+$_{[Calc]}$ | Structure | TAMRA | | Trp | |
|---|---|---|---|---|---|---|
| | | | EC1.5 (μM) | % Fold Act | EC1.5 (μM) | % Fold Act |
| 746 | 398 | | A | A | C | B |
| 747 | 402 | | A | A | NT | NT |
| 748 | 451 | | A | A | B | B |
| 749 | 420 | | A | A | B | B |
| 750 | 428 | | A | A | NT | NT |
| 751 | 430 | | A | A | NT | NT |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 752 | 420 | 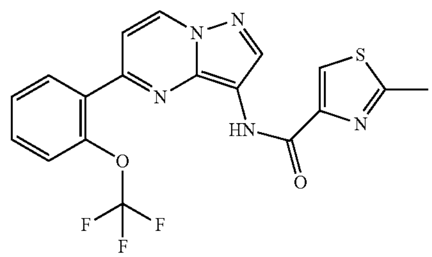 [SMILES: Cc1nc(C(=O)Nc2cnn3ccc(-c4ccccc4OC(F)(F)F)nc23)cs1] | B | A | B | B |
| 753 | 427 | 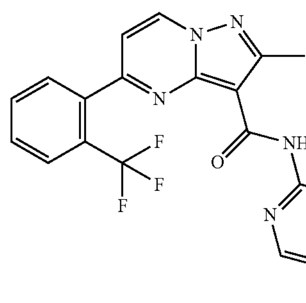 | B | A | NT | NT |
| 754 | 418 | 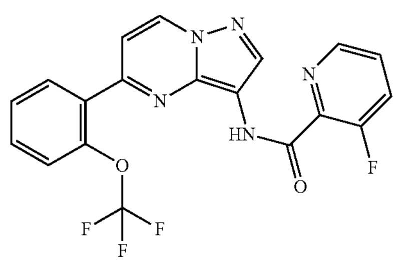 [SMILES: O=C(Nc1cnn2ccc(-c3ccccc3OC(F)(F)F)nc12)c1ncccc1F] | A | A | B | B |
| 755 | 436 | 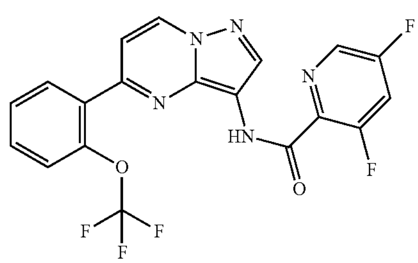 [SMILES: O=C(Nc1cnn2ccc(-c3ccccc3OC(F)(F)F)nc12)c1ncc(F)cc1F] | A | A | B | B |
| 756 | 420 | 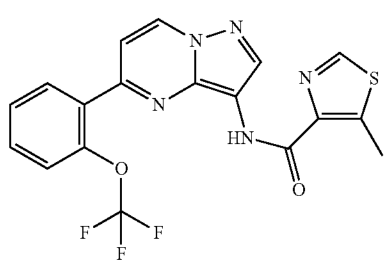 [SMILES: Cc1scnc1C(=O)Nc1cnn2ccc(-c3ccccc3OC(F)(F)F)nc12] | B | A | NT | NT |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 757 | 448 | 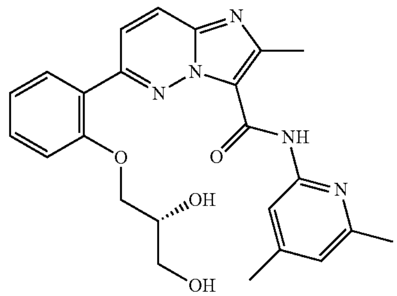 [SMILES: Cc1cc(C)nc(NC(=O)c2c(C)nc3ccc(-c4ccccc4OC[C@H](O)CO)nn23)c1] | B | A | NT | NT |
| 758 | 438 | 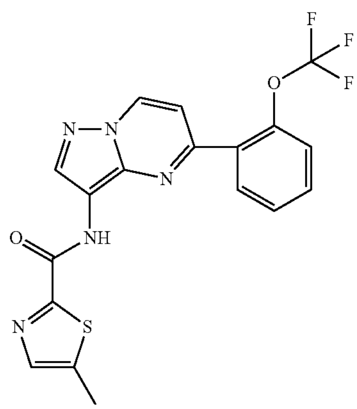 [SMILES: Cc1cnc(C(=O)Nc2cnn3ccc(-c4ccccc4OC(F)(F)F)nc23)s1] | A | A | B | B |
| 759 | 375 | 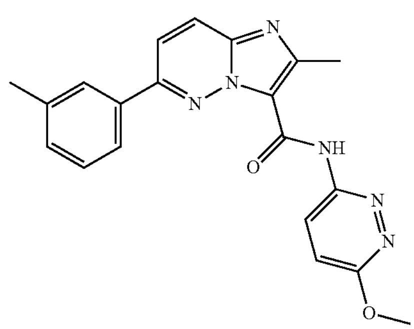 | A | B | NT | NT |
| 760 | 389 | 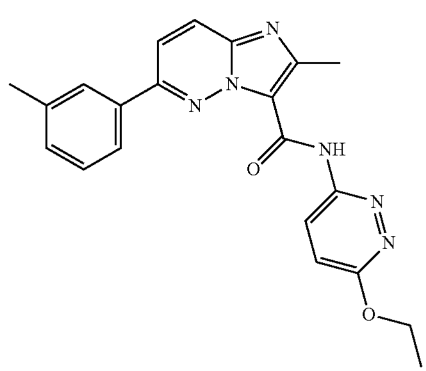 [SMILES: CCOc1ccc(NC(=O)c2c(C)nc3ccc(-c4cccc(C)c4)nn23)nn1] | A | B | ND | ND |

TABLE 1-continued
Compounds of Formula (I).
| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 761 | 379 | 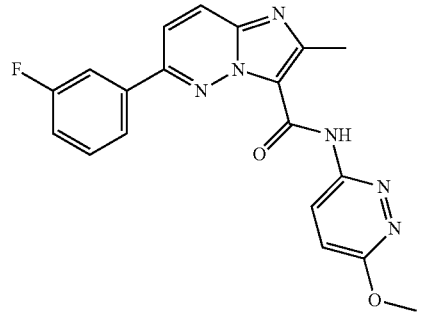 [SMILES: COc1ccc(NC(=O)c2c(C)nc3ccc(-c4cccc(F)c4)nn23)nn1] | C | B | A | B |
| 762 | 393 | 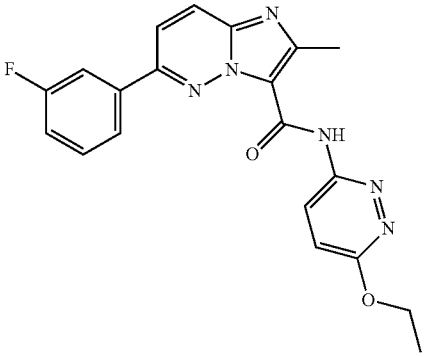 [SMILES: CCOc1ccc(NC(=O)c2c(C)nc3ccc(-c4cccc(F)c4)nn23)nn1] | B | B | NT | NT |
| 763 | 409 | 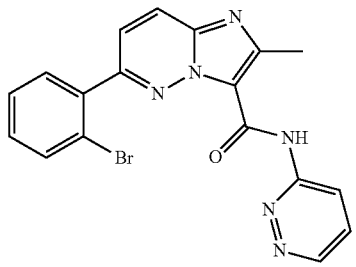 [SMILES: Cc1nc2ccc(-c3ccccc3Br)nn2c1C(=O)Nc1cccnn1] | A | A | NT | NT |
| 764 | 423 | 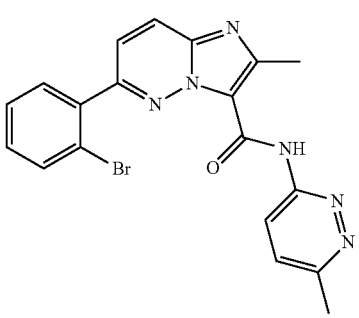 | A | A | ND | ND |

TABLE 1-continued

Compounds of Formula (I).

| Compound No | [M + H]+$_{[Calc]}$ | Structure | TAMRA EC1.5 (µM) | % Fold Act | Trp EC1.5 (µM) | % Fold Act |
|---|---|---|---|---|---|---|
| 765 | 439 | | A | A | NT | NT |
| 766 | 345 | | A | B | A | B |
| 767 | 349 | | B | B | A | A |
| 768 | 416 | | A | A | NT | NT |
| 769 | 467 | | A | A | NT | NT |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 770 | 474 | 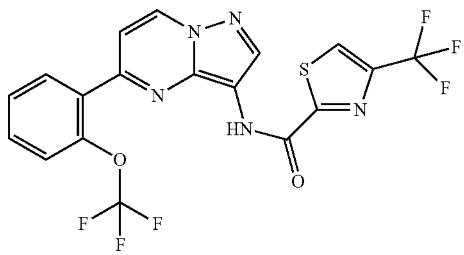 [SMILES: O=C(Nc1cnn2ccc(-c3ccccc3OC(F)(F)F)nc12)c1nc(C(F)(F)F)cs1] | B | A | C | B |
| 771 | 448 | 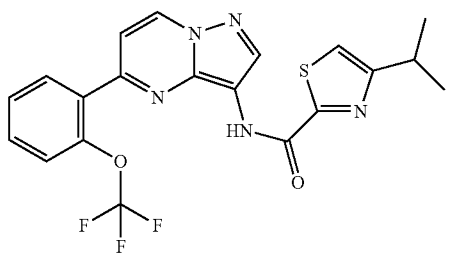 [SMILES: CC(C)c1csc(C(=O)Nc2cnn3ccc(-c4ccccc4OC(F)(F)F)nc23)n1] | A | A | NT | NT |
| 772 | 420 | 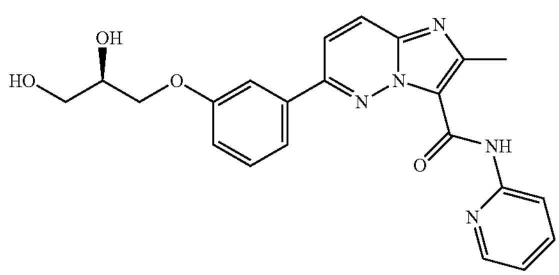 [SMILES: Cc1nc2ccc(-c3cccc(OC[C@H](O)CO)c3)nn2c1C(=O)Nc1ccccn1] | B | A | B | A |
| 773 | 489 | 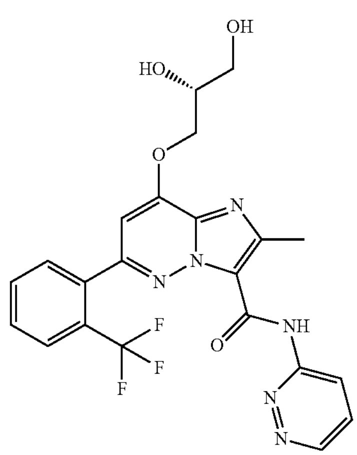 [SMILES: Cc1nc2c(OC[C@H](O)CO)cc(-c3ccccc3C(F)(F)F)nn2c1C(=O)Nc1cccnn1] | A | A | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 774 | 421 | 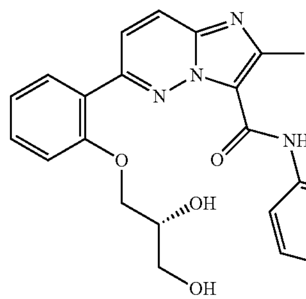 | A | B | NT | NT |
| 775 | 421 | 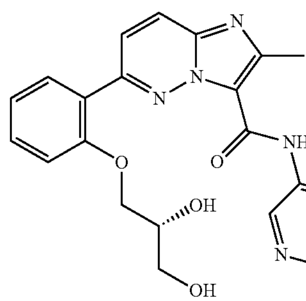 | A | A | NT | NT |
| 776 | 417 | 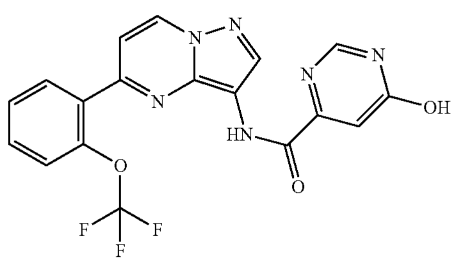 [SMILES: O=C(Nc1cnn2ccc(-c3ccccc3OC(F)(F)F)nc12)c1cc(O)ncn1] | B | A | C | B |
| 777 | 427 | 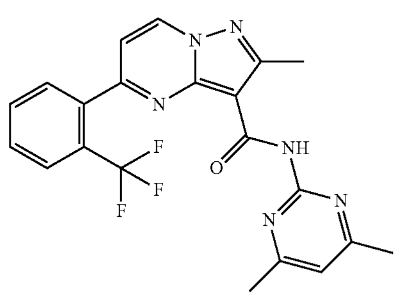 [SMILES: Cc1cc(C)nc(NC(=O)c2c(C)nn3ccc(-c4ccccc4C(F)(F)F)nc23)n1] | A | A | NT | NT |
| 778 | 429 | 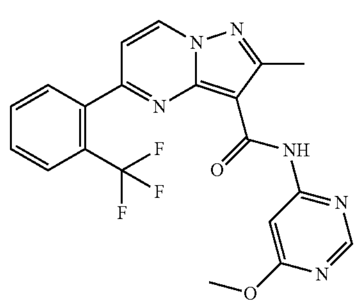 [SMILES: COc1cc(NC(=O)c2c(C)nn3ccc(-c4ccccc4C(F)(F)F)nc23)ncn1] | A | A | A | B |

TABLE 1-continued

Compounds of Formula (I).

| Compound No | [M + H]+[Calc] | Structure | TAMRA | | Trp | |
| --- | --- | --- | --- | --- | --- | --- |
| | | | EC1.5 (µM) | % Fold Act | EC1.5 (µM) | % Fold Act |
| 779 | 416 | 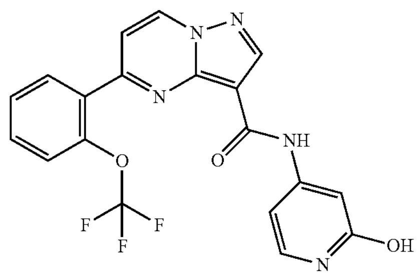 [SMILES: O=C(Nc1ccnc(O)c1)c1cnn2ccc(-c3ccccc3OC(F)(F)F)nc12] | A | A | A | A |
| 780 | 460 | 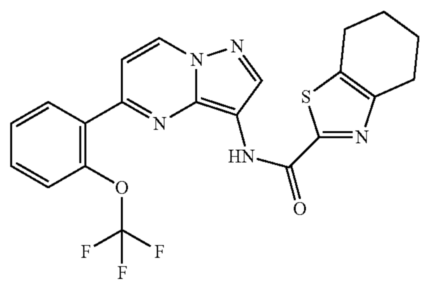 [SMILES: O=C(Nc1cnn2ccc(-c3ccccc3OC(F)(F)F)nc12)c1nc2c(s1)CCCC2] | A | A | NT | NT |
| 781 | 406 | 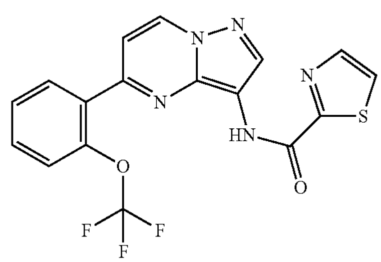 [SMILES: O=C(Nc1cnn2ccc(-c3ccccc3OC(F)(F)F)nc12)c1nccs1] | B | A | NT | NT |
| 782 | 420 | 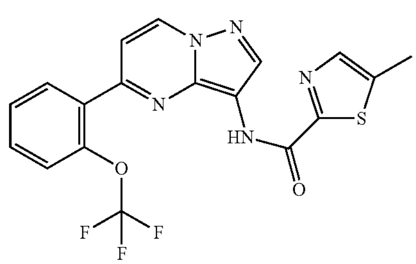 [SMILES: Cc1cnc(C(=O)Nc2cnn3ccc(-c4ccccc4OC(F)(F)F)nc23)s1] | A | A | C | B |
| 783 | 475 | 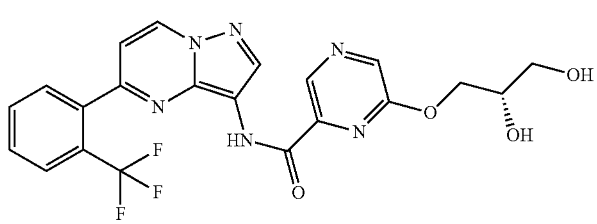 [SMILES: O=C(Nc1cnn2ccc(-c3ccccc3C(F)(F)F)nc12)c1cncc(OC[C@@H](O)CO)n1] | A | A | NT | NT |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 784 | 414 | 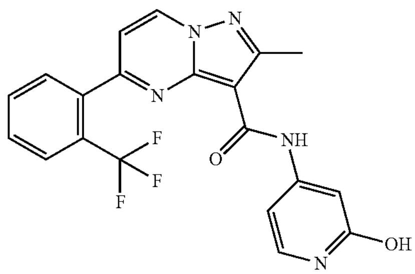 [SMILES: Cc1nn2ccc(-c3ccccc3C(F)(F)F)nc2c1C(=O)Nc1ccnc(O)c1] | A | A | A | A |
| 785 | 406 | 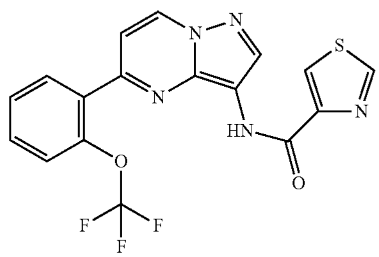 [SMILES: O=C(Nc1cnn2ccc(-c3ccccc3OC(F)(F)F)nc12)c1cscn1] | B | A | C | B |
| 786 | 443 | 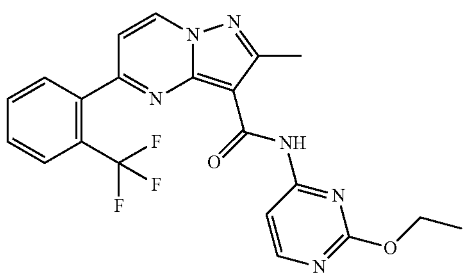 [SMILES: CCOc1nccc(NC(=O)c2c(C)nn3ccc(-c4ccccc4C(F)(F)F)nc23)n1] | A | A | NT | NT |
| 787 | 427 | 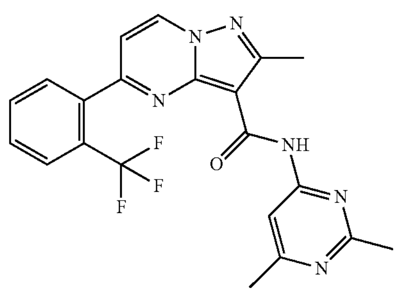 [SMILES: Cc1cc(NC(=O)c2c(C)nn3ccc(-c4ccccc4C(F)(F)F)nc23)nc(C)n1] | A | A | NT | NT |
| 788 | 434 | 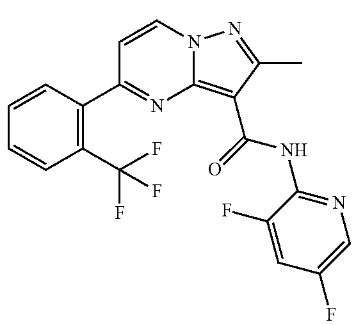 [SMILES: Cc1nn2ccc(-c3ccccc3C(F)(F)F)nc2c1C(=O)Nc1ncc(F)cc1F] | B | A | B | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 789 | 416 | | A | A | NT | NT |
| 790 | 434 | | A | A | A | A |
| 791 | 448 | | A | A | B | B |
| 792 | 434 | | A | A | NT | NT |
| 793 | 429 | | A | A | NT | NT |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 794 | 399 | 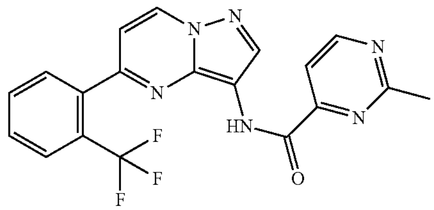 [SMILES: Cc1nccc(C(=O)Nc2cnn3ccc(-c4ccccc4C(F)(F)F)nc23)n1] | A | A | B | B |
| 795 | 413 | 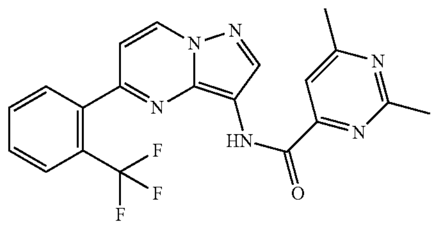 [SMILES: Cc1cc(C(=O)Nc2cnn3ccc(-c4ccccc4C(F)(F)F)nc23)nc(C)n1] | A | A | NT | NT |
| 796 | 427 | 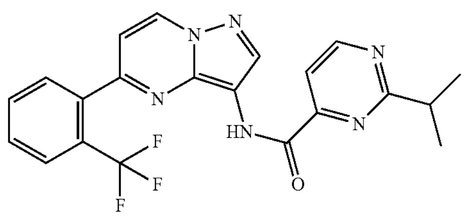 [SMILES: CC(C)c1nccc(C(=O)Nc2cnn3ccc(-c4ccccc4C(F)(F)F)nc23)n1] | A | A | B | B |
| 797 | 431 | 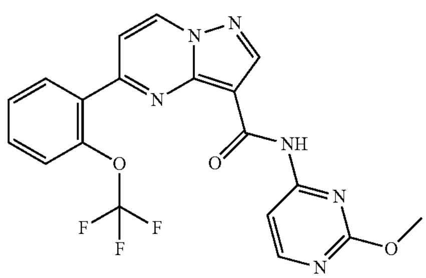 [SMILES: COc1nccc(NC(=O)c2cnn3ccc(-c4ccccc4OC(F)(F)F)nc23)n1] | A | A | A | A |
| 798 | 434 | 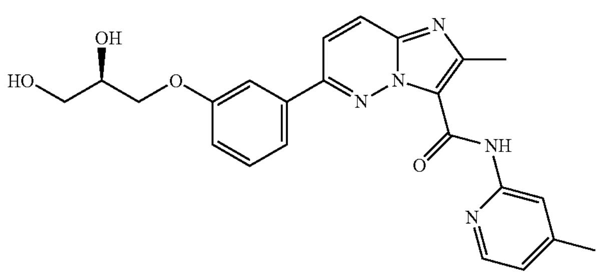 [SMILES: Cc1ccnc(NC(=O)c2c(C)nc3ccc(-c4cccc(OC[C@H](O)CO)c4)nn23)c1] | A | A | NT | NT |
| 799 | 445 | 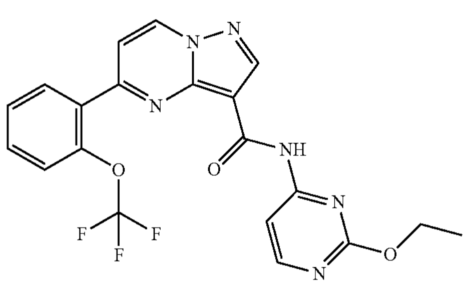 [SMILES: CCOc1nccc(NC(=O)c2cnn3ccc(-c4ccccc4OC(F)(F)F)nc23)n1] | NT | NT | NT | NT |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 800 | 399 | | B | A | C | B |
| 801 | 413 | | A | A | NT | NT |
| 802 | 390 | | B | A | C | B |
| 803 | 404 | | B | A | C | B |
| 804 | 420 | | A | A | NT | NT |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 805 | 434 | 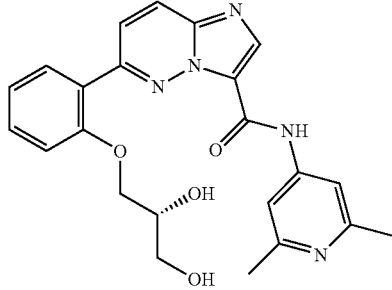 [SMILES: Cc1cc(NC(=O)c2cnc3ccc(-c4ccccc4OC[C@H](O)CO)nn23)cc(C)n1] | A | A | NT | NT |
| 806 | 413 | 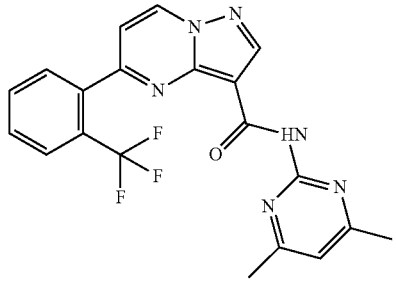 [SMILES: Cc1cc(C)nc(NC(=O)c2cnn3ccc(-c4ccccc4C(F)(F)F)nc23)n1] | A | A | B | A |
| 807 | 429 | 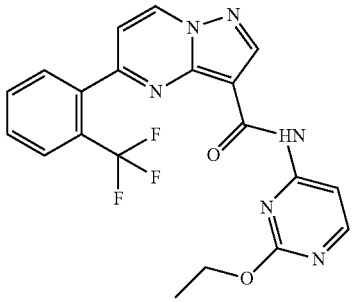 [SMILES: CCOc1nccc(NC(=O)c2cnn3ccc(-c4ccccc4C(F)(F)F)nc23)n1] | A | A | NT | NT |
| 808 | 432 | 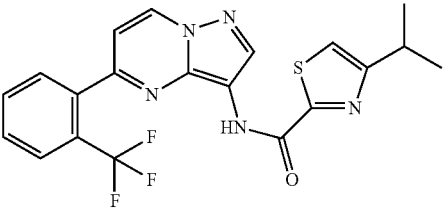 [SMILES: CC(C)c1csc(C(=O)Nc2cnn3ccc(-c4ccccc4C(F)(F)F)nc23)n1] | A | A | B | B |
| 809 | 458 | 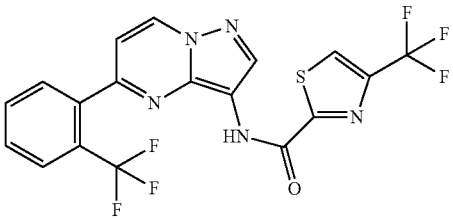 [SMILES: O=C(Nc1cnn2ccc(-c3ccccc3C(F)(F)F)nc12)c1nc(C(F)(F)F)cs1] | A | A | C | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 810 | 444 | 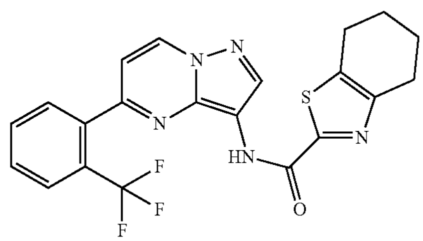 [SMILES: O=C(Nc1cnn2ccc(-c3ccccc3C(F)(F)F)nc12)c1nc2c(s1)CCCC2] | A | A | NT | NT |
| 811 | 420 | 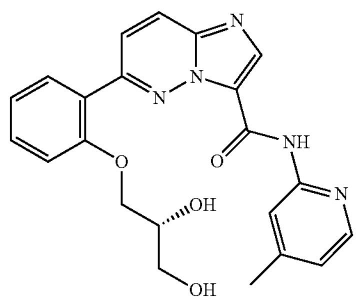 [SMILES: Cc1ccnc(NC(=O)c2cnc3ccc(-c4ccccc4OC[C@H](O)CO)nn23)c1] | A | A | NT | NT |
| 812 | 406 | 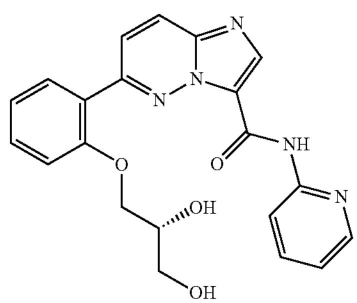 [SMILES: O=C(Nc1ccccn1)c1cnc2ccc(-c3ccccc3OC[C@H](O)CO)nn12] | A | A | A | A |
| 813 | 401 | 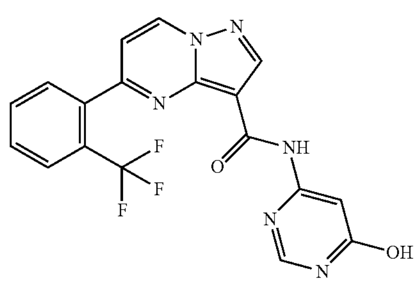 [SMILES: O=C(Nc1cc(O)ncn1)c1cnn2ccc(-c3ccccc3C(F)(F)F)nc12] | A | A | NT | NT |
| 814 | 424 | 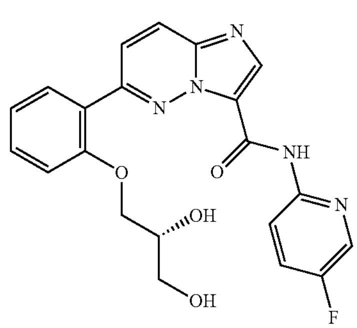 [SMILES: O=C(Nc1ccc(F)cn1)c1cnc2ccc(-c3ccccc3OC[C@H](O)CO)nn12] | B | A | B | B |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 815 | 420 | | A | A | A | A |
| 816 | 434 | | A | A | A | A |
| 817 | 434 | | A | A | NT | NT |
| 818 | 449 | | A | A | B | B |

TABLE 1-continued
Compounds of Formula (I).
| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 819 | 438 | 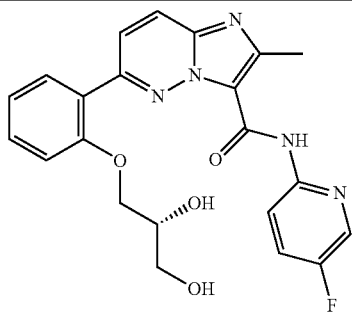 | A | A | NT | NT |
| 820 | 426 | 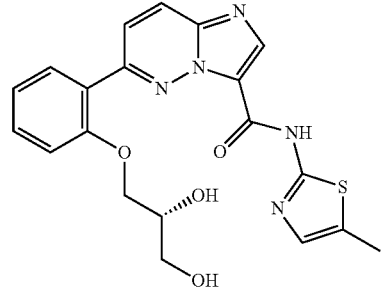 [SMILES: Cc1cnc(NC(=O)c2cnc3ccc(-c4ccccc4OC[C@H](O)CO)nn23)s1] | B | A | B | B |
| 821 | 438 | 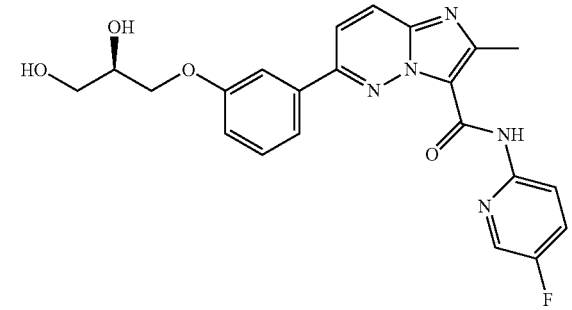 | B | B | A | B |
| 822 | 438 | 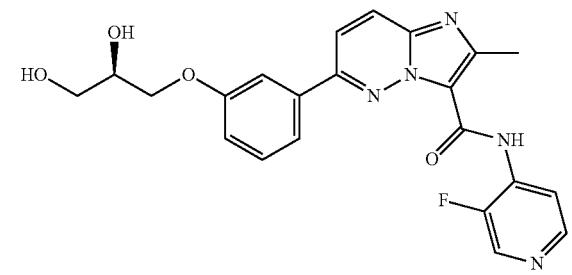 [SMILES: Cc1nc2ccc(-c3cccc(OC[C@H](O)CO)c3)nn2c1C(=O)Nc1ccncc1F] | A | B | NT | NT |
| 823 | 440 | 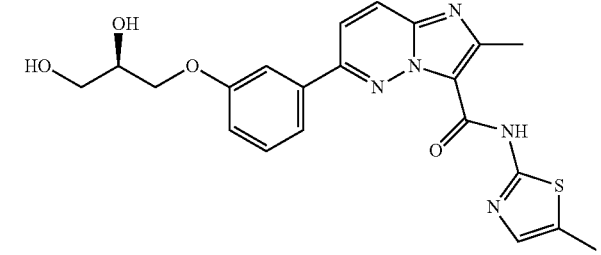 [SMILES: Cc1cnc(NC(=O)c2c(C)nc3ccc(-c4cccc(OC[C@H](O)CO)c4)nn23)s1] | A | B | A | B |

TABLE 1-continued

Compounds of Formula (I).

| Compound No | [M + H]+_[Calc] | Structure | TAMRA EC1.5 (μM) | TAMRA % Fold Act | Trp EC1.5 (μM) | Trp % Fold Act |
|---|---|---|---|---|---|---|
| 824 | 422 | 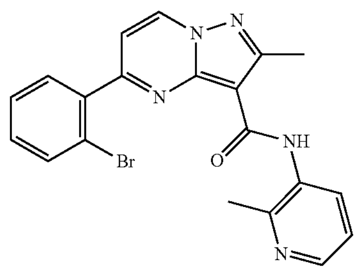 [SMILES: Cc1ncccc1NC(=O)c1c(C)nn2ccc(-c3ccccc3Br)nc12] | B | A | A | A |
| 825 | 422 | 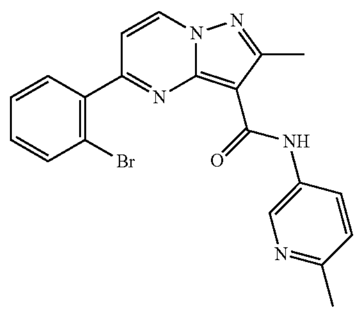 [SMILES: Cc1ccc(NC(=O)c2c(C)nn3ccc(-c4ccccc4Br)nc23)cn1] | NT | NT | ND | ND |
| 826 | 436 | 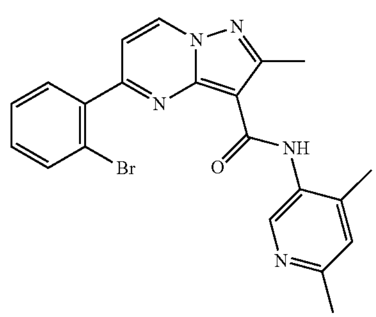 [SMILES: Cc1cc(C)c(NC(=O)c2c(C)nn3ccc(-c4ccccc4Br)nc23)cn1] | B | A | A | B |
| 827 | 422 | 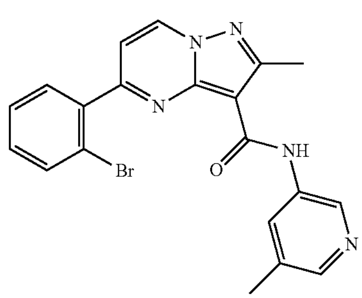 [SMILES: Cc1cncc(NC(=O)c2c(C)nn3ccc(-c4ccccc4Br)nc23)c1] | A | A | A | B |
| 828 | 401 | 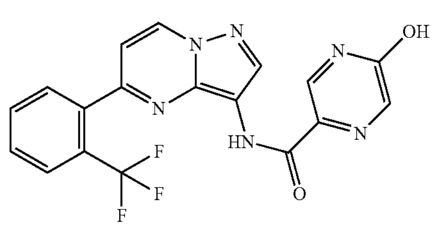 [SMILES: O=C(Nc1cnn2ccc(-c3ccccc3C(F)(F)F)nc12)c1cnc(O)cn1] | A | A | C | B |

TABLE 1-continued
Compounds of Formula (I).
| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 829 | 440 | 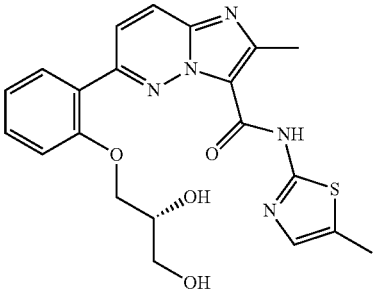 [SMILES: Cc1cnc(NC(=O)c2c(C)nc3ccc(-c4ccccc4OC[C@H](O)CO)nn23)s1] | A | A | A | B |
| 830 | 401 | 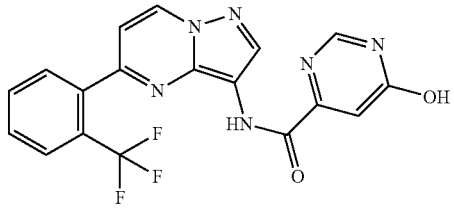 [SMILES: O=C(Nc1cnn2ccc(-c3ccccc3C(F)(F)F)nc12)c1cc(O)ncn1] | A | A | C | B |
| 831 | 424 | 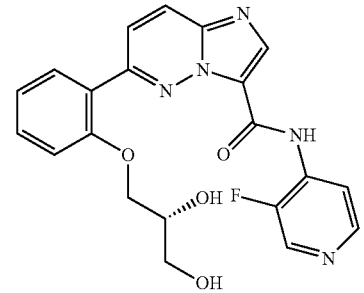 [SMILES: O=C(Nc1ccncc1F)c1cnc2ccc(-c3ccccc3OC[C@H](O)CO)nn12] | B | A | B | B |
| 832 | 435 | 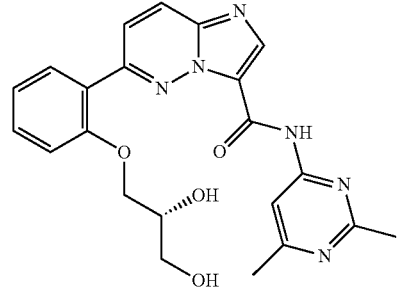 [SMILES: Cc1cc(NC(=O)c2cnc3ccc(-c4ccccc4OC[C@H](O)CO)nn23)nc(C)n1] | A | A | B | B |
| 833 | 407 | 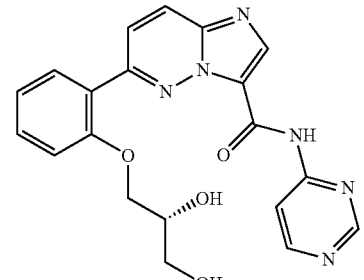 | B | A | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 834 | 516 | | NT | NT | A | A |
| 835 | 506 | | NT | NT | A | A |
| 836 | 327 | | NT | NT | B | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 837 | 327 | 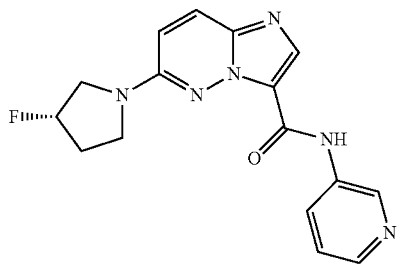 [SMILES: O=C(Nc1cccnc1)c1cnc2ccc(N3CC[C@H](F)C3)nn12] | NT | NT | B | B |
| 838 | 345 | 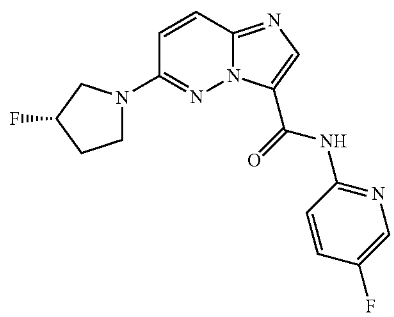 [SMILES: O=C(Nc1ccc(F)cn1)c1cnc2ccc(N3CC[C@H](F)C3)nn12] | NT | NT | B | B |
| 839 | 345 | 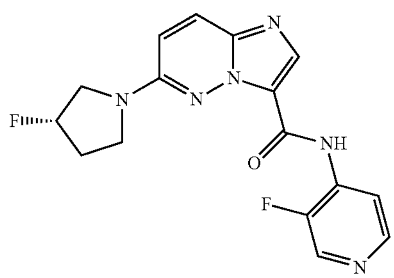 [SMILES: O=C(Nc1ccncc1F)c1cnc2ccc(N3CC[C@H](F)C3)nn12] | NT | NT | B | B |
| 840 | 341 | 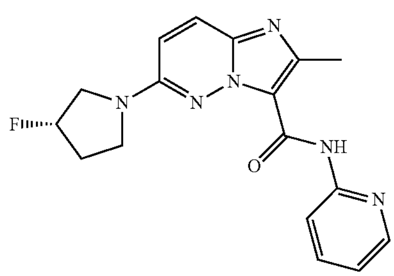 [SMILES: Cc1nc2ccc(N3CC[C@H](F)C3)nn2c1C(=O)Nc1ccccn1] | NT | NT | B | A |
| 841 | 341 | 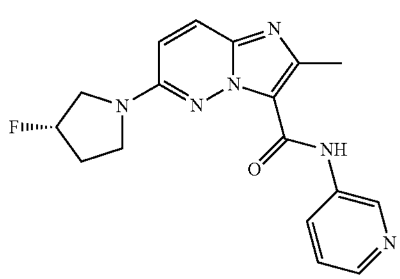 [SMILES: Cc1nc2ccc(N3CC[C@H](F)C3)nn2c1C(=O)Nc1cccnc1] | NT | NT | A | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 842 | 488 | 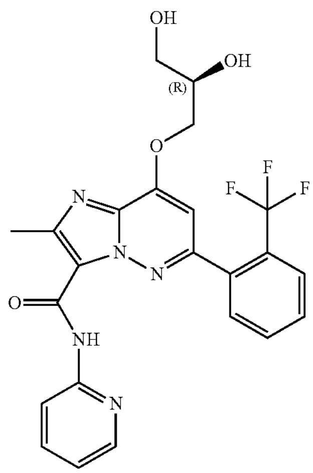 | NT | NT | A | A |
| 843 | 506 | 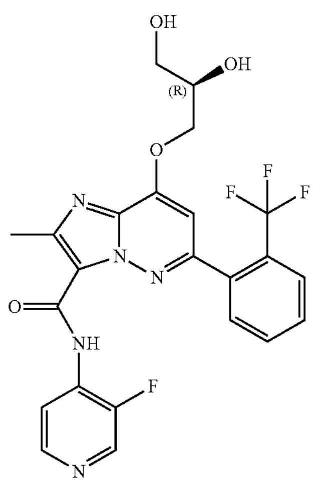 | NT | NT | A | A |
| 844 | 359 | 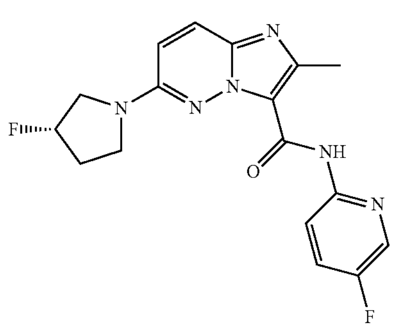 [SMILES: Cc1nc2ccc(N3CC[C@H](F)C3)nn2c1C(=O)Nc1ccc(F)cn1] | NT | NT | B | B |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 845 | 342 | 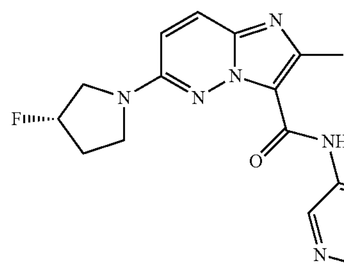 | NT | NT | B | B |
| 846 | 359 | 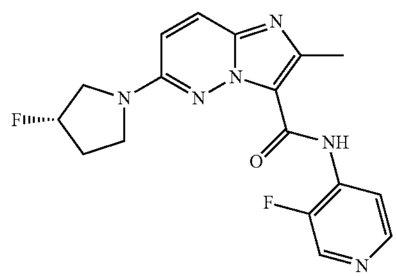 [SMILES: Cc1nc2ccc(N3CC[C@H](F)C3)nn2c1C(=O)Nc1ccncc1F] | NT | NT | A | B |
| 847 | 406 | 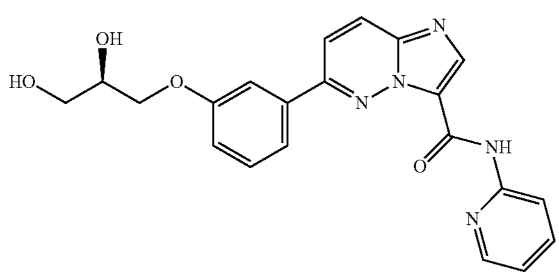 [SMILES: O=C(Nc1ccccn1)c1cnc2ccc(-c3cccc(OC[C@H](O)CO)c3)nn12] | NT | NT | A | A |
| 848 | 420 | 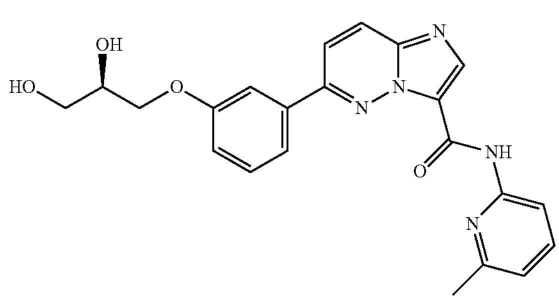 | NT | NT | A | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 849 | 502 | | NT | NT | A | A |
| 850 | 517 | | NT | NT | A | A |
| 851 | 328 | | NT | NT | B | B |
| 852 | 342 | | NT | NT | B | A |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 853 | 328 | | NT | NT | C | B |
| 854 | 328 | | NT | NT | B | B |
| 855 | 342 | | NT | NT | B | A |
| 856 | 328 | | NT | NT | B | B |
| 857 | 342 | | NT | NT | A | A |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 858 | 406 | 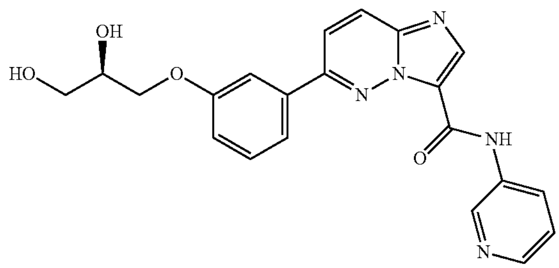 | NT | NT | B | B |
| 859 | 502 | 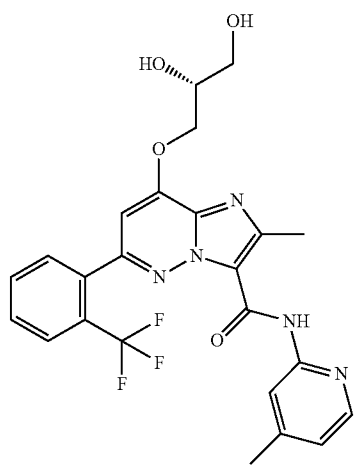 [SMILES: Cc1ccnc(NC(=O)c2c(C)nc3c(OC[C@H](O)CO)cc(-c4ccccc4C(F)(F)F)nn23)c1] | NT | NT | A | A |
| 860 | 516 | 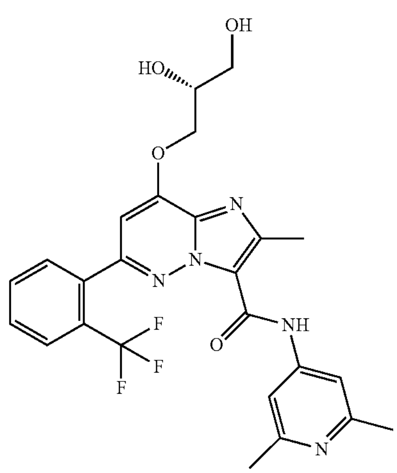 [SMILES: Cc1cc(NC(=O)c2c(C)nc3c(OC[C@H](O)CO)cc(-c4ccccc4C(F)(F)F)nn23)cc(C)n1] | NT | NT | A | A |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 861 | 508 | 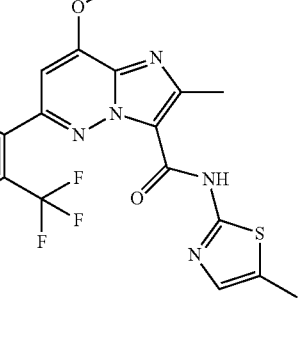 | NT | NT | A | A |
| 862 | 488 | 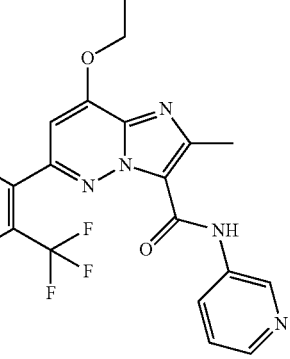 | NT | NT | A | A |
| 863 | 488 | 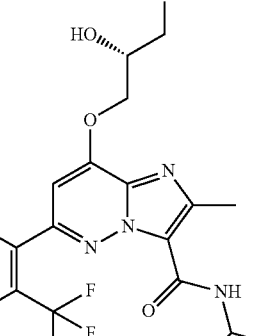 | NT | NT | A | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 864 | 502 | 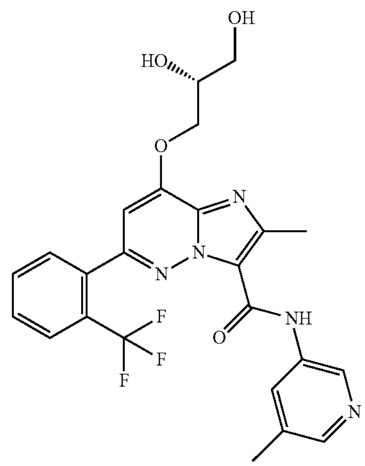 [SMILES: Cc1cncc(NC(=O)c2c(C)nc3c(OC[C@H](O)CO)cc(-c4ccccc4C(F)(F)F)nn23)c1] | NT | NT | A | A |
| 865 | 502 | 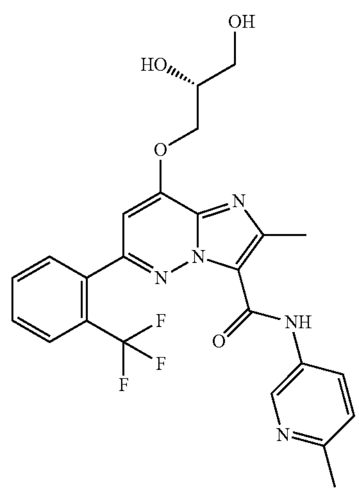 [SMILES: Cc1ccc(NC(=O)c2c(C)nc3c(OC[C@H](O)CO)cc(-c4ccccc4C(F)(F)F)nn23)cn1] | NT | NT | A | A |
| 866 | 352 | 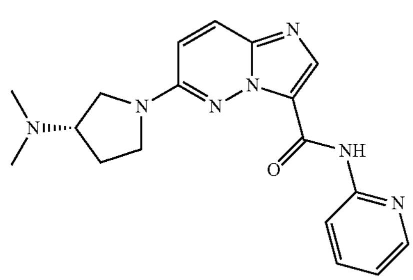 [SMILES: CN(C)[C@H]1CCN(c2ccc3ncc(C(=O)Nc4ccccn4)n3n2)C1] | NT | NT | B | A |
| 867 | 366 | 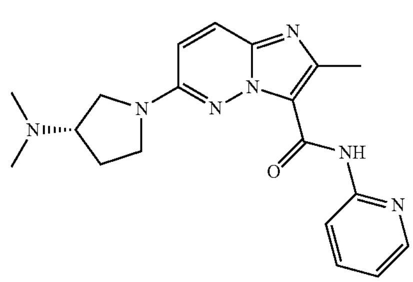 [SMILES: Cc1nc2ccc(N3CC[C@H](N(C)C)C3)nn2c1C(=O)Nc1ccccn1] | NT | NT | B | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 868 | 352 | 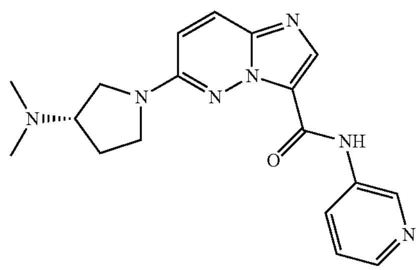 [SMILES: CN(C)[C@H]1CCN(c2ccc3ncc(C(=O)Nc4cccnc4)n3n2)C1] | NT | NT | B | B |
| 869 | 370 | 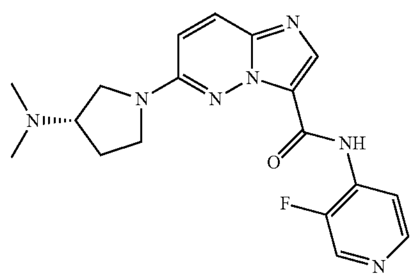 [SMILES: CN(C)[C@H]1CCN(c2ccc3ncc(C(=O)Nc4ccncc4F)n3n2)C1] | NT | NT | B | B |
| 870 | 384 | 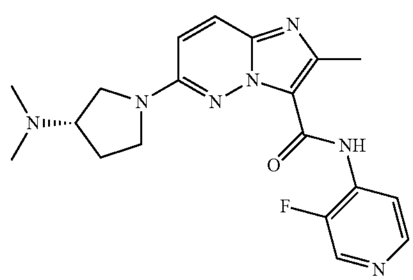 [SMILES: Cc1nc2ccc(N3CC[C@H](N(C)C)C3)nn2c1C(=O)Nc1ccncc1F] | NT | NT | C | B |
| 871 | 367 | 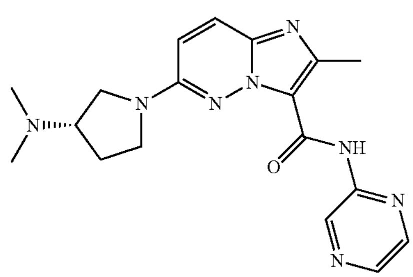 | NT | NT | B | B |
| 872 | 384 | 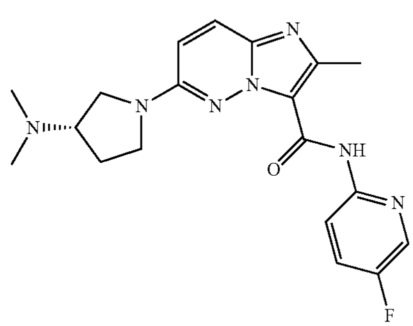 [SMILES: Cc1nc2ccc(N3CC[C@H](N(C)C)C3)nn2c1C(=O)Nc1ccc(F)cn1] | NT | NT | C | B |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 873 | 353 | | NT | NT | B | A |
| 874 | 370 | | NT | NT | A | B |
| 875 | 420 | | NT | NT | C | B |
| 876 | 449 | | NT | NT | A | A |
| 877 | 366 | | NT | NT | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 878 | 449 | | NT | NT | B | B |
| 879 | 353 | | NT | NT | B | B |
| 880 | 367 | | NT | NT | B | B |
| 881 | 367 | | NT | NT | C | B |
| 882 | 353 | | NT | NT | B | B |

TABLE 1-continued
Compounds of Formula (I).
| Compound No | [M + H]+$_{[Calc]}$ | Structure | TAMRA EC1.5 (µM) | % Fold Act | Trp EC1.5 (µM) | % Fold Act |
|---|---|---|---|---|---|---|
| 883 | 424 | 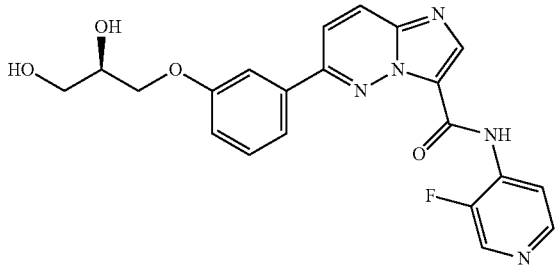 | NT | NT | A | B |
| 884 | 424 | 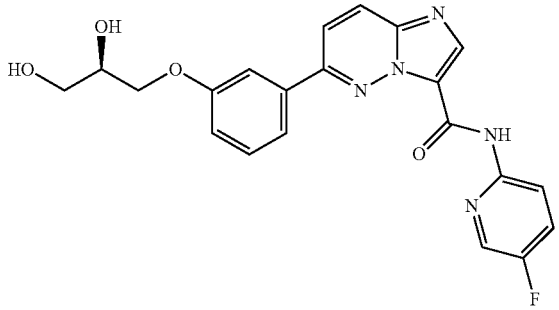 [SMILES: O=C(Nc1ccc(F)cn1)c1cnc2ccc(-c3cccc(OC[C@H](O)CO)c3)nn12] | NT | NT | B | B |
| 885 | 367 | 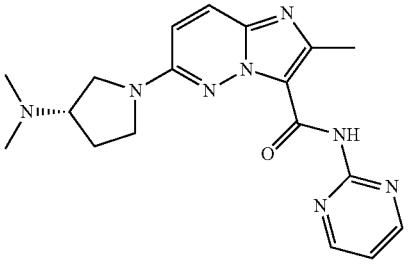 [SMILES: Cc1nc2ccc(N3CC[C@H](N(C)C)C3)nn2c1C(=O)Nc1ncccn1] | NT | NT | B | B |
| 886 | 353 | 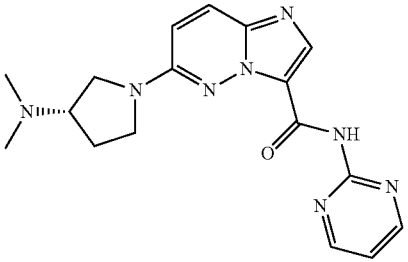 [SMILES: CN(C)[C@H]1CCN(c2ccc3ncc(C(=O)Nc4ncccn4)n3n2)C1] | NT | NT | B | B |
| 887 | 407 | 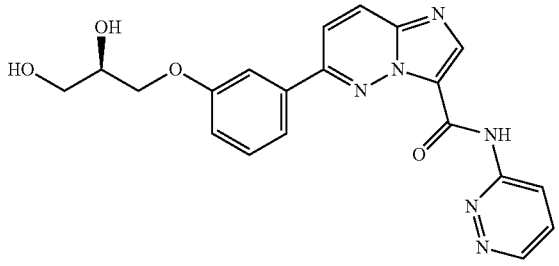 [SMILES: O=C(Nc1cccnn1)c1cnc2ccc(-c3cccc(OC[C@H](O)CO)c3)nn12] | NT | NT | A | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 888 | 328 | 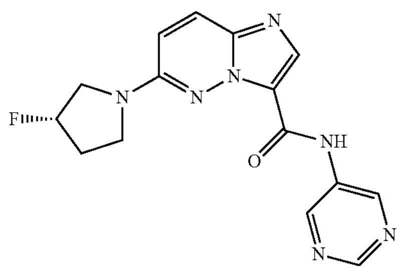 [SMILES: O=C(Nc1cncnc1)c1cnc2ccc(N3CC[C@H](F)C3)nn12] | NT | NT | C | B |
| 889 | 341 | 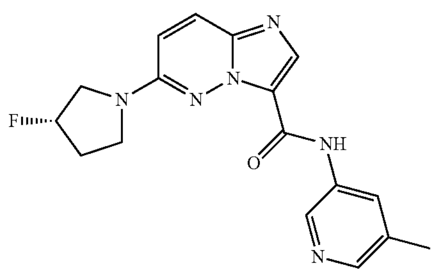 [SMILES: Cc1cncc(NC(=O)c2cnc3ccc(N4CC[C@H](F)C4)nn23)c1] | NT | NT | B | B |
| 890 | 345 | 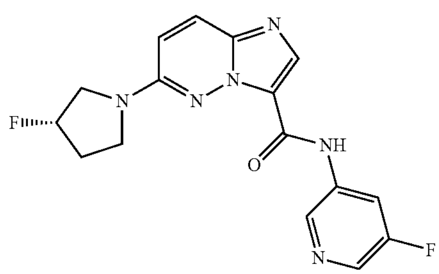 [SMILES: O=C(Nc1cncc(F)c1)c1cnc2ccc(N3CC[C@H](F)C3)nn12] | NT | NT | B | B |
| 891 | 330 | 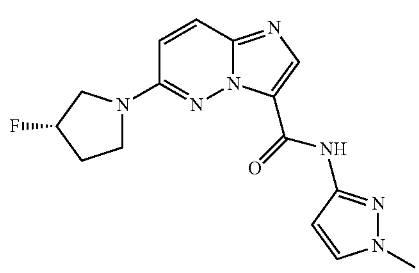 [SMILES: Cn1ccc(NC(=O)c2cnc3ccc(N4CC[C@H](F)C4)nn23)n1] | NT | NT | B | A |
| 892 | 361 | 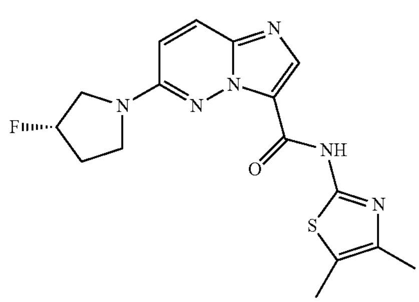 [SMILES: Cc1nc(NC(=O)c2cnc3ccc(N4CC[C@H](F)C4)nn23)sc1C] | NT | NT | A | B |

TABLE 1-continued
Compounds of Formula (I).
| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 893 | 356 | 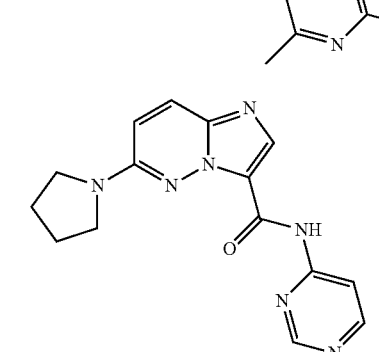 | NT | NT | C | B |
| 894 | 310 | 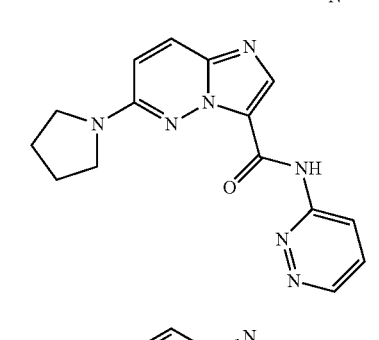 | NT | NT | B | B |
| 895 | 310 | 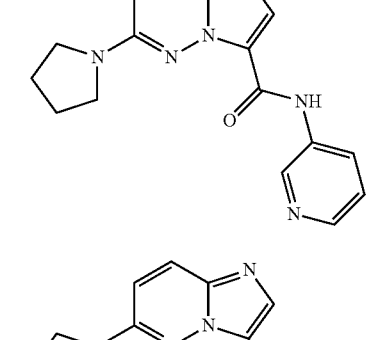 | NT | NT | C | B |
| 896 | 309 | 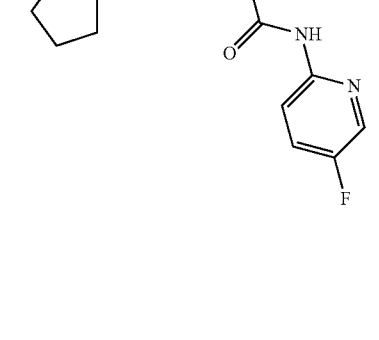 | NT | NT | B | B |
| 897 | 327 | 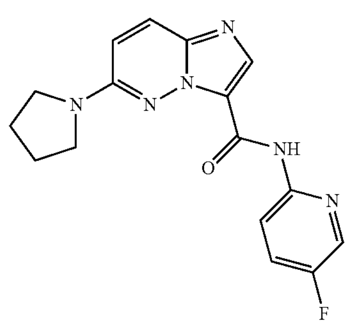 [SMILES: O=C(Nc1ccc(F)cn1)c1cnc2ccc(N3CCCC3)nn12] | NT | NT | C | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 898 | 327 | | NT | NT | C | B |
| 900 | 409 | | NT | NT | A | B |
| 901 | 405 | | NT | NT | A | A |
| 902 | 392 | | NT | NT | A | A |
| 903 | 363 | | NT | NT | C | B |

TABLE 1-continued
Compounds of Formula (I).
| Compound No | [M + H]+$_{[Calc]}$ | Structure | TAMRA EC1.5 (μM) | TAMRA % Fold Act | Trp EC1.5 (μM) | Trp % Fold Act |
|---|---|---|---|---|---|---|
| 904 | 346 | 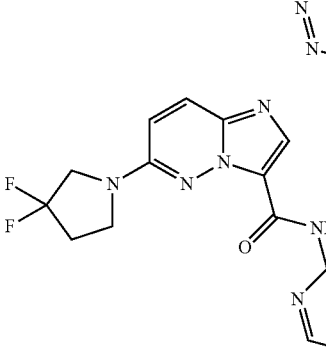 | NT | NT | B | A |
| 905 | 346 | 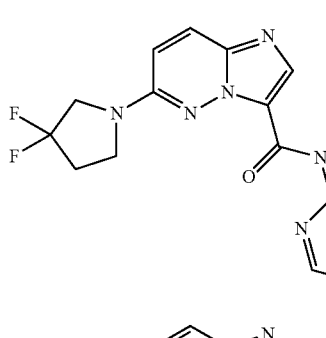 | NT | NT | B | B |
| 906 | 346 | 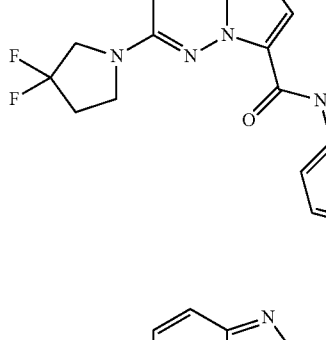 | NT | NT | B | B |
| 907 | 363 | 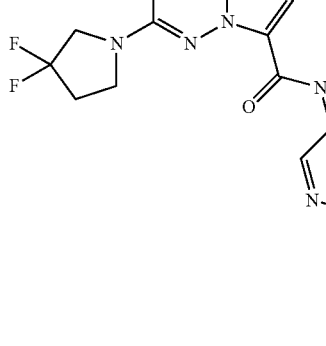 | NT | NT | B | B |
| 908 | 345 |  | NT | NT | B | B |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 909 | 345 | | NT | NT | B | A |
| 910 | 409 | | NT | NT | A | A |
| 911 | 370 | | NT | NT | A | A |
| 912 | 331 | | NT | NT | B | B |
| 913 | 331 | | NT | NT | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 914 | 349 | 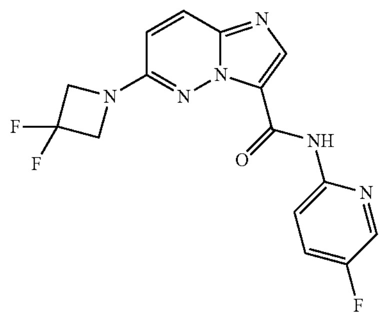 [SMILES: O=C(Nc1ccc(F)cn1)c1cnc2ccc(N3CC(F)(F)C3)nn12] | NT | NT | C | B |
| 915 | 349 | 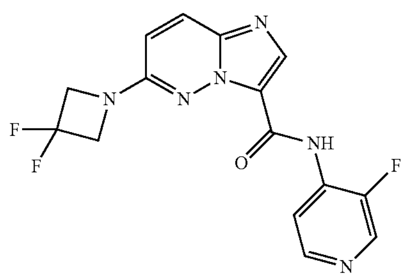 [SMILES: O=C(Nc1ccncc1F)c1cnc2ccc(N3CC(F)(F)C3)nn12] | NT | NT | C | B |
| 916 | 332 | 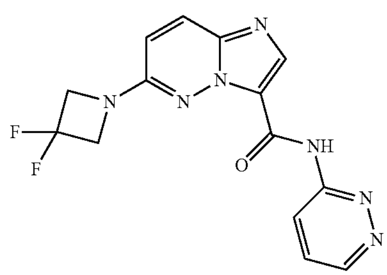 [SMILES: O=C(Nc1cccnn1)c1cnc2ccc(N3CC(F)(F)C3)nn12] | NT | NT | C | B |
| 917 | 418 | 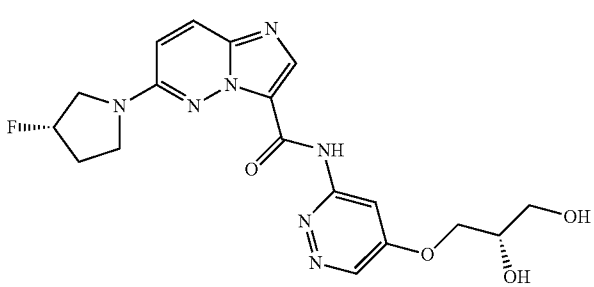 [SMILES: O=C(Nc1cc(OC[C@@H](O)CO)cnn1)c1cnc2ccc(N3CC[C@H](F)C3)nn12] | NT | NT | B | B |
| 918 | 358 | 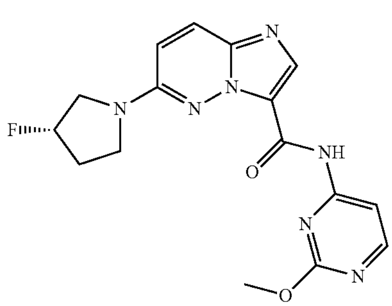 [SMILES: COc1nccc(NC(=O)c2cnc3ccc(N4CC[C@H](F)C4)nn23)n1] | NT | NT | B | B |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 919 | 395 | 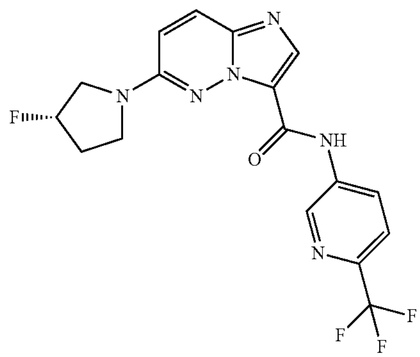 [SMILES: O=C(Nc1ccc(C(F)(F)F)nc1)c1cnc2ccc(N3CC[C@H](F)C3)nn12] | NT | NT | C | B |
| 920 | 341 | 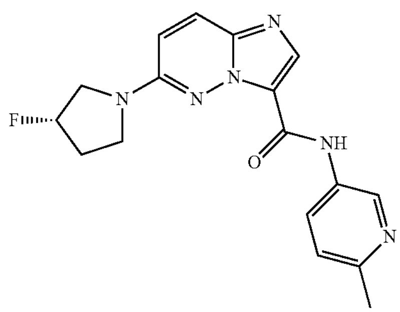 [SMILES: Cc1ccc(NC(=O)c2cnc3ccc(N4CC[C@H](F)C4)nn23)cn1] | NT | NT | B | B |
| 921 | 332 | 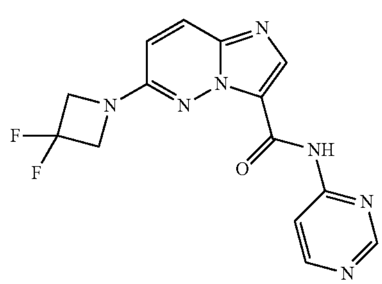 [SMILES: O=C(Nc1ccncn1)c1cnc2ccc(N3CC(F)(F)C3)nn12] | NT | NT | C | B |
| 922 | 358 | 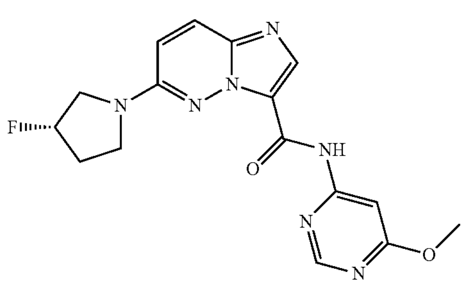 [SMILES: COc1cc(NC(=O)c2cnc3ccc(N4CC[C@H](F)C4)nn23)ncn1] | NT | NT | C | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 923 | 371 | | NT | NT | A | A |
| 924 | 371 | | NT | NT | B | B |
| 926 | 332 | | NT | NT | C | B |
| 927 | 359 | | NT | NT | B | A |
| 928 | 359 | | NT | NT | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 929 | 377 | 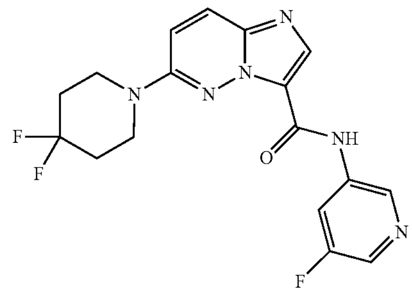 [SMILES: O=C(Nc1cncc(F)c1)c1cnc2ccc(N3CCC(F)(F)CC3)nn12] | NT | NT | B | A |
| 930 | 360 | 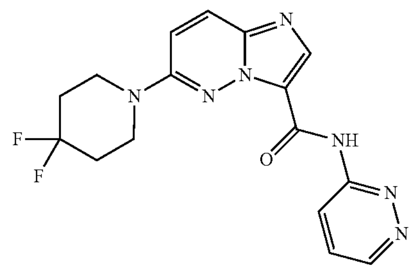 [SMILES: O=C(Nc1cccnn1)c1cnc2ccc(N3CCC(F)(F)CC3)nn12] | NT | NT | B | A |
| 931 | 409 | 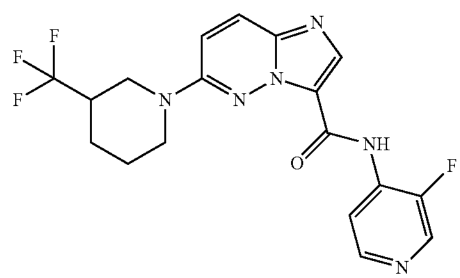 [SMILES: O=C(Nc1ccncc1F)c1cnc2ccc(N3CCCC(C(F)(F)F)C3)nn12] | NT | NT | A | A |
| 932 | 391 | 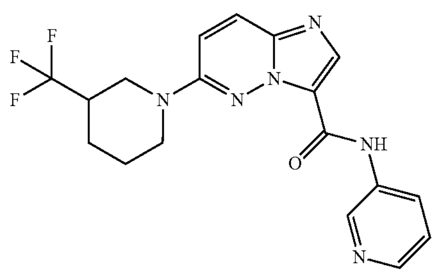 [SMILES: O=C(Nc1cccnc1)c1cnc2ccc(N3CCCC(C(F)(F)F)C3)nn12] | NT | NT | A | A |
| 933 | 339 | 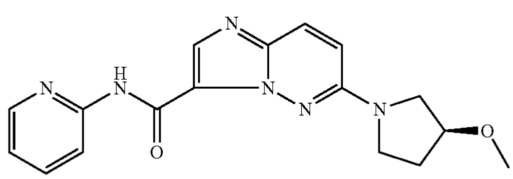 [SMILES: CO[C@H]1CCN(c2ccc3ncc(C(=O)Nc4ccccn4)n3n2)C1] | NT | NT | B | B |
| 934 | 339 | 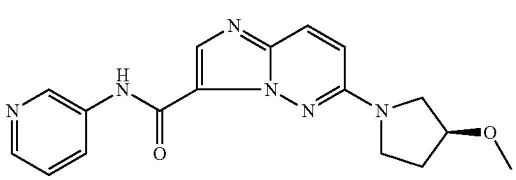 [SMILES: CO[C@H]1CCN(c2ccc3ncc(C(=O)Nc4cccnc4)n3n2)C1] | NT | NT | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 935 | 357 | 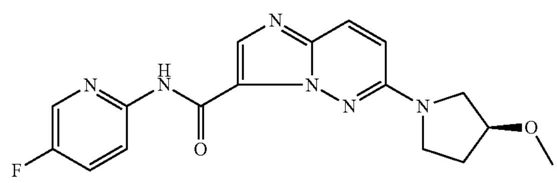 [SMILES: CO[C@H]1CCN(c2ccc3ncc(C(=O)Nc4ccc(F)cn4)n3n2)C1] | NT | NT | B | B |
| 936 | 357 | 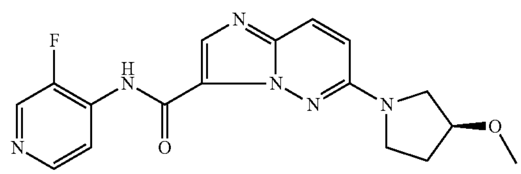 [SMILES: CO[C@H]1CCN(c2ccc3ncc(C(=O)Nc4ccncc4F)n3n2)C1] | NT | NT | B | B |
| 937 | 357 | 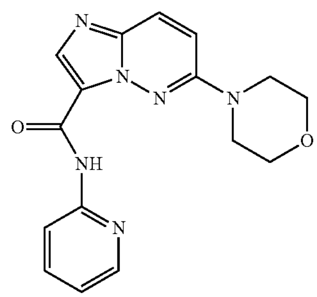 [SMILES: O=C(Nc1ccccn1)c1cnc2ccc(N3CCOCC3)nn12] | NT | NT | B | A |
| 938 | 325 | 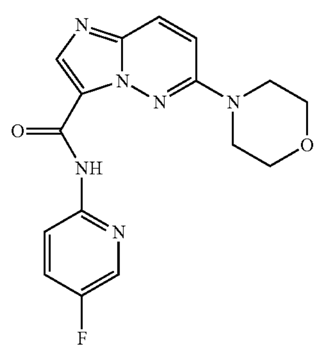 [SMILES: O=C(Nc1ccc(F)cn1)c1cnc2ccc(N3CCOCC3)nn12] | NT | NT | B | B |
| 939 | 343 | 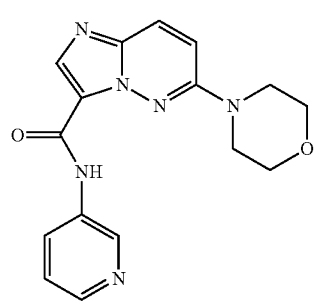 [SMILES: O=C(Nc1cccnc1)c1cnc2ccc(N3CCOCC3)nn12] | NT | NT | B | B |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 940 | 325 | | NT | NT | C | B |
| 941 | 343 | | NT | NT | B | B |
| 942 | 326 | | NT | NT | B | B |
| 943 | 343 | | NT | NT | B | B |

TABLE 1-continued

Compounds of Formula (I).

| | | | TAMRA | | Trp | |
|---|---|---|---|---|---|---|
| Compound No | [M + H]+[Calc] | Structure | EC1.5 (μM) | % Fold Act | EC1.5 (μM) | % Fold Act |
| 944 | 340 | | NT | NT | B | B |
| 945 | 391 | | NT | NT | A | A |
| 946 | 338 | | NT | NT | C | B |
| 947 | 355 | | NT | NT | B | B |
| 948 | 337 | | NT | NT | B | B |

TABLE 1-continued
Compounds of Formula (I).
| Compound No | [M + H]+[Cale] | Structure | TAMRA EC1.5 (µM) | % Fold Act | Trp EC1.5 (µM) | % Fold Act |
|---|---|---|---|---|---|---|
| 949 | 355 | 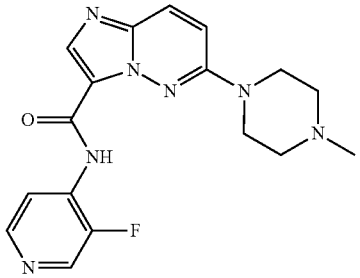 [SMILES: CN1CCN(c2ccc3ncc(C(=O)Nc4ccncc4F)n3n2)CC1] | NT | NT | C | B |
| 950 | 338 | 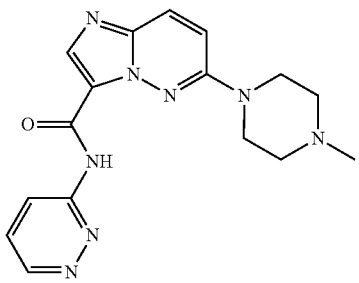 [SMILES: CN1CCN(c2ccc3ncc(C(=O)Nc4cccnn4)n3n2)CC1] | NT | NT | C | B |
| 951 | 355 | 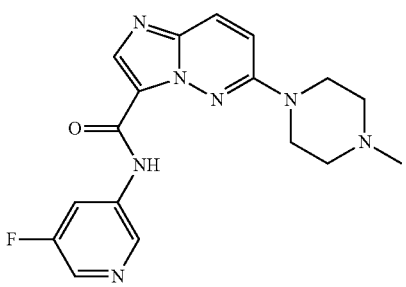 [SMILES: CN1CCN(c2ccc3ncc(C(=O)Nc4cncc(F)c4)n3n2)CC1] | NT | NT | C | B |
| 952 | 336 | 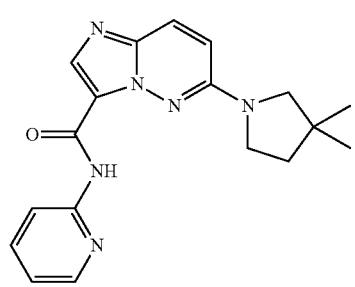 [SMILES: CC1(C)CCN(c2ccc3ncc(C(=O)Nc4ccccn4)n3n2)C1] | NT | NT | B | A |
| 953 | 336 | 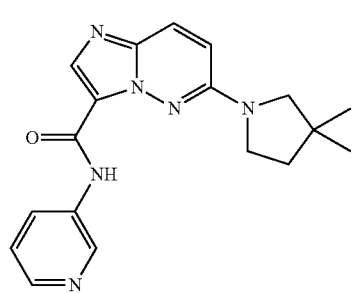 [SMILES: CC1(C)CCN(c2ccc3ncc(C(=O)Nc4cccnn4)n3n2)C1] | NT | NT | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 954 | 354 | | NT | NT | B | B |
| 955 | 337 | | NT | NT | B | A |
| 956 | 354 | | NT | NT | B | B |
| 957 | 390 | | NT | NT | A | A |
| 958 | 376 | | NT | NT | A | A |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 959 | 394 | 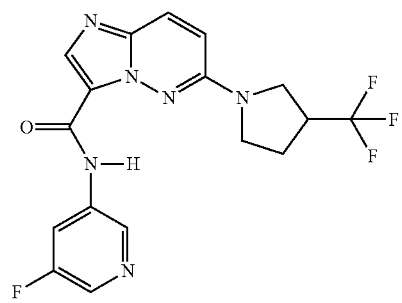 [SMILES: O=C(Nc1cncc(F)c1)c1cnc2ccc(N3CCC(C(F)(F)F)C3)nn12] | NT | NT | A | A |
| 960 | 354 | 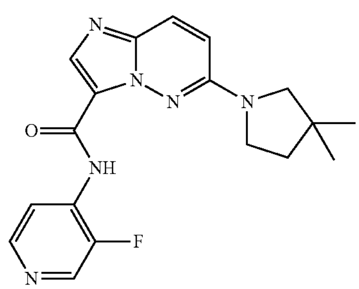 [SMILES: CC1(C)CCN(c2ccc3ncc(C(=O)Nc4ccncc4F)n3n2)C1] | NT | NT | A | B |
| 961 | 325 | 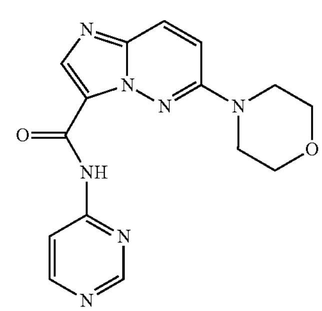 [SMILES: O=C(Nc1ccncn1)c1cnc2ccc(N3CCOCC3)nn12] | NT | NT | C | B |
| 962 | 376 | 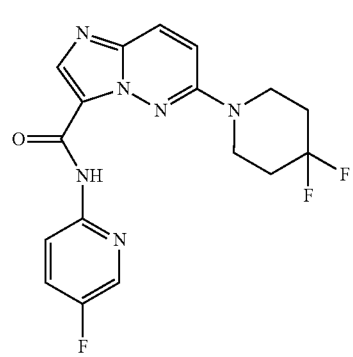 [SMILES: O=C(Nc1ccc(F)cn1)c1cnc2ccc(N3CCC(F)(F)CC3)nn12] | NT | NT | B | B |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 963 | 376 | 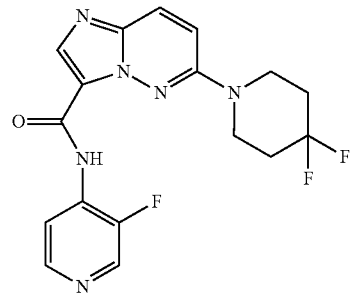 [SMILES: O=C(Nc1ccncc1F)c1cnc2ccc(N3CCC(F)(F)CC3)nn12] | NT | NT | B | B |
| 964 | 359 | 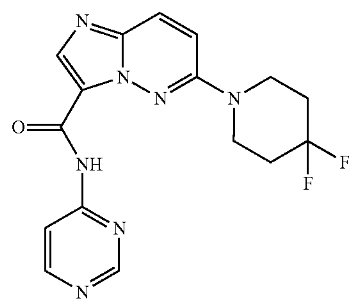 [SMILES: O=C(Nc1ccncn1)c1cnc2ccc(N3CCC(F)(F)CC3)nn12] | NT | NT | B | B |
| 965 | 424 | 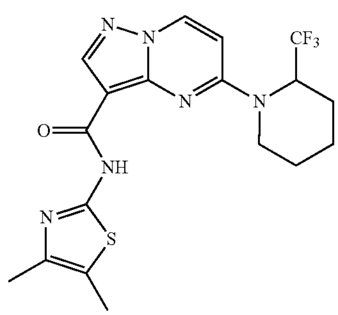 [SMILES: Cc1nc(NC(=O)c2cnn3ccc(N4CCCCC4C(F)(F)F)nc23)sc1C] | NT | NT | B | A |
| 966 | 376 | 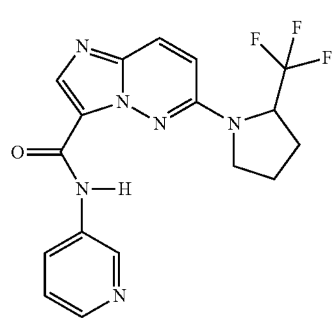 [SMILES: O=C(Nc1cccnc1)c1cnc2ccc(N3CCCC3C(F)(F)F)nn12] | NT | NT | A | A |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 967 | 394 | | NT | NT | B | A |
| 968 | 377 | | NT | NT | A | A |
| 969 | 410 | | NT | NT | A | A |
| 970 | 377 | | NT | NT | A | A |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 971 | 338 | | NT | NT | C | B |
| 972 | 337 | | NT | NT | B | B |
| 973 | 339 | | NT | NT | C | B |
| 974 | 376 | | NT | NT | A | A |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 975 | 322 | 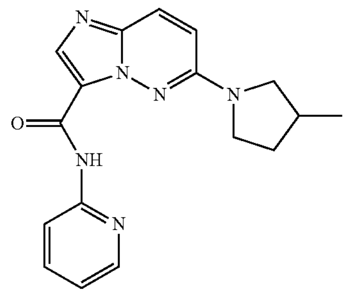 [SMILES: CC1CCN(c2ccc3ncc(C(=O)Nc4ccccn4)n3n2)C1] | NT | NT | B | B |
| 976 | 322 | 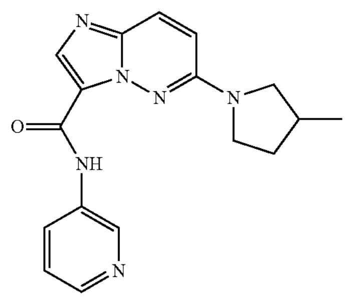 [SMILES: CC1CCN(c2ccc3ncc(C(=O)Nc4cccnc4)n3n2)C1] | NT | NT | B | A |
| 977 | 340 | 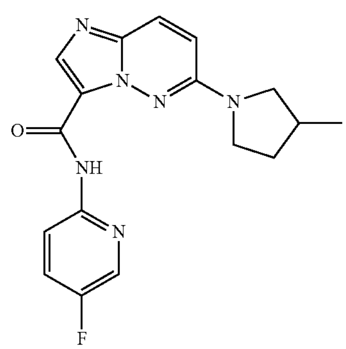 [SMILES: CC1CCN(c2ccc3ncc(C(=O)Nc4ccc(F)cn4)n3n2)C1] | NT | NT | B | B |
| 978 | 323 | 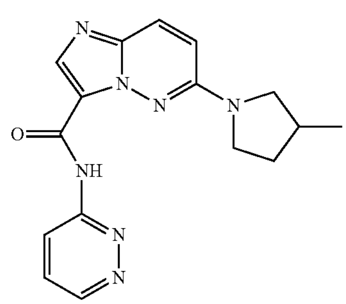 [SMILES: CC1CCN(c2ccc3ncc(C(=O)Nc4cccnn4)n3n2)C1] | NT | NT | A | A |

TABLE 1-continued
Compounds of Formula (I).
| Compound No | [M + H]+[Calc] | Structure | TAMRA EC1.5 (µM) | % Fold Act | Trp EC1.5 (µM) | % Fold Act |
|---|---|---|---|---|---|---|
| 979 | 340 | 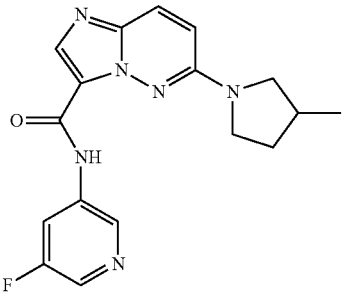 [SMILES: CC1CCN(c2ccc3ncc(C(=O)Nc4cncc(F)c4)n3n2)C1] | NT | NT | A | A |
| 980 | 358 | 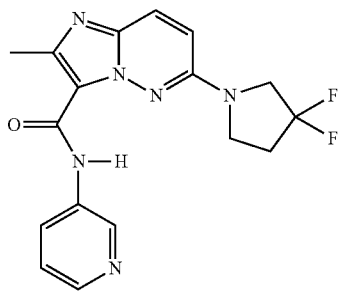 | NT | NT | B | A |
| 981 | 324 | 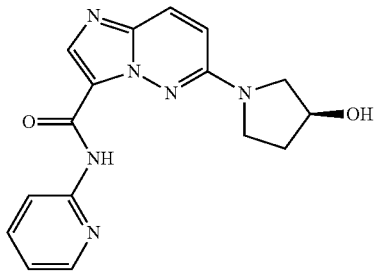 [SMILES: O=C(Nc1ccccn1)c1cnc2ccc(N3CC[C@H](O)C3)nn12] | NT | NT | B | B |
| 982 | 324 | 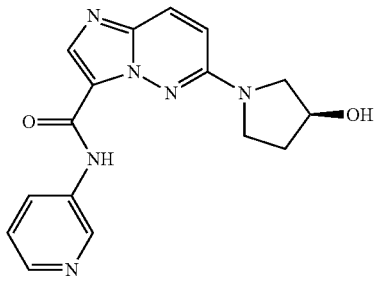 [SMILES: O=C(Nc1cccnc1)c1cnc2ccc(N3CC[C@H](O)C3)nn12] | NT | NT | B | B |
| 983 | 342 | 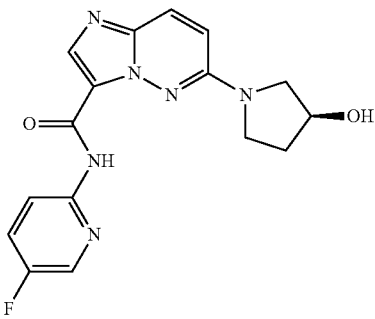 [SMILES: O=C(Nc1ccc(F)cn1)c1cnc2ccc(N3CC[C@H](O)C3)nn12] | NT | NT | B | B |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 984 | 325 | 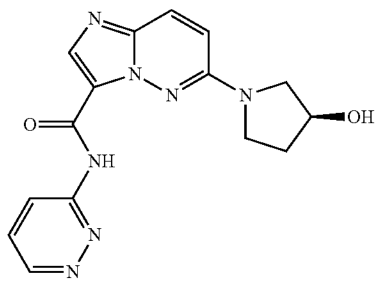 [SMILES: O=C(Nc1cccnn1)c1cnc2ccc(N3CC[C@H](O)C3)nn12] | NT | NT | B | B |
| 985 | 342 | 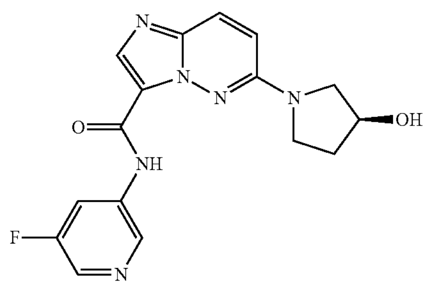 [SMILES: O=C(Nc1cncc(F)c1)c1cnc2ccc(N3CC[C@H](O)C3)nn12] | NT | NT | B | B |
| 986 | 340 | 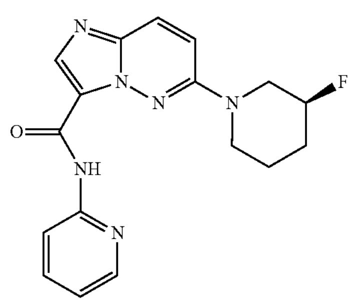 [SMILES: O=C(Nc1ccccn1)c1cnc2ccc(N3CCC[C@H](F)C3)nn12] | NT | NT | A | A |
| 987 | 340 | 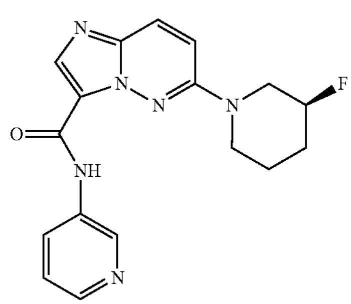 [SMILES: O=C(Nc1cccnc1)c1cnc2ccc(N3CCC[C@H](F)C3)nn12] | NT | NT | B | A |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 988 | 358 | 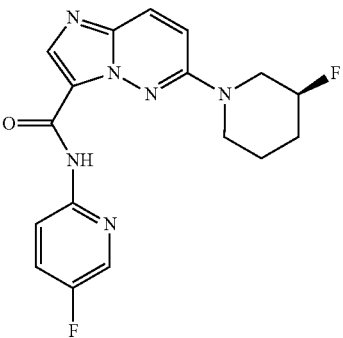 [SMILES: O=C(Nc1ccc(F)cn1)c1cnc2ccc(N3CCC[C@H](F)C3)nn12] | NT | NT | B | A |
| 989 | 341 | 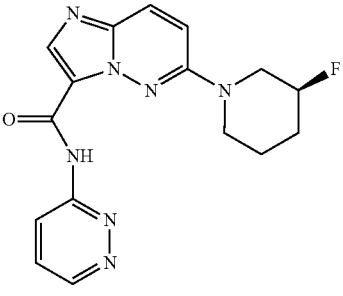 [SMILES: O=C(Nc1cccnn1)c1cnc2ccc(N3CCC[C@H](F)C3)nn12] | NT | NT | B | A |
| 990 | 358 | 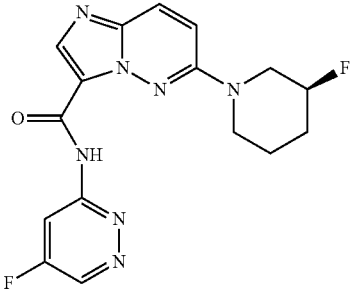 [SMILES: O=C(Nc1cc(F)cnn1)c1cnc2ccc(N3CCC[C@H](F)C3)nn12] | NT | NT | A | A |
| 991 | 376 | 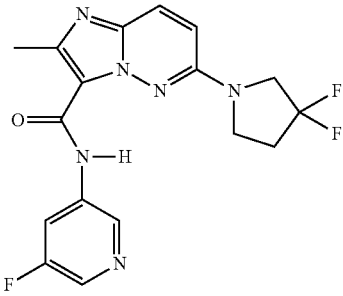 [SMILES: Cc1nc2ccc(N3CCC(F)(F)C3)nn2c1C(=O)Nc1cncc(F)c1] | NT | NT | B | B |

TABLE 1-continued

Compounds of Formula (I).

| Compound No | [M + H]+[Calc] | Structure | TAMRA EC1.5 (μM) | % Fold Act | Trp EC1.5 (μM) | % Fold Act |
|---|---|---|---|---|---|---|
| 992 | 323 | 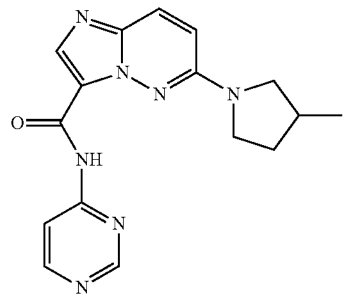 [SMILES: CC1CCN(c2ccc3ncc(C(=O)Nc4ccncn4)n3n2)C1] | NT | NT | C | B |
| 993 | 341 | 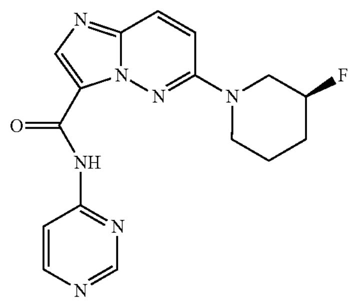 [SMILES: O=C(Nc1ccncn1)c1cnc2ccc(N3CCC[C@H](F)C3)nn12] | NT | NT | B | A |
| 994 | 373 | 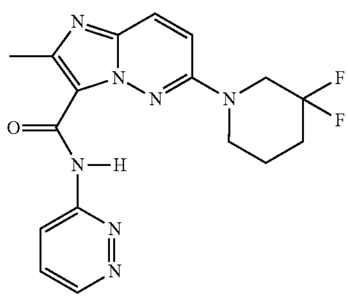 [SMILES: Cc1nc2ccc(N3CCCC(F)(F)C3)nn2c1C(=O)Nc1cccnn1] | NT | NT | A | A |
| 995 | 352 | 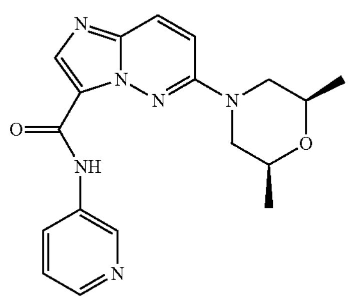 [SMILES: C[C@@H]1CN(c2ccc3ncc(C(=O)Nc4cccnc4)n3n2)C[C@H](C)O1] | NT | NT | B | A |
| 996 | 353 | 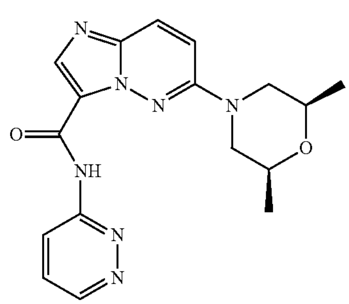 [SMILES: C[C@@H]1CN(c2ccc3ncc(C(=O)Nc4cccnn4)n3n2)C[C@H](C)O1] | NT | NT | B | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 997 | 370 | 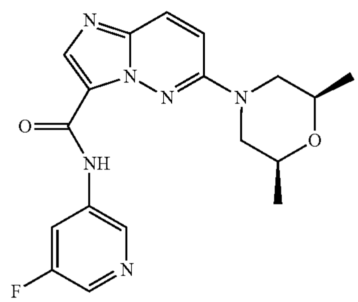 [SMILES: C[C@@H]1CN(c2ccc3ncc(C(=O)Nc4cncc(F)c4)n3n2)C[C@H](C)O1] | NT | NT | B | A |
| 998 | 391 | 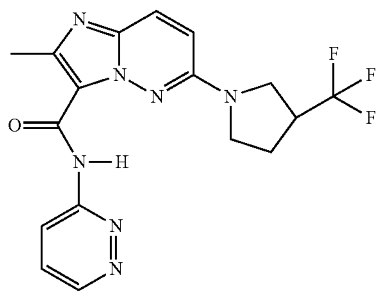 [SMILES: Cc1nc2ccc(N3CCC(C(F)(F)F)C3)nn2c1C(=O)Nc1cccnn1] | NT | NT | A | A |
| 999 | 376 | 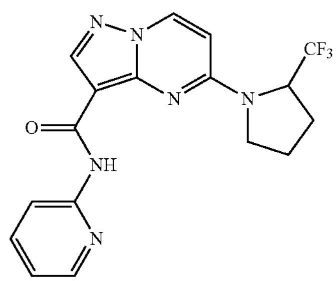 [SMILES: O=C(Nc1ccccn1)c1cnn2ccc(N3CCCC3C(F)(F)F)nc12] | NT | NT | A | A |
| 1000 | 376 | 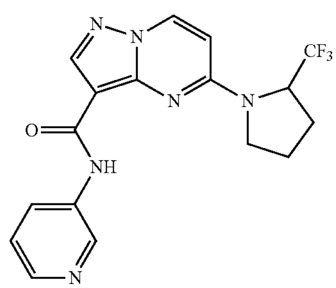 [SMILES: O=C(Nc1cccnc1)c1cnn2ccc(N3CCCC3C(F)(F)F)nc12] | NT | NT | A | A |
| 1001 | 394 | 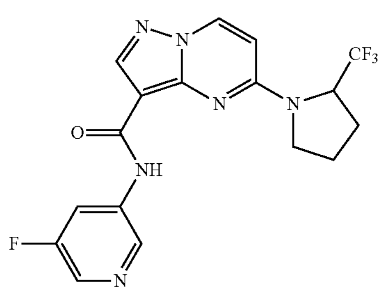 [SMILES: O=C(Nc1cncc(F)c1)c1cnn2ccc(N3CCCC3C(F)(F)F)nc12] | NT | NT | A | A |

TABLE 1-continued

Compounds of Formula (I).

| Compound No | [M + H]+ [Calc] | Structure | TAMRA EC1.5 (µM) | TAMRA % Fold Act | Trp EC1.5 (µM) | Trp % Fold Act |
|---|---|---|---|---|---|---|
| 1002 | 338 | 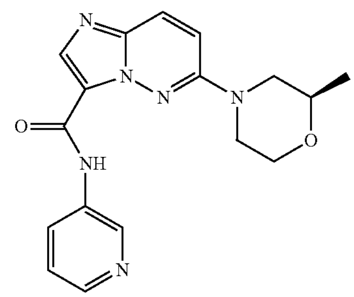 [SMILES: C[C@@H]1CN(c2ccc3ncc(C(=O)Nc4cccnc4)n3n2)CCO1] | NT | NT | B | A |
| 1003 | 339 | 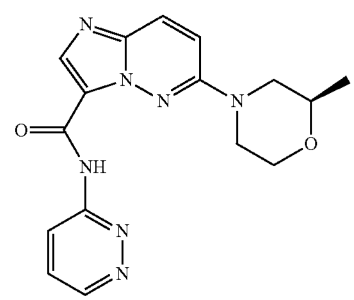 [SMILES: C[C@@H]1CN(c2ccc3ncc(C(=O)Nc4cccnn4)n3n2)CCO1] | NT | NT | B | A |
| 1004 | 356 | 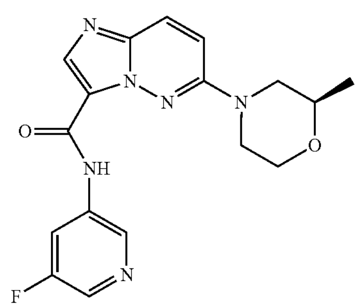 [SMILES: C[C@@H]1CN(c2ccc3ncc(C(=O)Nc4cncc(F)c4)n3n2)CCO1] | NT | NT | B | A |
| 1005 | 359 | 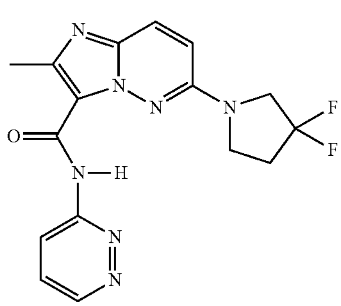 [SMILES: Cc1nc2ccc(N3CCC(F)(F)C3)nn2c1C(=O)Nc1cccnn1] | NT | NT | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1006 | 391 | 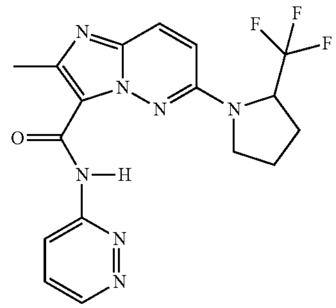 [SMILES: Cc1nc2ccc(N3CCCC3C(F)(F)F)nn2c1C(=O)Nc1cccnn1] | NT | NT | B | A |
| 1007 | 390 | 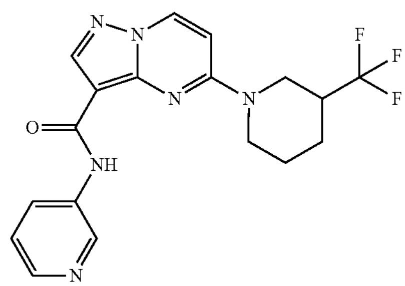 [SMILES: O=C(Nc1cccnc1)c1cnn2ccc(N3CCCC(C(F)(F)F)C3)nc12] | NT | NT | A | A |
| 1008 | 390 | 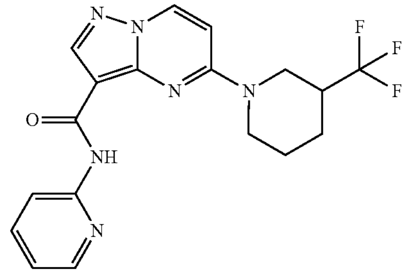 [SMILES: O=C(Nc1ccccn1)c1cnn2ccc(N3CCCC(C(F)(F)F)C3)nc12] | NT | NT | B | A |
| 1009 | 408 | 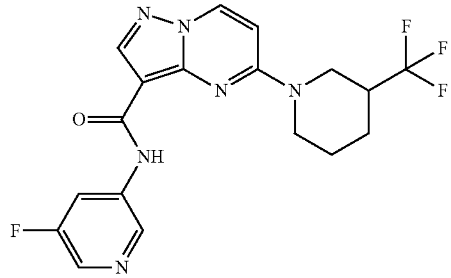 [SMILES: O=C(Nc1cncc(F)c1)c1cnn2ccc(N3CCCC(C(F)(F)F)C3)nc12] | NT | NT | A | A |
| 1010 | 408 | 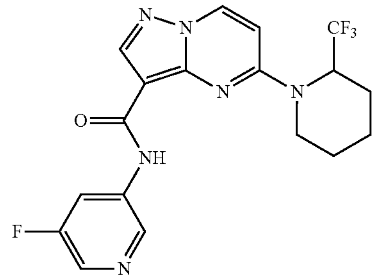 [SMILES: O=C(Nc1cncc(F)c1)c1cnn2ccc(N3CCCCC3C(F)(F)F)nc12] | NT | NT | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1011 | 376 | | NT | NT | A | A |
| 1012 | 376 | | NT | NT | A | A |
| 1013 | 394 | | NT | NT | A | A |
| 1014 | 377 | | NT | NT | A | A |
| 1015 | 390 | | NT | NT | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1016 | 390 | | NT | NT | A | A |
| 1017 | 408 | | NT | NT | A | A |
| 1018 | 391 | | NT | NT | A | A |
| 1019 | 376 | | NT | NT | B | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1020 | 429 | | NT | NT | A | A |
| 1021 | 391 | | NT | NT | B | A |
| 1022 | 377 | | NT | NT | B | A |
| 1023 | 391 | | NT | NT | B | A |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 1024 | 407 | 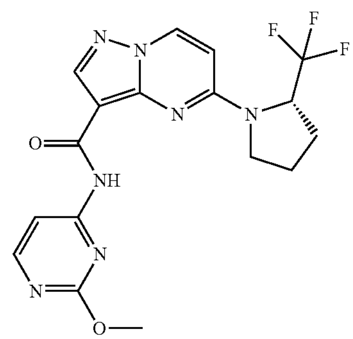 [SMILES: COc1nccc(NC(=O)c2cnn3ccc(N4CCC[C@H]4C(F)(F)F)nc23)n1] | NT | NT | A | A |
| 1025 | 377 | 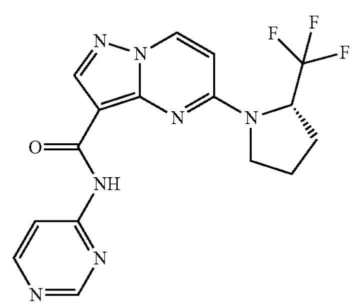 | NT | NT | A | A |
| 1026 | 376 | 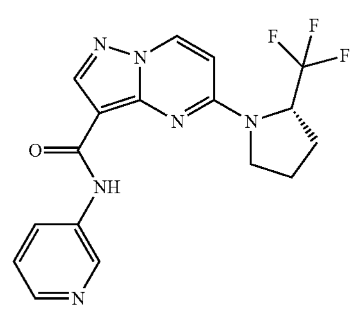 [SMILES: O=C(Nc1cccnc1)c1cnn2ccc(N3CCC[C@H]3C(F)(F)F)nc12] | NT | NT | A | A |
| 1027 | 390 | 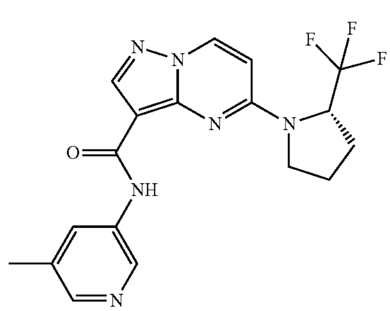 [SMILES: Cc1cncc(NC(=O)c2cnn3ccc(N4CCC[C@H]4C(F)(F)F)nc23)c1] | NT | NT | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1028 | 394 | | NT | NT | A | A |
| 1029 | 376 | | NT | NT | A | A |
| 1030 | 377 | | NT | NT | A | A |
| 1031 | 377 | | NT | NT | A | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1032 | 410 | | NT | NT | A | A |
| 1033 | 424 | | NT | NT | A | A |
| 1034 | 391 | | NT | NT | A | A |
| 1035 | 390 | | NT | NT | A | A |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 1036 | 404 | | NT | NT | A | A |
| 1037 | 322 | | NT | NT | B | A |
| 1038 | 356 | | NT | NT | B | B |
| 1039 | 340 | | NT | NT | B | A |

TABLE 1-continued

Compounds of Formula (I).

| | | | TAMRA | | Trp | |
|---|---|---|---|---|---|---|
| Compound No | [M + H]+$_{[Calc]}$ | Structure | EC1.5 (μM) | % Fold Act | EC1.5 (μM) | % Fold Act |
| 1040 | 323 | | NT | NT | B | A |
| 1041 | 323 | | NT | NT | B | B |
| 1042 | 323 | | NT | NT | B | B |
| 1043 | 353 | | NT | NT | B | B |
| 1044 | 322 | | NT | NT | B | A |

TABLE 1-continued

Compounds of Formula (I).

| Compound No | [M + H]+[Calc] | Structure | TAMRA | | Trp | |
|---|---|---|---|---|---|---|
| | | | EC1.5 (μM) | % Fold Act | EC1.5 (μM) | % Fold Act |
| 1045 | 336 | | NT | NT | B | B |
| 1046 | 391 | | NT | NT | A | A |
| 1047 | 390 | | NT | NT | A | A |
| 1048 | 391 | | NT | NT | A | A |

TABLE 1-continued
Compounds of Formula (I).
| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1049 | 421 | 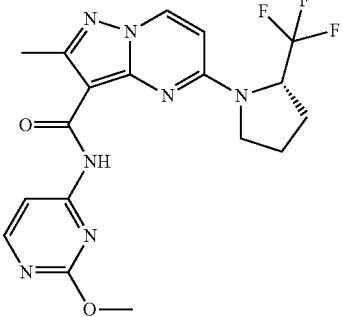 | NT | NT | A | A |
| 1050 | 408 | 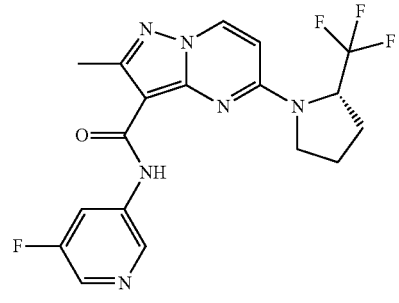 [SMILES: Cc1nn2ccc(N3CCC[C@H]3C(F)(F)F)nc2c1C(=O)Nc1cncc(F)c1] | NT | NT | A | A |
| 1051 | 353 | 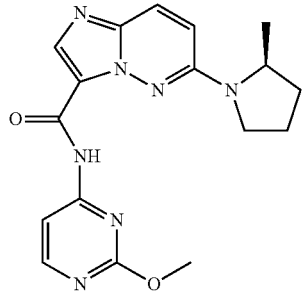 [SMILES: COc1nccc(NC(=O)c2cnc3ccc(N4CCC[C@@H]4C)nn23)n1] | NT | NT | C | B |
| 1052 | 340 | 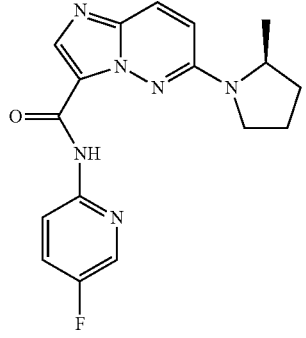 [SMILES: C[C@H]1CCCN1c1ccc2ncc(C(=O)Nc3ccc(F)cn3)n2n1] | NT | NT | B | B |

TABLE 1-continued
Compounds of Formula (I).
| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1053 | 322 | 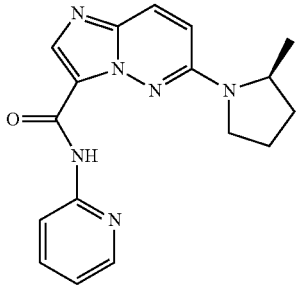 [SMILES: C[C@H]1CCCN1c1ccc2ncc(C(=O)Nc3ccccn3)n2n1] | NT | NT | B | A |
| 1054 | 323 | 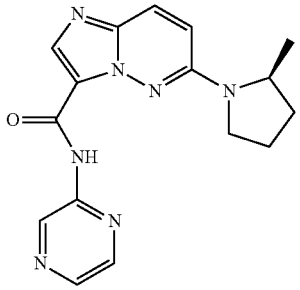 [SMILES: C[C@H]1CCCN1c1ccc2ncc(C(=O)Nc3cnccn3)n2n1] | NT | NT | C | B |
| 1055 | 323 | 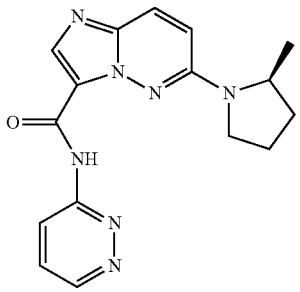 [SMILES: C[C@H]1CCCN1c1ccc2ncc(C(=O)Nc3cccnn3)n2n1] | NT | NT | B | A |
| 1056 | 322 | 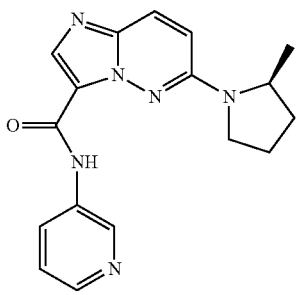 [SMILES: C[C@H]1CCCN1c1ccc2ncc(C(=O)Nc3cccnc3)n2n1] | NT | NT | B | B |
| 1057 | 323 | 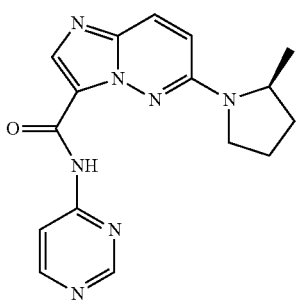 [SMILES: C[C@H]1CCCN1c1ccc2ncc(C(=O)Nc3ccncn3)n2n1] | NT | NT | C | B |

TABLE 1-continued

Compounds of Formula (I).

| Compound No | [M + H]+[Calc] | Structure | TAMRA EC1.5 (µM) | % Fold Act | Trp EC1.5 (µM) | % Fold Act |
|---|---|---|---|---|---|---|
| 1058 | 336 | 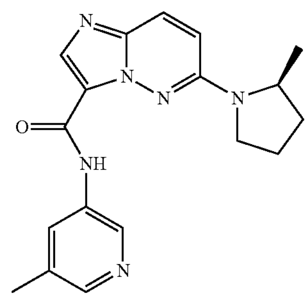 [SMILES: Cc1cncc(NC(=O)c2cnc3ccc(N4CCC[C@@H]4C)nn23)c1] | NT | NT | B | B |
| 1059 | 340 | 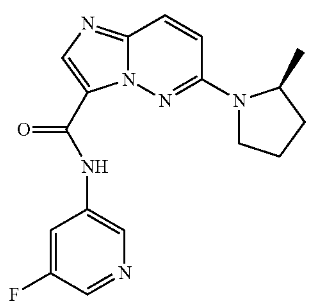 [SMILES: C[C@H]1CCCN1c1ccc2ncc(C(=O)Nc3cncc(F)c3)n2n1] | NT | NT | B | B |
| 1060 | 390 | 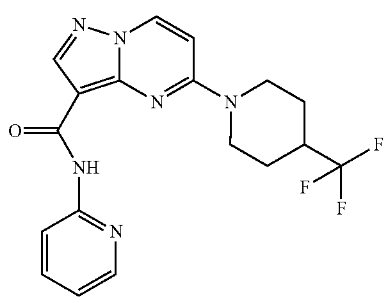 [SMILES: O=C(Nc1ccccn1)c1cnn2ccc(N3CCC(C(F)(F)F)CC3)nc12] | NT | NT | A | A |
| 1061 | 391 | 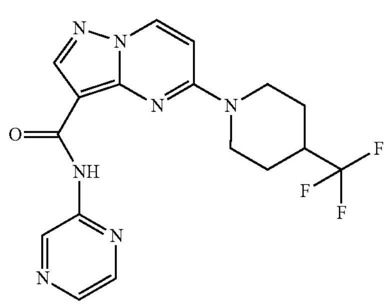 [SMILES: O=C(Nc1cnccn1)c1cnn2ccc(N3CCC(C(F)(F)F)CC3)nc12] | NT | NT | B | A |

TABLE 1-continued

Compounds of Formula (I).

| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1062 | 391 | | NT | NT | A | A |
| 1063 | 391 | | NT | NT | A | A |
| 1064 | 421 | | NT | NT | A | A |
| 1065 | 424 | | NT | NT | B | A |

TABLE 1-continued

Compounds of Formula (I).

| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 1066 | 390 | 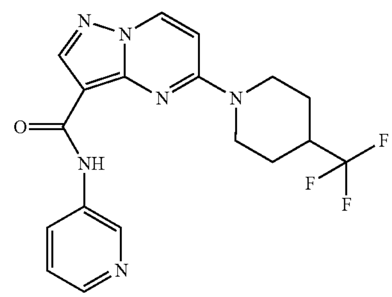 [SMILES: O=C(Nc1cccnc1)c1cnn2ccc(N3CCC(C(F)(F)F)CC3)nc12] | NT | NT | A | A |
| 1067 | 408 | 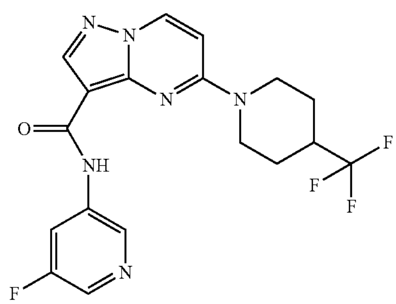 [SMILES: O=C(Nc1cncc(F)c1)c1cnn2ccc(N3CCC(C(F)(F)F)CC3)nc12] | NT | NT | B | A |
| 1068 | 391 | 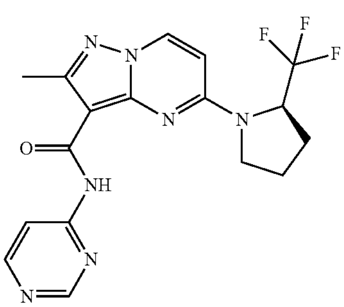 [SMILES: Cc1nn2ccc(N3CCC[C@@H]3C(F)(F)F)nc2c1C(=O)Nc1ccncn1] | NT | NT | B | A |
| 1069 | 408 | 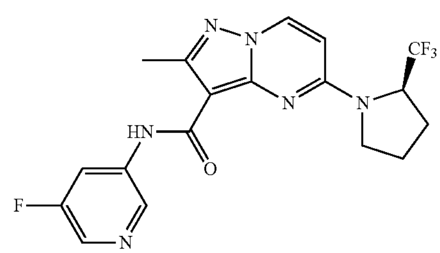 [SMILES: Cc1nn2ccc(N3CCC[C@@H]3C(F)(F)F)nc2c1C(=O)Nc1cncc(F)c1] | NT | NT | A | A |
| 1070 | 390 | 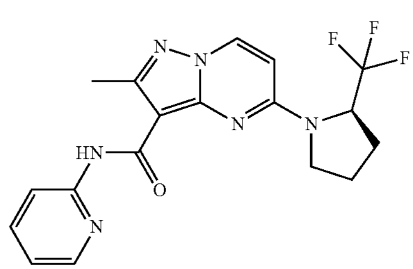 [SMILES: Cc1nn2ccc(N3CCC[C@@H]3C(F)(F)F)nc2c1C(=O)Nc1ccccn1] | NT | NT | B | A |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 1071 | 390 | 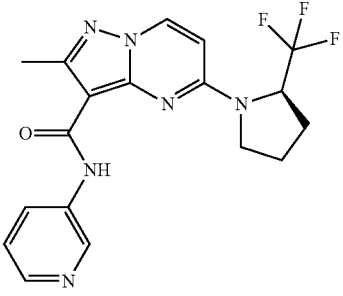 [SMILES: Cc1nn2ccc(N3CCC[C@@H]3C(F)(F)F)nc2c1C(=O)Nc1cccnc1] | NT | NT | A | A |
| 1072 | 404 | 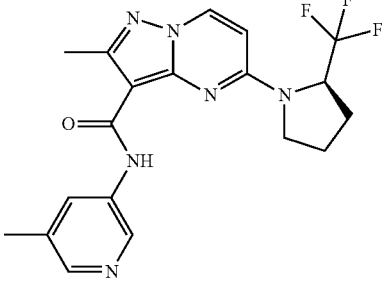 | NT | NT | A | A |
| 1073 | 404 | 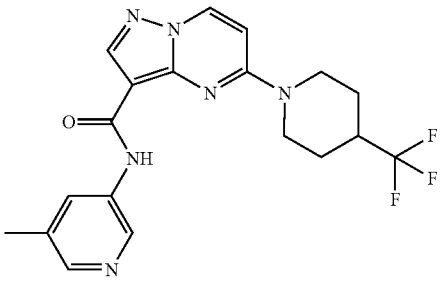 [SMILES: Cc1cncc(NC(=O)c2cnn3ccc(N4CCC(C(F)(F)F)CC4)nc23)c1] | NT | NT | A | A |
| 1074 | 457 | 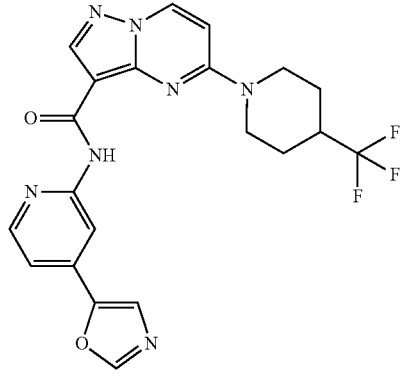 [SMILES: O=C(Nc1cc(-c2cnco2)ccn1)c1cnn2ccc(N3CCC(C(F)(F)F)CC3)nc12] | NT | NT | A | A |

TABLE 1-continued

Compounds of Formula (I).

| Compound No | [M + H]+[Calc] | Structure | TAMRA EC1.5 (µM) | TAMRA % Fold Act | Trp EC1.5 (µM) | Trp % Fold Act |
|---|---|---|---|---|---|---|
| 1075 | 391 | 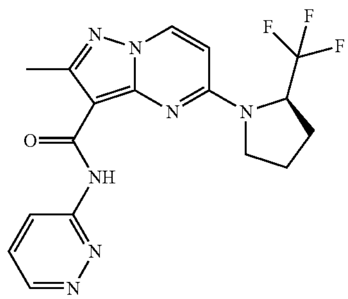 [SMILES: Cc1nn2ccc(N3CCC[C@@H]3C(F)(F)F)nc2c1C(=O)Nc1cccnn1] | NT | NT | B | A |
| 1076 | 376 | 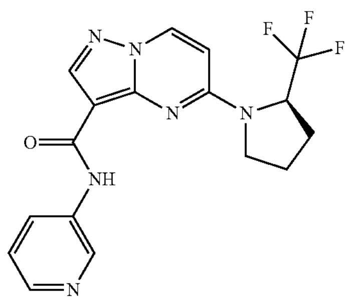 [SMILES: O=C(Nc1cccnc1)c1cnn2ccc(N3CCC[C@@H]3C(F)(F)F)nc12] | NT | NT | B | A |
| 1077 | 390 | 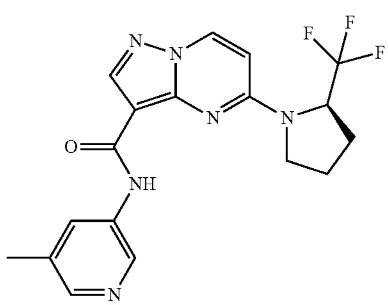 [SMILES: Cc1cncc(NC(=O)c2cnn3ccc(N4CCC[C@@H]4C(F)(F)F)nc23)c1] | NT | NT | A | A |
| 1078 | 377 | 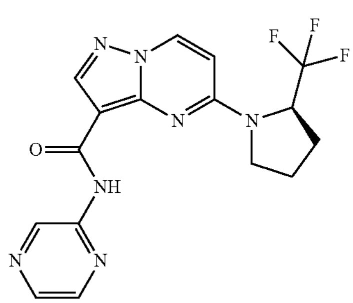 [SMILES: O=C(Nc1cnccn1)c1cnn2ccc(N3CCC[C@@H]3C(F)(F)F)nc12] | NT | NT | B | A |

TABLE 1-continued
Compounds of Formula (I).
| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1079 | 377 | 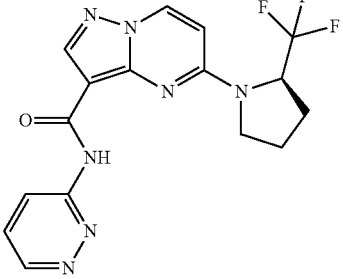 | NT | NT | B | A |
| 1080 | 407 | 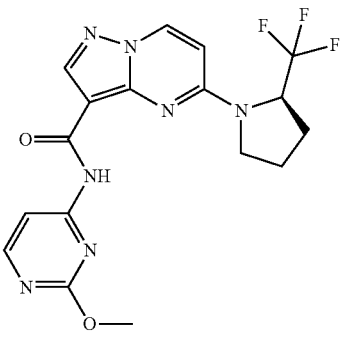 [SMILES: COc1nccc(NC(=O)c2cnn3ccc(N4CCC[C@@H]4C(F)(F)F)nc23)n1] | NT | NT | B | A |
| 1081 | 443 | 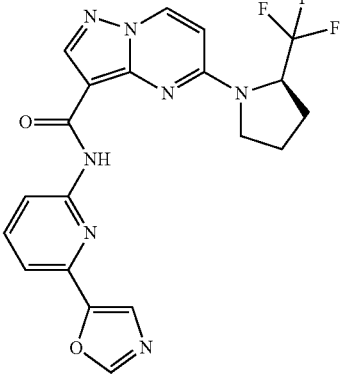 | NT | NT | A | A |
| 1082 | 424 | 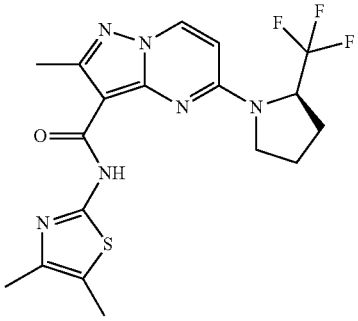 [SMILES: Cc1nc(NC(=O)c2c(C)nn3ccc(N4CCC[C@@H]4C(F)(F)F)nc23)sc1C] | NT | NT | A | A |

TABLE 1-continued
Compounds of Formula (I).
| Compound No | [M + H]+$_{[Calc]}$ | Structure | TAMRA EC1.5 (μM) | % Fold Act | Trp EC1.5 (μM) | % Fold Act |
|---|---|---|---|---|---|---|
| 1083 | 457 | 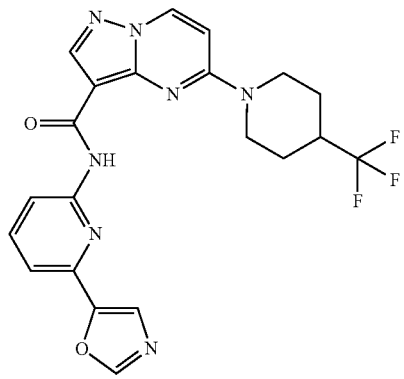 [SMILES: O=C(Nc1cccc(-c2cnco2)n1)c1cnn2ccc(N3CCC(C(F)(F)F)CC3)nc12] | NT | NT | A | A |
| 1084 | 391 | 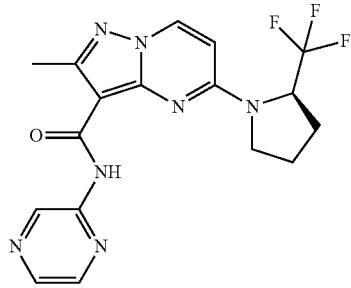 [SMILES: Cc1nn2ccc(N3CCC[C@@H]3C(F)(F)F)nc2c1C(=O)Nc1cnccn1] | NT | NT | B | A |
| 1085 | 421 | 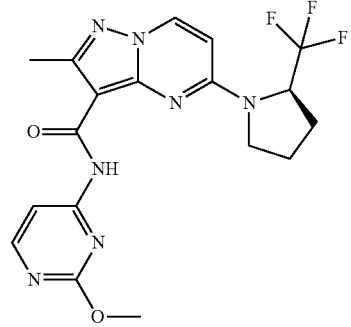 [SMILES: COc1nccc(NC(=O)c2c(C)nn3ccc(N4CCC[C@@H]4C(F)(F)F)nc23)n1] | NT | NT | A | A |
| 1086 | 457 | 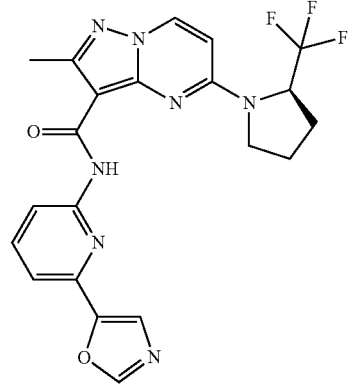 [SMILES: Cc1nn2ccc(N3CCC[C@@H]3C(F)(F)F)nc2c1C(=O)Nc1cccc(-c2cnco2)n1] | NT | NT | A | A |

TABLE 1-continued
Compounds of Formula (I).
| Compound No | [M + H]+[Calc] | Structure | TAMRA EC1.5 (μM) | TAMRA % Fold Act | Trp EC1.5 (μM) | Trp % Fold Act |
|---|---|---|---|---|---|---|
| 1087 | 457 | 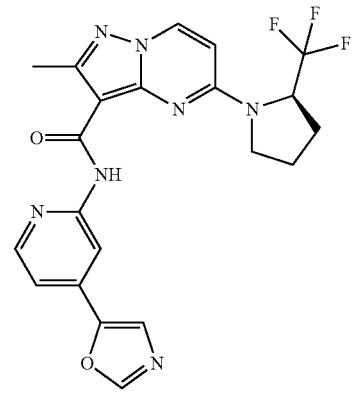 [SMILES: Cc1nn2ccc(N3CCC[C@@H]3C(F)(F)F)nc2c1C(=O)Nc1cc(-c2cnco2)ccn1] | NT | NT | A | A |
| 1088 | 410 | 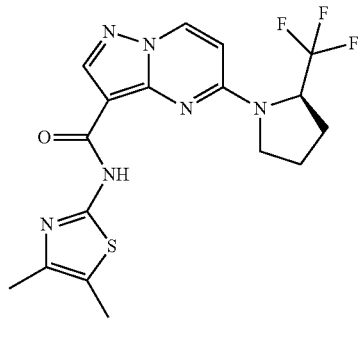 [SMILES: Cc1nc(NC(=O)c2cnn3ccc(N4CCC[C@@H]4C(F)(F)F)nc23)sc1C] | NT | NT | B | A |
| 1089 | 394 | 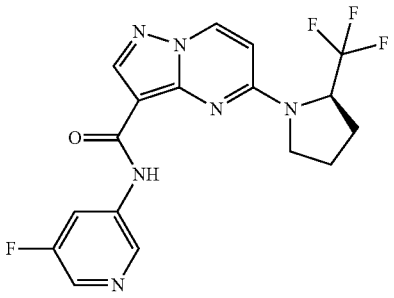 [SMILES: O=C(Nc1cncc(F)c1)c1cnn2ccc(N3CCC[C@@H]3C(F)(F)F)nc12] | NT | NT | B | B |
| 1090 | 376 | 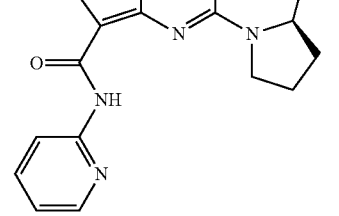 | NT | NT | C | B |

TABLE 1-continued
Compounds of Formula (I).
| Compound No | [M + H]+[Calc] | Structure | TAMRA EC1.5 (μM) | % Fold Act | Trp EC1.5 (μM) | % Fold Act |
|---|---|---|---|---|---|---|
| 1091 | 443 | 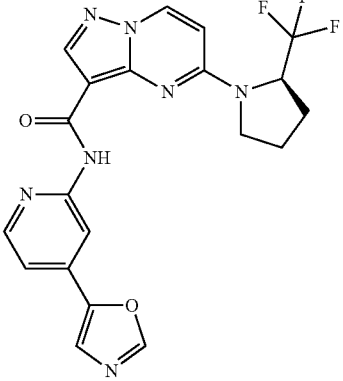 | NT | NT | B | A |
| 1092 | 429 | 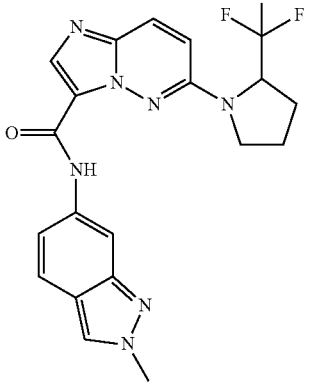 | NT | NT | A | A |
| 1093 | 377 | 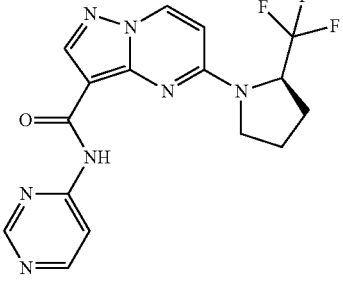 | NT | NT | B | B |
| 1094 | 445 | 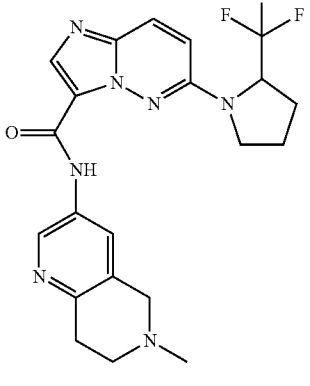 | NT | NT | B | A |

TABLE 1-continued

Compounds of Formula (I).

| Compound No | [M + H]+[Calc] | Structure | TAMRA EC1.5 (μM) | Fold Act | Trp EC1.5 (μM) | % Fold Act |
|---|---|---|---|---|---|---|
| 1095 | 432 | 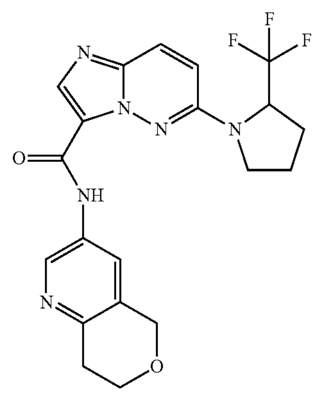 [SMILES: O=C(Nc1cnc2c(c1)COCC2)c1cnc2ccc(N3CCCC3C(F)(F)F)nn12] | NT | NT | B | A |
| 1096 | 436 | 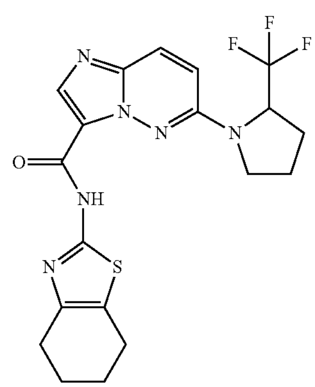 [SMILES: O=C(Nc1nc2c(s1)CCCC2)c1cnc2ccc(N3CCCC3C(F)(F)F)nn12] | NT | NT | A | A |
| 1097 | 431 | 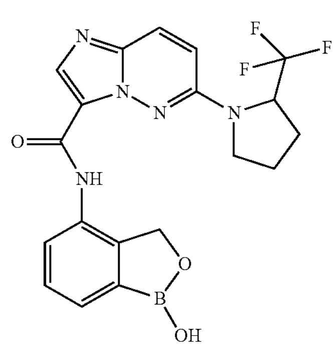 [SMILES: O=C(Nc1cccc2c1COB2O)c1cnc2ccc(N3CCCC3C(F)(F)F)nn12] | NT | NT | B | A |

TABLE 1-continued

Compounds of Formula (I).

| Compound No | [M + H]+$_{[Calc]}$ | Structure | TAMRA EC1.5 (µM) | % Fold Act | Trp EC1.5 (µM) | % Fold Act |
|---|---|---|---|---|---|---|
| 1098 | 443 | 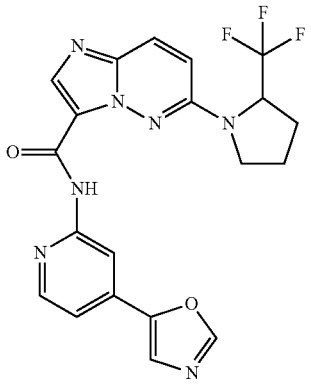 [SMILES: O=C(Nc1cc(-c2cnco2)ccn1)c1cnc2ccc(N3CCCC3C(F)(F)F)nn12] | NT | NT | A | A |
| 1099 | 443 | 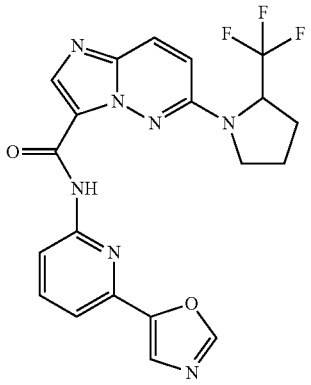 [SMILES: O=C(Nc1cccc(-c2cnco2)n1)c1cnc2ccc(N3CCCC3C(F)(F)F)nn12] | NT | NT | A | A |

In certain embodiments, the compound is any one of Compound Numbers 14, 94, 97, 98, 99, 100, 105, 119, 143, 159, 164, 165, 224, 225, 226, 230, 233, 301, 308, 318, 342, 344, 355, 370, 379, 424, 474, 479, 537, 577, 581, 586, 601, 638, 661, 665, 668, 684, 703, 761, 801, 806, 811, 812, 870, 880, 890, 918, 924, 925 928, 945, 953, 957, 958, 959, 966, 968, 969, 970, 974, 978, 979, 986, 990, 994, 998, 999, 1000, 1001, 1005, 1007, 1009, 1010, 1011, 1012, 1013, 1014, 1015, 1016, 1017, 1018, 1020, 1024, 1025, 1026, 1027, 1028, 1029, 1030, 1031, 1032, 1033, 1034, 1035, 1036, 1046, 1047, 1048, 1049, 1050, 1060, 1062, 1063, 1064, 1066, 1069, 1071, 1072, 1073, 1074, 1077, 1080, 1081, 1082, 1083, 1085, 1086, 1087, 1092, 1096 and 1098.

EQUIVALENTS

The present invention provides among other things sirtuin-modulating compounds and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

We claim:
1. A compound which is
| Compound No | Structure |
|---|---|
| 1 | 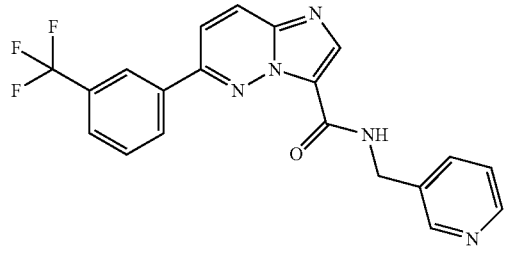 [SMILES: O=C(NCc1cccnc1)c1cnc2ccc(-c3cccc(C(F)(F)F)c3)nn12] |
| 2 | 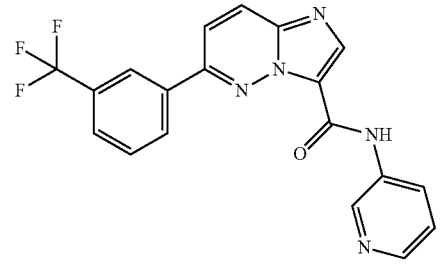 [SMILES: O=C(Nc1cccnc1)c1cnc2ccc(-c3cccc(C(F)(F)F)c3)nn12] |
| 3 | 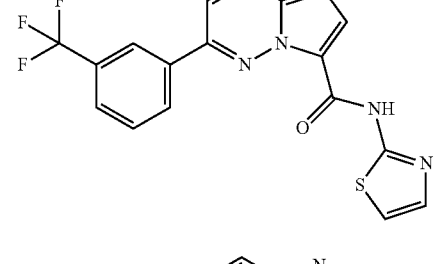 |
| 4 | 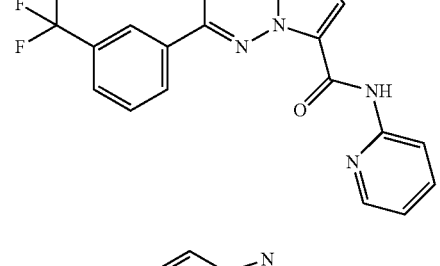 |
| 5 | 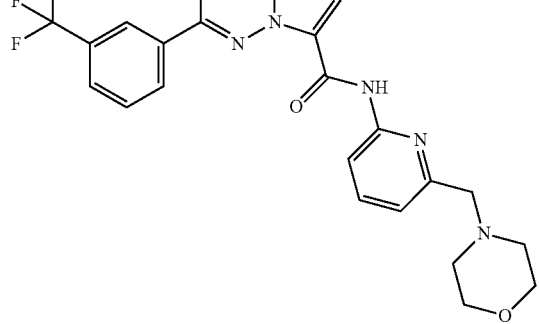 |

-continued

| Compound No | Structure |
|---|---|
| 6 | 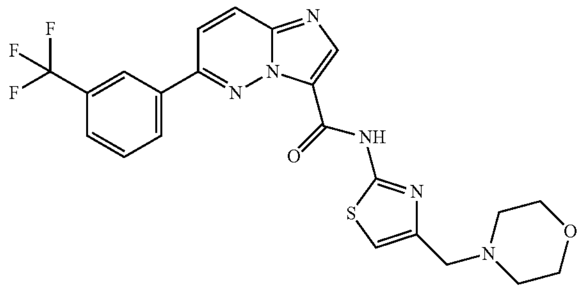 [SMILES: O=C(Nc1nc(CN2CCOCC2)cs1)c1cnc2ccc(-c3cccc(C(F)(F)F)c3)nn12] |
| 7 | 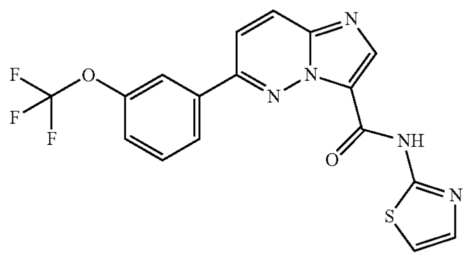 [SMILES: O=C(Nc1nccs1)c1cnc2ccc(-c3cccc(OC(F)(F)F)c3)nn12] |
| 8 | 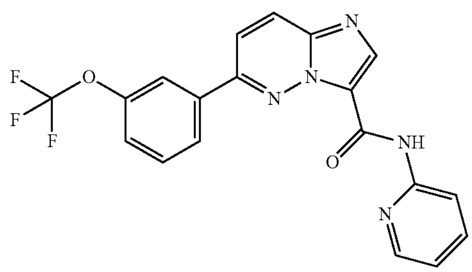 [SMILES: O=C(Nc1ccccn1)c1cnc2ccc(-c3cccc(OC(F)(F)F)c3)nn12] |
| 9 | 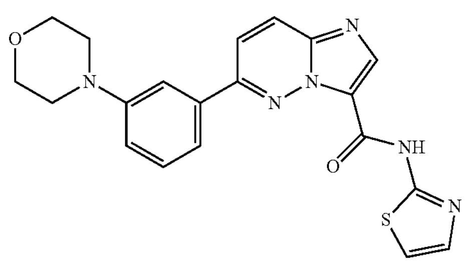 [SMILES: O=C(Nc1nccs1)c1cnc2ccc(-c3cccc(N4CCOCC4)c3)nn12] |
| 10 | 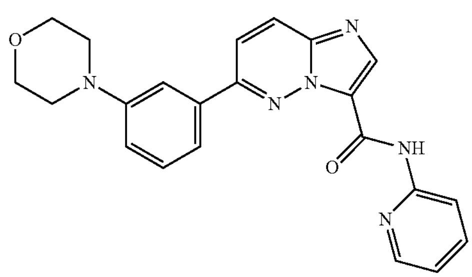 [SMILES: O=C(Nc1ccccn1)c1cnc2ccc(-c3cccc(N4CCOCC4)c3)nn12] |
| 11 | 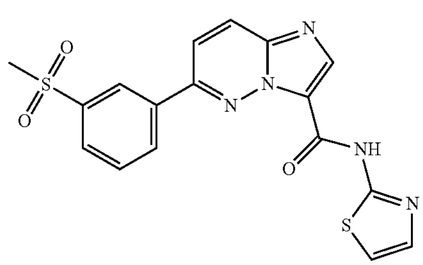 [SMILES: CS(=O)(=O)c1cccc(-c2ccc3ncc(C(=O)Nc4nccs4)n3n2)c1] |

-continued
| Compound No | Structure |
|---|---|
| 12 | 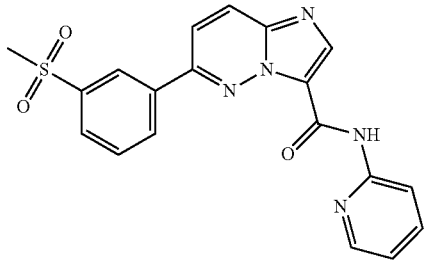 [SMILES: CS(=O)(=O)c1cccc(-c2ccc3ncc(C(=O)Nc4ccccn4)n3n2)c1] |
| 13 | 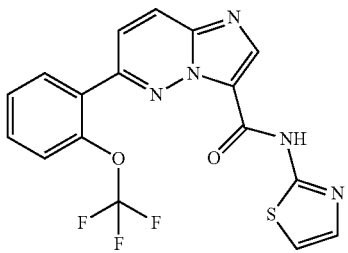 [SMILES: O=C(Nc1nccs1)c1cnc2ccc(-c3ccccc3OC(F)(F)F)nn12] |
| 14 | 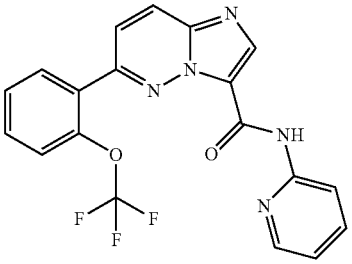 |
| 15 | 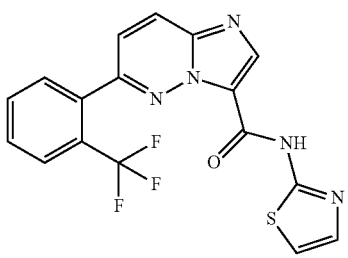 [SMILES: O=C(Nc1nccs1)c1cnc2ccc(-c3ccccc3C(F)(F)F)nn12] |
| 16 | 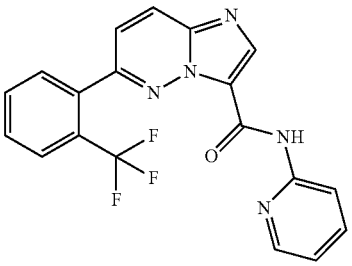 [SMILES: O=C(Nc1ccccn1)c1cnc2ccc(-c3ccccc3C(F)(F)F)nn12] |

-continued
| Compound No | Structure |
|---|---|
| 17 | 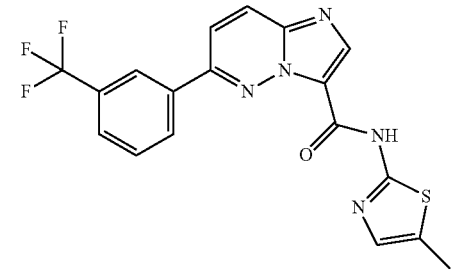 [SMILES: Cc1cnc(NC(=O)c2cnc3ccc(-c4cccc(C(F)(F)F)c4)nn23)s1] |
| 18 | 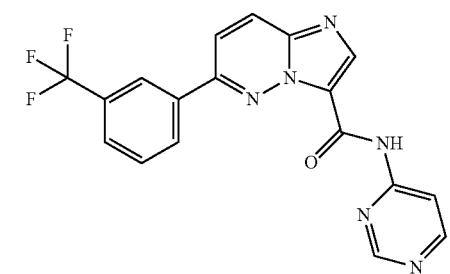 [SMILES: O=C(Nc1ccncn1)c1cnc2ccc(-c3cccc(C(F)(F)F)c3)nn12] |
| 19 | 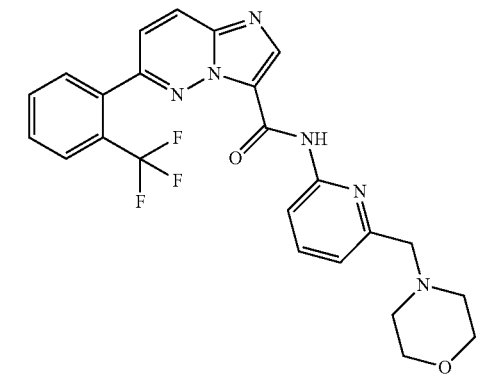 [SMILES: O=C(Nc1cccc(CN2CCOCC2)n1)c1cnc2ccc(-c3ccccc3C(F)(F)F)nn12] |
| 20 | 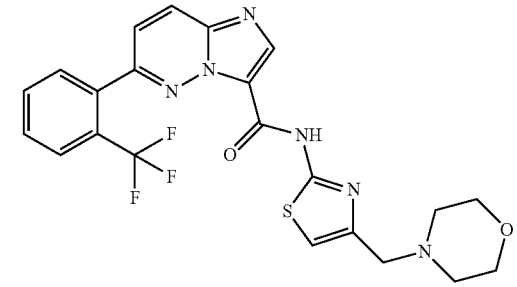 |
| 21 | 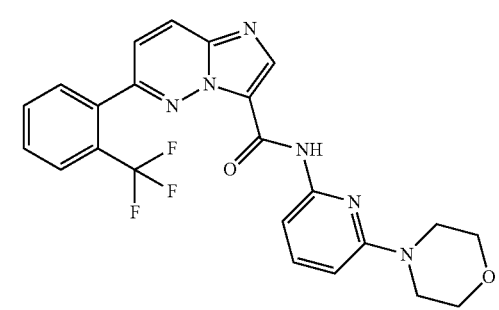 [SMILES: O=C(Nc1cccc(N2CCOCC2)n1)c1cnc2ccc(-c3ccccc3C(F)(F)F)nn12] |

-continued
| Compound No | Structure |
|---|---|
| 22 | 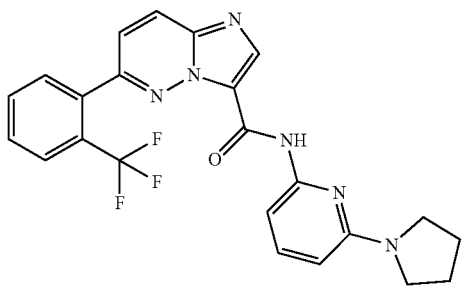 [SMILES: O=C(Nc1cccc(N2CCCC2)n1)c1cnc2ccc(-c3ccccc3C(F)(F)F)nn12] |
| 23 | 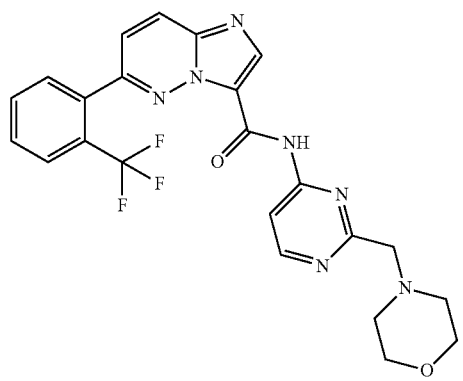 |
| 24 | 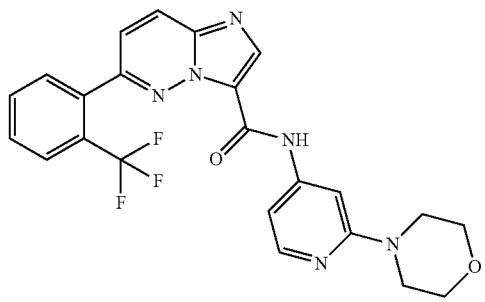 [SMILES: O=C(Nc1ccnc(N2CCOCC2)c1)c1cnc2ccc(-c3ccccc3C(F)(F)F)nn12] |
| 25 | 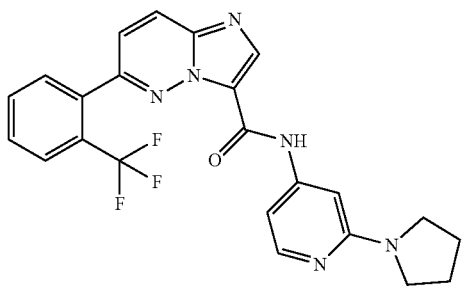 [SMILES: O=C(Nc1ccnc(N2CCCC2)c1)c1cnc2ccc(-c3ccccc3C(F)(F)F)nn12] |

-continued
| Compound No | Structure |
|---|---|
| 26 | 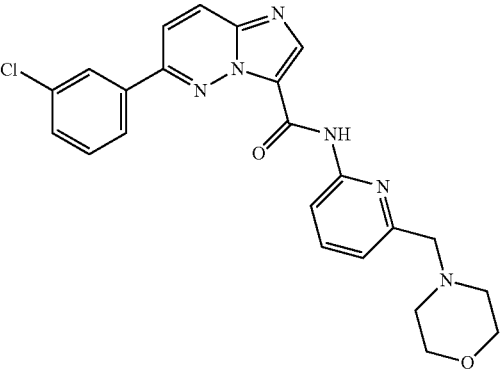 [SMILES: O=C(Nc1cccc(CN2CCOCC2)n1)c1cnc2ccc(-c3cccc(Cl)c3)nn12] |
| 27 | 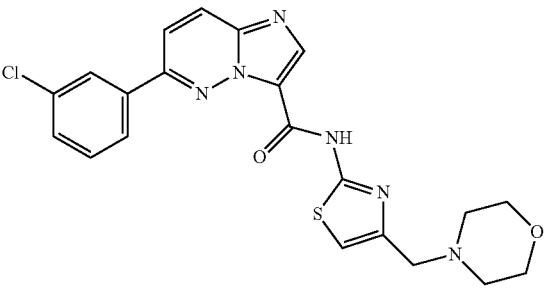 [SMILES: O=C(Nc1nc(CN2CCOCC2)cs1)c1cnc2ccc(-c3cccc(Cl)c3)nn12] |
| 28 | 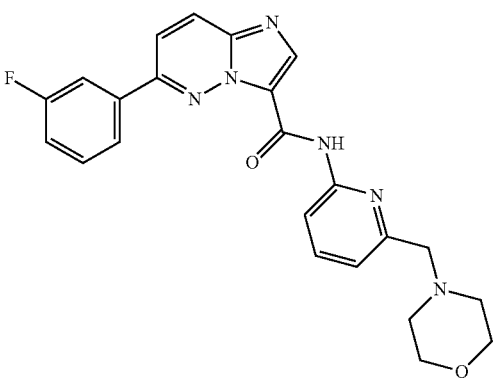 [SMILES: O=C(Nc1cccc(CN2CCOCC2)n1)c1cnc2ccc(-c3cccc(F)c3)nn12] |
| 29 | 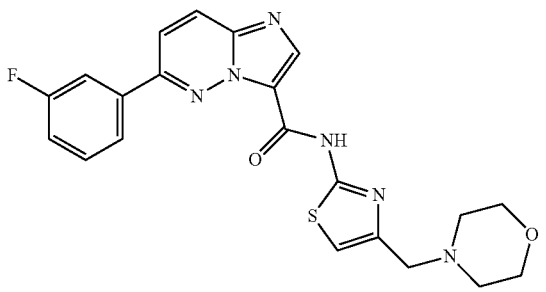 [SMILES: O=C(Nc1nc(CN2CCOCC2)cs1)c1cnc2ccc(-c3cccc(F)c3)nn12] |

| Compound No | Structure |
|---|---|
| 30 | 6-(2,5-difluorophenyl)-N-(6-(morpholinomethyl)pyridin-2-yl)imidazo[1,2-b]pyridazine-3-carboxamide |
| 31 | 6-(2,5-difluorophenyl)-N-(4-(morpholinomethyl)thiazol-2-yl)imidazo[1,2-b]pyridazine-3-carboxamide |
| 32 | 6-(2-(difluoromethyl)phenyl)-N-(pyridin-2-yl)imidazo[1,2-b]pyridazine-3-carboxamide |
| 33 | 6-(2-(difluoromethyl)phenyl)-N-(thiazol-2-yl)imidazo[1,2-b]pyridazine-3-carboxamide |
| 34 | 6-(2-(difluoromethyl)phenyl)-N-(6-(morpholinomethyl)pyridin-2-yl)imidazo[1,2-b]pyridazine-3-carboxamide |

-continued
| Compound No | Structure |
|---|---|
| 35 | 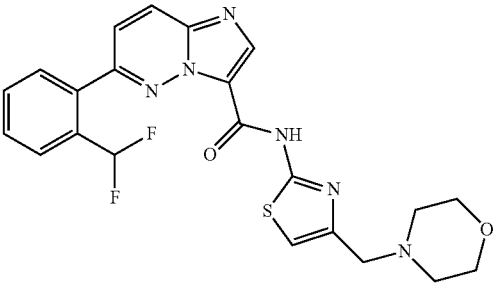 [SMILES: O=C(Nc1nc(CN2CCOCC2)cs1)c1cnc2ccc(-c3ccccc3C(F)F)nn12] |
| 36 | 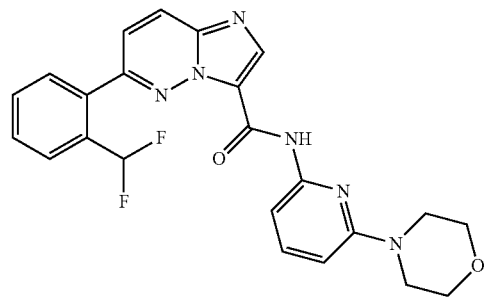 [SMILES: O=C(Nc1cccc(N2CCOCC2)n1)c1cnc2ccc(-c3ccccc3C(F)F)nn12] |
| 37 | 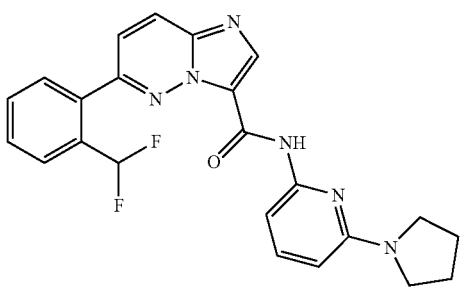 [SMILES: O=C(Nc1cccc(N2CCCC2)n1)c1cnc2ccc(-c3ccccc3C(F)F)nn12] |
| 38 | 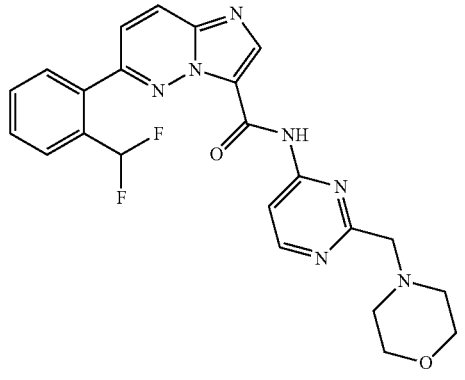 [SMILES: O=C(Nc1ccnc(CN2CCOCC2)n1)c1cnc2ccc(-c3ccccc3C(F)F)nn12] |
| 39 | 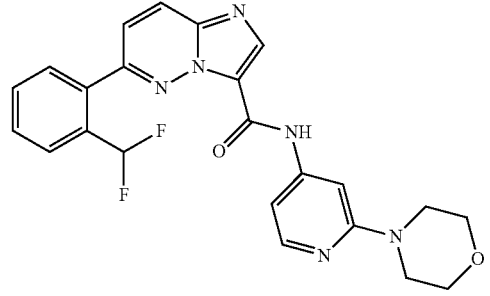 [SMILES: O=C(Nc1ccnc(N2CCOCC2)c1)c1cnc2ccc(-c3ccccc3C(F)F)nn12] |

-continued
| Compound No | Structure |
|---|---|
| 40 | 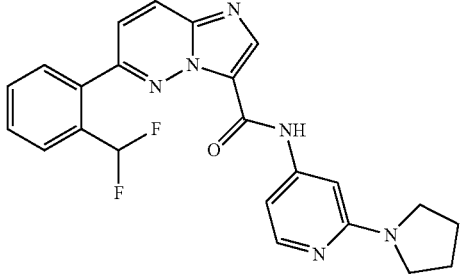 [SMILES: O=C(Nc1ccnc(N2CCCC2)c1)c1cnc2ccc(-c3ccccc3C(F)F)nn12] |
| 41 | 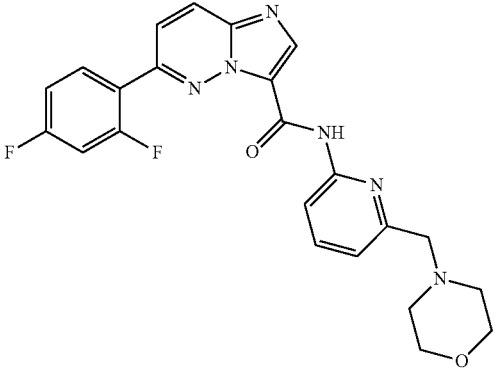 [SMILES: O=C(Nc1cccc(CN2CCOCC2)n1)c1cnc2ccc(-c3ccc(F)cc3F)nn12] |
| 42 | 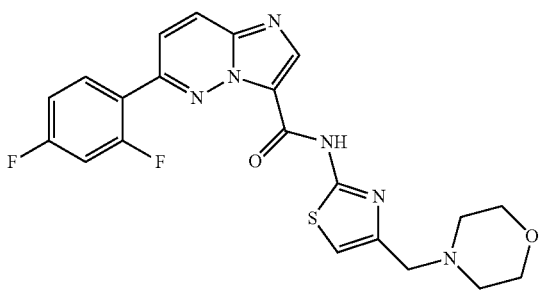 [SMILES: O=C(Nc1nc(CN2CCOCC2)cs1)c1cnc2ccc(-c3ccc(F)cc3F)nn12] |
| 43 | 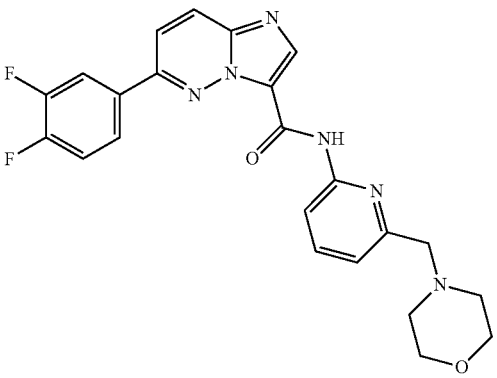 [SMILES: O=C(Nc1cccc(CN2CCOCC2)n1)c1cnc2ccc(-c3ccc(F)c(F)c3)nn12] |

| Compound No | Structure |
|---|---|
| 44 | 6-(3,4-difluorophenyl)-N-(4-(morpholinomethyl)thiazol-2-yl)imidazo[1,2-b]pyridazine-3-carboxamide |
| 45 | 6-(3,5-difluorophenyl)-N-(6-(morpholinomethyl)pyridin-2-yl)imidazo[1,2-b]pyridazine-3-carboxamide |
| 46 | 6-(3,5-difluorophenyl)-N-(4-(morpholinomethyl)thiazol-2-yl)imidazo[1,2-b]pyridazine-3-carboxamide |
| 47 | 6-(2,3-difluorophenyl)-N-(6-(morpholinomethyl)pyridin-2-yl)imidazo[1,2-b]pyridazine-3-carboxamide |
| 48 | 6-(2,3-difluorophenyl)-N-(4-(morpholinomethyl)thiazol-2-yl)imidazo[1,2-b]pyridazine-3-carboxamide |

-continued
| Compound No | Structure |
|---|---|
| 49 | 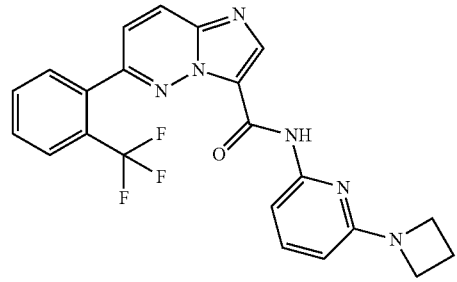 [SMILES: O=C(Nc1cccc(N2CCC2)n1)c1cnc2ccc(-c3ccccc3C(F)(F)F)nn12] |
| 50 | 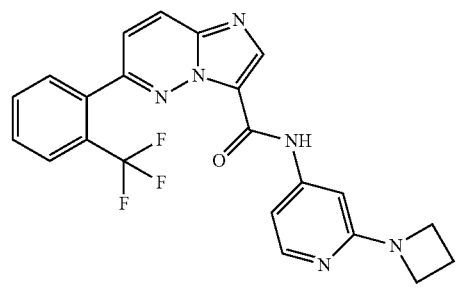 [SMILES: O=C(Nc1ccnc(N2CCC2)c1)c1cnc2ccc(-c3ccccc3C(F)(F)F)nn12] |
| 51 | 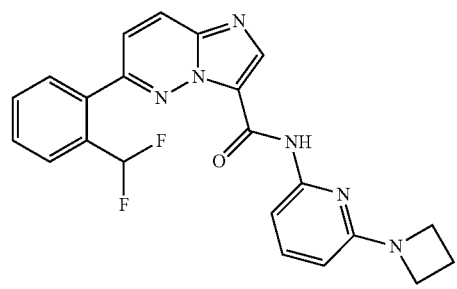 [SMILES: O=C(Nc1cccc(N2CCC2)n1)c1cnc2ccc(-c3ccccc3C(F)F)nn12] |
| 52 | 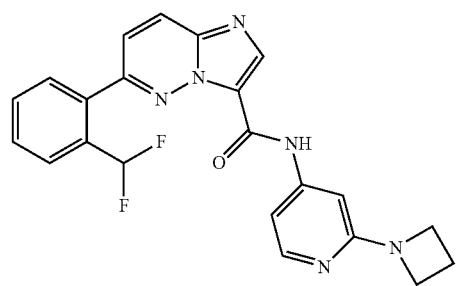 [SMILES: O=C(Nc1ccnc(N2CCC2)c1)c1cnc2ccc(-c3ccccc3C(F)F)nn12] |
| 69 | 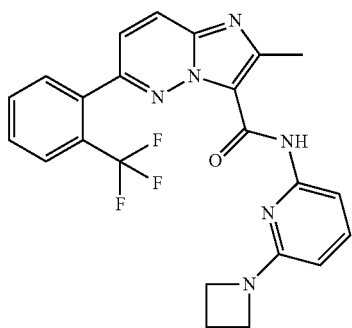 [SMILES: Cc1nc2ccc(-c3ccccc3C(F)(F)F)nn2c1C(=O)Nc1cccc(N2CCC2)n1] |

| Compound No | Structure |
|---|---|
| 70 | 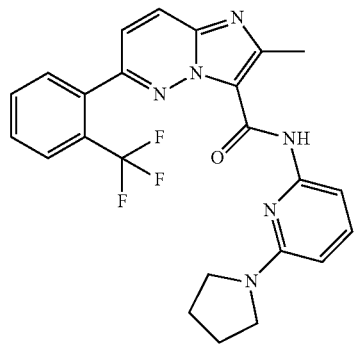 [SMILES: Cc1nc2ccc(-c3ccccc3C(F)(F)F)nn2c1C(=O)Nc1cccc(N2CCCC2)n1] |
| 71 | 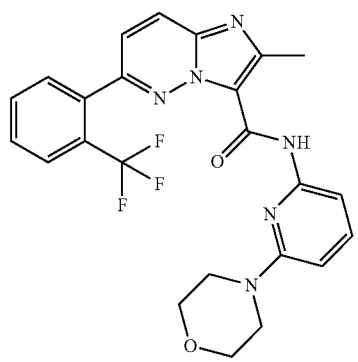 [SMILES: Cc1nc2ccc(-c3ccccc3C(F)(F)F)nn2c1C(=O)Nc1cccc(N2CCOCC2)n1] |
| 72 | 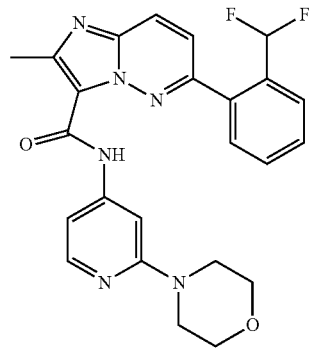 [SMILES: Cc1nc2ccc(-c3ccccc3C(F)F)nn2c1C(=O)Nc1ccnc(N2CCOCC2)c1] |
| 74 | 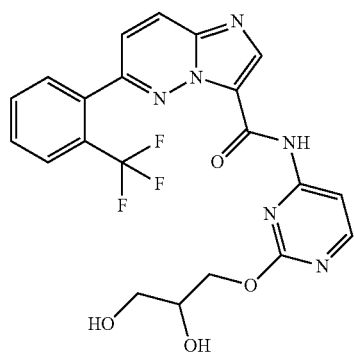 [SMILES: O=C(Nc1ccnc(OCC(O)CO)n1)c1cnc2ccc(-c3ccccc3C(F)(F)F)nn12] |

-continued
| Compound No | Structure |
|---|---|
| 75 | 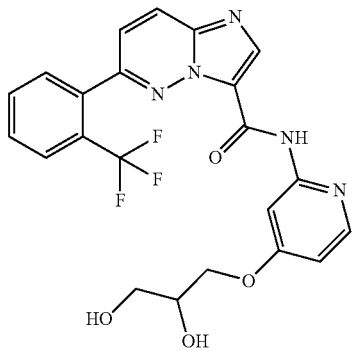 |
| 76 | 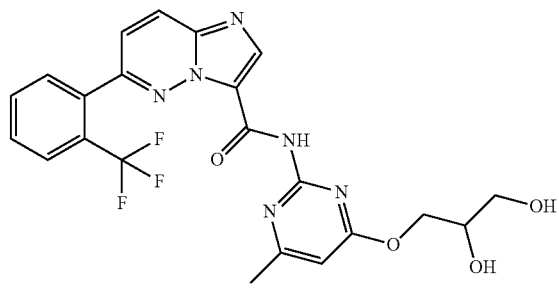 [SMILES: Cc1cc(OCC(O)CO)nc(NC(=O)c2cnc3ccc(-c4ccccc4C(F)(F)F)nn23)n1] |
| 77 | 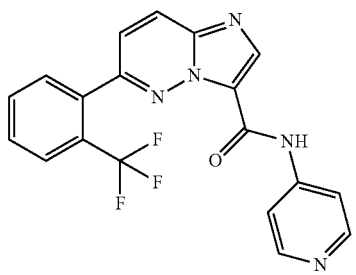 [SMILES: O=C(Nc1ccncc1)c1cnc2ccc(-c3ccccc3C(F)(F)F)nn12] |
| 78 | 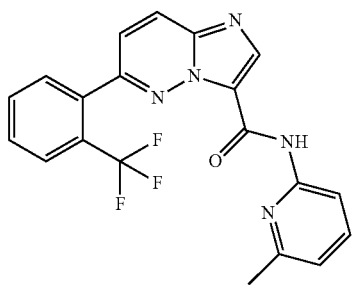 [SMILES: Cc1cccc(NC(=O)c2cnc3ccc(-c4ccccc4C(F)(F)F)nn23)n1] |
| 79 | 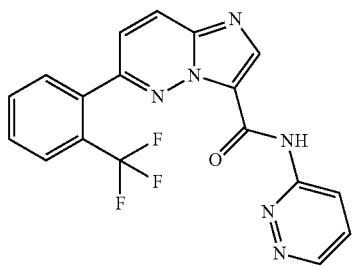 [SMILES: O=C(Nc1cccnn1)c1cnc2ccc(-c3ccccc3C(F)(F)F)nn12] |

-continued

| Compound No | Structure |
|---|---|
| 80 | 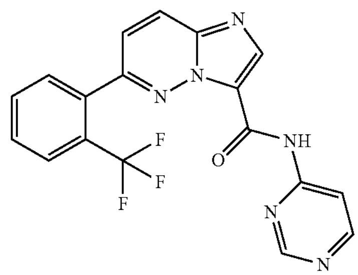 [SMILES: O=C(Nc1ccncn1)c1cnc2ccc(-c3ccccc3C(F)(F)F)nn12] |
| 81 | 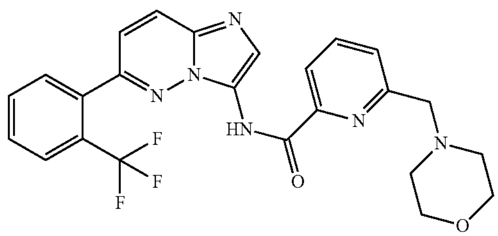 [SMILES: O=C(Nc1cnc2ccc(-c3ccccc3C(F)(F)F)nn12)c1cccc(CN2CCOCC2)n1] |
| 82 | 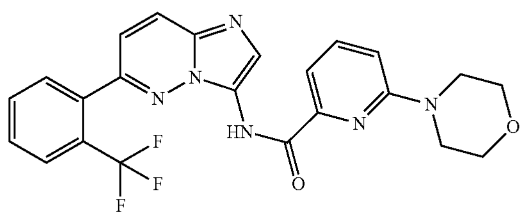 |
| 83 | 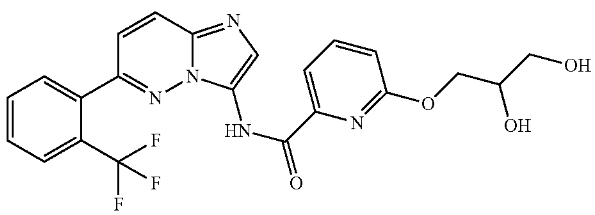 [SMILES: O=C(Nc1cnc2ccc(-c3ccccc3C(F)(F)F)nn12)c1cccc(OCC(O)CO)n1] |
| 84 | 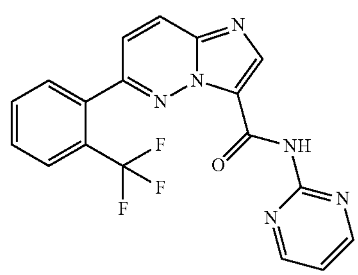 [SMILES: O=C(Nc1ncccn1)c1cnc2ccc(-c3ccccc3C(F)(F)F)nn12] |
| 85 | 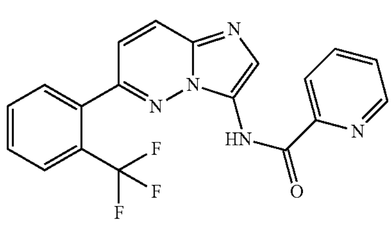 |

-continued
| Compound No | Structure |
|---|---|
| 86 | 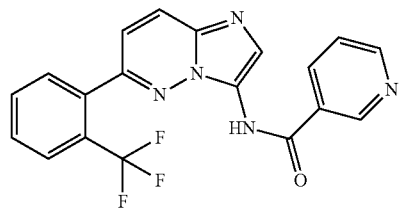 [SMILES: O=C(Nc1cnc2ccc(-c3ccccc3C(F)(F)F)nn12)c1cccnc1] |
| 87 | 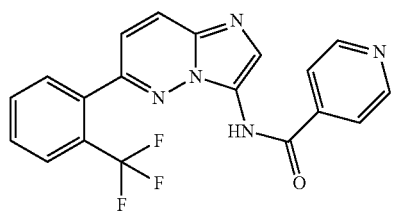 |
| 88 | 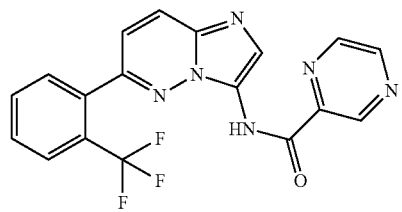 [SMILES: O=C(Nc1cnc2ccc(-c3ccccc3C(F)(F)F)nn12)c1cnccn1] |
| 89 | 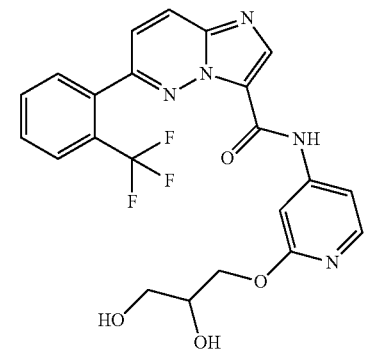 |
| 90 | 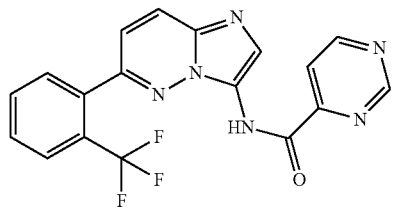 [SMILES: O=C(Nc1cnc2ccc(-c3ccccc3C(F)(F)F)nn12)c1ccncn1] |
| 91 | 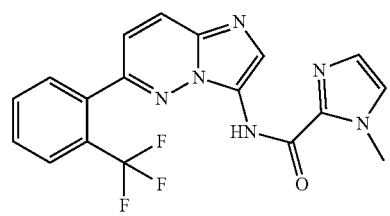 [SMILES: Cn1ccnc1C(=O)Nc1cnc2ccc(-c3ccccc3C(F)(F)F)nn12] |

-continued

| Compound No | Structure |
|---|---|
| 92 | (structure) |
| 93 | (structure) |
| 94 | (structure) |
| 95 | (structure) |
| 96 | (structure) |
| 97 | (structure) |

-continued
| Compound No | Structure |
|---|---|
| 98 | 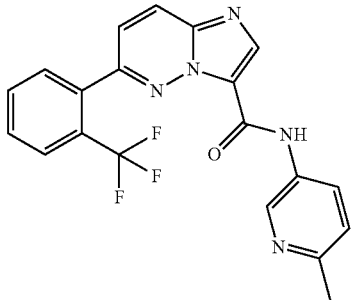 [SMILES: Cc1ccc(NC(=O)c2cnc3ccc(-c4ccccc4C(F)(F)F)nn23)cn1] |
| 99 | 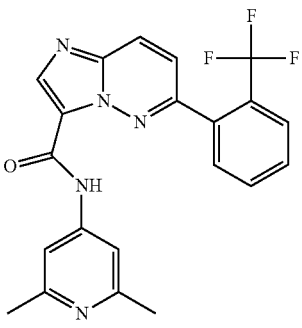 [SMILES: Cc1cc(NC(=O)c2cnc3ccc(-c4ccccc4C(F)(F)F)nn23)cc(C)n1] |
| 100 | 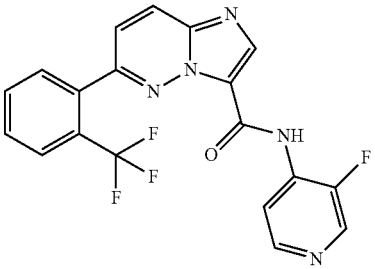 [SMILES: O=C(Nc1ccncc1F)c1cnc2ccc(-c3ccccc3C(F)(F)F)nn12] |
| 101 | 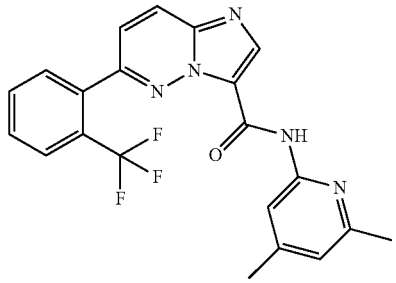 [SMILES: Cc1cc(C)nc(NC(=O)c2cnc3ccc(-c4ccccc4C(F)(F)F)nn23)c1] |
| 102 | 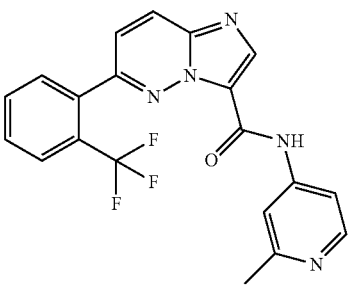 [SMILES: Cc1cc(NC(=O)c2cnc3ccc(-c4ccccc4C(F)(F)F)nn23)ccn1] |

-continued
| Compound No | Structure |
|---|---|
| 103 | 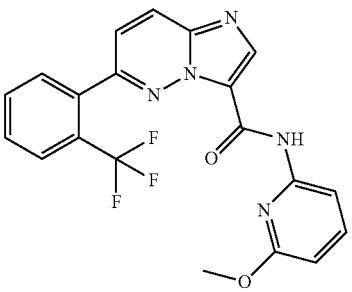 [SMILES: COc1cccc(NC(=O)c2cnc3ccc(-c4ccccc4C(F)(F)F)nn23)n1] |
| 104 | 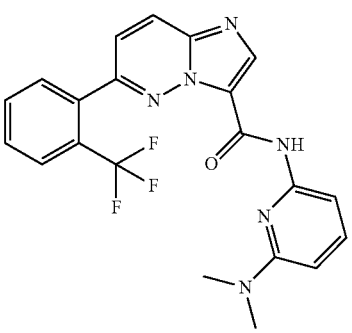 [SMILES: CN(C)c1cccc(NC(=O)c2cnc3ccc(-c4ccccc4C(F)(F)F)nn23)n1] |
| 105 | 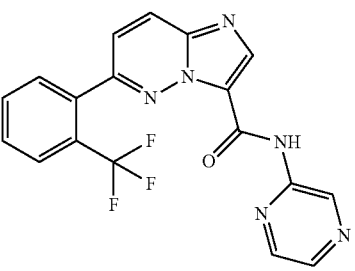 [SMILES: O=C(Nc1cnccn1)c1cnc2ccc(-c3ccccc3C(F)(F)F)nn12] |
| 106 | 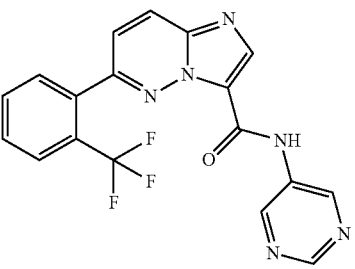 [SMILES: O=C(Nc1cncnc1)c1cnc2ccc(-c3ccccc3C(F)(F)F)nn12] |
| 107 | 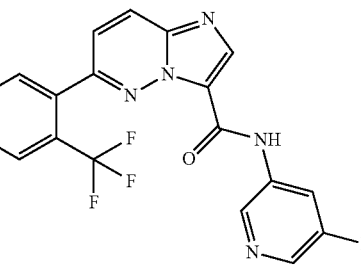 |

| Compound No | Structure |
|---|---|
| 108 | 6-(2-(trifluoromethyl)phenyl)imidazo[1,2-b]pyridazine-3-carboxamide with N-(pyridin-3-yl) |
| 109 | 6-(2-(trifluoromethyl)phenyl)imidazo[1,2-b]pyridazine-3-carboxamide with N-(5-methylthiazol-2-yl) |
| 110 | 6-(2-(trifluoromethyl)phenyl)imidazo[1,2-b]pyridazine-3-carboxamide with N-(5-fluoropyridin-2-yl) |
| 111 | 6-(2-(trifluoromethyl)phenyl)imidazo[1,2-b]pyridazine-3-carboxamide with N-(3,5-difluoropyridin-2-yl) |
| 112 | 6-(2-(trifluoromethyl)phenyl)imidazo[1,2-b]pyridazine-3-carboxamide with N-(1-methyl-1H-pyrazol-3-yl) |

-continued

| Compound No | Structure |
|---|---|
| 113 | 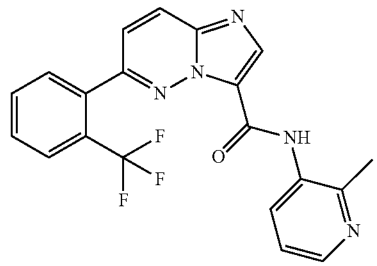 [SMILES: Cc1ncccc1NC(=O)c1cnc2ccc(-c3ccccc3C(F)(F)F)nn12] |
| 114 | 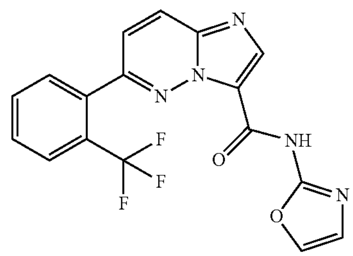 |
| 115 | 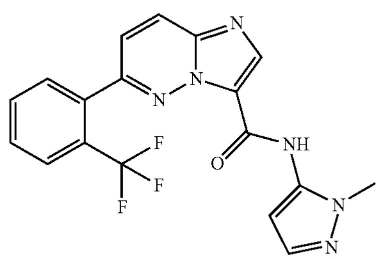 [SMILES: Cn1nccc1NC(=O)c1cnc2ccc(-c3ccccc3C(F)(F)F)nn12] |
| 116 | 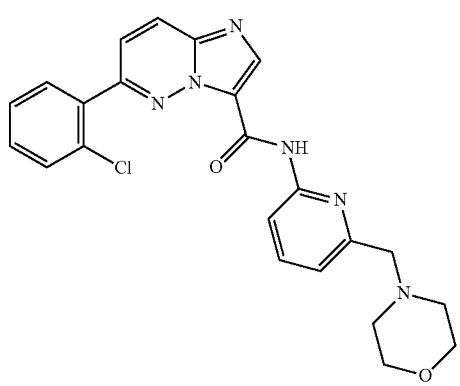 |
| 117 | 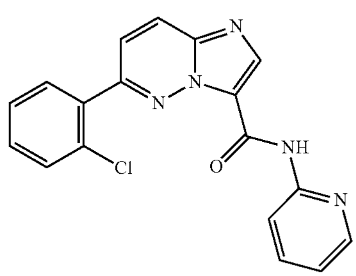 [SMILES: O=C(Nc1ccccn1)c1cnc2ccc(-c3ccccc3Cl)nn12] |

-continued
| Compound No | Structure |
|---|---|
| 118 | 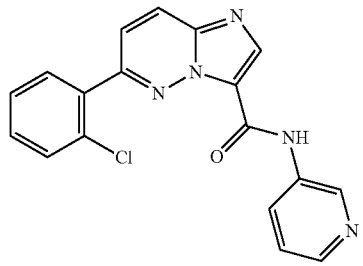 [SMILES: O=C(Nc1cccnc1)c1cnc2ccc(-c3ccccc3Cl)nn12] |
| 119 | 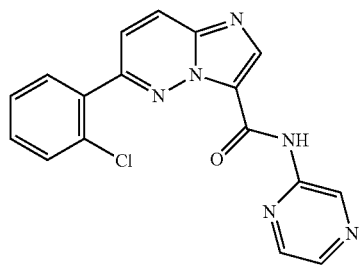 [SMILES: O=C(Nc1cnccn1)c1cnc2ccc(-c3ccccc3Cl)nn12] |
| 120 | 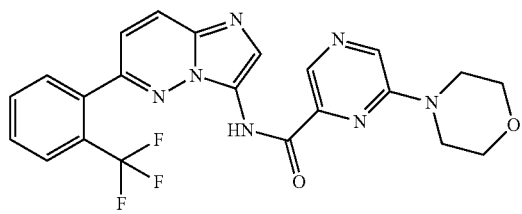 [SMILES: O=C(Nc1cnc2ccc(-c3ccccc3C(F)(F)F)nn12)c1cncc(N2CCOCC2)n1] |
| 121 | 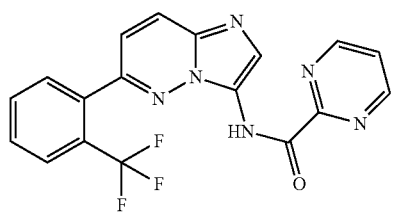 [SMILES: O=C(Nc1cnc2ccc(-c3ccccc3C(F)(F)F)nn12)c1ncccn1] |
| 122 | 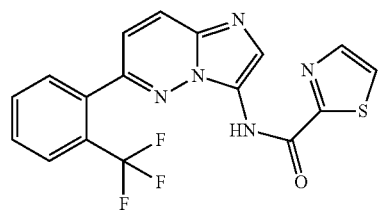 [SMILES: O=C(Nc1cnc2ccc(-c3ccccc3C(F)(F)F)nn12)c1nccs1] |
| 123 | 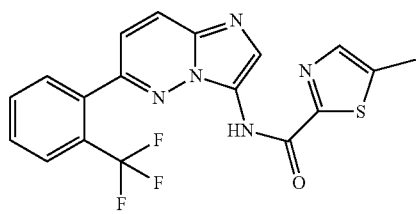 [SMILES: Cc1cnc(C(=O)Nc2cnc3ccc(-c4ccccc4C(F)(F)F)nn23)s1] |

| Compound No | Structure |
|---|---|
| 124 | 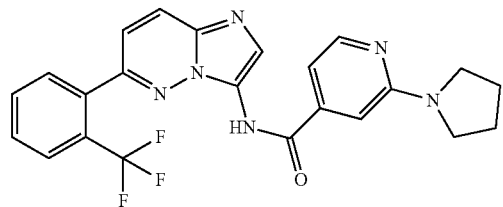 [SMILES: O=C(Nc1cnc2ccc(-c3ccccc3C(F)(F)F)nn12)c1ccnc(N2CCCC2)c1] |
| 125 | 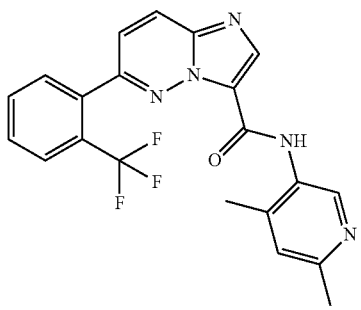 [SMILES: Cc1cc(C)c(NC(=O)c2cnc3ccc(-c4ccccc4C(F)(F)F)nn23)cn1] |
| 126 | 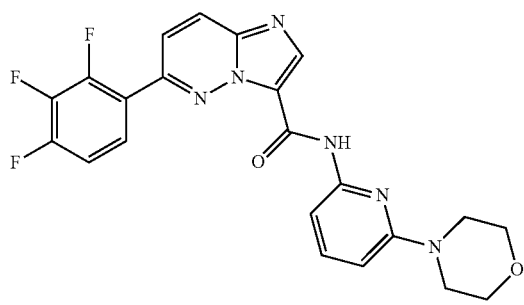 [SMILES: O=C(Nc1cccc(N2CCOCC2)n1)c1cnc2ccc(-c3ccc(F)c(F)c3F)nn12] |
| 127 | 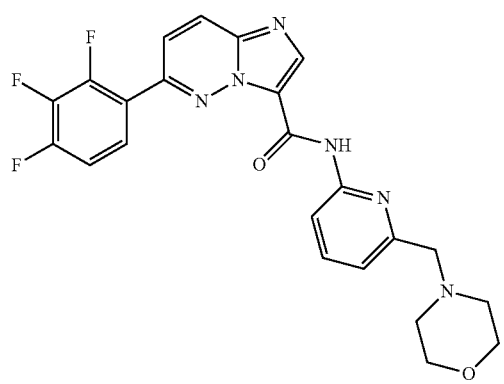 [SMILES: O=C(Nc1cccc(CN2CCOCC2)n1)c1cnc2ccc(-c3ccc(F)c(F)c3F)nn12] |
| 128 | 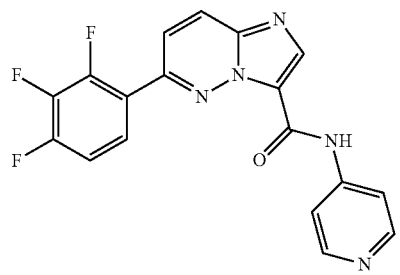 [SMILES: O=C(Nc1ccncc1)c1cnc2ccc(-c3ccc(F)c(F)c3F)nn12] |

-continued
| Compound No | Structure |
|---|---|
| 129 | 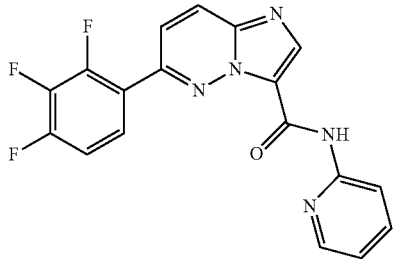 [SMILES: O=C(Nc1ccccn1)c1cnc2ccc(-c3ccc(F)c(F)c3F)nn12] |
| 130 | 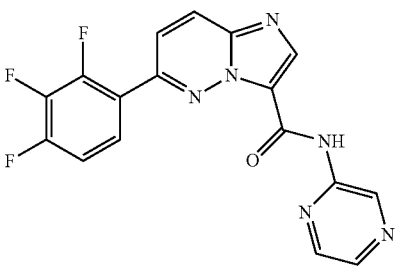 |
| 131 | 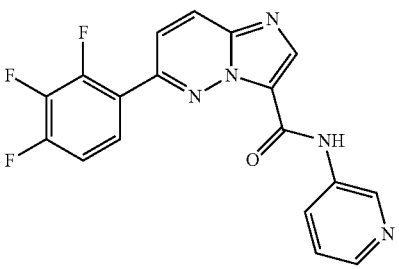 [SMILES: O=C(Nc1cccnc1)c1cnc2ccc(-c3ccc(F)c(F)c3F)nn12] |
| 132 | 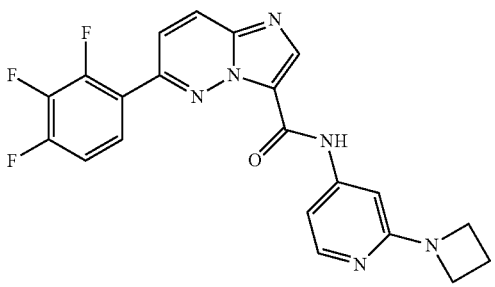 [SMILES: O=C(Nc1ccnc(N2CCC2)c1)c1cnc2ccc(-c3ccc(F)c(F)c3F)nn12] |
| 133 | 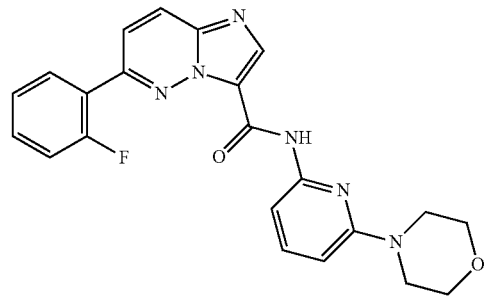 [SMILES: O=C(Nc1cccc(N2CCOCC2)n1)c1cnc2ccc(-c3ccccc3F)nn12] |

-continued
| Compound No | Structure |
|---|---|
| 134 | 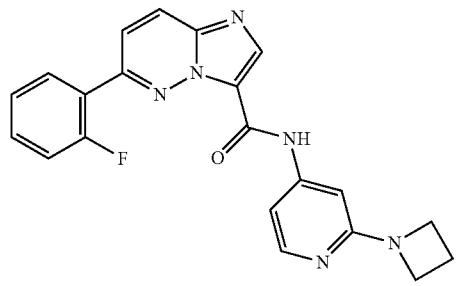 [SMILES: O=C(Nc1ccnc(N2CCC2)c1)c1cnc2ccc(-c3ccccc3F)nn12] |
| 135 | 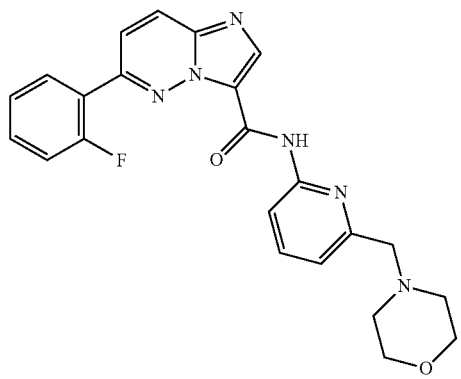 |
| 136 | 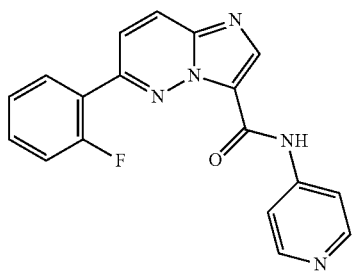 [SMILES: O=C(Nc1ccncc1)c1cnc2ccc(-c3ccccc3F)nn12] |
| 137 | 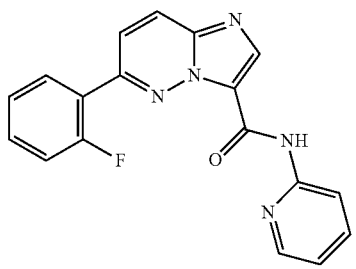 [SMILES: O=C(Nc1ccccn1)c1cnc2ccc(-c3ccccc3F)nn12] |
| 138 | 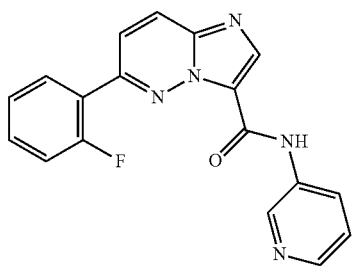 [SMILES: O=C(Nc1cccnc1)c1cnc2ccc(-c3ccccc3F)nn12] |

-continued
| Compound No | Structure |
|---|---|
| 139 | 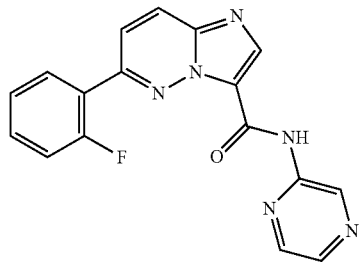 [SMILES: O=C(Nc1cnccn1)c1cnc2ccc(-c3ccccc3F)nn12] |
| 140 | 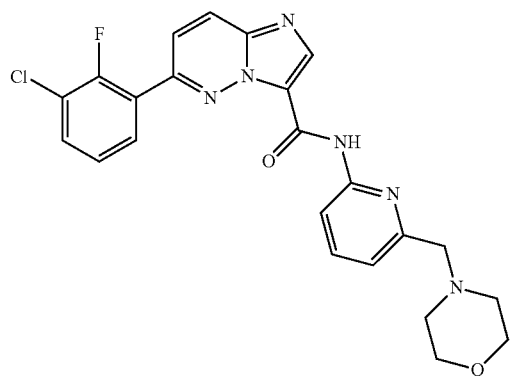 [SMILES: O=C(Nc1cccc(CN2CCOCC2)n1)c1cnc2ccc(-c3cccc(Cl)c3F)nn12] |
| 141 | 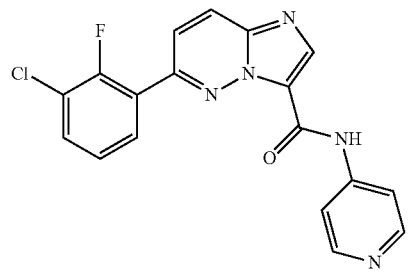 [SMILES: O=C(Nc1ccncc1)c1cnc2ccc(-c3cccc(Cl)c3F)nn12] |
| 142 | 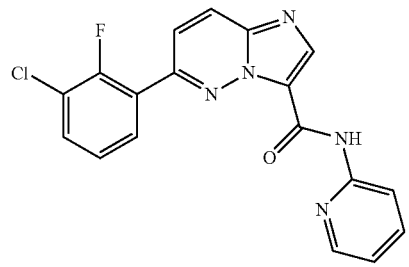 [SMILES: O=C(Nc1ccccn1)c1cnc2ccc(-c3cccc(Cl)c3F)nn12] |
| 143 | 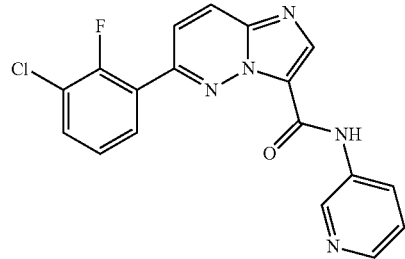 [SMILES: O=C(Nc1cccnc1)c1cnc2ccc(-c3cccc(Cl)c3F)nn12] |

-continued

| Compound No | Structure |
|---|---|
| 144 | *[chemical structure]* |
| 145 | *[chemical structure]* |
| 146 | *[chemical structure]* |
| 147 | *[chemical structure]* |
| 148 | *[chemical structure]* |
| 149 | *[chemical structure]* |

| Compound No | Structure |
|---|---|
| 150 | [6-(2-(trifluoromethyl)phenyl)imidazo[1,2-b]pyridazine-3-carboxamide with N-(5-(morpholinomethyl)thiazol-2-yl)] |
| 151 | [6-(2-(trifluoromethyl)phenyl)imidazo[1,2-b]pyridazine-3-carboxamide with N-(5-morpholinothiazol-2-yl)] |
| 152 | [6-(2-(trifluoromethyl)phenyl)imidazo[1,2-b]pyridazine-3-carboxamide with N-(4-methylthiazol-2-yl)] |
| 153 | [6-(2-(trifluoromethyl)phenyl)imidazo[1,2-b]pyridazine-3-carboxamide with N-(1-methyl-1H-pyrazol-4-yl)] |
| 154 | [6-(2-(trifluoromethyl)phenyl)imidazo[1,2-b]pyridazine-3-carboxamide with N-(1-(2-methoxyethyl)-1H-pyrazol-4-yl)] |

| Compound No | Structure |
|---|---|
| 155 | *6-(2-(trifluoromethyl)phenyl)imidazo[1,2-b]pyridazine-3-carboxamide, N-(1-(2-(dimethylamino)ethyl)-1H-pyrazol-4-yl)* |
| 156 | *6-(2-(trifluoromethyl)phenyl)imidazo[1,2-b]pyridazine-3-carboxamide, N-(1-(2-methoxyethyl)-6-oxo-1,6-dihydropyridin-3-yl)* |
| 157 | *6-(3-chloro-2-fluorophenyl)imidazo[1,2-b]pyridazine-3-carboxamide, N-(pyrazin-2-yl)* |
| 158 | *6-(3-chloro-2-fluorophenyl)imidazo[1,2-b]pyridazine-3-carboxamide, N-(6-morpholinopyridin-2-yl)* |
| 159 | *6-(3-chloro-2-fluorophenyl)imidazo[1,2-b]pyridazine-3-carboxamide, N-(2-(azetidin-1-yl)pyridin-4-yl)* |

-continued

| Compound No | Structure |
|---|---|
| 160 | 6-(2-chloro-6-fluorophenyl)-N-(6-(morpholinomethyl)pyridin-2-yl)imidazo[1,2-b]pyridazine-3-carboxamide |
| 161 | 6-(2-chloro-6-fluorophenyl)-N-(pyridin-4-yl)imidazo[1,2-b]pyridazine-3-carboxamide |
| 162 | 6-(2-chloro-6-fluorophenyl)-N-(pyridin-2-yl)imidazo[1,2-b]pyridazine-3-carboxamide |
| 163 | 6-(2-chloro-6-fluorophenyl)-N-(pyridin-3-yl)imidazo[1,2-b]pyridazine-3-carboxamide |
| 164 | 6-(2-chloro-6-fluorophenyl)-N-(6-morpholinopyridin-2-yl)imidazo[1,2-b]pyridazine-3-carboxamide |

| Compound No | Structure |
|---|---|
| 165 | 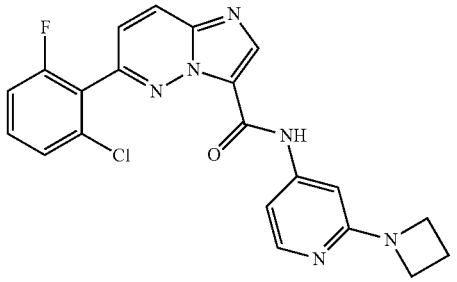 [SMILES: O=C(Nc1ccnc(N2CCC2)c1)c1cnc2ccc(-c3c(F)cccc3Cl)nn12] |
| 166 | 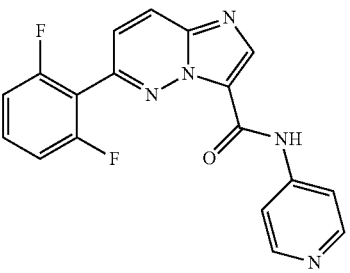 [SMILES: O=C(Nc1ccncc1)c1cnc2ccc(-c3c(F)cccc3F)nn12] |
| 167 | 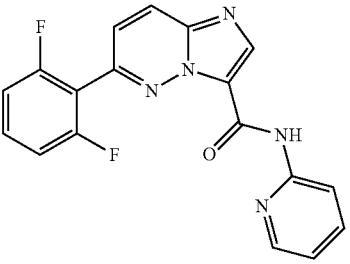 [SMILES: O=C(Nc1ccccn1)c1cnc2ccc(-c3c(F)cccc3F)nn12] |
| 168 | 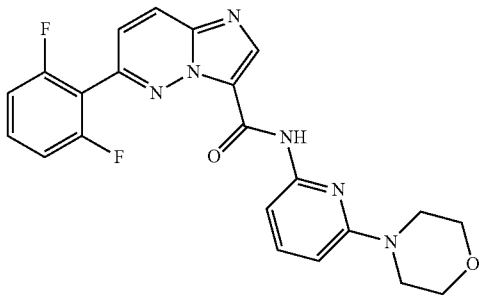 [SMILES: O=C(Nc1cccc(N2CCOCC2)n1)c1cnc2ccc(-c3c(F)cccc3F)nn12] |
| 169 | 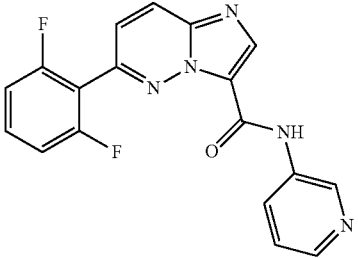 [SMILES: O=C(Nc1cccnc1)c1cnc2ccc(-c3c(F)cccc3F)nn12] |

-continued
| Compound No | Structure |
|---|---|
| 170 | 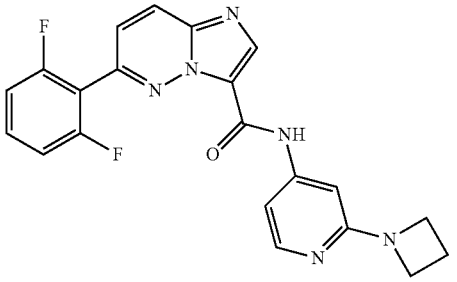 |
| 171 | 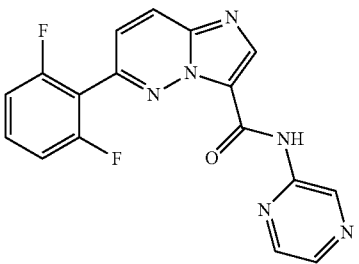 |
| 172 | 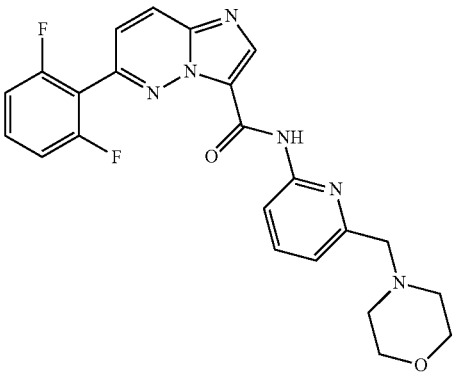 |
| 173 | 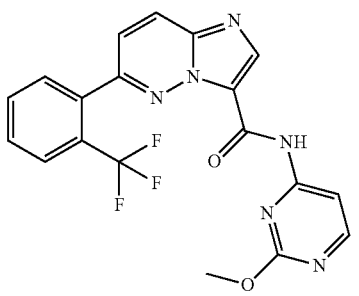 [SMILES: COc1nccc(NC(=O)c2cnc3ccc(-c4ccccc4C(F)(F)F)nn23)n1] |
| 174 | 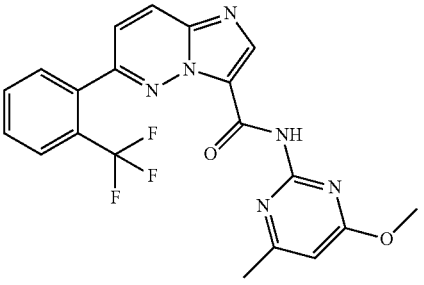 [SMILES: COc1cc(C)nc(NC(=O)c2cnc3ccc(-c4ccccc4C(F)(F)F)nn23)n1] |

| Compound No | Structure |
|---|---|
| 175 | 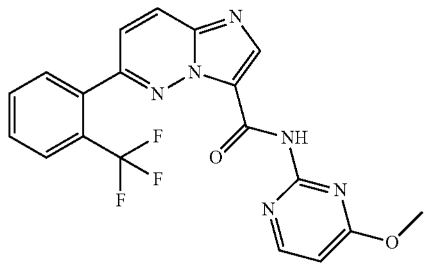 [SMILES: COc1ccnc(NC(=O)c2cnc3ccc(-c4ccccc4C(F)(F)F)nn23)n1] |
| 176 | 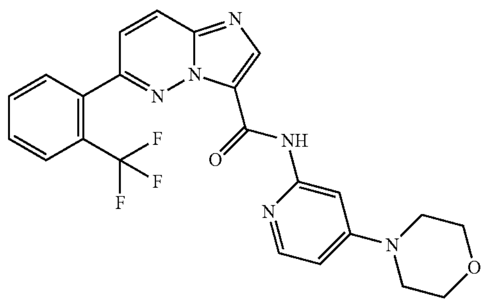 [SMILES: O=C(Nc1cc(N2CCOCC2)ccn1)c1cnc2ccc(-c3ccccc3C(F)(F)F)nn12] |
| 177 | 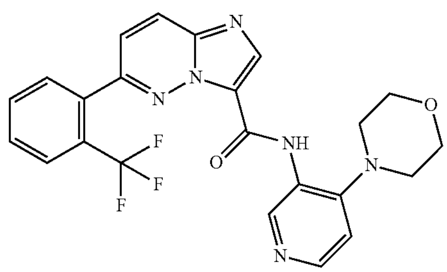 [SMILES: O=C(Nc1cnccc1N1CCOCC1)c1cnc2ccc(-c3ccccc3C(F)(F)F)nn12] |
| 178 | 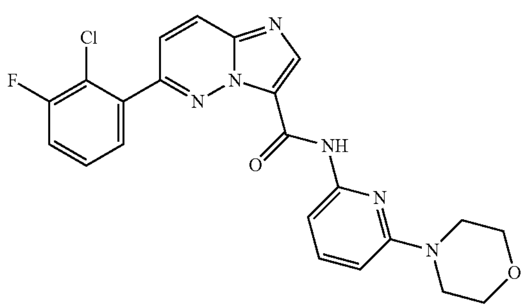 [SMILES: O=C(Nc1cccc(N2CCOCC2)n1)c1cnc2ccc(-c3cccc(F)c3Cl)nn12] |
| 179 | 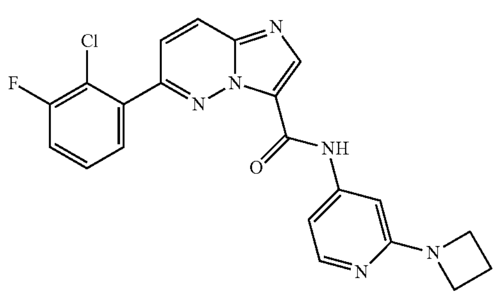 [SMILES: O=C(Nc1ccnc(N2CCC2)c1)c1cnc2ccc(-c3cccc(F)c3Cl)nn12] |

| Compound No | Structure |
|---|---|
| 180 | 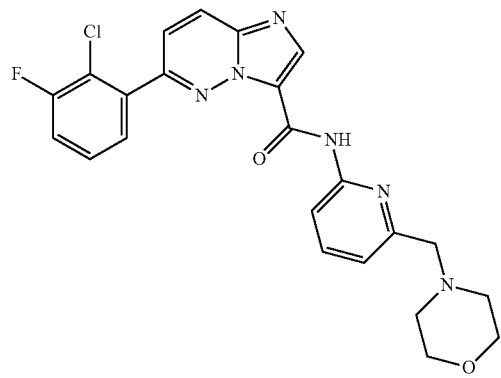 |
| 181 | 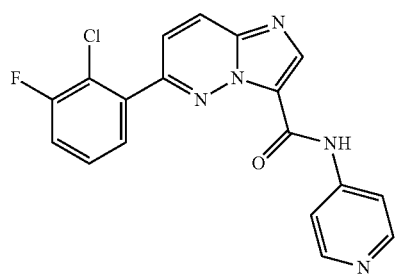 [SMILES: O=C(Nc1ccncc1)c1cnc2ccc(-c3cccc(F)c3Cl)nn12] |
| 182 | 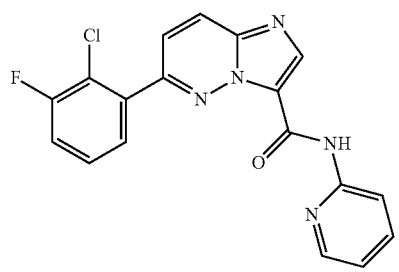 [SMILES: O=C(Nc1ccccn1)c1cnc2ccc(-c3cccc(F)c3Cl)nn12] |
| 183 | 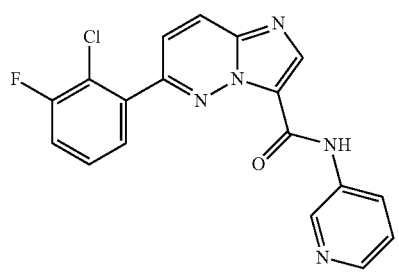 [SMILES: O=C(Nc1cccnc1)c1cnc2ccc(-c3cccc(F)c3Cl)nn12] |
| 184 | 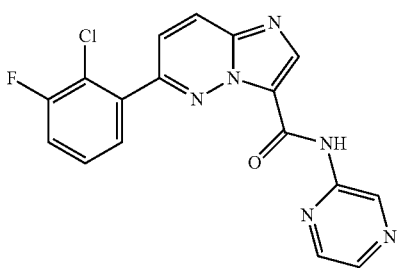 [SMILES: O=C(Nc1cnccn1)c1cnc2ccc(-c3cccc(F)c3Cl)nn12] |

| Compound No | Structure |
|---|---|
| 185 | (structure) |
| 186 | (structure) |
| 187 | (structure) |
| 188 | (structure) |
| 189 | (structure) |

-continued
| Compound No | Structure |
|---|---|
| 190 | 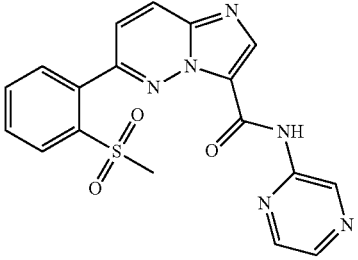 [SMILES: CS(=O)(=O)c1ccccc1-c1ccc2ncc(C(=O)Nc3cnccn3)n2n1] |
| 191 | 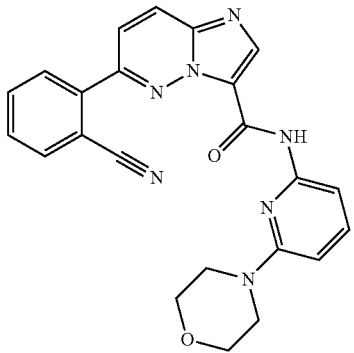 [SMILES: N#Cc1ccccc1-c1ccc2ncc(C(=O)Nc3cccc(N4CCOCC4)n3)n2n1] |
| 192 | 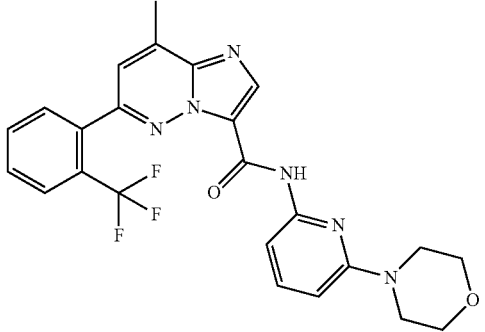 [SMILES: Cc1cc(-c2ccccc2C(F)(F)F)nn2c(C(=O)Nc3cccc(N4CCOCC4)n3)cnc12] |
| 193 | 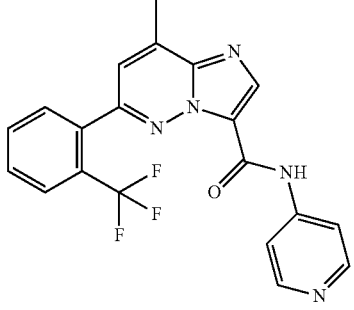 |
| 194 | 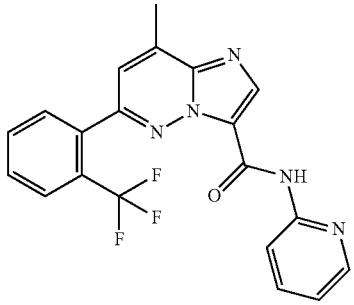 [SMILES: Cc1cc(-c2ccccc2C(F)(F)F)nn2c(C(=O)Nc3ccccn3)cnc12] |

| Compound No | Structure |
|---|---|
| 195 | 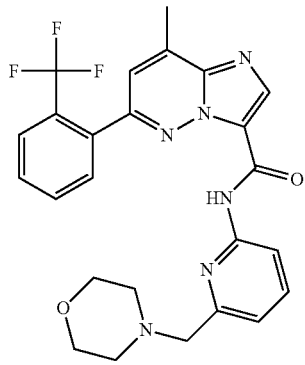 [SMILES: Cc1cc(-c2ccccc2C(F)(F)F)nn2c(C(=O)Nc3cccc(CN4CCOCC4)n3)cnc12] |
| 196 | 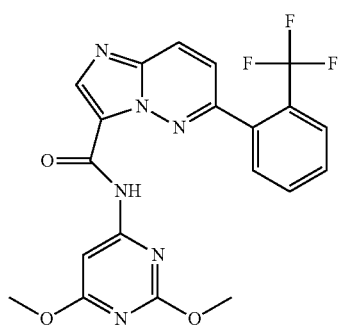 [SMILES: COc1cc(NC(=O)c2cnc3ccc(-c4ccccc4C(F)(F)F)nn23)nc(OC)n1] |
| 197 | 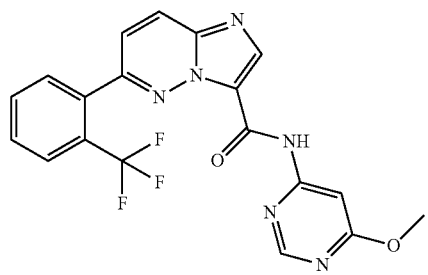 |
| 198 | 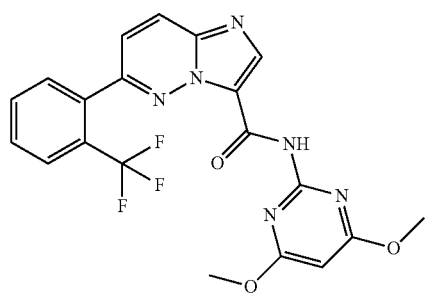 [SMILES: COc1cc(OC)nc(NC(=O)c2cnc3ccc(-c4ccccc4C(F)(F)F)nn23)n1] |

-continued
| Compound No | Structure |
|---|---|
| 199 | 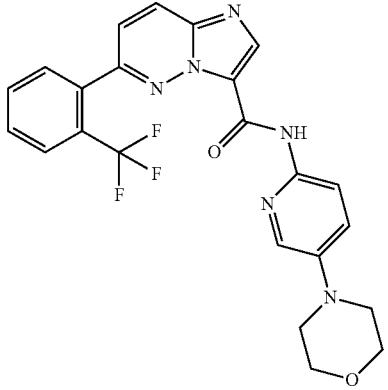 [SMILES: O=C(Nc1ccc(N2CCOCC2)cn1)c1cnc2ccc(-c3ccccc3C(F)(F)F)nn12] |
| 200 | 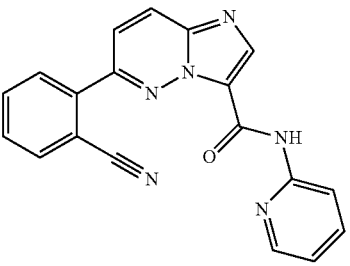 [SMILES: N#Cc1ccccc1-c1ccc2ncc(C(=O)Nc3ccccn3)n2n1] |
| 201 | 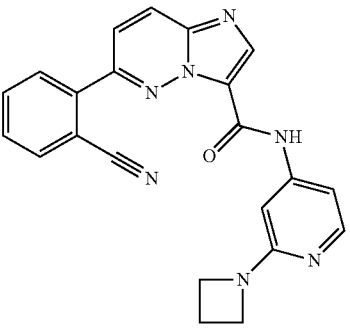 [SMILES: N#Cc1ccccc1-c1ccc2ncc(C(=O)Nc3ccnc(N4CCC4)c3)n2n1] |
| 202 | 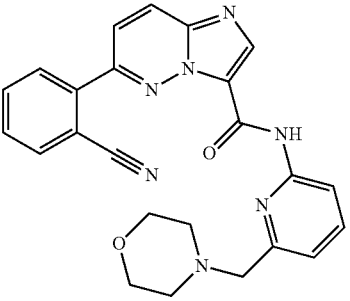 [SMILES: N#Cc1ccccc1-c1ccc2ncc(C(=O)Nc3cccc(CN4CCOCC4)n3)n2n1] |
| 203 | 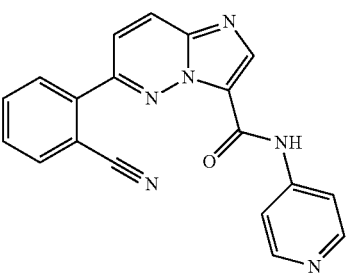 [SMILES: N#Cc1ccccc1-c1ccc2ncc(C(=O)Nc3ccncc3)n2n1] |

-continued

| Compound No | Structure |
|---|---|
| 204 | 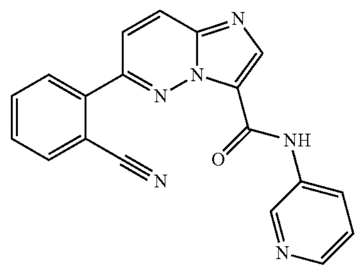 [SMILES: N#Cc1ccccc1-c1ccc2ncc(C(=O)Nc3cccnc3)n2n1] |
| 205 | 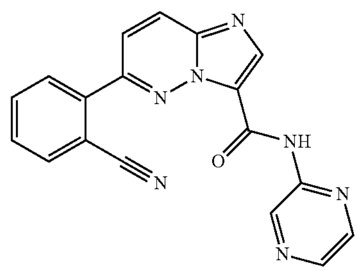 [SMILES: N#Cc1ccccc1-c1ccc2ncc(C(=O)Nc3cnccn3)n2n1] |
| 206 | 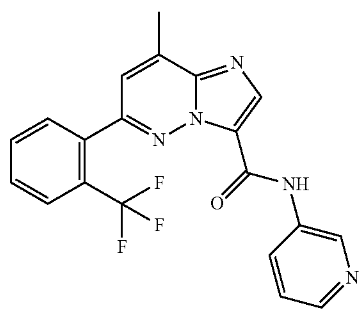 [SMILES: Cc1cc(-c2ccccc2C(F)(F)F)nn2c(C(=O)Nc3cccnc3)cnc12] |
| 207 | 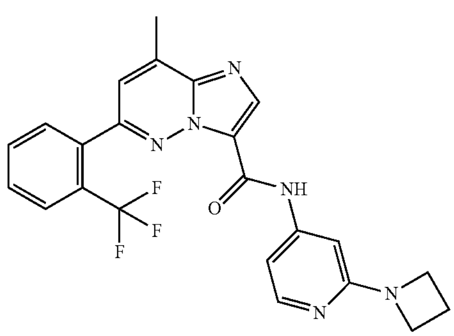 [SMILES: Cc1cc(-c2ccccc2C(F)(F)F)nn2c(C(=O)Nc3ccnc(N4CCC4)c3)cnc12] |
| 208 | 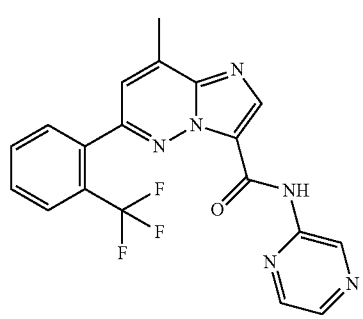 [SMILES: Cc1cc(-c2ccccc2C(F)(F)F)nn2c(C(=O)Nc3cnccn3)cnc12] |

-continued
| Compound No | Structure |
|---|---|
| 209 | 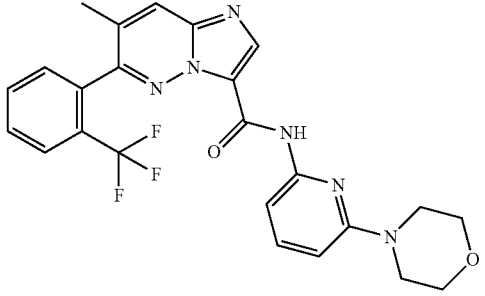 [SMILES: Cc1cc2ncc(C(=O)Nc3cccc(N4CCOCC4)n3)n2nc1-c1ccccc1C(F)(F)F] |
| 210 | 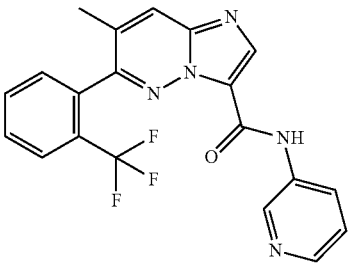 [SMILES: Cc1cc2ncc(C(=O)Nc3cccnc3)n2nc1-c1ccccc1C(F)(F)F] |
| 211 | 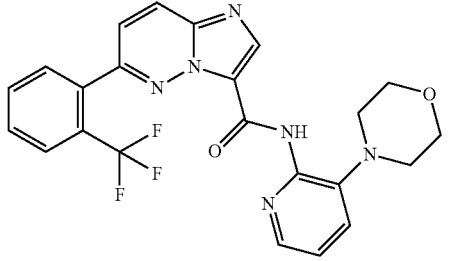 [SMILES: O=C(Nc1ncccc1N1CCOCC1)c1cnc2ccc(-c3ccccc3C(F)(F)F)nn12] |
| 212 | 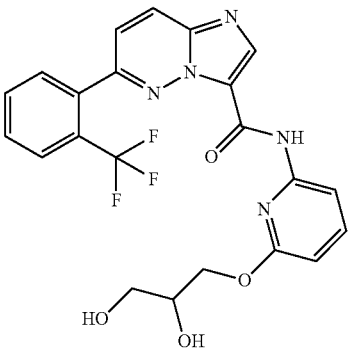 |
| 213 | 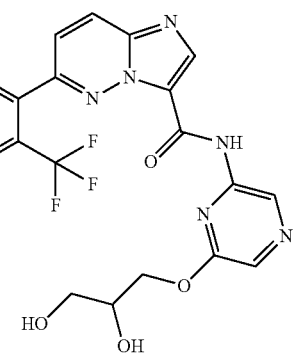 |

-continued
| Compound No | Structure |
|---|---|
| 214 | 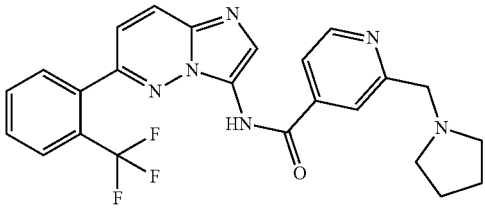 [SMILES: O=C(Nc1cnc2ccc(-c3ccccc3C(F)(F)F)nn12)c1ccnc(CN2CCCC2)c1] |
| 215 | 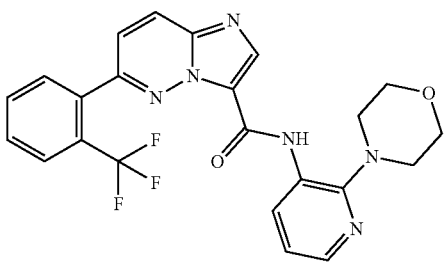 [SMILES: O=C(Nc1cccnc1N1CCOCC1)c1cnc2ccc(-c3ccccc3C(F)(F)F)nn12] |
| 216 | 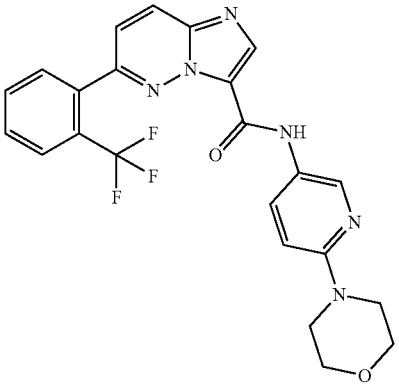 [SMILES: O=C(Nc1ccc(N2CCOCC2)nc1)c1cnc2ccc(-c3ccccc3C(F)(F)F)nn12] |
| 217 | 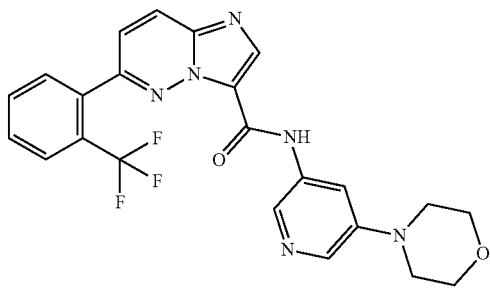 [SMILES: O=C(Nc1cncc(N2CCOCC2)c1)c1cnc2ccc(-c3ccccc3C(F)(F)F)nn12] |
| 218 | 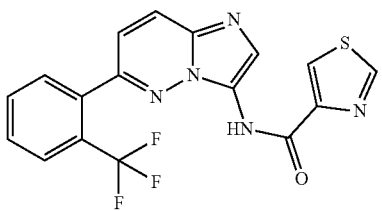 [SMILES: O=C(Nc1cnc2ccc(-c3ccccc3C(F)(F)F)nn12)c1cscn1] |
| 219 | 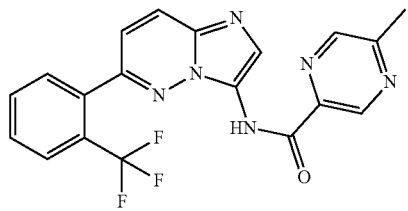 [SMILES: Cc1cnc(C(=O)Nc2cnc3ccc(-c4ccccc4C(F)(F)F)nn23)cn1] |

-continued
| Compound No | Structure |
|---|---|
| 220 | 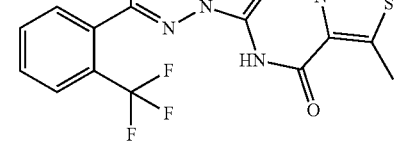 |
| 221 | 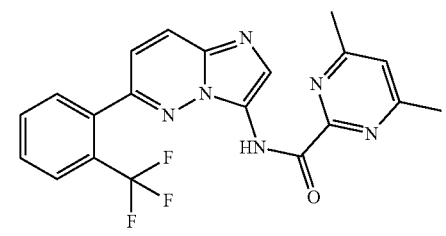 [SMILES: Cc1cc(C)nc(C(=O)Nc2cnc3ccc(-c4ccccc4C(F)(F)F)nn23)n1] |
| 222 | 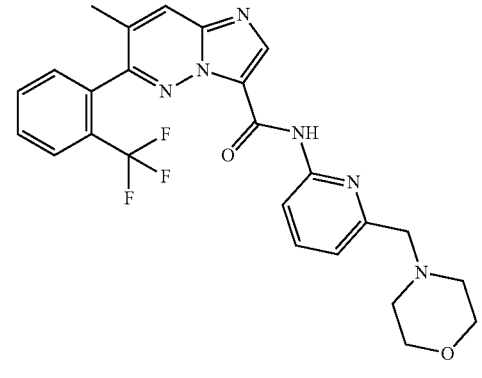 [SMILES: Cc1cc2ncc(C(=O)Nc3cccc(CN4CCOCC4)n3)n2nc1-c1ccccc1C(F)(F)F] |
| 223 | 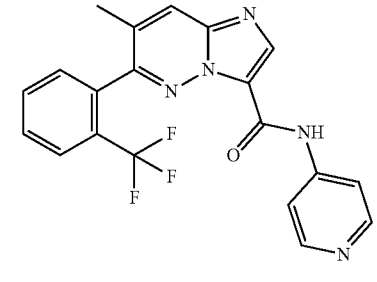 [SMILES: Cc1cc2ncc(C(=O)Nc3ccncc3)n2nc1-c1ccccc1C(F)(F)F] |
| 224 | 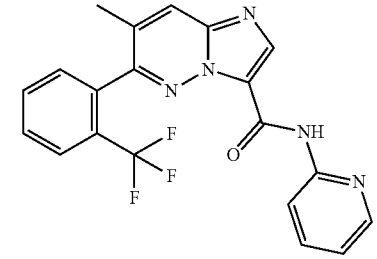 [SMILES: Cc1cc2ncc(C(=O)Nc3ccccn3)n2nc1-c1ccccc1C(F)(F)F] |

-continued

| Compound No | Structure |
|---|---|
| 225 | 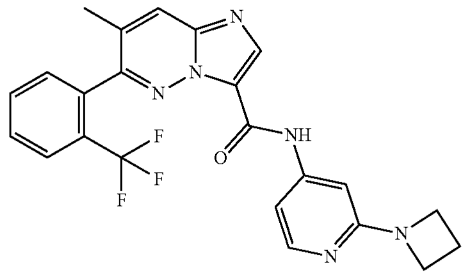 [SMILES: Cc1cc2ncc(C(=O)Nc3ccnc(N4CCC4)c3)n2nc1-c1ccccc1C(F)(F)F] |
| 226 | 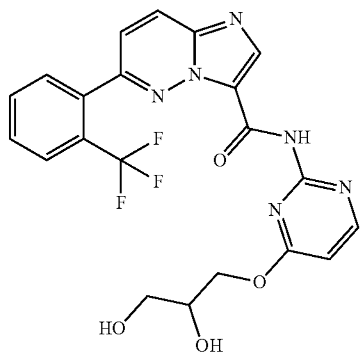 [SMILES: O=C(Nc1nccc(OCC(O)CO)n1)c1cnc2ccc(-c3ccccc3C(F)(F)F)nn12] |
| 227 | 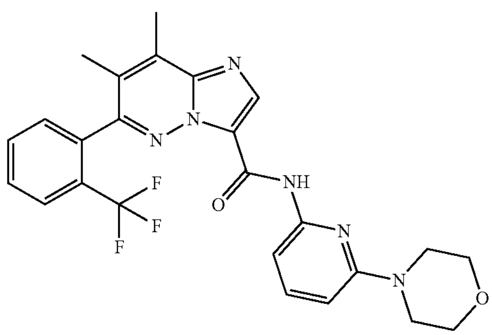 [SMILES: Cc1c(-c2ccccc2C(F)(F)F)nn2c(C(=O)Nc3cccc(N4CCOCC4)n3)cnc2c1C] |
| 228 | 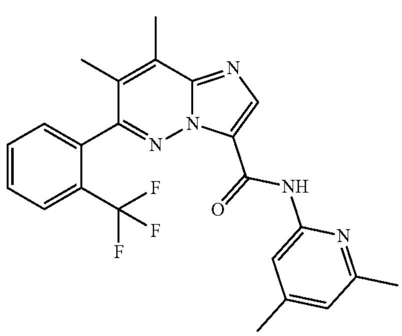 [SMILES: Cc1cc(C)nc(NC(=O)c2cnc3c(C)c(C)c(-c4ccccc4C(F)(F)F)nn23)c1] |

| Compound No | Structure |
|---|---|
| 229 | 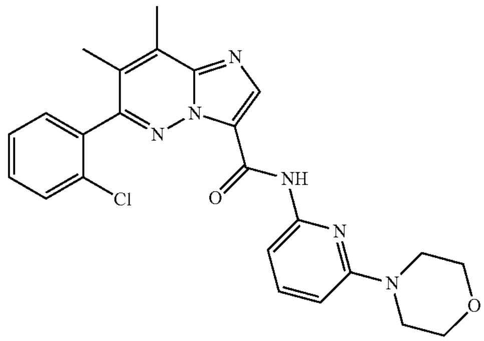 [SMILES: Cc1c(-c2ccccc2Cl)nn2c(C(=O)Nc3cccc(N4CCOCC4)n3)cnc2c1C] |
| 230 | 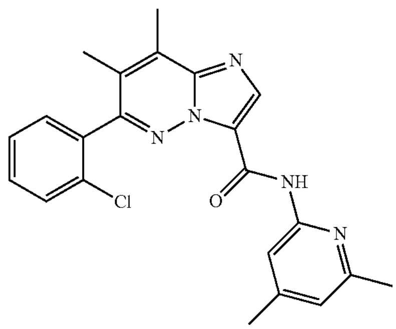 [SMILES: Cc1cc(C)nc(NC(=O)c2cnc3c(C)c(C)c(-c4ccccc4Cl)nn23)c1] |
| 231 | 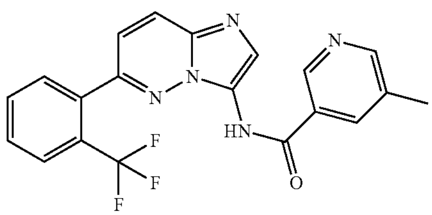 [SMILES: Cc1cncc(C(=O)Nc2cnc3ccc(-c4ccccc4C(F)(F)F)nn23)c1] |
| 232 | 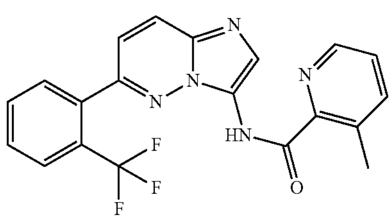 [SMILES: Cc1cccnc1C(=O)Nc1cnc2ccc(-c3ccccc3C(F)(F)F)nn12] |
| 233 | 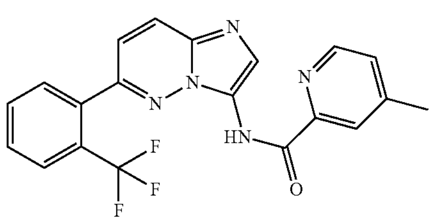 [SMILES: Cc1ccnc(C(=O)Nc2cnc3ccc(-c4ccccc4C(F)(F)F)nn23)c1] |
| 234 | 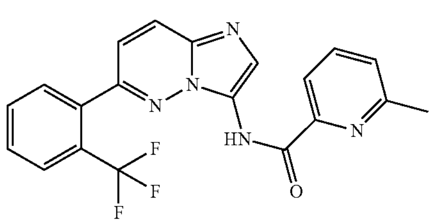 [SMILES: Cc1cccc(C(=O)Nc2cnc3ccc(-c4ccccc4C(F)(F)F)nn23)n1] |

| Compound No | Structure |
|---|---|
| 235 | 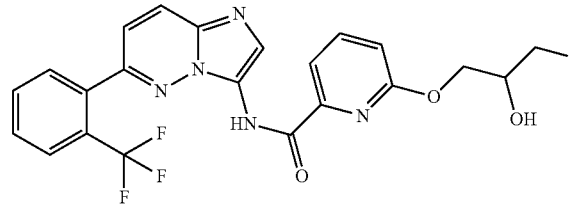 |
| 236 | 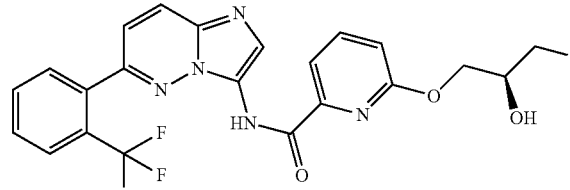 |
| 237 | 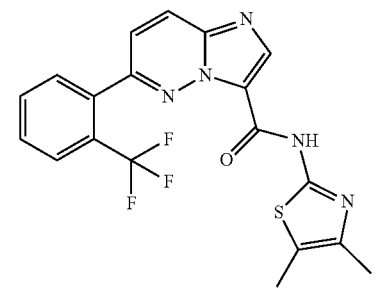 [SMILES: Cc1nc(NC(=O)c2cnc3ccc(-c4ccccc4C(F)(F)F)nn23)sc1C] |
| 238 | 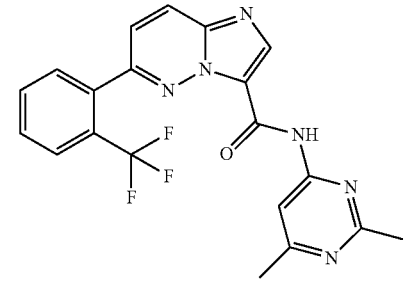 [SMILES: Cc1cc(NC(=O)c2cnc3ccc(-c4ccccc4C(F)(F)F)nn23)nc(C)n1] |
| 242 | 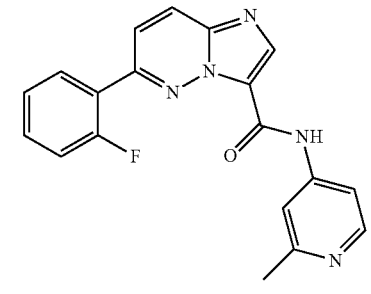 |
| 243 | 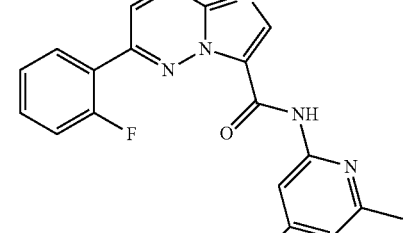 |

-continued
| Compound No | Structure |
|---|---|
| 244 | 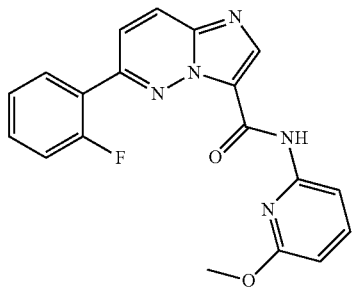 [SMILES: COc1cccc(NC(=O)c2cnc3ccc(-c4ccccc4F)nn23)n1] |
| 245 | 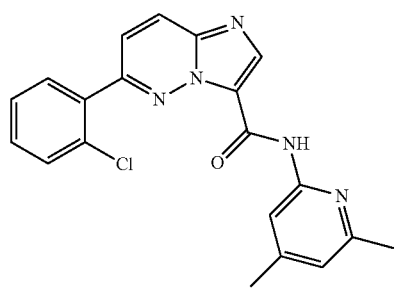 [SMILES: Cc1cc(C)nc(NC(=O)c2cnc3ccc(-c4ccccc4Cl)nn23)c1] |
| 246 | 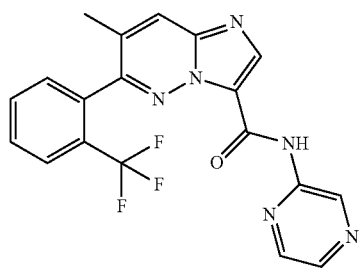 [SMILES: Cc1cc2ncc(C(=O)Nc3cnccn3)n2nc1-c1ccccc1C(F)(F)F] |
| 247 | 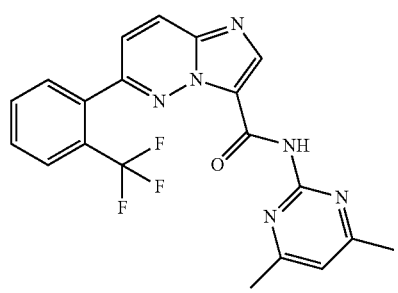 [SMILES: Cc1cc(C)nc(NC(=O)c2cnc3ccc(-c4ccccc4C(F)(F)F)nn23)n1] |
| 248 | 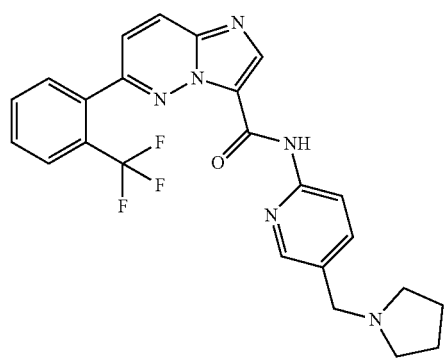 [SMILES: O=C(Nc1ccc(CN2CCCC2)cn1)c1cnc2ccc(-c3ccccc3C(F)(F)F)nn12] |

-continued

| Compound No | Structure |
|---|---|
| 257 | 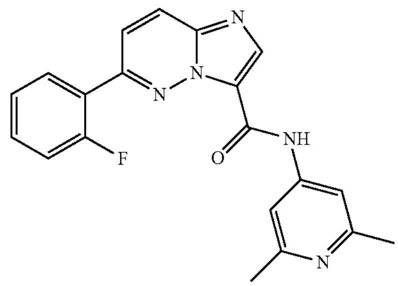 [SMILES: Cc1cc(NC(=O)c2cnc3ccc(-c4ccccc4F)nn23)cc(C)n1] |
| 258 | 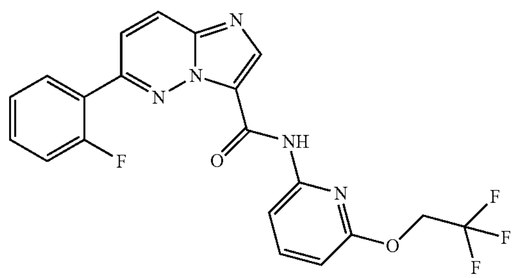 [SMILES: O=C(Nc1cccc(OCC(F)(F)F)n1)c1cnc2ccc(-c3ccccc3F)nn12] |
| 259 | 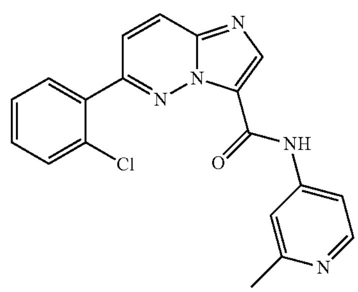 [SMILES: Cc1cc(NC(=O)c2cnc3ccc(-c4ccccc4Cl)nn23)ccn1] |
| 260 | 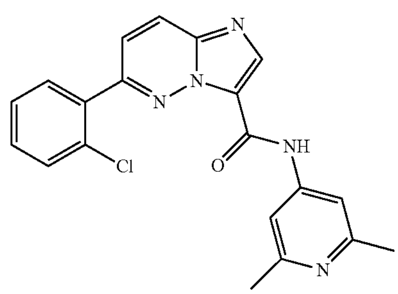 [SMILES: Cc1cc(NC(=O)c2cnc3ccc(-c4ccccc4Cl)nn23)cc(C)n1] |
| 261 | 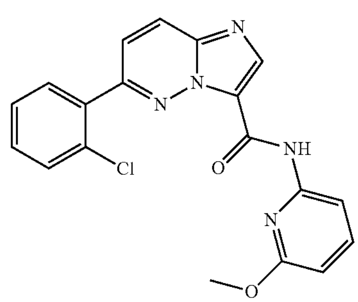 [SMILES: COc1cccc(NC(=O)c2cnc3ccc(-c4ccccc4Cl)nn23)n1] |

| Compound No | Structure |
|---|---|
| 262 | 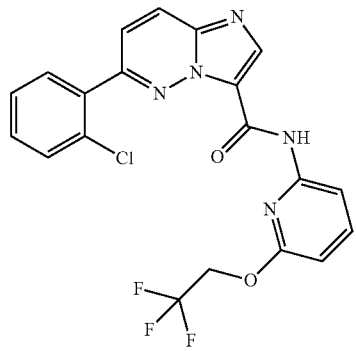 [SMILES: O=C(Nc1cccc(OCC(F)(F)F)n1)c1cnc2ccc(-c3ccccc3Cl)nn12] |
| 263 | 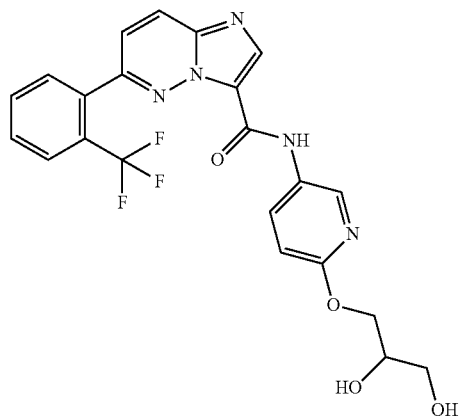 [SMILES: O=C(Nc1ccc(OCC(O)CO)nc1)c1cnc2ccc(-c3ccccc3C(F)(F)F)nn12] |
| 264 | 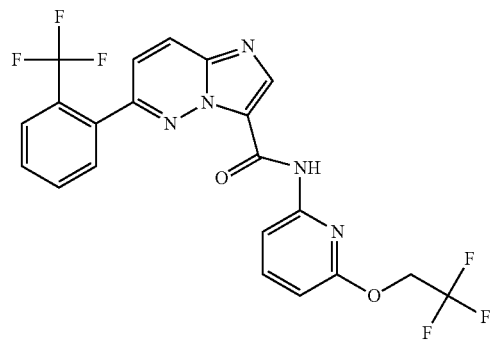 [SMILES: O=C(Nc1cccc(OCC(F)(F)F)n1)c1cnc2ccc(-c3ccccc3C(F)(F)F)nn12] |
| 270 | 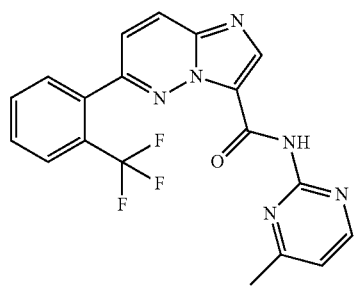 |

| Compound No | Structure |
|---|---|
| 271 | 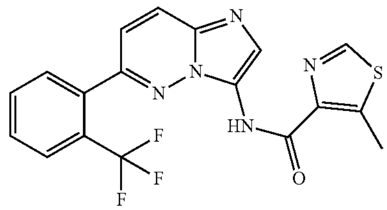 [SMILES: Cc1scnc1C(=O)Nc1cnc2ccc(-c3ccccc3C(F)(F)F)nn12] |
| 272 | 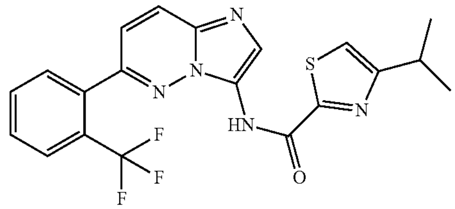 [SMILES: CC(C)c1csc(C(=O)Nc2cnc3ccc(-c4ccccc4C(F)(F)F)nn23)n1] |
| 273 | 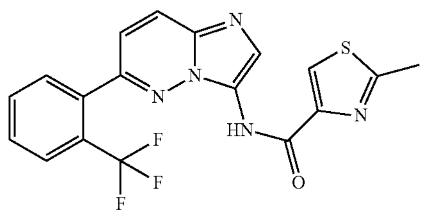 [SMILES: Cc1nc(C(=O)Nc2cnc3ccc(-c4ccccc4C(F)(F)F)nn23)cs1] |
| 274 | 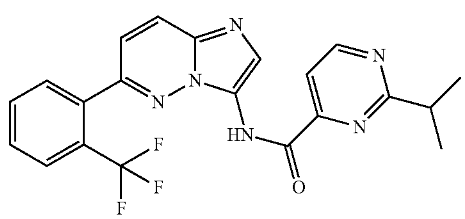 [SMILES: CC(C)c1nccc(C(=O)Nc2cnc3ccc(-c4ccccc4C(F)(F)F)nn23)n1] |
| 275 | 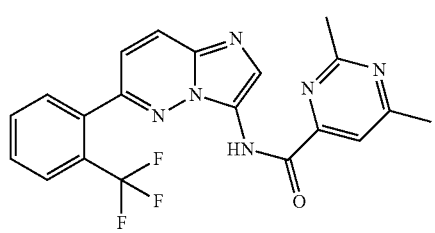 [SMILES: Cc1cc(C(=O)Nc2cnc3ccc(-c4ccccc4C(F)(F)F)nn23)nc(C)n1] |
| 276 | 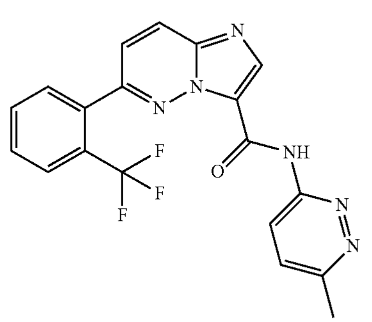 [SMILES: Cc1ccc(NC(=O)c2cnc3ccc(-c4ccccc4C(F)(F)F)nn23)nn1] |

-continued

| Compound No | Structure |
|---|---|
| 277 | 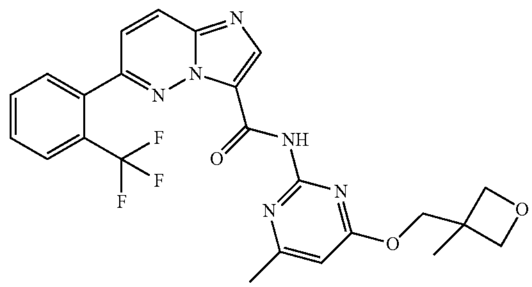 [SMILES: Cc1cc(OCC2(C)COC2)nc(NC(=O)c2cnc3ccc(-c4ccccc4C(F)(F)F)nn23)n1] |
| 278 | 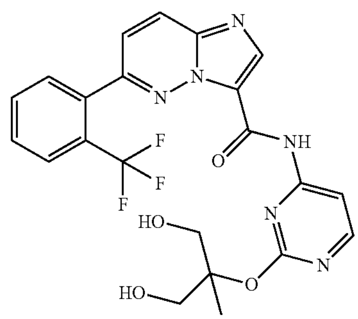 [SMILES: CC(CO)(CO)Oc1nccc(NC(=O)c2cnc3ccc(-c4ccccc4C(F)(F)F)nn23)n1] |
| 279 | 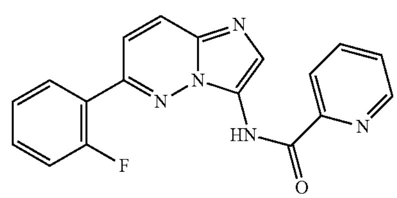 [SMILES: O=C(Nc1cnc2ccc(-c3ccccc3F)nn12)c1ccccn1] |
| 280 | 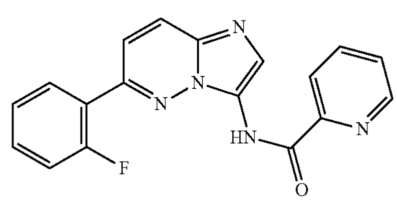 [SMILES: O=C(Nc1cnc2ccc(-c3ccccc3F)nn12)c1ccccn1] |
| 281 | 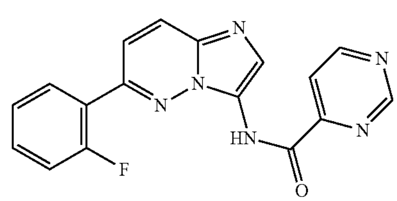 [SMILES: O=C(Nc1cnc2ccc(-c3ccccc3F)nn12)c1ccncn1] |
| 282 | 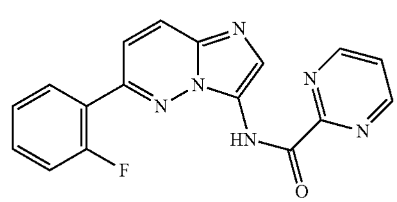 [SMILES: O=C(Nc1cnc2ccc(-c3ccccc3F)nn12)c1ncccn1] |

-continued

| Compound No | Structure |
|---|---|
| 283 | 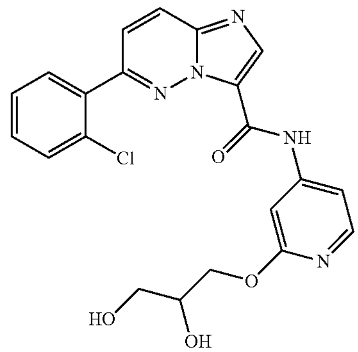 [SMILES: O=C(Nc1ccnc(OCC(O)CO)c1)c1cnc2ccc(-c3ccccc3Cl)nn12] |
| 284 | 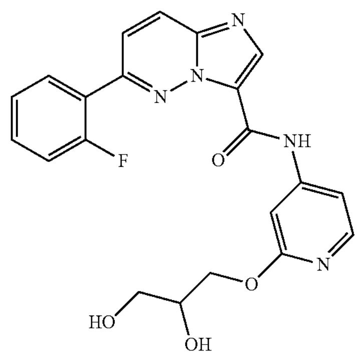 [SMILES: O=C(Nc1ccnc(OCC(O)CO)c1)c1cnc2ccc(-c3ccccc3F)nn12] |
| 285 | 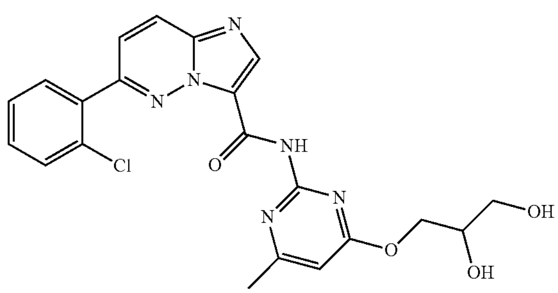 [SMILES: Cc1cc(OCC(O)CO)nc(NC(=O)c2cnc3ccc(-c4ccccc4Cl)nn23)n1] |
| 286 | 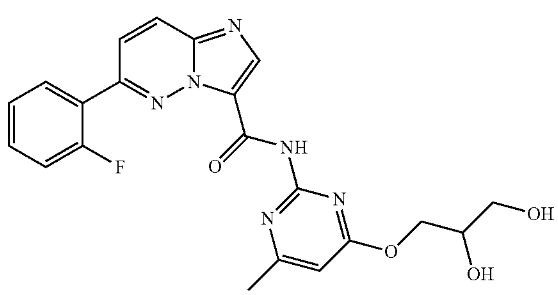 [SMILES: Cc1cc(OCC(O)CO)nc(NC(=O)c2cnc3ccc(-c4ccccc4F)nn23)n1] |
| 287 | 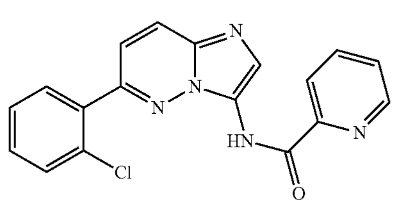 |

-continued

| Compound No | Structure |
|---|---|
| 288 | 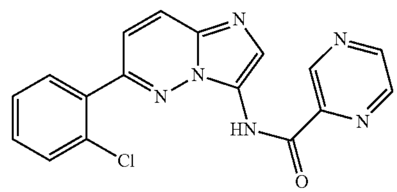 [SMILES: O=C(Nc1cnc2ccc(-c3ccccc3Cl)nn12)c1cnccn1] |
| 289 | 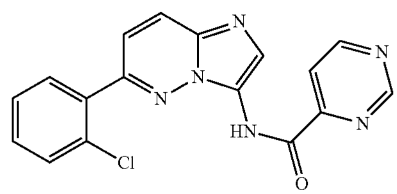 [SMILES: O=C(Nc1cnc2ccc(-c3ccccc3Cl)nn12)c1ccncn1] |
| 290 | 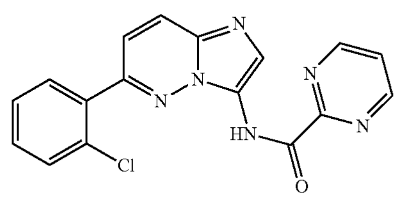 [SMILES: O=C(Nc1cnc2ccc(-c3ccccc3Cl)nn12)c1ncccn1] |
| 291 | 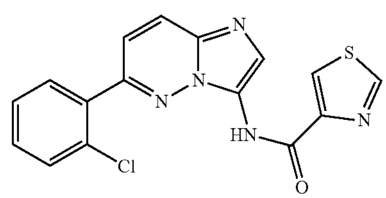 [SMILES: O=C(Nc1cnc2ccc(-c3ccccc3Cl)nn12)c1cscn1] |
| 292 | 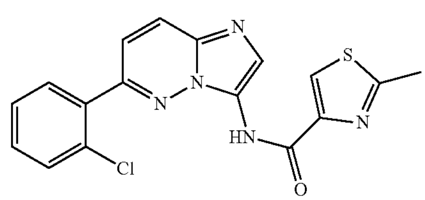 [SMILES: Cc1nc(C(=O)Nc2cnc3ccc(-c4ccccc4Cl)nn23)cs1] |
| 293 | 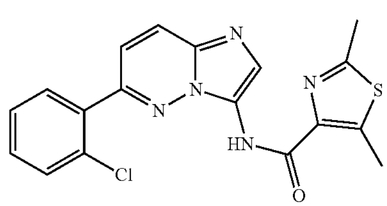 [SMILES: Cc1nc(C(=O)Nc2cnc3ccc(-c4ccccc4Cl)nn23)c(C)s1] |
| 294 | 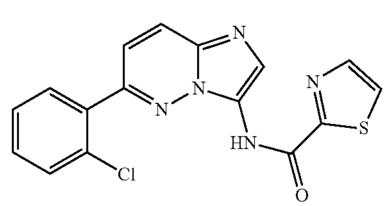 [SMILES: O=C(Nc1cnc2ccc(-c3ccccc3Cl)nn12)c1nccs1] |

| Compound No | Structure |
|---|---|
| 295 | (structure) |
| 296 | (structure) |
| 297 | (structure) |
| 298 | (structure) |
| 299 | (structure) |

| Compound No | Structure |
|---|---|
| 300 | 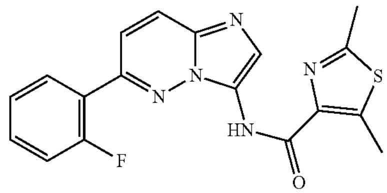 [SMILES: Cc1nc(C(=O)Nc2cnc3ccc(-c4ccccc4F)nn23)c(C)s1] |
| 301 | 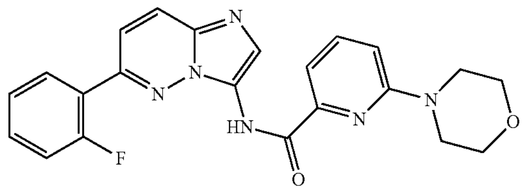 [SMILES: O=C(Nc1cnc2ccc(-c3ccccc3F)nn12)c1cccc(N2CCOCC2)n1] |
| 302 | 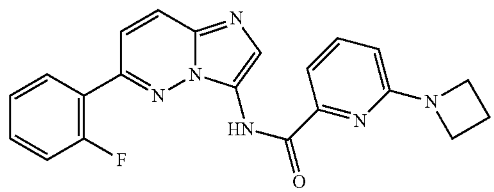 [SMILES: O=C(Nc1cnc2ccc(-c3ccccc3F)nn12)c1cccc(N2CCC2)n1] |
| 303 | 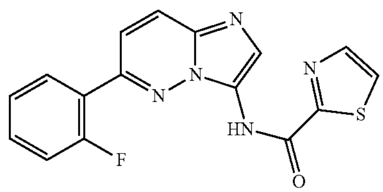 [SMILES: O=C(Nc1cnc2ccc(-c3ccccc3F)nn12)c1nccs1] |
| 304 | 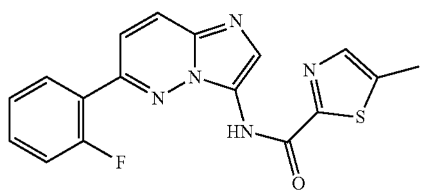 [SMILES: Cc1cnc(C(=O)Nc2cnc3ccc(-c4ccccc4F)nn23)s1] |
| 305 | 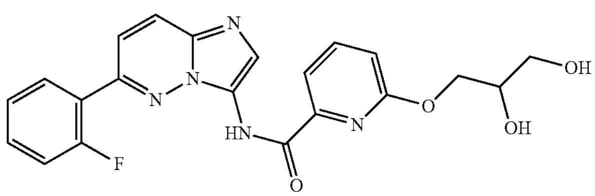 [SMILES: O=C(Nc1cnc2ccc(-c3ccccc3F)nn12)c1cccc(OCC(O)CO)n1] |
| 306 | 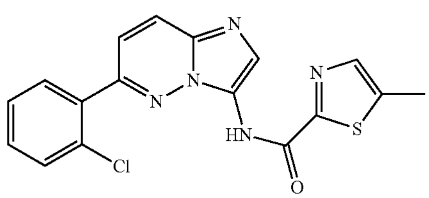 [SMILES: Cc1cnc(C(=O)Nc2cnc3ccc(-c4ccccc4Cl)nn23)s1] |
| 307 | 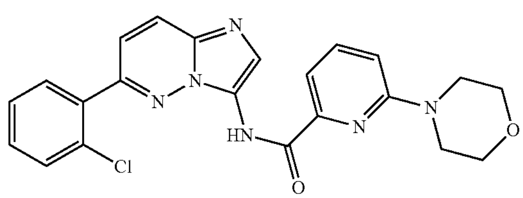 [SMILES: O=C(Nc1cnc2ccc(-c3ccccc3Cl)nn12)c1cccc(N2CCOCC2)n1] |

| Compound No | Structure |
|---|---|
| 308 | 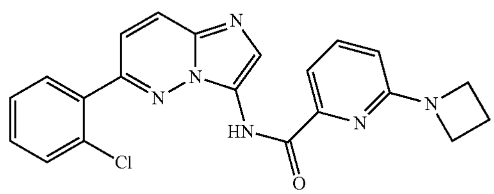 [SMILES: O=C(Nc1cnc2ccc(-c3ccccc3Cl)nn12)c1cccc(N2CCC2)n1] |
| 309 | 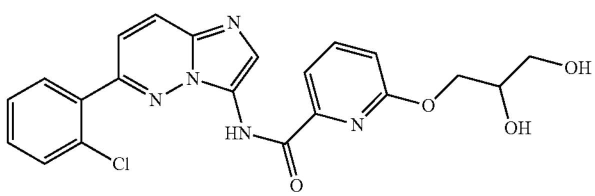 [SMILES: O=C(Nc1cnc2ccc(-c3ccccc3Cl)nn12)c1cccc(OCC(O)CO)n1] |
| 310 | 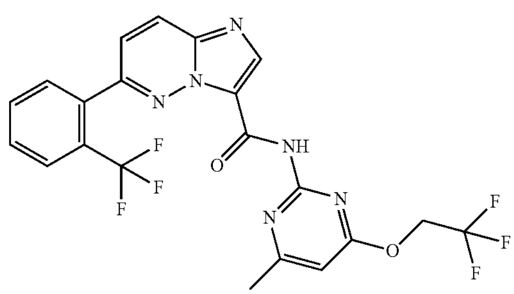 [SMILES: Cc1cc(OCC(F)(F)F)nc(NC(=O)c2cnc3ccc(-c4ccccc4C(F)(F)F)nn23)n1] |
| 311 | 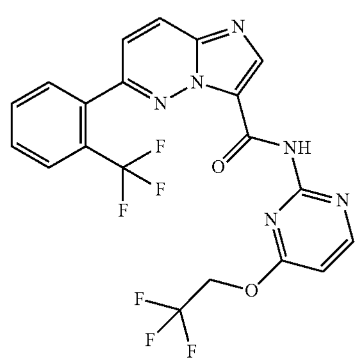 [SMILES: O=C(Nc1nccc(OCC(F)(F)F)n1)c1cnc2ccc(-c3ccccc3C(F)(F)F)nn12] |
| 312 | 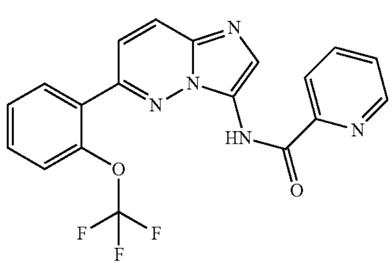 [SMILES: O=C(Nc1cnc2ccc(-c3ccccc3OC(F)(F)F)nn12)c1ccccn1] |
| 313 | 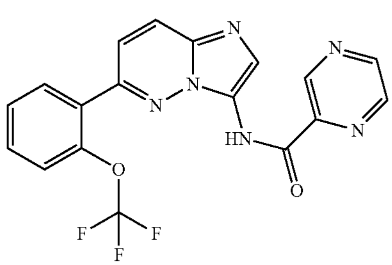 [SMILES: O=C(Nc1cnc2ccc(-c3ccccc3OC(F)(F)F)nn12)c1cnccn1] |

-continued

| Compound No | Structure |
|---|---|
| 314 | (structure) |
| 315 | (structure) |
| 316 | (structure) |
| 317 | (structure) |
| 318 | (structure) |
| 319 | (structure) |

-continued

| Compound No | Structure |
|---|---|
| 320 | 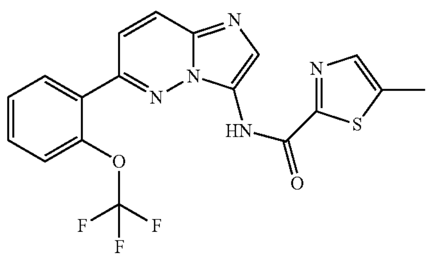 [SMILES: Cc1cnc(C(=O)Nc2cnc3ccc(-c4ccccc4OC(F)(F)F)nn23)s1] |
| 321 | 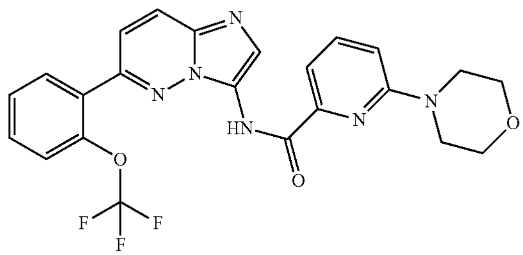 [SMILES: O=C(Nc1cnc2ccc(-c3ccccc3OC(F)(F)F)nn12)c1cccc(N2CCOCC2)n1] |
| 322 | 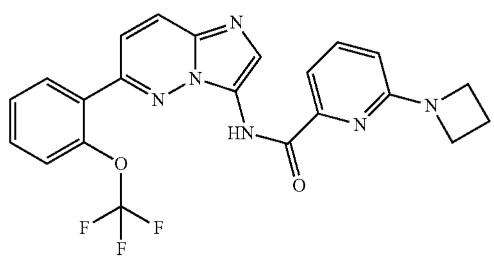 [SMILES: O=C(Nc1cnc2ccc(-c3ccccc3OC(F)(F)F)nn12)c1cccc(N2CCC2)n1] |
| 323 | 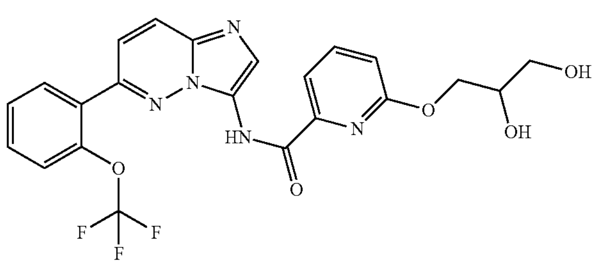 [SMILES: O=C(Nc1cnc2ccc(-c3ccccc3OC(F)(F)F)nn12)c1cccc(OCC(O)CO)n1] |
| 324 | 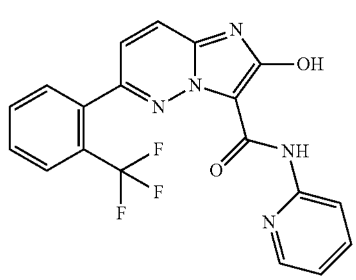 [SMILES: O=C(Nc1ccccn1)c1c(O)nc2ccc(-c3ccccc3C(F)(F)F)nn12] |

-continued

| Compound No | Structure |
|---|---|
| 325 | 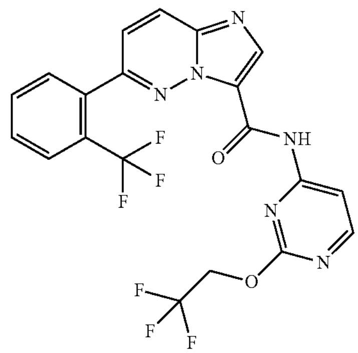 [SMILES: O=C(Nc1ccnc(OCC(F)(F)F)n1)c1cnc2ccc(-c3ccccc3C(F)(F)F)nn12] |
| 326 | 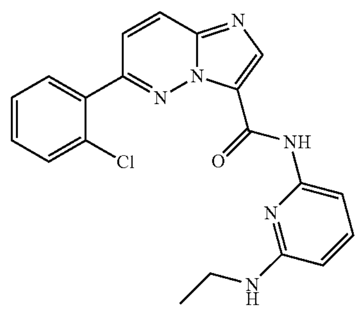 [SMILES: CCNc1cccc(NC(=O)c2cnc3ccc(-c4ccccc4Cl)nn23)n1] |
| 327 | 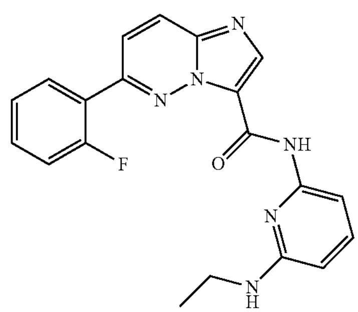 [SMILES: CCNc1cccc(NC(=O)c2cnc3ccc(-c4ccccc4F)nn23)n1] |
| 328 | 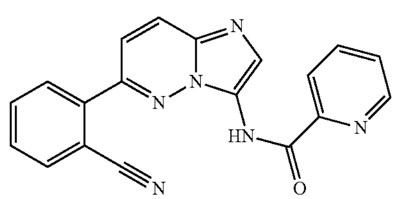 [SMILES: N#Cc1ccccc1-c1ccc2ncc(NC(=O)c3ccccn3)n2n1] |
| 329 | 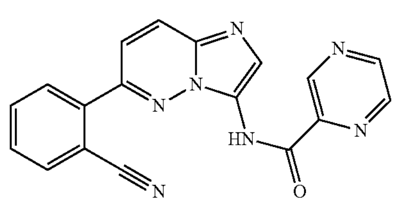 [SMILES: N#Cc1ccccc1-c1ccc2ncc(NC(=O)c3cnccn3)n2n1] |
| 330 | 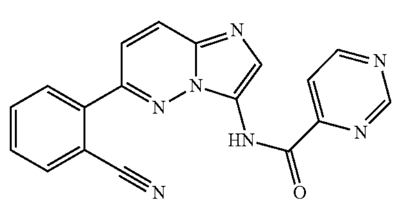 [SMILES: N#Cc1ccccc1-c1ccc2ncc(NC(=O)c3ccncn3)n2n1] |

| Compound No | Structure |
|---|---|
| 331 | (imidazo[1,2-b]pyridazine with 2-cyanophenyl substituent, 3-NHC(O)-pyrimidin-2-yl) |
| 332 | (imidazo[1,2-b]pyridazine with 2-cyanophenyl substituent, 3-NHC(O)-thiazol-4-yl) |
| 333 | (imidazo[1,2-b]pyridazine with 2-cyanophenyl substituent, 3-NHC(O)-(2-methylthiazol-4-yl)) |
| 334 | (imidazo[1,2-b]pyridazine with 2-cyanophenyl substituent, 3-NHC(O)-(2,5-dimethylthiazol-4-yl)) |
| 335 | (imidazo[1,2-b]pyridazine with 2-cyanophenyl substituent, 3-NHC(O)-thiazol-2-yl) |
| 336 | (imidazo[1,2-b]pyridazine with 2-cyanophenyl substituent, 3-NHC(O)-(5-methylthiazol-2-yl)) |
| 337 | (imidazo[1,2-b]pyridazine with 2-cyanophenyl substituent, 3-NHC(O)-(6-morpholinopyridin-2-yl)) |
| 338 | (imidazo[1,2-b]pyridazine with 2-cyanophenyl substituent, 3-NHC(O)-(6-azetidin-1-yl-pyridin-2-yl)) |

| Compound No | Structure |
|---|---|
| 339 | 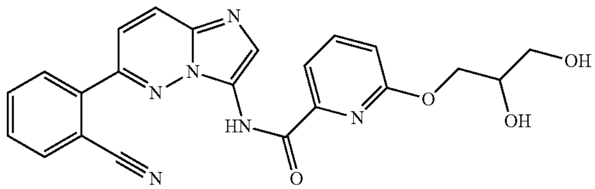 [SMILES: N#Cc1ccccc1-c1ccc2ncc(NC(=O)c3cccc(OCC(O)CO)n3)n2n1] |
| 340 | 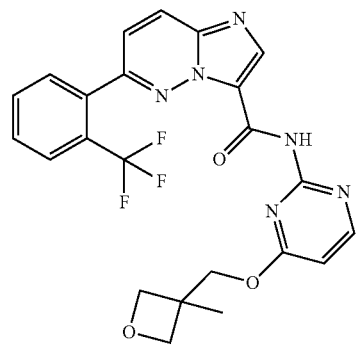 [SMILES: CC1(COc2ccnc(NC(=O)c3cnc4ccc(-c5ccccc5C(F)(F)F)nn34)n2)COC1] |
| 341 | 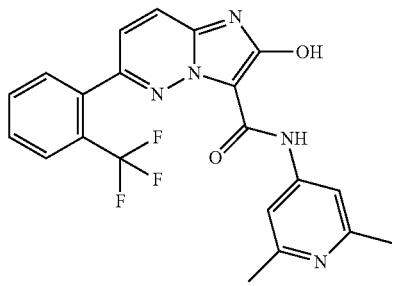 [SMILES: Cc1cc(NC(=O)c2c(O)nc3ccc(-c4ccccc4C(F)(F)F)nn23)cc(C)n1] |
| 342 | 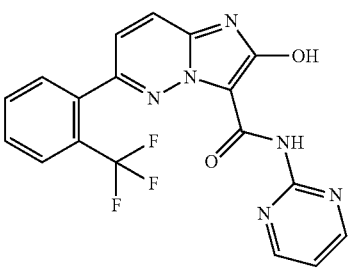 [SMILES: O=C(Nc1ncccn1)c1c(O)nc2ccc(-c3ccccc3C(F)(F)F)nn12] |
| 343 | 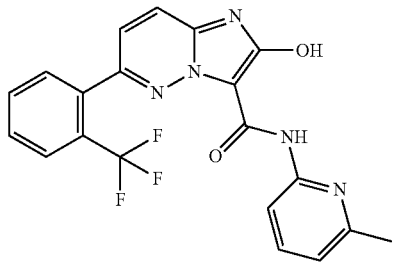 [SMILES: Cc1cccc(NC(=O)c2c(O)nc3ccc(-c4ccccc4C(F)(F)F)nn23)n1] |

US 9,957,271 B2
823                                                                                                          824
-continued
| Compound No | Structure |
|---|---|
| 344 | 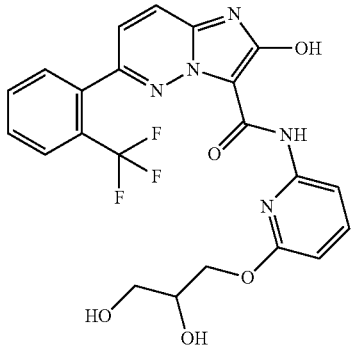 [SMILES: O=C(Nc1cccc(OCC(O)CO)n1)c1c(O)nc2ccc(-c3ccccc3C(F)(F)F)nn12] |
| 345 | 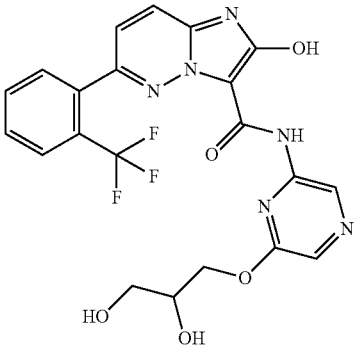 [SMILES: O=C(Nc1cncc(OCC(O)CO)n1)c1c(O)nc2ccc(-c3ccccc3C(F)(F)F)nn12] |
| 346 | 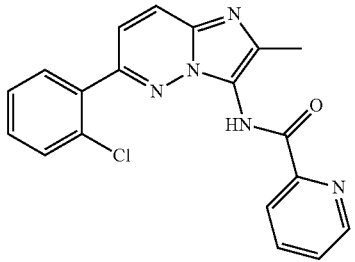 [SMILES: Cc1nc2ccc(-c3ccccc3Cl)nn2c1NC(=O)c1ccccn1] |
| 347 | 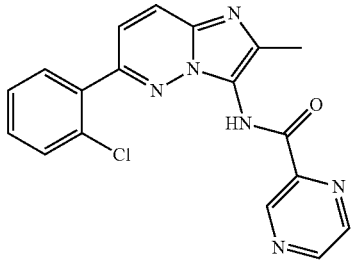 |
| 348 | 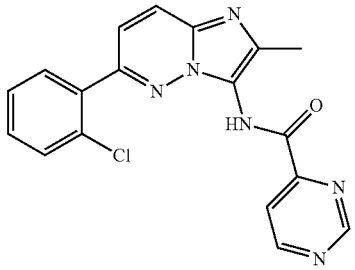 [SMILES: Cc1nc2ccc(-c3ccccc3Cl)nn2c1NC(=O)c1ccncn1] |

-continued
| Compound No | Structure |
|---|---|
| 349 | 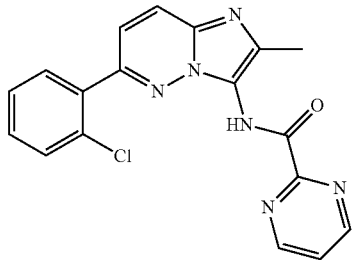 [SMILES: Cc1nc2ccc(-c3ccccc3Cl)nn2c1NC(=O)c1ncccn1] |
| 350 | 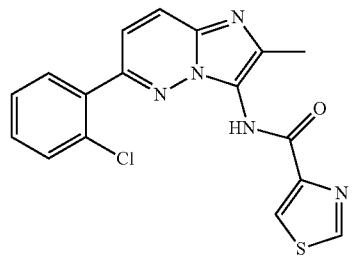 [SMILES: Cc1nc2ccc(-c3ccccc3Cl)nn2c1NC(=O)c1cscn1] |
| 351 | 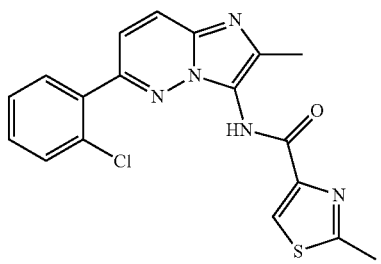 [SMILES: Cc1nc(C(=O)Nc2c(C)nc3ccc(-c4ccccc4Cl)nn23)cs1] |
| 352 | 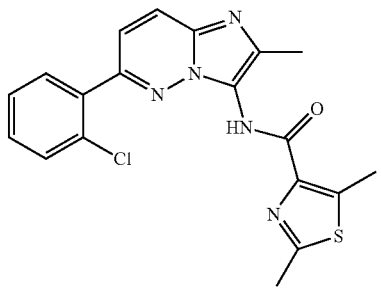 [SMILES: Cc1nc(C(=O)Nc2c(C)nc3ccc(-c4ccccc4Cl)nn23)c(C)s1] |
| 353 | 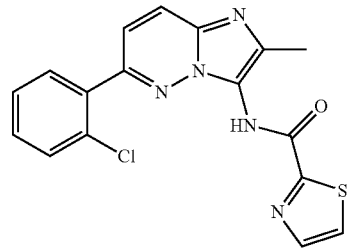 [SMILES: Cc1nc2ccc(-c3ccccc3Cl)nn2c1NC(=O)c1nccs1] |

-continued
| Compound No | Structure |
|---|---|
| 354 | 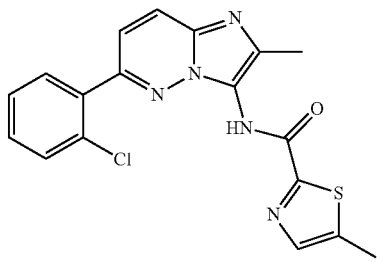 [SMILES: Cc1cnc(C(=O)Nc2c(C)nc3ccc(-c4ccccc4Cl)nn23)s1] |
| 355 | 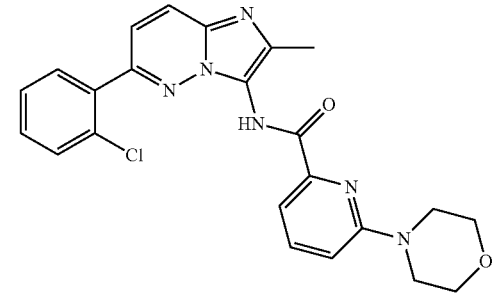 [SMILES: Cc1nc2ccc(-c3ccccc3Cl)nn2c1NC(=O)c1cccc(N2CCOCC2)n1] |
| 356 | 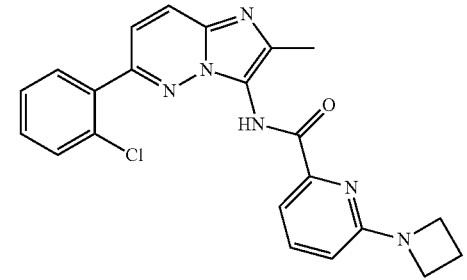 [SMILES: Cc1nc2ccc(-c3ccccc3Cl)nn2c1NC(=O)c1cccc(N2CCC2)n1] |
| 357 | 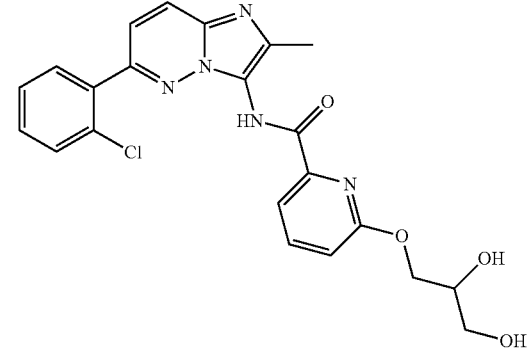 [SMILES: Cc1nc2ccc(-c3ccccc3Cl)nn2c1NC(=O)c1cccc(OCC(O)CO)n1] |
| 358 | 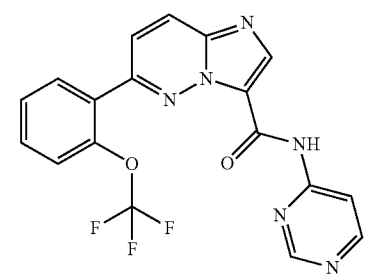 [SMILES: O=C(Nc1ccncn1)c1cnc2ccc(-c3ccccc3OC(F)(F)F)nn12] |

| Compound No | Structure |
|---|---|
| 359 | 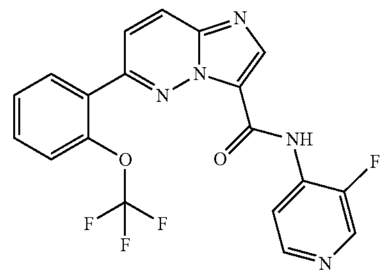 [SMILES: O=C(Nc1ccncc1F)c1cnc2ccc(-c3ccccc3OC(F)(F)F)nn12] |
| 360 | 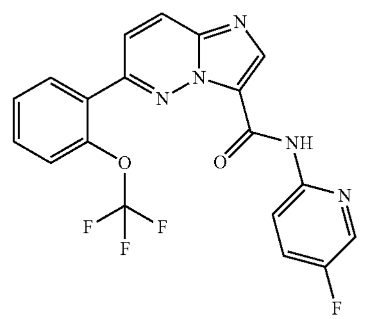 [SMILES: O=C(Nc1ccc(F)cn1)c1cnc2ccc(-c3ccccc3OC(F)(F)F)nn12] |
| 361 | 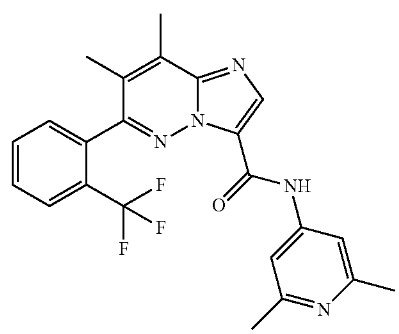 [SMILES: Cc1cc(NC(=O)c2cnc3c(C)c(C)c(-c4ccccc4C(F)(F)F)nn23)cc(C)n1] |
| 362 | 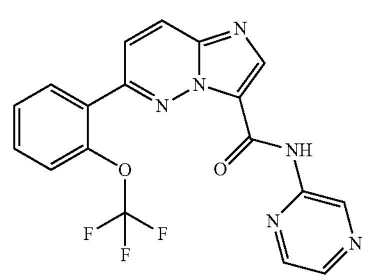 [SMILES: O=C(Nc1cnccn1)c1cnc2ccc(-c3ccccc3OC(F)(F)F)nn12] |
| 363 | 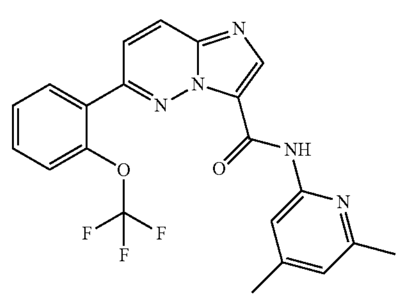 [SMILES: Cc1cc(C)nc(NC(=O)c2cnc3ccc(-c4ccccc4OC(F)(F)F)nn23)c1] |

| Compound No | Structure |
|---|---|
| 364 | 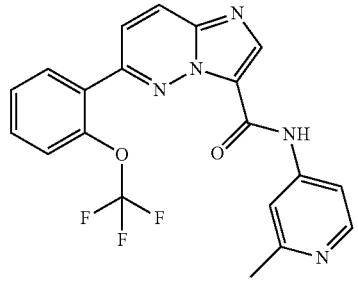 [SMILES: Cc1cc(NC(=O)c2cnc3ccc(-c4ccccc4OC(F)(F)F)nn23)ccn1] |
| 365 | 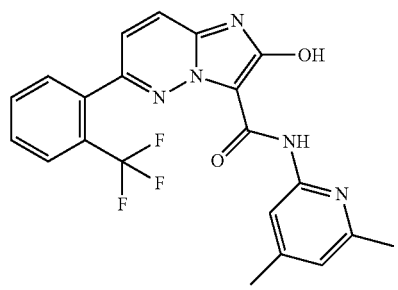 [SMILES: Cc1cc(C)nc(NC(=O)c2c(O)nc3ccc(-c4ccccc4C(F)(F)F)nn23)c1] |
| 366 | 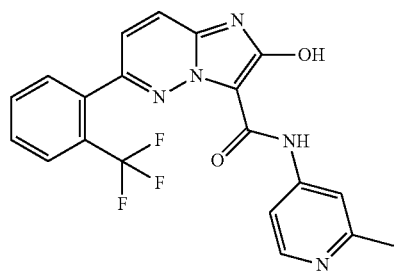 [SMILES: Cc1cc(NC(=O)c2c(O)nc3ccc(-c4ccccc4C(F)(F)F)nn23)ccn1] |
| 367 | 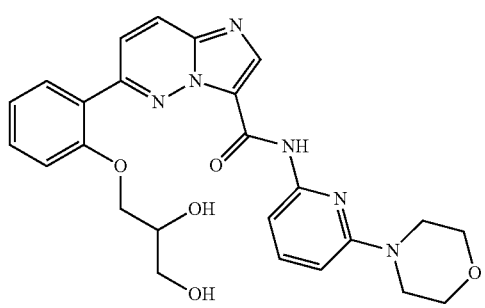 [SMILES: O=C(Nc1cccc(N2CCOCC2)n1)c1cnc2ccc(-c3ccccc3OCC(O)CO)nn12] |
| 368 | 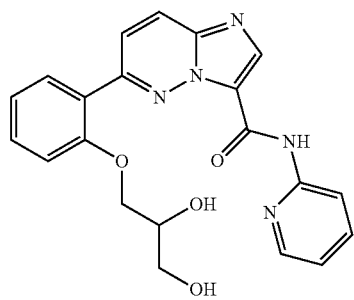 [SMILES: O=C(Nc1ccccn1)c1cnc2ccc(-c3ccccc3OCC(O)CO)nn12] |

-continued

| Compound No | Structure |
|---|---|
| 369 | 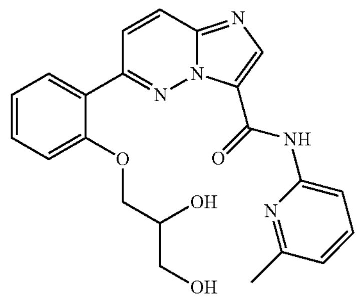 [SMILES: Cc1cccc(NC(=O)c2cnc3ccc(-c4ccccc4OCC(O)CO)nn23)n1] |
| 370 | 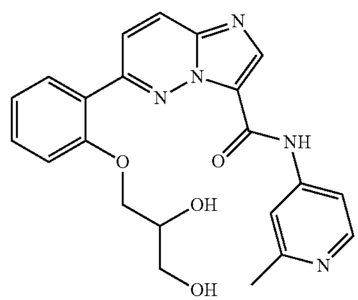 [SMILES: Cc1cc(NC(=O)c2cnc3ccc(-c4ccccc4OCC(O)CO)nn23)ccn1] |
| 371 | 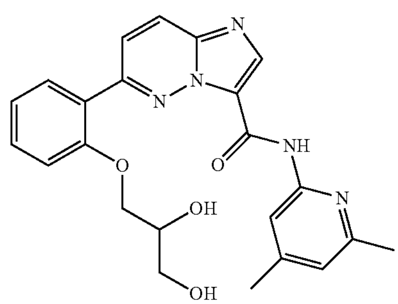 [SMILES: Cc1cc(C)nc(NC(=O)c2cnc3ccc(-c4ccccc4OCC(O)CO)nn23)c1] |
| 372 | 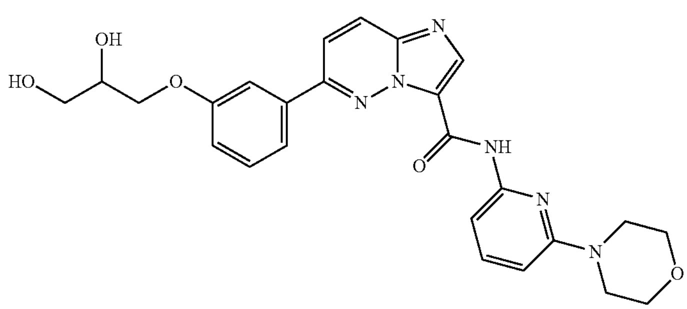 [SMILES: O=C(Nc1cccc(N2CCOCC2)n1)c1cnc2ccc(-c3cccc(OCC(O)CO)c3)nn12] |
| 373 | 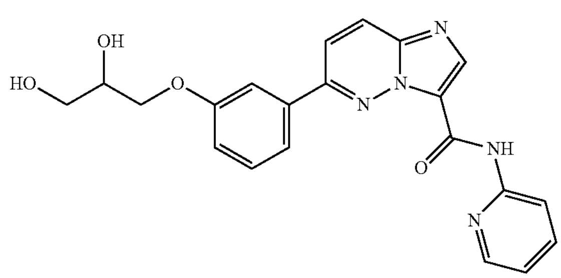 [SMILES: O=C(Nc1ccccn1)c1cnc2ccc(-c3cccc(OCC(O)CO)c3)nn12] |

-continued
| Compound No | Structure |
|---|---|
| 374 | 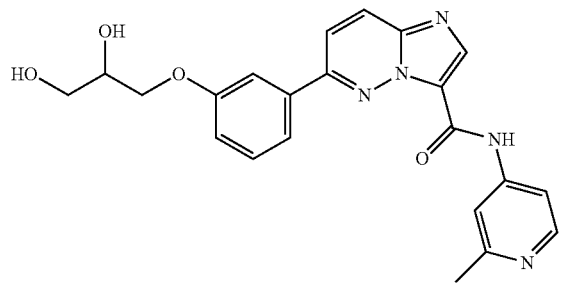 |
| 375 | 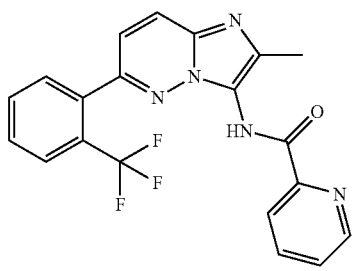 |
| 376 | 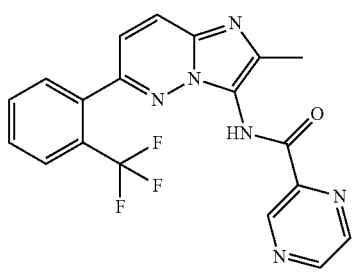 |
| 377 | 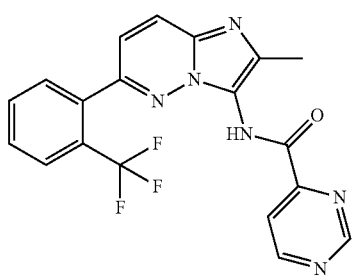 [SMILES: Cc1nc2ccc(-c3ccccc3C(F)(F)F)nn2c1NC(=O)c1ccncn1] |
| 378 | 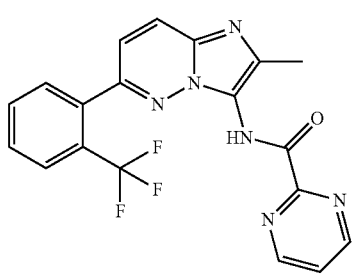 [SMILES: Cc1nc2ccc(-c3ccccc3C(F)(F)F)nn2c1NC(=O)c1ncccn1] |

| Compound No | Structure |
|---|---|
| 379 | 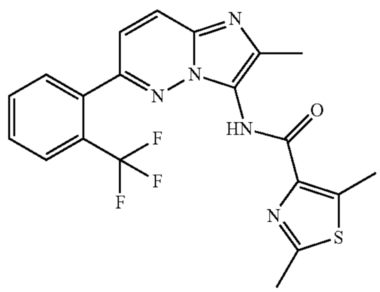 [SMILES: Cc1nc(C(=O)Nc2c(C)nc3ccc(-c4ccccc4C(F)(F)F)nn23)c(C)s1] |
| 380 | 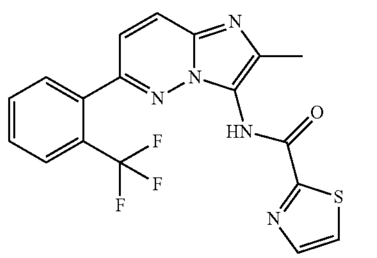 [SMILES: Cc1nc2ccc(-c3ccccc3C(F)(F)F)nn2c1NC(=O)c1nccs1] |
| 381 | 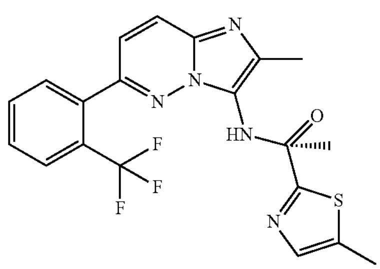 |
| 382 | 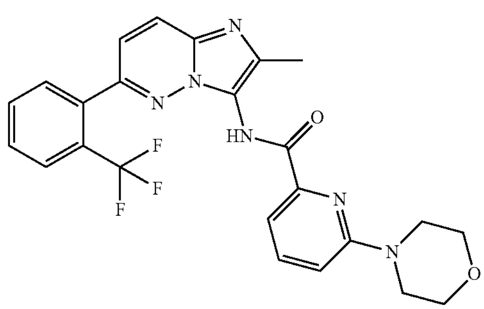 [SMILES: Cc1nc2ccc(-c3ccccc3C(F)(F)F)nn2c1NC(=O)c1cccc(N2CCOCC2)n1] |
| 383 | 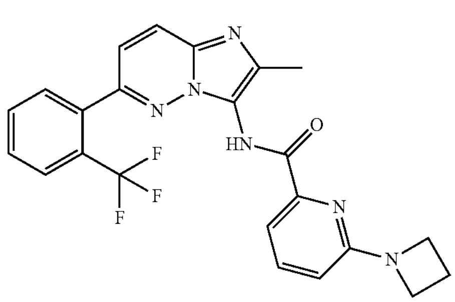 [SMILES: Cc1nc2ccc(-c3ccccc3C(F)(F)F)nn2c1NC(=O)c1cccc(N2CCC2)n1] |

-continued
| Compound No | Structure |
|---|---|
| 384 | 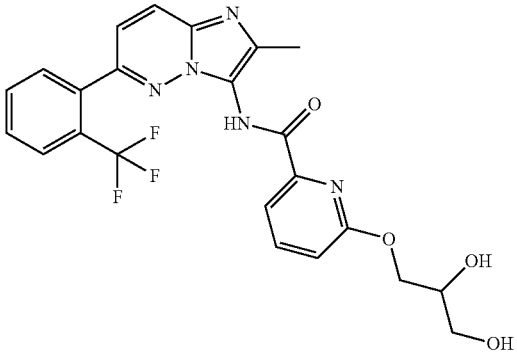 [SMILES: Cc1nc2ccc(-c3ccccc3C(F)(F)F)nn2c1NC(=O)c1cccc(OCC(O)CO)n1] |
| 385 | 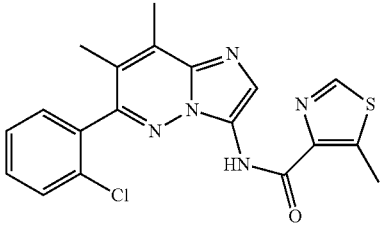 [SMILES: Cc1scnc1C(=O)Nc1cnc2c(C)c(C)c(-c3ccccc3Cl)nn12] |
| 386 | 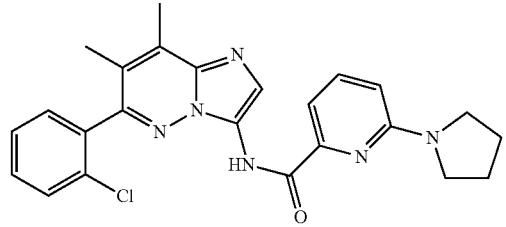 [SMILES: Cc1c(-c2ccccc2Cl)nn2c(NC(=O)c3cccc(N4CCCC4)n3)cnc2c1C] |
| 387 | 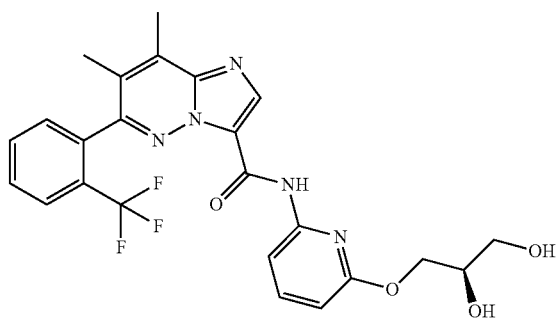 [SMILES: Cc1c(-c2ccccc2C(F)(F)F)nn2c(C(=O)Nc3cccc(OC[C@H](O)CO)n3)cnc2c1C] |
| 388 | 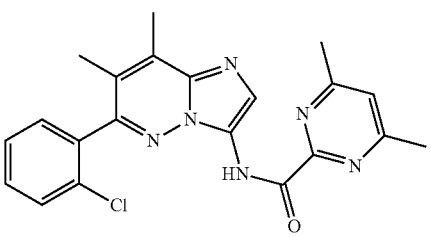 [SMILES: Cc1cc(C)nc(C(=O)Nc2cnc3c(C)c(C)c(-c4ccccc4Cl)nn23)n1] |

-continued

| Compound No | Structure |
|---|---|
| 389 | 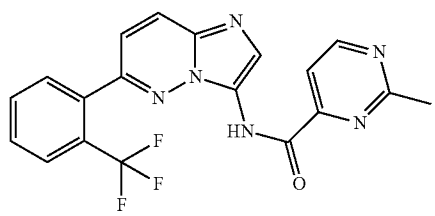 [SMILES: Cc1nccc(C(=O)Nc2cnc3ccc(-c4ccccc4C(F)(F)F)nn23)n1] |
| 390 | 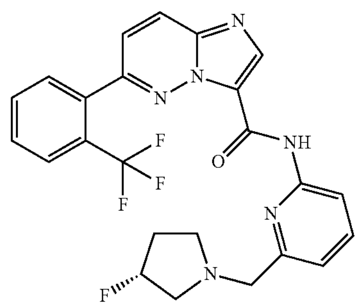 [SMILES: O=C(Nc1cccc(CN2CC[C@@H](F)C2)n1)c1cnc2ccc(-c3ccccc3C(F)(F)F)nn12] |
| 391 | 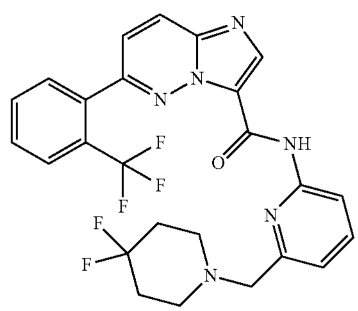 [SMILES: O=C(Nc1cccc(CN2CCC(F)(F)CC2)n1)c1cnc2ccc(-c3ccccc3C(F)(F)F)nn12] |
| 392 | 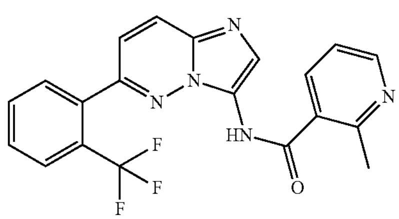 [SMILES: Cc1ncccc1C(=O)Nc1cnc2ccc(-c3ccccc3C(F)(F)F)nn12] |
| 393 | 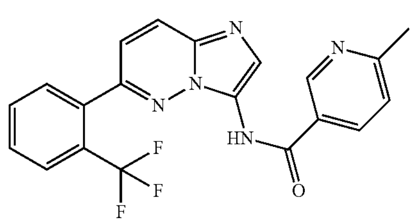 [SMILES: Cc1ccc(C(=O)Nc2cnc3ccc(-c4ccccc4C(F)(F)F)nn23)cn1] |
| 394 | 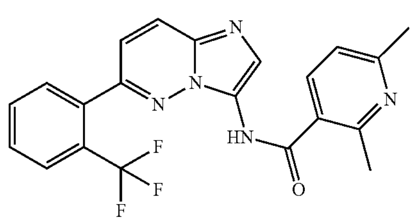 [SMILES: Cc1ccc(C(=O)Nc2cnc3ccc(-c4ccccc4C(F)(F)F)nn23)c(C)n1] |

| Compound No | Structure |
|---|---|
| 395 | 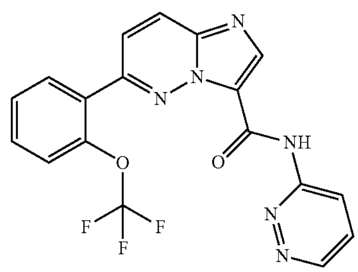 [SMILES: O=C(Nc1cccnn1)c1cnc2ccc(-c3ccccc3OC(F)(F)F)nn12] |
| 396 | 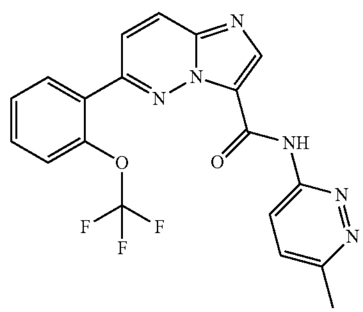 [SMILES: Cc1ccc(NC(=O)c2cnc3ccc(-c4ccccc4OC(F)(F)F)nn23)nn1] |
| 397 | 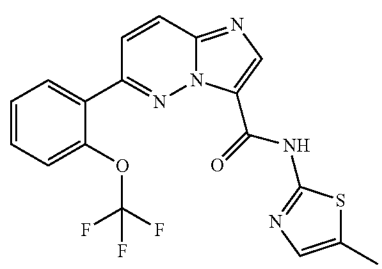 [SMILES: Cc1cnc(NC(=O)c2cnc3ccc(-c4ccccc4OC(F)(F)F)nn23)s1] |
| 398 | 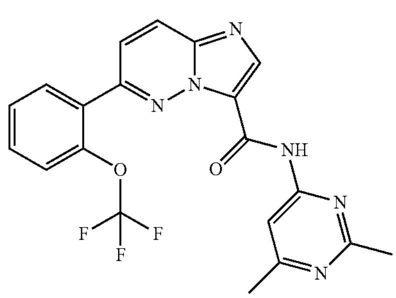 [SMILES: Cc1cc(NC(=O)c2cnc3ccc(-c4ccccc4OC(F)(F)F)nn23)nc(C)n1] |
| 399 | 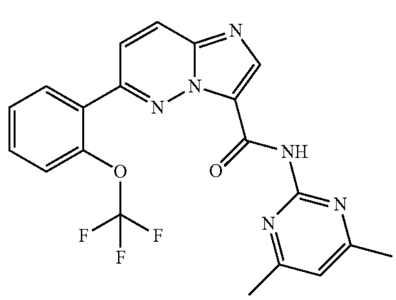 [SMILES: Cc1cc(C)nc(NC(=O)c2cnc3ccc(-c4ccccc4OC(F)(F)F)nn23)n1] |

-continued

| Compound No | Structure |
|---|---|
| 400 | 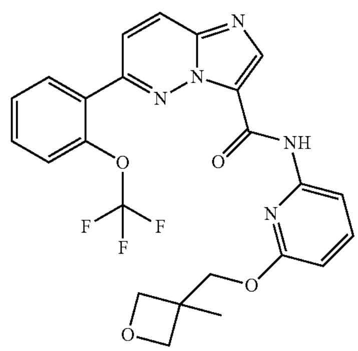 [SMILES: CC1(COc2cccc(NC(=O)c3cnc4ccc(-c5ccccc5OC(F)(F)F)nn34)n2)COC1] |
| 401 | 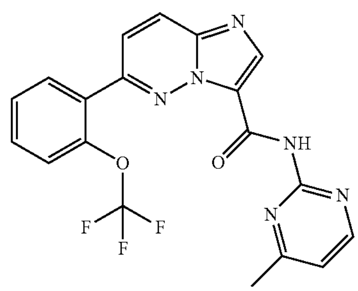 [SMILES: Cc1ccnc(NC(=O)c2cnc3ccc(-c4ccccc4OC(F)(F)F)nn23)n1] |
| 402 | 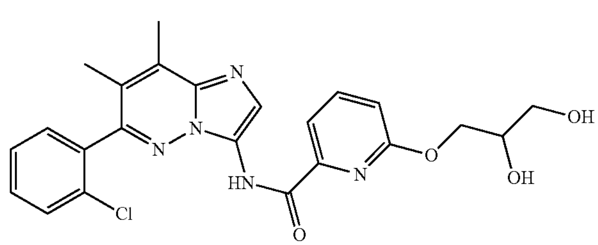 [SMILES: Cc1c(-c2ccccc2Cl)nn2c(NC(=O)c3cccc(OCC(O)CO)n3)cnc2c1C] |
| 403 | 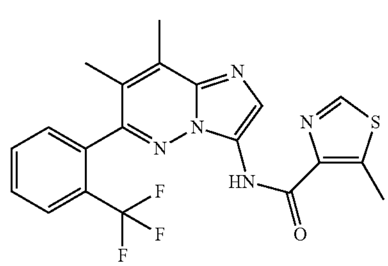 [SMILES: Cc1scnc1C(=O)Nc1cnc2c(C)c(C)c(-c3ccccc3C(F)(F)F)nn12] |
| 404 | 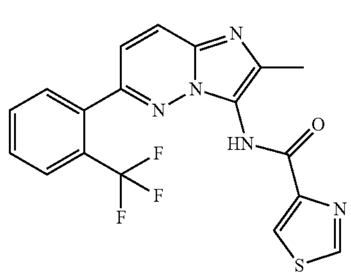 [SMILES: Cc1nc2ccc(-c3ccccc3C(F)(F)F)nn2c1NC(=O)c1cscn1] |

-continued
| Compound No | Structure |
|---|---|
| 405 | 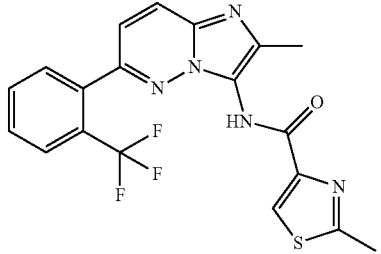 [SMILES: Cc1nc(C(=O)Nc2c(C)nc3ccc(-c4ccccc4C(F)(F)F)nn23)cs1] |
| 406 | 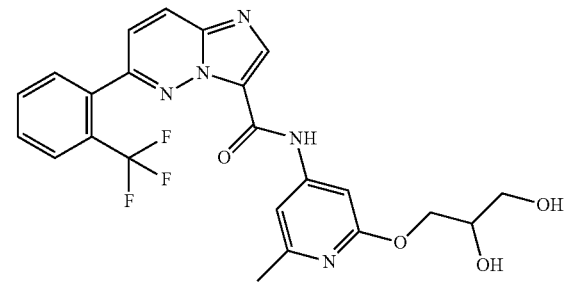 [SMILES: Cc1cc(NC(=O)c2cnc3ccc(-c4ccccc4C(F)(F)F)nn23)cc(OCC(O)CO)n1] |
| 407 | 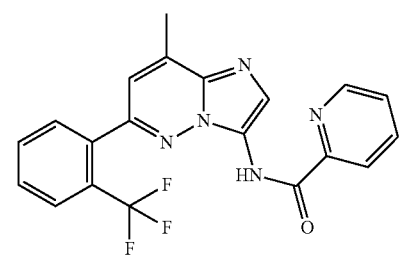 [SMILES: Cc1cc(-c2ccccc2C(F)(F)F)nn2c(NC(=O)c3ccccn3)cnc12] |
| 408 | 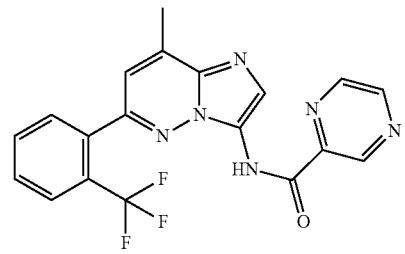 [SMILES: Cc1cc(-c2ccccc2C(F)(F)F)nn2c(NC(=O)c3cnccn3)cnc12] |
| 409 | 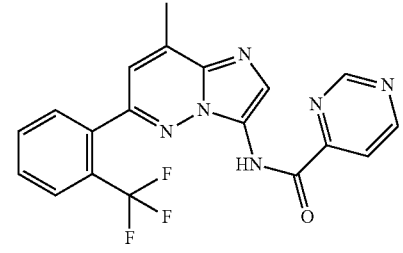 [SMILES: Cc1cc(-c2ccccc2C(F)(F)F)nn2c(NC(=O)c3ccncn3)cnc12] |
| 410 | 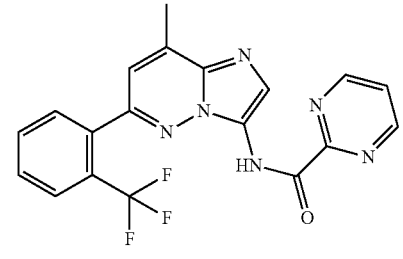 [SMILES: Cc1cc(-c2ccccc2C(F)(F)F)nn2c(NC(=O)c3ncccn3)cnc12] |

| Compound No | Structure |
|---|---|
| 411 | 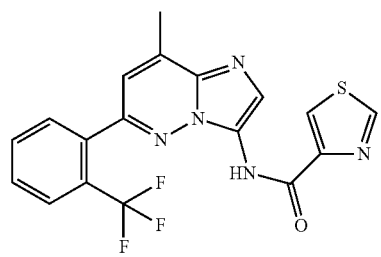 [SMILES: Cc1cc(-c2ccccc2C(F)(F)F)nn2c(NC(=O)c3cscn3)cnc12] |
| 412 | 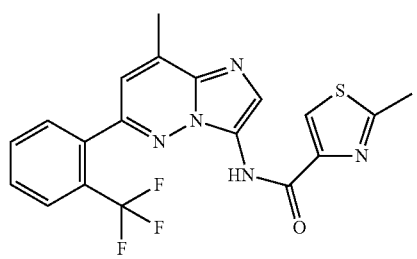 [SMILES: Cc1nc(C(=O)Nc2cnc3c(C)cc(-c4ccccc4C(F)(F)F)nn23)cs1] |
| 413 | 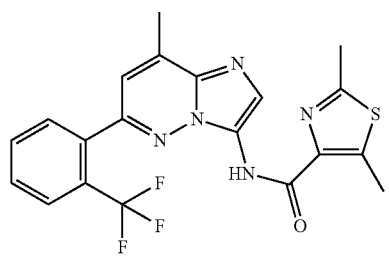 [SMILES: Cc1nc(C(=O)Nc2cnc3c(C)cc(-c4ccccc4C(F)(F)F)nn23)c(C)s1] |
| 414 | 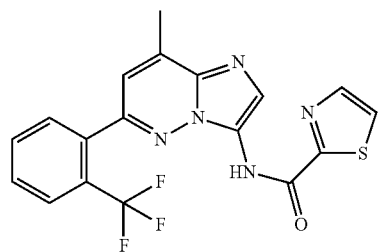 [SMILES: Cc1cc(-c2ccccc2C(F)(F)F)nn2c(NC(=O)c3nccs3)cnc12] |
| 415 | 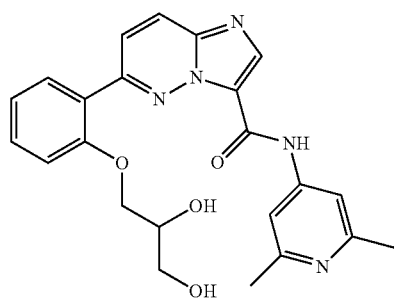 [SMILES: Cc1cc(NC(=O)c2cnc3ccc(-c4ccccc4OCC(O)CO)nn23)cc(C)n1] |

| Compound No | Structure |
|---|---|
| 416 | 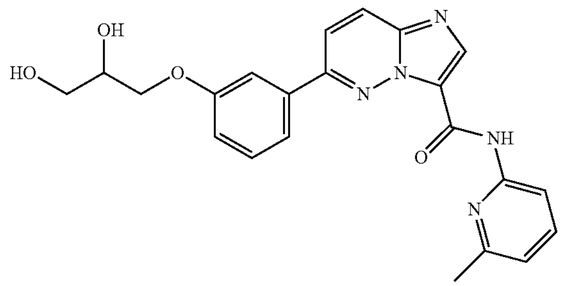 [SMILES: Cc1cccc(NC(=O)c2cnc3ccc(-c4cccc(OCC(O)CO)c4)nn23)n1] |
| 417 | 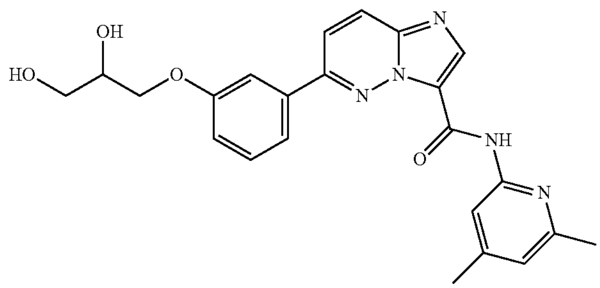 [SMILES: Cc1cc(C)nc(NC(=O)c2cnc3ccc(-c4cccc(OCC(O)CO)c4)nn23)c1] |
| 418 | 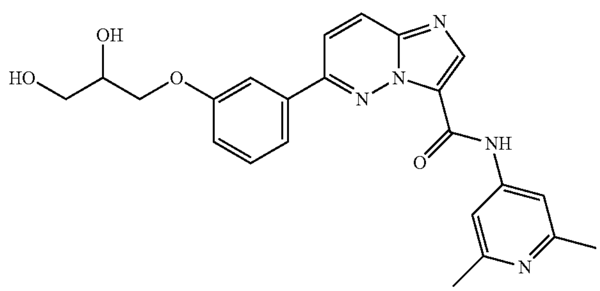 [SMILES: Cc1cc(NC(=O)c2cnc3ccc(-c4cccc(OCC(O)CO)c4)nn23)cc(C)n1] |
| 419 | 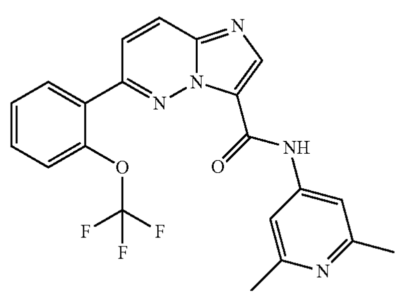 [SMILES: Cc1cc(NC(=O)c2cnc3ccc(-c4ccccc4OC(F)(F)F)nn23)cc(C)n1] |
| 420 | 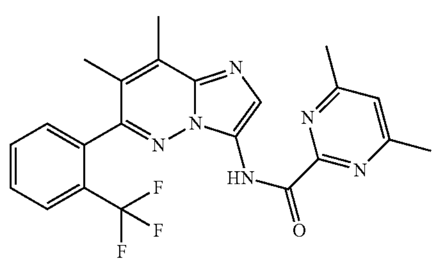 [SMILES: Cc1cc(C)nc(C(=O)Nc2cnc3c(C)c(C)c(-c4ccccc4C(F)(F)F)nn23)n1] |

-continued
| Compound No | Structure |
|---|---|
| 421 | 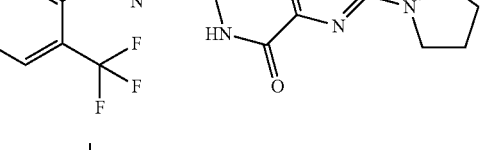 |
| 422 | 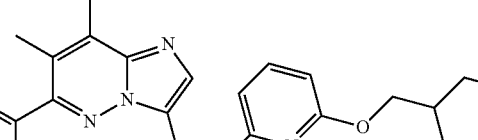 |
| 423 | 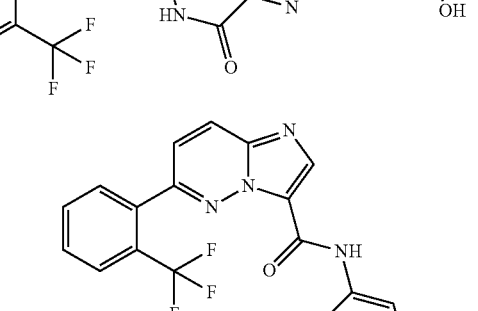 |
| 424 | 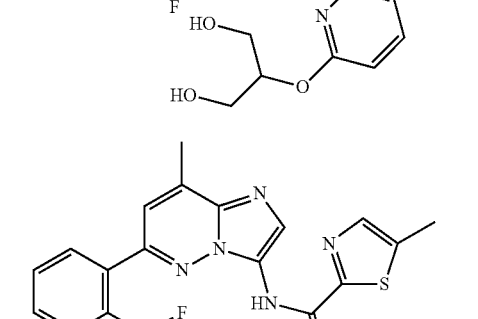 |
| 425 | 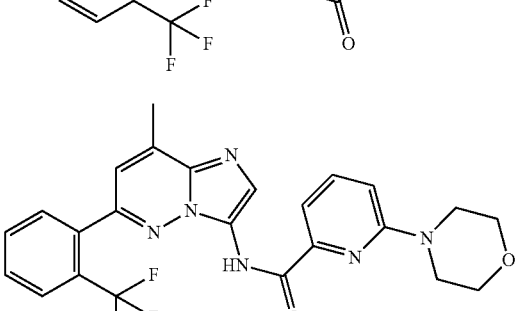 |
| 426 | 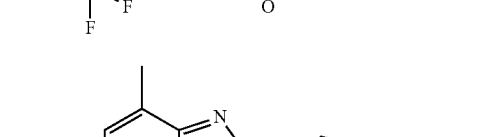 |

| Compound No | Structure |
|---|---|
| 427 | 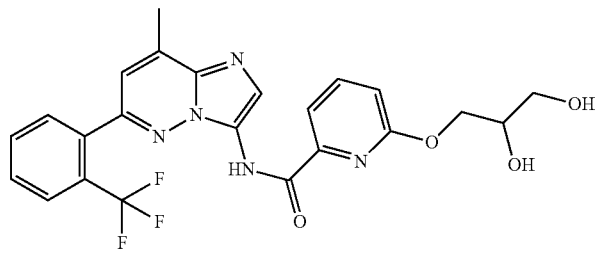 [SMILES: Cc1cc(-c2ccccc2C(F)(F)F)nn2c(NC(=O)c3cccc(OCC(O)CO)n3)cnc12] |
| 428 | 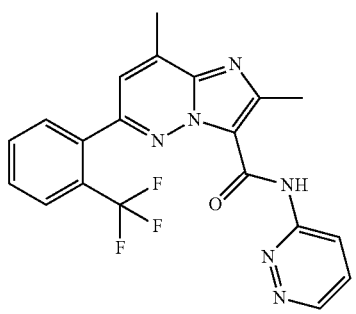 [SMILES: Cc1nc2c(C)cc(-c3ccccc3C(F)(F)F)nn2c1C(=O)Nc1cccnn1] |
| 429 | 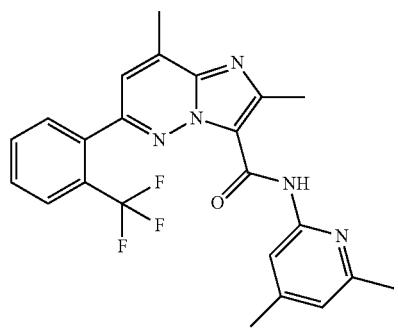 [SMILES: Cc1cc(C)nc(NC(=O)c2c(C)nc3c(C)cc(-c4ccccc4C(F)(F)F)nn23)c1] |
| 430 | 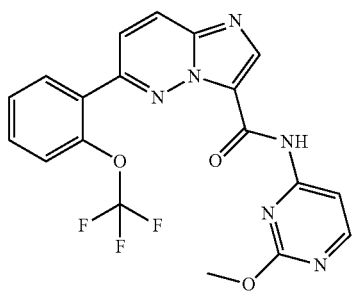 [SMILES: COc1nccc(NC(=O)c2cnc3ccc(-c4ccccc4OC(F)(F)F)nn23)n1] |
| 431 | 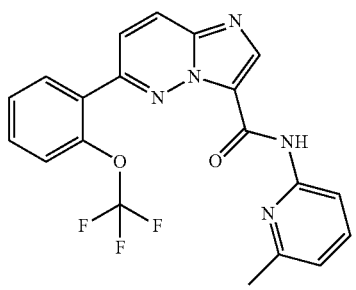 [SMILES: Cc1cccc(NC(=O)c2cnc3ccc(-c4ccccc4OC(F)(F)F)nn23)n1] |

| Compound No | Structure |
|---|---|
| 432 | (structure) |
| 433 | (structure) |
| 434 | (structure) |
| 435 | (structure) |
| 436 | (structure) |
| 437 | (structure) |

| Compound No | Structure |
|---|---|
| 438 | 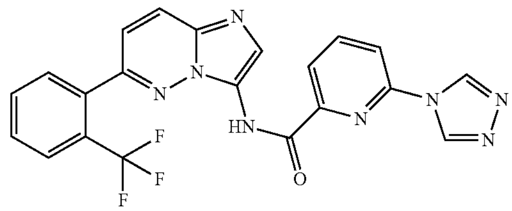 [SMILES: O=C(Nc1cnc2ccc(-c3ccccc3C(F)(F)F)nn12)c1cccc(-n2cnnc2)n1] |
| 439 | 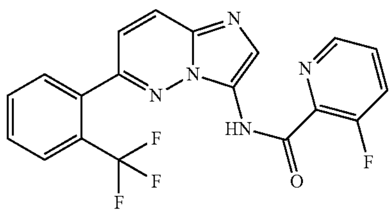 |
| 440 | 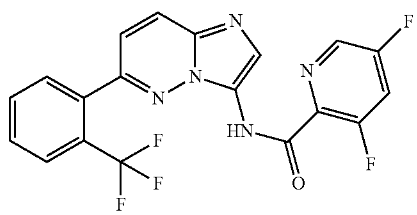 [SMILES: O=C(Nc1cnc2ccc(-c3ccccc3C(F)(F)F)nn12)c1ncc(F)cc1F] |
| 441 | 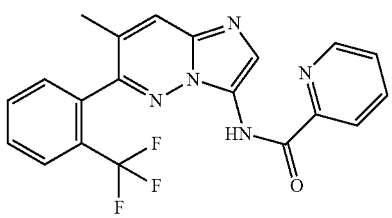 [SMILES: Cc1cc2ncc(NC(=O)c3ccccn3)n2nc1-c1ccccc1C(F)(F)F] |
| 442 | 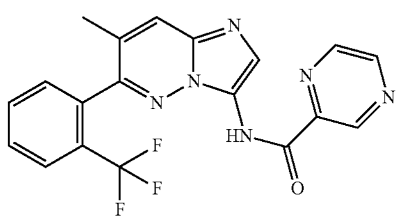 [SMILES: Cc1cc2ncc(NC(=O)c3cnccn3)n2nc1-c1ccccc1C(F)(F)F] |
| 443 | 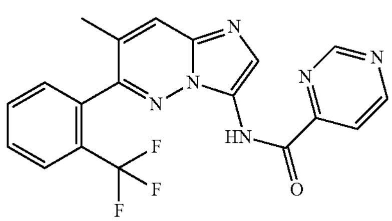 [SMILES: Cc1cc2ncc(NC(=O)c3ccncn3)n2nc1-c1ccccc1C(F)(F)F] |
| 444 | 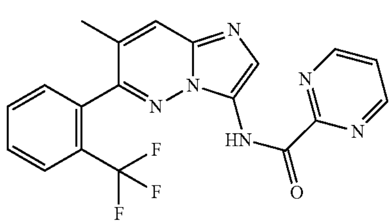 [SMILES: Cc1cc2ncc(NC(=O)c3ncccn3)n2nc1-c1ccccc1C(F)(F)F] |

-continued

| Compound No | Structure |
|---|---|
| 445 | 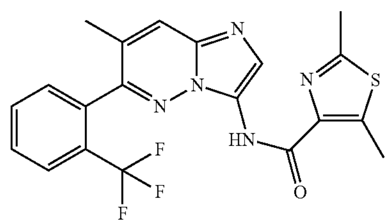 [SMILES: Cc1nc(C(=O)Nc2cnc3cc(C)c(-c4ccccc4C(F)(F)F)nn23)c(C)s1] |
| 446 | 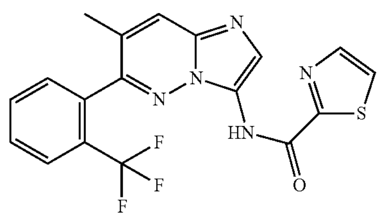 [SMILES: Cc1cc2ncc(NC(=O)c3nccs3)n2nc1-c1ccccc1C(F)(F)F] |
| 447 | 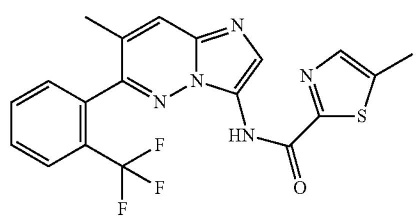 [SMILES: Cc1cnc(C(=O)Nc2cnc3cc(C)c(-c4ccccc4C(F)(F)F)nn23)s1] |
| 448 | 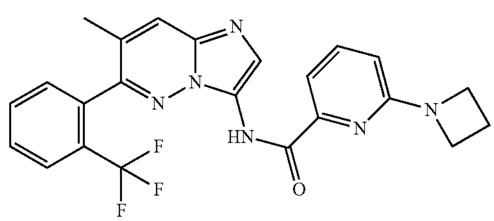 [SMILES: Cc1cc2ncc(NC(=O)c3cccc(N4CCC4)n3)n2nc1-c1ccccc1C(F)(F)F] |
| 449 | 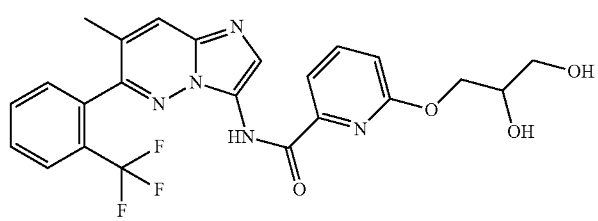 [SMILES: Cc1cc2ncc(NC(=O)c3cccc(OCC(O)CO)n3)n2nc1-c1ccccc1C(F)(F)F] |
| 457 | 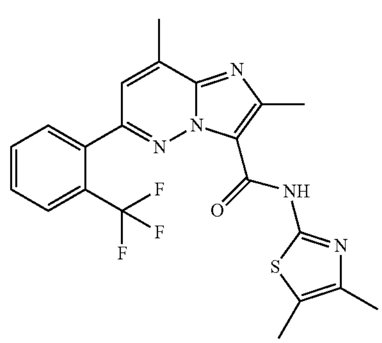 [SMILES: Cc1nc(NC(=O)c2c(C)nc3c(C)cc(-c4ccccc4C(F)(F)F)nn23)sc1C] |

-continued
| Compound No | Structure |
|---|---|
| 458 | 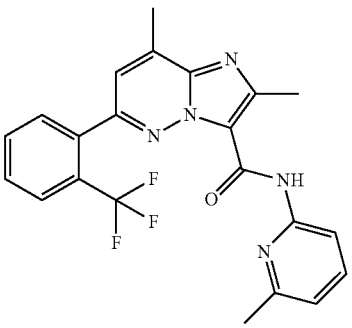 [SMILES: Cc1cccc(NC(=O)c2c(C)nc3c(C)cc(-c4ccccc4C(F)(F)F)nn23)n1] |
| 459 | 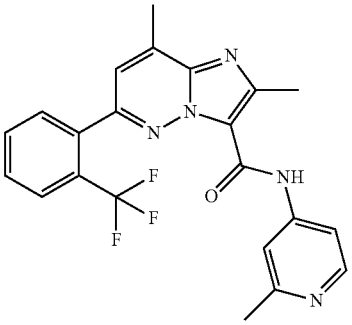 [SMILES: Cc1cc(NC(=O)c2c(C)nc3c(C)cc(-c4ccccc4C(F)(F)F)nn23)ccn1] |
| 460 | 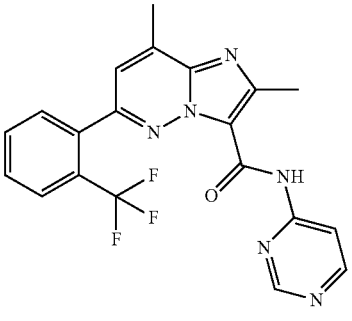 [SMILES: Cc1nc2c(C)cc(-c3ccccc3C(F)(F)F)nn2c1C(=O)Nc1ccncn1] |
| 461 | 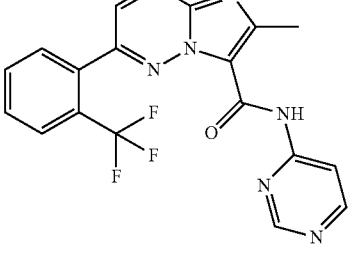 |
| 462 | 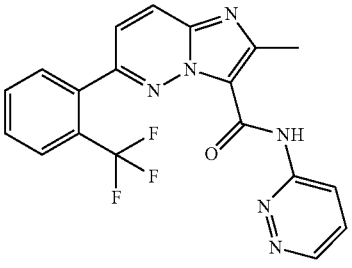 [SMILES: Cc1nc2ccc(-c3ccccc3C(F)(F)F)nn2c1C(=O)Nc1cccnn1] |

-continued
| Compound No | Structure |
|---|---|
| 463 | 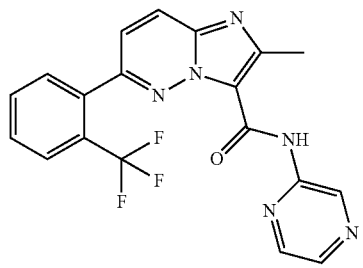 [SMILES: Cc1nc2ccc(-c3ccccc3C(F)(F)F)nn2c1C(=O)Nc1cnccn1] |
| 464 | 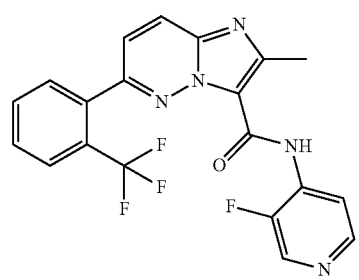 [SMILES: Cc1nc2ccc(-c3ccccc3C(F)(F)F)nn2c1C(=O)Nc1ccncc1F] |
| 465 | 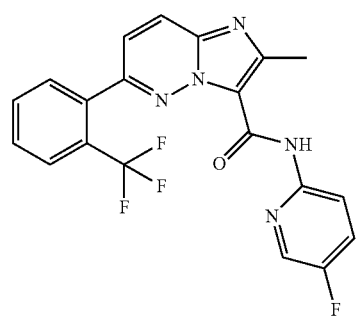 [SMILES: Cc1nc2ccc(-c3ccccc3C(F)(F)F)nn2c1C(=O)Nc1ccc(F)cn1] |
| 466 | 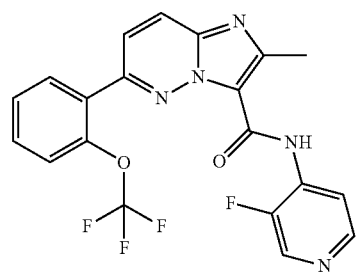 [SMILES: Cc1nc2ccc(-c3ccccc3OC(F)(F)F)nn2c1C(=O)Nc1ccncc1F] |
| 467 | 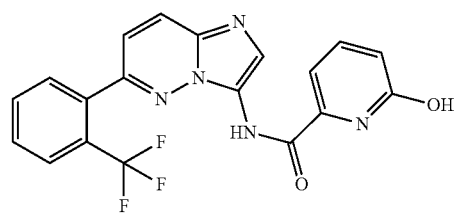 [SMILES: O=C(Nc1cnc2ccc(-c3ccccc3C(F)(F)F)nn12)c1cccc(O)n1] |

| Compound No | Structure |
|---|---|
| 468 | 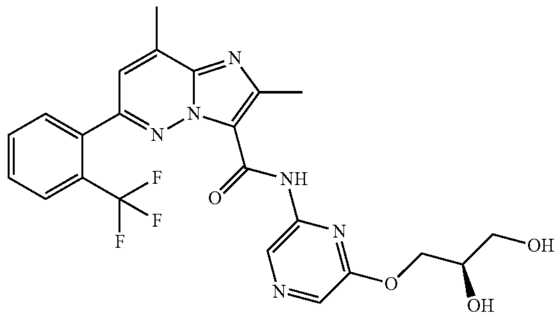 [SMILES: Cc1nc2c(C)cc(-c3ccccc3C(F)(F)F)nn2c1C(=O)Nc1cncc(OC[C@H](O)CO)n1] |
| 469 | 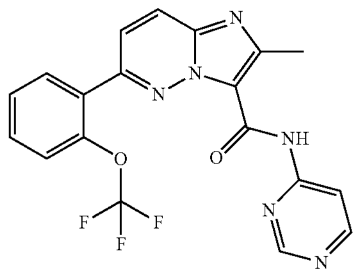 [SMILES: Cc1nc2ccc(-c3ccccc3OC(F)(F)F)nn2c1C(=O)Nc1ccncn1] |
| 470 | 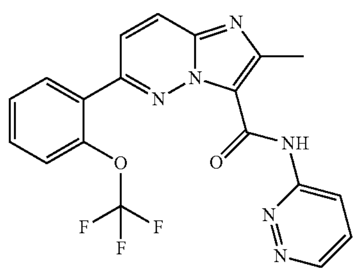 [SMILES: Cc1nc2ccc(-c3ccccc3OC(F)(F)F)nn2c1C(=O)Nc1cccnn1] |
| 471 | 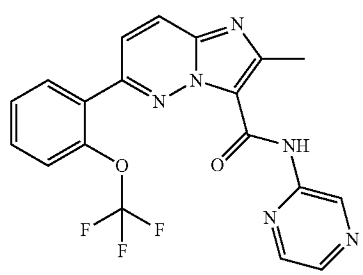 [SMILES: Cc1nc2ccc(-c3ccccc3OC(F)(F)F)nn2c1C(=O)Nc1cnccn1] |
| 472 | 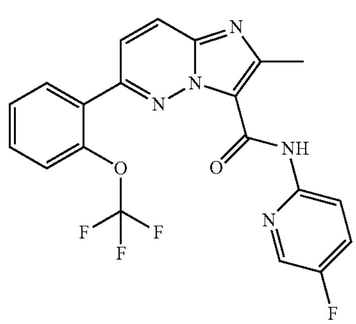 [SMILES: Cc1nc2ccc(-c3ccccc3OC(F)(F)F)nn2c1C(=O)Nc1ccc(F)cn1] |

| Compound No | Structure |
|---|---|
| 473 | 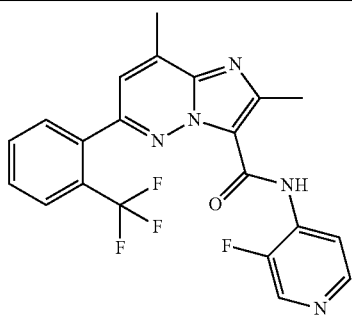 |
| 474 | 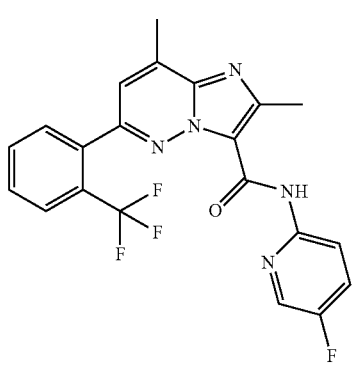 [SMILES: Cc1nc2c(C)cc(-c3ccccc3C(F)(F)F)nn2c1C(=O)Nc1ccc(F)cn1] |
| 475 | 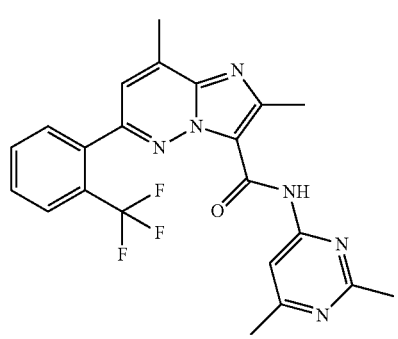 |
| 476 | 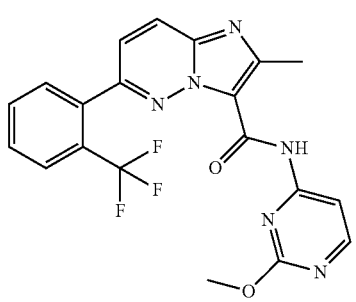 [SMILES: COc1nccc(NC(=O)c2c(C)nc3ccc(-c4ccccc4C(F)(F)F)nn23)n1] |
| 477 | 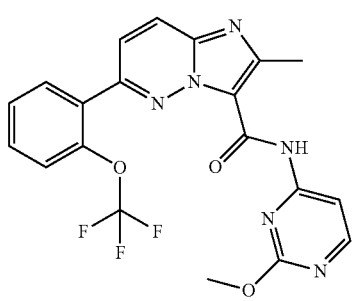 [SMILES: COc1nccc(NC(=O)c2c(C)nc3ccc(-c4ccccc4OC(F)(F)F)nn23)n1] |

| Compound No | Structure |
|---|---|
| 478 | 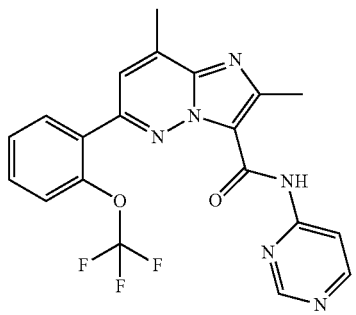 [SMILES: Cc1nc2c(C)cc(-c3ccccc3OC(F)(F)F)nn2c1C(=O)Nc1ccncn1] |
| 479 | 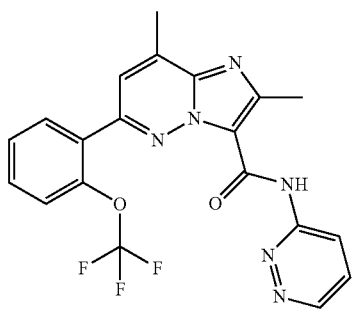 [SMILES: Cc1nc2c(C)cc(-c3ccccc3OC(F)(F)F)nn2c1C(=O)Nc1cccnn1] |
| 480 | 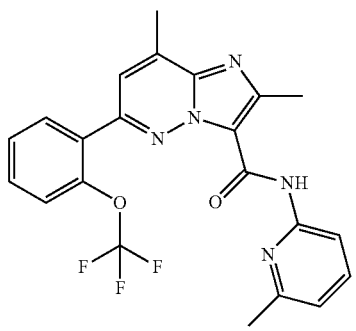 [SMILES: Cc1cccc(NC(=O)c2c(C)nc3c(C)cc(-c4ccccc4OC(F)(F)F)nn23)n1] |
| 481 | 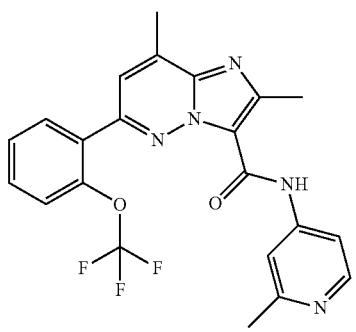 [SMILES: Cc1cc(NC(=O)c2c(C)nc3c(C)cc(-c4ccccc4OC(F)(F)F)nn23)ccn1] |

| Compound No | Structure |
|---|---|
| 482 | 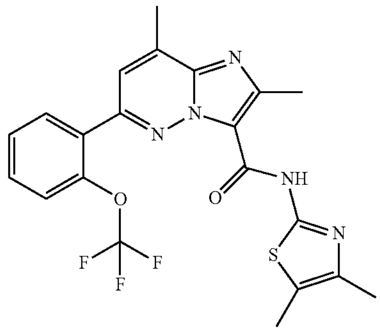 [SMILES: Cc1nc(NC(=O)c2c(C)nc3c(C)cc(-c4ccccc4OC(F)(F)F)nn23)sc1C] |
| 493 | 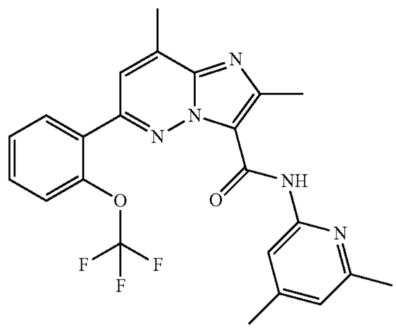 [SMILES: Cc1cc(C)nc(NC(=O)c2c(C)nc3c(C)cc(-c4ccccc4OC(F)(F)F)nn23)c1] |
| 494 | 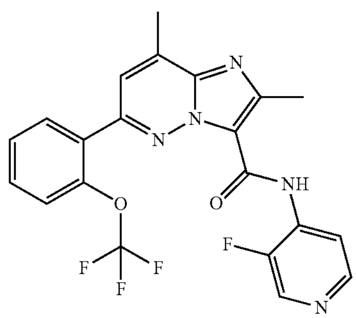 [SMILES: Cc1nc2c(C)cc(-c3ccccc3OC(F)(F)F)nn2c1C(=O)Nc1ccncc1F] |
| 495 | 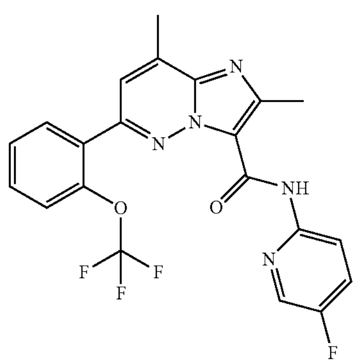 [SMILES: Cc1nc2c(C)cc(-c3ccccc3OC(F)(F)F)nn2c1C(=O)Nc1ccc(F)cn1] |
| 496 | 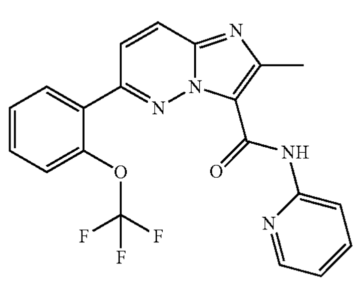 [SMILES: Cc1nc2ccc(-c3ccccc3OC(F)(F)F)nn2c1C(=O)Nc1ccccn1] |

-continued
| Compound No | Structure |
|---|---|
| 497 | 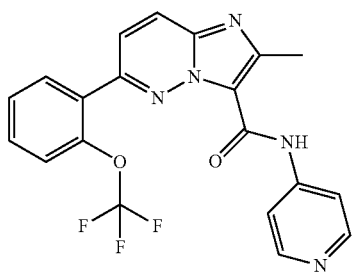 |
| 498 | 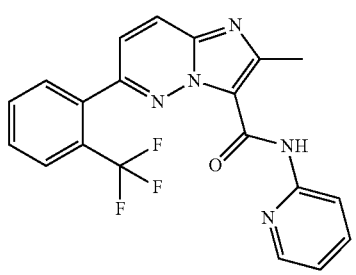 [SMILES: Cc1nc2ccc(-c3ccccc3C(F)(F)F)nn2c1C(=O)Nc1ccccn1] |
| 499 | 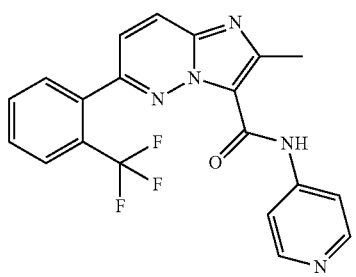 |
| 514 | 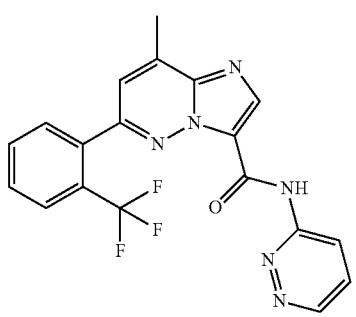 [SMILES: Cc1cc(-c2ccccc2C(F)(F)F)nn2c(C(=O)Nc3cccnn3)cnc12] |
| 515 | 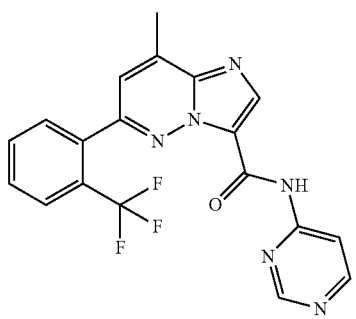 [SMILES: Cc1cc(-c2ccccc2C(F)(F)F)nn2c(C(=O)Nc3ccncn3)cnc12] |

| Compound No | Structure |
|---|---|
| 516 | 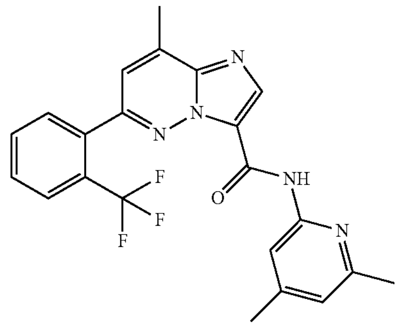 [SMILES: Cc1cc(C)nc(NC(=O)c2cnc3c(C)cc(-c4ccccc4C(F)(F)F)nn23)c1] |
| 528 | 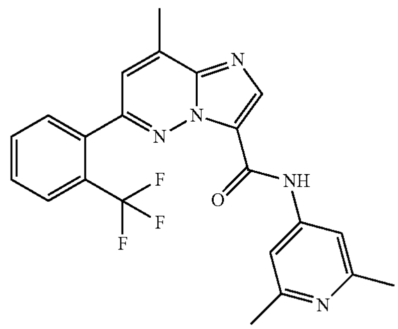 [SMILES: Cc1cc(NC(=O)c2cnc3c(C)cc(-c4ccccc4C(F)(F)F)nn23)cc(C)n1] |
| 537 | 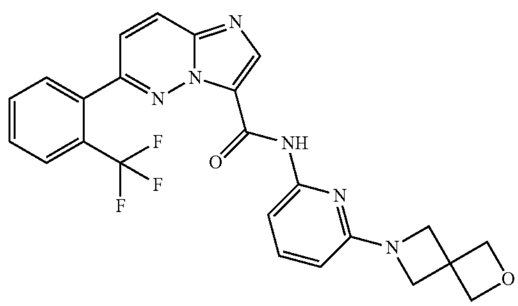 [SMILES: O=C(Nc1cccc(N2CC3(COC3)C2)n1)c1cnc2ccc(-c3ccccc3C(F)(F)F)nn12] |
| 538 | 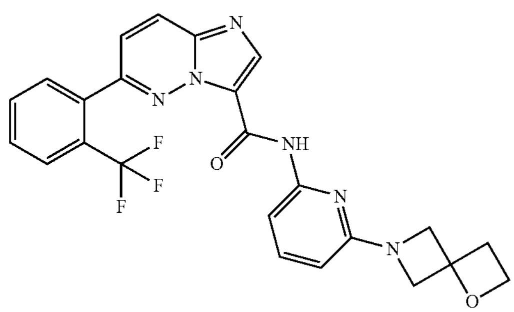 [SMILES: O=C(Nc1cccc(N2CC3(CCO3)C2)n1)c1cnc2ccc(-c3ccccc3C(F)(F)F)nn12] |
| 539 | 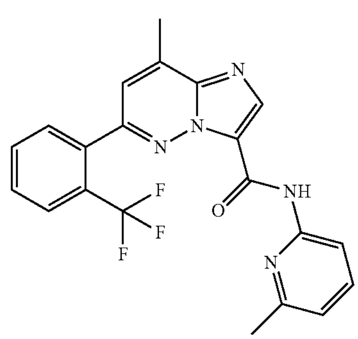 [SMILES: Cc1cccc(NC(=O)c2cnc3c(C)cc(-c4ccccc4C(F)(F)F)nn23)n1] |

| Compound No | Structure |
|---|---|
| 540 | 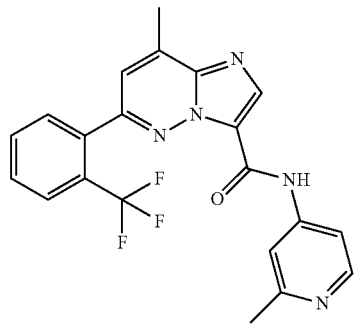 [SMILES: Cc1cc(NC(=O)c2cnc3c(C)cc(-c4ccccc4C(F)(F)F)nn23)ccn1] |
| 541 | 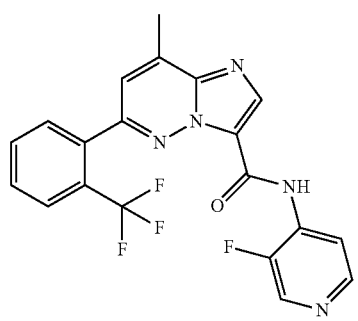 [SMILES: Cc1cc(-c2ccccc2C(F)(F)F)nn2c(C(=O)Nc3ccncc3F)cnc12] |
| 542 | 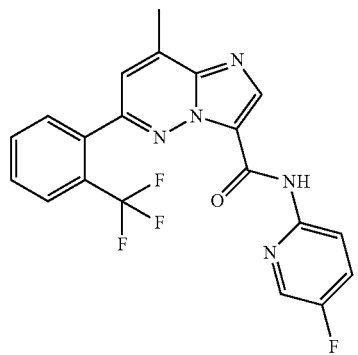 [SMILES: Cc1cc(-c2ccccc2C(F)(F)F)nn2c(C(=O)Nc3ccc(F)cn3)cnc12] |
| 543 | 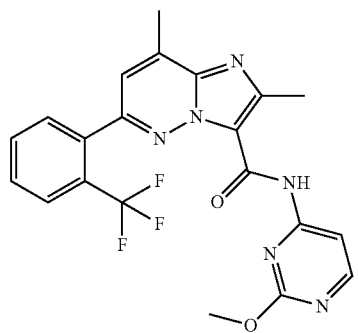 [SMILES: COc1nccc(NC(=O)c2c(C)nc3c(C)cc(-c4ccccc4C(F)(F)F)nn23)n1] |

| Compound No | Structure |
|---|---|
| 544 | 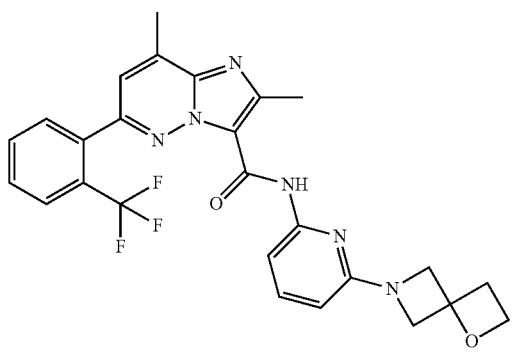 [SMILES: Cc1nc2c(C)cc(-c3ccccc3C(F)(F)F)nn2c1C(=O)Nc1cccc(N2CC3(CCO3)C2)n1] |
| 545 | 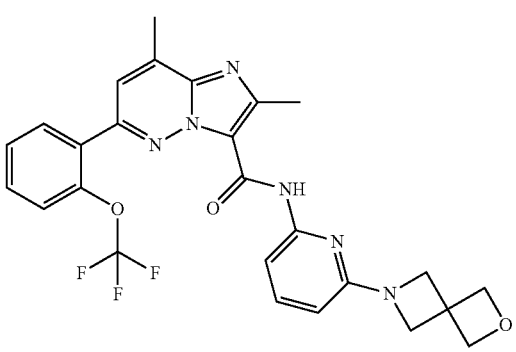 [SMILES: Cc1nc2c(C)cc(-c3ccccc3OC(F)(F)F)nn2c1C(=O)Nc1cccc(N2CC3(COC3)C2)n1] |
| 546 | 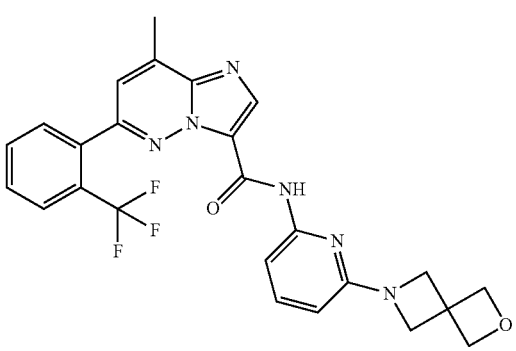 [SMILES: Cc1cc(-c2ccccc2C(F)(F)F)nn2c(C(=O)Nc3cccc(N4CC5(COC5)C4)n3)cnc12] |
| 553 | 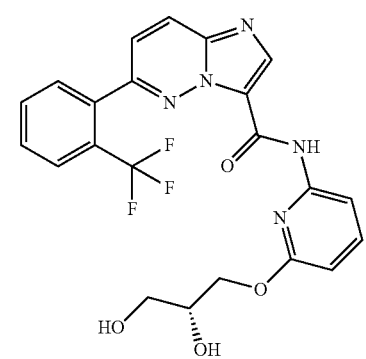 [SMILES: O=C(Nc1cccc(OC[C@H](O)CO)n1)c1cnc2ccc(-c3ccccc3C(F)(F)F)nn12] |

| Compound No | Structure |
|---|---|
| 554 | 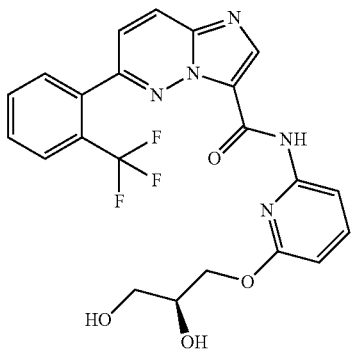 [SMILES: O=C(Nc1cccc(OC[C@@H](O)CO)n1)c1cnc2ccc(-c3ccccc3C(F)(F)F)nn12] |
| 555 | 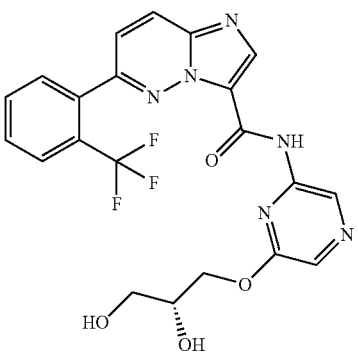 [SMILES: O=C(Nc1cncc(OC[C@H](O)CO)n1)c1cnc2ccc(-c3ccccc3C(F)(F)F)nn12] |
| 556 | 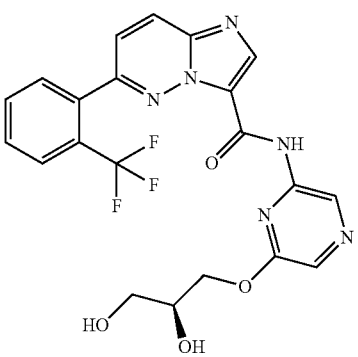 [SMILES: O=C(Nc1cncc(OC[C@@H](O)CO)n1)c1cnc2ccc(-c3ccccc3C(F)(F)F)nn12] |
| 557 | 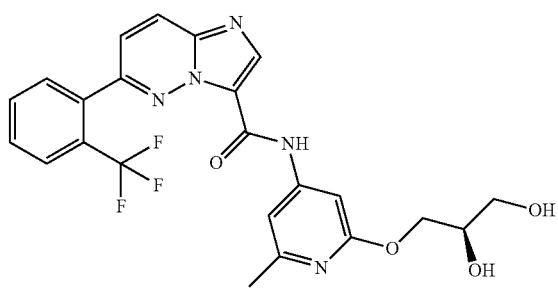 [SMILES: Cc1cc(NC(=O)c2cnc3ccc(-c4ccccc4C(F)(F)F)nn23)cc(OC[C@H](O)CO)n1] |

-continued
| Compound No | Structure |
|---|---|
| 558 | 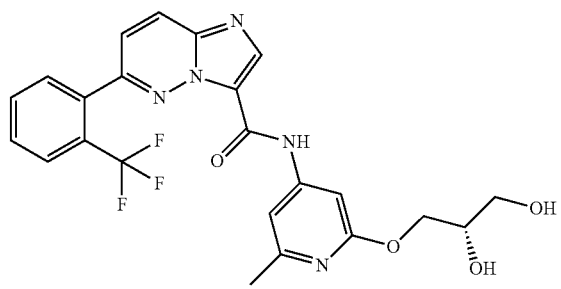 [SMILES: Cc1cc(NC(=O)c2cnc3ccc(-c4ccccc4C(F)(F)F)nn23)cc(OC[C@@H](O)CO)n1] |
| 561 | 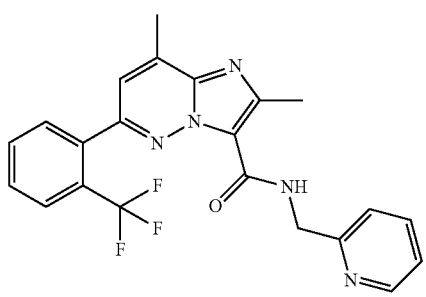 [SMILES: Cc1nc2c(C)cc(-c3ccccc3C(F)(F)F)nn2c1C(=O)NCc1ccccn1] |
| 86 | 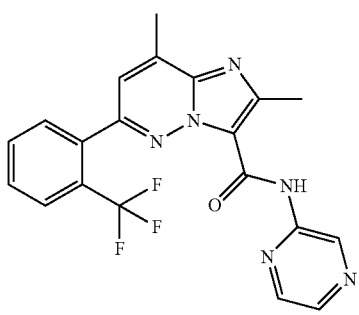 [SMILES: Cc1nc2c(C)cc(-c3ccccc3C(F)(F)F)nn2c1C(=O)Nc1cnccn1] |
| 587 | 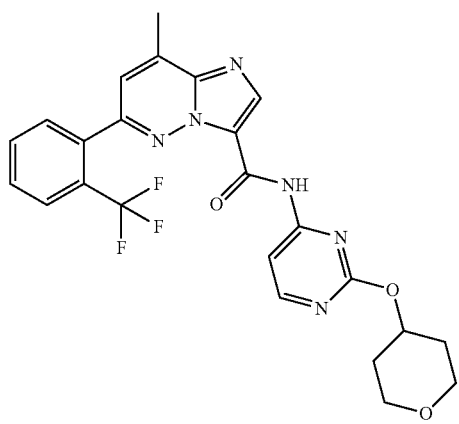 [SMILES: Cc1cc(-c2ccccc2C(F)(F)F)nn2c(C(=O)Nc3ccnc(OC4CCOCC4)n3)cnc12] |

| Compound No | Structure |
|---|---|
| 588 | 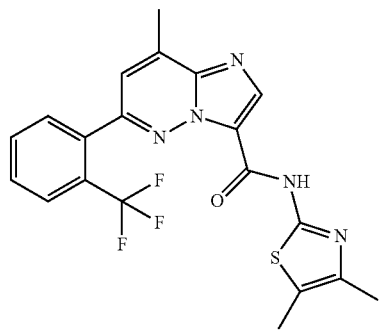 [SMILES: Cc1nc(NC(=O)c2cnc3c(C)cc(-c4ccccc4C(F)(F)F)nn23)sc1C] |
| 589 | 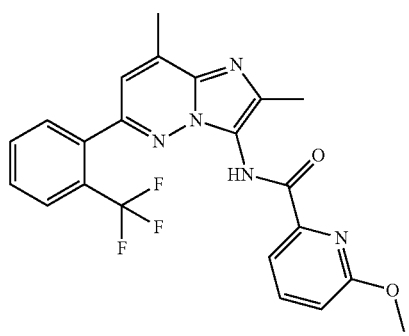 [SMILES: COc1cccc(C(=O)Nc2c(C)nc3c(C)cc(-c4ccccc4C(F)(F)F)nn23)n1] |
| 562 | 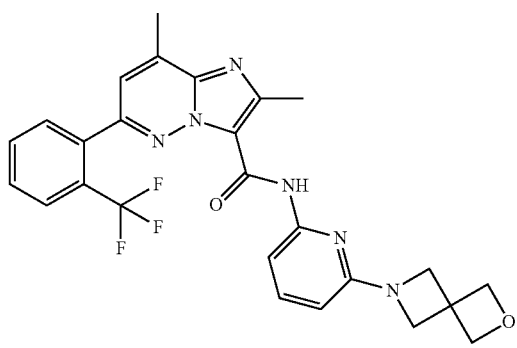 [SMILES: Cc1nc2c(C)cc(-c3ccccc3C(F)(F)F)nn2c1C(=O)Nc1cccc(N2CC3(COC3)C2)n1] |
| 590 | 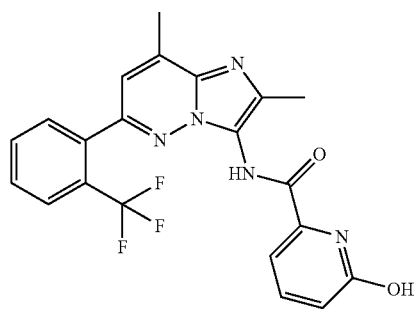 [SMILES: Cc1nc2c(C)cc(-c3ccccc3C(F)(F)F)nn2c1NC(=O)c1cccc(O)n1] |

| Compound No | Structure |
|---|---|
| 591 | 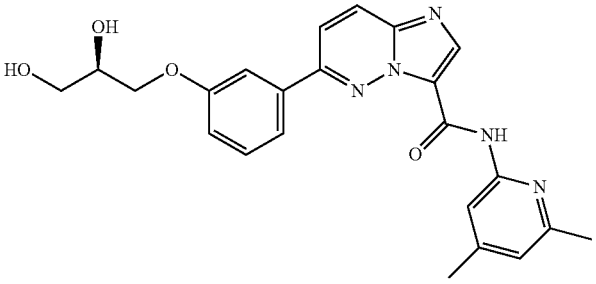 [SMILES: Cc1cc(C)nc(NC(=O)c2cnc3ccc(-c4cccc(OC[C@H](O)CO)c4)nn23)c1] |
| 592 | 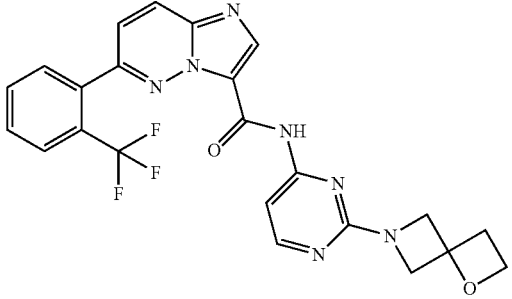 |
| 593 | 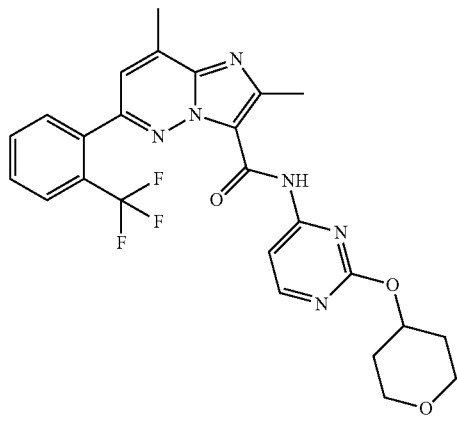 [SMILES: Cc1nc2c(C)cc(-c3ccccc3C(F)(F)F)nn2c1C(=O)Nc1ccnc(OC2CCOCC2)n1] |
| 594 | 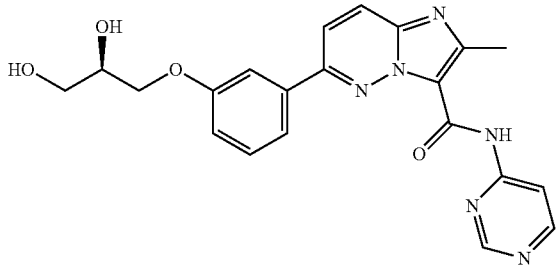 [SMILES: Cc1nc2ccc(-c3cccc(OC[C@H](O)CO)c3)nn2c1C(=O)Nc1ccncn1] |
| 595 | 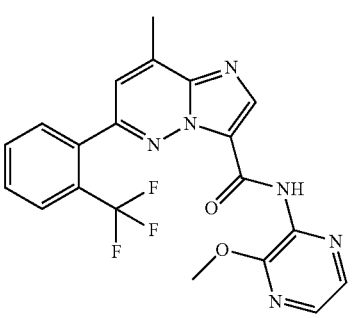 [SMILES: COc1nccnc1NC(=O)c1cnc2c(C)cc(-c3ccccc3C(F)(F)F)nn12] |

-continued
| Compound No | Structure |
|---|---|
| 596 | 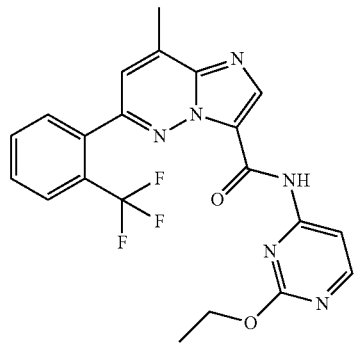 [SMILES: CCOc1nccc(NC(=O)c2cnc3c(C)cc(-c4ccccc4C(F)(F)F)nn23)n1] |
| 597 | 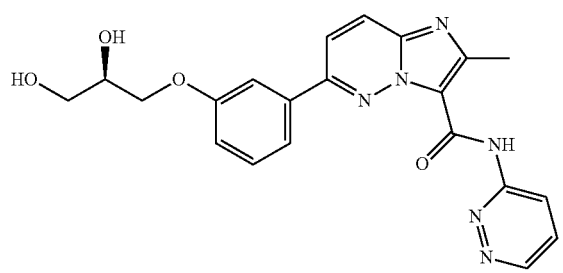 |
| 598 | 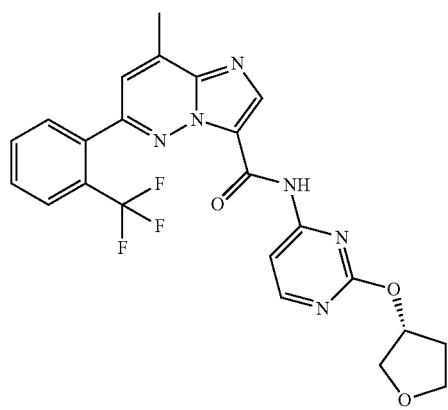 [SMILES: Cc1cc(-c2ccccc2C(F)(F)F)nn2c(C(=O)Nc3ccnc(O[C@@H]4CCOC4)n3)cnc12] |
| 600 | 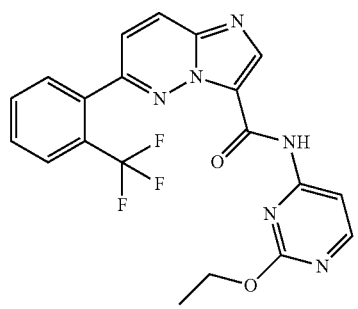 [SMILES: CCOc1nccc(NC(=O)c2cnc3ccc(-c4ccccc4C(F)(F)F)nn23)n1] |

-continued
| Compound No | Structure |
|---|---|
| 601 | 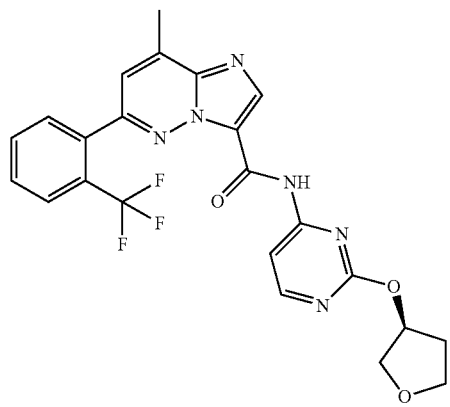 [SMILES: Cc1cc(-c2ccccc2C(F)(F)F)nn2c(C(=O)Nc3ccnc(O[C@H]4CCOC4)n3)cnc12] |
| 602 | 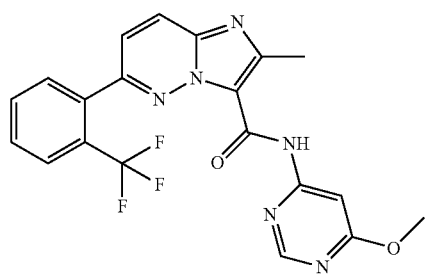 |
| 615 | 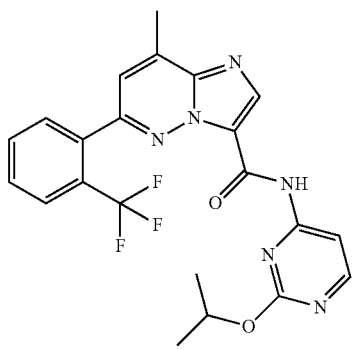 [SMILES: Cc1cc(-c2ccccc2C(F)(F)F)nn2c(C(=O)Nc3ccnc(OC(C)C)n3)cnc12] |
| 627 | 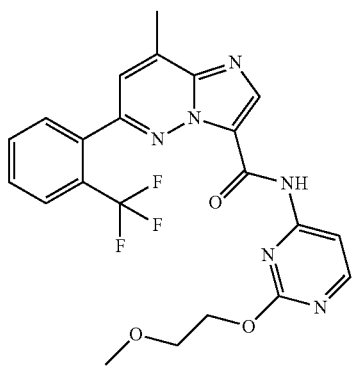 [SMILES: COCCOc1nccc(NC(=O)c2cnc3c(C)cc(-c4ccccc4C(F)(F)F)nn23)n1] |

-continued

| Compound No | Structure |
|---|---|
| 634 | 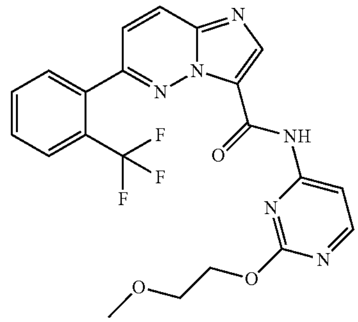 [SMILES: COCCOc1nccc(NC(=O)c2cnc3ccc(-c4ccccc4C(F)(F)F)nn23)n1] |
| 645 | 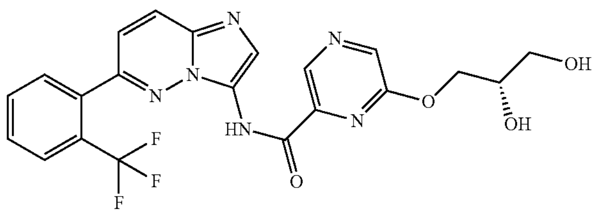 [SMILES: O=C(Nc1cnc2ccc(-c3ccccc3C(F)(F)F)nn12)c1cncc(OC[C@@H](O)CO)n1] |
| 646 | 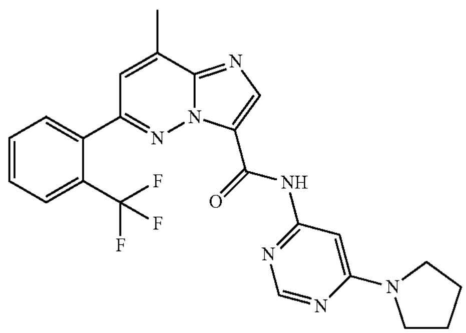 [SMILES: Cc1cc(-c2ccccc2C(F)(F)F)nn2c(C(=O)Nc3cc(N4CCCC4)ncn3)cnc12] |
| 647 | 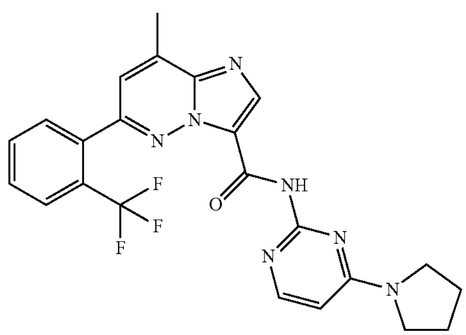 [SMILES: Cc1cc(-c2ccccc2C(F)(F)F)nn2c(C(=O)Nc3nccc(N4CCCC4)n3)cnc12] |
| 662 | 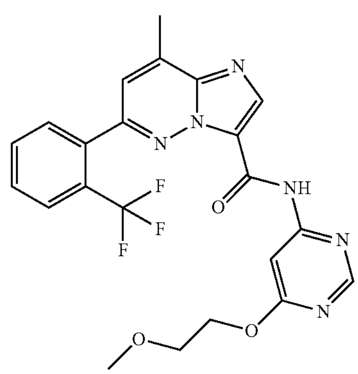 [SMILES: COCCOc1cc(NC(=O)c2cnc3c(C)cc(-c4ccccc4C(F)(F)F)nn23)ncn1] |

| Compound No | Structure |
|---|---|
| 663 | 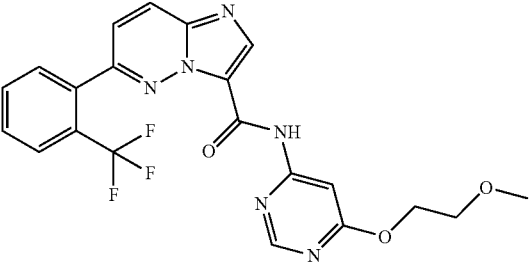 [SMILES: COCCOc1cc(NC(=O)c2cnc3ccc(-c4ccccc4C(F)(F)F)nn23)ncn1] |
| 664 | 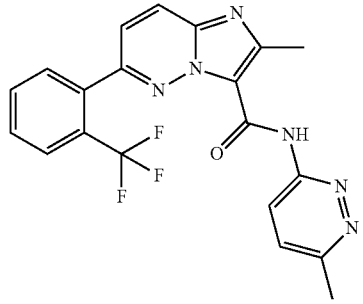 [SMILES: Cc1ccc(NC(=O)c2c(C)nc3ccc(-c4ccccc4C(F)(F)F)nn23)nn1] |
| 665 | 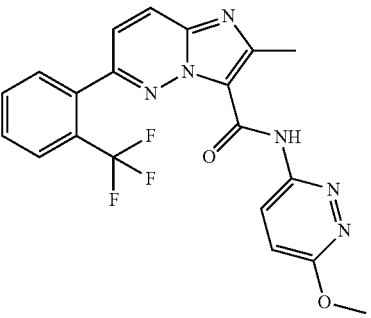 [SMILES: COc1ccc(NC(=O)c2c(C)nc3ccc(-c4ccccc4C(F)(F)F)nn23)nn1] |
| 666 | 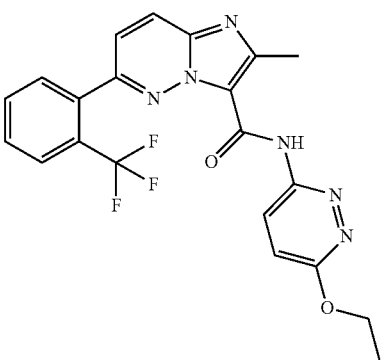 [SMILES: CCOc1ccc(NC(=O)c2c(C)nc3ccc(-c4ccccc4C(F)(F)F)nn23)nn1] |
| 667 | 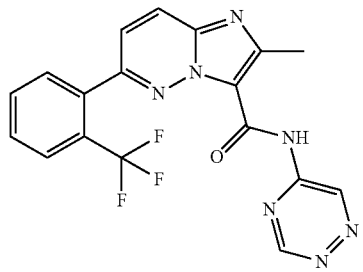 [SMILES: Cc1nc2ccc(-c3ccccc3C(F)(F)F)nn2c1C(=O)Nc1cnncn1] |

| Compound No | Structure |
|---|---|
| 668 | 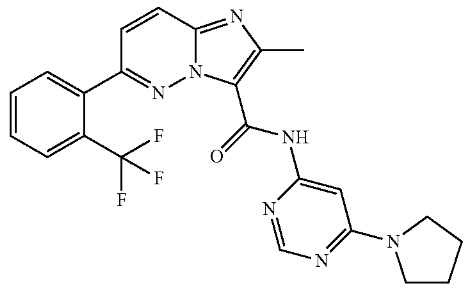 |
| 669 | 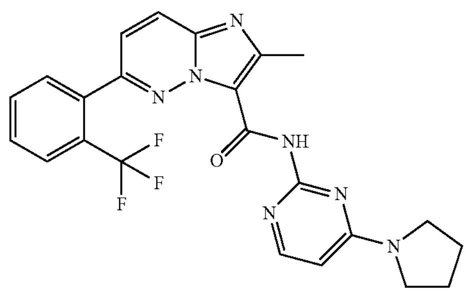 [SMILES: Cc1nc2ccc(-c3ccccc3C(F)(F)F)nn2c1C(=O)Nc1nccc(N2CCCC2)n1] |
| 670 | 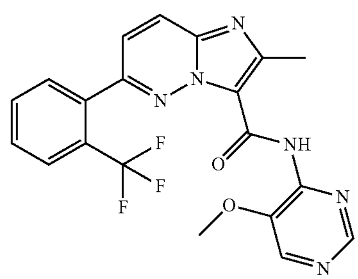 [SMILES: COc1cncnc1NC(=O)c1c(C)nc2ccc(-c3ccccc3C(F)(F)F)nn12] |
| 671 | 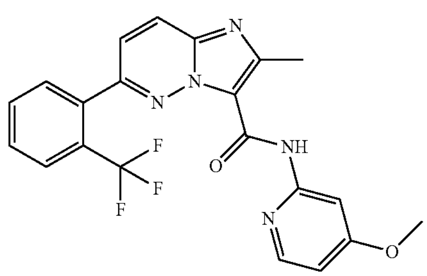 [SMILES: COc1ccnc(NC(=O)c2c(C)nc3ccc(-c4ccccc4C(F)(F)F)nn23)c1] |
| 672 | 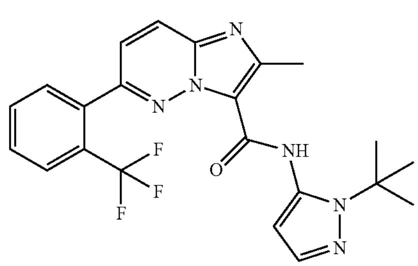 [SMILES: Cc1nc2ccc(-c3ccccc3C(F)(F)F)nn2c1C(=O)Nc1ccnn1C(C)(C)C] |

-continued

| Compound No | Structure |
|---|---|
| 673 | 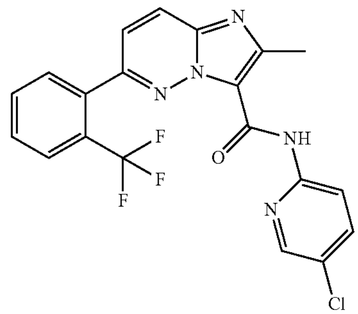 [SMILES: Cc1nc2ccc(-c3ccccc3C(F)(F)F)nn2c1C(=O)Nc1ccc(Cl)cn1] |
| 674 | 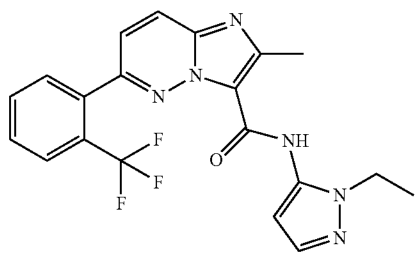 [SMILES: CCn1nccc1NC(=O)c1c(C)nc2ccc(-c3ccccc3C(F)(F)F)nn12] |
| 675 | 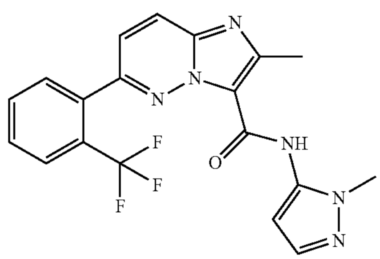 [SMILES: Cc1nc2ccc(-c3ccccc3C(F)(F)F)nn2c1C(=O)Nc1ccnn1C] |
| 676 | 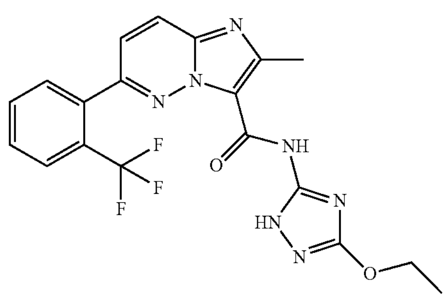 [SMILES: CCOc1n[nH]c(NC(=O)c2c(C)nc3ccc(-c4ccccc4C(F)(F)F)nn23)n1] |
| 677 | 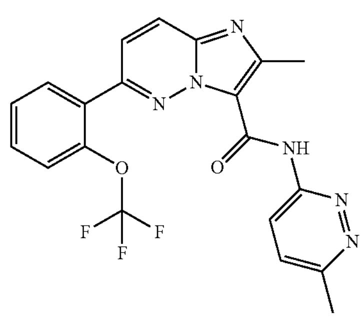 [SMILES: Cc1ccc(NC(=O)c2c(C)nc3ccc(-c4ccccc4OC(F)(F)F)nn23)nn1] |

| Compound No | Structure |
|---|---|
| 678 | 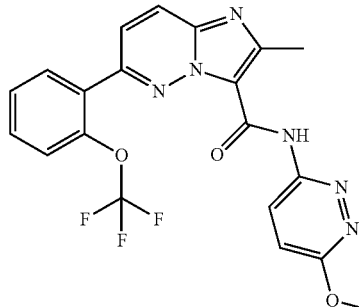 |
| 679 | 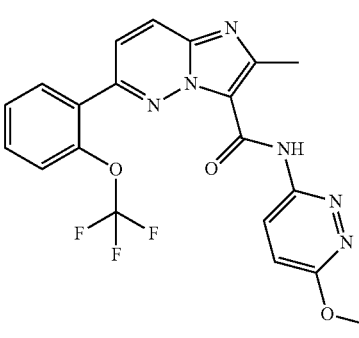 |
| 680 | 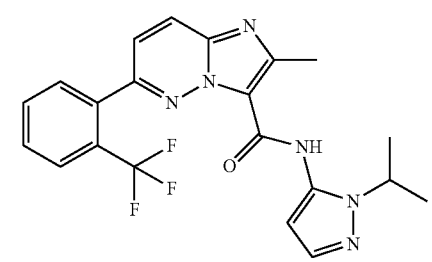 [SMILES: Cc1nc2ccc(-c3ccccc3C(F)(F)F)nn2c1C(=O)Nc1ccnn1C(C)C] |
| 681 | 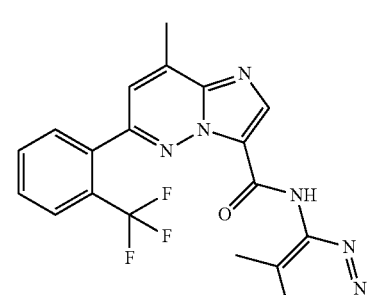 |

| Compound No | Structure |
|---|---|
| 691 | 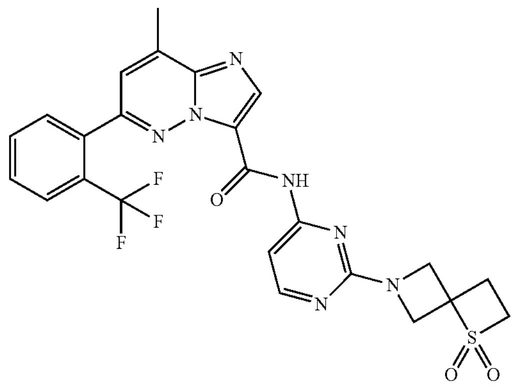 [SMILES: Cc1cc(-c2ccccc2C(F)(F)F)nn2c(C(=O)Nc3ccnc(N4CC5(CCS5(=O)=O)C4)n3)cnc12] |
| 692 | 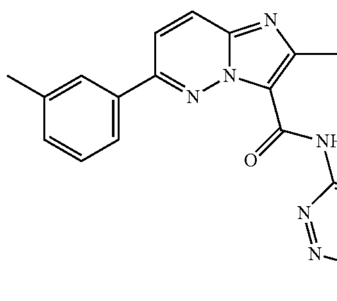 |
| 693 | 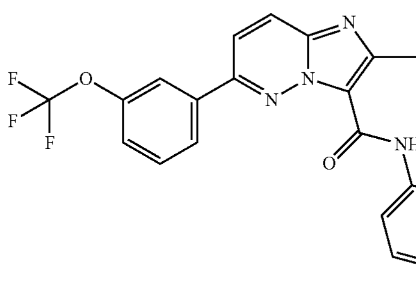 |
| 694 | 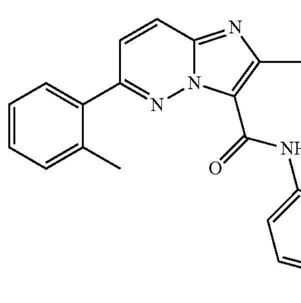 |
| 704 | 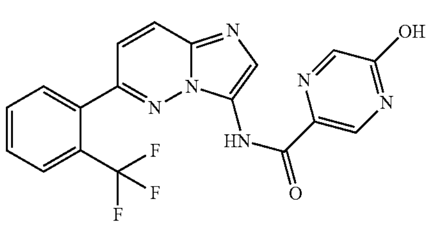 [SMILES: O=C(Nc1cnc2ccc(-c3ccccc3C(F)(F)F)nn12)c1cnc(O)cn1] |

-continued

| Compound No | Structure |
|---|---|
| 705 | 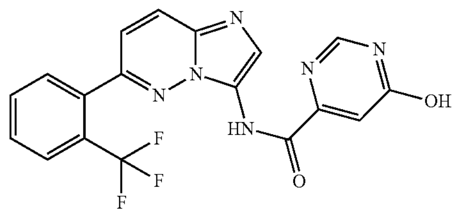 [SMILES: O=C(Nc1cnc2ccc(-c3ccccc3C(F)(F)F)nn12)c1cc(O)ncn1] |
| 706 | 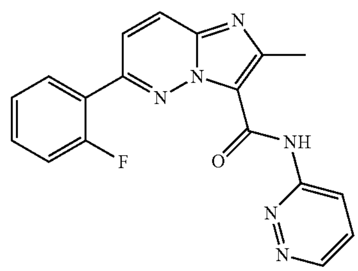 |
| 715 | 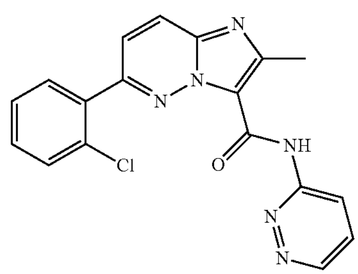 |
| 716 | 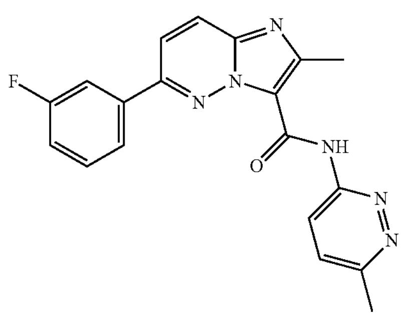 [SMILES: Cc1ccc(NC(=O)c2c(C)nc3ccc(-c4cccc(F)c4)nn23)nn1] |
| 717 | 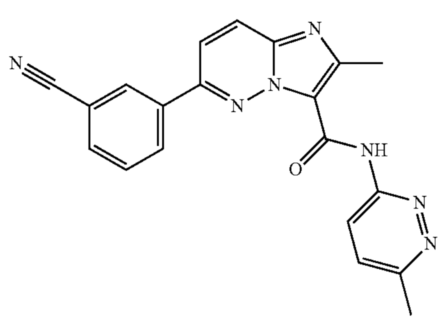 [SMILES: Cc1ccc(NC(=O)c2c(C)nc3ccc(-c4cccc(C#N)c4)nn23)nn1] |

-continued
| Compound No | Structure |
|---|---|
| 718 | 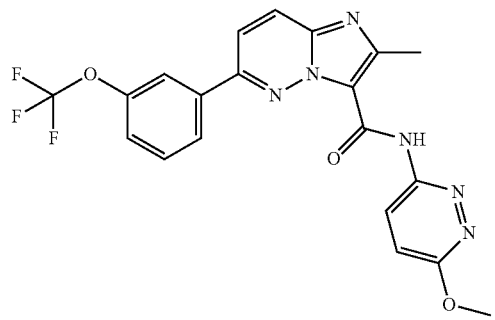 [SMILES: COc1ccc(NC(=O)c2c(C)nc3ccc(-c4cccc(OC(F)(F)F)c4)nn23)nn1] |
| 719 | 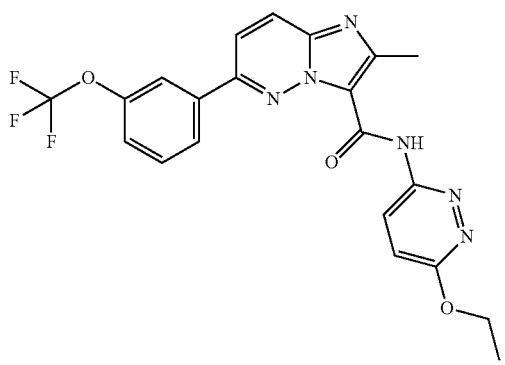 [SMILES: CCOc1ccc(NC(=O)c2c(C)nc3ccc(-c4cccc(OC(F)(F)F)c4)nn23)nn1] |
| 720 | 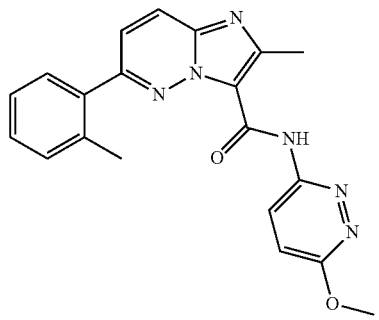 [SMILES: COc1ccc(NC(=O)c2c(C)nc3ccc(-c4ccccc4C)nn23)nn1] |
| 721 | 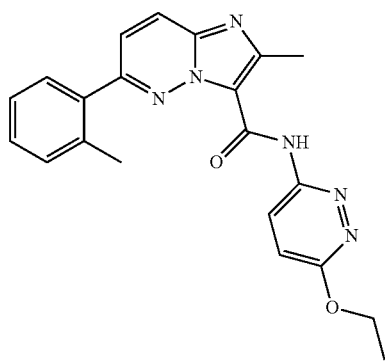 [SMILES: CCOc1ccc(NC(=O)c2c(C)nc3ccc(-c4ccccc4C)nn23)nn1] |

| Compound No | Structure |
|---|---|
| 729 | 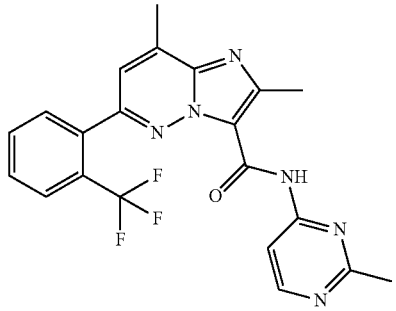 [SMILES: Cc1nccc(NC(=O)c2c(C)nc3c(C)cc(-c4ccccc4C(F)(F)F)nn23)n1] |
| 730 | 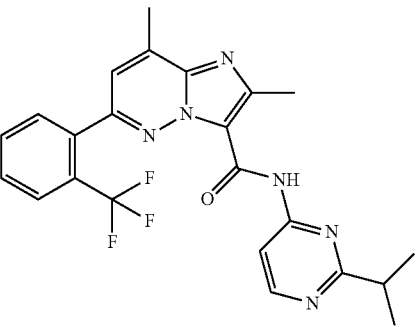 [SMILES: Cc1nc2c(C)cc(-c3ccccc3C(F)(F)F)nn2c1C(=O)Nc1ccnc(C(C)C)n1] |
| 731 | 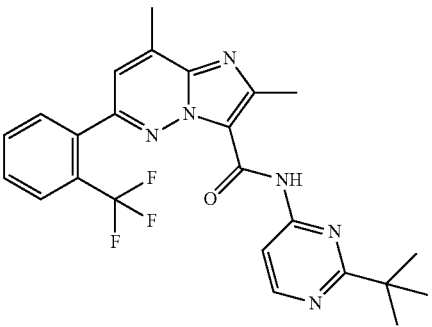 [SMILES: Cc1nc2c(C)cc(-c3ccccc3C(F)(F)F)nn2c1C(=O)Nc1ccnc(C(C)(C)C)n1] |
| 732 | 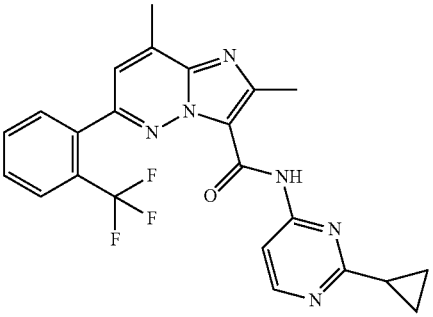 [SMILES: Cc1nc2c(C)cc(-c3ccccc3C(F)(F)F)nn2c1C(=O)Nc1ccnc(C2CC2)n1] |

-continued
| Compound No | Structure |
|---|---|
| 733 | 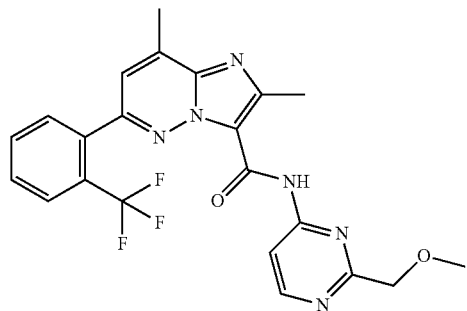 [SMILES: COCc1nccc(NC(=O)c2c(C)nc3c(C)cc(-c4ccccc4C(F)(F)F)nn23)n1] |
| 738 | 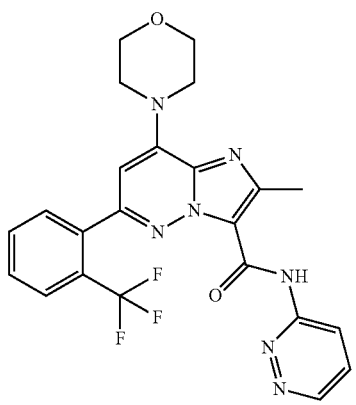 [SMILES: Cc1nc2c(N3CCOCC3)cc(-c3ccccc3C(F)(F)F)nn2c1C(=O)Nc1cccnn1] |
| 739 | 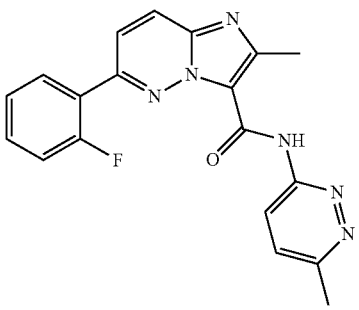 [SMILES: Cc1ccc(NC(=O)c2c(C)nc3ccc(-c4ccccc4F)nn23)nn1] |
| 740 | 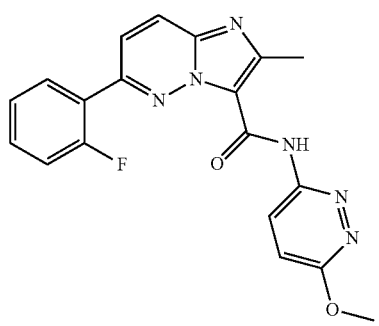 |

-continued
| Compound No | Structure |
|---|---|
| 741 | 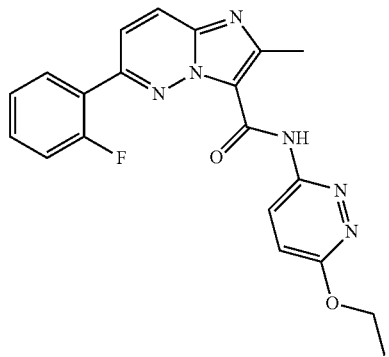 |
| 742 | 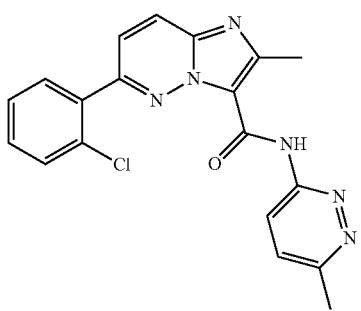 |
| 743 | 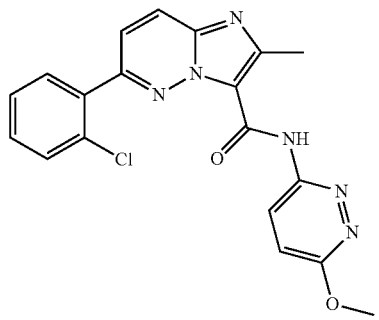 |
| 744 | 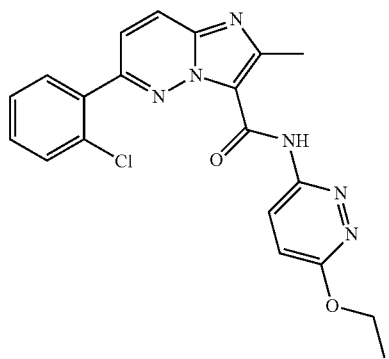 [SMILES: CCOc1ccc(NC(=O)c2c(C)nc3ccc(-c4ccccc4Cl)nn23)nn1] |

| Compound No | Structure |
|---|---|
| 745 | 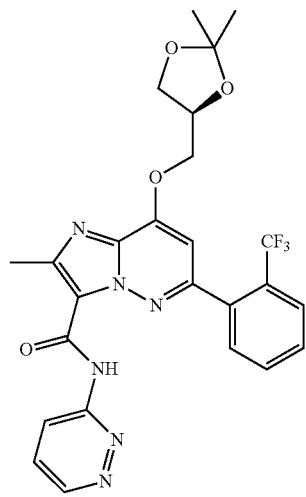 [SMILES: Cc1nc2c(OC[C@H]3COC(C)(C)O3)cc(-c3ccccc3C(F)(F)F)nn2c1C(=O)Nc1cccnn1] |
| 757 | 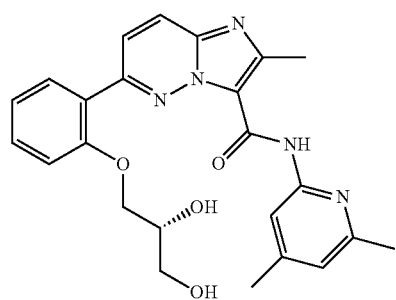 [SMILES: Cc1cc(C)nc(NC(=O)c2c(C)nc3ccc(-c4ccccc4OC[C@H](O)CO)nn23)c1] |
| 759 | 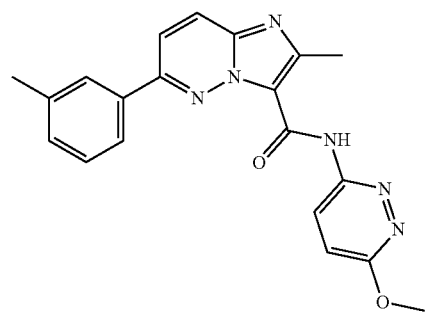 |
| 760 | 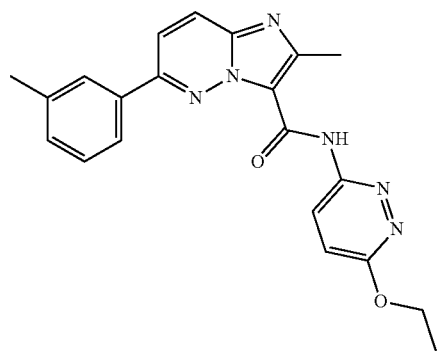 [SMILES: CCOc1ccc(NC(=O)c2c(C)nc3ccc(-c4cccc(C)c4)nn23)nn1] |

-continued

| Compound No | Structure |
|---|---|
| 761 | 6-(3-fluorophenyl)-2-methyl-N-(6-methoxypyridazin-3-yl)imidazo[1,2-b]pyridazine-3-carboxamide |
| 762 | 6-(3-fluorophenyl)-2-methyl-N-(6-ethoxypyridazin-3-yl)imidazo[1,2-b]pyridazine-3-carboxamide |
| 763 | 6-(2-bromophenyl)-2-methyl-N-(pyridazin-3-yl)imidazo[1,2-b]pyridazine-3-carboxamide |
| 764 | 6-(2-bromophenyl)-2-methyl-N-(6-methylpyridazin-3-yl)imidazo[1,2-b]pyridazine-3-carboxamide |
| 765 | 6-(2-bromophenyl)-2-methyl-N-(6-methoxypyridazin-3-yl)imidazo[1,2-b]pyridazine-3-carboxamide |

-continued
| Compound No | Structure |
|---|---|
| 766 | 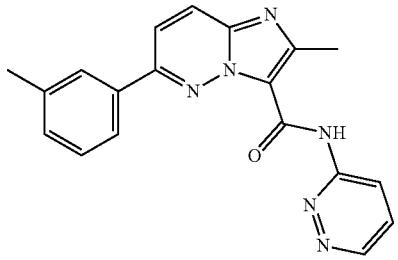 [SMILES: Cc1cccc(-c2ccc3nc(C)c(C(=O)Nc4cccnn4)n3n2)c1] |
| 767 | 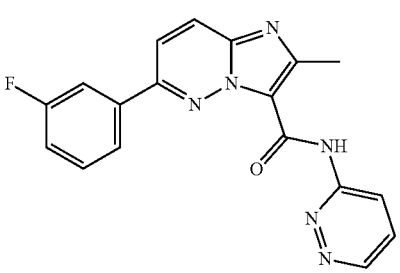 [SMILES: Cc1nc2ccc(-c3cccc(F)c3)nn2c1C(=O)Nc1cccnn1] |
| 772 | 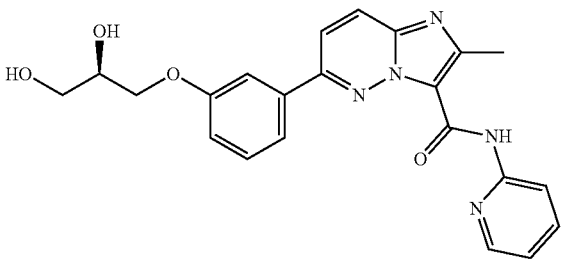 [SMILES: Cc1nc2ccc(-c3cccc(OC[C@H](O)CO)c3)nn2c1C(=O)Nc1ccccn1] |
| 773 | 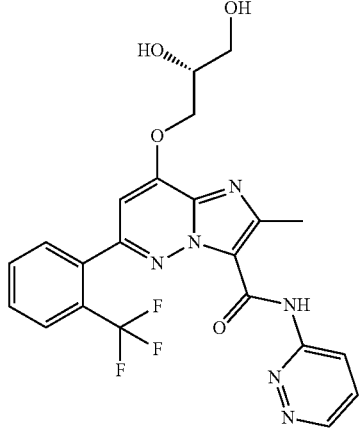 [SMILES: Cc1nc2c(OC[C@H](O)CO)cc(-c3ccccc3C(F)(F)F)nn2c1C(=O)Nc1cccnn1] |
| 774 | 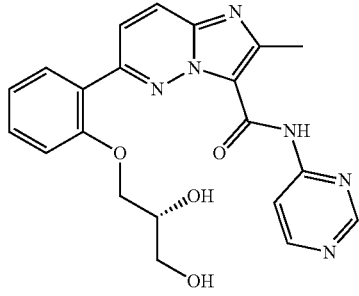 [SMILES: Cc1nc2ccc(-c3ccccc3OC[C@H](O)CO)nn2c1C(=O)Nc1ccncn1] |

| Compound No | Structure |
|---|---|
| 775 | 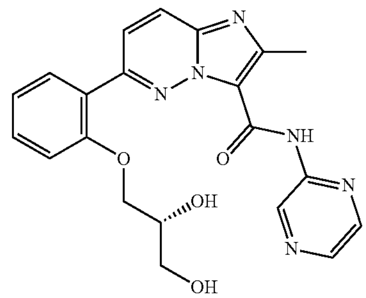 [SMILES: Cc1nc2ccc(-c3ccccc3OC[C@H](O)CO)nn2c1C(=O)Nc1cnccn1] |
| 790 | 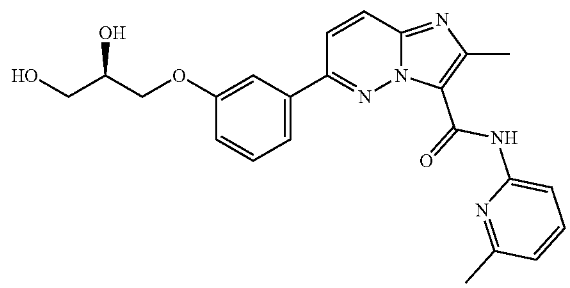 [SMILES: Cc1cccc(NC(=O)c2c(C)nc3ccc(-c4cccc(OC[C@H](O)CO)c4)nn23)n1] |
| 791 | 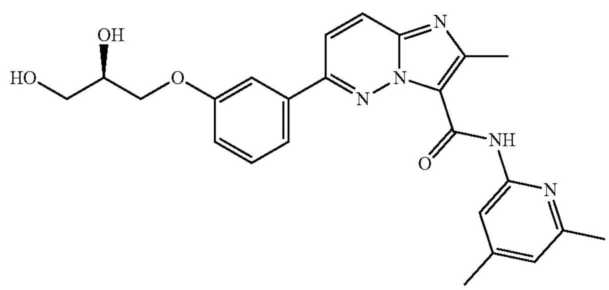 [SMILES: Cc1cc(C)nc(NC(=O)c2c(C)nc3ccc(-c4cccc(OC[C@H](O)CO)c4)nn23)c1] |
| 792 | 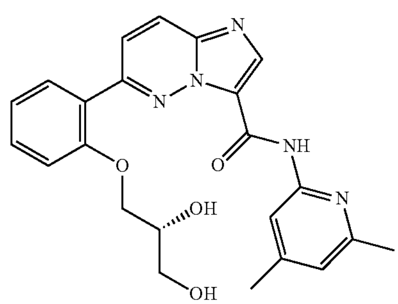 [SMILES: Cc1cc(C)nc(NC(=O)c2cnc3ccc(-c4ccccc4OC[C@H](O)CO)nn23)c1] |
| 798 | 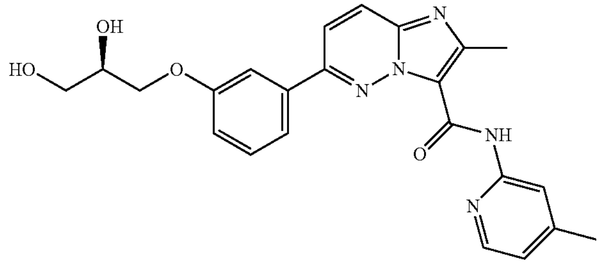 [SMILES: Cc1ccnc(NC(=O)c2c(C)nc3ccc(-c4cccc(OC[C@H](O)CO)c4)nn23)c1] |

| Compound No | Structure |
|---|---|
| 804 | 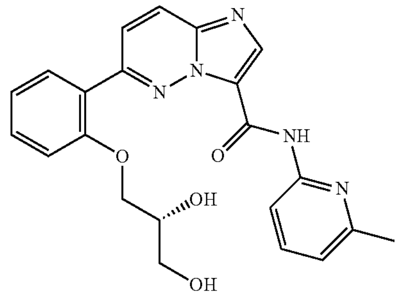 [SMILES: Cc1cccc(NC(=O)c2cnc3ccc(-c4ccccc4OC[C@H](O)CO)nn23)n1] |
| 805 | 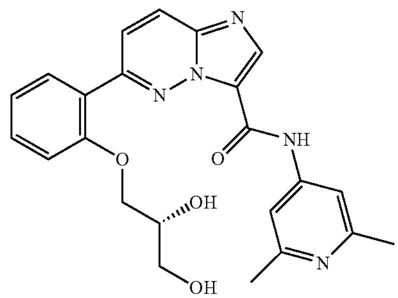 [SMILES: Cc1cc(NC(=O)c2cnc3ccc(-c4ccccc4OC[C@H](O)CO)nn23)cc(C)n1] |
| 811 | 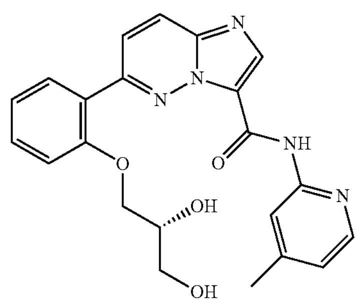 [SMILES: Cc1ccnc(NC(=O)c2cnc3ccc(-c4ccccc4OC[C@H](O)CO)nn23)c1] |
| 812 | 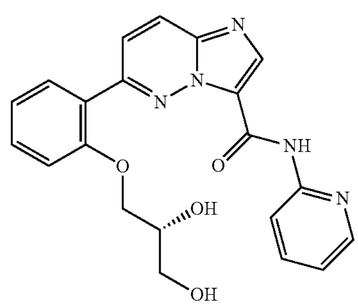 [SMILES: O=C(Nc1ccccn1)c1cnc2ccc(-c3ccccc3OC[C@H](O)CO)nn12] |
| 814 | 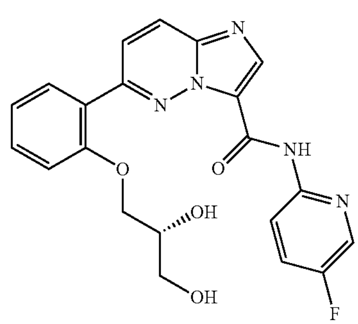 [SMILES: O=C(Nc1ccc(F)cn1)c1cnc2ccc(-c3ccccc3OC[C@H](O)CO)nn12] |

-continued

| Compound No | Structure |
|---|---|
| 815 | 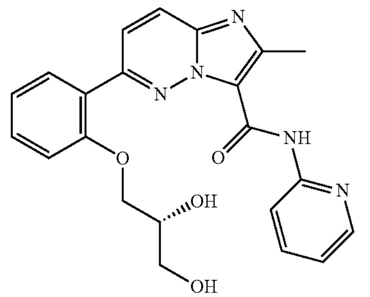 [SMILES: Cc1nc2ccc(-c3ccccc3OC[C@H](O)CO)nn2c1C(=O)Nc1ccccn1] |
| 816 | 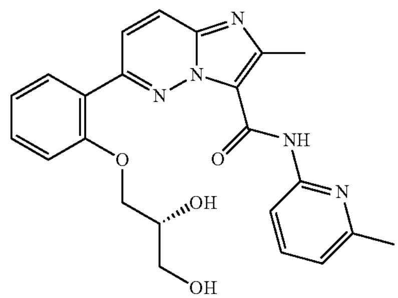 [SMILES: Cc1cccc(NC(=O)c2c(C)nc3ccc(-c4ccccc4OC[C@H](O)CO)nn23)n1] |
| 817 | 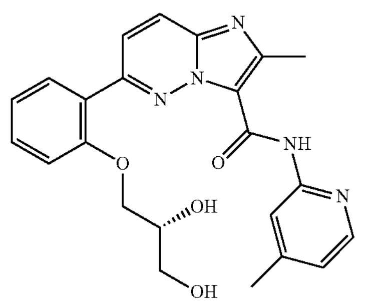 [SMILES: Cc1ccnc(NC(=O)c2c(C)nc3ccc(-c4ccccc4OC[C@H](O)CO)nn23)c1] |
| 818 | 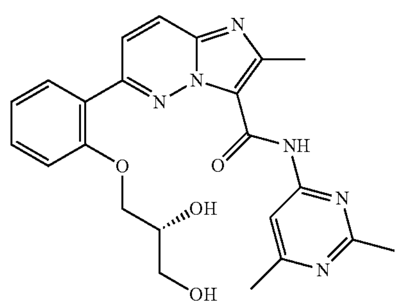 |
| 819 | 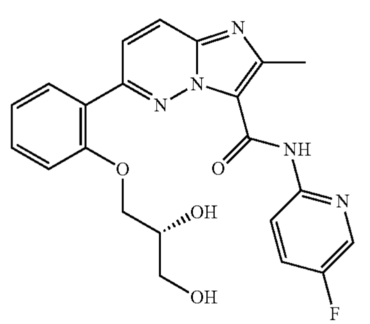 [SMILES: Cc1nc2ccc(-c3ccccc3OC[C@H](O)CO)nn2c1C(=O)Nc1ccc(F)cn1] |

| Compound No | Structure |
|---|---|
| 820 | 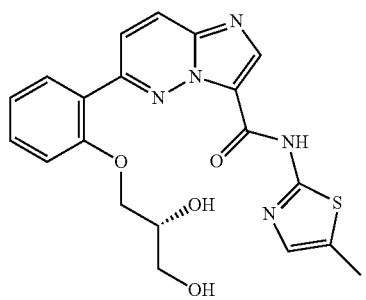 [SMILES: Cc1cnc(NC(=O)c2cnc3ccc(-c4ccccc4OC[C@H](O)CO)nn23)s1] |
| 821 | 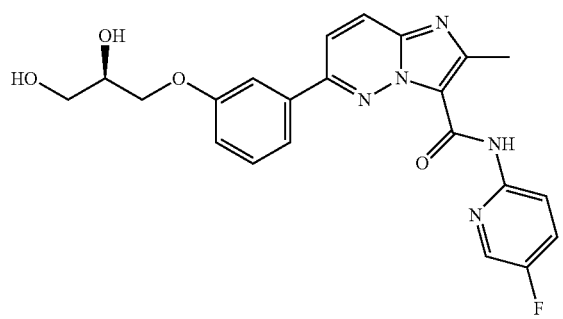 [SMILES: Cc1nc2ccc(-c3cccc(OC[C@H](O)CO)c3)nn2c1C(=O)Nc1ccc(F)cn1] |
| 822 | 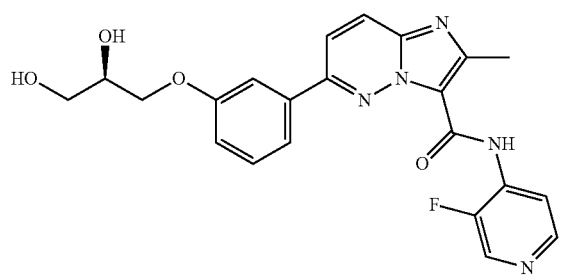 [SMILES: Cc1nc2ccc(-c3cccc(OC[C@H](O)CO)c3)nn2c1C(=O)Nc1ccncc1F] |
| 823 | 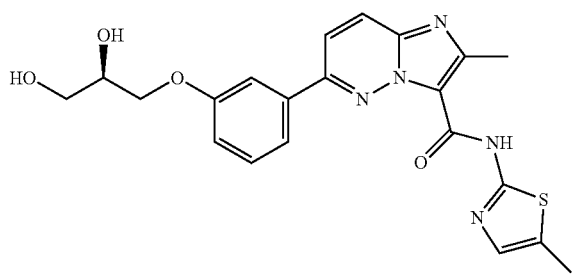 [SMILES: Cc1cnc(NC(=O)c2c(C)nc3ccc(-c4cccc(OC[C@H](O)CO)c4)nn23)s1] |
| 829 | 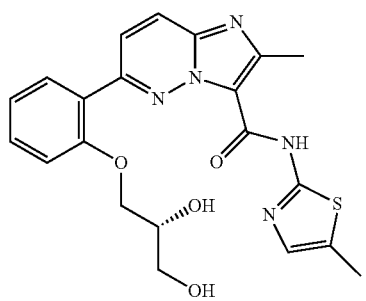 [SMILES: Cc1cnc(NC(=O)c2c(C)nc3ccc(-c4ccccc4OC[C@H](O)CO)nn23)s1] |

-continued
| Compound No | Structure |
|---|---|
| 831 | 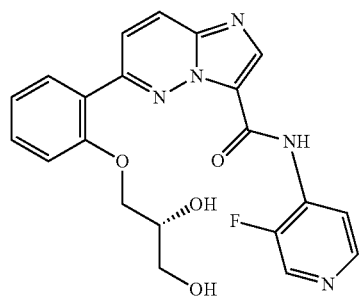 [SMILES: O=C(Nc1ccncc1F)c1cnc2ccc(-c3ccccc3OC[C@H](O)CO)nn12] |
| 832 | 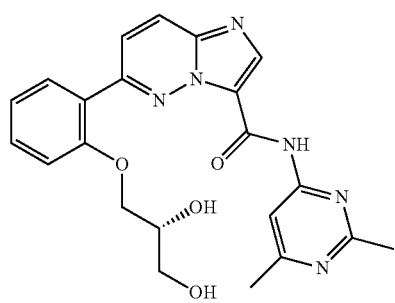 [SMILES: Cc1cc(NC(=O)c2cnc3ccc(-c4ccccc4OC[C@H](O)CO)nn23)nc(C)n1] |
| 833 | 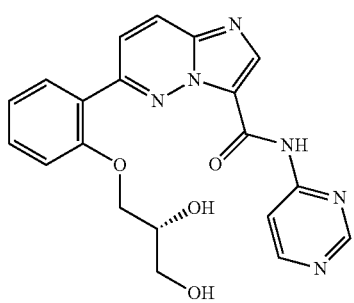 [SMILES: O=C(Nc1ccncn1)c1cnc2ccc(-c3ccccc3OC[C@H](O)CO)nn12] |
| 834 | 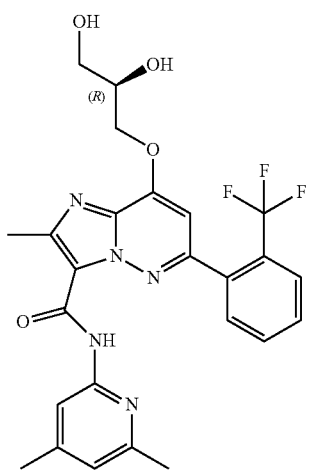 |

-continued
| Compound No | Structure |
|---|---|
| 835 | 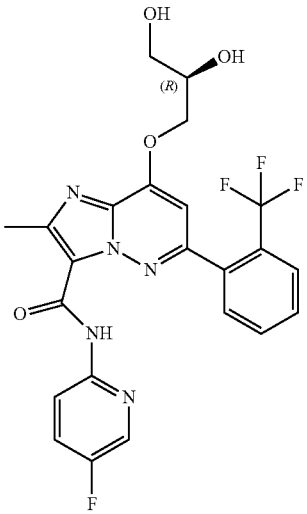 |
| 842 | 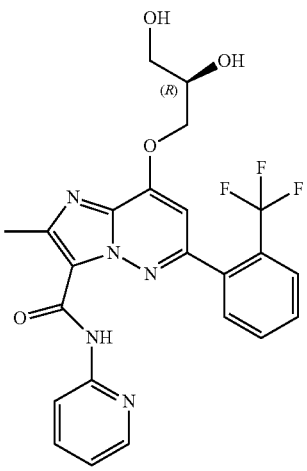 |
| 843 | 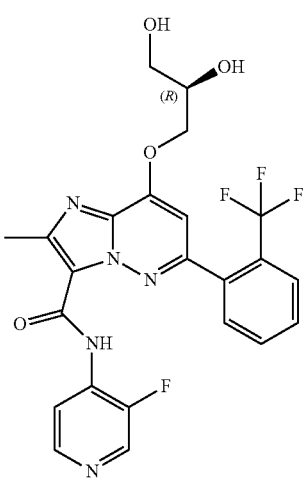 |

-continued
| Compound No | Structure |
|---|---|
| 847 | 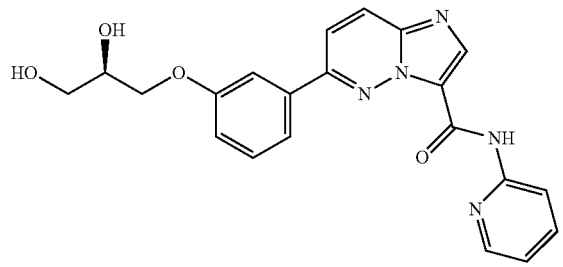 [SMILES: O=C(Nc1ccccn1)c1cnc2ccc(-c3cccc(OC[C@H](O)CO)c3)nn12] |
| 848 | 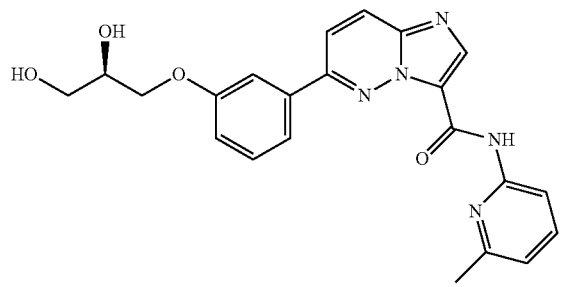 [SMILES: Cc1cccc(NC(=O)c2cnc3ccc(-c4cccc(OC[C@H](O)CO)c4)nn23)n1] |
| 849 | 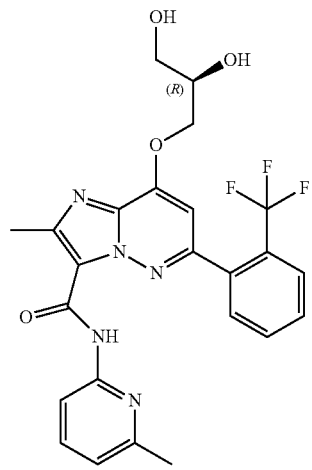 |
| 850 | 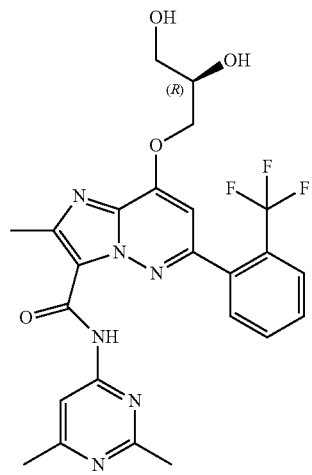 |

-continued

| Compound No | Structure |
|---|---|
| 847 | 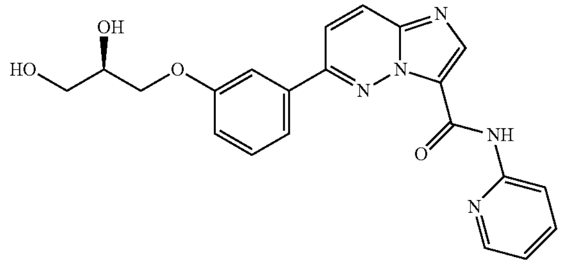 [SMILES: O=C(Nc1ccccn1)c1cnc2ccc(-c3cccc(OC[C@H](O)CO)c3)nn12] |
| 848 | 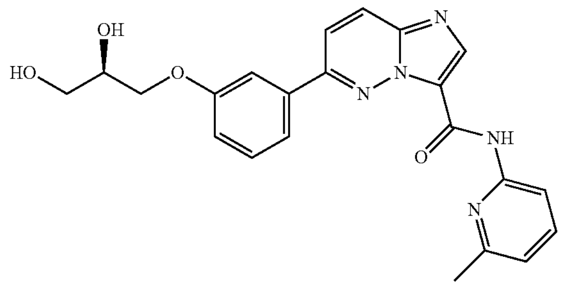 [SMILES: Cc1cccc(NC(=O)c2cnc3ccc(-c4cccc(OC[C@H](O)CO)c4)nn23)n1] |
| 849 | 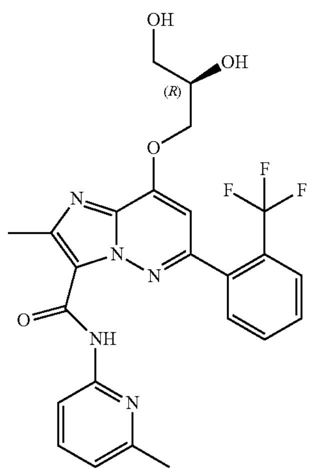 |
| 850 | 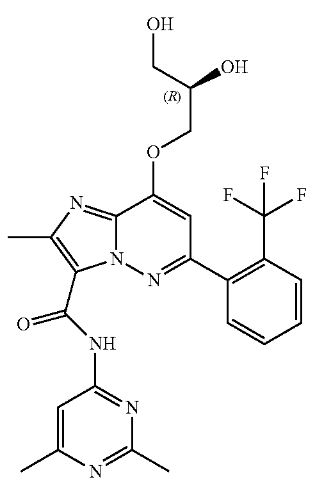 |

| Compound No | Structure |
|---|---|
| 858 | 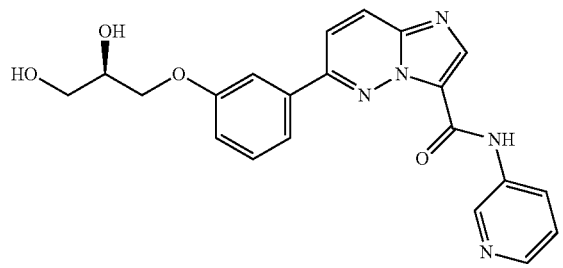 [SMILES: O=C(Nc1cccnc1)c1cnc2ccc(-c3cccc(OC[C@H](O)CO)c3)nn12] |
| 859 | 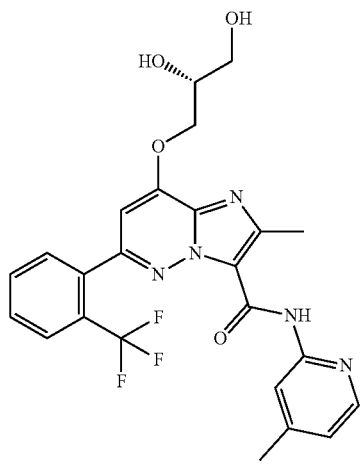 [SMILES: Cc1ccnc(NC(=O)c2c(C)nc3c(OC[C@H](O)CO)cc(-c4ccccc4C(F)(F)F)nn23)c1] |
| 860 | 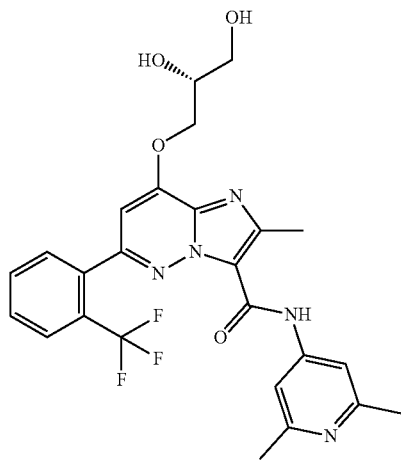 [SMILES: Cc1cc(NC(=O)c2c(C)nc3c(OC[C@H](O)CO)cc(-c4ccccc4C(F)(F)F)nn23)cc(C)n1] |

-continued
| Compound No | Structure |
|---|---|
| 861 | 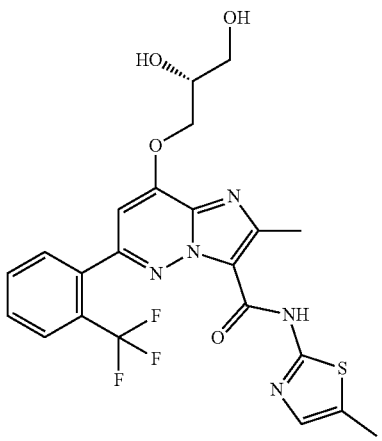 [SMILES: Cc1cnc(NC(=O)c2c(C)nc3c(OC[C@H](O)CO)cc(-c4ccccc4C(F)(F)F)nn23)s1] |
| 862 | 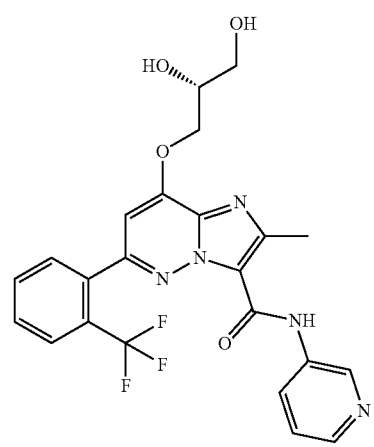 [SMILES: Cc1nc2c(OC[C@H](O)CO)cc(-c3ccccc3C(F)(F)F)nn2c1C(=O)Nc1cccnc1] |
| 863 | 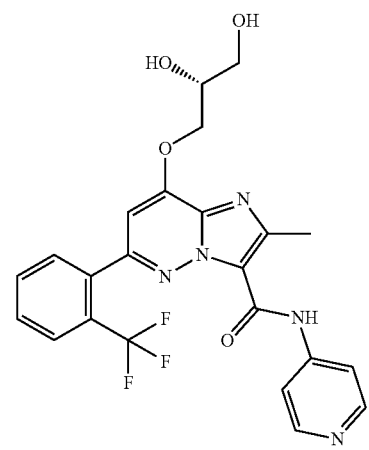 [SMILES: Cc1nc2c(OC[C@H](O)CO)cc(-c3ccccc3C(F)(F)F)nn2c1C(=O)Nc1ccncc1] |

-continued
| Compound No | Structure |
|---|---|
| 864 | 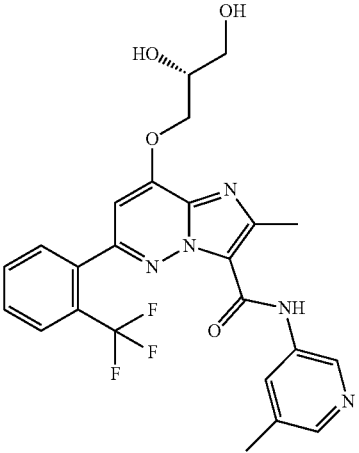 [SMILES: Cc1cncc(NC(=O)c2c(C)nc3c(OC[C@H](O)CO)cc(-c4ccccc4C(F)(F)F)nn23)c1] |
| 865 | 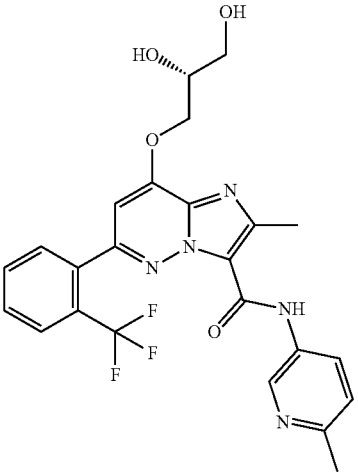 [SMILES: Cc1ccc(NC(=O)c2c(C)nc3c(OC[C@H](O)CO)cc(-c4ccccc4C(F)(F)F)nn23)cn1] |
| 875 | 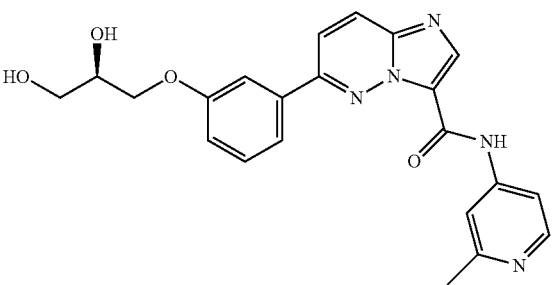 |
| 876 | 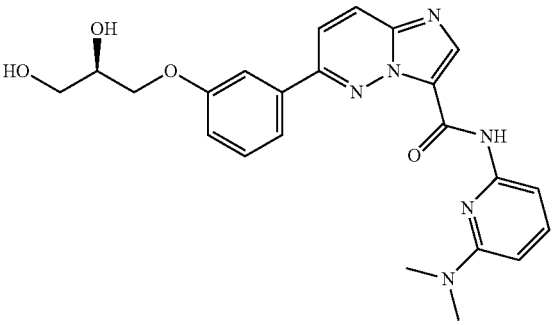 [SMILES: CN(C)c1cccc(NC(=O)c2cnc3ccc(-c4cccc(OC[C@H](O)CO)c4)nn23)n1] |

| Compound No | Structure |
|---|---|
| 878 | 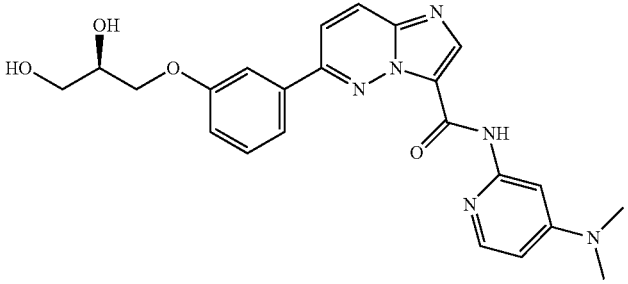 [SMILES: CN(C)c1ccnc(NC(=O)c2cnc3ccc(-c4cccc(OC[C@H](O)CO)c4)nn23)c1] |
| 883 | 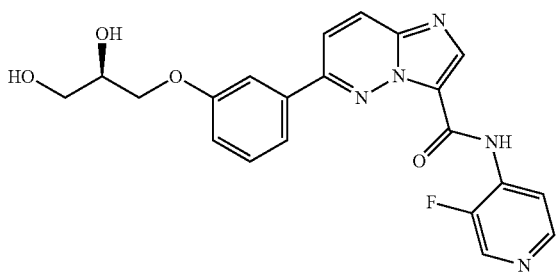 [SMILES: O=C(Nc1ccncc1F)c1cnc2ccc(-c3cccc(OC[C@H](O)CO)c3)nn12] |
| 884 | 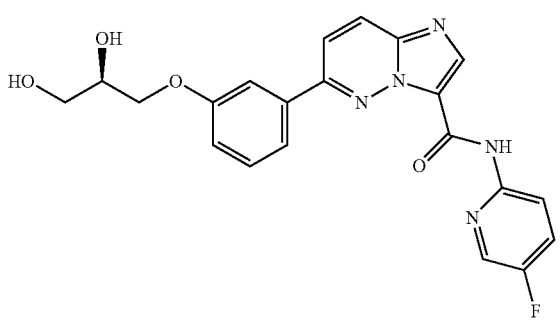 [SMILES: O=C(Nc1ccc(F)cn1)c1cnc2ccc(-c3cccc(OC[C@H](O)CO)c3)nn12] |
|  | 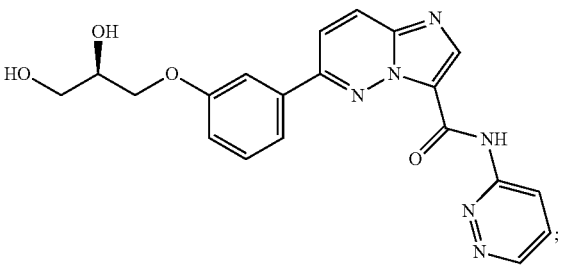 [SMILES: O=C(Nc1cccnn1)c1cnc2ccc(-c3cccc(OC[C@H](O)CO)c3)nn12] |
or a pharmaceutically acceptable salt thereof.

2. A pharmaceutical composition comprising a compound according to claim 1 and at least one pharmaceutically acceptable excipient, carrier or diluent.

3. A compound which is

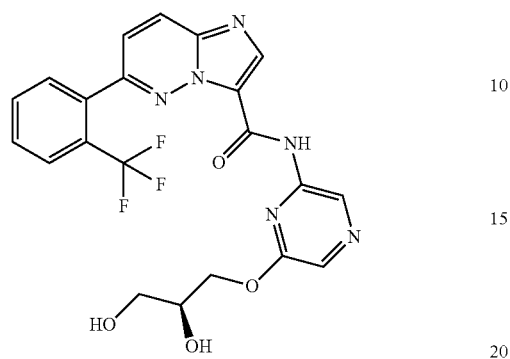

or a pharmaceutically acceptable salt thereof.

4. A pharmaceutical composition comprising a compound according to claim 3 and at least one pharmaceutically acceptable excipient, carrier or diluent.

* * * * *